(12) United States Patent
Chen et al.

(10) Patent No.: US 11,696,956 B2
(45) Date of Patent: *Jul. 11, 2023

(54) BICYCLIC PEPTIDE LIGANDS SPECIFIC FOR EPHA2

(71) Applicant: BicycleTx Limited, Cambridge (GB)

(72) Inventors: Liuhong Chen, Cambridge (GB); Philip Huxley, Cambridge (GB); Silvia Pavan, Cambridge (GB); Katerine Van Rietschoten, Cambridge (GB)

(73) Assignee: BicycleTx Limited, Cambridge (GB)

( * ) Notice: Subject to any disclaimer, the term of this patent is extended or adjusted under 35 U.S.C. 154(b) by 188 days.

This patent is subject to a terminal disclaimer.

(21) Appl. No.: 16/771,186

(22) PCT Filed: Dec. 19, 2018

(86) PCT No.: PCT/GB2018/053678
§ 371 (c)(1),
(2) Date: Jun. 9, 2020

(87) PCT Pub. No.: WO2019/122863
PCT Pub. Date: Jun. 27, 2019

(65) Prior Publication Data
US 2022/0289792 A1 Sep. 15, 2022

(30) Foreign Application Priority Data

Dec. 19, 2017 (GB) .................... 1721259
Mar. 14, 2018 (GB) .................... 1804102
Nov. 14, 2018 (GB) .................... 1818603

(51) Int. Cl.
| | | |
|---|---|---|
| A61K 47/64 | (2017.01) | |
| A61K 38/10 | (2006.01) | |
| C07K 7/08 | (2006.01) | |
| A61P 35/00 | (2006.01) | |
| A61K 47/65 | (2017.01) | |
| A61K 38/05 | (2006.01) | |
| A61K 47/62 | (2017.01) | |

(52) U.S. Cl.
CPC .......... *A61K 47/6415* (2017.08); *A61K 38/05* (2013.01); *A61K 38/10* (2013.01); *A61K 47/62* (2017.08); *A61K 47/64* (2017.08); *A61K 47/65* (2017.08); *A61P 35/00* (2018.01); *C07K 7/08* (2013.01)

(58) Field of Classification Search
CPC ........ A61K 38/12; A61K 38/05; A61K 38/10; A61K 47/6415; C07K 7/54; C07K 7/08
See application file for complete search history.

(56) References Cited

U.S. PATENT DOCUMENTS

| | | | |
|---|---|---|---|
| 8,685,890 B2 | 4/2014 | Winter et al. | |
| 9,868,767 B2 | 1/2018 | Pei et al. | |
| 10,919,937 B2 | 2/2021 | Beswick et al. | |
| 11,306,123 B2 | 4/2022 | Mudd et al. | |
| 11,312,749 B2 | 4/2022 | Mudd et al. | |
| 11,332,500 B2 | 5/2022 | Mudd et al. | |
| 2017/0190743 A1 | 7/2017 | Pei et al. | |
| 2019/0184025 A1 | 6/2019 | Chen et al. | |
| 2019/0307836 A1 | 10/2019 | Keen et al. | |
| 2019/0389906 A1 * | 12/2019 | Beswick | A61K 38/10 |
| 2020/0338203 A1 | 10/2020 | Chen et al. | |
| 2021/0040154 A1 | 2/2021 | Mudd et al. | |
| 2021/0069287 A1 | 3/2021 | Mudd et al. | |
| 2021/0101937 A1 | 4/2021 | Mudd et al. | |
| 2021/0147484 A1 | 5/2021 | Beswick et al. | |
| 2021/0261620 A1 | 8/2021 | Teufel et al. | |
| 2021/0299210 A2 | 9/2021 | Keen et al. | |
| 2022/0184222 A1 | 6/2022 | Bennett et al. | |

FOREIGN PATENT DOCUMENTS

| | | | |
|---|---|---|---|
| WO | 2009098450 A2 | 8/2009 | |
| WO | 2016067035 A1 | 5/2016 | |
| WO | WO-2016174103 A1 * | 11/2016 | ............... C07K 7/06 |
| WO | 2017191460 A1 | 11/2017 | |
| WO | 2018115203 A1 | 6/2018 | |
| WO | 2019122860 A1 | 6/2019 | |
| WO | 2019122861 A1 | 6/2019 | |

(Continued)

OTHER PUBLICATIONS

Merritt et al., Analysis of EphA2 expression and mutant p53 in ovarian cancer, Cancer Biology and Therapy, pp. 1357-1360; 2006 (Year: 2006).*

Center for Diseases, "What Can I Do to Reduce My Risk of Ovarian Cancer", 2021 (Year: 2021).*

Bennett et al., "Abstract 5855: Bicycle Drug Conjugates targeting EphA2 for the treatment of solid tumors: Discovery and selection of BT5528," Cancer Research. 2018 <<http://cancerres.aacrjournals.org/content/78/13_Supplement/5855>>.

PCT International Search Report and Written Opinion for PCT/GB2018/05367 dated Mar. 20, 2018.

Bennett et al., "Abstract 5855: Bicycle Drug Conjugates Targeting EphA2 for the Treatment of Solid Tumors: Discovery and Selection of BT5528," Cancer Research, 2018, 4 Pages.

(Continued)

*Primary Examiner* — Lianko G Garyu
(74) *Attorney, Agent, or Firm* — Dechert LLP; Andrea L. C. Reid; Gang Wang

(57) ABSTRACT

The present invention relates to polypeptides which are covalently bound to non-aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder characterised by overexpression of EphA2 in diseased tissue (such as a tumour).

19 Claims, 21 Drawing Sheets

Specification includes a Sequence Listing.

(56) References Cited

FOREIGN PATENT DOCUMENTS

| WO | 2019122863 A1 | 6/2019 |
|---|---|---|
| WO | 2019193328 A1 | 10/2019 |
| WO | 2019243313 A1 | 12/2019 |
| WO | 2020084305 A1 | 4/2020 |
| WO | 2020201753 A1 | 10/2020 |
| WO | 2021019243 A1 | 2/2021 |
| WO | 2021019245 A1 | 2/2021 |
| WO | 2021064428 A1 | 4/2021 |
| WO | 2021105694 A1 | 6/2021 |
| WO | 2021250418 A1 | 12/2021 |

OTHER PUBLICATIONS

Annunziata et al., "Phase 1, open-label study of MEDI-547 in patients with relapsed or refractory solid tumors," Invest. New. Drugs. 2013;31(1):77-84.
Bennett et al., "Development of BT1718, a Bicycle Drug Conjugate (BDC) targeting MT1-MMP for treatment of solid tumours," European Journal of Cancer. 2016;69(1):S21.
Bennett, "BT5528, an EphA2-Targeting Bicycle Toxin Conjugate (BTC): Profound Efficacy Without Bleeding and Coagulation Abnormalities in Animal Models," Association for Cancer Research Annual Meeting, 2019, 11 Pages.
Chen et al., "Peptide Ligands Stabilized by Small Molecules," Angewandte Chemie International Edition. 2014;56(6):1602-1606.
Deonarain et al., "Small-Format Drug Conjugates: A Viable Alternative to ADCs for Solid Tumours?" Antibodies (Basel). 2018;7(2):16.
Deyle et al., "Phage Selection of Cyclic Peptides for Application in Research and Drug Development," Accounts of Chemical Research, 2017, vol. 50(8), pp. 1866-1874.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13):5144.
Heinis et al., "Phage-encoded combinatorial chemical libraries based on bicyclic peptides," Nat Chem Biol. 2009;5(7):502-7.
Mitra et al., "Structure-Activity Relationship Analysis of Peptides Targeting the EphA2 Receptor," Biochemistry. 2010;49(31):6687-95.
Mudd et al., "Identification and Optimization of EphA2-Selective Biccyles for the Delivery of Cytotoxic Payloads," J Med Chem. 2020; 63(8) 4107-4116.
PCT International Search Report and Written Opinion for PCT/GB2018/053678 dated Mar. 20, 2019.
PCT International Search Report for PCT Application No. PCT/EP2019/065993, mailed by the European Patent Office dated Sep. 24, 2019, 5 Pages.
PCT International Search Report for PCT Application No. PCT/GB2020/051829, mailed by the European Patent Office dated Oct. 30, 2020, 5 Pages.
Shi et al., "One-Bead-Two-Compound Thioether Bridged Macrocyclic [gamma]-AApeptide Screening Library Against EphA2," J. Med. Chem. 2017;60(22):9290-9298.
U.S. Appl. No. 16/771,186, filed Jun. 9, 2020.
U.S. Appl. No. 17/590,875, filed Feb. 2, 2022.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.
U.S. Appl. No. 17/655,822, filed Mar. 22, 2022.
U.S. Appl. No. 17/663,169, filed May 12, 2022.
U.S. Appl. No. 17/779,226, filed May 24, 2022.
Wu et al., "Design and Characterization of Novel EphA2 Agonists for Targeted Delivery of Chemotherapy to Cancer Cells," Chem. Biol. 2015;22(7):876-887.

* cited by examiner

BICYCLIC PEPTIDE LIGANDS SPECIFIC FOR EPHA2

CROSS-REFERENCE TO RELATED APPLICATIONS

This application is a U.S. national stage application under 35 U.S.C. § 371 of International Application No. PCT/GB2018/053678, filed Dec. 19, 2018, which claims priority under 35 U.S.C. § 119 to United Kingdom Application No. GB1721259.8, filed Dec. 19, 2017, United Kingdom Application No. GB1804102.0, filed Mar. 14, 2018, and United Kingdom Application No. GB1818603.1, filed Nov. 14, 2018, each of which is incorporated herein by reference in its entirety.

SEQUENCE LISTING

A Sequence Listing was submitted electronically via EFS in the form of a txt file on Jun. 9, 2020 and named "174752_SL.txt" (28,061 bytes), the contents of which are incorporated herein by reference in their entirety.

FIELD OF THE INVENTION

The present invention relates to polypeptides which are covalently bound to non-aromatic molecular scaffolds such that two or more peptide loops are subtended between attachment points to the scaffold. In particular, the invention describes peptides which are high affinity binders of the Eph receptor tyrosine kinase A2 (EphA2). The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder characterised by overexpression of EphA2 in diseased tissue (such as a tumour).

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, (MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example TATA (1,1',1''-(1,3,5-triazinane-1,3,5-triyl) triprop-2-en-1-one, Heinis et al. Angew Chem, Int Ed. 2014; 53:1602-1606).

Phage display-based combinatorial approaches have been developed to generate and screen large libraries of bicyclic peptides to targets of interest (Heinis et al. (2009), Nat Chem Biol 5 (7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for EphA2 comprising a polypeptide comprising at least three cysteine residues, separated by at least two loop sequences, and a non-aromatic molecular scaffold which forms covalent bonds with the cysteine residues of the polypeptide such that at least two polypeptide loops are formed on the molecular scaffold.

According to a further aspect of the invention, there is provided a drug conjugate comprising a peptide ligand as defined herein conjugated to one or more effector and/or functional groups.

According to a further aspect of the invention, there is provided a pharmaceutical composition comprising a peptide ligand or a drug conjugate as defined herein in combination with one or more pharmaceutically acceptable excipients.

According to a further aspect of the invention, there is provided a peptide ligand or drug conjugate as defined herein for use in preventing, suppressing or treating a disease or disorder characterised by overexpression of EphA2 in diseased tissue (such as a tumour).

Figure 1:
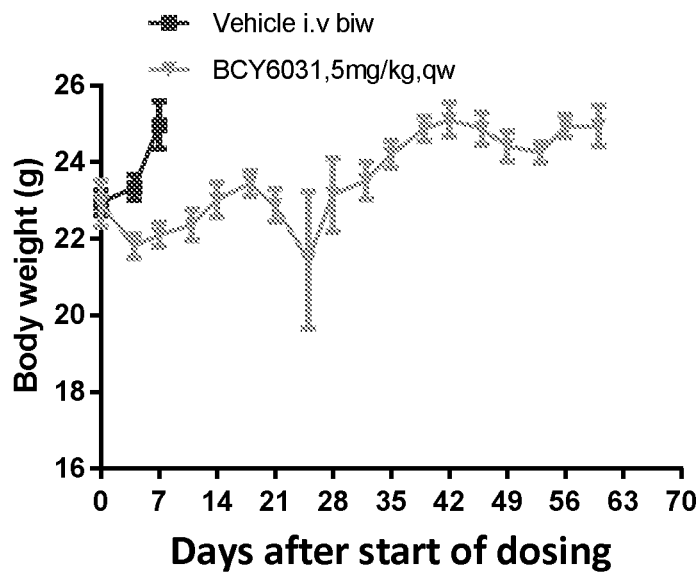
FIG. 1: Body weight changes after administering BCY6031 to female Balb/C nude mice bearing LU-01-0046 tumor. Data points represent group mean body weight.

Where error bars are present in the above Figures, these represent standard error of the mean (SEM).

DETAILED DESCRIPTION OF THE INVENTION

In one embodiment, said loop sequences comprise 2, 3, 5, 6 or 7 amino acid acids.

In a further embodiment, said loop sequences comprise three cysteine residues separated by two loop sequences one of which consists of 2 amino acids and the other of which consists of 7 amino acids (such as those listed in Table 4).

In a further embodiment, said loop sequences comprise three cysteine residues separated by two loop sequences both of which consist of 5 amino acids (such as those listed in Tables 3 and 4).

In a further embodiment, said loop sequences comprise three cysteine residues separated by two loop sequences both of which consist of 6 amino acids (such as those listed in Tables 3 to 5).

In a further embodiment, said loop sequences comprise three cysteine residues separated by two loop sequences both of which consist of 6 amino acids (such as those listed in Table 10).

In a further embodiment, said loop sequences comprise three cysteine residues separated by two loop sequences one of which consists of 7 amino acids and the other of which consists of 3 amino acids (such as those listed in Table 4).

In a further embodiment, said loop sequences comprise three cysteine residues separated by two loop sequences one of which consists of 6 amino acids and the other of which consists of 7 amino acids (such as those listed in Table 5).

In one embodiment, the peptide ligand comprises an amino acid sequence selected from:

$$C_i\text{-}X_1\text{-}C_{ii}\text{-}X_2\text{-}C_{iii}$$

wherein $X_1$ and $X_2$ represent the amino acid residues between the cysteine residues listed in Tables 3 to 5 and $C_i$, $C_{ii}$ and $C_{iii}$ represent first, second and third cysteine residues, respectively or a pharmaceutically acceptable salt thereof.

In a further embodiment, the peptide ligand comprises an amino acid sequence selected from one or more of the peptide ligands listed in one or more Tables 3 to 5.

In a further embodiment, the peptide ligand comprises an amino acid sequence selected from:

$$C_i\text{-}X_1\text{-}C_{ii}\text{-}X_2\text{-}C_{iii}$$

wherein $X_1$ and $X_2$ represent the amino acid residues between the cysteine residues listed in Table 10 and $C_i$, $C_{ii}$ and $C_{iii}$ represent first, second and third cysteine residues, respectively or a pharmaceutically acceptable salt thereof.

In a further embodiment, the peptide ligand comprises an amino acid sequence selected from one or more of the peptide ligands listed in Table 10.

In one embodiment, said loop sequences comprise three cysteine residues separated by two loop sequences both of which consist of 6 amino acids and the peptide ligand has an amino acid sequence selected from:

$C_{i+1(HyP)}LVNPLC_{ii}$LHP(D-Asp)W(HArg)$C_{iii}$ (SEQ ID NO: 1); and
$C_i$PLVNPLC$_{ii}$LHPGWTCH$_{iii}$ (SEQ ID NO: 97);

wherein HyP is hydroxyproline, HArg is homoarginine and $C_i$, $C_{ii}$ and $C_{iii}$ represent first, second and third cysteine residues, respectively or a pharmaceutically acceptable salt thereof.

In a further embodiment, said loop sequences comprise three cysteine residues separated by two loop sequences both of which consist of 6 amino acids and the peptide ligand has the following amino acid sequence:

$C_{i+1(HyP)}LVNPLC_{ii}$LHP(D-Asp)W(HArg)$C_{iii}$ (SEQ ID NO: 1);

wherein HyP is hydroxyproline, HArg is homoarginine and $C_i$, $C_{ii}$ and $C_{iii}$ represent first, second and third cysteine residues, respectively or a pharmaceutically acceptable salt thereof.

In one embodiment, the peptide ligand of the invention is a peptide ligand which is other than the amino acid sequence:

$C_{i+1(HyP)}LVNPLC_{ii}$LHP(D-Asp)W(HArg)$C_{iii}$ (SEQ ID NO: 1).

In one embodiment, said loop sequences comprise three cysteine residues separated by two loop sequences both of which consist of 6 amino acids and the peptide ligand has an amino acid sequence selected from:

(β-Ala)-Sar$_{10}$-A(HArg)D-C$_i$(HyP)LVNPLC$_{ii}$LHP(D-Asp)W(HArg)C$_{iii}$ (SEQ ID NO: 2)
(BCY6099; Compound 66); and
(β-Ala)-Sar$_{10}$-A(HArg)D-C$_i$PLVNPLC$_{ii}$LHPGWTC$_{iii}$ ((β-Ala)-Sar$_{10}$-
(SEQ ID NO: 11))
(BCY6014; Compound 67);

wherein Sar is sarcosine, HArg is homoarginine and HyP is hydroxyproline.

In a further embodiment, said loop sequences comprise three cysteine residues separated by two loop sequences both of which consist of 6 amino acids and the peptide ligand has the following amino acid sequence:

(β-Ala)-Sar$_{10}$-A(HArg)D-C$_i$(HyP)LVNPLC$_{ii}$LHP(D-Asp)W(HArg)C$_{iii}$ (SEQID NO: 2)
(BCY6099; Compound 66);

wherein Sar is sarcosine, HArg is homoarginine and HyP is hydroxyproline.

In one embodiment, the peptide ligand of the invention is a peptide ligand which is other than the amino acid sequence:

(β-Ala)-Sar$_{10}$-A(HArg)D-C$_i$(HyP)LVNPLC$_{ii}$LHP(D-Asp)W(HArg)C$_{iii}$ (SEQ ID NO: 2)
(BCY6099; Compound 66).

In one embodiment, the molecular scaffold is selected from 1,1',1''-(1,3,5-triazinane-1,3,5-triyl)triprop-2-en-1-one (TATA) and the peptide ligand is selected from any one of the peptide ligands listed in Tables 3 to 5.

In an alternative embodiment, the molecular scaffold is selected from 1,1',1''-(1,3,5-triazinane-1,3,5-triyl)triprop-2-en-1-one (TATA) and the peptide ligand is selected from any one of the peptide ligands listed in Table 10.

In one embodiment, the molecular scaffold is selected from 1,1',1''-(1,3,5-triazinane-1,3,5-triyl)triprop-2-en-1-one (TATA) and the peptide ligand is selected from:

(β-Ala)-Sar₁₀-A(HArg)D-C$_i$(HyP)LVNPLC$_{ii}$LHP(D-Asp)W(HArg)C$_{iii}$ (SEQ ID NO: 2)
(BCY6099; Compound 66); and
(β-Ala)-Sar₁₀-A(HArg)D-C$_{PLVNPLCii}$LHPGWTC$_{iii}$ ((β-Ala)-Sar₁₀- (SEQ ID NO: 11))
(BCY6014; Compound 67);

wherein Sar is sarcosine, HArg is homoarginine and HyP is hydroxyproline.

In a further embodiment, the molecular scaffold is selected from 1,1',1"-(1,3,5-triazinane-1,3,5-triyl)triprop-2-en-1-one (TATA) and the peptide ligand is:

(β-Ala)-Sar₁₀-A(HArg)D-C$_i$(HyP)LVNPLC$_{ii}$LHP(D-Asp)W(HArg)C$_{iii}$
(SEQ ID NO: 2);

wherein Sar is sarcosine, HArg is homoarginine and HyP is hydroxyproline.

In one embodiment, the peptide ligand is selected from any one of Compounds 1-113 or a pharmaceutically acceptable salt thereof.

In a further embodiment, the peptide ligand is Compound 66 (BCY6099) or Compound 67 (BCY6014) or a pharmaceutically acceptable salt thereof.

In a yet further embodiment, the peptide ligand is Compound 66 (BCY6099) or a pharmaceutically acceptable salt thereof.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Nomenclature
Numbering

When referring to amino acid residue positions within the peptides of the invention, cysteine residues (C$_i$, C$_{ii}$ and C$_{iii}$) are omitted from the numbering as they are invariant, therefore, the numbering of amino acid residues within the peptides of the invention is referred to as below:

-C$_i$-HyP$_1$-L$_2$-V$_3$-N$_4$-P$_5$-L$_6$-C$_{ii}$-L$_7$-H$_8$-P$_9$-(D-Asp)$_{10}$-W$_{11}$-(HArg)$_{12}$-C$_{iii}$-
(SEQ ID NO: 1).

For the purpose of this description, all bicyclic peptides are assumed to be cyclised with 1,1',1"-(1,3,5-triazinane-1,3,5-triyl)triprop-2-en-1-one (TATA) yielding a tri-substituted 1,1',1"-(1,3,5-triazinane-1,3,5-triyl)tripropan-1-one structure. Cyclisation with TATA occurs on C$_i$, C$_{ii}$, and C$_{iii}$.

Molecular Format

N- or C-terminal extensions to the bicycle core sequence are added to the left or right side of the sequence, separated by a hyphen. For example, an N-terminal (β-Ala)-Sar₁₀-Ala tail would be denoted as:

(β-Ala)-Sar₁₀-A-(SEQ ID NO: X).

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus become C-terminus and vice versa) and their stereochemistry is likewise also reversed (i.e. D-amino acids become L-amino acids and vice versa).

Peptide Ligands

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as C$_i$, C$_{ii}$ and C$_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent;

Selectivity. Certain peptide ligands of the invention demonstrate good selectivity over other Eph receptor tyrosine kinases, such as EphA1, EphA3, EphA4, EphA5, EphA6, EphA7 and EphB1 and factor XIIA, carbonic anhydrase 9 and CD38 (selectivity data for selected peptide ligands of the invention may be seen in Tables 7 and 14). It should also be noted that selected peptide ligands of the invention exhibit cross reactivity with other species (eg mouse and rat) to permit testing in animal models (Tables 3 to 6 and 15); and Safety. Bleeding events have been reported in pre-clinical in vivo models and clinical trials with EphA2 Antibody Drug Conjugates. For example, a phase 1, open-label study with MEDI-547 was halted due to bleeding and coagulation events that occurred in 5 of 6 patients (Annunziata et al, Invest New Drugs (2013) 31:77-84). The bleeding events observed in patients were consistent with effects on the coagulation system observed in rat and monkey pre-clinical studies: increased activated partial thromboplastin time and increased fibrinogen/fibrin degradation product (Annunziata et al IBID). Overt bleeding events were reportedly seen in toxicology studies in monkeys (Annunziata et al, IBID). Taken together these results imply that MEDI-547 causes Disseminated Intravascular Coagulation (DIC) in both preclinical species and patients. The BDCs reported here have short in vivo half lives (<30 minutes) and are therefore intrinsically less likely to give rise to DIC in patients. Results shown here (see BIOLOGICAL DATA sections 5 and 6 and Table 20) demonstrate that selected Bicycle Drug Conjugates of the invention have no effect on coagulation parameters and gave rise to no bleeding events in pre-clinical studies.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, C$\square$-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise $\square$-turn conformations (Tugyi et al (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio)isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the EphA2 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Non-Aromatic Molecular Scaffold

References herein to the term "non-aromatic molecular scaffold" refer to any molecular scaffold as defined herein which does not contain an aromatic (i.e. unsaturated) carbocyclic or heterocyclic ring system.

Suitable examples of non-aromatic molecular scaffolds are described in Heinis et al (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

An example of an α unsaturated carbonyl containing compound is 1,1',1''-(1,3,5-triazinane-1,3,5-triyl)triprop-2-en-1-one (TATA) (Angewandte Chemie, International Edition (2014), 53(6), 1602-1606).

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one particular embodiment of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

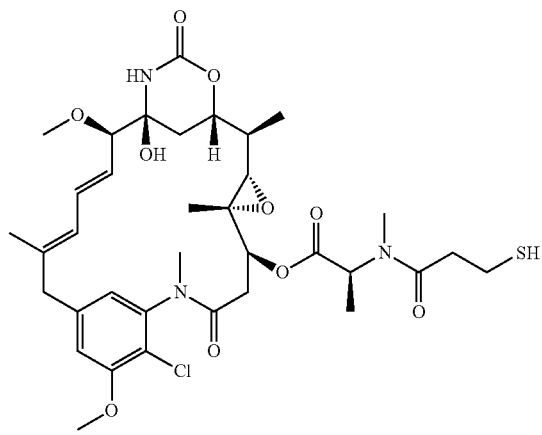

Monomethyl auristatin E (MMAE) is a synthetic antineoplastic agent and has the following structure:

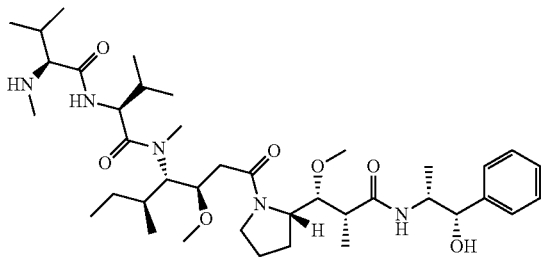 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In one yet further particular embodiment of the invention, the cytotoxic agent is selected from maytansinoids (such as DM1). Data is presented herein in Table 6 which demonstrates the effects of peptide ligands conjugated to toxins containing DM1.

In one embodiment, the cytotoxic agent is linked to the bicyclic peptide by a cleavable bond, such as a disulphide bond or a protease sensitive bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

In one embodiment, the drug conjugate additionally comprises a linker between said peptide ligand and said cytotoxic agents.

In one embodiment, the cytotoxic agent and linker is selected from any combinations of those described in WO 2016/067035 (the cytotoxic agents and linkers thereof are herein incorporated by reference).

In one embodiment the cytotoxic agent is selected from DM1 or MMAE.

In one embodiment, the linker between said cytotoxic agent and said bicyclic peptide comprises one or more amino acid residues. Thus, in one embodiment, the cytotoxic agent is MMAE and the linker is selected from: -Val-Cit-, -Trp-Cit-, -Val-Lys-, -D-Trp-Cit-, -Ala-Ala-Asn-, D-Ala-Phe-Lys- or -Glu-Pro-Cit-Gly-hPhe-Tyr-Leu- (SEQ ID NO: 98). In a further embodiment, the cytotoxic agent is MMAE and the linker is selected from: -Val-Cit-, -Trp-Cit-, -Val-Lys- or -D-Trp-Cit-. In a yet further embodiment, the cytotoxic agent is MMAE and the linker is -Val-Cit- or -Val-Lys-. In a still yet further embodiment, the cytotoxic agent is MMAE and the linker is -Val-Cit-.

In an alternative embodiment, the linker between said cytoxic agent comprises a disulfide bond, such as a cleavable disulfide bond. Thus, in a further embodiment, the cytotoxic agent is DM1 and the linker is selected from: —S—S—, —SS(SO$_3$H)—, —SS-(Me)-, -(Me)-SS-(Me)-, —SS-(Me$_2$)- or —SS-(Me)-SO$_3$H—. In a further embodiment, the cytotoxic agent is DM1 and the linker comprises an —S—S— moiety, such as (N-succinimidyl 3-(2-pyridyldithio)propionate (SPDB), or an —SS(SO$_3$H)— moiety, such as SO$_3$H-SPDB.

In an alternative embodiment, the cytotoxic agent comprises a non-cleavable cytotoxic agent. Thus, in one embodiment the cytotoxic agent is non-cleavable MMAE (such as the cytotoxic agent within BCY6063) or non-cleavable DM1 (such as the cytotoxic agent within BCY6064).

In one embodiment, the cytotoxic agent is DM1 and the drug conjugate comprises a compound of formula (A):

(A), wherein said bicycle is selected from BCY6099 as defined herein. This BDC is known herein as BCY6027. Data is presented herein which demonstrates excellent competition binding for BCY6027 in the EphA2 competition binding assay as shown in Table 6.

In an alternative embodiment, the cytotoxic agent is DM1 and the drug conjugate comprises a compound of formula (B), wherein said bicycle is selected from BCY6099 as defined herein. This BDC is known herein as BCY6028. Data is presented herein which demonstrates excellent competition binding for BCY6028 in the EphA2 competition binding assay as shown in Table 6.

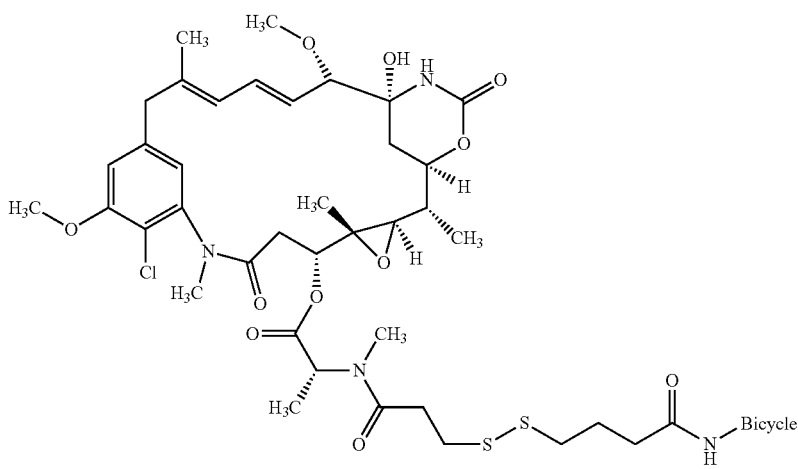

(A)

wherein said bicycle is selected from any one of BCY6099 and BCY6014 as defined herein.

In an alternative embodiment, the cytotoxic agent is DM1 and the drug conjugate comprises a compound of formula (B):

In an alternative embodiment, the cytotoxic agent is DM1 and the drug conjugate comprises a compound of formula (A), wherein said bicycle is selected from BCY6014 as defined herein. This BDC is known herein as BCY6031. Data is presented herein which demonstrates excellent com-

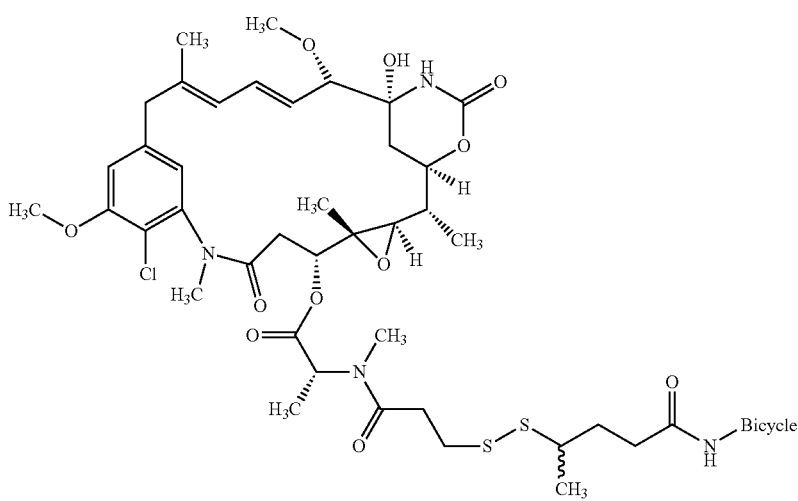

(B)

wherein said bicycle is selected from any one of BCY6099 and BCY6014 as defined herein.

In an alternative embodiment, the cytotoxic agent is DM1 and the drug conjugate comprises a compound of formula petition binding for BCY6031 in the EphA2 competition binding assay as shown in Table 6. Data is also presented herein in Table 11 and FIGS. 1 and 2 which demonstrate that BCY6031 treatment completely eradicated non-small cell lung carcinomas from day 32 and no tumour regrowth occurred following dosing suspension on day 28.

In an alternative embodiment, the cytotoxic agent is DM1 and the drug conjugate comprises a compound of formula (B), wherein said bicycle is selected from BCY6014 as defined herein. This BDC is known herein as BCY6032. Data is presented herein which demonstrates excellent competition binding for BCY6032 in the EphA2 competition binding assay as shown in Table 6.

In an alternative embodiment, the cytotoxic agent is MMAE or DM1 and the drug conjugate is selected from any of the BDCs listed in Table 11. Data is presented herein which shows that these BDCs exhibited excellent cross reactivity between human, mouse and rodent EphA2 as shown in Table 11.

In a further embodiment, the cytotoxic agent is MMAE or DM1 and the drug conjugate is selected from any of the BDCs listed in Table 13.

In a further embodiment, the cytotoxic agent is MMAE or DM1 and the drug conjugate is selected from BCY6033, BCY6082, BCY6136 and BCY6173. Data is presented herein which shows that these four Bicycle Drug Conjugates exhibited no significant binding to: closely related human homologs EphA1, EphA3, EphA4, EphA5, EphA6, EphA7 and EphB4; mouse EphA3 and EphA4; and rat EphA3 and EphB1 as shown in Tables 14 and 15.

In a yet further embodiment, the drug conjugate is selected from any one of: BCY6031, BCY6033, BCY6082, BCY6135, BCY6136, BCY6173, BCY6174 and BCY6175:

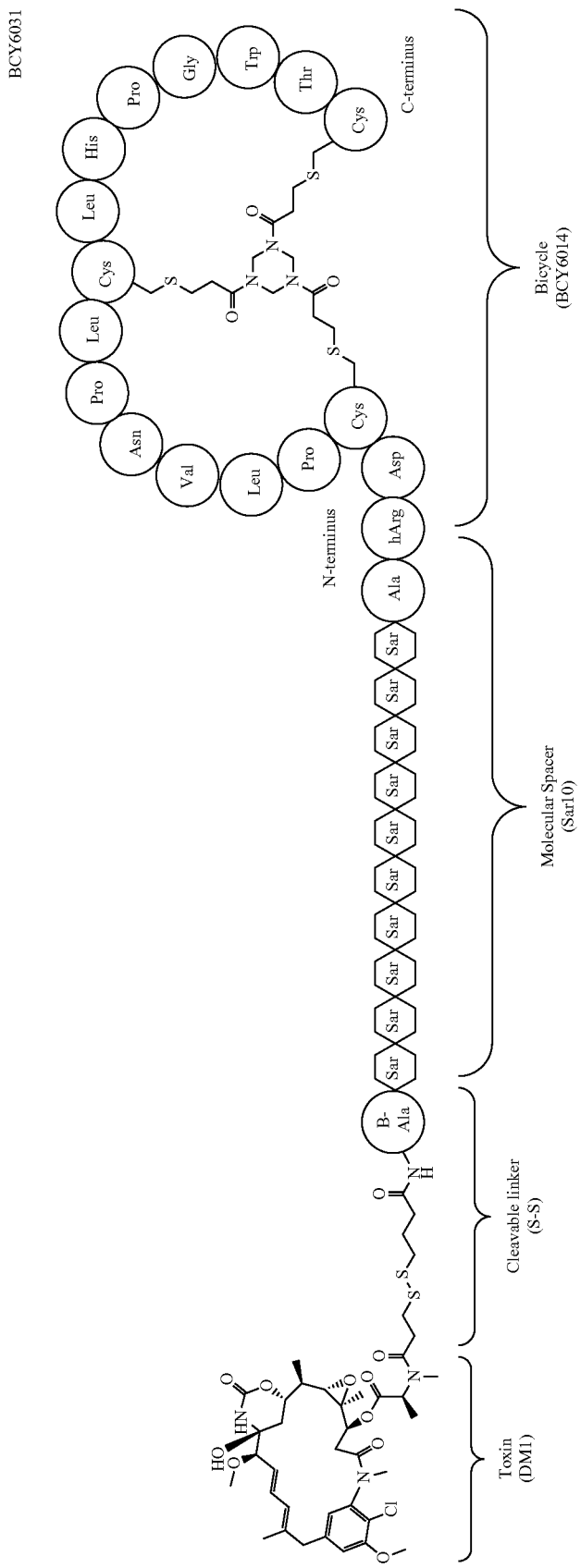

-continued
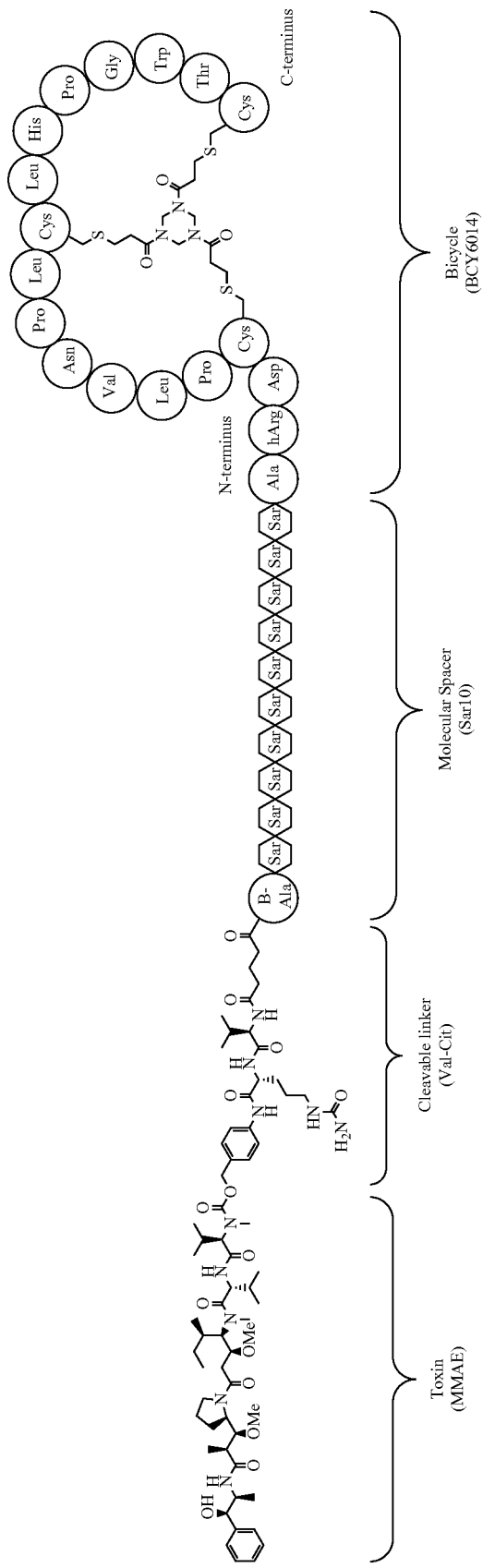

-continued
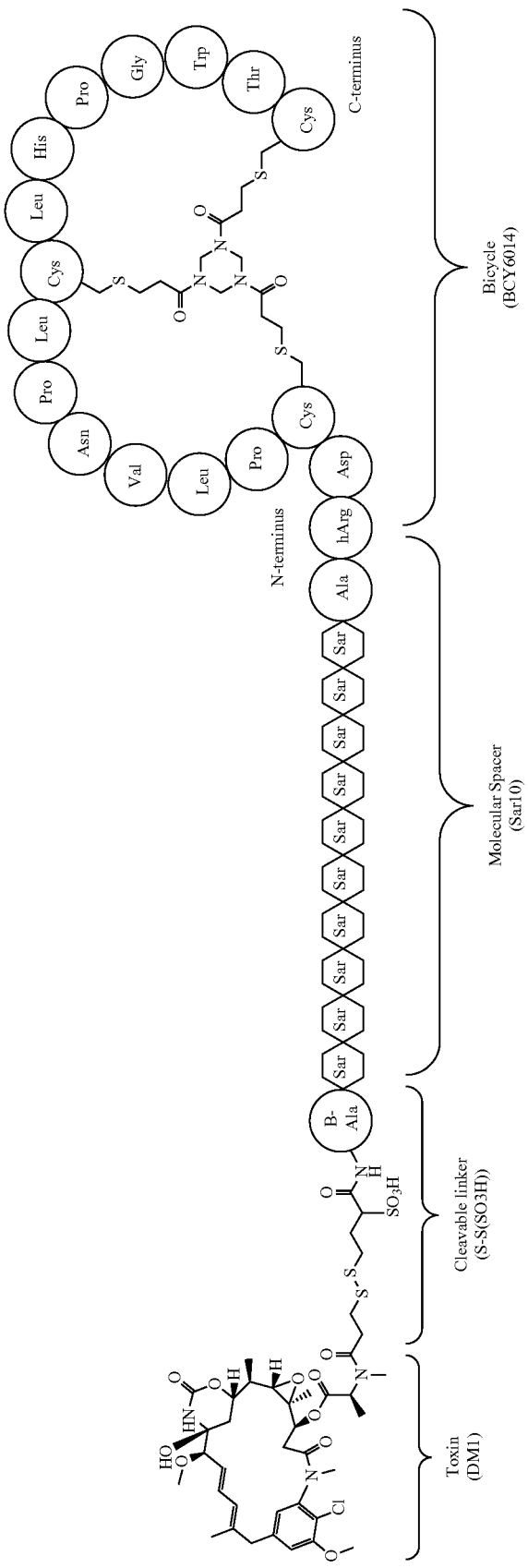

-continued
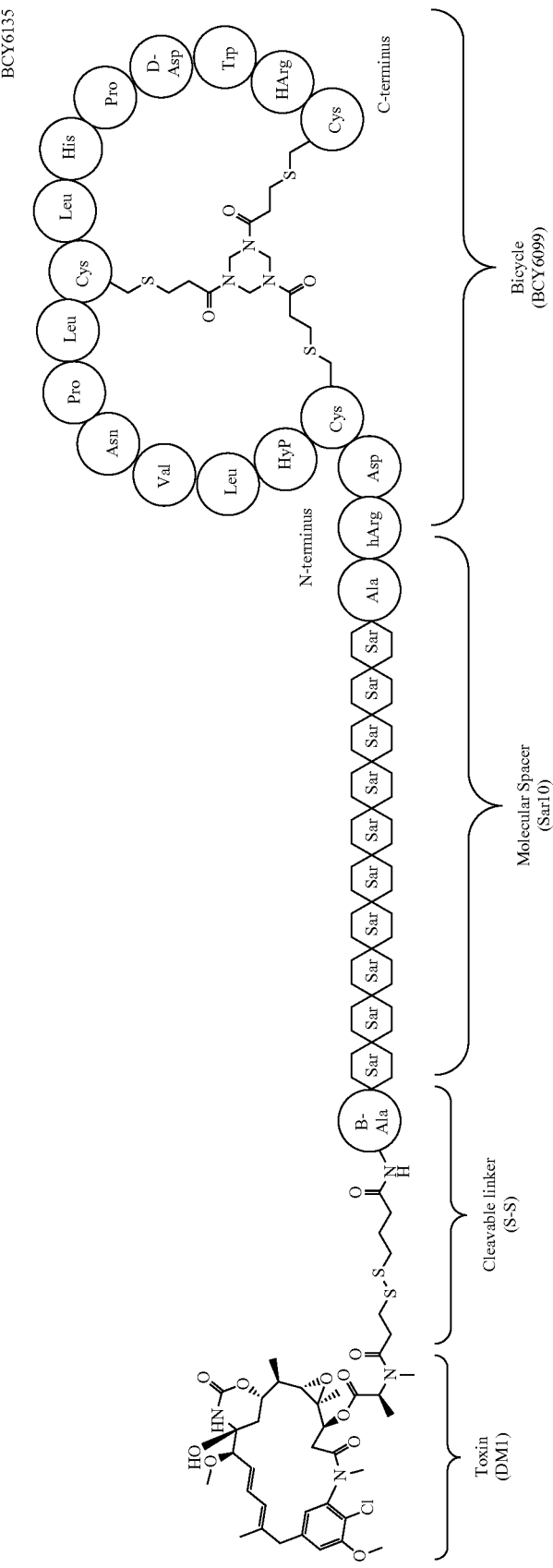

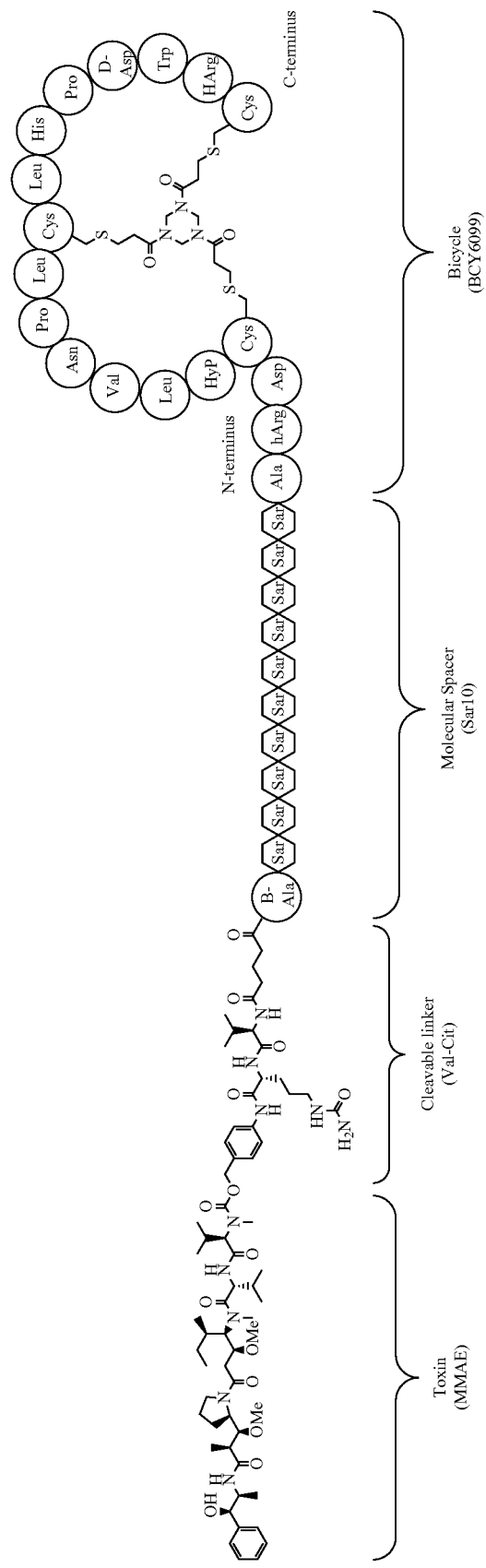

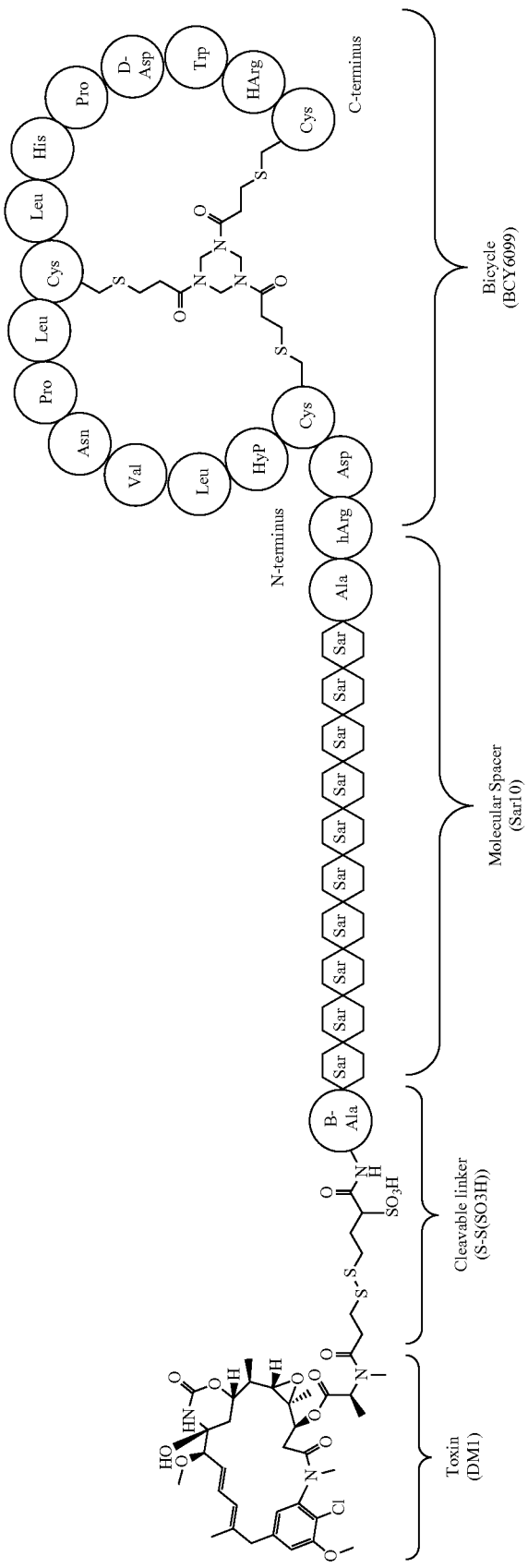

-continued
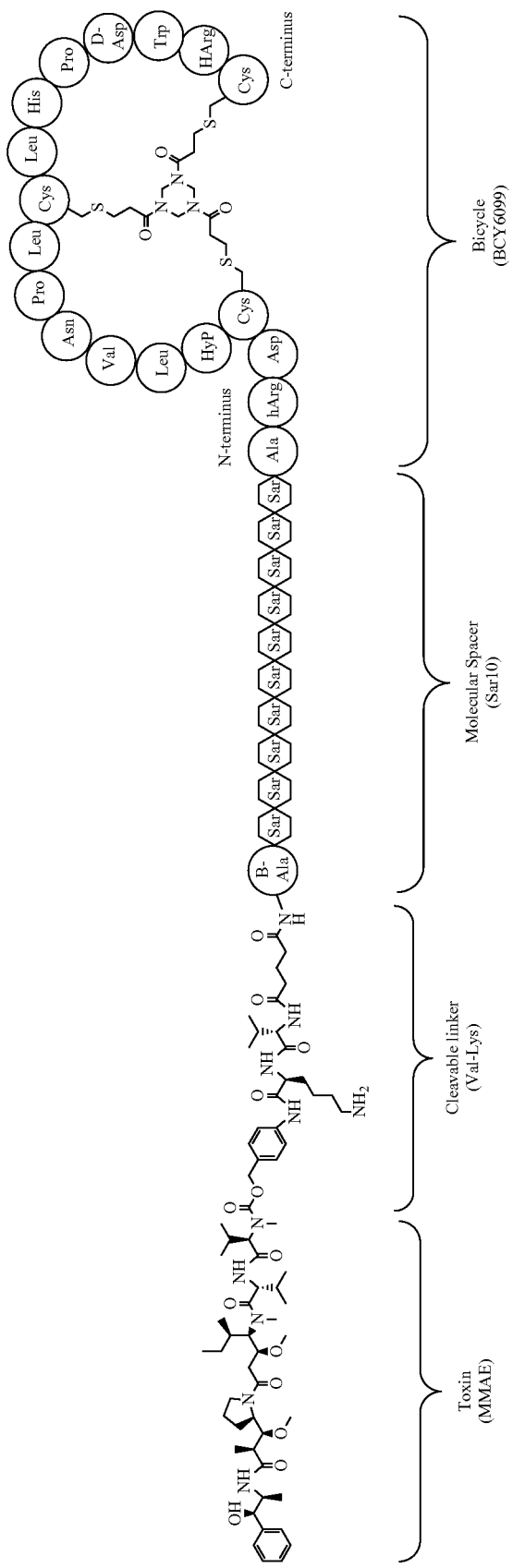

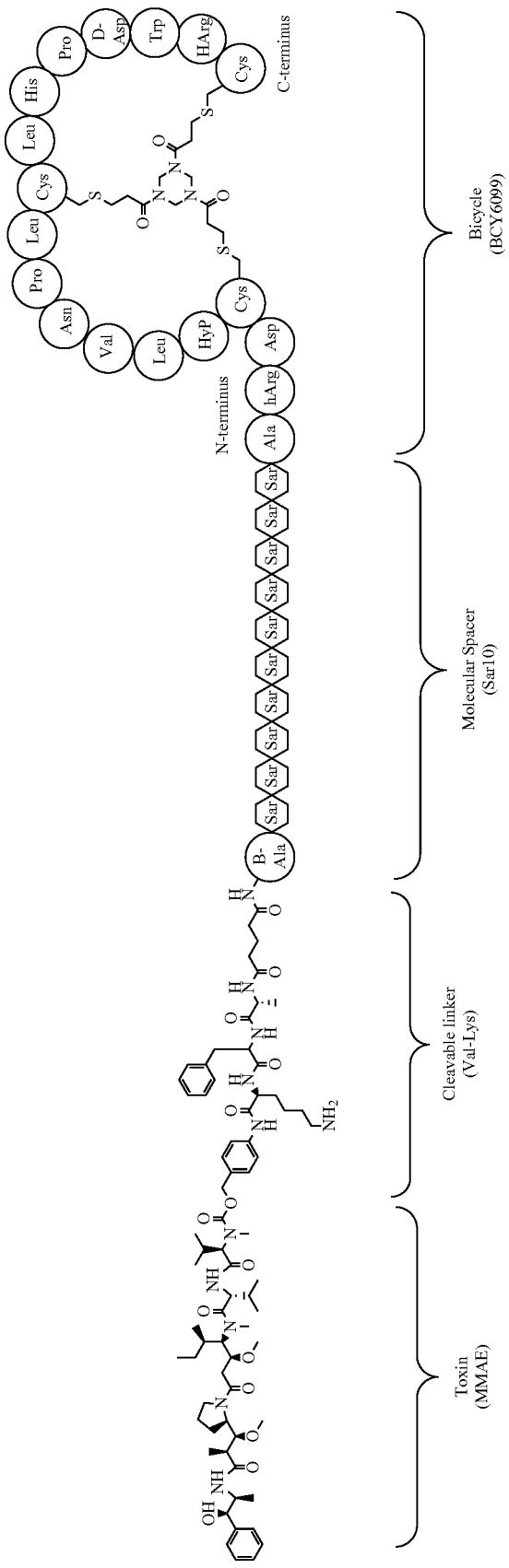

In one embodiment, the drug conjugate is other than BCY6027, BCY6028, BCY6135, BCY6136, BCY6173, BCY6174 and BCY6175.

Figure 23:
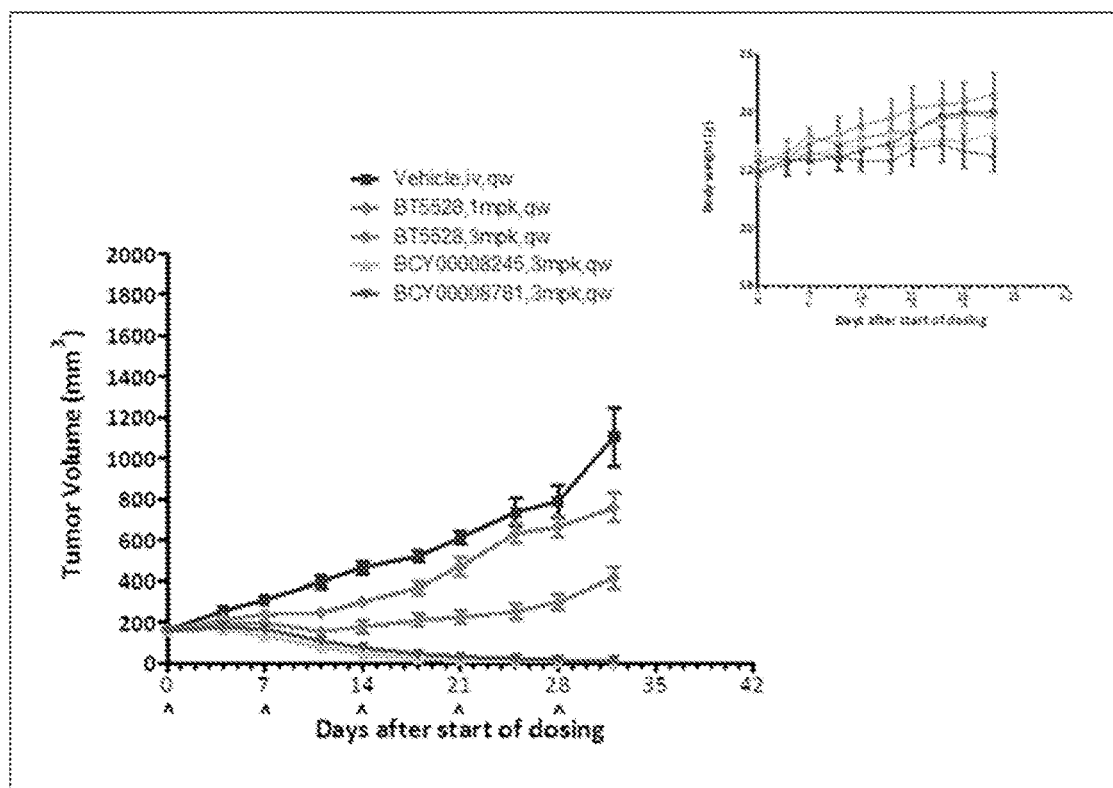
FIG. 23: Body weight changes and tumor volume traces after administering BCY6136 (referred to in FIG. 23 as BT5528), BCY8245 or BCY8781 to female BALB/c nude mice bearing LU-01-0412 xenograft. Data points represent group mean tumor volume (left panel) and body weight (right panel).
Figure 24:
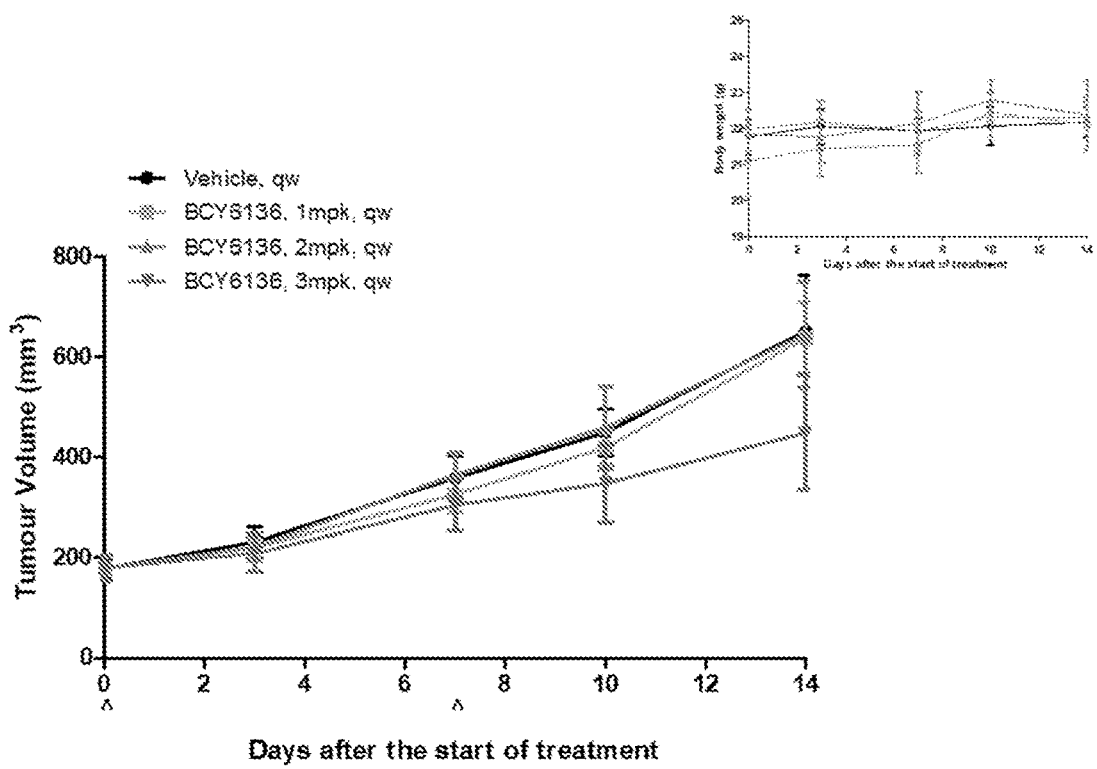
FIG. 24: Body weight changes and tumor volume traces after administering BCY6136 to female Balb/c nude mice bearing LU-01-0486 xenograft. Data points represent group mean body weight.

In a still yet further embodiment, the drug conjugate is BCY6136. Data is presented herein in Studies 7 and 8 which show that BCY6136 showed significant and potent anti-tumor activity in the PC-3 xenograft prostate cancer model (see FIGS. 7 to 10 and Tables 21 to 24). Data is also provided herein which show that BCY6136 demonstrated potent antitumor activity in the NCI-H1975 xenograft lung cancer (NSCLC) model (see FIGS. 11 to 13 and Tables 25 to 30). Data is also presented herein in Studies 10 and 11 which show that BCY6136 demonstrated potent anti-tumor effect in both large and small tumour size LU-01-0251 PDX lung cancer (NSCLC) models (see FIGS. 14 and 15 and Tables 31 to 34) wherein complete tumor regression was observed. Data is also presented herein in Study 12 which show that BCY6136 demonstrated significant anti-tumor effect in the LU-01-0046 PDX lung cancer (NSCLC) model (see FIG. 16 and Tables 35 and 36) wherein complete tumor regression was observed for BCY6136. Data is also presented herein in Study 13 which show that BCY6136 demonstrated dose dependent anti-tumor activity in the LU-01-0046 PDX lung cancer (NSCLC) model (see FIG. 17 and Tables 37 and 38). Data is also presented herein in Study 14 which show BCY6136 eradicated tumors in the LU-01-0046 PDX lung cancer (NSCLC) model (see FIGS. 18 to 22 and Tables 39 to 42). Data is also presented herein in Studies 15 and 16 which demonstrate the effects of BCY6136 in two models which make use of cell lines with low/negligible EphA2 expression (namely Lu-01-0412 and Lu-01-0486). This data is shown in FIGS. 23 and 24 and Tables 43 to 46 and demonstrate that BCY6136 had no effect upon tumor regression in either cell line but BCYs BCY8245 and BCY8781, which bind to a target highly expressed in the Lu-01-0412 cell line, completely eradicated the tumour. Data is presented herein in Study 17 which show that BCY6136 demonstrated potent antitumor activity in the MDA-MB-231 xenograft breast cancer model (see FIGS. 25 to 27 and Tables 47 to 50). Data is also presented herein in Study 18 which demonstrates the effects of BCY6136 in a breast cancer model which makes use of a cell line with low/negligible EphA2 expression (namely EMT6). This data is shown in FIG. 28 and Tables 51 and 52 and demonstrates that BCY6136 had no effect upon tumor regression in this cell line. Data is also presented herein in Study 19 which show that BCY6136 demonstrated significant antitumor activity in the NCI-N87 xenograft gastric cancer model (see FIG. 29 and Tables 53 and 54). Data is also presented herein in Study 20 which show that BCY6136 demonstrated significant antitumor activity in the SK-OV-3 xenograft ovarian cancer model (see FIG. 30 and Tables 55 and 56) compared with the ADC MEDI-547 which demonstrated moderate antitumour activity. Data is also presented herein in Study 21 which show that BCY6136 demonstrated significant antitumor activity in the OE-21 xenograft oesophageal cancer model (see FIG. 31 and Tables 57 and 58). Data is also presented herein in Study 22 which show that BCY6136 demonstrated dose-dependent antitumor activity in the MOLP-8 xenograft multiple myeloma model and BCY6082 demonstrated significant antitumor activity (see FIGS. 32 and 33 and Tables 59 and 60). Data is also presented herein in Study 23 which show that BCY6136 demonstrated potent antitumor activity in the HT-1080 xenograft fibrosarcoma model (see FIGS. 34 to 41 and Tables 61 and 62).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as EphA2 binding agents.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLoS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder characterised by overexpression of EphA2 in diseased tissue (such as a tumour).

According to a further aspect of the invention, there is provided a method of preventing, suppressing or treating a disease or disorder characterised by overexpression of EphA2 in diseased tissue (such as a tumour), which comprises administering to a patient in need thereof an effector group and drug conjugate of the peptide ligand as defined herein.

In one embodiment, the EphA2 is mammalian EphA2. In a further embodiment, the mammalian EphA2 is human EphA2.

In one embodiment, the disease or disorder characterised by overexpression of EphA2 in diseased tissue is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from: breast cancer, lung cancer, gastric cancer, pancreatic cancer, prostate cancer, liver cancer, glioblastoma and angiogenesis.

In a further embodiment, the cancer is selected from: prostate cancer, lung cancer (such as non-small cell lung carcinomas (NSCLC)), breast cancer (such as triple negative breast cancer), gastric cancer, ovarian cancer, oesophageal cancer, multiple myeloma and fibrosarcoma.

In a yet further embodiment, the cancer is prostate cancer. Data is presented herein in Studies 7 and 8 which show that BCY6033 and BCY6136 showed significant and potent anti-tumor activity in the PC-3 xenograft prostate cancer model (see FIGS. 7 to 10 and Tables 21 to 24).

In a yet further embodiment, the drug conjugate is useful for preventing, suppressing or treating solid tumours such as fibrosarcomas and breast, and non-small cell lung carcinomas.

In a yet further embodiment, the cancer is selected from lung cancer, such as non-small cell lung carcinomas (NSCLC). Data is presented herein which demonstrates that a BDC of the invention (BCY6031) completely eradicated non-small cell lung carcinomas from day 32 and no tumour regrowth occurred following dosing suspension on day 28. This data clearly demonstrates the clinical utility of the BDCs of the present invention in cancers such as lung cancers, in particular non-small cell lung carcinomas. Data is also presented herein in Study 9 which show that BCY6033 demonstrated dose dependent anti-tumor activity, BCY6082 demonstrated significant antitumor activity and BCY6136 demonstrated potent antitumor activity in the NCI-H1975 xenograft lung cancer (NSCLC) model (see FIGS. 11 to 13 and Tables 25 to 30). Data is also presented herein in Studies 10 and 11 which show that BCY6136 demonstrated potent anti-tumor effect in both large and small tumour size LU-01-0251 PDX lung cancer (NSCLC) models (see FIGS. 14 and 15 and Tables 31 to 34) wherein complete tumor regression was observed. Data is also presented herein in Study 12 which show that BCY6033, BCY6136, BCY6082 and BCY6031 demonstrated significant anti-tumor effect in the LU-01-0046 PDX lung cancer (NSCLC) model (see FIG. 16 and Tables 35 and 36) wherein complete tumor regression was observed for BCY6033 and BCY6136. Data is also presented herein in Study 13 which show that BCY6136 demonstrated dose dependent anti-tumor activity in the LU-01-0046 PDX lung cancer (NSCLC) model (see FIG. 17 and Tables 37 and 38). Data is also presented herein in Study 14 which show that BCY6082 demonstrated dose dependent antitumor activity, BCY6031 and BCY6173 demonstrated antitumor activity and BCY6033, BCY6136 and BCY6175 eradicated tumors in the LU-01-0046 PDX lung cancer (NSCLC) model (see FIGS. 18 to 22 and Tables 39 to 42). Data is also presented herein in Studies 15 and 16 which demonstrate the effects of BCY6136 in two models which make use of cell lines with low/negligible EphA2 expression (namely Lu-01-0412 and Lu-01-0486). This data is shown in FIGS. 23 and 24 and Tables 43 to 46 and demonstrate that BCY6136 had no effect upon tumor regression in either cell line but BCYs BCY8245 and BCY8781, which bind to a target highly expressed in the Lu-01-0412 cell line, completely eradicated the tumour. In a further embodiment, the cancer is breast cancer. In a yet further embodiment, the breast cancer is triple negative breast cancer. Data is presented herein in Study 17 which show that BCY6082 demonstrated antitumor activity, BCY6033 demonstrated dose dependent antitumor activity and BCY6136 demonstrated potent antitumor activity in the MDA-MB-231 xenograft breast cancer model (see FIGS. 25 to 27 and Tables 47 to 50). Data is also presented herein in Study 18 which demonstrates the effects of BCY6136 in a breast cancer model which makes use of a cell line with low/negligible EphA2 expression (namely EMT6). This data is shown in FIG. 28 and Tables 51 and 52 and demonstrates that BCY6136 had no effect upon tumor regression in this cell line. In an alternative embodiment, the breast cancer is Herceptin resistant breast cancer. Without being bound by theory, EphA2 is believed to be implicated in the resistance to Herceptin, therefore, an EphA2-targeting entity has potential utility in patients who have failed to respond to Herceptin.

In a further embodiment, the cancer is gastric cancer. Data is presented herein in Study 19 which show that BCY6136 demonstrated significant antitumor activity in the NCI-N87 xenograft gastric cancer model (see FIG. 29 and Tables 53 and 54).

In a further embodiment, the cancer is ovarian cancer. Data is presented herein in Study 20 which show that BCY6136 demonstrated significant antitumor activity in the SK-OV-3 xenograft ovarian cancer model (see FIG. 30 and Tables 55 and 56) compared with the ADC MEDI-547 which demonstrated moderate antitumour activity.

In a further embodiment, the cancer is oesophageal cancer. Data is presented herein in Study 21 which show that BCY6136 demonstrated significant antitumor activity in the OE-21 xenograft oesophageal cancer model (see FIG. 31 and Tables 57 and 58).

In a further embodiment, the cancer is multiple myeloma. Data is presented herein in Study 22 which show that BCY6136 demonstrated dose-dependent antitumor activity in the MOLP-8 xenograft multiple myeloma model and BCY6082 demonstrated significant antitumor activity (see FIGS. 32 and 33 and Tables 59 and 60).

In a further embodiment, the cancer is fibrosarcoma. Data is presented herein in Study 23 which show that BCY6173, BCY6135, BCY6174 and BCY6175 demonstrated dose dependent antitumor activity and BCY6082, BCY6031, BCY6033 and BCY6136 demonstrated potent antitumor activity in the HT-1080 xenograft fibrosarcoma model (see FIGS. 34 to 41 and Tables 61 and 62).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Furthermore, data is presented herein which demonstrates an association between copy number variation (CNV) and gene expression for EphA2 from multiple tumor types. Thus, according to a further aspect of the invention, there is provided a method of preventing, suppressing or treating cancer, which comprises administering to a patient in need thereof an effector group and drug conjugate of the peptide ligand as defined herein, wherein said patient is identified as having an increased copy number variation (CNV) of EphA2.

In one embodiment, the cancer is selected from those identified herein as having increased CNV of EphA2. In a further embodiment, the cancer is breast cancer.

The invention is further described below with reference to the following examples.

EXAMPLES

| Abbreviations | Name | Precursor Name | Precursor CAS | Supplier |
|---|---|---|---|---|
| 1Nal | 1-Naphthylalanine | Fmoc-3-(1-naphthyl)-L-alanine | 96402-49-2 | Fluorochem |
| 2FuAla | 2-Furylalanine | Fmoc-L-2-furylalanine | 159611-02-6 | Combi Blocks |
| 2Nal | 2-Naphthylalanine | Fmoc-3-(2-naphthyl)-L-alanine | 112883-43-9 | Alfa Aesar |

-continued

| Abbreviations | Name | Precursor Name | Precursor CAS | Supplier |
|---|---|---|---|---|
| 3,3-DPA | 3,3-Diphenylalanine | fmoc-3,3-diphenylalanine | 189937-46-0 | Alfa Aesar |
| 3,4-DCPhe | 3,4-Dichlorophenylalanine | Fmoc-3,4-dichloro-L-phenylalanine | 17766-59-5 | PolyPeptide |
| 3Pal | 3-(3-Pyridyl)-Alanine | N-Fmoc-3-(3-pyridyl)-Lβnine | 175453-07-3 | Fluorochem |
| 4,4-BPA | 4,4'-Biphenylalanine | Fmoc-L-4,4'-Biphenylalanine | 199110-64-0 | Alfa Aesar |
| 4BenzylPro | 4-Benzyl-pyrrolidine-2-carboxylic acid | Fmoc-4-Benzyl-pyrrolidine-2-carboxylic acid | | PolyPeptide |
| 4BrPhe | 4-Bromophenylalanine | Fmoc-4-Bromo-L-phenylalanine | 198561-04-5 | PolyPeptide |
| 4FlPro | 4-Fluoro-pyrrolidine-2-carboxylic acid | Fmoc-4-fluoro-pyrrolidine-2-carboxylic acid | 203866-19-7 | PolyPeptide |
| 4MeoPhe | 4-Methoxyphenylalanine | Fmoc-4-Methoxyphenylalanine | 77128-72-4 | Iris Biotech |
| 4Pal | 3-(4-Pyridyl)-Alanine | N-Fmoc-3-(4-pyridyl)-L-alanine | 169555-95-7 | Fluorochem |
| 4PhenylPro | 4-Phenyl-pyrrolidine-2-carboxylic acid | Fmoc-4-phenyl-pyrrolidine-2-carboxylic acid | 269078-71-9 | Cambridge Bioscience |
| Ac | Acetyl | | | |
| AC3C | 1-Aminocyclopropane-1-carboxylic acid | 1-(Fmoc-amino)cyclopropanecarboxylic acid | 126705-22-4 | Iris Biotech |
| AC4C | 1-Amino-1-cyclobutanecarboxylic acid | 1-(Fmoc-amino)-cyclobutylcarboxylic acid | 885951-77-9 | Fluorochem |
| AC5C | 1-Amino-1-cyclopentanecarboxylic acid | 1-(Fmoc-amino)cyclopentanecarboxylic acid | 117322-30-2 | Iris Biotech |
| AF488 | AlexaFluor488 | AlexaFluor488-NHS Ester | | Fisher Scientific |
| Aib | 2-Aminoisobutyric acid | Fmoc-α-aminoisobutyric acid | 94744-50-0 | Fluorochem |
| Aza-Gly | Azaglycine | | | |
| Aze | Azetidine | Fmoc-L-azetidine-2-carboxylic acid | 136552-06-2 | Combi Blocks |
| β-Ala | β-Alanine | Fmoc-β-alanine | 35737-10-1 | Fluorochem |
| β-AlaSO$_3$H | β-Alanine(SO$_3$H) | Fmoc-alpha-sulfo-beta-Alanine | 1005412-03-2 | Iris Biotech |
| C5g | Cyclopentylglycine | Fmoc-L-cyclopentylglycine | 220497-61-0 | Fluorochem |
| Cba | β-Cyclobutylalanine | Fmoc-β-cyclobutyl-L-alanine | 478183-62-9 | IRIS Biotech GmbH |
| Cpa | β-Cyclopropylalanine | Fmoc-β-cyclopropyl-L-alanine | 214750-76-2 | Fluorochem |
| Cpg | Cyclopropylglycine | Fmoc-L-cycloproprylglycine | 1212257-18-5 | Apollo Scientific |
| Cya | Cysteic acid | Fmoc-L-cysteic acid | 320384-09-6 | |
| D-3,3-DPA | 3,3-diphenyl-D-alanine | Fmoc-3,3-diphenyl-D-alanine | 189937-46-0 | Chem-Impex international |
| D-Arg | D-Arginine | Fmoc-D-Arginine(Pbf) | 187618-60-6 | Iris Biotech |
| D-Asp | D-Aspartic acid | Fmoc-D-aspartic acid 4-tert-butyl ester | 112883-39-3 | Sigma aldrich |
| D-Cya | D-cysteic acid | Fmoc-D-cysteic acid | | Costom synthesis |
| D-K | D-Lysine | Fmoc-D-Lysine(Boc) | 92122-45-7 | Sigma Aldrich |
| DOTA | 1,4,7,10-tetraazacyclododecane-1,4,7,10-tetraacetic acid | | | |
| Fl | 5(6)-carboxyfluorescein | | | Sigma |
| HArg | HomoArginine | Fmoc-L-HomoArg(Pbf)-OH | 401915-53-5 | Fluorochem |
| HPhe | HomoPhenylalanine | Fmoc-L-Homophenylalanine | 132684-59-4 | Iris Biotech |
| HyP | Hydroxyproline | Fmoc-Hydroxyproline(tBu)-OH | 122996-47-8 | Sigma |

-continued

| Abbreviations | Name | Precursor Name | Precursor CAS | Supplier |
|---|---|---|---|---|
| hSerMe | HomoSerine(methyl) | Fmoc-O-methyl-L-homoserine | 173212-86-7 | Iris Biotech |
| Lys(Dde) | Lysine(Dde) | N-α-Fmoc-N-ε-1-(4,4-dimethyl-2,6-dioxocyclohex-1-ylidene)ethyl-L-lysine | 150629-67-7 | Sigma Aldrich |
| NO2Phe | 4-Nitrophenylalanine | Fmoc-4-nitro-L-phenylalanine | 95753-55-2 | PolyPeptide |
| Phg | Phenylglycine | Fmoc-L-phenylglycine | 102410-65-1 | Combi Blocks |
| Pip | Pipecolic acid | Fmoc-L-Pipecolic acid | 86069-86-5 | Peptech |
| Sar | Sarcosine, such that $Sar_x$ represents x Sar residues | Fmoc-Sarcosine-OH | 77128-70-2 | Sigma |
| tBuGly | Tert-leucine | Fmoc-L-tert-leucine | 132684-60-7 | Fluorochem |
| Thi | 2-Thienylalanine | Fmoc-2-Thienylalanine | 130309-35-2 | Novabiochem |
| ThiAz | 3-(1,2,4-triazol-1-yl)-Alanine | Fmoc-3-(1,2,4-triazol-1-yl)-Ala-OH | 1217449-37-0 | Sigma |
| ΨAla | Reduced amide on backbone | | | |

Materials and Methods

Peptide Synthesis

Peptides were synthesized by solid phase synthesis. Rink Amide MBHA Resin was used. To a mixture containing Rink Amide MBHA (0.4-0.45 mmol/g) and Fmoc-Cys(Trt)-OH (3.0 eq) was added DMF, then DIC (3 eq) and HOAt (3 eq) were added and mixed for 1 hour. 20% piperidine in DMF was used for deblocking. Each subsequent amino acid was coupled with 3 eq using activator reagents, DIC (3.0 eq) and HOAT (3.0 eq) in DMF. The reaction was monitored by ninhydrin color reaction or tetrachlor color reaction. After synthesis completion, the peptide resin was washed with DMF×3, MeOH×3, and then dried under $N_2$ bubbling overnight. The peptide resin was then treated with 92.5% TFA/2.5% TIS/2.5% EDT/2.5% $H_2O$ for 3 h. The peptide was precipitated with cold isopropyl ether and centrifuged (3 min at 3000 rpm). The pellet was washed twice with isopropyl ether and the crude peptide was dried under vacuum for 2 hours and then lyophilised. The lyophilised powder was dissolved in of ACN/$H_2O$ (50:50), and a solution of 100 mM TATA in ACN was added, followed by ammonium bicarbonate in $H_2O$ (1 M) and the solution mixed for 1 h. Once the cyclisation was complete, the reaction was quenched with 1 M aq. Cysteine hydrochloride (10 eq relative to TATA), then mixed and left to stand for an hour. The solution was lyophilised to afford crude product. The crude peptide was purified by Preparative HPLC and lyophilized to give the product All amino acids, unless noted otherwise, were used in the L-configurations.

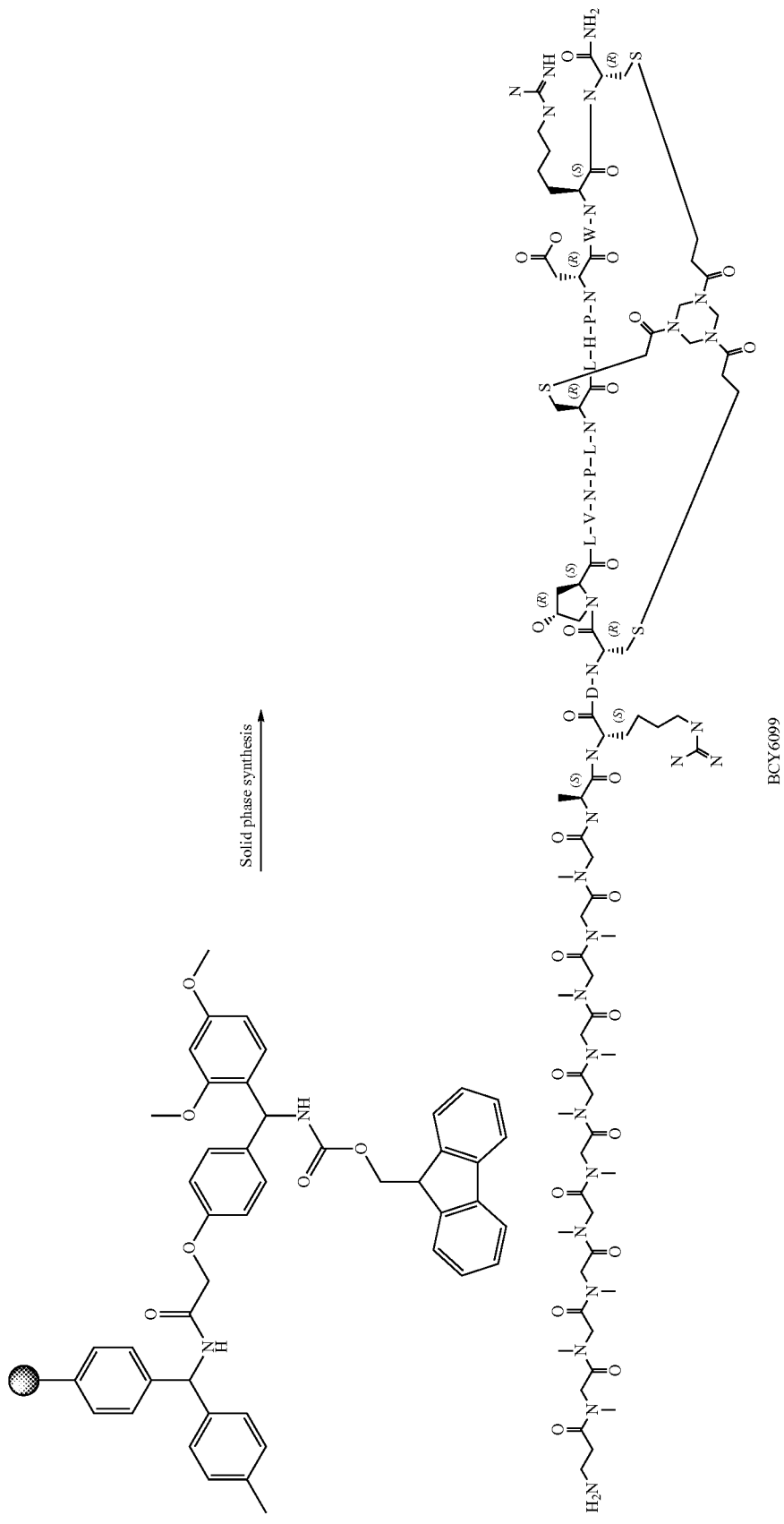

Sequence: (β-Ala)-Sar$_{10}$-(SEQ ID NO: 2)-CONH$_2$ 8.0 g of resin was used to generate 2.1 g BCY6099 (99.2% purity; 16.3% yield) as a white solid.

|  | BCY6099 Analytical Data |
| --- | --- |
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 15-45% B over 20 minutes, then 3 min 95% B |
| Retention Time: | 11.31 min |
| LCMS (ESI): | m/z 1061.8 [M + 3H]$^{3+}$, 796.5 [M + 4H]$^{4+}$ |
| Peptide mw | 3183.68 |

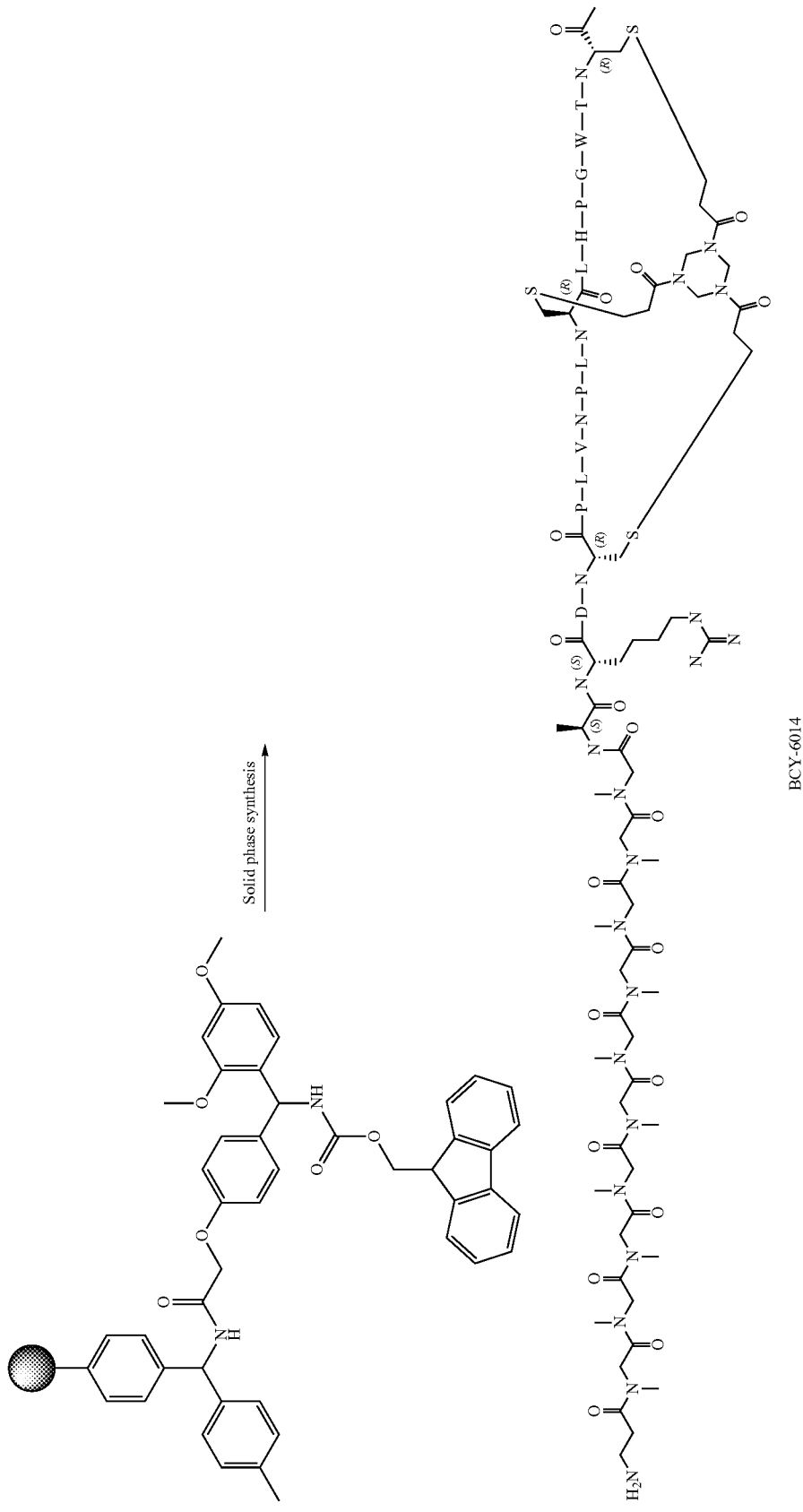

Sequence: (β-Ala)-Sar$_{10}$-(SEQ ID NO: 11)-CONH$_2$ 4.79 g of resin was used to generate 1.07 g BCY6014 (Q1: 131.9 mg, 97.99% purity; Q2: 141.7 mg, 99.04% purity; Q3: 800.7 mg, 92.35% purity; 16.9% yield) as white a solid.

|  | BCY6014 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 9.95 min |
| LCMS (ESI): | m/z 1013.8 [M + 3H]$^{3+}$, 760.4 [M + 4H]$^{4+}$ |
| Peptide mw | 3039.53 |

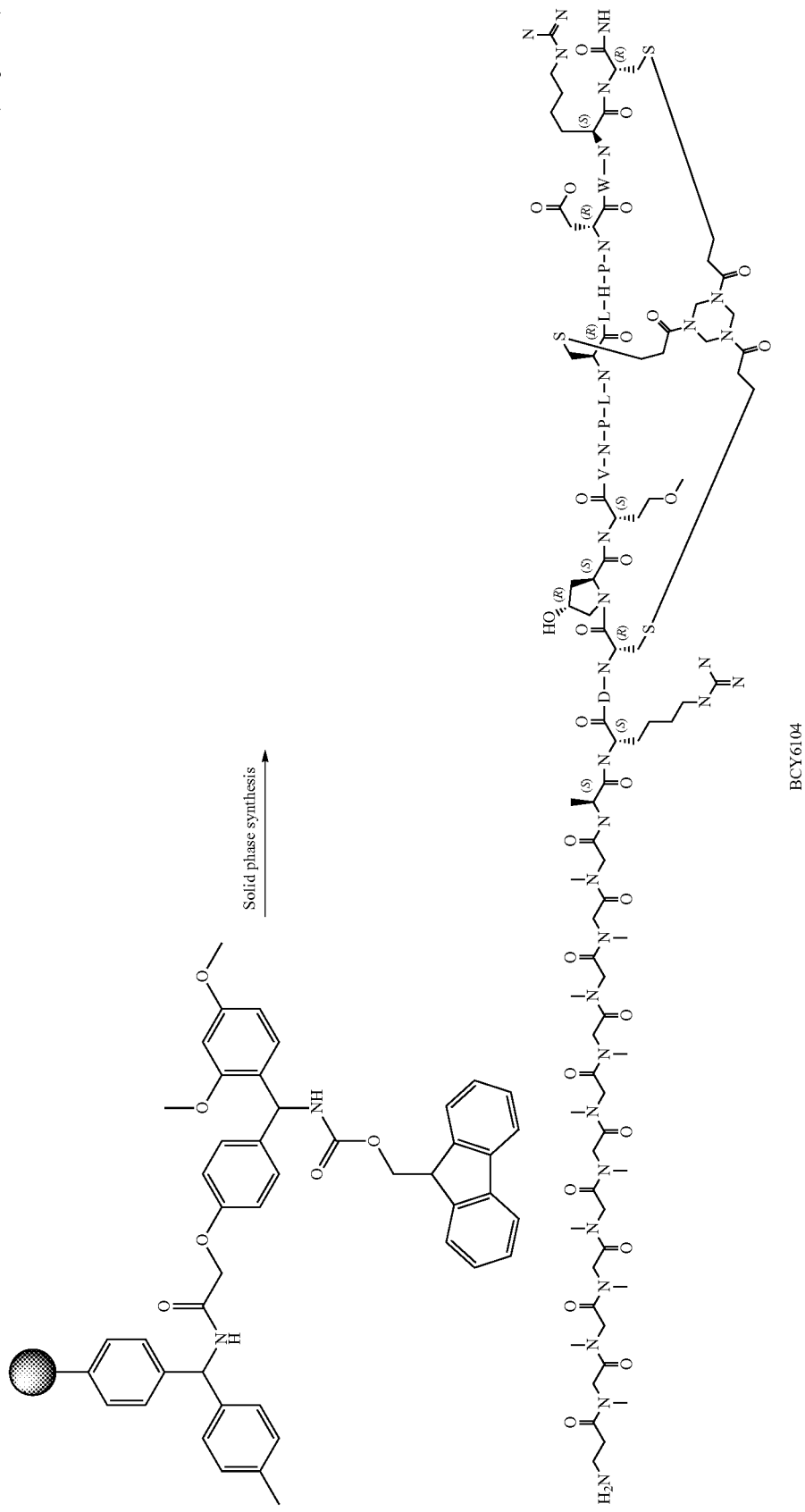

4.44 g of resin was used to generate 700 mg BCY6104 (95.87% purity, 10.5% yield) as white a solid.

|  | BCY6104 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 7.06 min |
| LCMS (ESI): | m/z 1062.1 $[M + 3H]^{3+}$, 796.8 $[M + 4H]^{4+}$ |
| Peptide mw | 3185.65 |

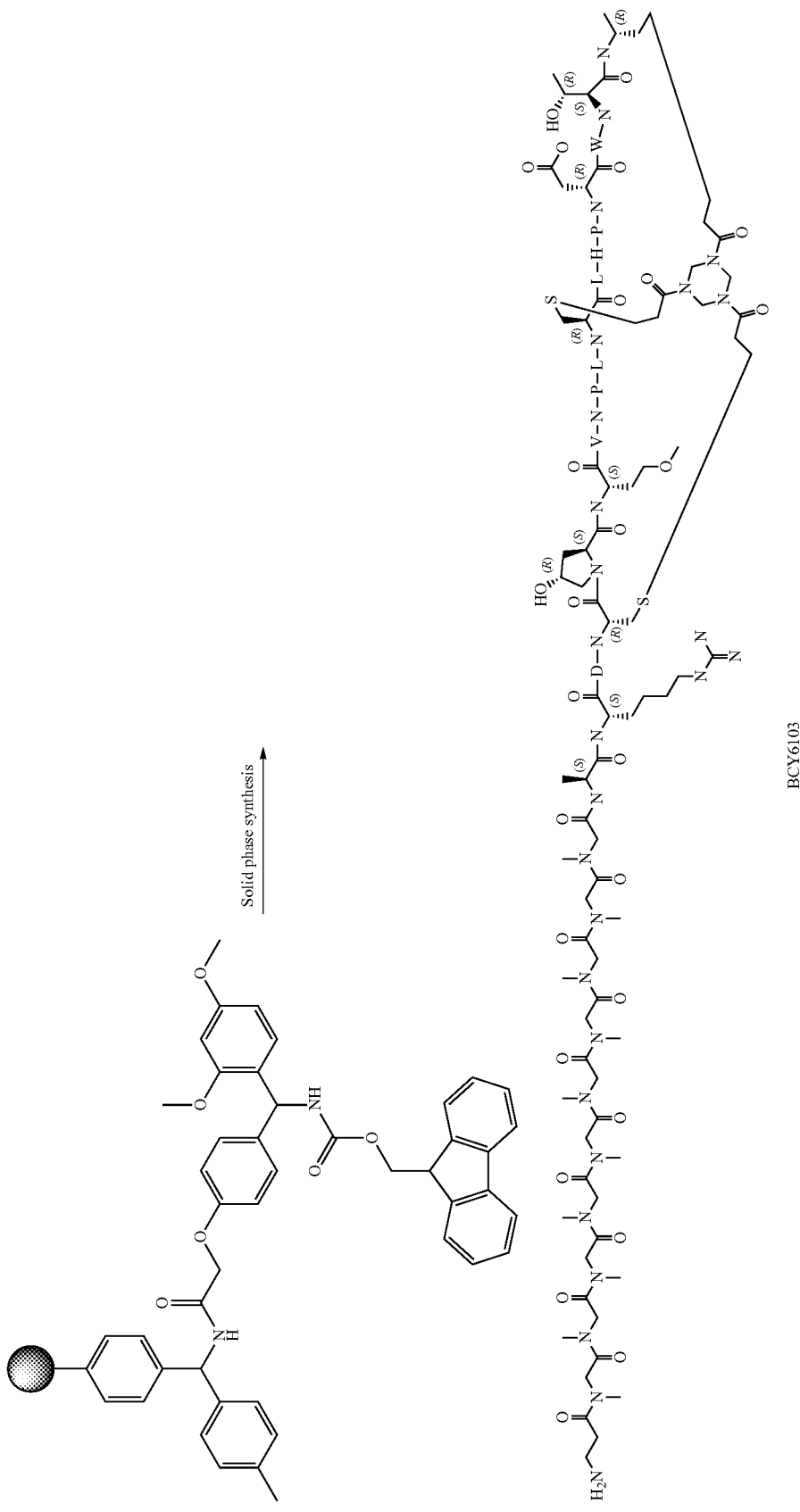
Sequence: (β-Ala)-Sar₁₀-A(HArg)DC(HyP)(Hse(Me))VNPLCLHP(D-Asp)WTC ((β-Ala)-Sar₁₀-(SEQ ID NO: 86))
BCY6103 (Compound 100)
BCY6103

4.44 g of resin was used to generate 700 mg BCY6103 (98.9% purity, 11.1% yield) as white a solid.

|  | BCY6103 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 8.02 min |
| LCMS (ESI): | m/z 1039.1 $[M + 3H]^{3+}$, 779.5 $[M + 4H]^{4+}$ |
| Peptide mw | 3117.55 |

Sequence: (β-Ala)-Sar10-A(HArg)DC(HyP)LVNPLCLHP(D-Ala)WTC ((β-Ala)-Sar10-(SEQ ID NO: 87))
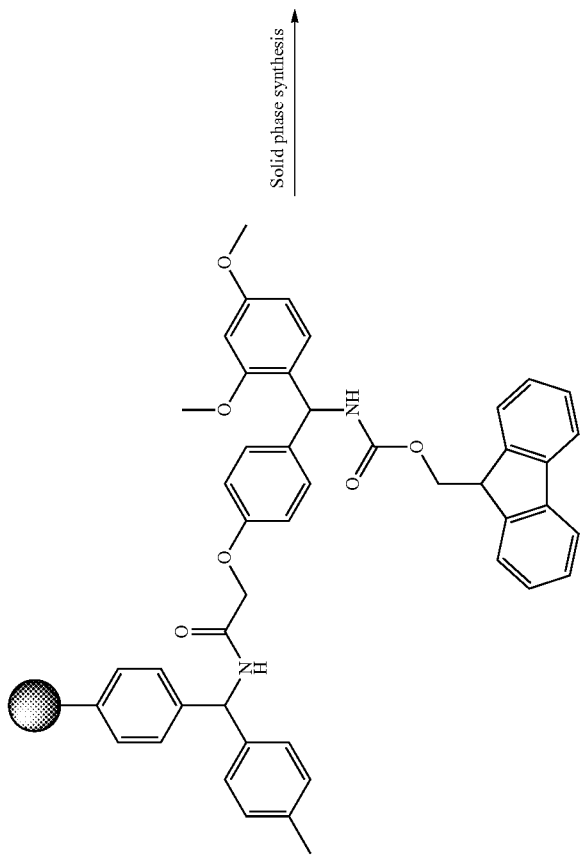
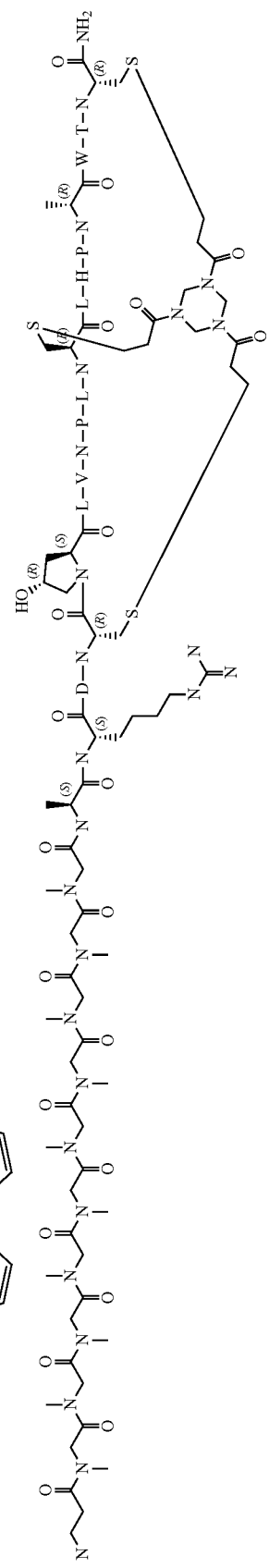
BCY6101 (Compound 101)
BCY6101

4.44 g of resin was used to generate 700 mg BCY6101 (95.9% purity, 10.9% yield) as white a solid.

|  | BCY6101 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 9.79 min |
| LCMS (ESI): | m/z 1023.6 $[M + 3H]^{3+}$, 768.0 $[M + 4H]^{4+}$ |
| Peptide mw | 3069.55 |

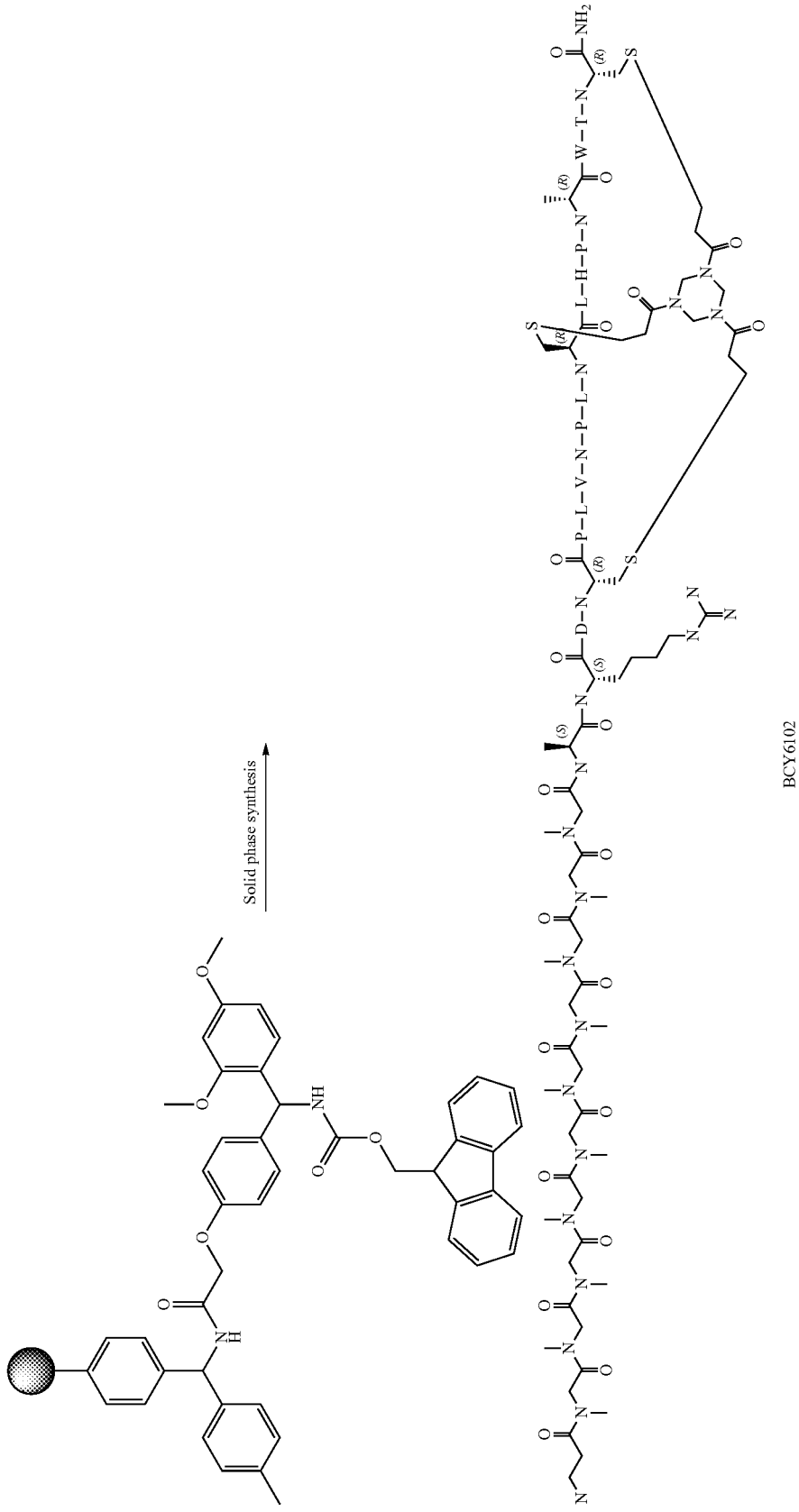

4.44 g of resin was used to generate 900 mg BCY6102 (95.9% purity, 14.1% yield) as white a solid.

|  | BCY6102 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 9.89 min |
| LCMS (ESI): | m/z 1018 $[M + 3H]^{3+}$, 763.9 $[M + 4H]^{4+}$ |
| Peptide mw | 3053.56 |

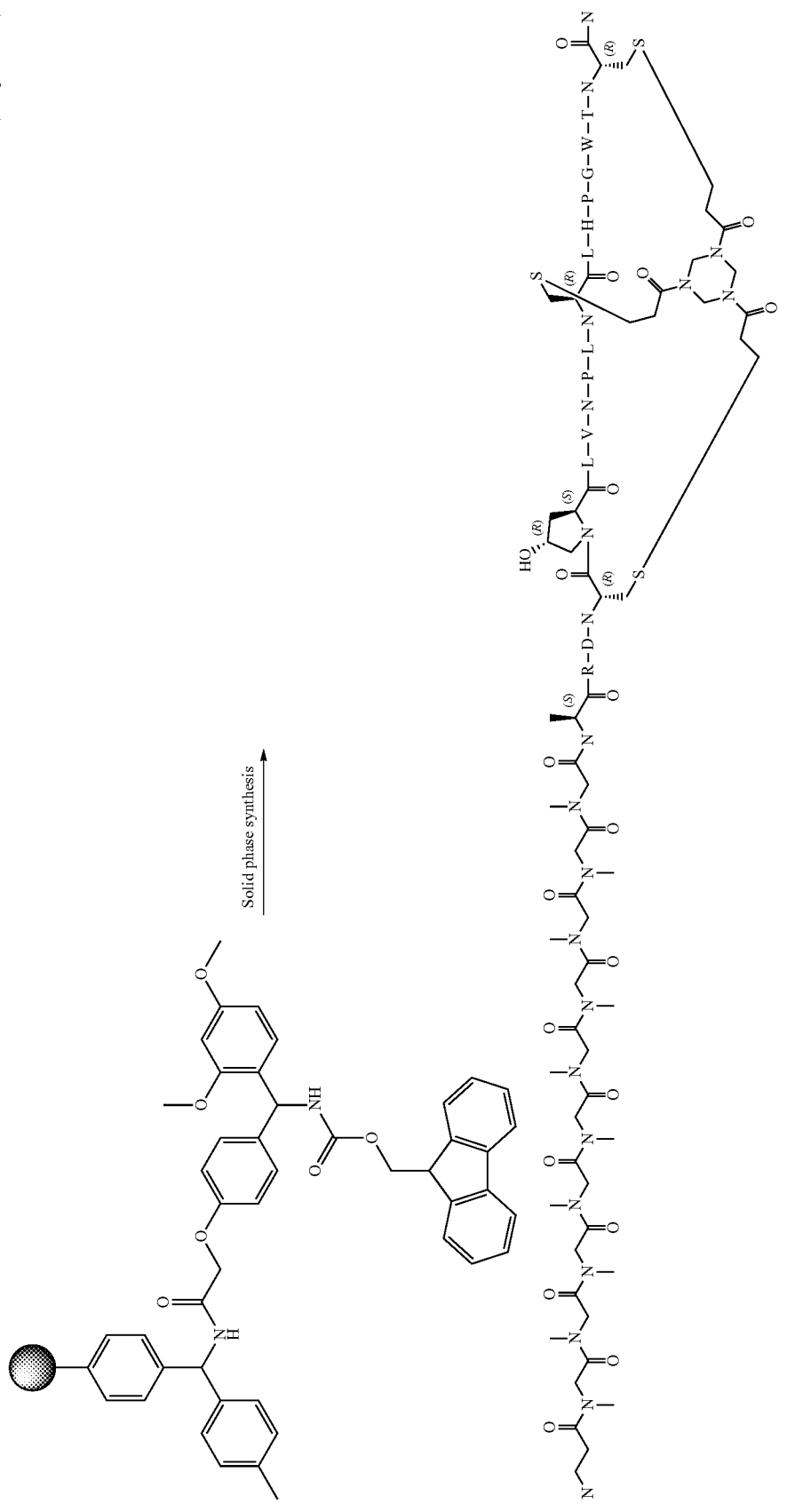

4.44 g of resin was used to generate 900 mg BCY6139 (97.4% purity, 11.2% yield) as white a solid.

|  | BCY6139 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 8.95 min |
| LCMS (ESI): | m/z 1014.6 $[M + 3H]^{3+}$, 761.2 $[M + 4H]^{4+}$ |
| Peptide mw | 3042.51 |

Sequence: (β-Ala)-Sar₁₀-ARDCPLVNPLCL(D-3,3-DPA)PGWTC ((β-Ala)-Sar₁₀-(SEQ ID NO: 90))
BCY6138 (Compound 104)
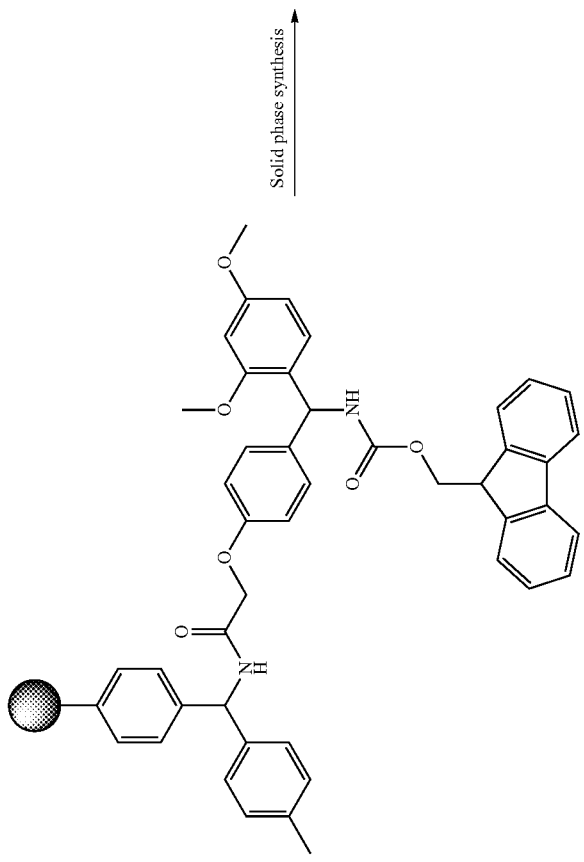
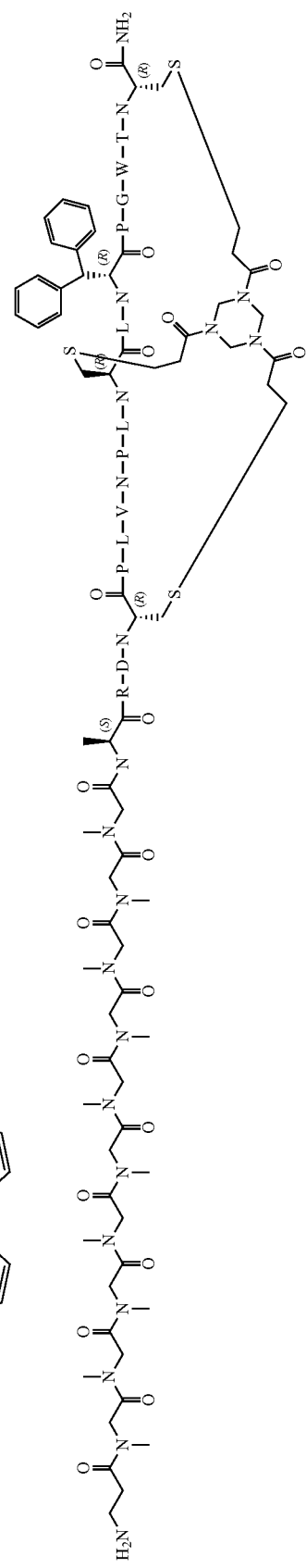

1.11 g of resin was used to generate 200 mg BCY6138 (95.2% purity, 12.2% yield) as white a solid.

|  | BCY6138 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 20 minutes, then 3 min 95% B |
| Retention Time: | 14.46 min |
| LCMS (ESI): | m/z 1037.6 $[M + 3H]^{3+}$ |
| Peptide mw | 3111.63 |

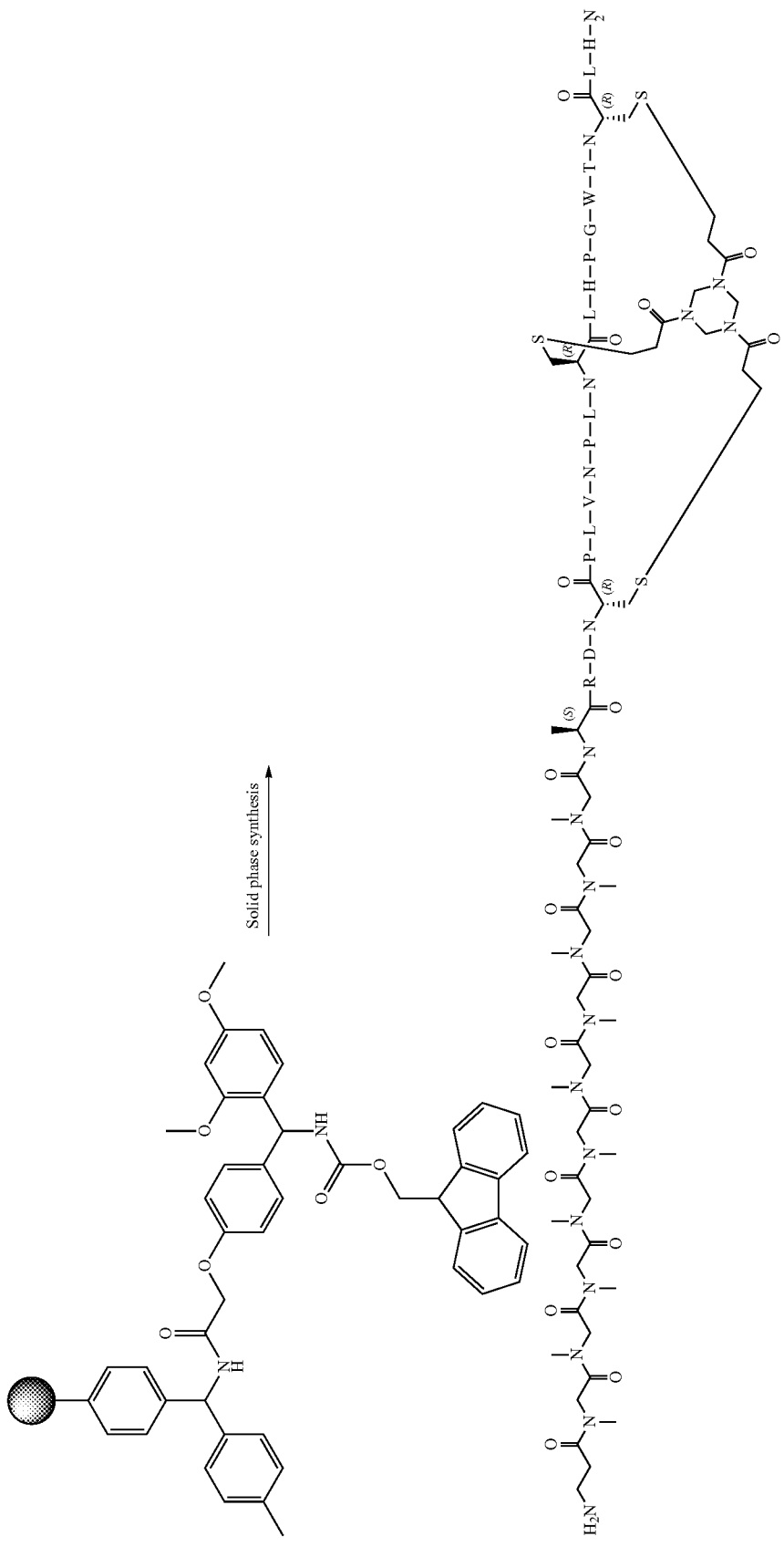

4.44 g of resin was used to generate 600 mg BCY6137 (98.9% purity, 9.06% yield) as white a solid.
| BCY6137 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| BCY6137 Analytical Data | |
|---|---|
| Method: | 20-50% B over 20 minutes, then 3 min 95% B |
| Retention Time: | 14.46 min |
| LCMS (ESI): | m/z 1092.7 $[M + 3H]^{3+}$, 819.6 $[M + 4H]^{4+}$ |
| Peptide mw | 3275.8 |
BCY6042 (Compound 91)
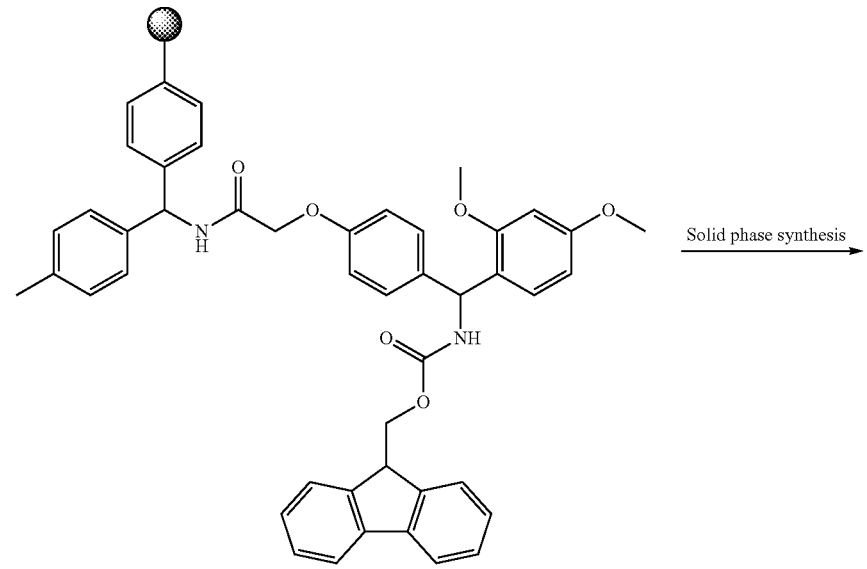
Solid phase synthesis →
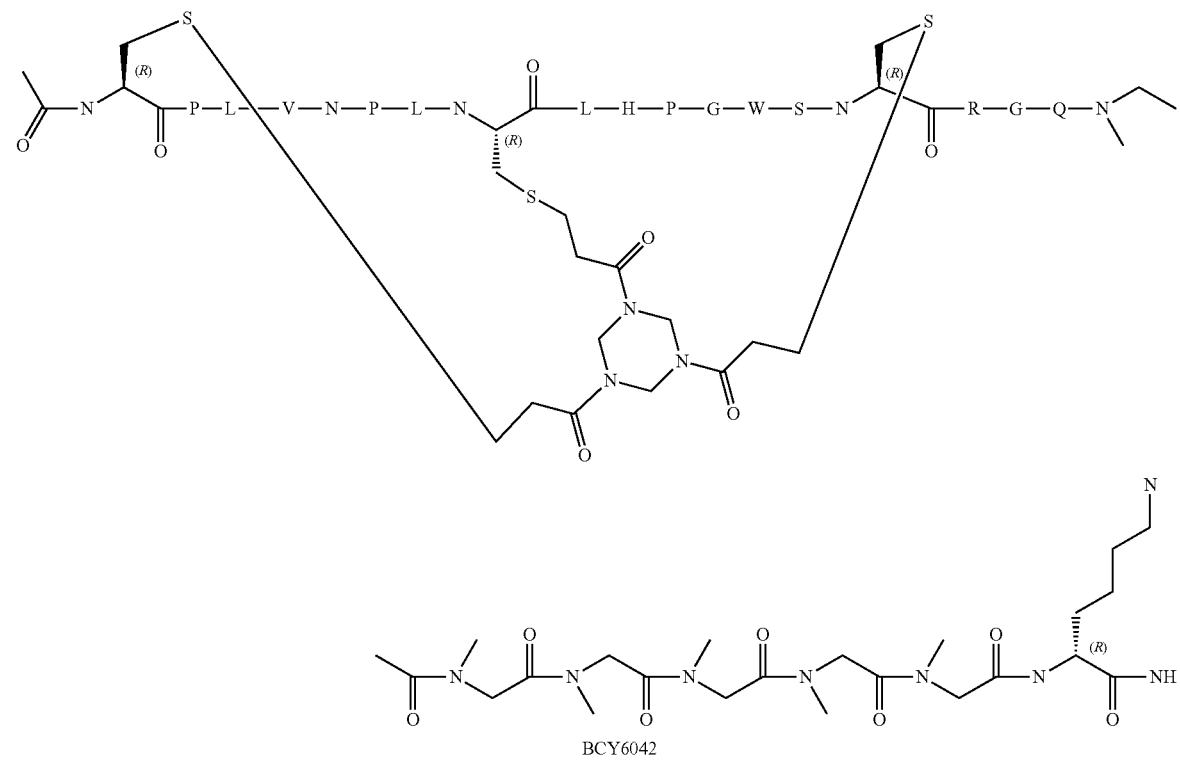
BCY6042

85

Sequence: Ac-(SEQ ID NO: 14)-Sar₆-(D-K)

1.11 g of resin was used to generate 99.2 ma BCY6042 (99.2% purity 7.0% yield) as white a solid

| BCY6042 Analytical Data | |
|---|---|
| Mobile Phase: | A: 0.1% TFA in H2O B: 0.1% TFA in ACN |
| Flow: | 1.0 ml/min |

86

-continued

| BCY6042 Analytical Data | |
|---|---|
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 9.12 min |
| LCMS (ESI): | m/z 943.5 [M + 3H]³⁺ |
| Peptide mw | 2825.31 |

BCY6019 (Compound 77)

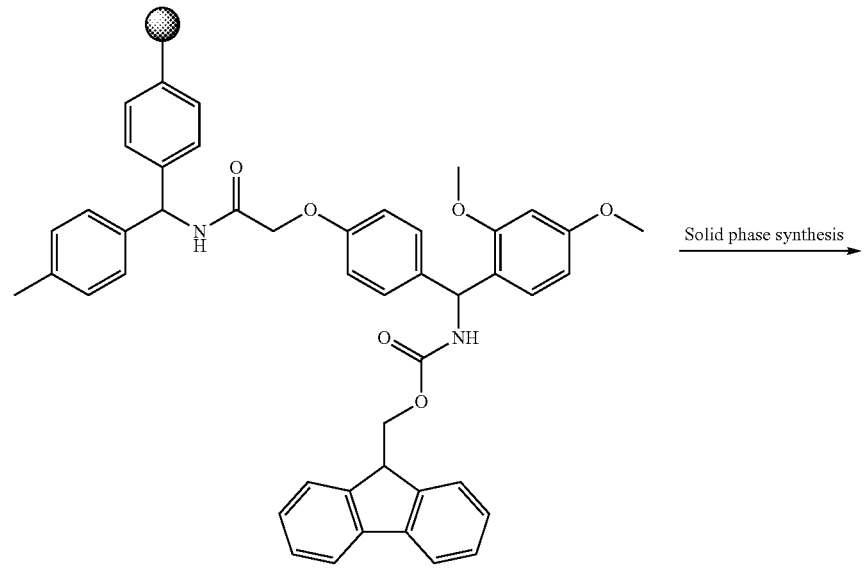

Solid phase synthesis

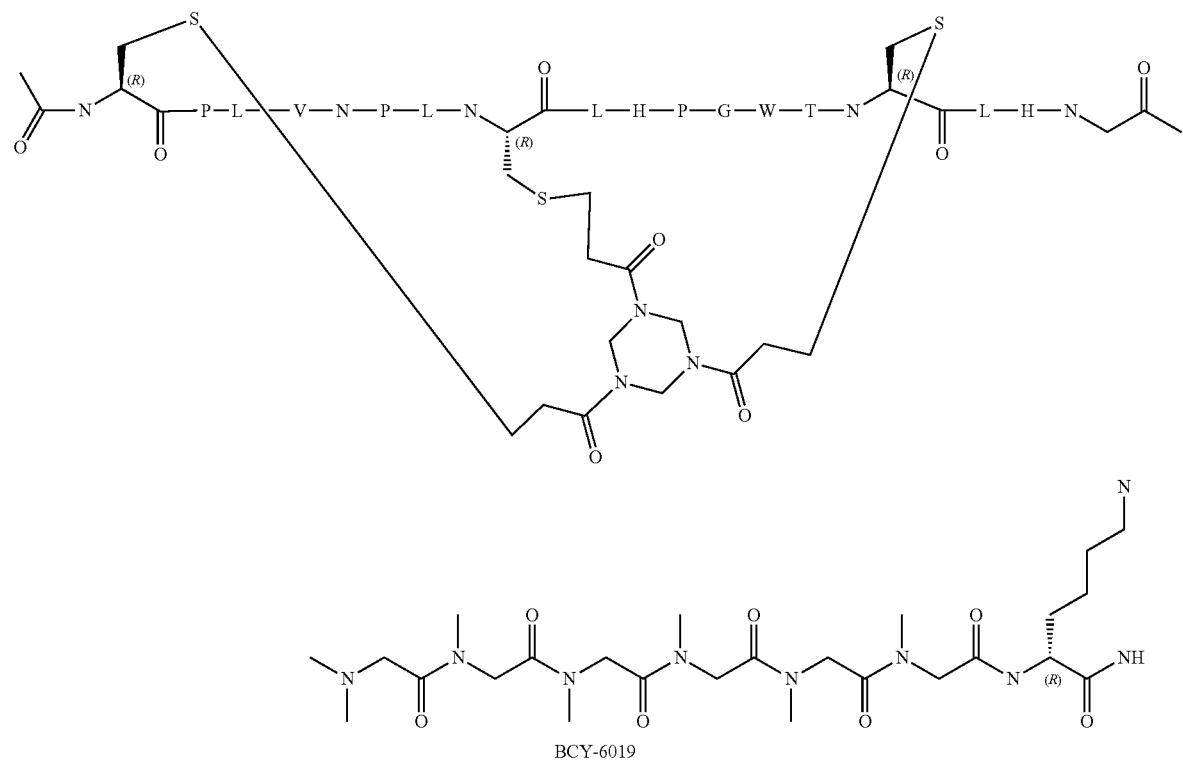

BCY-6019

Sequence: Ac-(SEQ ID NO: 12)-Sar$_6$-(D-K)

4.79 g of resin was used to generate 732.0 mg BCY6019 (92.82% purity, 12.2% yield) as white a solid.

|  | BCY6019 Analytical Data |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 11.36 min |
| LCMS (ESI): | m/z 935.5 $[M + 3H]^{3+}$ |
| Peptide mw | 2805.32 |

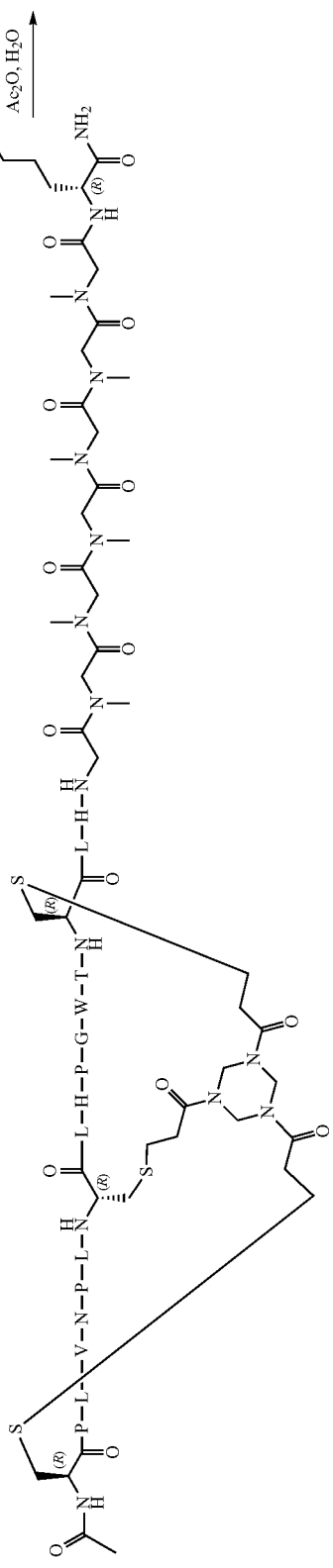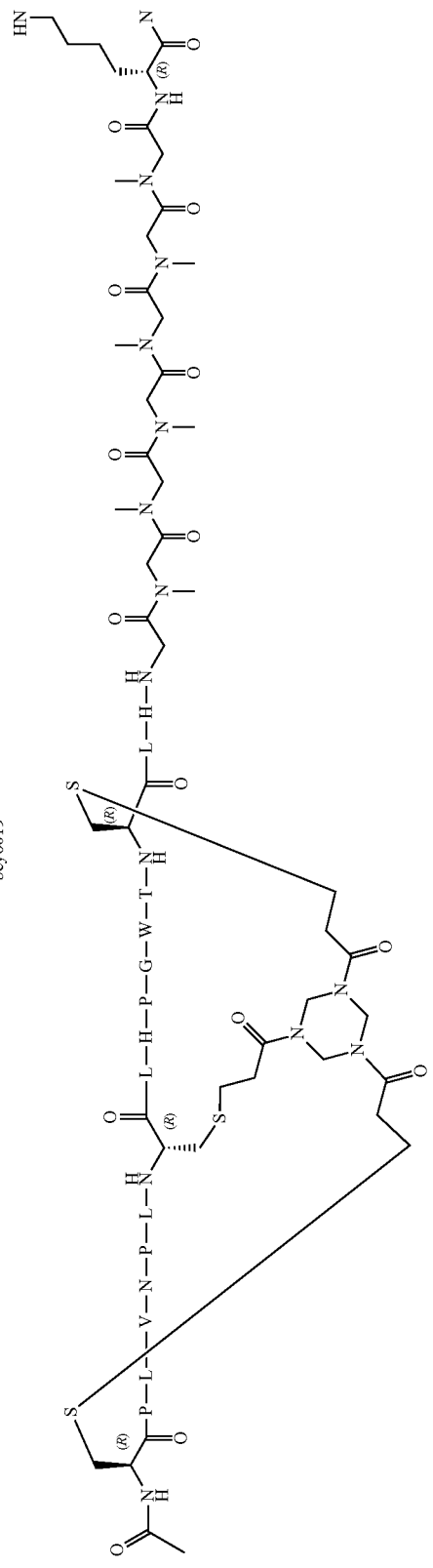

Sequence: Ac-(SEQ ID NO: 12)-Sar₆-(D-K[Ac])

To a solution of BCY6019 (0.05 g, 17.82 μmol, 1.00 eq) in H₂O (3 mL) was adjusted PH=11 by Na₂CO₃ (aq) and added acetyl acetate (5.46 mg, 53.46 μmol, 5.01 μL, 3.00 eq). The mixture was stirred at 15° C. for 1 hr. LC-MS showed BCY6019 was consumed completely and one main peak with desired MS was detected. The reaction was adjusted PH=7 by 1N HCl and directly purified by prep-HPLC (TFA condition). Compound BCY6059 (18.1 mg, 6.36 μmol, 35.67% yield) was obtained as a white solid.

| BCY6059 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 6.67 min |
| LCMS (ESI): | m/z 949.8 [M + 3H]³⁺ |
| Peptide mw | 2848.36 |

BCY6160 (Compound 107)

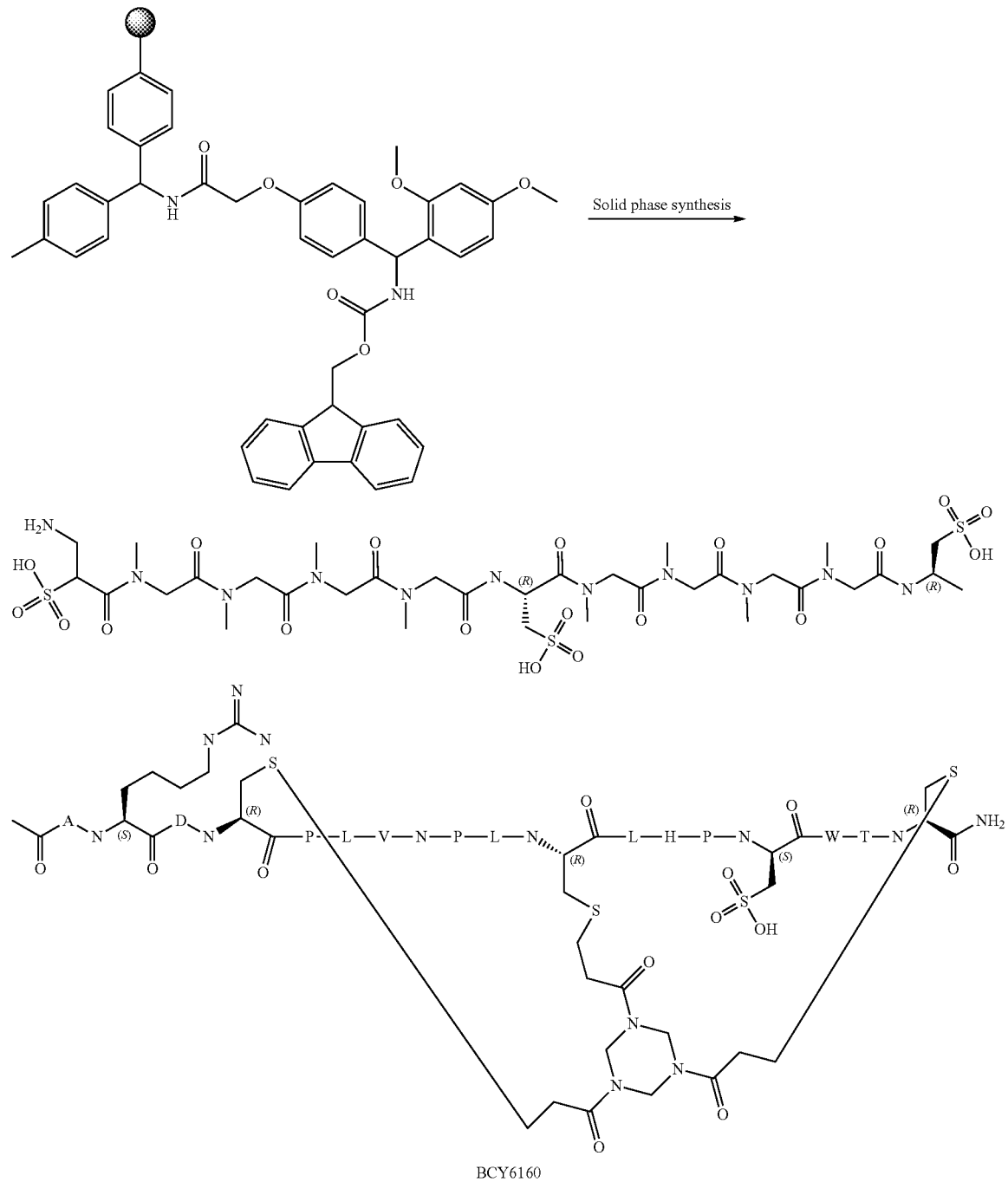

BCY6160

93

Sequence: (β-AlaSO₃H)-Sar₄-(Cya)-Sar₄-(Cya)-A(HArg)DCPLVNPLCLHP(D-Cya)WTC ((β-AlaSO₃H)-Sar₄-(Cya)-Sar₄-(Cya)-(SEQ ID NO: 92))

1.11 g of resin was used to generate 45.2 mg BCY6160 (95.5% purity, 2.5% yield) as white a solid.

| BCY6160 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 11.38 min |
| LCMS (ESI): | m/z 1124.9 [M + 3H]³⁺ |
| Peptide mw | 3376.83 |

94

Sequence: (β-Ala)-Sar₁₀-ARDCPLVN-PLCLHPGWTC ((β-Ala)-Sar₁₀-(SEQ ID NO: 10))

4.79 g of resin was used to generate 2.42 g BCY6009 (>88.92% purity, 36.0% yield) as white a solid.

| BCY6009 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 10.16 min |
| LCMS (ESI): | m/z 1008.9 [M + 3H]³⁺, 756.9 [M + 4H]⁴⁺ |
| Peptide mw | 3025.5 |

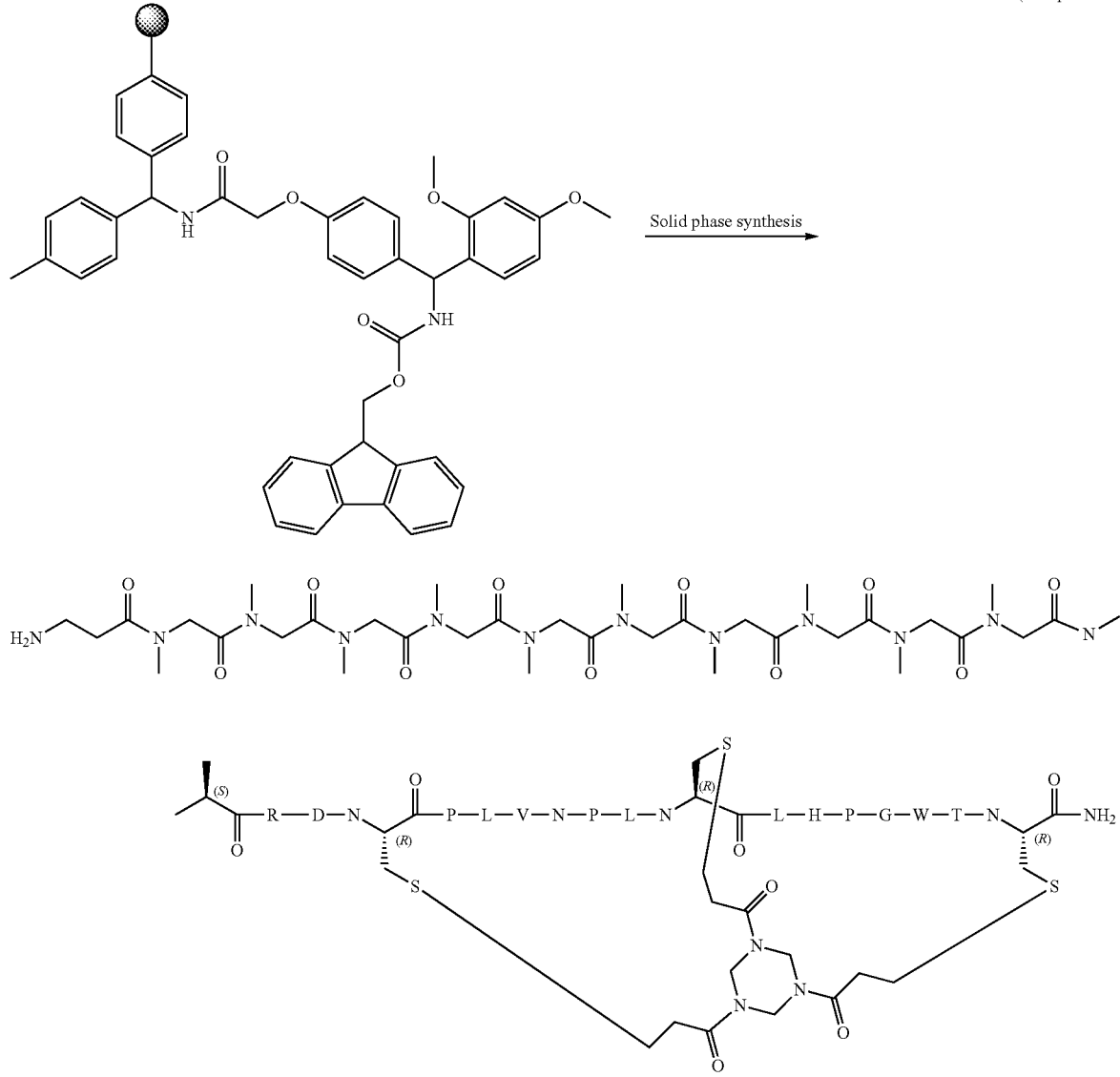

BCY6009 (Compound 108)

BCY-6009

BCY6017 (Compound 109)

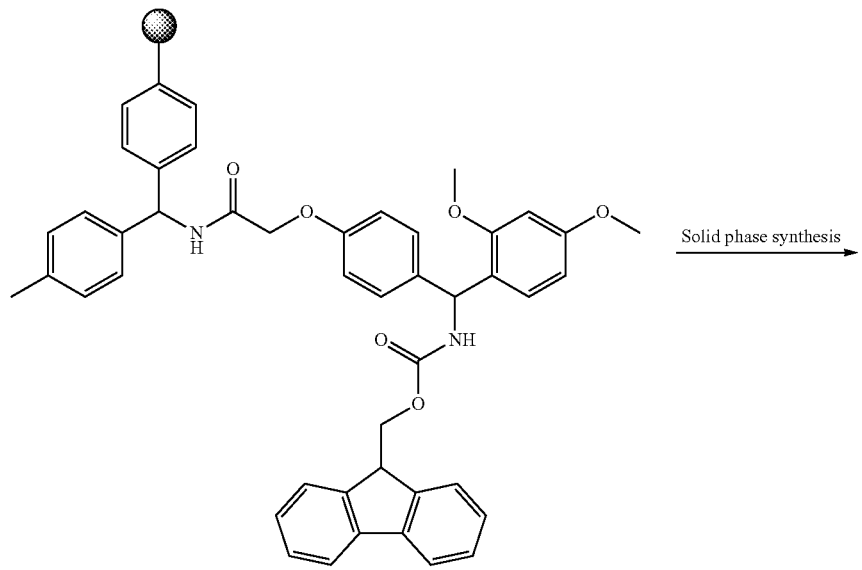

Solid phase synthesis

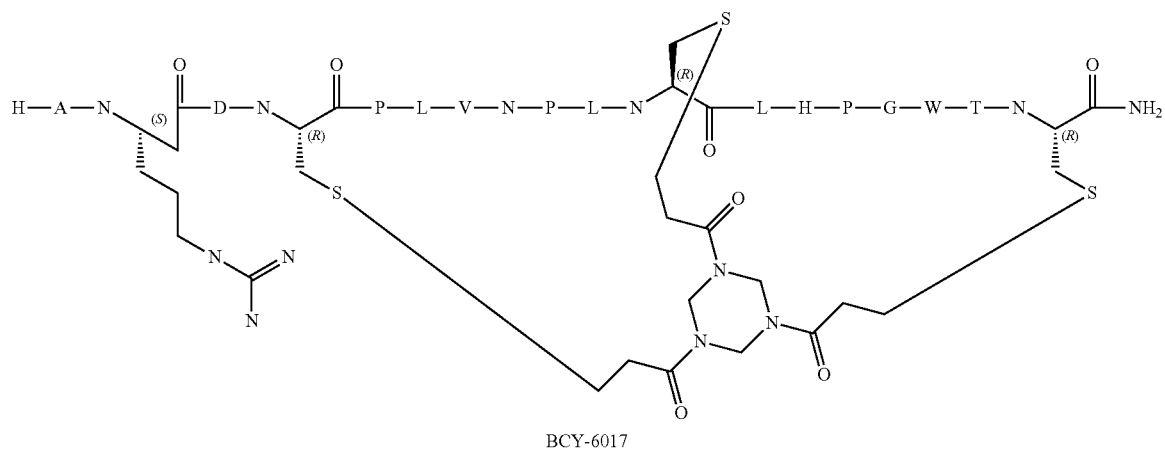

BCY-6017

Sequence: A(HArg)DCPLVNPLCLHPGWTC (SEQ ID NO: 11)

1.19 g of resin was used to generate 189.9 mg BCY6017 (95.05% purity, 16.8% yield) as white a solid.

| BCY6017 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 10.01 min |
| LCMS (ESI): | m/z 1129.1 $[M + 2H]^{2+}$, 753.0 $[M + 3H]^{3+}$ |
| Peptide mw | 2257.67 |

BCY6018 (Compound 110)

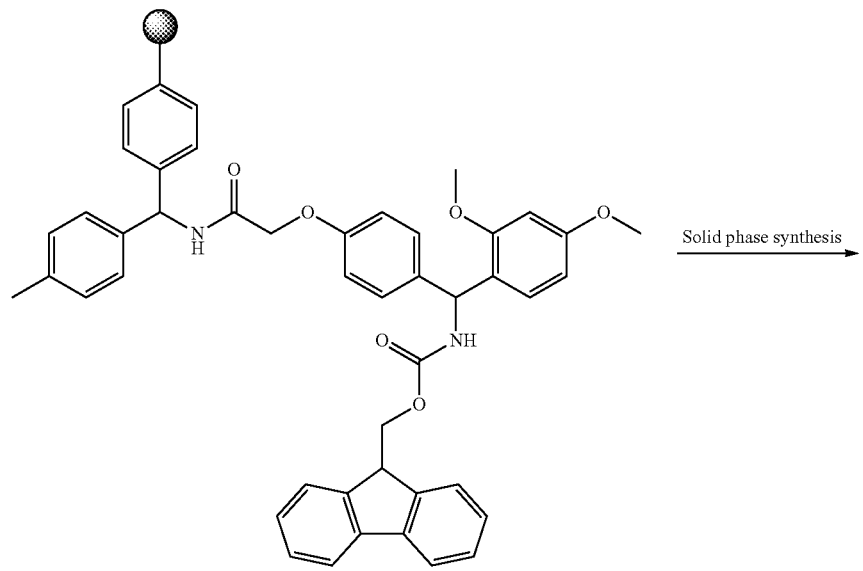

Solid phase synthesis

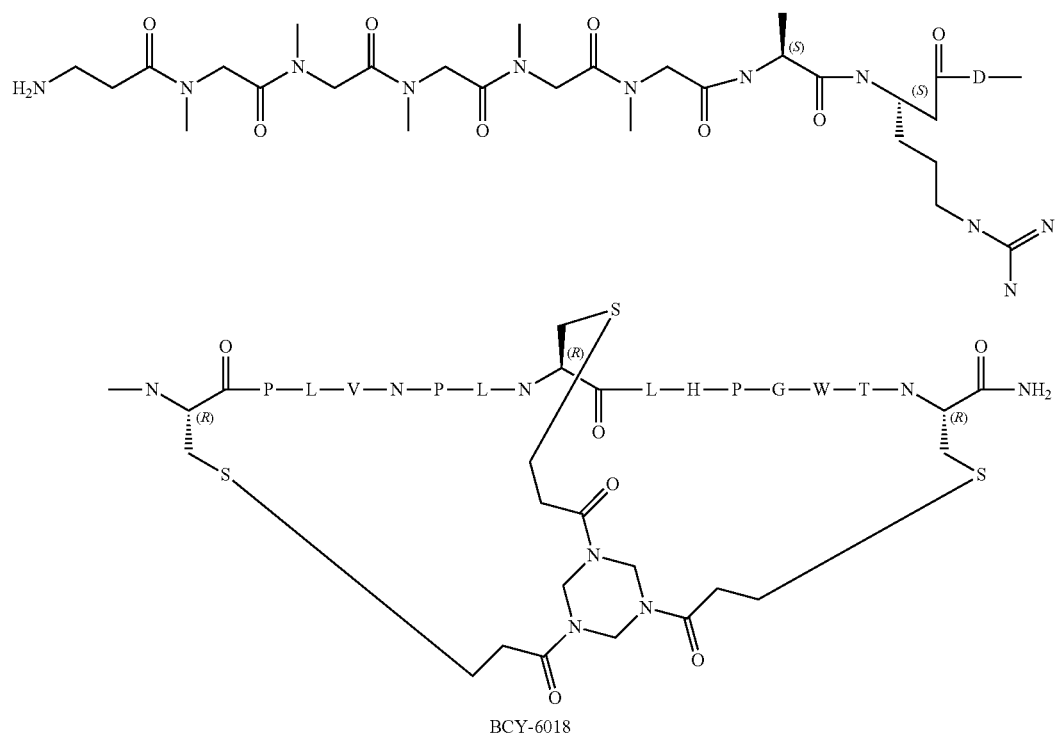

BCY-6018

Sequence: (β-Ala)-Sar₅-(SEQ ID NO: 11)

1.19 g of resin was used to generate 289.1 mg BCY6018 (97.92% purity, 21.0% yield) as white a solid.

| BCY6018 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6018 Analytical Data | |
|---|---|
| Method: | 20-50% B over 20 minutes, then 3 min 95% B |
| Retention Time: | 9.77 min |
| LCMS (ESI): | m/z 1342.9 [M + 2H]$^{2+}$, 895.3 [M + 3H]$^{3+}$ |
| Peptide mw | 2684.14 |

BCY6152 (Compound 111)

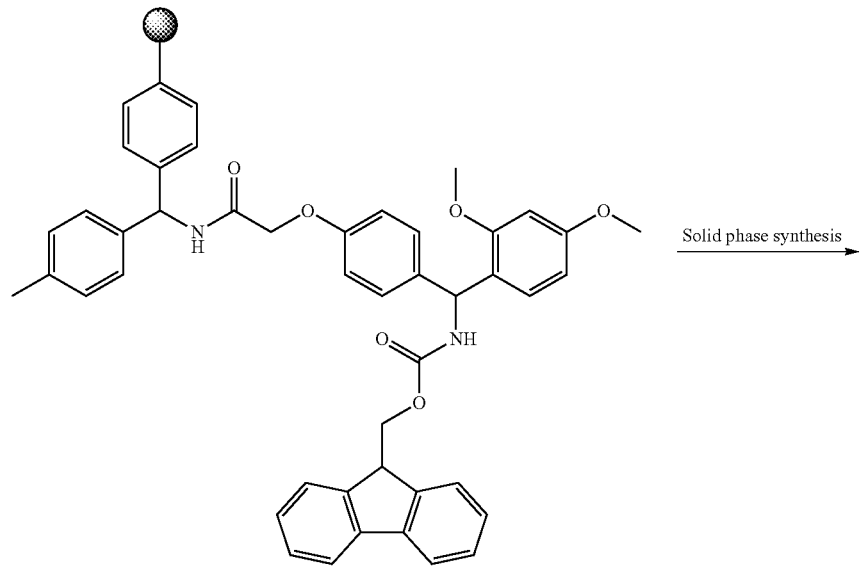

Solid phase synthesis

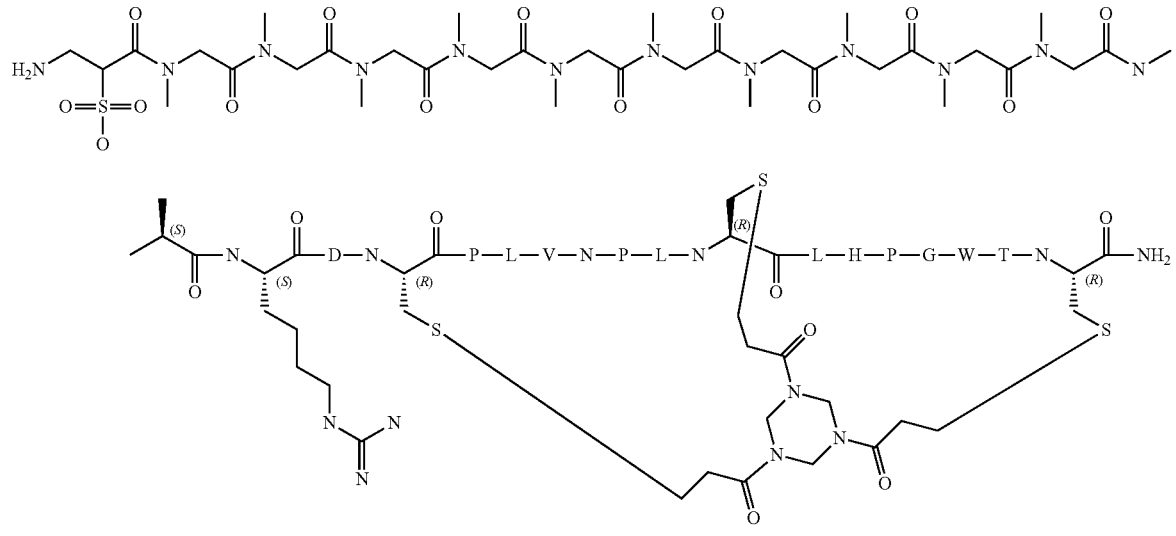

BCY6152

Sequence: (β-AlaSO₃H)-Sar₁₀-(SEQ ID NO: 11)

1.11 g of resin was used to generate 150.0 mg BCY6152 (98.75% purity; 9.5% yield) as white a solid.

| BCY6152 Analytical Data | |
|---|---|
| Mobile Phase: | A: 0.1% TFA in H2O B: 0.1% TFA in ACN |
| Flow: | 1.0 ml/min |

-continued

| BCY6152 Analytical Data | |
|---|---|
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 10.09 min |
| LCMS (ESI): | m/z 1040.3 [M + 3H]$^{3+}$ |
| Peptide mw | 3119.59 |

BCY6141 (Compound 112)

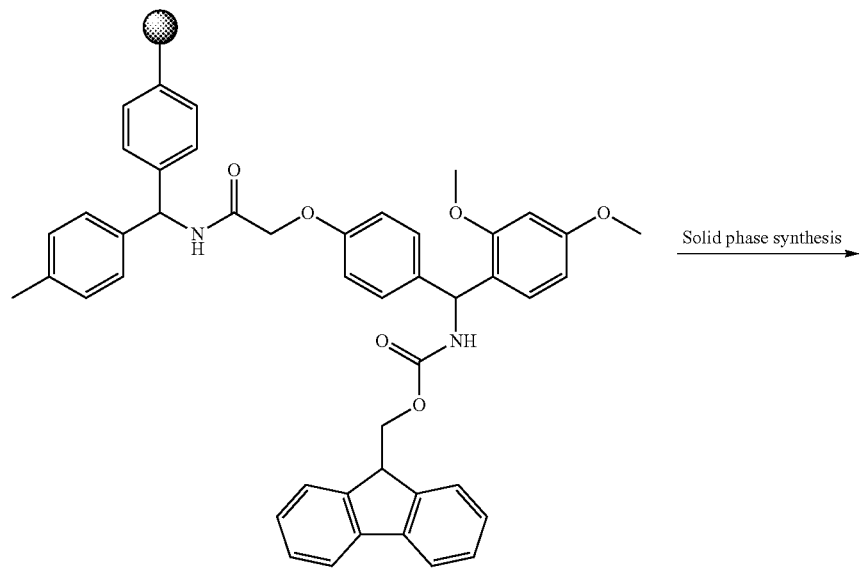

→ Solid phase synthesis

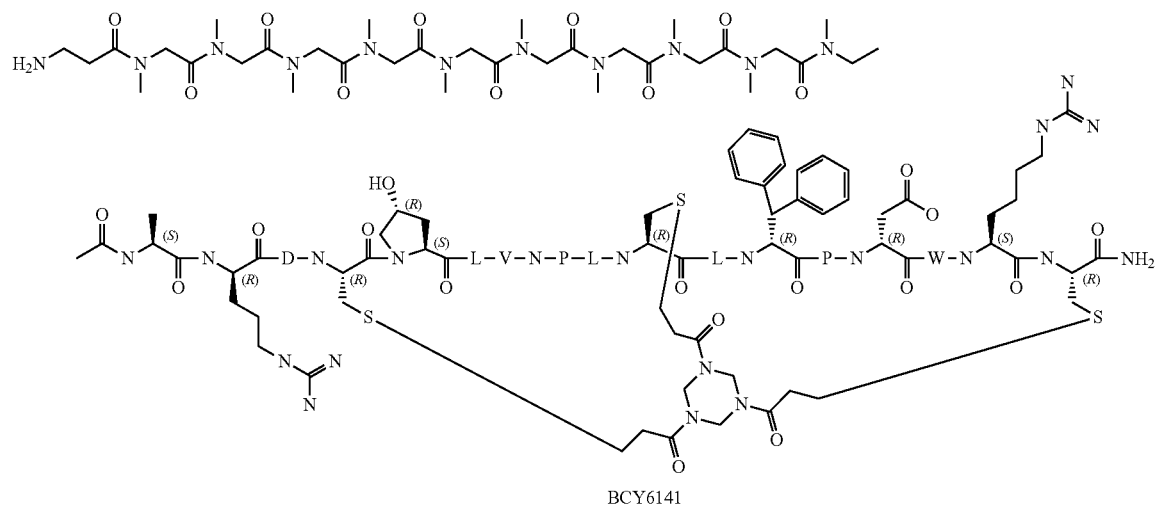

BCY6141

Sequence: (β-Ala)-Sar₁₀-A(D-Arg)DC(HyP)LVN-PLCL(D-3,3-DPA)P(D-Asp)W(HArg)C ((β-Ala)-Sar₁₀-(SEQ ID NO: 93))

1.11 g of resin was used to generate 120.0 mg BCY6141 (97.91% purity; 7.3% yield) as white a solid.

| BCY6141 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |

-continued

| BCY6141 Analytical Data | |
|---|---|
| Instrument: | Agilent 1200 HPLC-BE(1-614) |
| Method: | 28-68% B over 30 minutes, then 3 min 95% B |
| Retention Time: | 11.41 min |
| LCMS (ESI): | m/z 1085.5 [M + 3H]³⁺ |
| Peptide mw | 3255.78 |

BCY6026 (Compound 87)

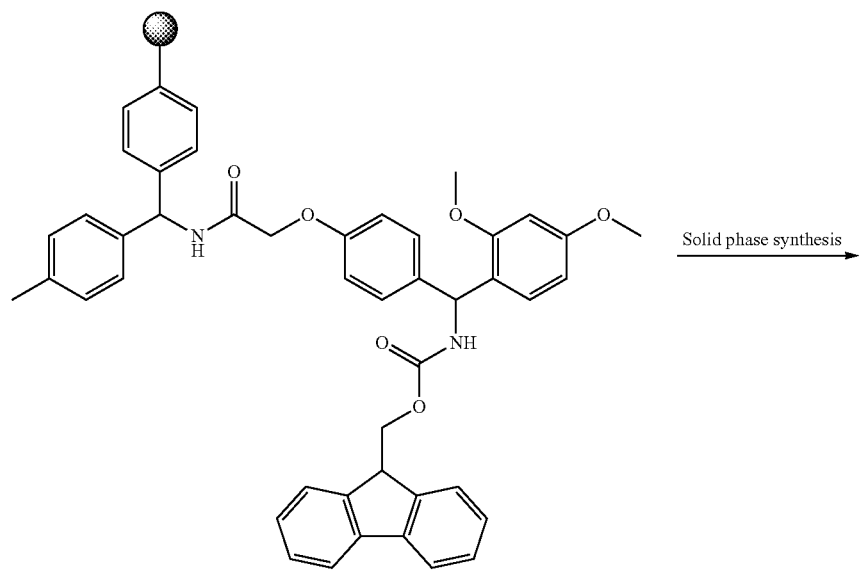

Solid phase synthesis →

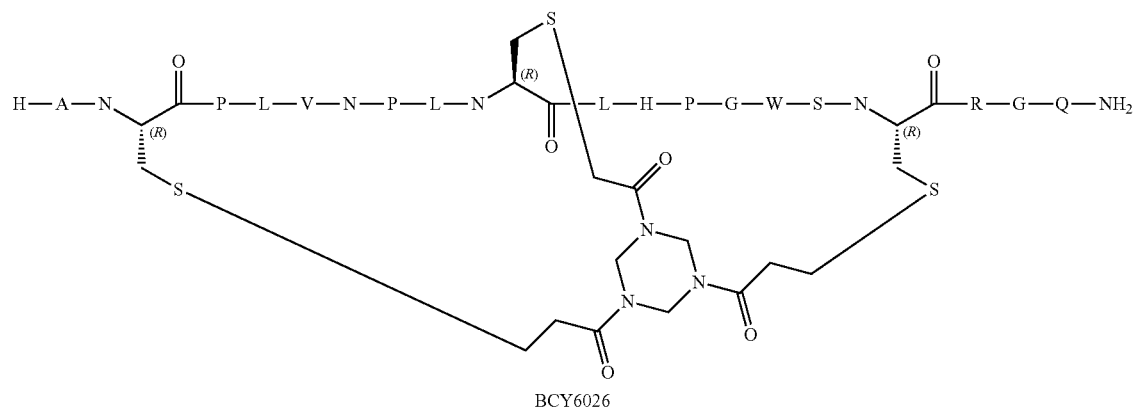

BCY6026

Sequence: ACPLVNPLCLHPGWSCRGQ (SEQ ID NO: 77)

1.11 g of resin was used to generate 285.0 mg BCY6026 (97.7% purity; 24.2% yield) as white a solid.

| BCY6026 Analytical Data | |
|---|---|
| Mobile Phase: | A: 0.1% TFA in H2O B: 0.1% TFA in ACN |
| Flow: | 1.0 ml/min |

-continued

| BCY6026 Analytical Data | |
|---|---|
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 9.31 min |
| LCMS (ESI): | m/z 1150 $[M + 2H]^{2+}$, 767.0 $[M + 3H]^{3+}$ |
| Peptide mw | 2299.71 |

BCY6153 (Compound 113)

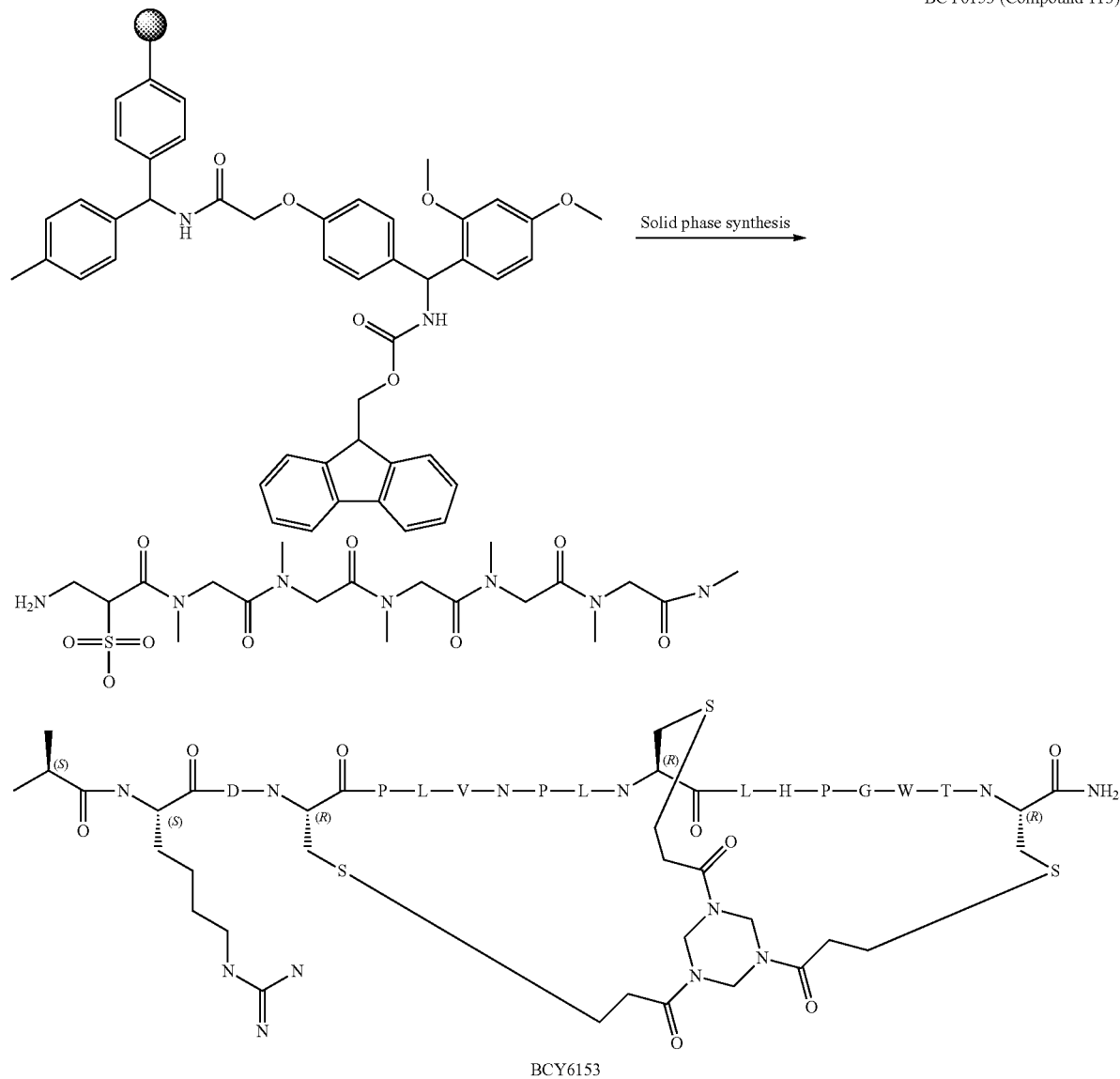

BCY6153

Sequence: (β-AlaSO₃H)-Sar₅-(SEQ ID NO: 11)

1.11 g of resin was used to generate 140.0 mg BCY6153 (98.59% purity; 9.9% yield) as white a solid.

| BCY6153 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 20-50% B over 20 minutes, then 3 min 95% B |
| Retention Time: | 10.33 min |
| LCMS (ESI): | m/z 1382.6 [M + 2H]$^{2+}$, 922.0 [M + 3H]$^{3+}$ |
| Peptide mw | 2764.2 |

Preparation of Bicyclic Peptide Drug Conjugates

Figure 3:
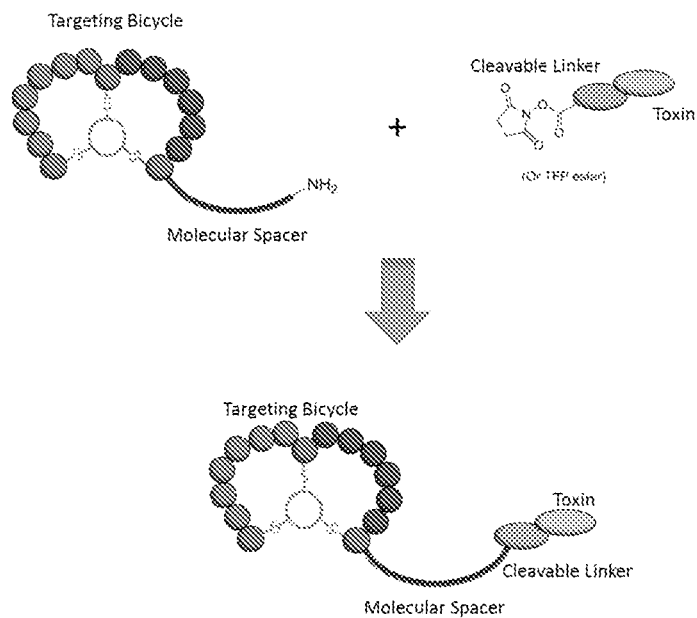
FIG. 3: General schematic demonstrating the concept of preparing Bicycle drug conjugates (BDCs).

The general schematic for preparing Bicycle drug conjugates (BDCs) is shown in FIG. 3 and Table A describes the component targeting bicycle and linker/toxin within each BDC.

TABLE A

| BDC (BCY No) | Targeting Bicycle (BCY No) | Linker/Toxin |
|---|---|---|
| 6136 | 6099 | ValCit-MMAE |
| 6033 | 6014 | |
| 6029 | 6009 | |
| 6122 | 6104 | |
| 6053 | 6018 | |
| 6049 | 6017 | |
| 6037 | 6019 | |
| 6030 | 6009 | TrpCit-MMAE |

TABLE A-continued

| BDC (BCY No) | Targeting Bicycle (BCY No) | Linker/Toxin |
|---|---|---|
| 6034 | 6014 | |
| 6050 | 6017 | |
| 6054 | 6018 | |
| 6038 | 6019 | |
| 6061 | 6014 | ValLys-MMAE |
| 6174 | 6099 | |
| 6062 | 6014 | D-TrpCit-MMAE |
| 6135 | 6099 | DM1-SS— |
| 6031 | 6014 | |
| 6134 | 6104 | |
| 6027 | 6009 | |
| 6047 | 6017 | |
| 6035 | 6019 | |
| 6051 | 6018 | |
| 6154 | 6152 | |
| 6155 | 6153 | |
| 6173 | 6099 | DM1-SS(SO3H)— |
| 6082 | 6014 | |
| 6150 | 6018 | |
| 6151 | 6104 | |
| 6162 | 6138 | |
| 6161 | 6137 | |
| 6032 | 6014 | DM1-SS—(Me)— |
| 6052 | 6018 | |
| 6048 | 6017 | |
| 6036 | 6019 | |
| 6028 | 6009 | |
| 6039 | 6014 | DM1-(Me)—SS—(Me)— |
| 6055 | 6014 | DM1-SS—(Me2)— |
| 6077 | 6014 | DM1-SS—(Me)—SO3H— |
| 6063 | 6014 | Non-cleavable (MMAE) |
| 6064 | 6014 | Non-cleavable (DM1) |
| 6105 | 6014 | MMAE-Ala-Ala-Asn |
| 6106 | 6014 | MMAE-D-Ala-Phe-Lys- |
| 6175 | 6099 | |
| 6107 | 6014 | MMAE-Glu-Pro-Cit-Gly-hPhe-Tyr-Leu- |

The synthesis of Bicyclic Peptide Drug Conjugates BCY6027, BCY6028, BCY6031 and BCY6032 listed in Table 6 were performed using the protocol disclosed in WO 2016/067035.

MMAE Series
Val-Cit-MMAE Series
Val-Cit-MMAE Linker

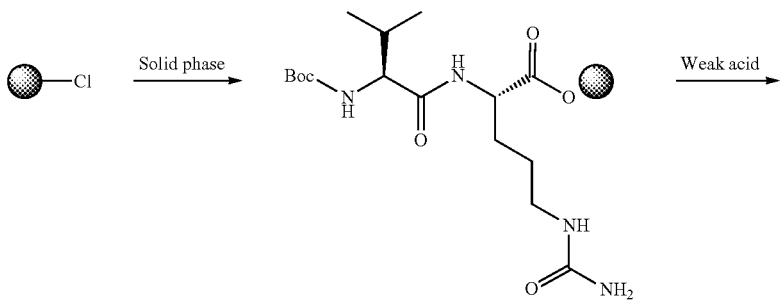

Activated bicycle peptides with formula (C) and (D):

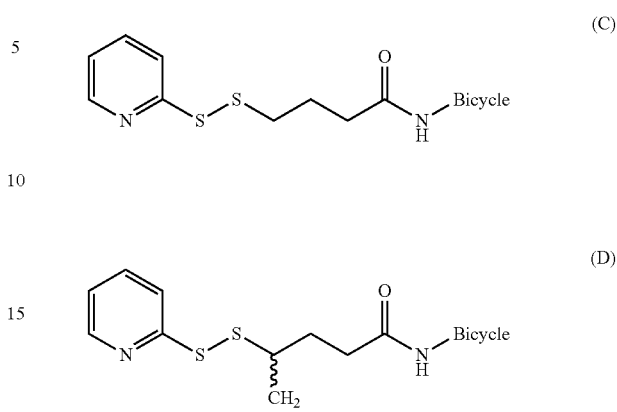

were synthesised by reacting the free amino group of the bicycle precursors with, respectively, SPP (N-succinimidyl 4-(2-pyridyldithio)pentanoate, Annova Chem) and SPDB (N-succinimidyl 3-(2-pyridyldithio)propionate, Annova Chem) in DMSO. Concentrations of bicycle precursors were 10 mM or higher, with a 1.3-fold excess of SPP or SPDB, and a 20-fold excess of diisopropylethylamine, at room temperature. The reaction was judged complete after 1 hour, as judged by LCMS. Purification was performed by reverse phase as described above. Appropriate fractions were lyophilised.

Activated bicycle peptides with formula (C) and (D) were disulphide exchanged with 1.15 equivalents of DM1 (as the free thiol), in semi aqueous conditions (50% dimethylacetamide and 50% 100 mM sodium acetate pH 5.0 supplemented with 2 mM EDTA) for 21 hours at room temperature under a nitrogen gas blanket. Concentrations of activated bicycle peptides with structure C and D in the reaction were at 10 mM or higher.

This was followed by standard reverse phase purification using a C18 column. Fractions at purity greater than 95% were isolated and lyophilised. The materials did not contain measurable quantities of free toxin.

-continued
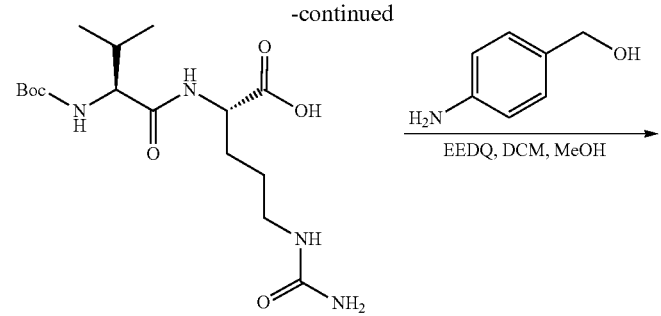
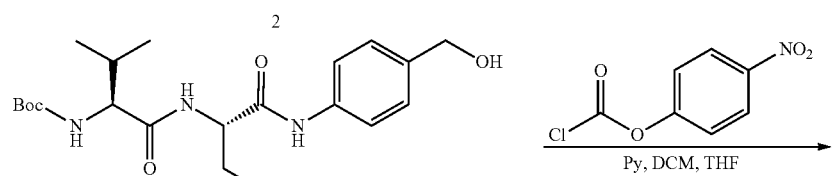
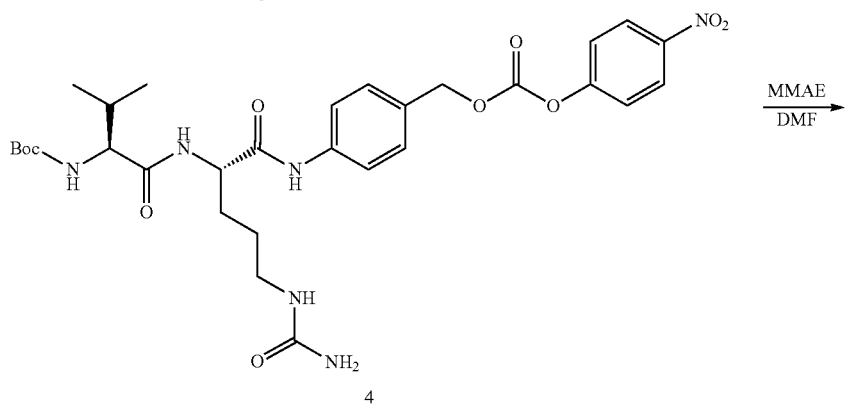
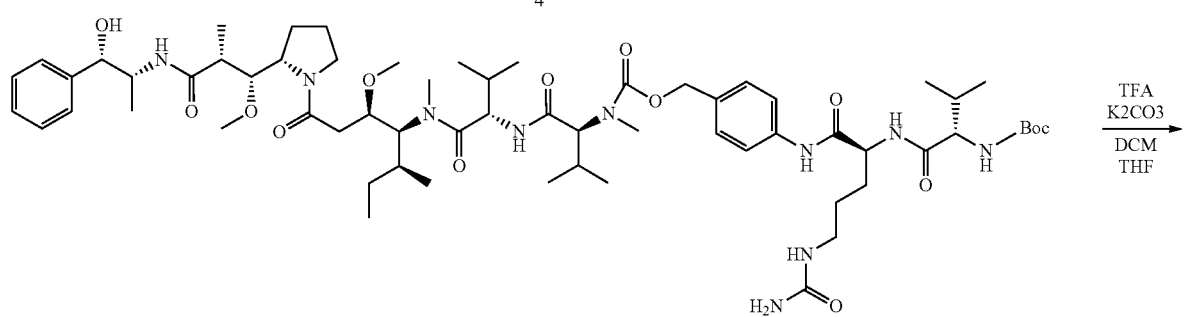
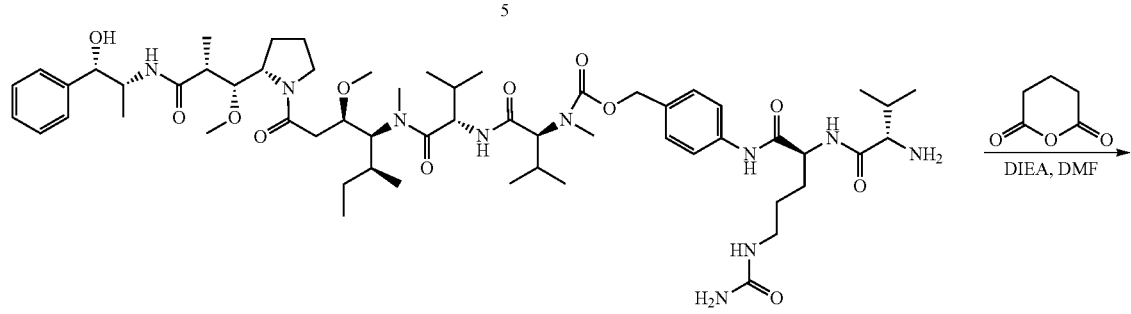

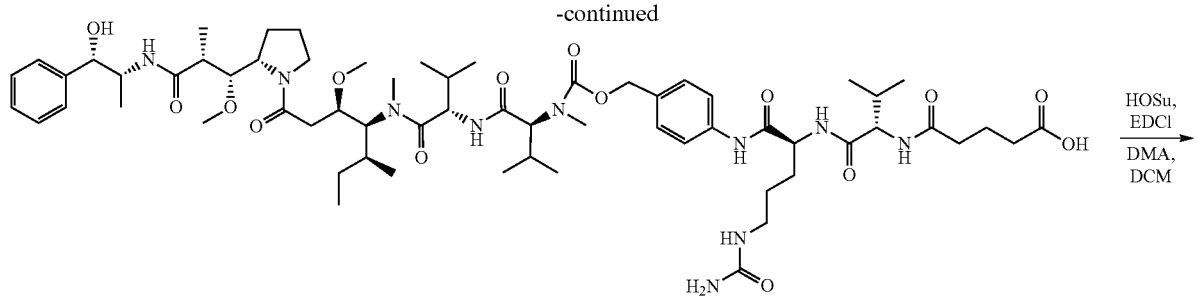

7

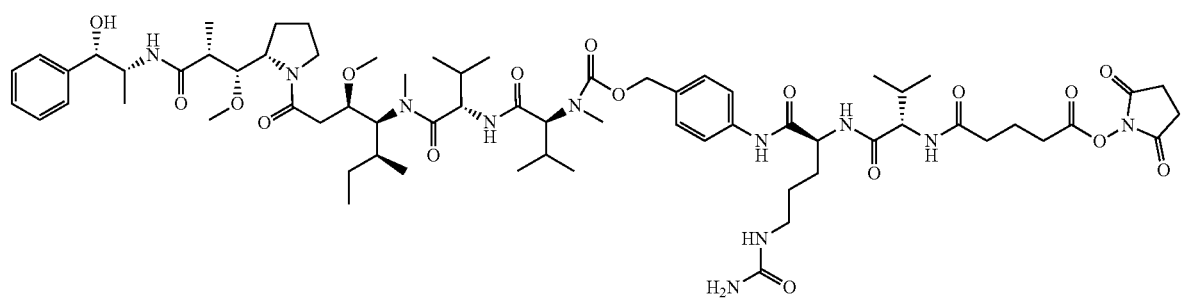

8

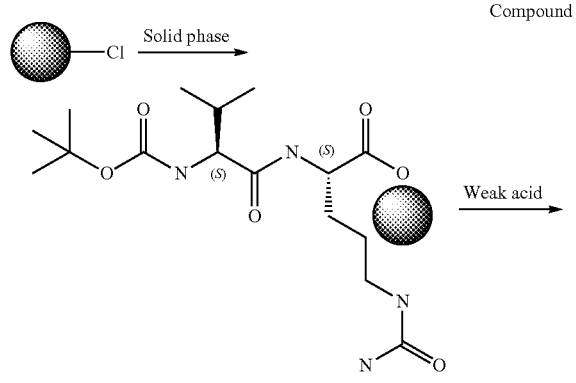

1

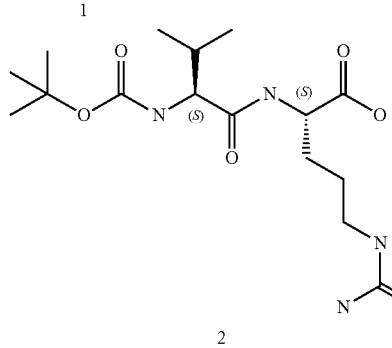

2

The peptide was synthesized by solid phase synthesis. 50 g CTC Resin (sub: 1.0 mmol/g) was used. To a mixture containing CTC Resin (50 mmol, 50 g, 1.0 mmol/g) and Fmoc-Cit-OH (19.8 g, 50 mmol, 1.0 eq) was added DCM (400 mL), then DIEA (6.00 eq) was added and mixed for 3 hours. And then MeOH (50 mL) was added and mixed for 30 min for capping. 20% piperidine in DMF was used for deblocking. Boc-Val-OH (32.5 g, 150 mmol, 3 eq) was coupled with 3 eq using HBTU (2.85 eq) and DIPEA (6.0 eq) in DMF (400 mL). The reaction was monitored by ninhydrin colour reaction test. After synthesis completion, the peptide resin was washed with DMF×3, MeOH×3, and then dried under $N_2$ bubbling overnight. After that the peptide resin was treated with 20% HFIP/DCM for 30 min for 2 times. The solution was removed on a rotary evaporator to give the crude. The crude peptide was dissolved in ACN/H2O, then lyophilized twice to give the peptide product (17.3 g crude).

| LCMS (ESI): | m/z 374.9 $[M + H]^+$ |
|---|---|
| Molecular weight | 374.44 |

Compound 3

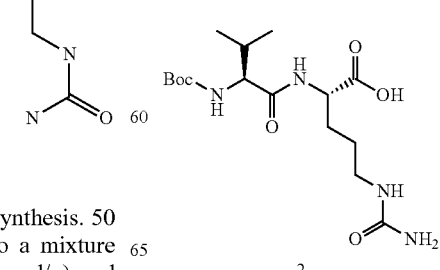

2

-continued

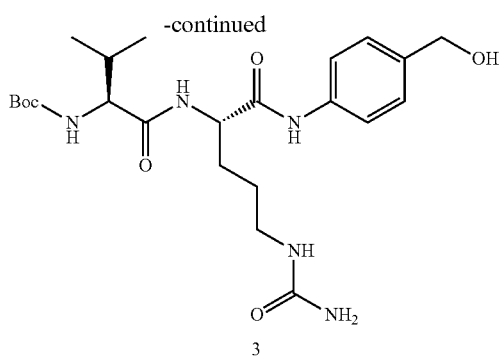

3

A solution of Compound 2 (4.00 g, 10.68 mmol, 1.00 eq) in DCM (40.00 mL) and MeOH (20.00 mL) was stirred at room temperature, then (4-aminophenyl)methanol (1.58 g, 12.82 mmol, 1.20 eq) and EEDQ (5.28 g, 21.37 mmol, 2.00 eq) were added and the mixture stirred in the dark for 9 hrs. TLC (dichloromethane/methanol=5/1, Rf=0.56) indicated one new spot had formed. The reaction mixture was concentrated under reduced pressure to remove solvent. The resulting residue was purified by flash silica gel chromatography (ISCO®; 120 g SepaFlash® Silica Flash Column, Eluent of 0~20% MeOH/DCM @ 80 mL/min). Compound 3 (3.00 g, 6.26 mmol, 58.57% yield) was obtained as a white solid.

| LCMS (ESI): | m/z 480.1 [M + H]+ |
|---|---|
| Molecular weight | 479.58 |

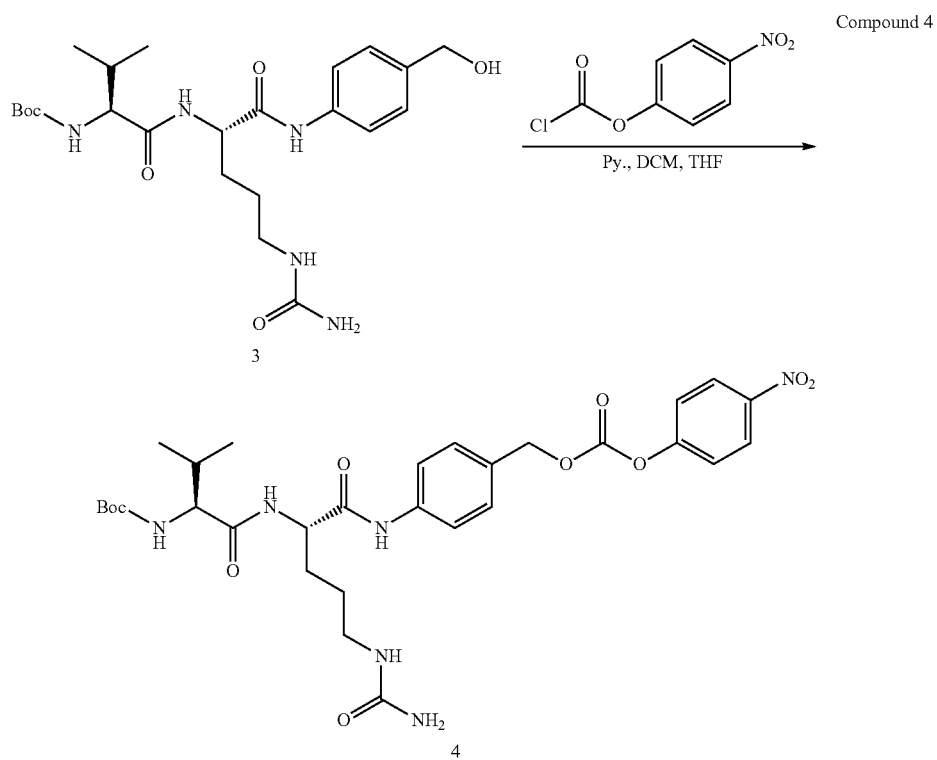

To a solution of Compound 3 (3.00 g, 6.26 mmol, 1.00 eq) in anhydrous THF (35.00 mL) and anhydrous DCM (15.00 mL) was added (4-nitrophenyl) chloroformate (6.31 g, 31.30 mmol, 5.00 eq) and pyridine (2.48 g, 31.30 mmol, 2.53 mL, 5.00 eq), and the mixture was stirred at 25° C. for 5 hrs. TLC (dichloromethane/methanol=10/1, Rf=0.55) indicated a new spot had formed. The reaction mixture was filtered, and the filtrate was concentrated under reduced pressure to give a residue. The residue was purified by flash silica gel chromatography (ISCO®; 120 g SepaFlash® Silica Flash Column, Eluent of 0~10% DCM/MeOH© 80 mL/min). Compound 4 (2.00 g, 3.10 mmol, 49.56% yield) was obtained as a white solid.

| LCMS (ESI): | m/z 667.3 [M + Na]+ |
|---|---|
| Molecular weight | 644.68 |

Compound 5

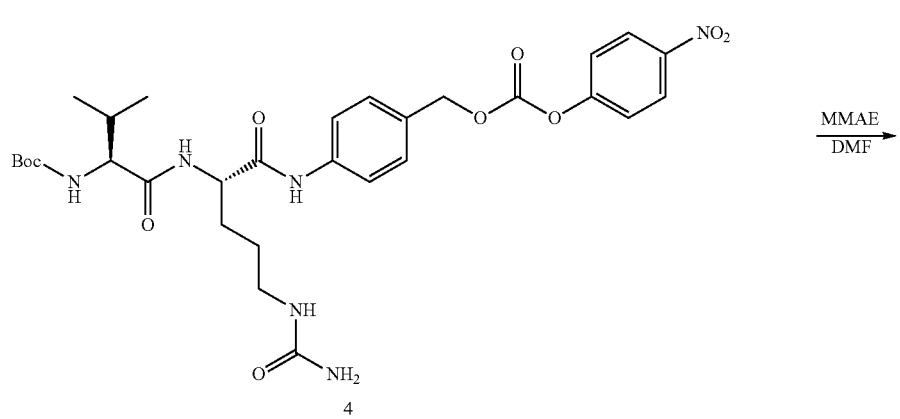

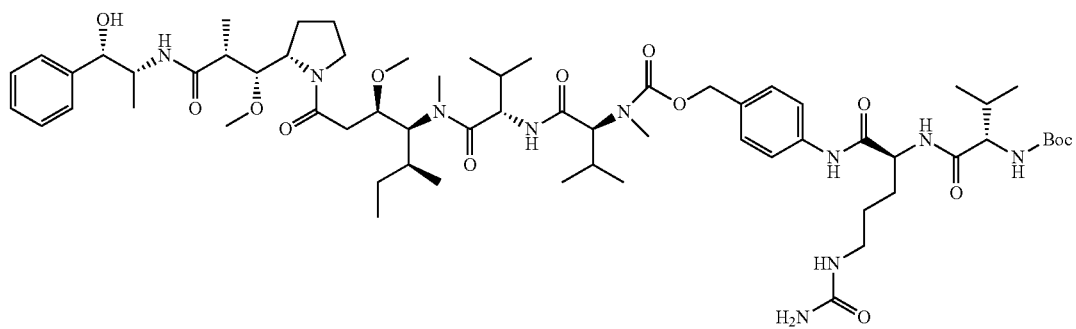

A mixture of Compound 4 (278.43 mg, 387.80 μmol, 1.00 eq) and DIEA (501.19 mg, 3.88 mmol, 677.29 μL, 10.00 eq) in DMF (5.00 mL) was stirred under nitrogen for 10 min. MMAE (250.00 mg, 387.80 μmol, 1.00 eq) and HOBt (52.40 mg, 387.80 μmol, 1.00 eq) were added and the mixture was stirred at 0° C. under nitrogen for 20 min and stirred at 30° C. for additional 18 hrs. LC-MS showed one main peak with desired mass was detected. The resulting mixture was purified by flash C18 gel chromatography (ISCO®; 130 g SepaFlash® C18 Flash Column, Eluent of 0~50% MeCN/H₂O @ 75 mL/min). Compound 5 (190.00 mg, 155.29 μmol, 40.04% yield) was obtained as a white solid.

| LCMS (ESI): | m/z 1223.4 [M + H]⁺ |
|---|---|
| Molecular weight | 1223.57 |

Compound 6

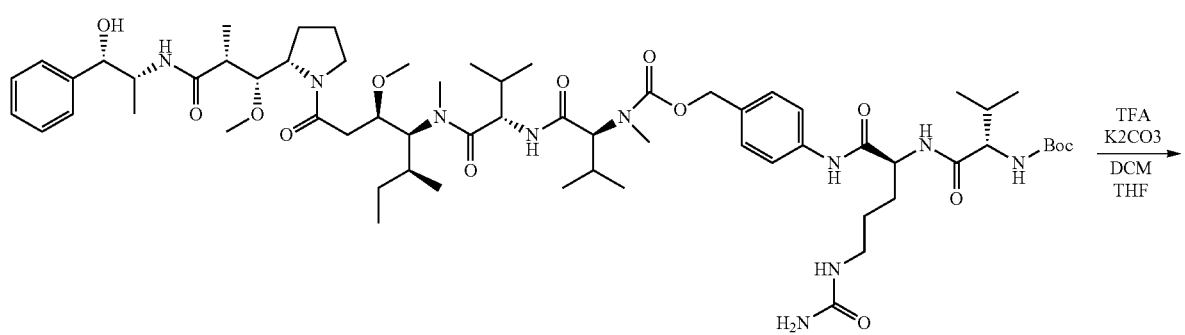

-continued

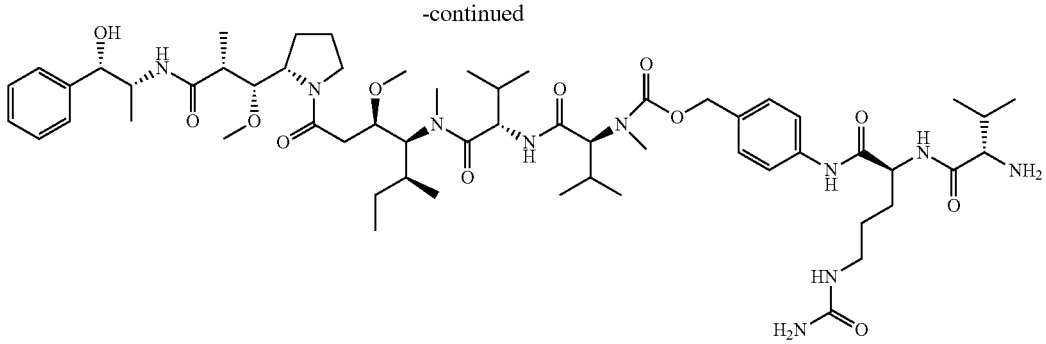

6

To a solution of Compound 5 (170.00 mg, 138.94 μmol, 1.00 eq) in DCM (2.70 mL) was added 2,2,2-trifluoroacetic acid (413.32 mg, 3.62 mmol, 268.39 μL, 26.09 eq), and the mixture was stirred at 25° C. for 1 hr. LC-MS showed Compound 5 was consumed completely. The mixture was concentrated under reduced pressure to give a residue. The residue was dissolved in THF (10.00 mL) and was added K$_2$CO$_3$ (192.03 mg, 1.39 mmol, 10.00 eq), the mixture was stirred at room temperature for additional 3 hrs. LC-MS showed one main peak with desired mass was detected. The resulting reaction mixture was concentrated under reduced pressure to remove solvent to give a residue. The residue was purified by flash C18 gel chromatography (ISCO®; 130 g SepaFlash® C18 Flash Column, Eluent of 0-50% MeCN/H$_2$O @ 75 mL/min). Compound 6 (110.00 mg, 97.92 μmol, 70.48% yield) was obtained as a white solid.

| LCMS (ESI): | m/z 1123.4 [M + H]$^+$ |
|---|---|
| Molecular weight | 1123.45 |

Compound 7

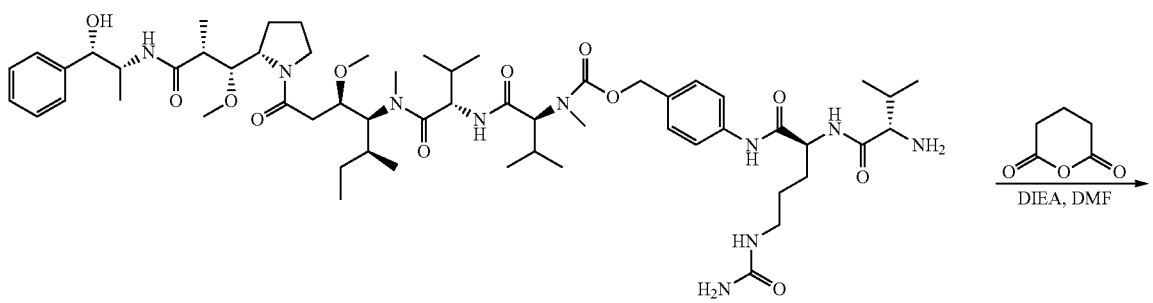

6

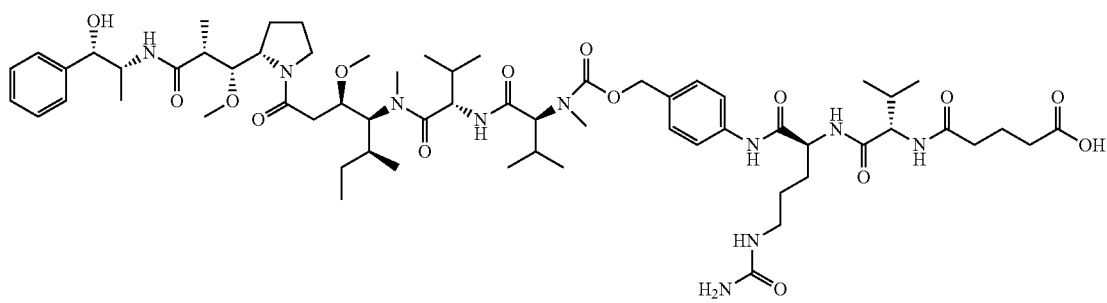

7

121

To a solution of Compound 6 (110.00 mg, 97.92 µmol, 1.00 eq) in DMA (5 mL), DIEA (25.31 mg, 195.83 µmol. 34.20 µL, 2.00 eq) and tetrahydropyran-2,6-dione (22.34 mg, 195.83 µmol, 2.00 eq). The mixture was stirred at room temperature for 18 hrs. LC-MS showed Compound 6 was consumed completely and one main peak with desired mass was detected. The reaction mixture was purified by flash C18 gel chromatography (ISCO®; 130 g SepaFlash® C18 Flash Column, Eluent of 0~50% MeCN/H$_2$O @ 75 mL/min). Compound 7 (100.00 mg, 80.81 µmol, 82.53% yield) was obtained as a white solid.

| LCMS (ESI): | m/z 1237.4 [M + H]$^+$ |
|---|---|
| Molecular weight | 1236.74 |

122

To a solution of Compound 7 (100.00 mg, 80.81 µmol, 1.00 eq) in DMA (4.5 mL) and DCM (1.5 mL) was added 1-hydroxypyrrolidine-2,5-dione (27.90 mg, 242.42 µmol, 3.00 eq) under N$_2$, the mixture was stirred at 0° C. for 30 min. EDCI (46.47 mg, 242.43 µmol, 3.00 eq) was added in the mixture, and the mixture was stirred at 25° C. for additional 16 hrs. LC-MS showed Compound 7 was consumed completely and one main peak with desired mass was detected. The reaction mixture was purified by flash C18 gel chromatography (ISCO®; 130 g SepaFlash® C18 Flash Column, Eluent of 0~50% MeCN/H$_2$O @ 75 mL/min). Compound 8 (90.00 mg, 60.69 µmol, 75.11% yield) was obtained as a white solid.

| LCMS (ESI): | m/z 1334.5 [M + H]$^+$ |
|---|---|
| Molecular weight | 1334.62 |

Compound 8 (MMAE-PABC-Cit-Val-Glutarate-NHS)

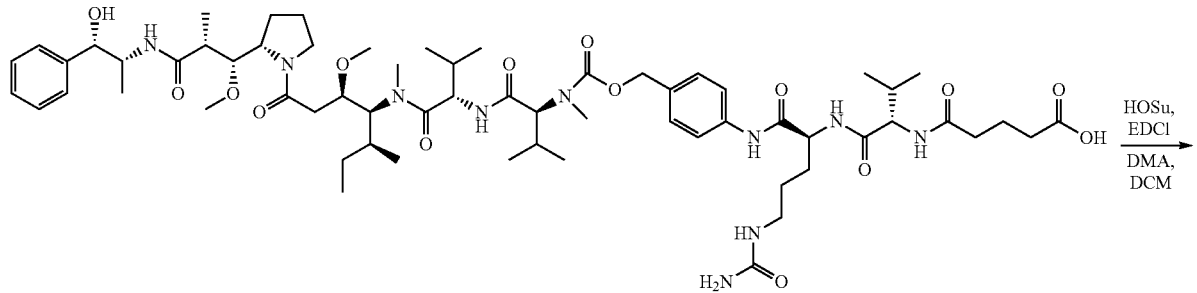

7

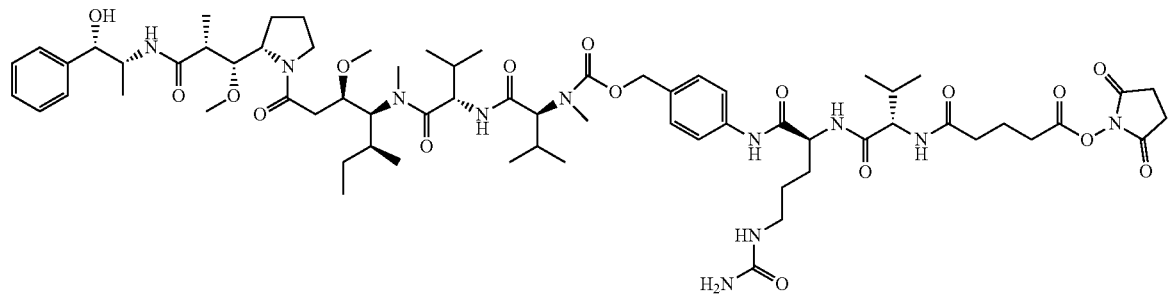

8

General Procedure for Coupling MMAE-PABC-Cit-Val-Glutarate-NHS with Targeting Bicycles To a solution of Bicycle (1.0-1.3 eq) in DMA was added DIEA (3 eq) and MMAE-PABC-Cit-Val-Glutarate-NHS (1 eq). The mixture was stirred at 25° C. for 18 hr. The reaction was monitored by LC-MS and once complete, was directly purified by preparative HPLC.

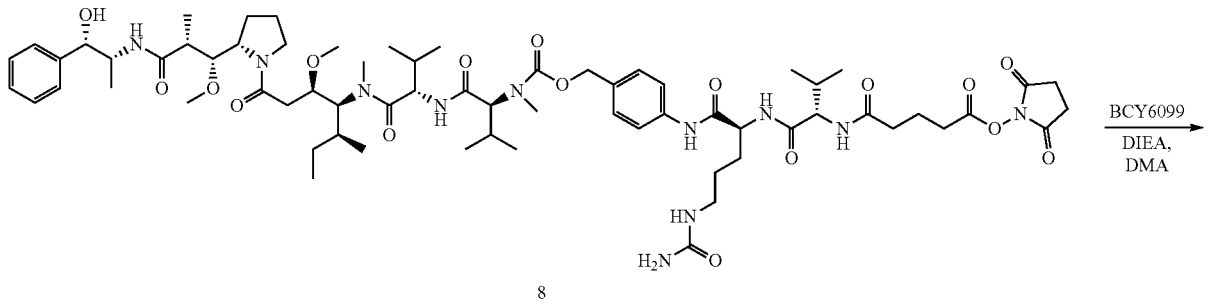

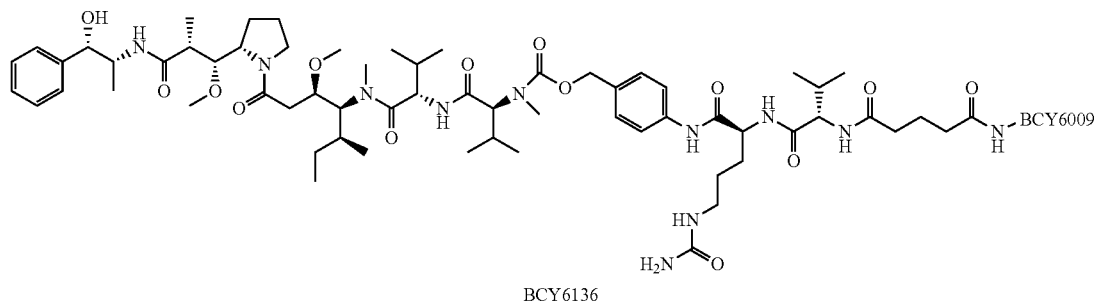

BCY6099 (71.5 mg, 22.48 μmol) was used as the bicycle reagent. Compound BCY6136 (40.9 mg, 9.05 μmol, 40.27% yield, 97.42% purity) was obtained as a white solid.

| BCY6136 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

| -continued | |
|---|---|
| BCY6136 Analytical Data | |
| Method: | 28-68% B over 30 minutes, then 3 min 95% B |
| Retention Time: | 11.35 min |
| LCMS (ESI): | m/z 1468.1 [M + 3H]$^{3+}$, 1101.2 [M + 4H]$^{4+}$, 881.3 [M + 5H]$^{5+}$ |
| Peptide mw | 4404.2 |

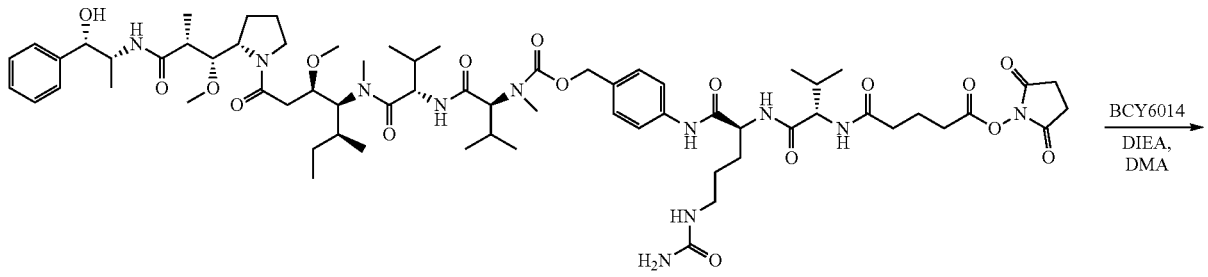

-continued

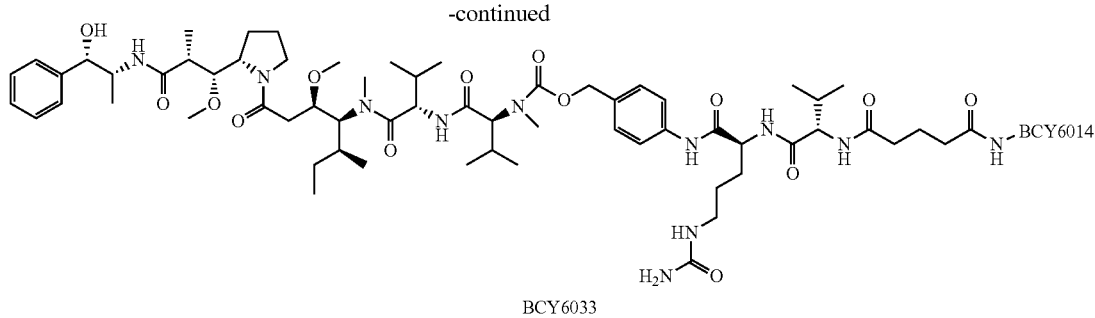

BCY6033

BCY6014 (70.00 mg, 22.47 μmol, 1.00 eq) was used as the bicycle reagent. Compound BCY6033 (33.90 mg, 7.96 μmol, 34.57% yield) was obtained as a white solid.

| BCY6033 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 35-65% B over 20 minutes, then 3 min 95% B |
| Retention Time: | 7.47 min |
| LCMS (ESI): | m/z 1065.2 [M + 4H]$^{4+}$, 852.2 [M + 5H]$^{5+}$ |
| Peptide mw | 4259.04 |

BCY6009 (70.0 mg, 22.47 μmol, 1 eq) was used as the bicycle reagent. Compound BCY6029 (32.9 mg, 7.75 μmol, 33.49% yield) was obtained as a white solid.

| BCY6029 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150*4.6 mm |
| Instrument: | Agilent 1200 HPLC-BE(1-614) |
| Method: | 35-65% B over 20 minutes, then 3 min 95% B |
| Retention Time: | 7.46 min |
| LCMS (ESI): | m/z 1061.7 [M + 4H]$^{4+}$ |
| Peptide mw | 4245.02 |

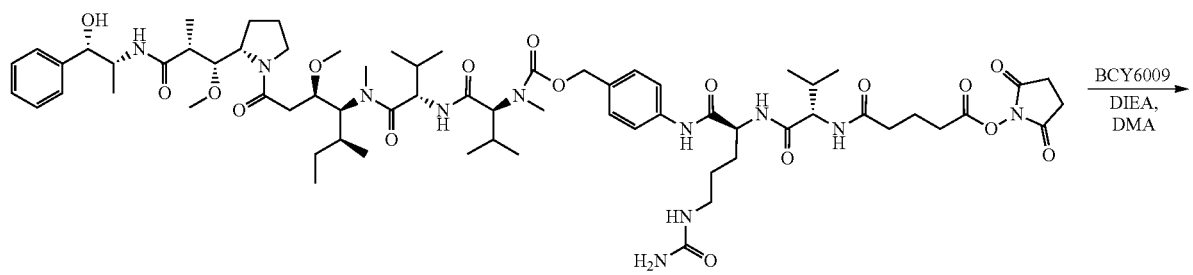

BCY6029

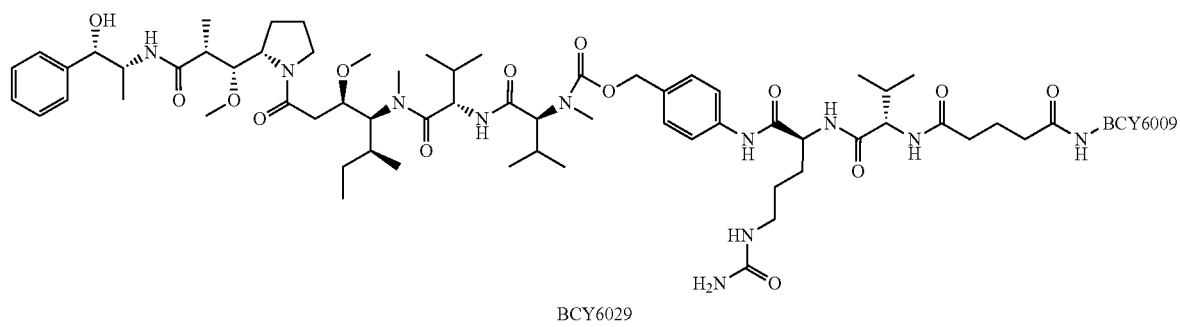

BCY6029

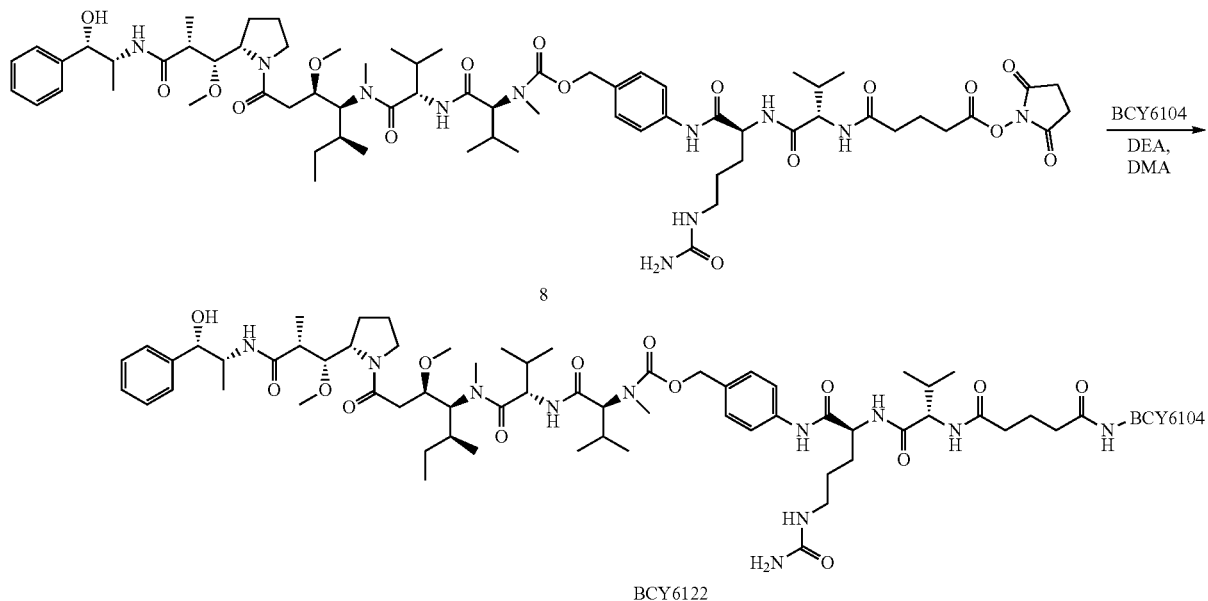
BCY6104 (71.59 mg, 22.48 μmol, 1.00 eq) was used as the bicycle reagent. Compound BCY6122 (38.30 mg, 8.57 μmol, 38.14% yield, 98.58% purity) was obtained as a white solid.
| BCY6122 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| -continued | |
|---|---|
| BCY6122 Analytical Data | |
| Instrument: | Agilent 1200 HPLC-BE(1-614) |
| Method: | 28-68% B over 30 minutes, then 3 min 95% B |
| Retention Time: | 10.72 min |
| LCMS (ESI): | m/z 1101.8 [M + 4H]$^{4+}$, 881.5 [M + 5H]$^{5+}$ |
| Peptide mw | 4406.18 |
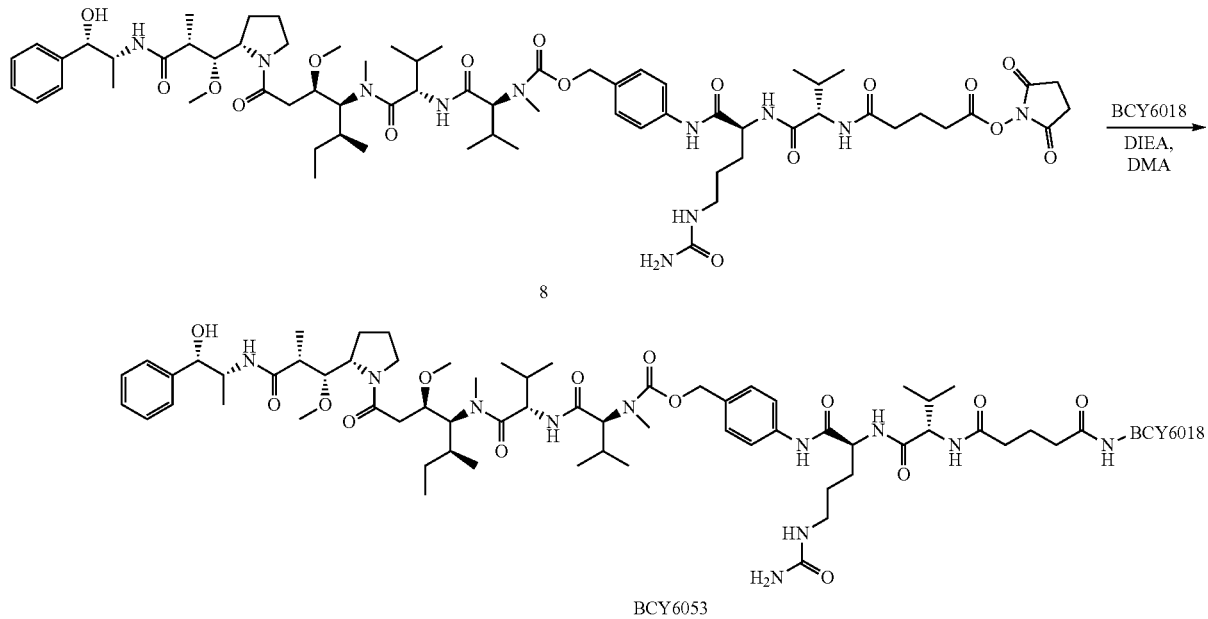

BCY6018 (72.40 mg, 26.97 µmol, 1.2 eq) was used as the bicycle reagent. Compound BCY6053 (38.3 mg, 9.81 µmol, 43.65% yield) was obtained as a white solid.

| BCY6053 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 12.95 min |
| LCMS (ESI): | m/z 1301.7 $[M + 3H]^{3+}$, 976.5 $[M + 4H]^{4+}$ |
| Peptide mw | 3905.67 |

BCY6017 (50.75 mg, 22.48 µmol, 1.2 eq) was used as the bicycle reagent. Compound BCY6049 (22.5 mg, 6.47 µmol, 34.54% yield) was obtained as a white solid.

| BCY6049 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 14.28 min |
| LCMS (ESI): | m/z 1159.6 $[M + 3H]^{3+}$, 869.8 $[M + 4H]^{4+}$ |
| Peptide mw | 3479.2 |

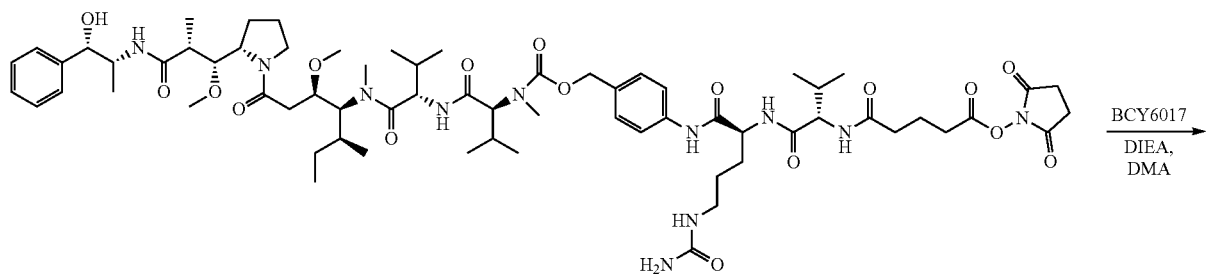

8

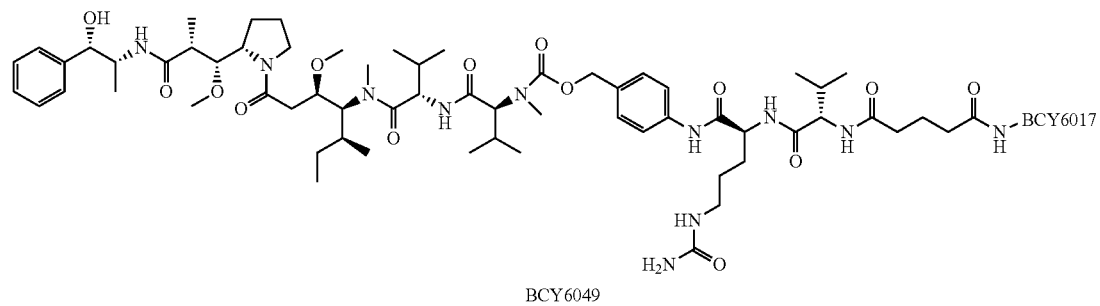

BCY6049

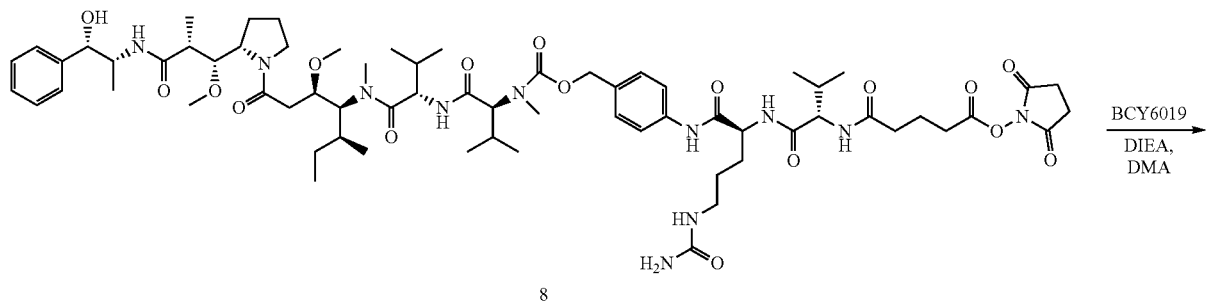

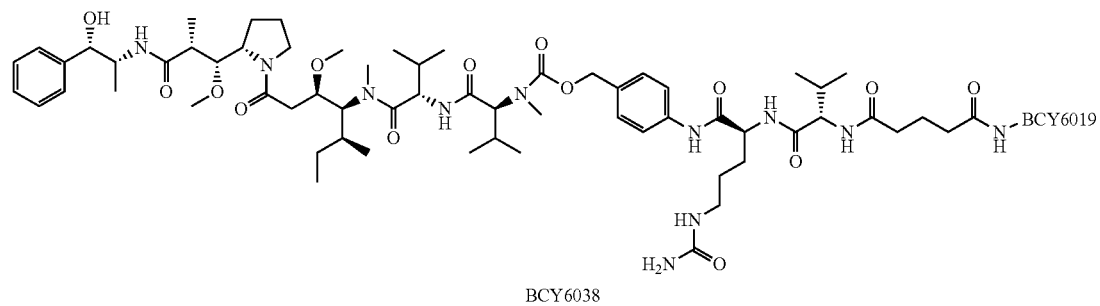

BCY6019 (65.00 mg, 22.47 μmol, 1.00 eq) was used as the bicycle reagent. Compound BCY6037 (26.80 mg, 6.66 μmol, 28.74% yield) was obtained as a white solid.

| BCY6037 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6037 Analytical Data | |
|---|---|
| Method: | 35-65% B over 20 minutes, then 3 min 95% B |
| Retention Time: | 8.79 min |
| LCMS (ESI): | m/z 1342.1 [M + 3H]$^{3+}$, 1006.6 [M + 4H]$^{4+}$ |
| Peptide mw | 4025.84 |

Trp-Cit-MMAE Series
Trp-Cit-MMAE Linker

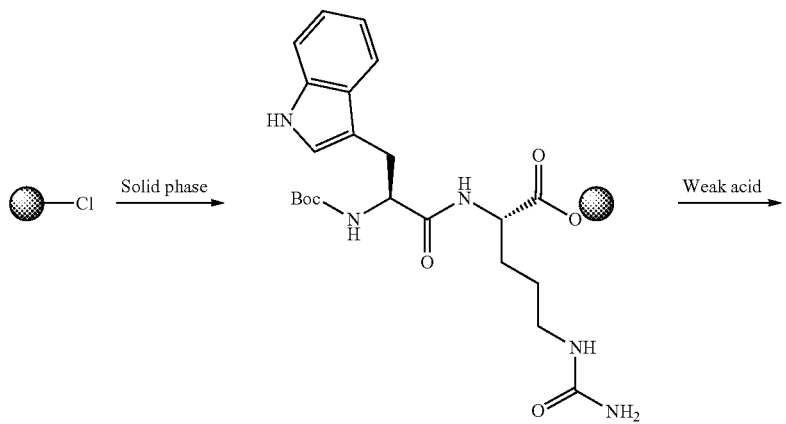

133                                          134
-continued
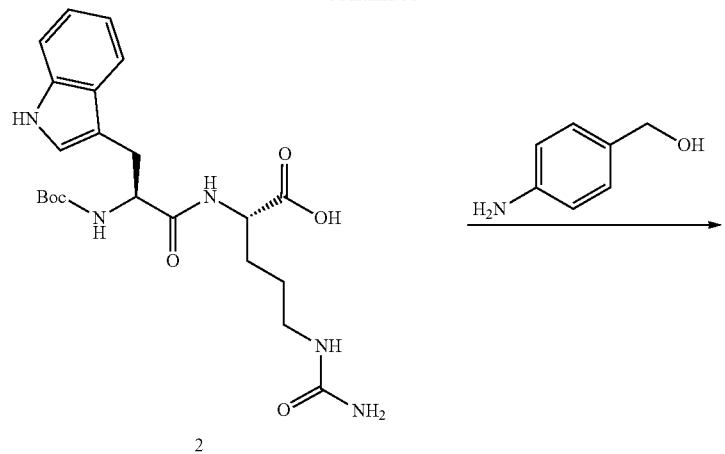
2
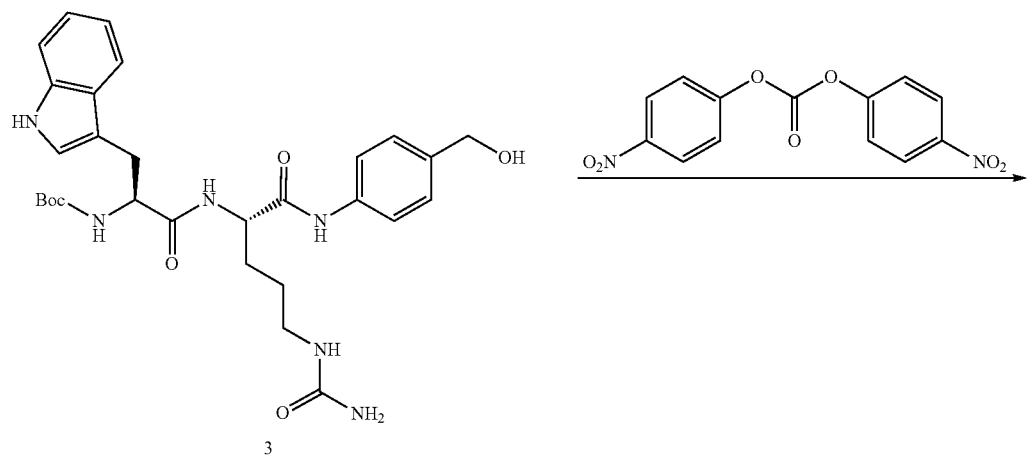
3
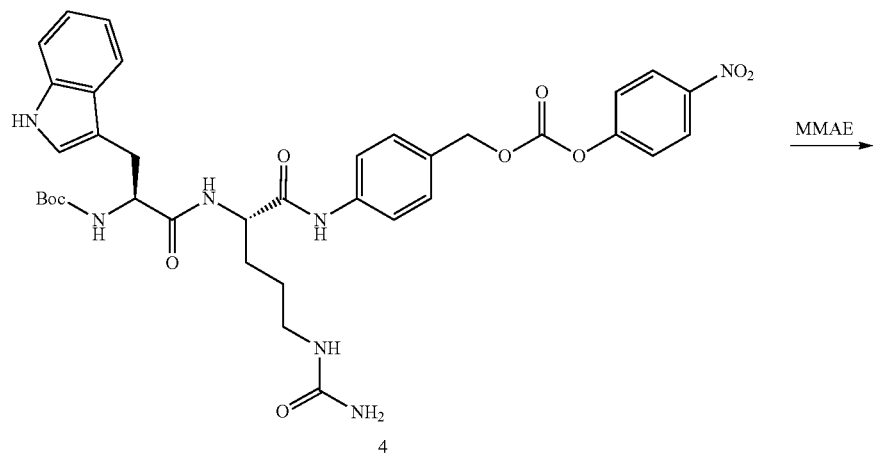
4

-continued
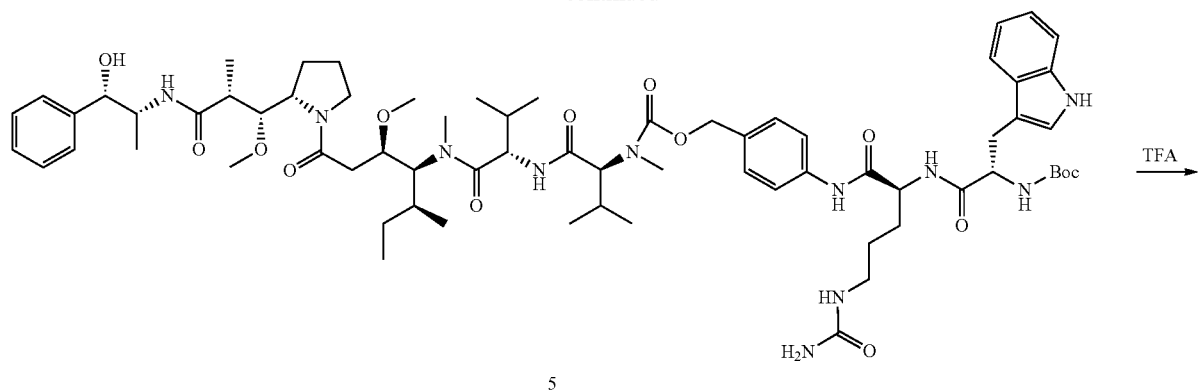
5
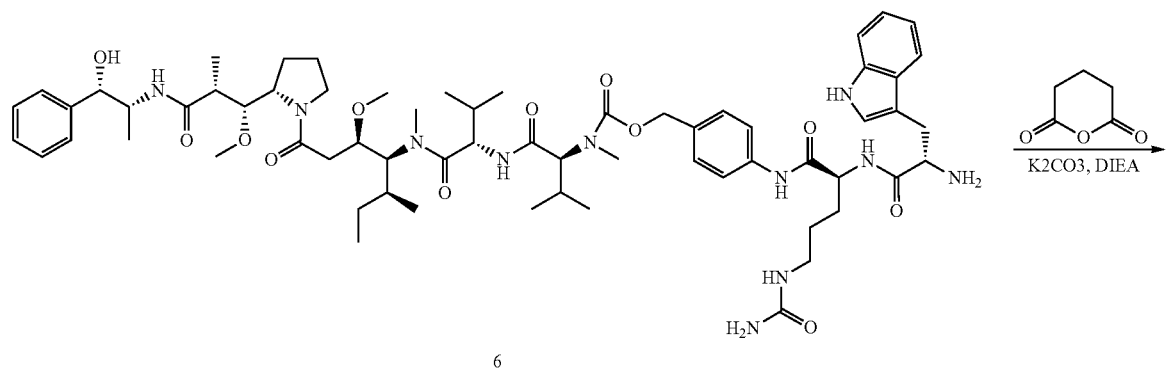
6
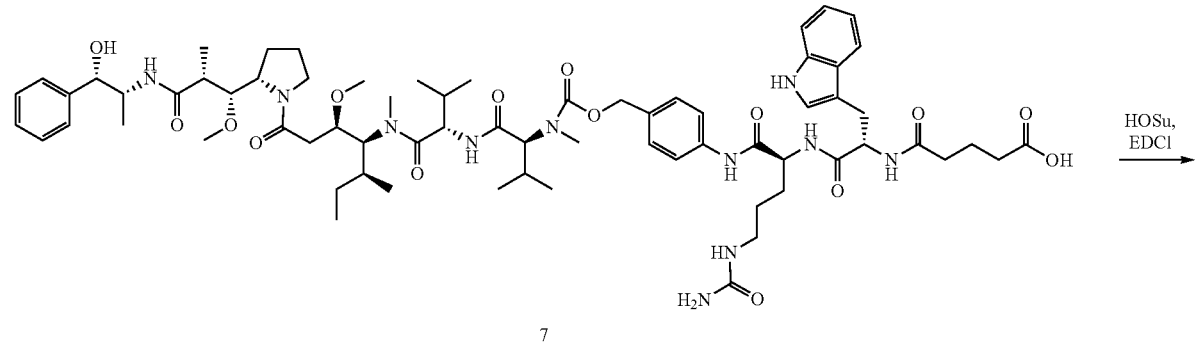
7
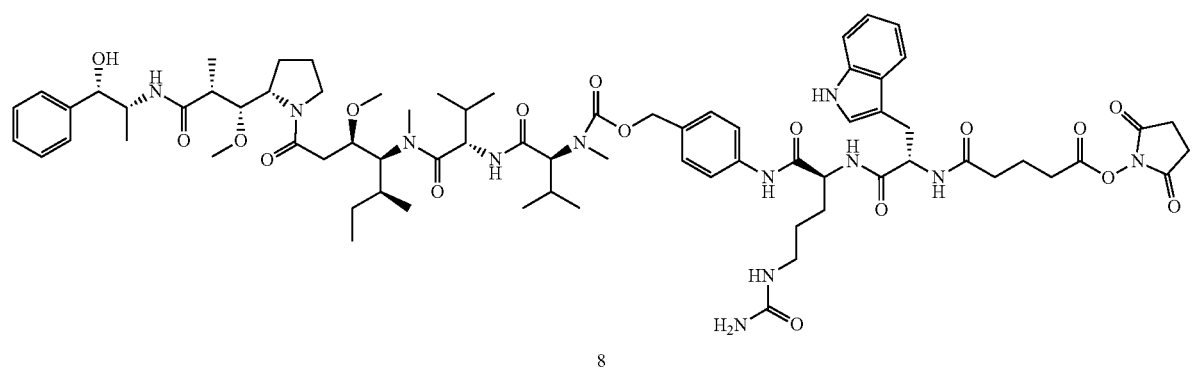
8

General Procedure for Preparation of 3

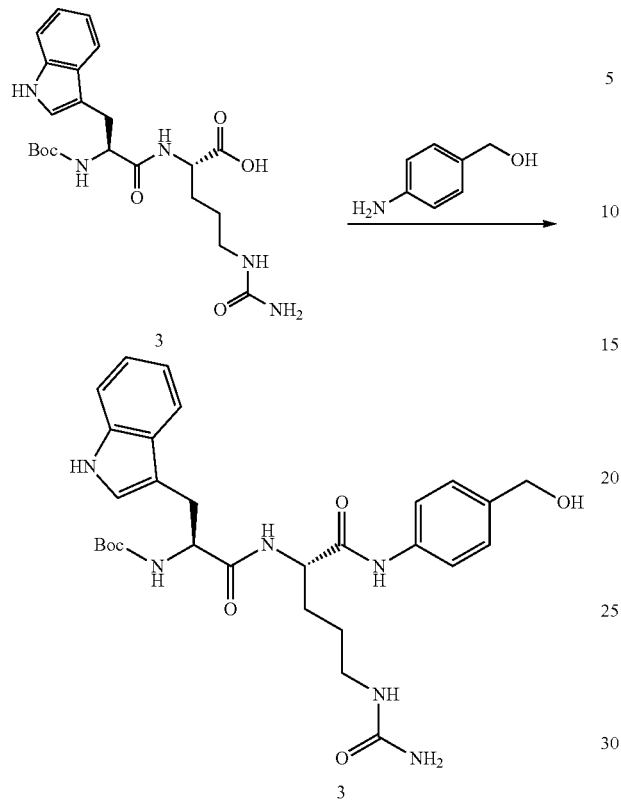

To a solution of compound 2 (4.00 g, 8.67 mmol, 1.00 eq), DIC (1.61 g, 12.78 mmol, 1.97 mL, 9.00 eq) and HOBt (10.54 g, 78.00 mmol, 9.00 eq) in DMF (30.00 mL) was added (4-aminophenyl)methanol (9.61 g, 78.00 mmol, 9.00 eq). The mixture was stirred at 15° C. for 1 hour. LC-MS showed compound 2 was consumed completely and one main peak with desired MS was detected. The mixture was purified by prep-HPLC. Compound 3 (4.20 g, 7.41 mmol, 85.49% yield) was obtained as a white solid.

| LCMS (ESI): | m/z 566.9 [M + H]$^+$ |
|---|---|
| Molecular weight | 566.66 |

General Procedure for Preparation of 4

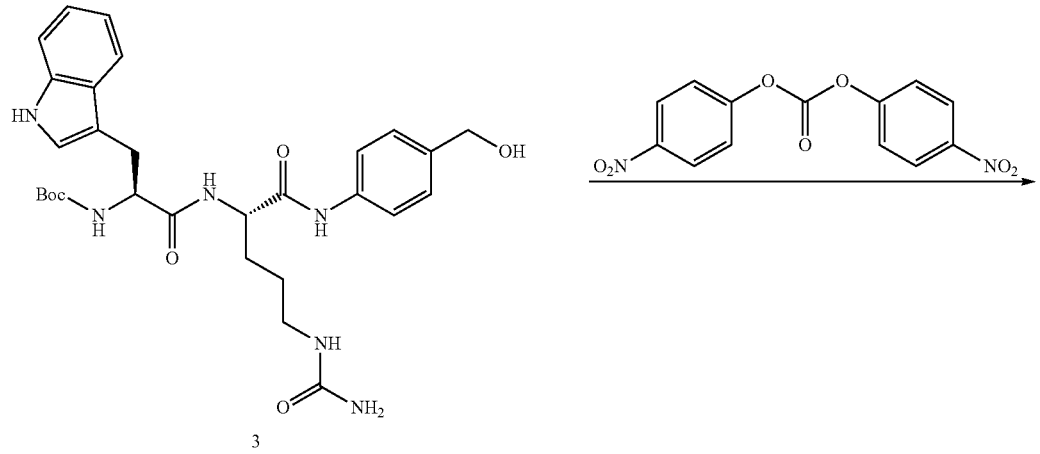

-continued

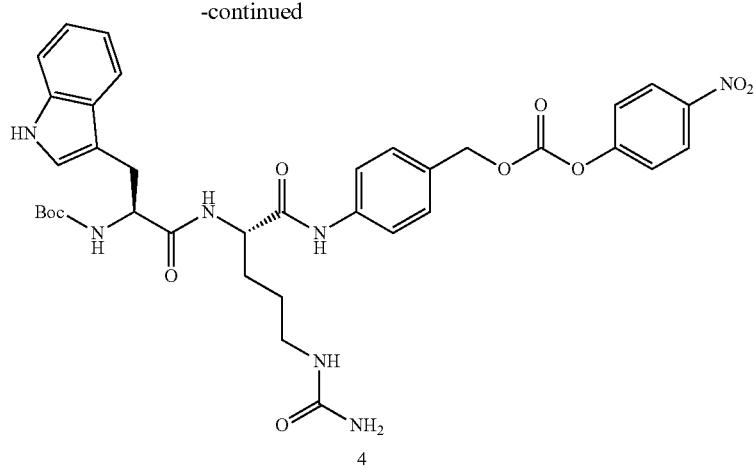

4

To a solution of compound 3 (4.20 g, 6.30 mmol, 1.00 eq), DIPEA (1.09 g, 8.40 mmol, 1.47 mL, 7.00 eq) in DMF (30.00 mL) was added bis(4-nitrophenyl) carbonate (11.50 g, 37.79 mmol, 6.00 eq) in one part. The mixture was stirred at 0-15° C. for 1.5 hour. LC-MS showed compound 3 was consumed completely and one main peak with desired MS was detected. Directly purified by prep-HPLC (TFA condition). Compound 4 (2.00 g, 2.40 mmol, 38.16% yield) was obtained as a white solid.

| LCMS (ESI): | m/z 732.0 [M + H]$^+$ |
| Molecular weight | 731.76 |

General Procedure for Preparation of 5

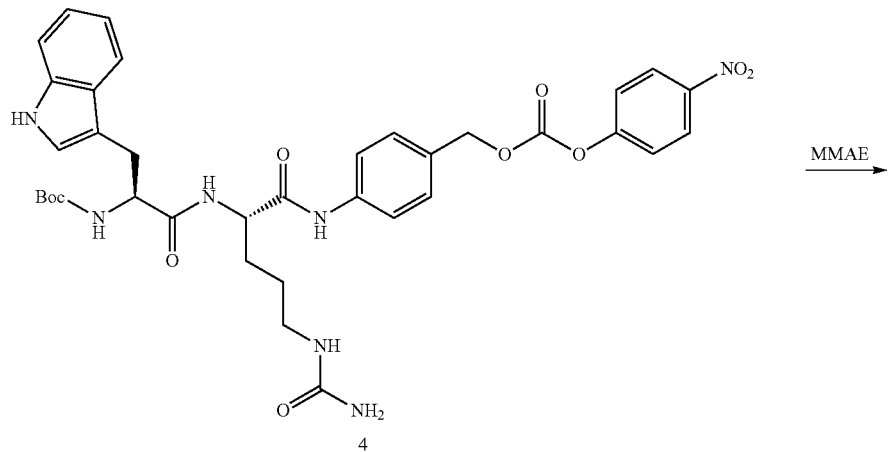

4

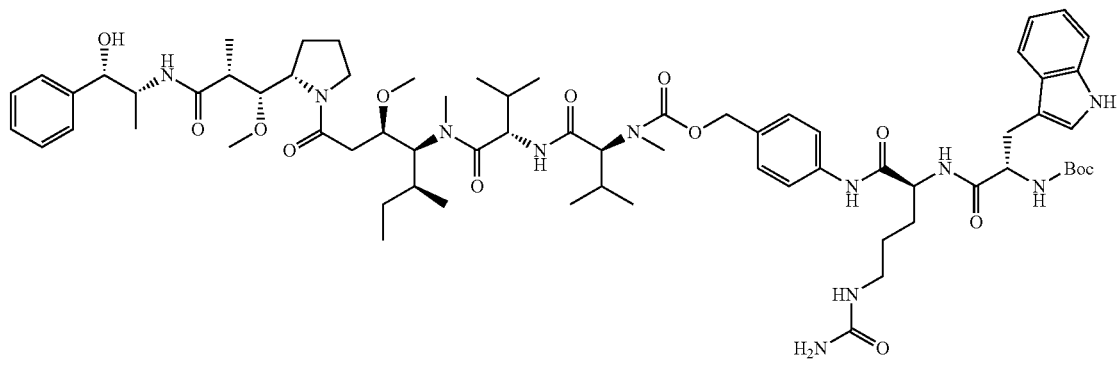

5

To a solution of compound 4 (300.00 mg, 360.63 μmol, 1.00 eq), DIEA (93.22 mg, 721.27 μmol, 125.97 μL, 3.00 eq) in DMF (10.00 mL) was added MMAE (233.03 mg, 324.57 μmol, 0.90 eq) and HOBt (48.73 mg, 360.63 μmol, 1.00 eq) at 0° C. The mixture was stirred at 30° C. for 18 hour. LC-MS showed compound 4 was consumed completely and one main peak with desired MS was detected. Directly purified by prep-HPLC (neutral condition). Compound 5 (250.00 mg, 190.75 μmol, 52.89% yield) was obtained as a yellow solid.

| LCMS (ESI): | m/z 1310.5 [M + H]+ |
|---|---|
| Molecular weight | 1310.65 |

General Procedure for Preparation of 6

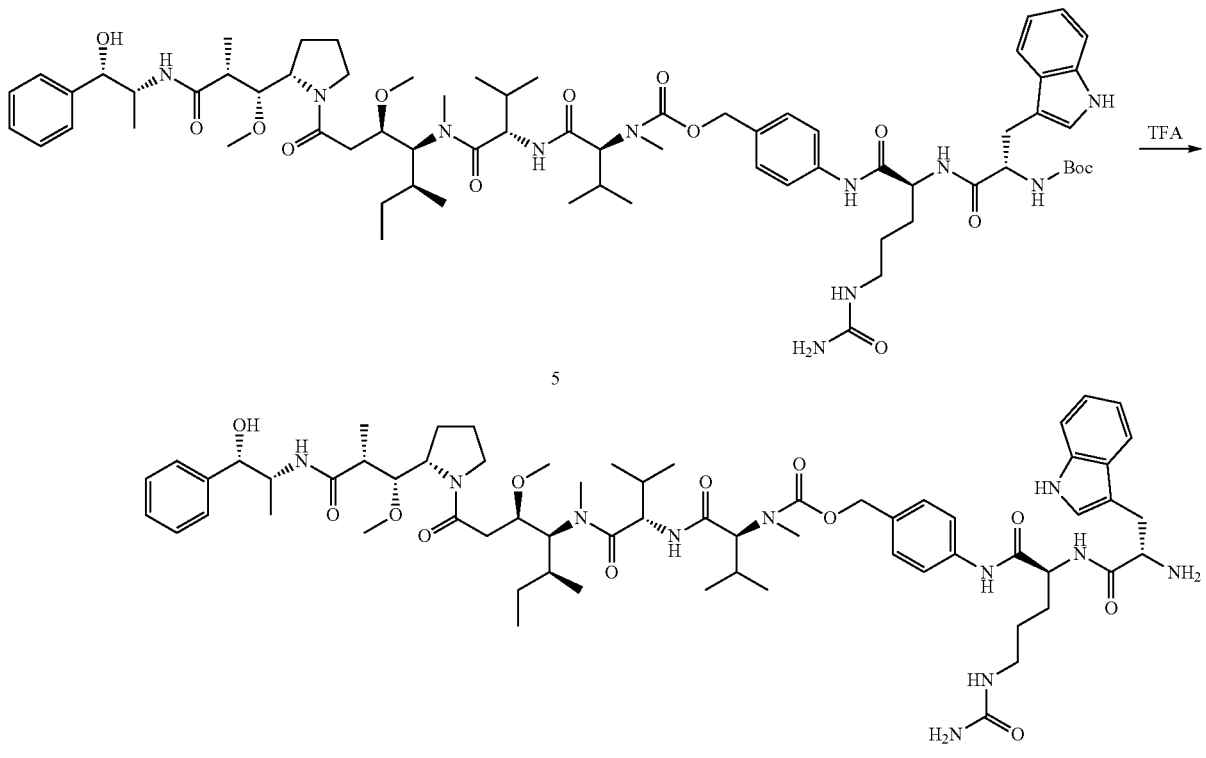

To a solution of compound 5 (240.00 mg, 183.12 μmol, 1.00 eq) in DCM (10.00 mL) was added TFA (1.54 g, 13.51 mmol, 1.00 mL, 73.76 eq). The mixture was stirred at 15° C. for 2 hour. And the mixture was concentrated under reduced pressure to remove solvent to give a residue, the residue was dissolved in THF and added $K_2CO_3$ and stirred at 15° C. for 2 h. LC-MS showed compound 5 was consumed completely and one main peak with desired MS was detected. The reaction mixture was concentrated under reduced pressure to remove solvent to give a residue. The residue was purified by prep-HPLC (neutral condition). The crude product 6 (125.00 mg, 94.37 μmol, 51.53% yield, TFA) was used into the next step without further purification.

| LCMS (ESI): | m/z 1210.4 [M + H]+ |
|---|---|
| Molecular weight | 1209.53 |

General Procedure for Preparation of 7

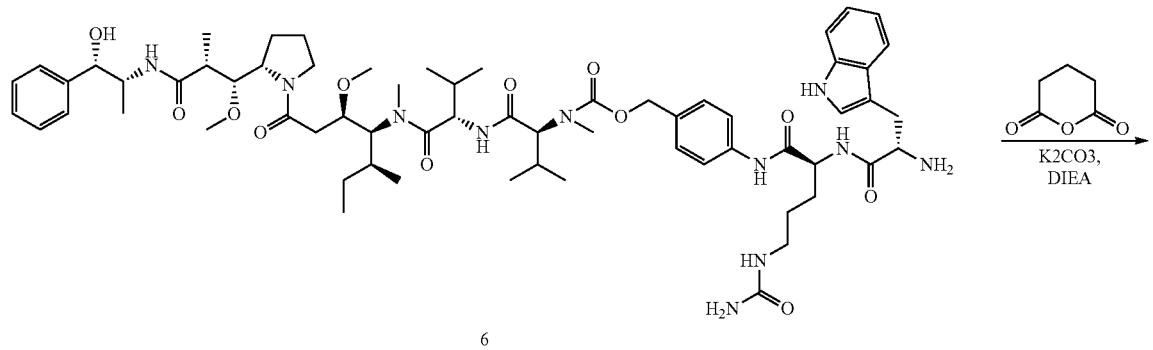

6

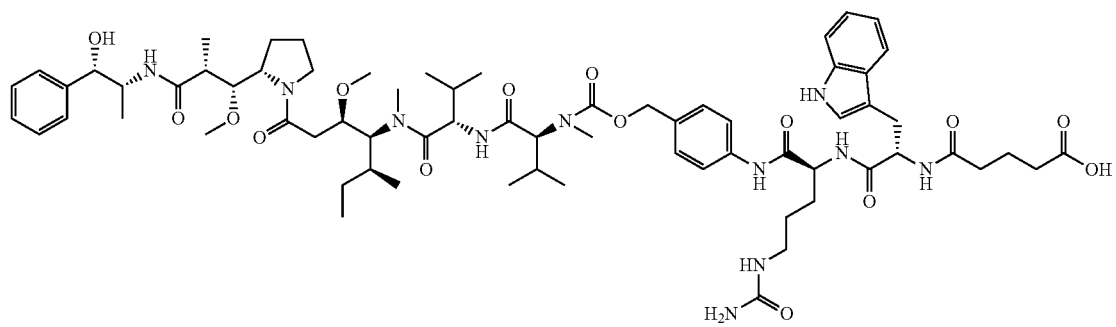

7

To a solution of compound 6 (125.00 mg, 94.37 µmol, 1.00 eq, TFA) in DMA (5.00 mL) was added DIEA (24.39 mg, 188.75 µmol, 32.96 µL, 2.00 eq), tetrahydropyran-2,6-dione (21.54 mg, 188.75 µmol, 2.00 eq). The mixture was stirred at 15° C. for 2 hour. LC-MS showed compound 6 was consumed completely and one main peak with desired MS was detected. Directly purified by prep-HPLC (neutral condition). Compound 7 (100.00 mg, 75.49 µmol, 80.00% yield) was obtained as a white solid.

| LCMS (ESI): | m/z 1324.5 [M + H]+ |
|---|---|
| Molecular weight | 1324.63 |

General Procedure for Preparation of 8 (MMAE-PABC-Cit-Trp-Glutarate-NHS)

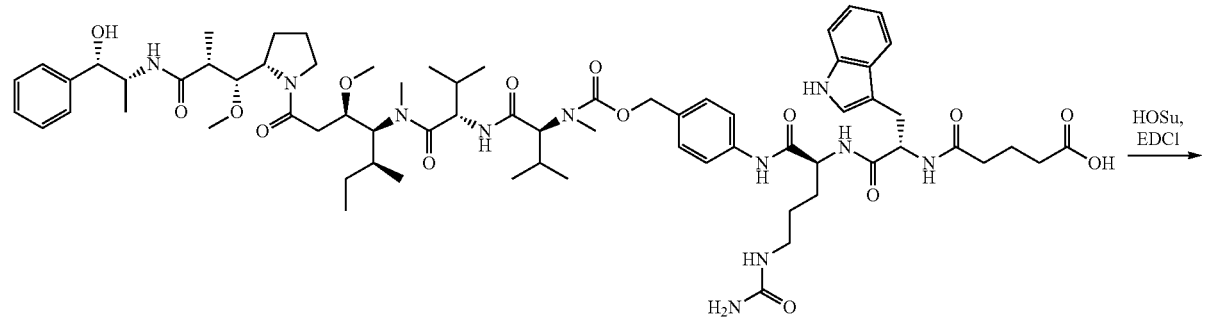

7

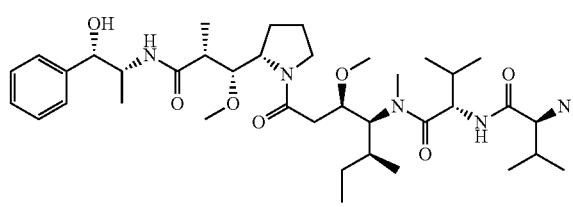

8

To a solution of compound 7 (100.00 mg, 75.49 µmol, 1.00 eq), 1-hydroxypyrrolidine-2, 5-dione (26.07 mg, 226.48 µmol, 3.00 eq) in DMA (3.00 mL) and DCM (1.00 mL) was added EDCI (43.42 mg, 226.48 µmol, 3.00 eq). The mixture was stirred at 15° C. for 4 hour. LC-MS showed compound 7 was consumed completely and one main peak with desired MS was detected. The DCM was removed. Directly was purified by prep-HPLC (neutral condition). Compound 8 (60.00 mg, 42.20 µmol, 55.91% yield) was obtained as a white solid.

| LCMS (ESI): | m/z 711.2 [M + 2H]$^{2+}$ |
|---|---|
| Molecular weight | 1421.7 |

General Procedure for Coupling MMAE-PABC-Cit-Trp-Glutarate-NHS with Targeting Bicycles To a solution of Bicycle (1.0-1.3 eq) in DMA was added DIEA (3 eq) and MMAE-PABC-Cit-Trp-Glutarate-NHS (1 eq). The mixture was stirred at 25° C. for 18 hr. The reaction was monitored by LC-MS and once complete, was directly purified by preparative HPLC.

BCY6030

BCY6009 (47.29 mg, 14.07 µmol, 1.00 eq) was used as the bicycle reagent. Compound BCY6030 (0.0156 g, 3.51 µmol, 24.93% yield, 97.41% purity) was obtained as a white solid.

| BCY6030 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 35-65% B over 20 minutes, then 3 min 95% B |
| Retention Time: | 7.90 min |
| LCMS (ESI): | m/z 1083.7 [M + 4H]$^{4+}$ |
| Peptide mw | 4332.17 |

BCY6030

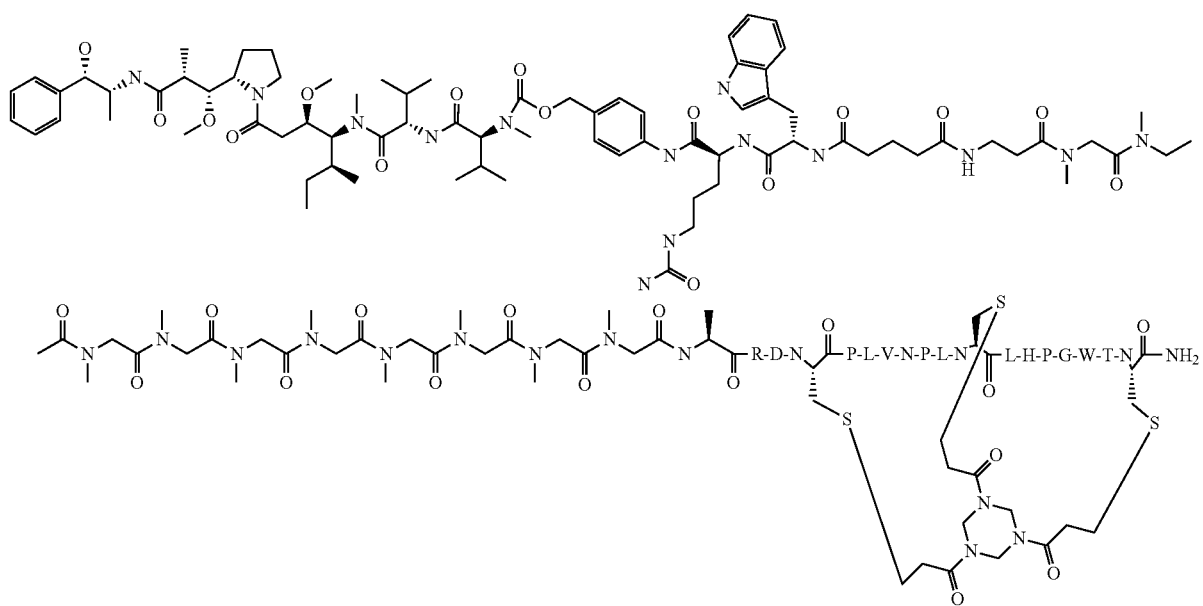

BCY6034

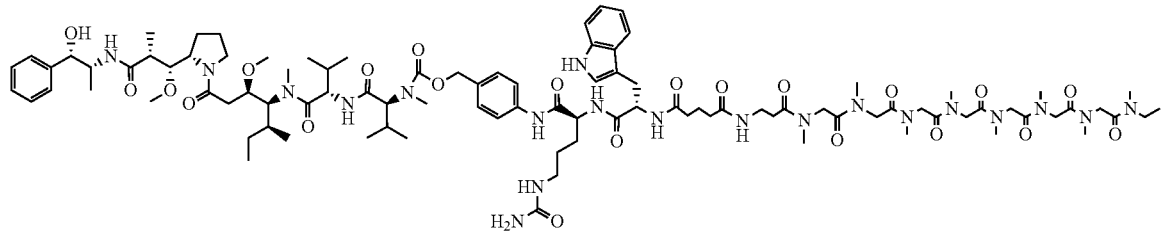

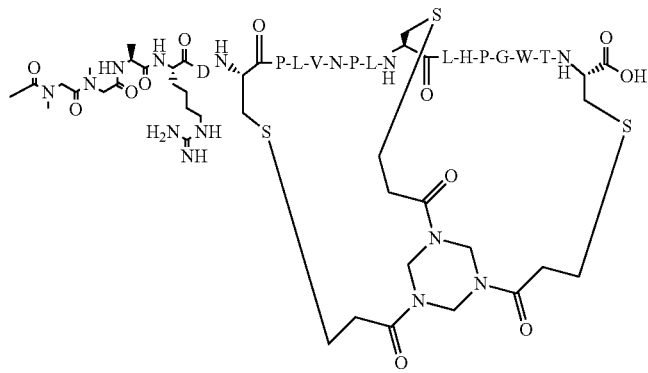

BCY6034

BCY6014 (88.21 mg, 23.21 μmol, 1.10 eq) was used as the bicycle reagent. Compound BCY6034 (27.70 mg, 6.05 μmol, 28.70% yield, 95.02% purity) was obtained as a white solid.

BCY6017 (57.17 mg, 25.32 μmol, 1.2 eq) was used as the bicycle reagent. Compound BCY6050 (0.0519 g, 14.56 μmol, 69.01% yield) was obtained as a white solid.

| BCY6034 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 30-60% B over 20 minutes, then 3 min 95% B |
| Retention Time: | 11.49 min |
| LCMS (ESI): | m/z 1449.3 $[M + 3H]^{3+}$, 1087.4 $[M + 4H]^{4+}$ |
| Peptide mw | 4346.13 |

| BCY6050 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 13.55 min |
| LCMS (ESI): | m/z 1188.5 $[M + 3H]^{3+}$, 891.7 $[M + 4H]^{4+}$ |
| Peptide mw | 3564.25 |

BCY6050

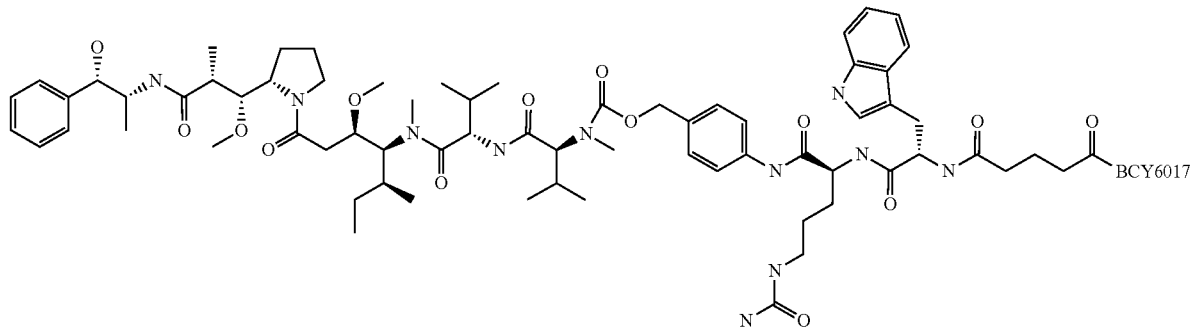

BCY6050

BCY6054

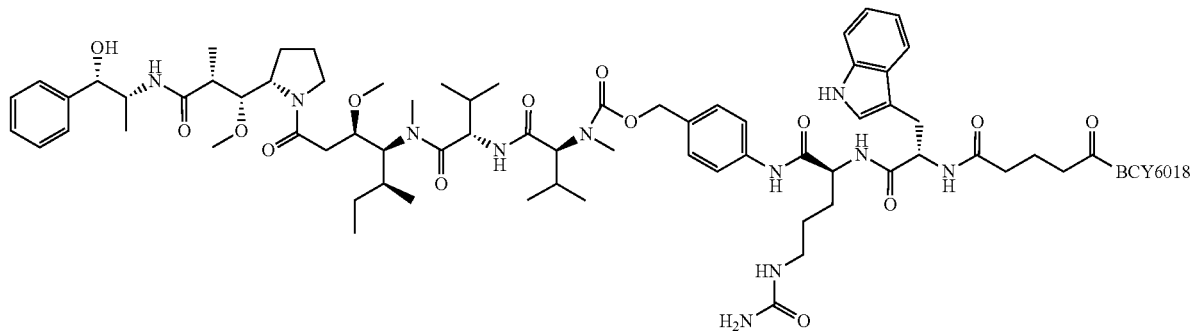

BCY6018 (67.97 mg, 25.32 μmol, 1.2 eq) was used as the bicycle reagent. Compound BCY6054 (40.10 mg, 10.05 μmol, 47.62% yield) was obtained as a white solid.

| BCY6054 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 13.73 min |
| LCMS (ESI): | m/z 1330.4 [M + 3H]$^{3+}$, 998.1 [M + 4H]$^{4+}$ |
| Peptide mw | 3990.72 |

BCY6019 (81.39 mg, 23.21 μmol, 1.10 eq) was used as the bicycle reagent. Compound BCY6038 (34.10 mg, 8.02 μmol, 38.00% yield, 96.68% purity) was obtained as a white solid.

| BCY6038 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 35-65% B over 20 minutes, then 3 min 95% B |
| Retention Time: | 9.56 min |
| LCMS (ESI): | m/z 1371.0 [M + 3H]$^{3+}$, 1028.3 [M + 4H]$^{4+}$ |
| Peptide mw | 4111.9 |

BCY6038

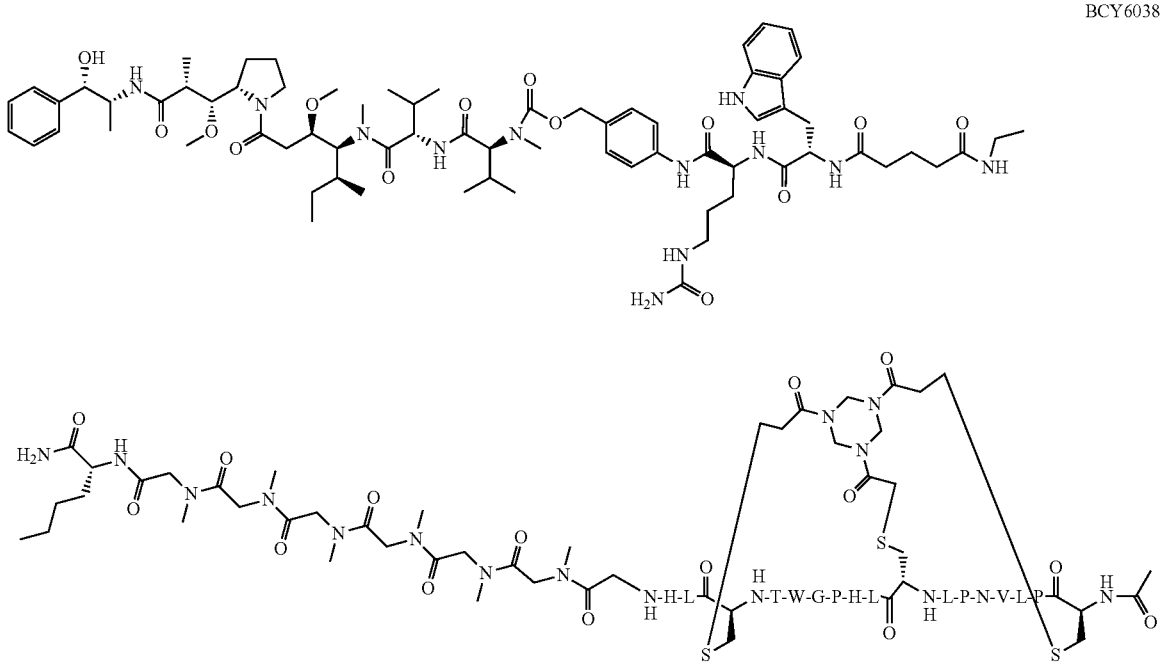

Val-Lys-MMAE Series
Val-Lys-MMAE Linker
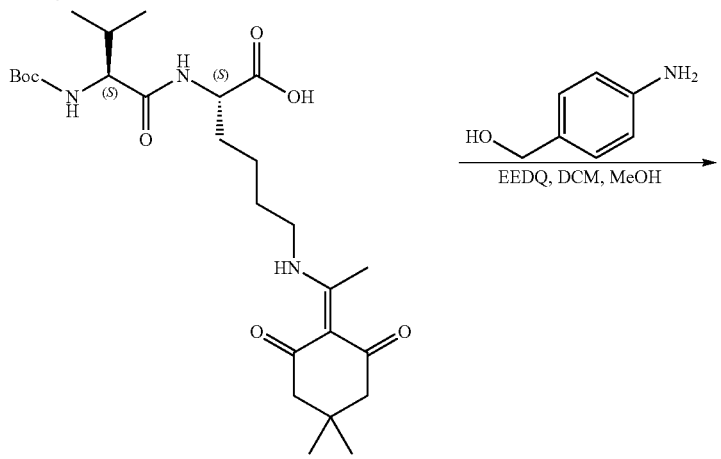
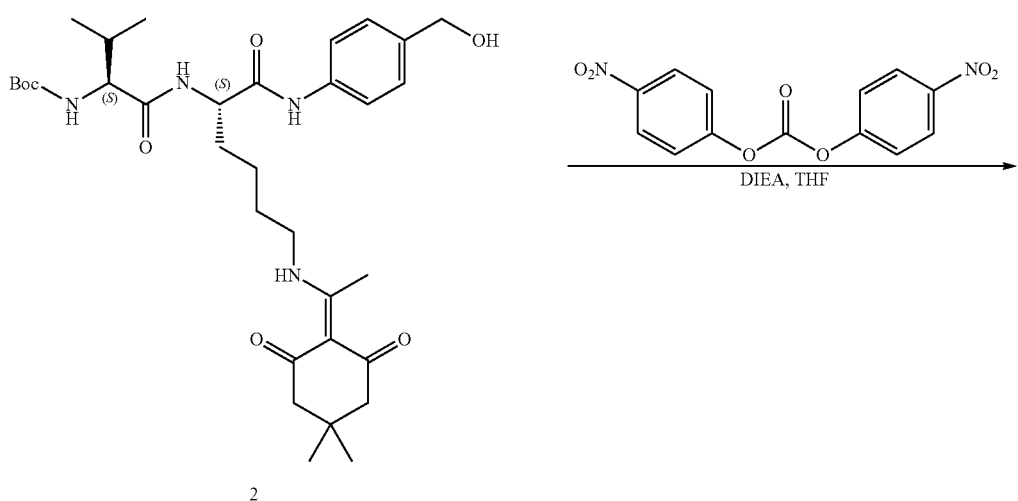
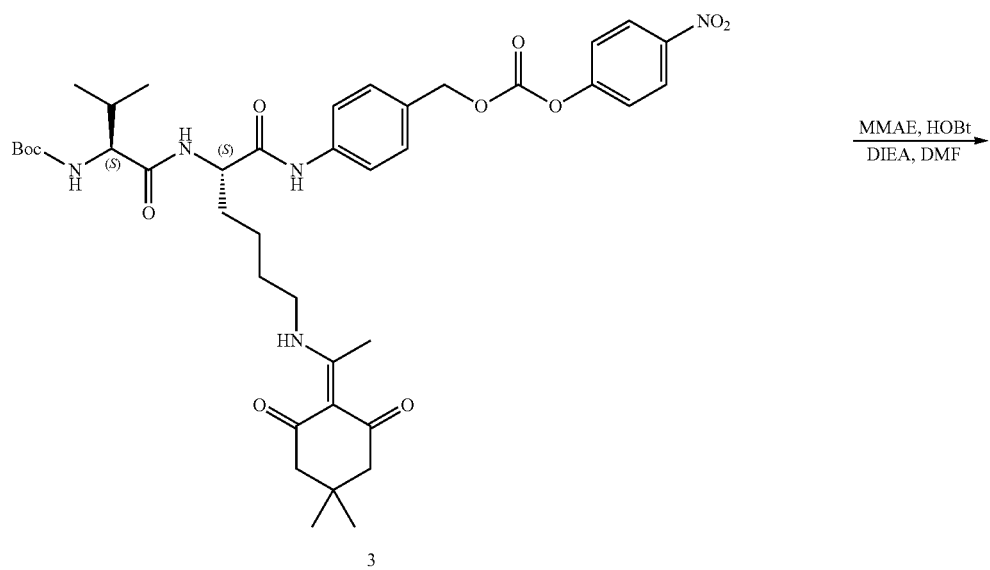

-continued
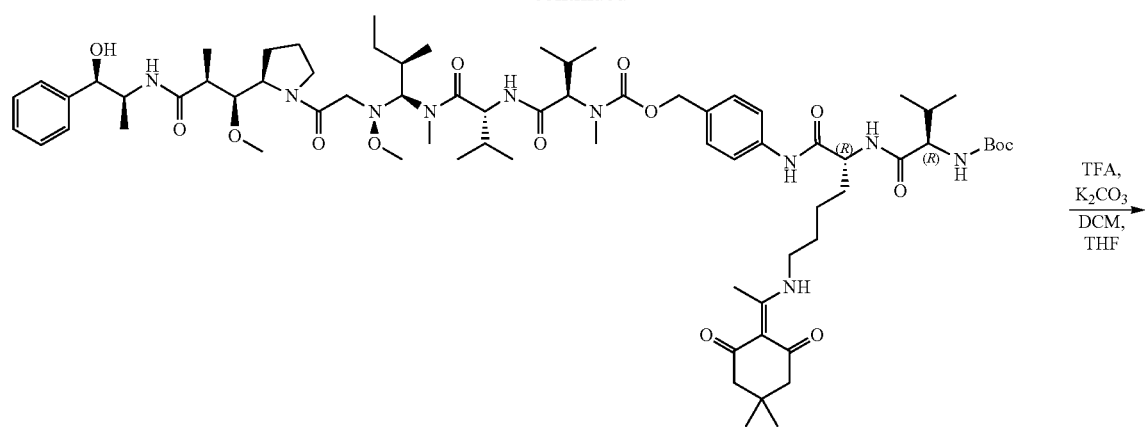
4
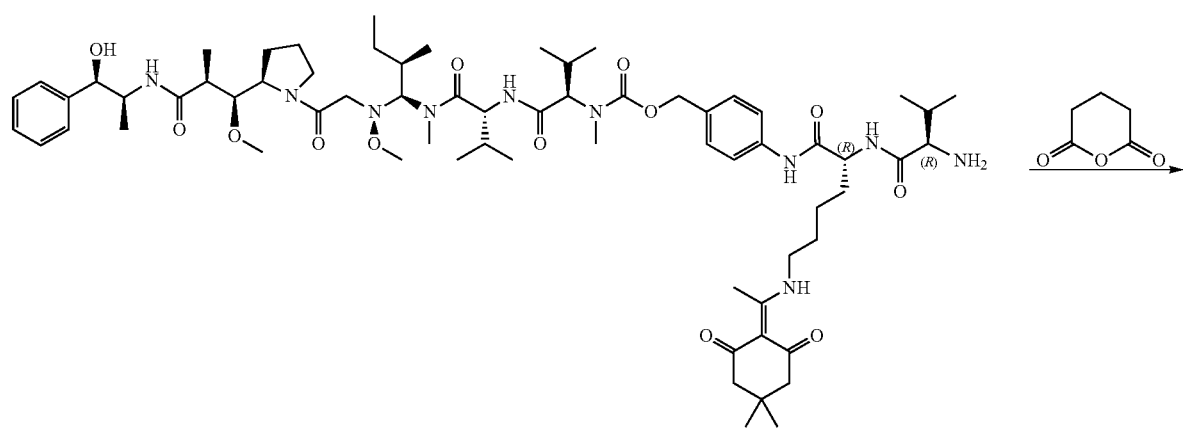
5
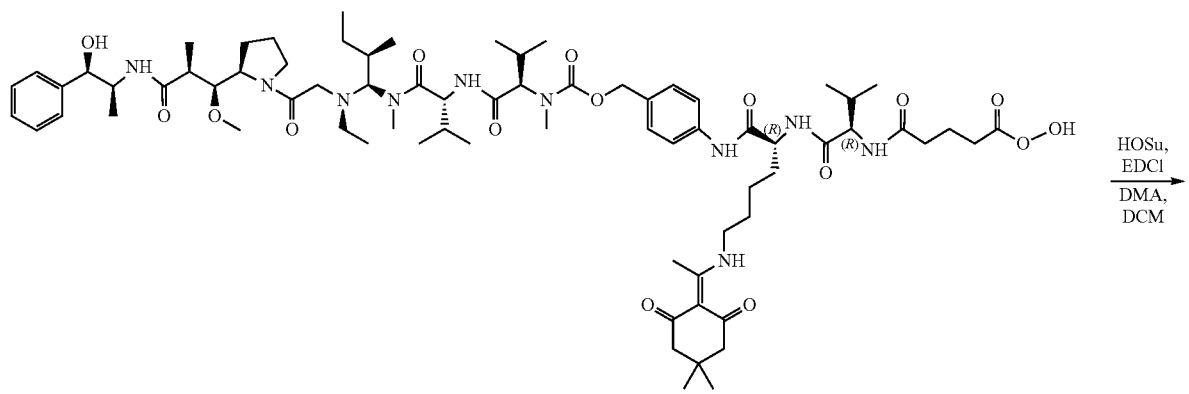
6

-continued

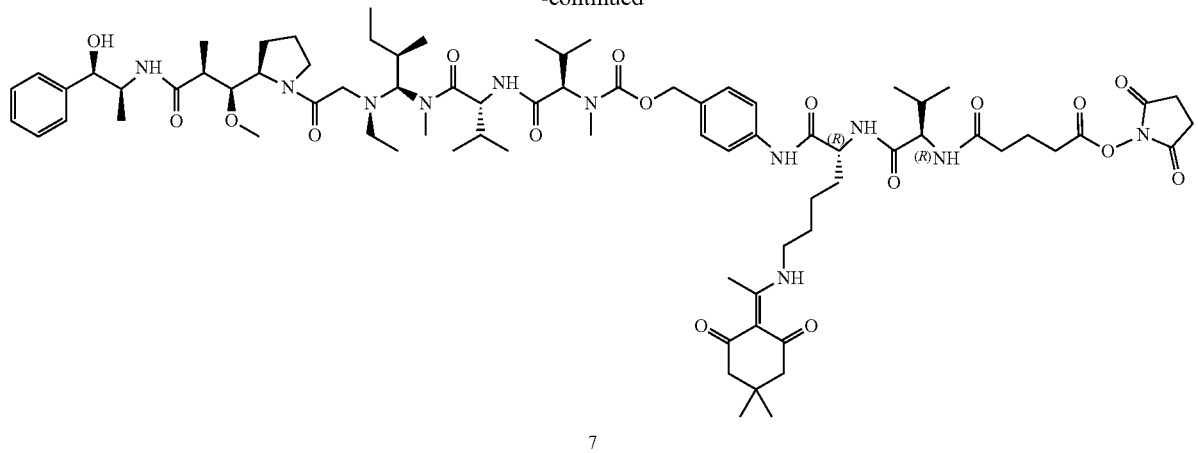

7

General Procedure for Preparation of Compound 2

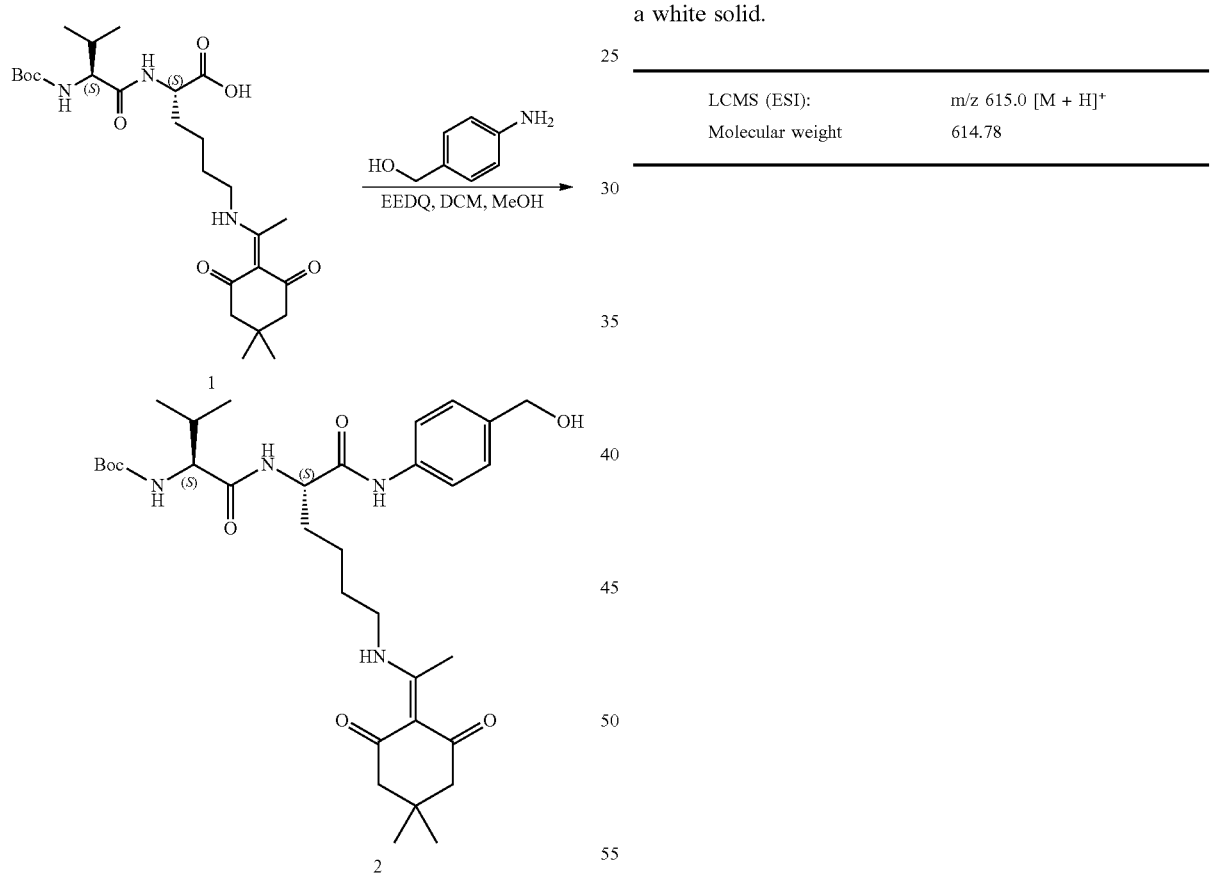

| LCMS (ESI): | m/z 615.0 [M + H]$^+$ |
| Molecular weight | 614.78 |

To a mixture of Compound 1 (3.00 g, 5.89 mmol, 1 eq) and (4-aminophenyl)methanol (869.93 mg, 7.06 mmol, 1.2 eq) in DCM (35 mL) and MeOH (18 mL) was added EEDQ (2.91 g, 11.77 mmol, 2 eq) in the dark under nitrogen, the mixture was stirred at 25° C. for 5 hr. LC-MS showed Compound 1 was consumed completely and one main peak with desired MS was detected. The resulting reaction mixture was concentrated under reduced pressure to give a residue. The residue was purified by flash silica gel chromatography (ISCO®; 120 g SepaFlash® Silica Flash Column, Eluent of 0~20% MeOH/DCM @ 80 mL/min). Compound 2 (2.2 g, 3.58 mmol, 60.79% yield) was obtained as a white solid.

General Procedure for Preparation of Compound 3

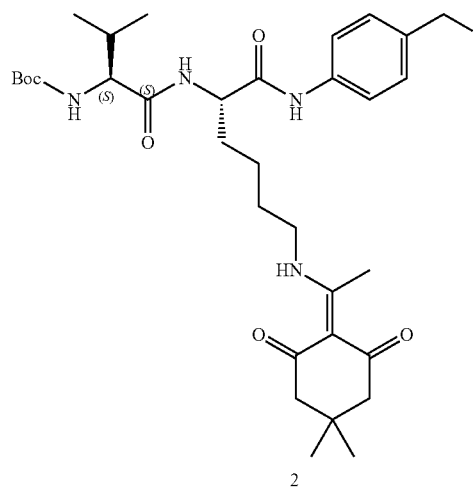

2

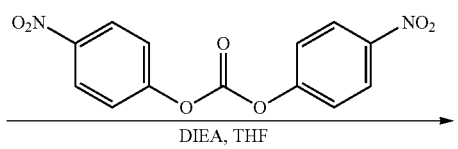

DIEA, THF

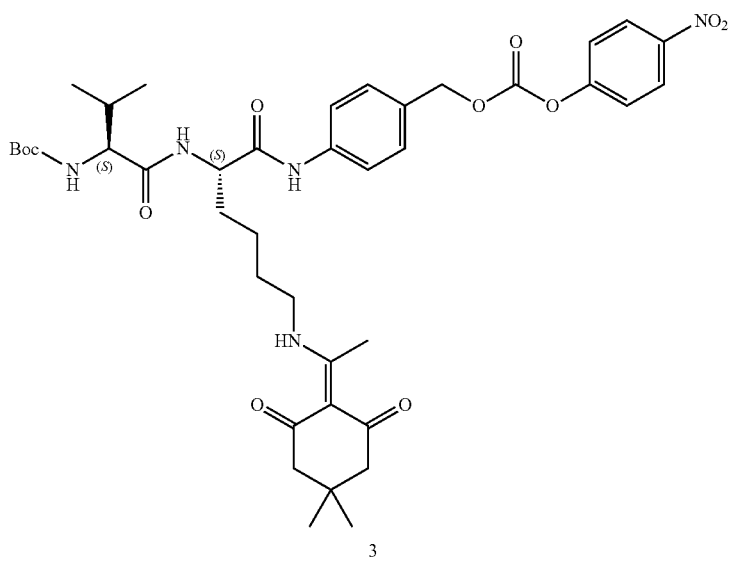

3

To a solution Compound 2 (500 mg, 813.31 μmol, 1 eq) in THF (10 mL) was added DIEA (630.69 mg, 4.88 mmol, 849.98 μL, 6 eq) at 0° C. under nitrogen with stirring for 30 mins. Then bis(4-nitrophenyl) carbonate (1.48 g, 4.88 mmol, 6 eq) was added thereto, the mixture was stirred at 25° C. under nitrogen for additional 21 hr. LC-MS showed one main peak with desired MS was detected. The resulting reaction mixture was concentrated under reduced pressure to give a residue. The residue was purified by flash silica gel chromatography (ISCO®; 40 g SepaFlash® Silica Flash Column, Eluent of 0~20% MeOH/DCM @ 40 mL/min). Compound 3 (500 mg, 641.13 μmol, 78.83% yield) was obtained as a yellow solid.

| | | |
|---|---|---|
| LCMS (ESI): | m/z 780.0 [M + H]$^+$ | |
| Molecular weight | 779.89 | |

General Procedure for Preparation of Compound 4

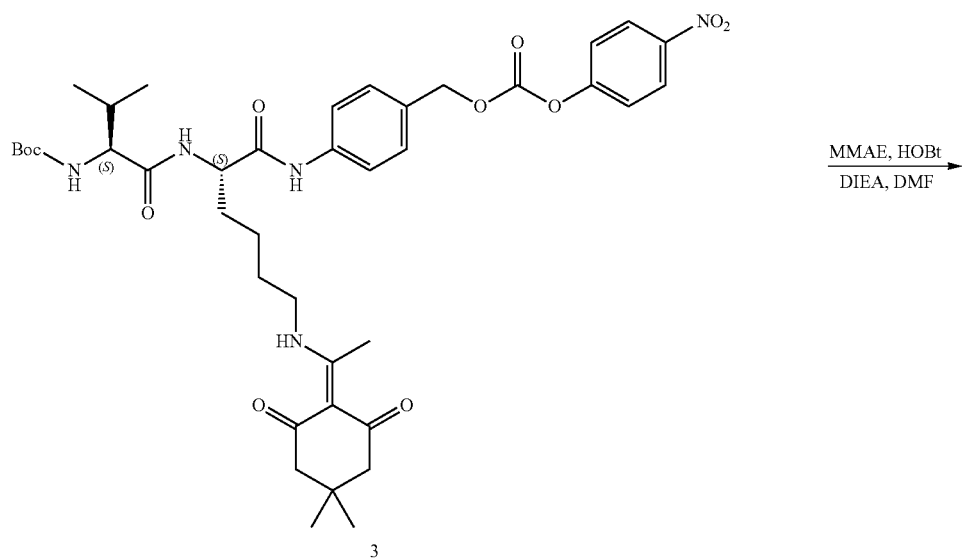

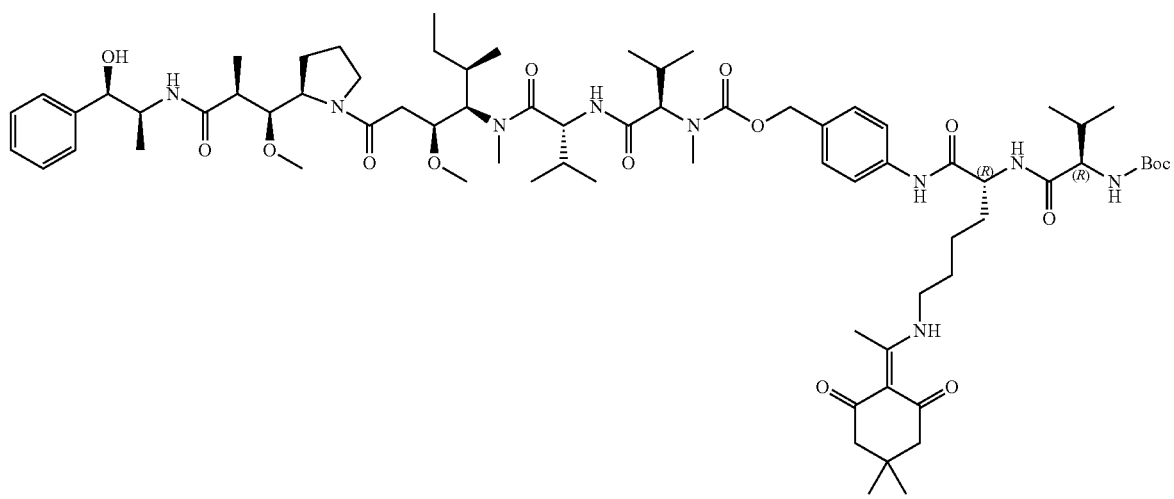

To a mixture of Compound 3 (500 mg, 512.90 μmol, 1.23 eq) in DMF (8 mL) was added DIEA (135.01 mg, 1.04 mmol, 181.95 μL, 2.5 eq) with stirring at 0° C. for 30 mins. Then MMAE (300 mg, 417.84 μmol, 1 eq) and HOBt (84.69 mg, 626.76 μmol, 1.5 eq) was added thereto, and the mixture was stirred at 40° C. for 15 hr. LC-MS showed compound 3 was consumed completely and one main peak with desired MS was detected. The residue was purified by flash C18 gel chromatography (ISCO®; 130 g SepaFlash® C18 Flash Column, Eluent of 0~60% MeCN/H2O @ 75 mL/min). Compound 4 (330 mg, 242.87 μmol, 58.13% yield) was obtained as a white solid.

| LCMS (ESI): | m/z 679.7 [M + 2H]$^{2+}$ |
|---|---|
| Molecular weight | 1358.77 |

General Procedure for Preparation of Compound 5

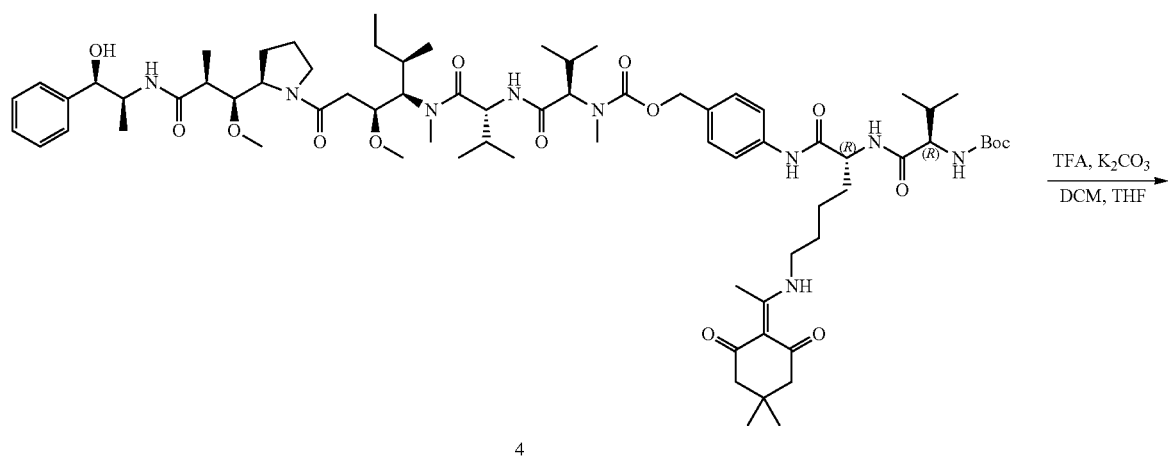

4

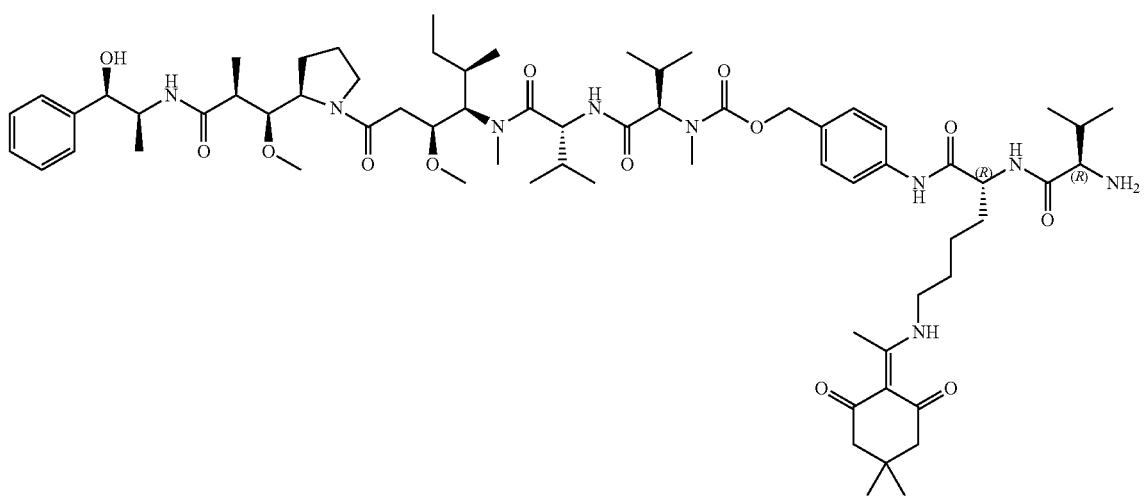

5

To a solution of Compound 4 (325 mg, 239.19 μmol, 1 eq) in DCM (18 mL) was added TFA (3.03 g, 26.60 mmol, 1.97 mL, 111.22 eq) at 0° C., the mixture was stirred at 25° C. for 2 hr. LC-MS showed compound 4 was consumed completely. Then the reaction mixture was concentrated under reduced pressure to give a residue, the residue was dissolved in THF (10 mL) and K$_2$CO$_3$ (661.16 mg, 4.78 mmol, 20 eq) was added thereto. The mixture was stirred at 25° C. for 15 hrs. LC-MS showed one main peak with desired MS was detected. The resulting reaction mixture was filtered and the filtrate was concentrated under reduced pressure to give a residue. The residue was purified by flash C18 gel chromatography (ISCO®; 130 g SepaFlash® C18 Flash Column, Eluent of 0~60% MeCN/H2O @ 75 mL/min). Compound 5 (170 mg, 135.07 μmol, 56.47% yield) was obtained as a white solid.

| | |
|---|---|
| LCMS (ESI): | m/z 629.7 [M + 2H]$^{2+}$ |
| Molecular weight | 1258.65 |

General Procedure for Preparation of Compound 6

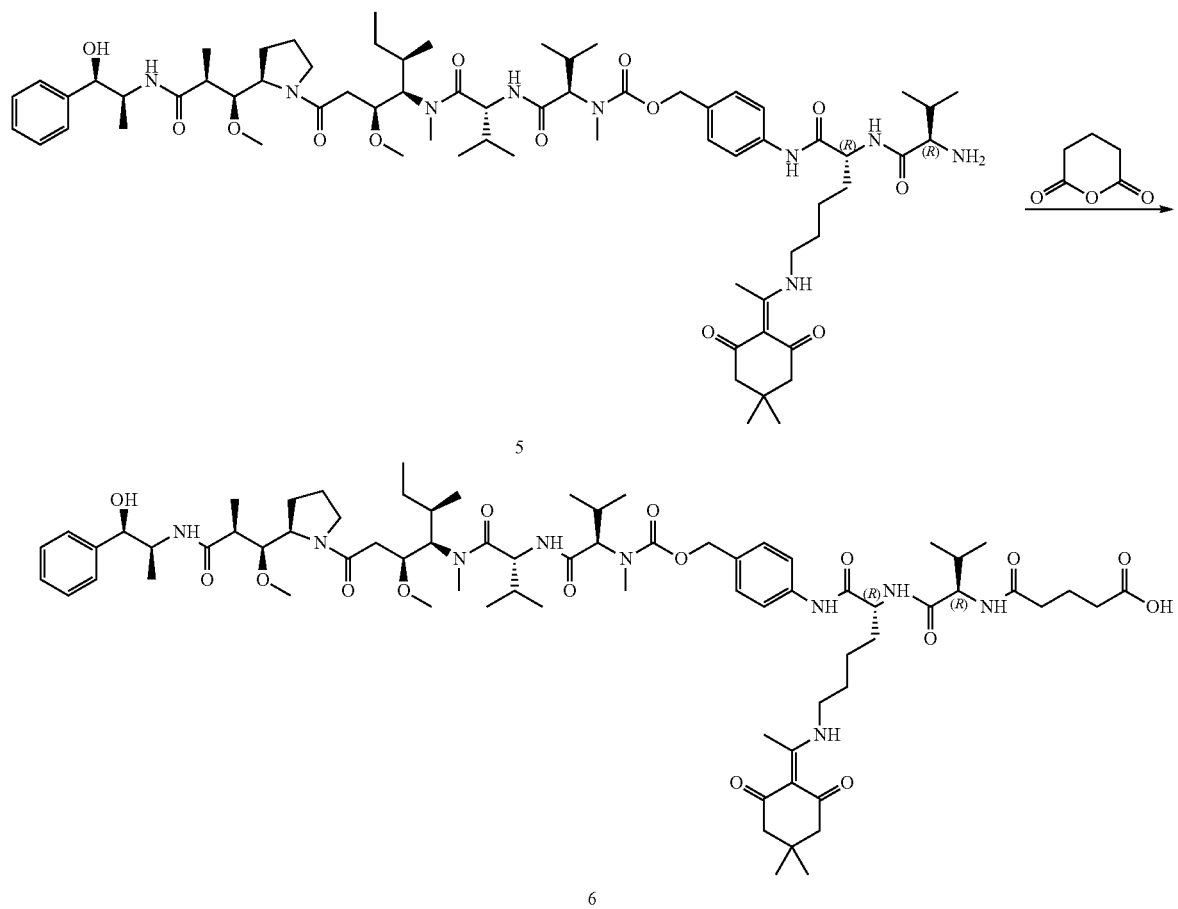

A round bottle containing a solution of compound 5 (140 mg, 111.23 μmol, 1 eq) in DMA (5 mL) was purged using a nitrogen balloon and added DIEA (28.75 mg, 222.46 μmol, 38.75 μL, 2 eq) at 0° C. with stirring for 10 mins, tetrahydropyran-2,6-dione (25.38 mg, 222.46 μmol, 2 eq) was added as a solution in DMA. The mixture was stirred at 25° C. for 12 hr. LC-MS showed compound 5 was consumed completely and one main peak with desired MS was detected. The resulting reaction mixture was purified by flash C18 gel chromatography (ISCO®; 43 g SepaFlash® C18 Flash Column, Eluent of 0~60% MeCN/H2O @ 40 mL/min). Compound 6 (120 mg, 87.42 μmol, 78.59% yield) was obtained as a white solid.

| LCMS (ESI): | m/z 686.7 [M + 2H]$^{2+}$ |
|---|---|
| Molecular weight | 1372.75 |

General Procedure for Preparation of Compound 7 (MMAE-PABC-Lys(Dde)-Val-Glutarate-NHS)

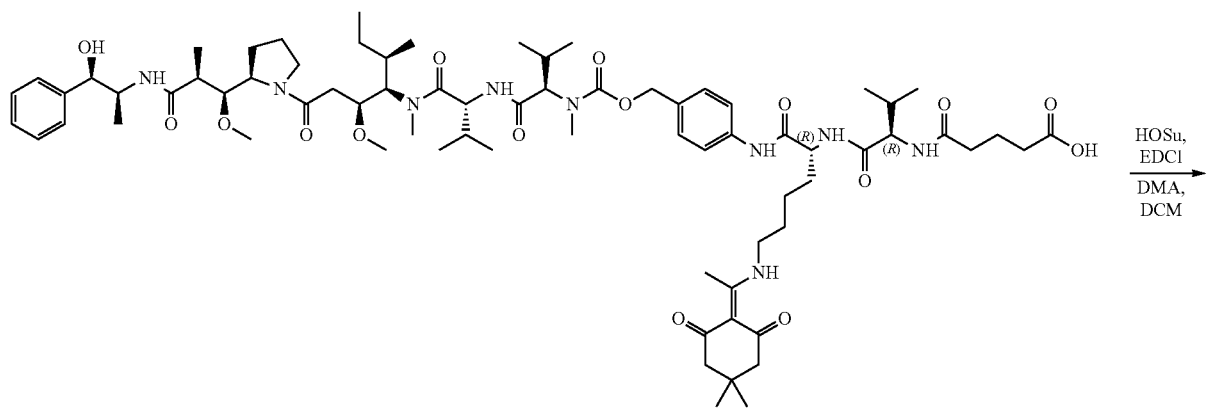

-continued

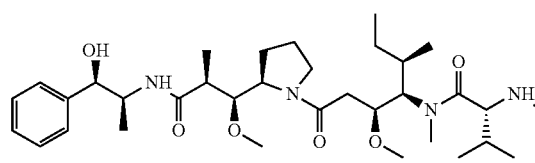

7

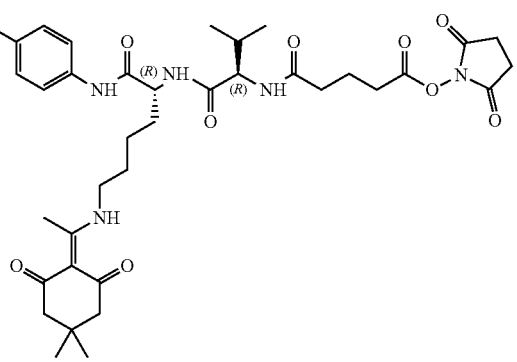

To a solution of compound 6 (120 mg, 87.42 μmol, 1 eq) in DMA (9 mL) and DCM (3 mL) was added 1-hydroxypyrrolidine-2,5-dione (30.18 mg, 262.25 μmol, 3 eq) with stirring, and EDCI (50.27 mg, 262.25 μmol, 3 eq) was added thereto, the mixture was stirred at 0° C. for 30 mins and at 25° C. for additional 19 hr. LC-MS showed compound 6 was consumed completely and one main peak with desired MS was detected. The resulting reaction mixture was concentrated under reduced pressure to remove DCM. The mixture was purified by flash C18 gel chromatography (ISCO®; 43 g SepaFlash® C18 Flash Column, Eluent of 0~60% MeCN/H2O @ 40 mL/min). Compound 7 (60 mg, 40.82 μmol, 46.70% yield) was obtained as a white solid.

| LCMS (ESI): | m/z 735.3 [M + 2H]$^{2+}$ |
|---|---|
| Molecular weight | 1469.83 |

General Procedure for Coupling MMAE-PABC-Lys (Dde)-Val-Glutarate-NHS with Targeting Bicycles

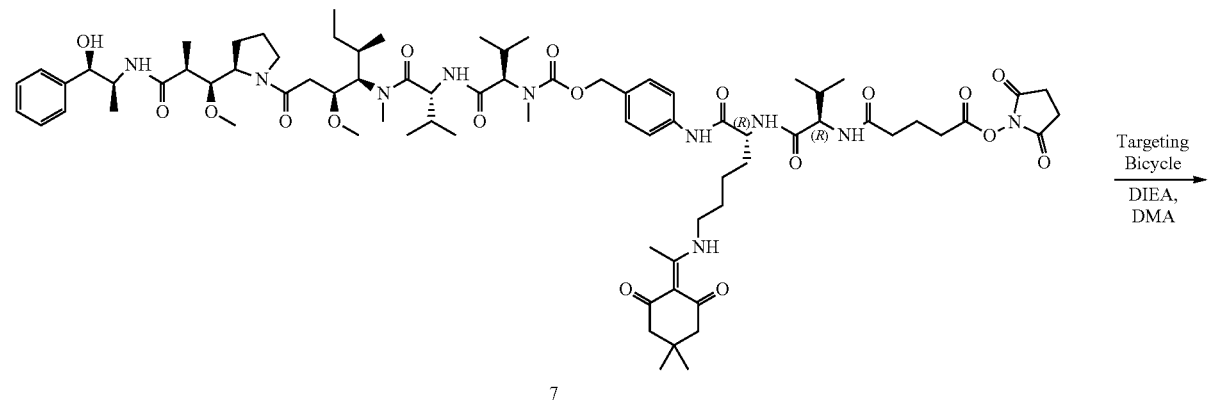

7

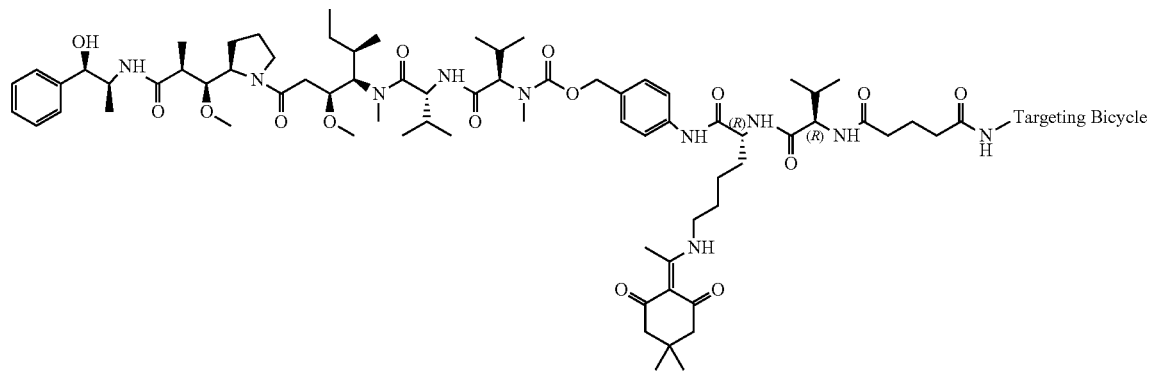

8

To a solution of Bicycle (1.0-1.3 eq) in DMA was added DIEA (3 eq) and MMAE-PABC-Lys(Dde)-Val-Glutarate-NHS (1 eq). The mixture was stirred at 25° C. for 18 hr. The reaction was monitored by LC-MS and once complete, was directly purified by preparative HPLC.

General Procedure for Dde Deprotection

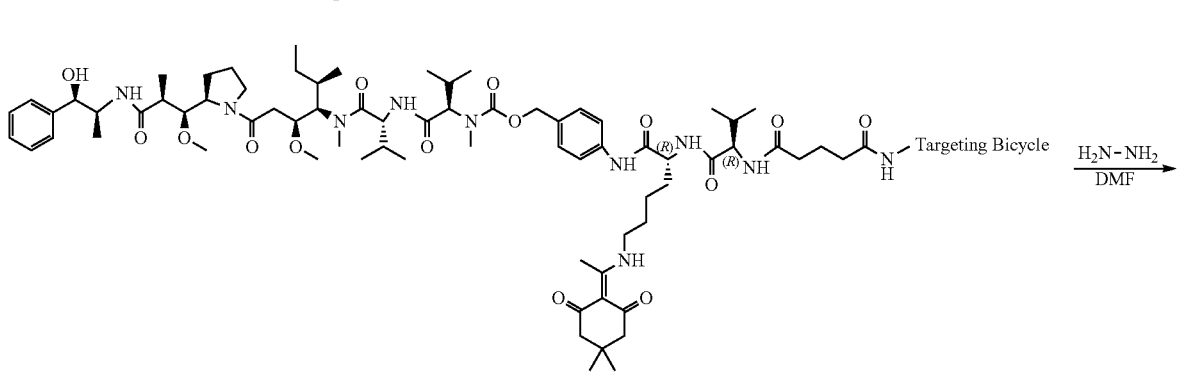

8

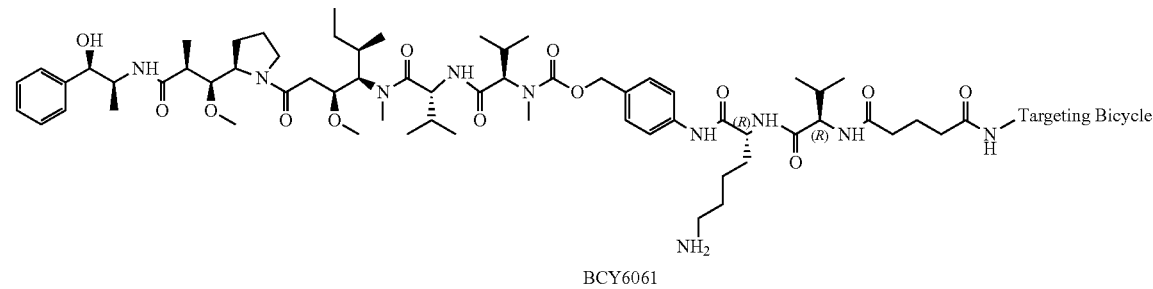

BCY6061

To a solution of Dde protected peptide (1 eq) in DMF was added hydrazine hydrate (6500 eq), and the mixture was stirred at 25° C. for 1 hr. LC-MS was used to monitor the reaction, and once complete, the mixture was purified by preparative HPLC and the clean fractions lyophilised.

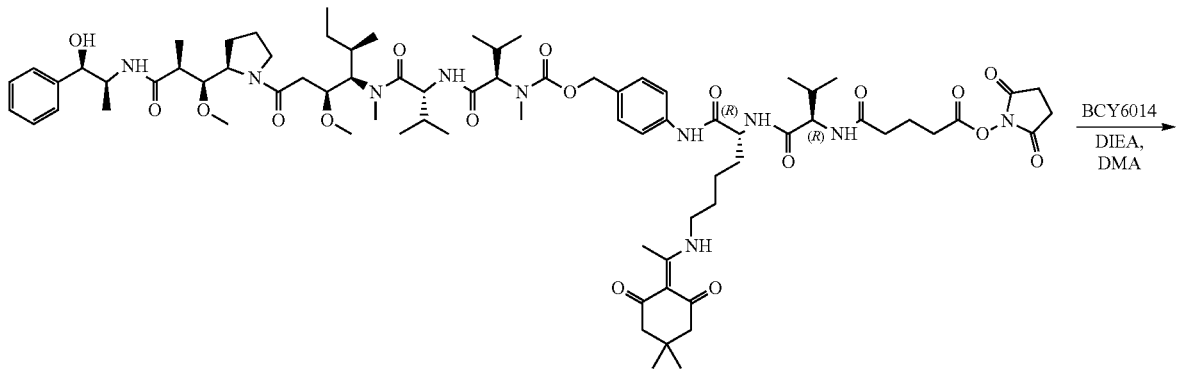

7

-continued

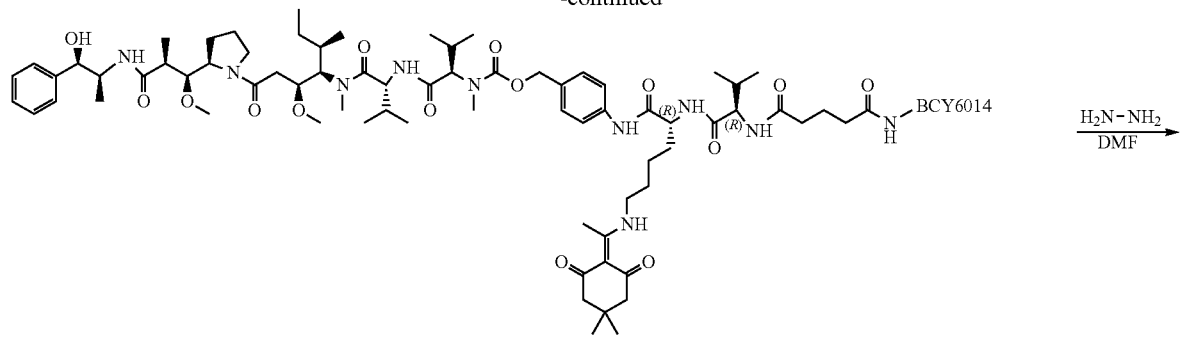

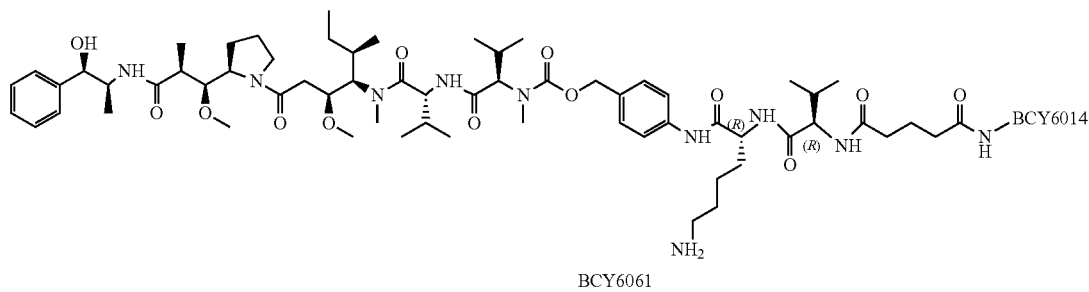
BCY6061

BCY6014 (124.12 mg, 40.82 μmol, 1.2 eq) was used as the bicycle reagent. Dde-BCY6038 (80 mg, 18.20 μmol, 53.51% yield) was obtained as a white solid.

| LCMS (ESI): | m/z 1099.0 [M + 4H]$^{4+}$, 879.4 [M + 5H]$^{5+}$ |
|---|---|
| Molecular weight | 4395.24 |

Dde-BCY6061 (78 mg, 17.75 μmol) was deprotected using hydrazine according to the general procedure to give BCY6061 (47.1 mg, 11.13 μmol, 62.73% yield) as a white solid.

| BCY6061 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 12.01 min |
| LCMS (ESI): | m/z 1058.1 [M + 4H]$^{4+}$, 846.5 [M + 5H]$^{5+}$ |
| Peptide mw | 4230.03 |

BCY6174

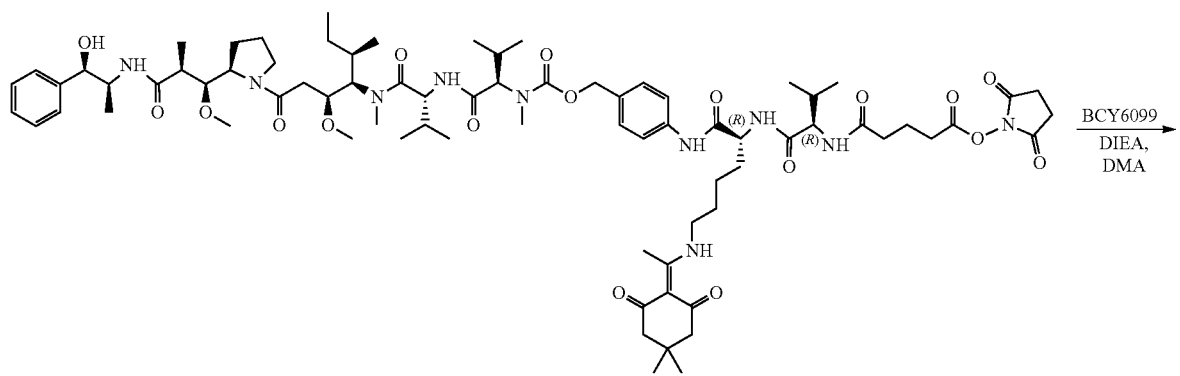

-continued

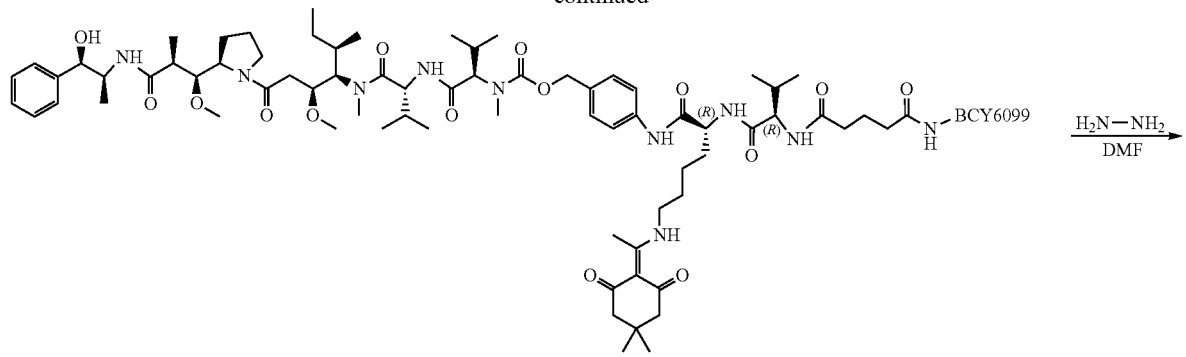

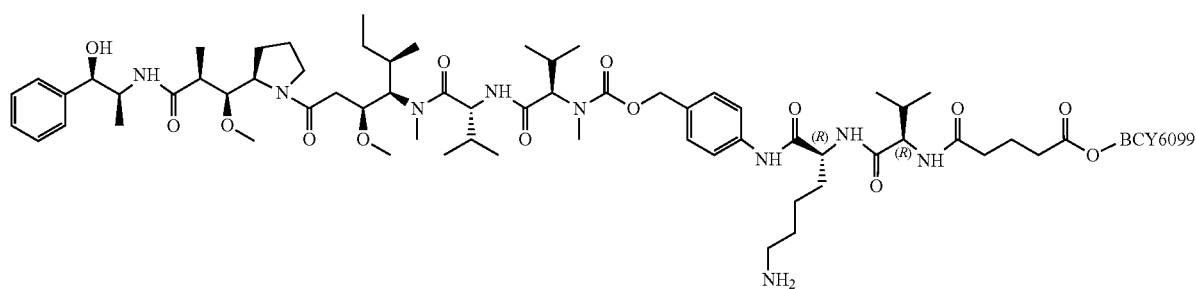

BCY6174

BCY6099 (389.77 mg, 122.47 μmol, 1.2 eq) was used as the bicycle reagent. Dde-BCY6174 (0.250 g, 55.10 μmol, 53.99% yield) was obtained as a white solid.

| LCMS (ESI): | m/z 1513.0 [M + 3H]$^{3+}$, 1135.0 [M + 4H]$^{4+}$, 908.2 [M + 5H]$^{5+}$ |
|---|---|
| Molecular weight | 4538.38 |

Dde-BCY6174 (0.250 g, 55.10 μmol, 1.0 eq) was deprotected using hydrazine according to the general procedure to give BCY6174 (0.1206 g, 27.45 μmol, 49.82% yield) as a white solid.

| BCY6174 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 9.85 min |
| LCMS (ESI): | m/z 1458.5 [M + 3H]$^{3+}$, 1094.1 [M + 4H]$^{4+}$, 875.4 [M + 5H]$^{5+}$ |
| Peptide mw | 4373.17 |

D-Trp-Cit-MMAE Series
D-Trp-Cit-MMAE Linker

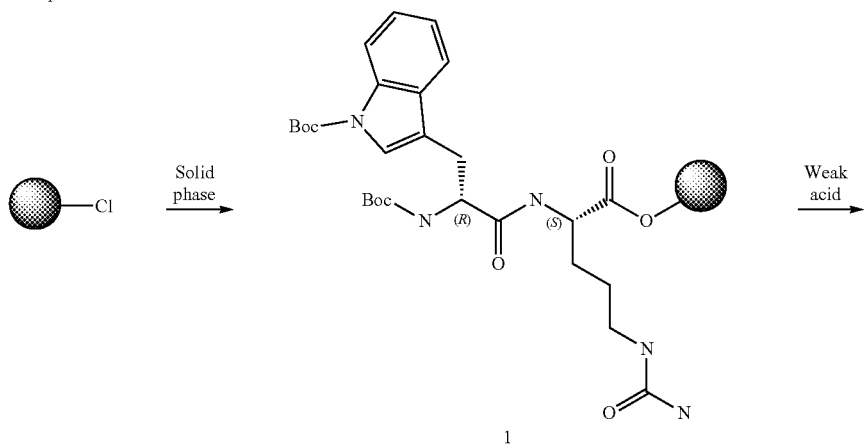

-continued
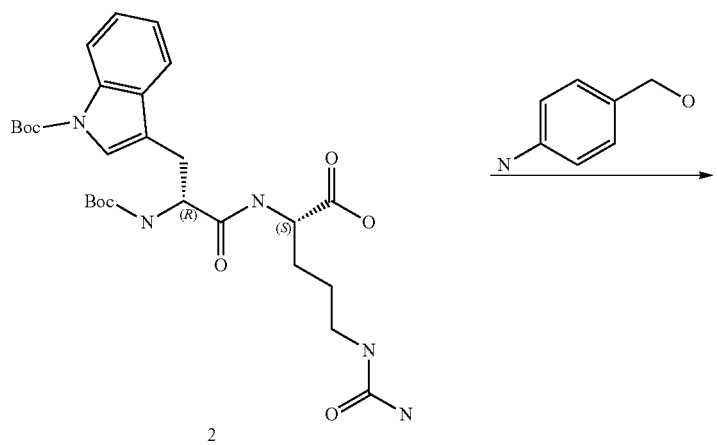
2
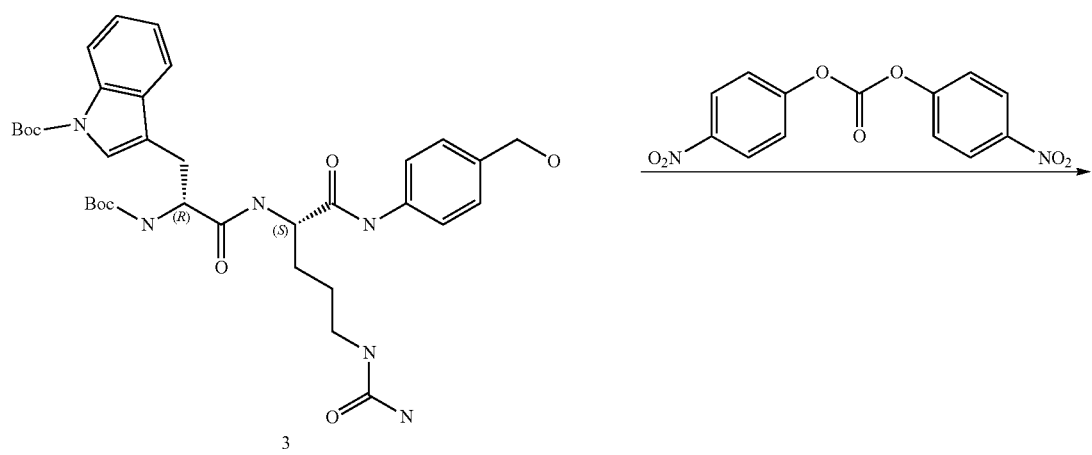
3
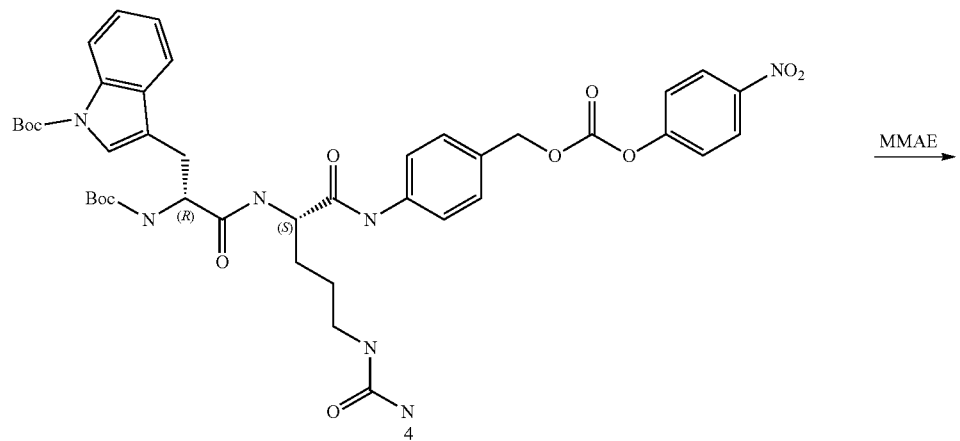
4
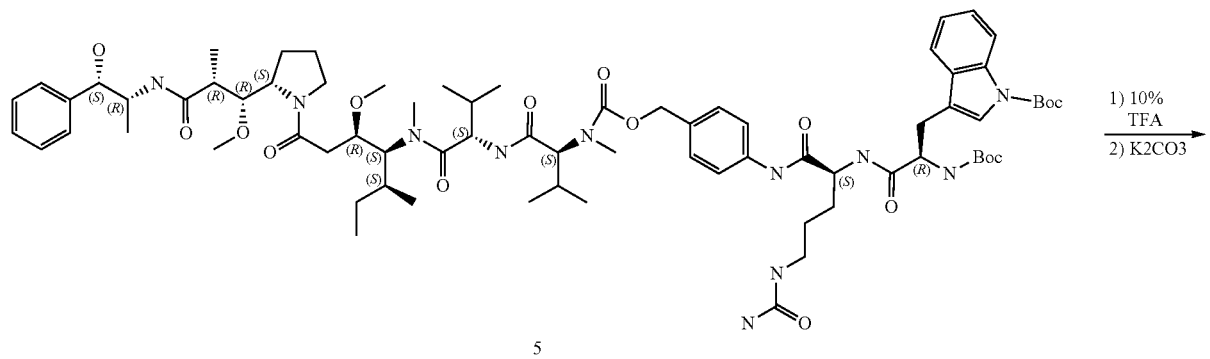
5

-continued
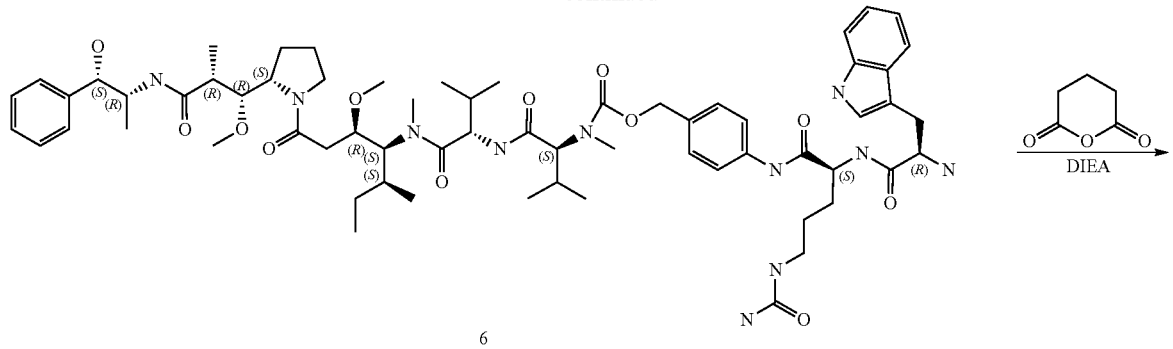
6
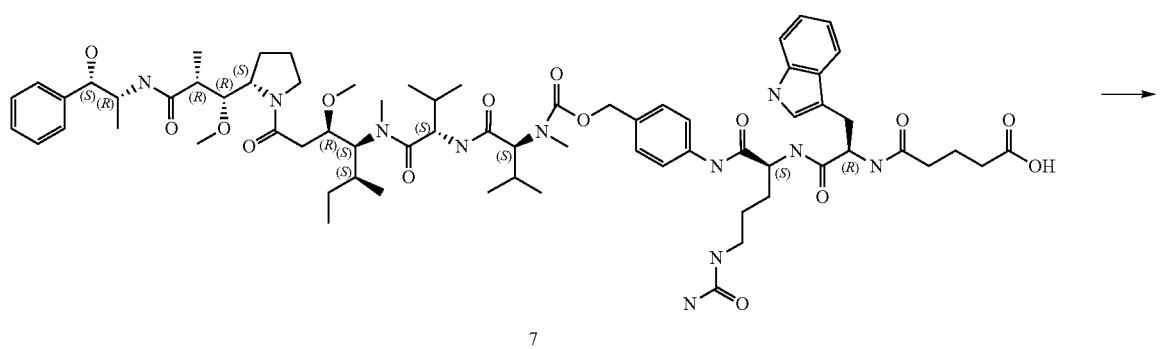
7
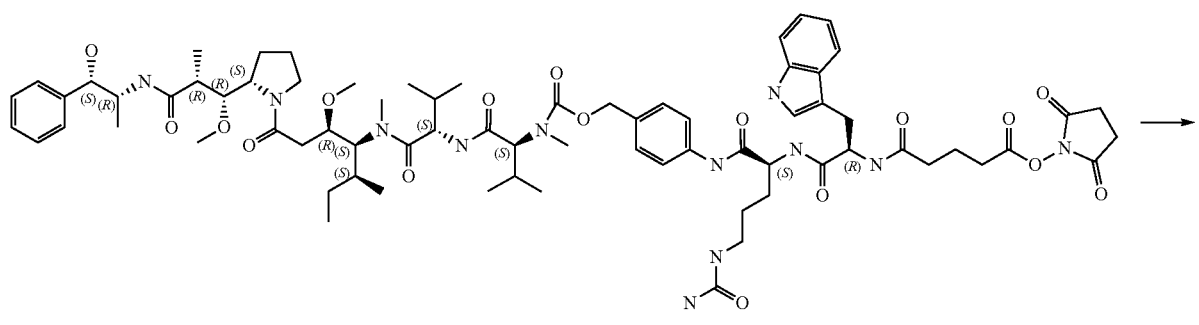
7
BCY6062
General Procedure for Preparation of Compound 3
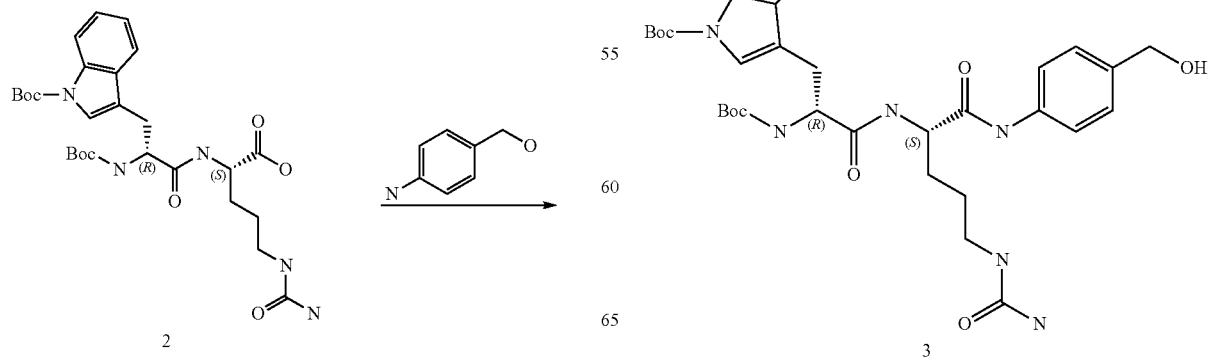

To a solution of compound 1 (2 g, 4.33 mmol, 1.00 eq), DIC (4.92 g, 39.00 mmol, 6.00 mL, 9.00 eq), HOBt (5.27 g, 39.00 mmol, 9.00 eq) in DMF (30.00 mL) was added (4-aminophenyl)methanol (4.80 g, 39.00 mmol, 9.00 eq). The mixture was stirred at 15° C. for 1 hour. LC-MS showed compound 1 was consumed completely and one main peak with desired MS was detected. Directly purified by prep-HPLC (neutral condition). Compound 2 (2 g, 3.53 mmol, 81.45% yield) was obtained as a white solid.

| LCMS (ESI): | m/z 666.9 [M + H]$^+$ |
|---|---|
| Molecular weight | 666.78 |

General Procedure for Preparation of Compound 4

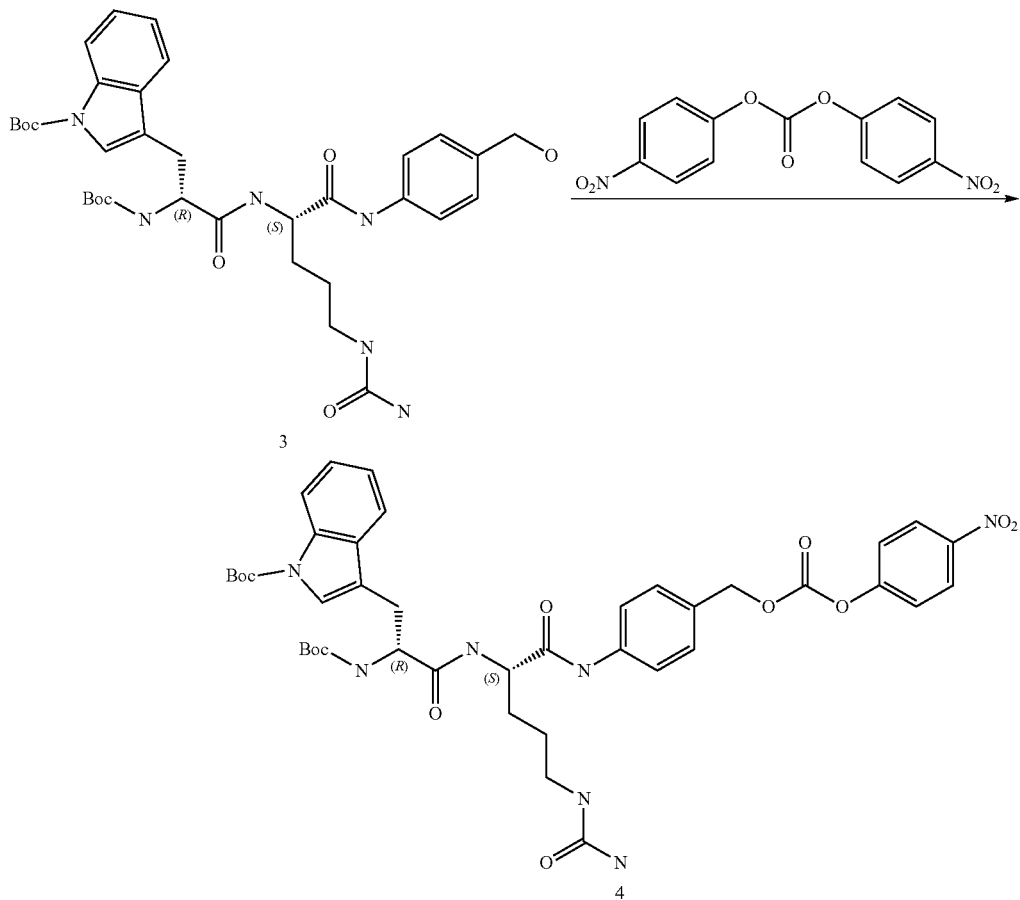

To a solution of compound 2 (2 g, 3.00 mmol, 1 eq), DIEA (2.71 g, 21.00 mmol, 3.66 mL, 7 eq) in DMF (20 mL) was added bis(4-nitrophenyl) carbonate (5.48 g, 18.00 mmol, 6 eq) in one part at 0° C. The mixture was stirred at 0-15° C. for 2 hr. LC-MS showed compound 2 was consumed completely and one main peak with desired MS was detected. Directly purified by prep-HPLC (neutral condition). Compound 3 (0.9 g, 1.08 mmol, 36.07% yield) was obtained as a yellow solid.

| LCMS (ESI): | m/z 832.0 [M + H]$^+$ |
|---|---|
| Molecular weight | 831.88 |

General Procedure for Preparation of Compound 5

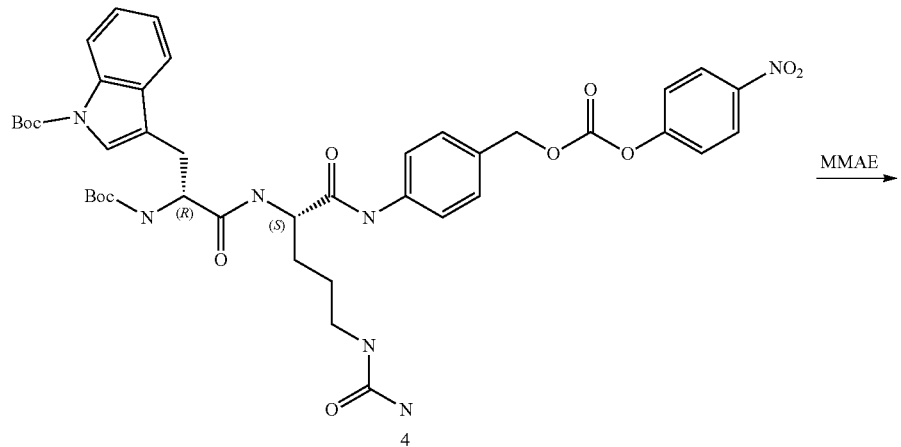

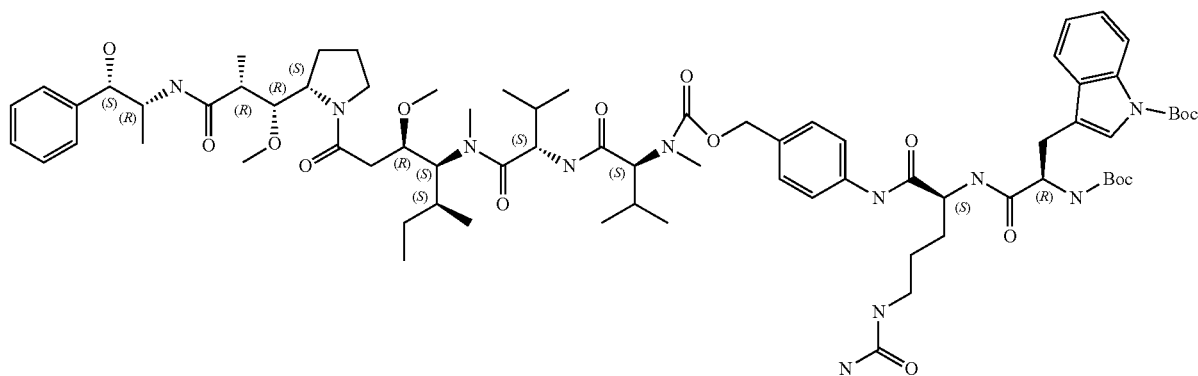

To a solution of compound 3 (350 mg, 420.74 μmol, 1.00 eq), HOBt (56.85 mg, 420.74 μmol, 1 eq) and DIEA (163.13 mg, 1.26 mmol, 219.86 μL, 3 eq) in DMF (10 mL) was added MMAE (302.08 mg, 420.74 μmol, 1 eq) at 0° C. The mixture was stirred at 40° C. for 18 hour. LC-MS showed compound 4 was consumed completely and one main peak with desired MS was detected. Directly purified by prep-HPLC (neutral condition). Compound 4 (0.22 g, 155.95 μmol, 37.06% yield) was obtained as a yellow solid.

| LCMS (ESI): | m/z 1410.5 [M + H]$^+$ |
| --- | --- |
|  | 705.7 [M + 2H]$^{2+}$ |
| Molecular weight | 1410.76 |

General Procedure for Preparation of Compound 6

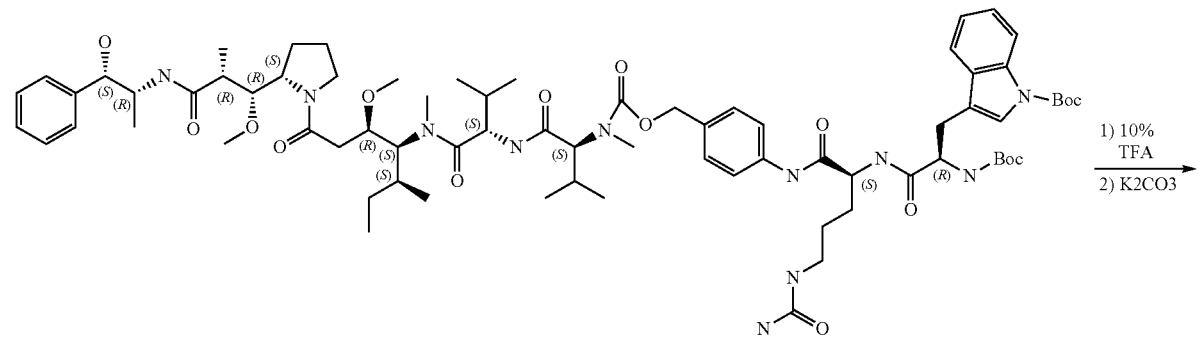

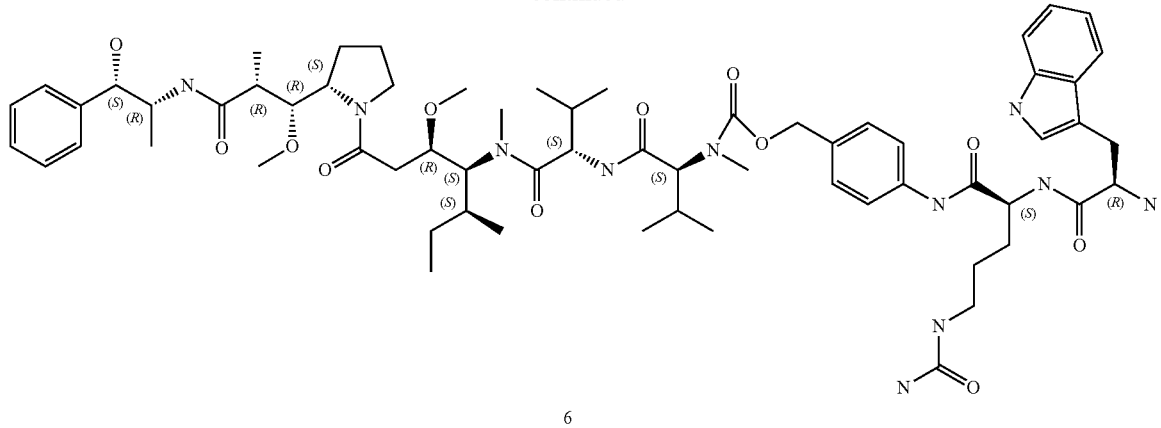

6

To a solution of compound 4 (0.21 g, 148.86 μmol, 1 eq) in DCM (9 mL) was added TFA (1.54 g, 13.51 mmol, 1 mL, 90.73 eq). The mixture was stirred at 15° C. for 4 h, and concentrated under reduced pressure to give a residue, dissolved in THF, then added $K_2CO_3$(s) and stirred at 15° C. for 16 h. LC-MS showed compound 4 was consumed completely and one main peak with desired MS was detected. The reaction mixture was filtered and concentrated under reduced pressure to give a residue. The residue was purified by prep-HPLC (neutral condition). Compound 5 (0.13 g, 102.02 μmol, 68.54% yield, 95% purity) was obtained as a white solid.

| LCMS (ESI): | m/z 1210.4 [M + H]$^+$, 605.8 [M + 2H]$^{2+}$ |
|---|---|
| Molecular weight | 1210.53 |

General Procedure for Preparation of Compound 7

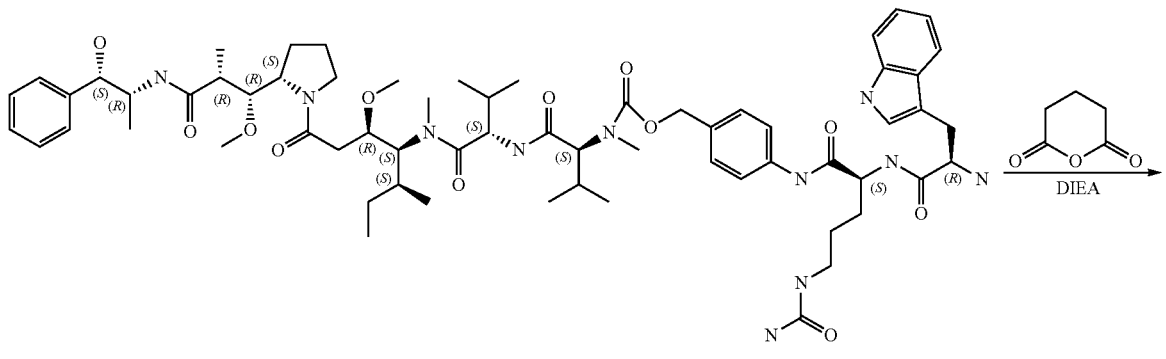

6

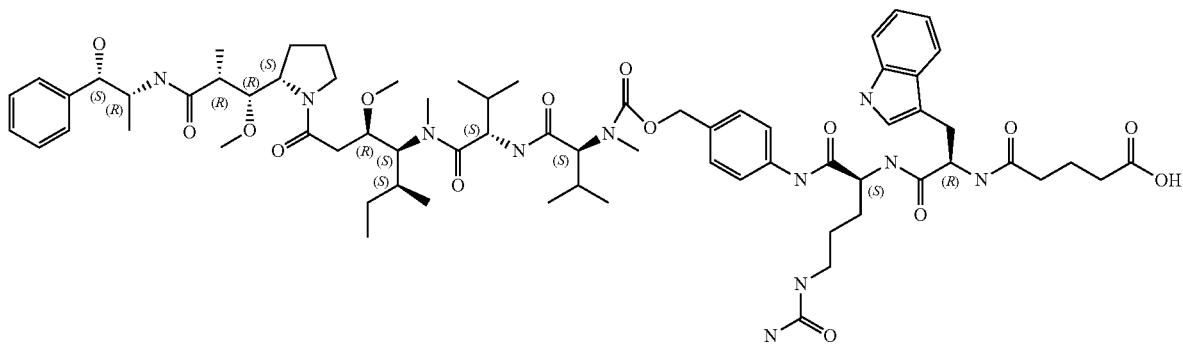

7

To a solution of compound 5 (0.12 g, 99.13 µmol, 1 eq) in DMA (5 mL) was added DIEA (38.44 mg, 297.40 µmol, 51.80 µL, 3 eq) and tetrahydropyran-2,6-dione (22.62 mg, 198.26 µmol, 2 eq). The mixture was stirred at 15° C. for 16 hr. LC-MS showed compound 5 was consumed completely and one main peak with desired MS was detected. Directly purified by prep-HPLC (neutral condition). Compound 6 (0.09 g, 67.94 µmol, 68.54% yield) was obtained as a white solid.

| LCMS (ESI): | m/z 662.7 [M + 2H]$^{2+}$ |
|---|---|
| Molecular weight | 1324.63 |

General Procedure for Preparation of Compound 8

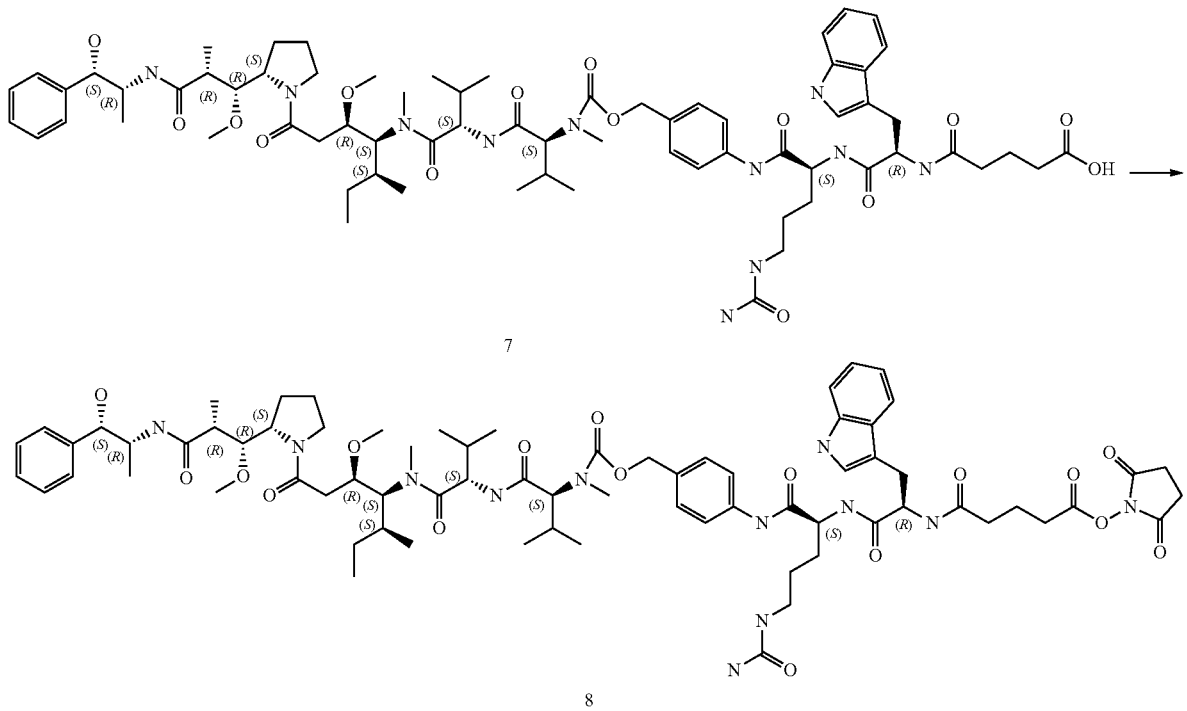

To a solution of compound 6 (0.09 g, 67.95 µmol, 1 eq), HOSu (23.46 mg, 203.84 µmol, 3 eq) in DMA (6 mL) and DCM (2 mL) was added EDCI (39.08 mg, 203.84 µmol, 3 eq). The mixture was stirred at 15° C. for 16 h. LC-MS showed compound 6 was consumed completely and one main peak with desired MS was detected. DCM was removed and directly purified by prep-HPLC (neutral condition). Compound 7 (0.06 g, 40.09 µmol, 59.01% yield, 95% purity) was obtained as a white solid.

| LCMS (ESI): | m/z 711.2 [M + 2H]$^{2+}$ |
|---|---|
| Molecular weight | 1421.7 |

BCY6062

To a solution of BCY6014 (76.99 mg, 25.32 µmol, 1.2 eq) in DMA (5 mL) was added DIEA (8.18 mg, 63.31 µmol, 11.03 µL, 3 eq), compound 7 (0.03 g, 21.10 µmol, 1 eq). The mixture was stirred at 15° C. for 16 hr. The reaction was monitored by LC-MS and once complete, the mixture was purified by preparative HPLC. BCY6062 (0.0255 g, 5.70 µmol, 27.01% yield, 97.15% purity) was obtained as a white solid.

| BCY6062 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 13.15 min |
| LCMS (ESI): | m/z 1449.2 [M + 3H]$^{3+}$, |
| | 1087.0 [M + 4H]$^{4+}$ |
| Peptide mw | 4346.13 |

DM1 Series
DM1-SS-Series
DM1-SPDP-TPF Linker
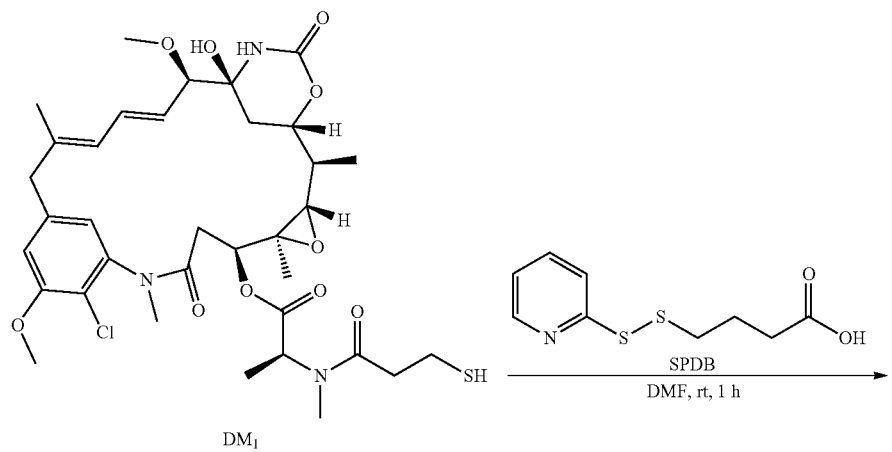
DM1
SPDB
DMF, rt, 1 h
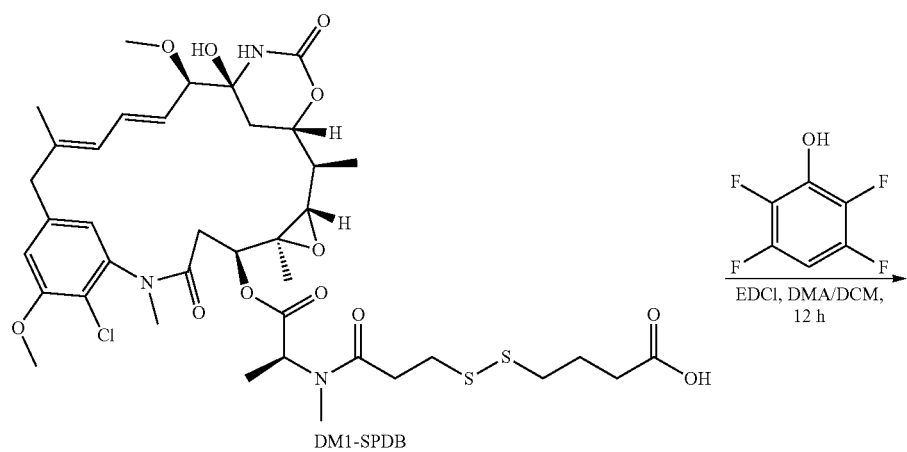
DM1-SPDB
EDCl, DMA/DCM,
12 h
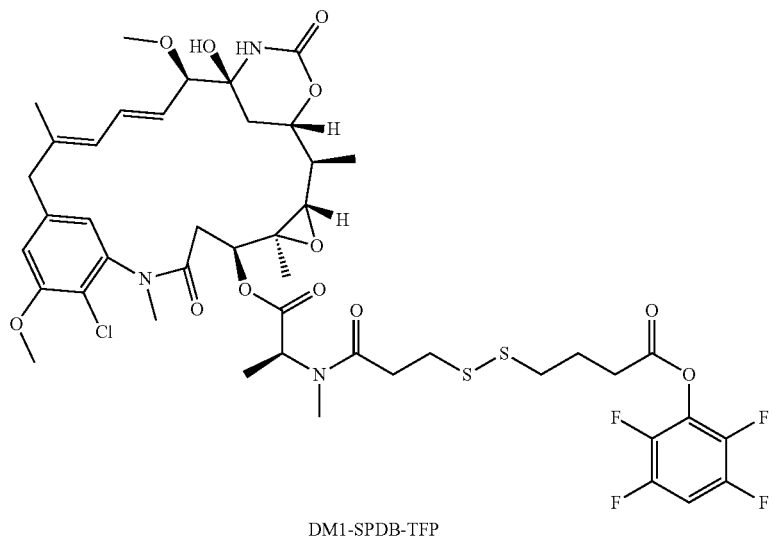
DM1-SPDB-TFP

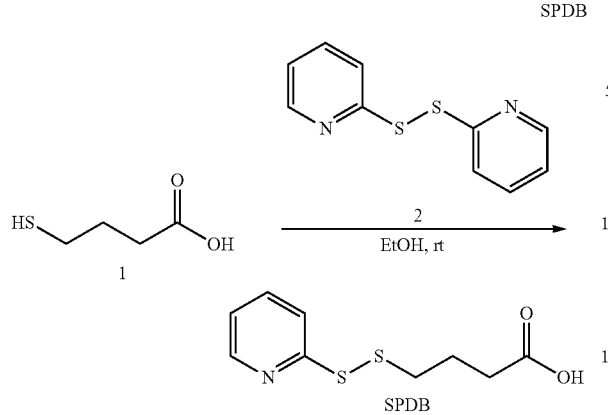

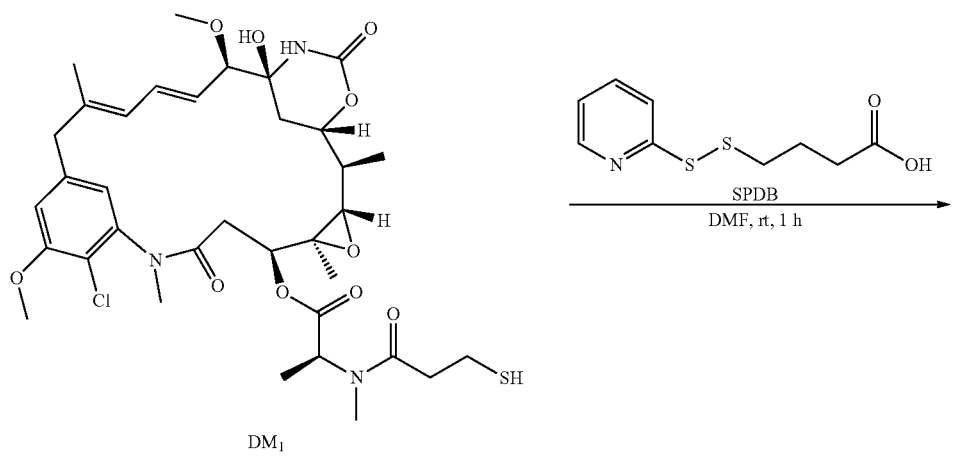

4-sulfanylbutanoic acid (4.50 g, 37.45 mmol, 1.00 eq). The mixture was stirred at 15° C. for 18 hours under N₂. LC-MS showed compound 1 was consumed completely and one main peak with desired mass was detected. The reaction mixture was concentrated under reduced pressure to remove solvent to give a residue. The residue was purified by preparative HPLC (C18 360 g, neutral condition). Compound SPDB (1.9 g, 8.29 mmol, 22.12% yield) was obtained as a yellow solid.

¹H NMR: ES6446-8-P1A 400 MHz CDCl₃

δ ppm 1.98 (q, J=7.09 Hz, 2H), 2.45 (t, J=7.15 Hz, 2H), 2.79 (t, J=7.03 Hz, 2H), 7.03 (dd, J=7.15, 4.89 Hz, 1H), 7.19 (s, 1H), 7.56-7.65 (m, 2H), 8.41 (d, J=4.52 Hz, 1H).

| LCMS (ESI): | m/z 230.0 [M + H]⁺ |
|---|---|
| Molecular weight | 229.31 |

To a solution of 2-(2-pyridyldisulfanyl)pyridine (12.37 g, 56.18 mmol, 1.50 eq) in EtOH (100.00 mL) was added

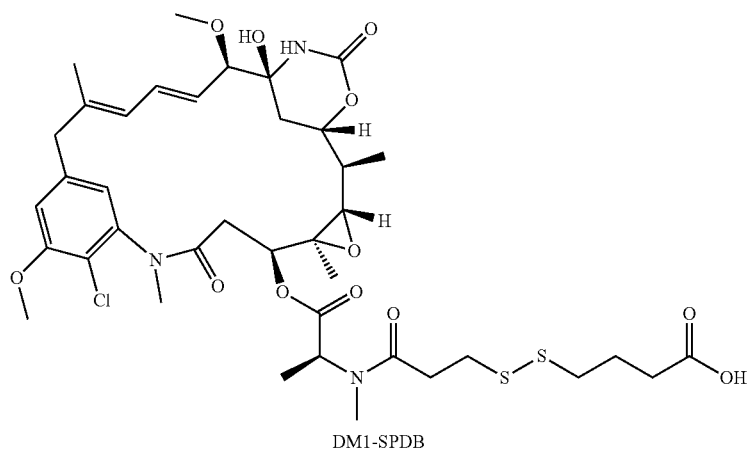

A mixture of DM1 (250.00 mg, 338.62 µmol, 1.00 eq) and 4-(2-pyridyldisulfanyl)butanoic acid (100.95 mg, 440.21 µmol, 1.30 eq) was added under nitrogen in a 50 mL of flask with DMF (10.00 mL) purged with $N_2$ for 30 mins. The mixture was stirred at room temperature for 1 hr. LC-MS showed that the DM1 was consumed completely and one main peak with desired mass was detected. The residue was purified by flash C18 gel chromatography (ISCO®; 120 g SepaFlash® C18 Flash Column, Eluent of 0-60% MeCN/$H_2O$ @ 85 mL/min). DM1-SPDB (120.00 mg, 140.11 µmol, 41.38% yield) was obtained as a white solid.

| LCMS (ESI): | m/z 838.0 [M + H − $H_2O$]$^+$ |
|---|---|
| Molecular weight | 856.44 |

To a solution of DM1-SPDB (120.00 mg, 140.11 µmol, 1.00 eq) and 2,3,5,6-tetrafluorophenol (69.81 mg, 420.34 µmol, 3.00 eq) in DCM (1.00 mL) and DMA (3.00 mL) was added EDCI (80.58 mg, 420.34 µmol, 3.00 eq). The mixture was stirred at 15° C. for 4 hours. LC-MS showed DM1-SPDB was consumed completely and one main peak with desired mass was detected. The DCM was removed and the residue The mixture was directly purified by preparative HPLC (neutral condition). Compound DM1-SPDB-TFP (60.00 mg, 59.73 µmol, 42.63% yield) was obtained as a white solid.

| LCMS (ESI): | m/z 985.9 [M + H − $H_2O$]$^+$ |
|---|---|
| Molecular weight | 1004.5 |

General Procedure for Coupling DM1-SPDB-TFP with Targeting Bicycles

To a solution of targeting Bicycle (1.1-1.3 eq) in DMA was added DIEA (3 eq) and DM1-SPDB-TFP (1 eq). The mixture was stirred at 25° C. for 18 hr. The reaction was monitored by LC-MS and once complete, the mixture was directly purified by preparative HPLC.

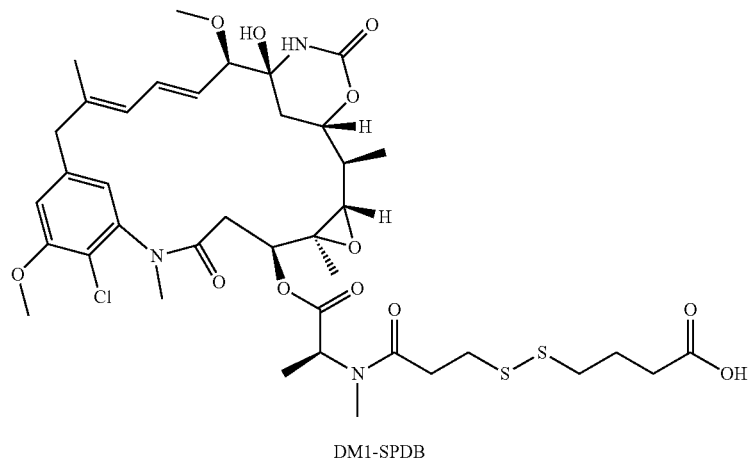

DM1-SPDB

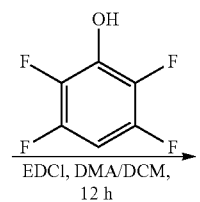

EDCl, DMA/DCM, 12 h

DM1-SPDB-TFP

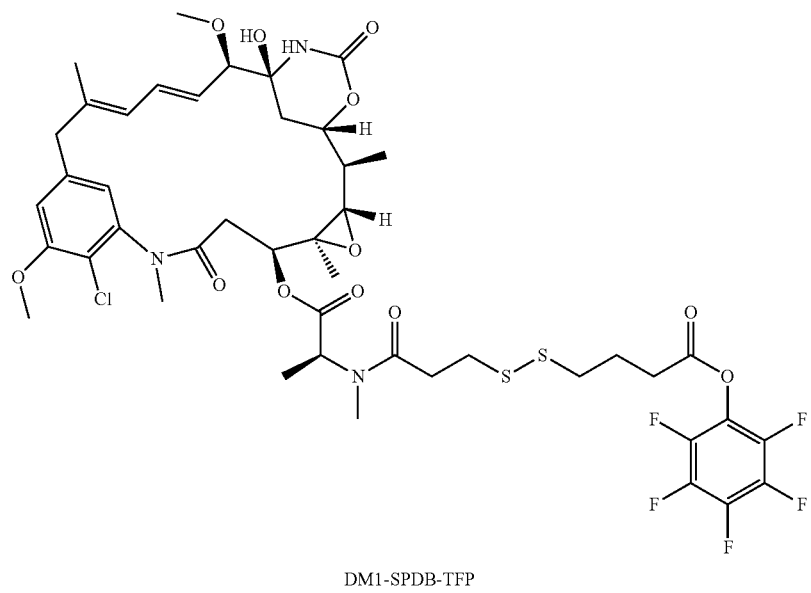

DM1-SPDB-TFP

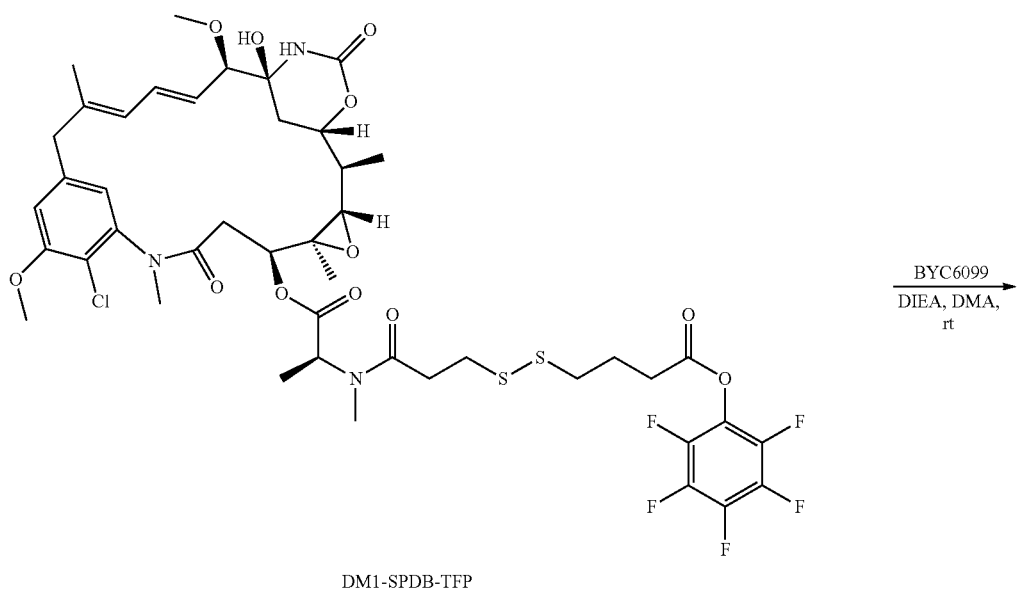

DM1-SPDB-TFP

BYC6099
DIEA, DMA, rt

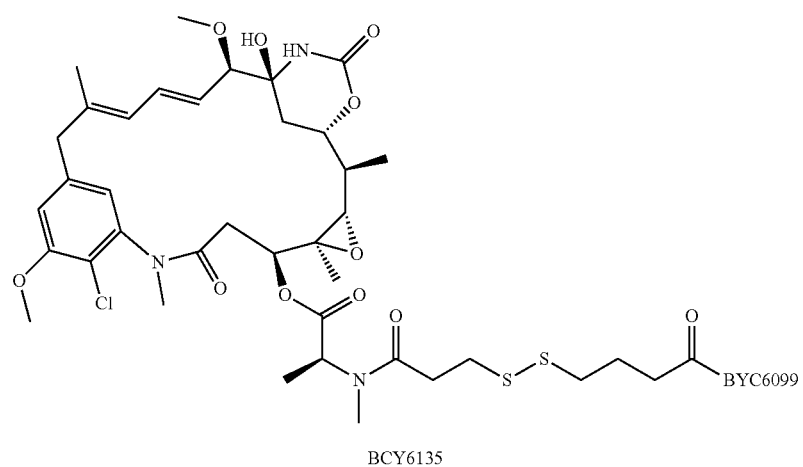

BCY6135

BCY6099 (114.1 mg, 35.84 μmol) was used as the bicycle reagent. 22.4 mg Compound BCY6135 (5.30 μmol, 17.74% yield, 95.14% purity) was obtained as a white solid.

| BCY6135 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |

-continued

| BCY6135 Analytical Data | |
|---|---|
| Retention Time: | 9.81 |
| LCMS (ESI): | m/z 1341.5 [M + 3H]$^{3+}$, 805.0 [M + 5H]$^{5+}$ |
| Peptide mw | 4021.08 |

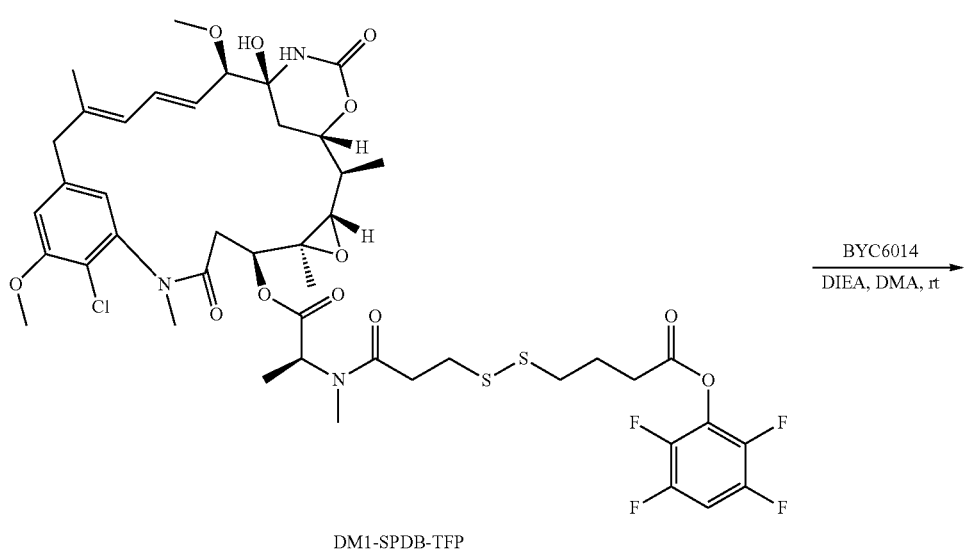

DM1-SPDB-TFP

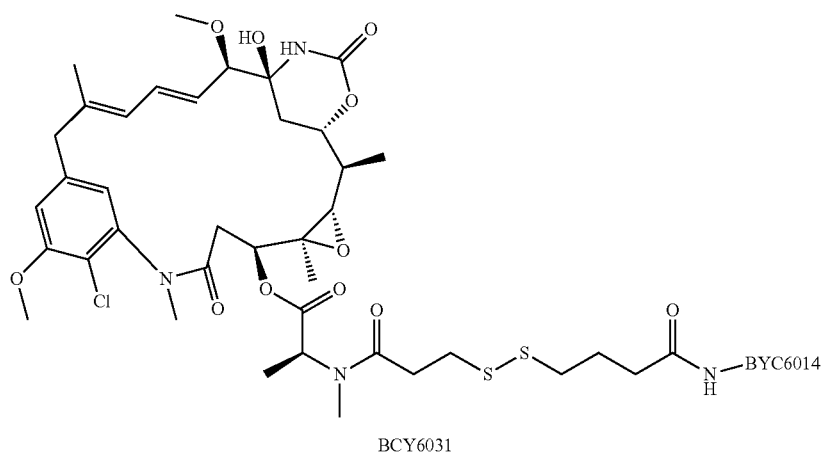

BCY6031

BCY6014 (121.07 mg, 39.82 μmol) was used as the bicycle reagent. 59.90 mg compound BCY6031 (14.67 μmol, 36.85% yield, 95.02% purity) was obtained as a white solid.

| BCY6031 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |

-continued

| BCY6031 Analytical Data | |
|---|---|
| Instrument: | Agilent 1200 HPLC-BE(1-614) |
| Method: | 35-65% B over 20 minutes, then 3 min 95% B |
| Retention Time: | 6.284 min |
| LCMS (ESI): | m/z 1286.4 [M + 3H − H2O]$^{3+}$, 965.6 [M + 4H − H2O]$^{4+}$ |
| Peptide mw | 3877.96 |

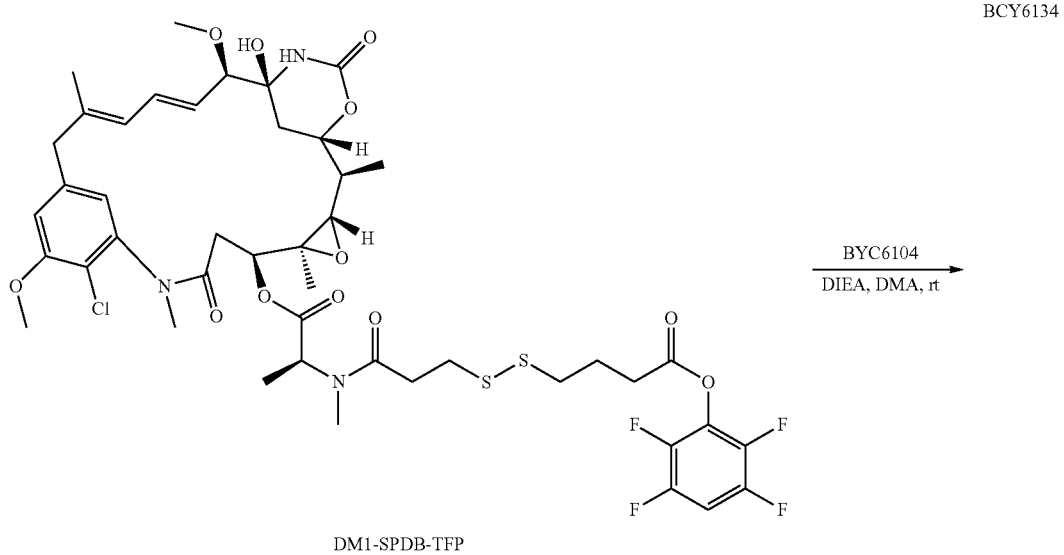
DM1-SPDB-TFP
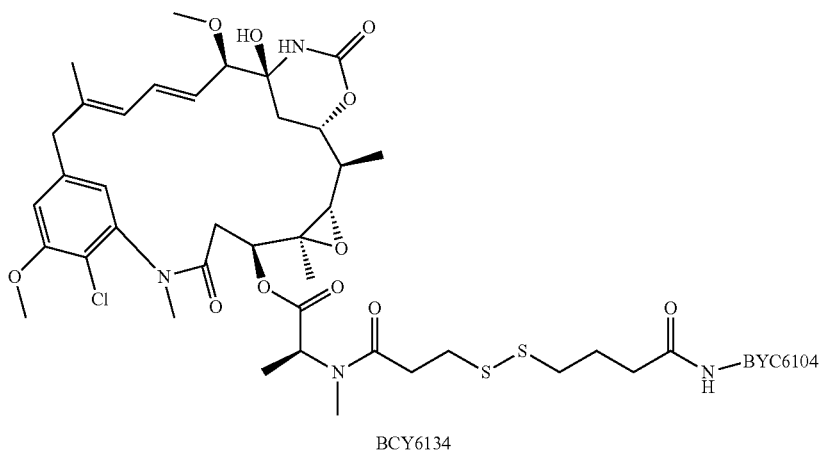
BCY6134
BCY6104 (95.11 mg, 29.87 μmol, 1 eq) was used as the bicycle reagent. BCY6134 (0.0232 g, 5.64 μmol, 18.89% yield, 97.82% purity) was obtained as a white solid.
| BCY6134 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6134 Analytical Data | |
|---|---|
| Method: | 28-68% B over 30 minutes, then 3 min 95% B |
| Retention Time: | 9.10 min |
| LCMS (ESI): | m/z 1001.8 [M + 4H − H2O]$^{4+}$ |
| Peptide mw | 4026.1 |

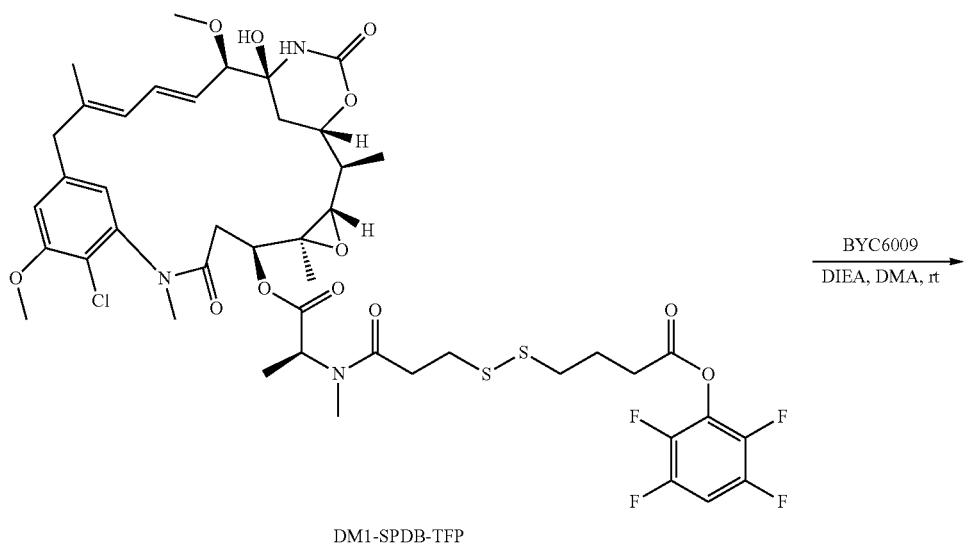

DM1-SPDB-TFP

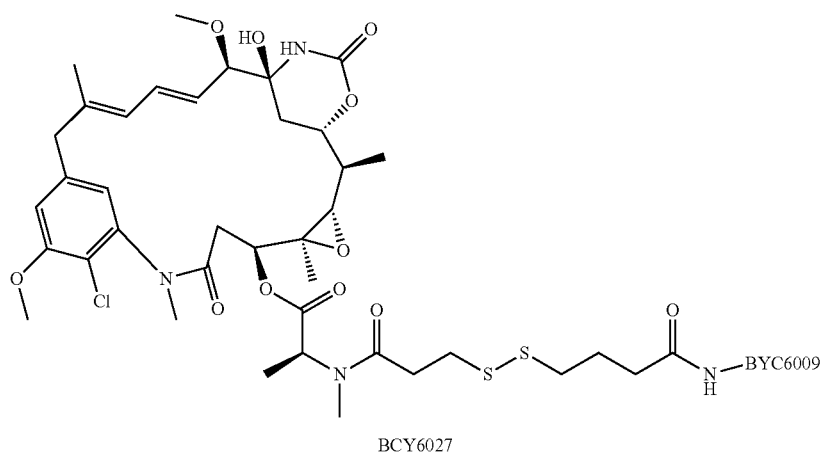

BCY6027

BCY6009 (60.24 mg, 19.91 μmol, 1.00 eq) was used as the bicycle reagent. BCY6027 (20.40 mg, 5.11 μmol, 25.69% yield, 96.88% purity) was obtained as a white solid.

| BCY6027 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6027 Analytical Data | |
|---|---|
| Method: | 35-65% B over 20 minutes, then 3 min 95% B |
| Retention Time: | 5.97 min |
| LCMS (ESI): | m/z 1932.1 $[M + 2H]^{2+}$, 1282.5 $[M + 3H - H2O]^{3+}$ |
| Peptide mw | 3863.99 |

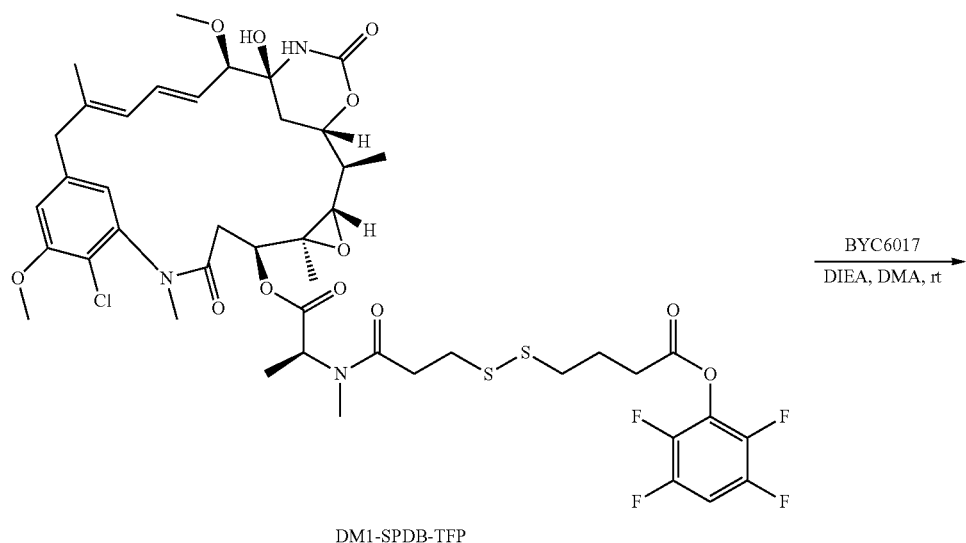

DM1-SPDB-TFP $\xrightarrow{\text{BYC6017}}_{\text{DIEA, DMA, rt}}$

BCY6047

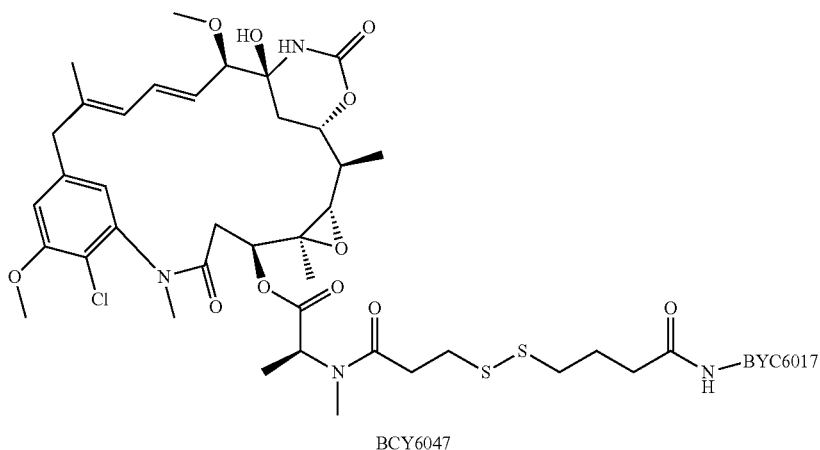

BCY6047

BCY6017 (61.81 mg, 27.38 μmol, 1.1 eq) was used as the bicycle reagent. BCY6047 (0.032 g, 10.34 μmol, 41.53% yield) was obtained as a white solid.

| BCY6047 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6047 Analytical Data | |
|---|---|
| Method: | 38-68% B over 30 minutes, then 3 min 95% B |
| Retention Time: | 12.28 min |
| LCMS (ESI): | m/z 1026.3 [M + 3H − H2O]$^{3+}$ |
| Peptide mw | 3096.1 |

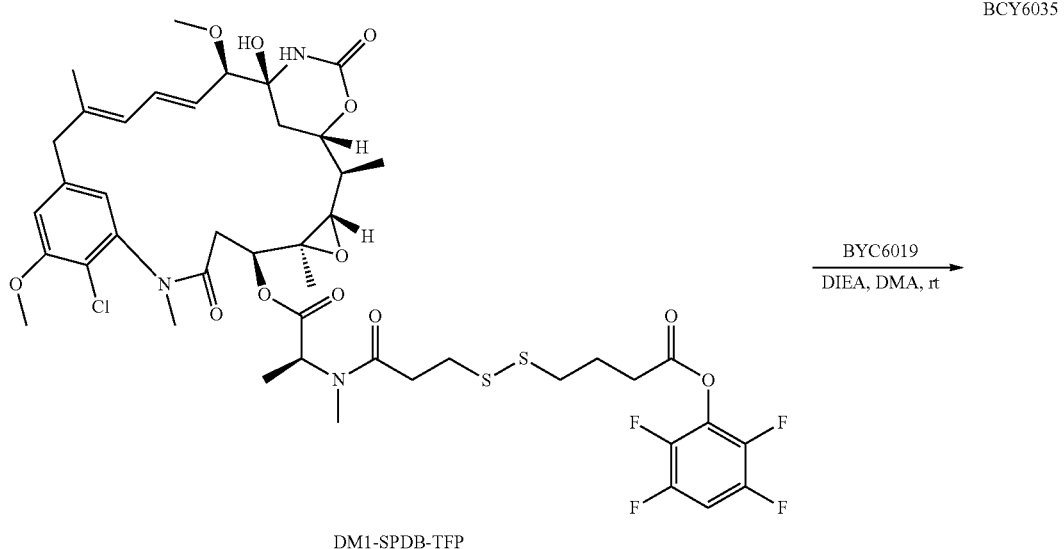

DM1-SPDB-TFP $\xrightarrow{\text{BYC6019}}$
DIEA, DMA, rt

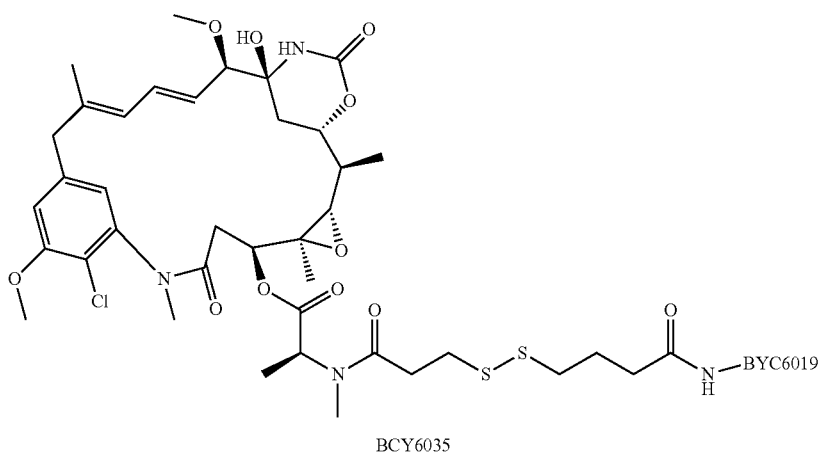

BCY6035

BCY6019 (115.22 mg, 32.86 μmol, 1.10 eq) was used as the bicycle reagent. BCY6035 (37.80 mg, 10.37 μmol, 34.73% yield) was obtained as a white solid.

| BCY6035 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6035 Analytical Data | |
|---|---|
| Method: | 35-65% B over 20 minutes, then 3 min 95% B |
| Retention Time: | 12.28 min |
| LCMS (ESI): | m/z 1208.8 [M + 3H − H2O]$^{3+}$, 911.5 [M + 4H]$^{4+}$ |
| Peptide mw | 3643.73 |

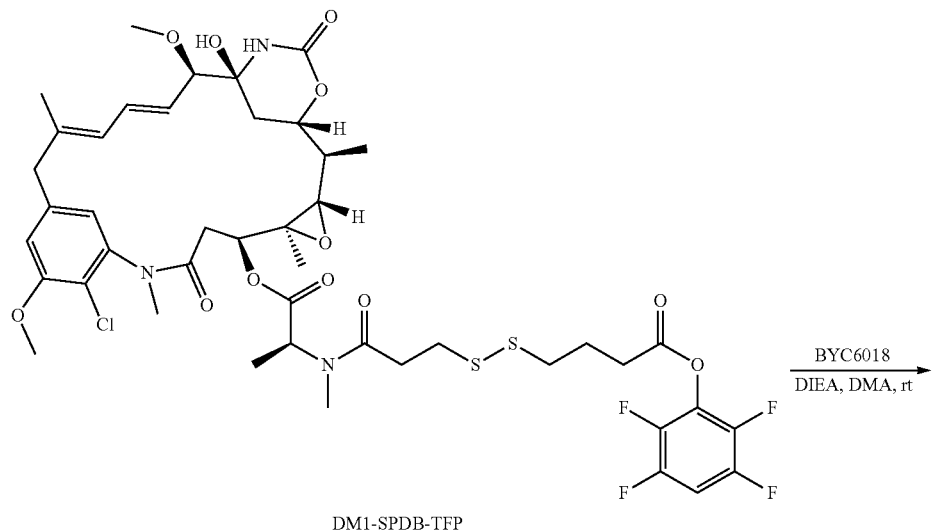
DM1-SPDB-TFP
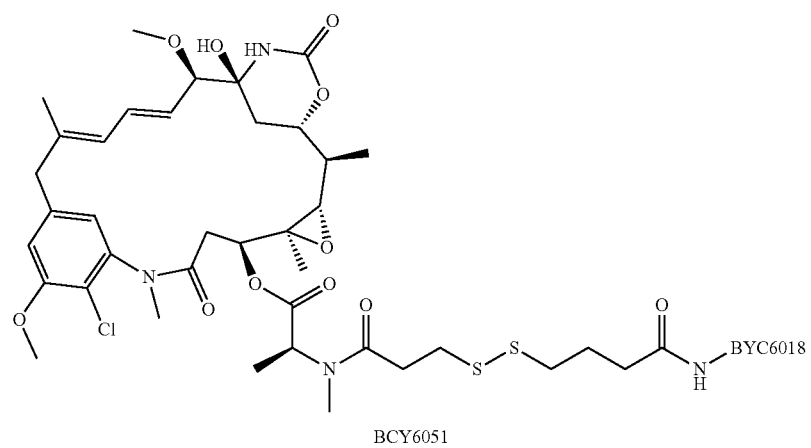
BCY6051
BCY6018 (73.48 mg, 27.38 μmol, 1.1 eq) was used as the bicycle reagent. BCY6051 (0.0582 g, 16.52 μmol, 66.39% yield) was obtained as a white solid.
| BCY6051 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
*-continued*
| BCY6051 Analytical Data | |
|---|---|
| Method: | 28-68% B over 30 minutes, then 3 min 95% B |
| Retention Time: | 11.37 min |
| LCMS (ESI): | m/z 880.5 $[M + 4H]^{4+}$ |
| Peptide mw | 3522.57 |

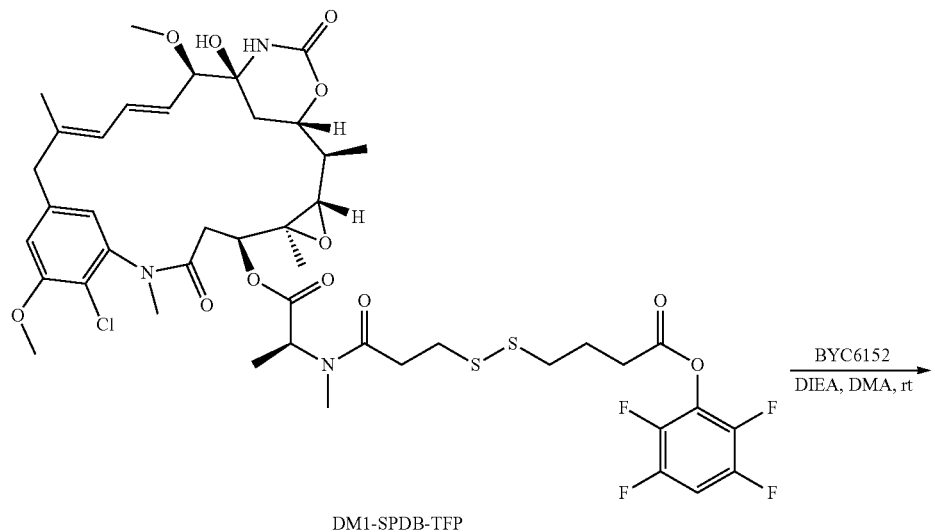

DM1-SPDB-TFP

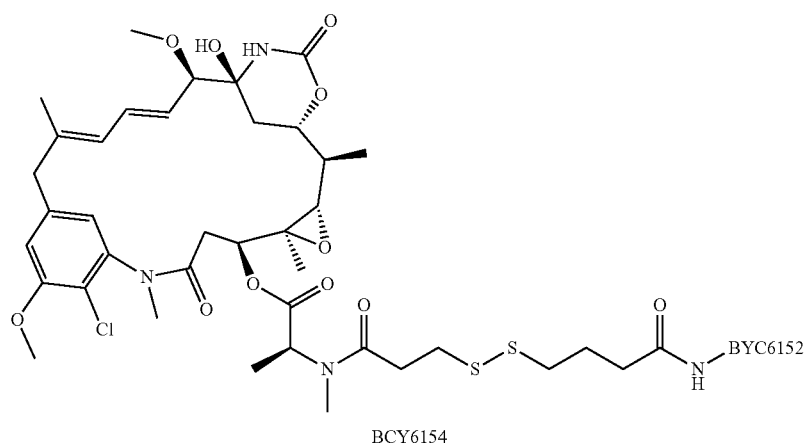

BCY6154

BCY6152 (93.17 mg, 29.87 μmol, 1 eq) was used as the bicycle reagent. BCY6154 (40.10 mg, 9.93 μmol, 33.27% yield, 98.06% purity) was obtained as a white solid.

| BCY6154 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6154 Analytical Data | |
|---|---|
| Method: | 28-68% B over 30 minutes, then 3 min 95% B |
| Retention Time: | 11.94 min |
| LCMS (ESI): | m/z 1313.8 [M + 3H − H2O]$^{3+}$, 985.8 [M + 4H − H2O]$^{4+}$ |
| Peptide mw | 3958.02 |

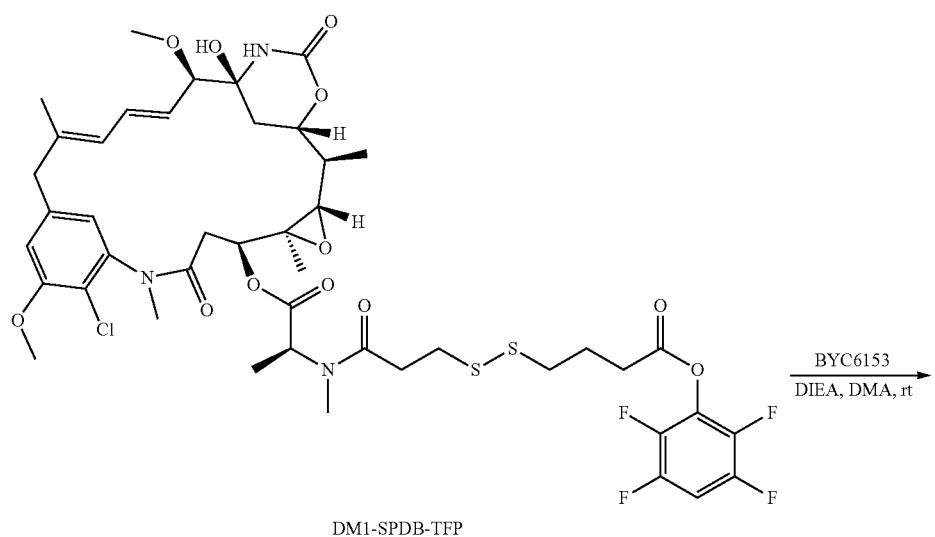
DM1-SPDB-TFP
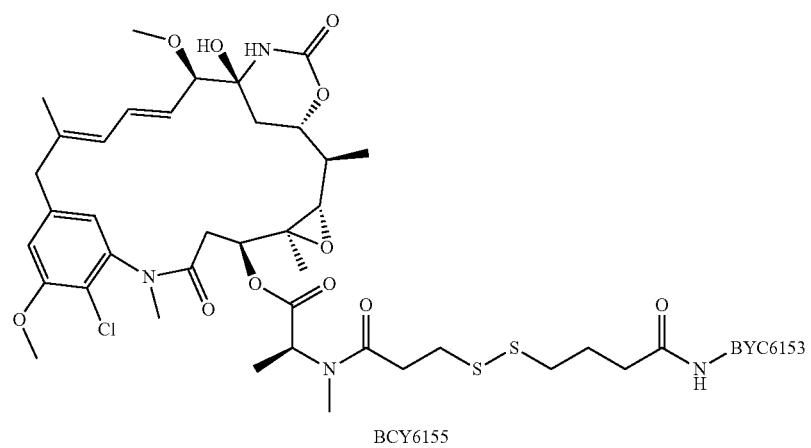
BCY6155
BCY6153 (82.55 mg, 29.87 μmol, 1 eq) was used as the bicycle reagent. BCY6155 (0.0312 g, 8.55 μmol, 28.62% yield, 98.69% purity) was obtained as a white solid.
| BCY6155 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6155 Analytical Data | |
|---|---|
| Method: | 28-68% B over 30 minutes, then 3 min 95% B |
| Retention Time: | 12.93 min |
| LCMS (ESI): | m/z 897.1 [M + 4H − H2O]$^{4+}$ |
| Peptide mw | 3602.63 |

DM1-SS(SO3H)-Series
DM1-SPDP(SO3H)-NHS Linker
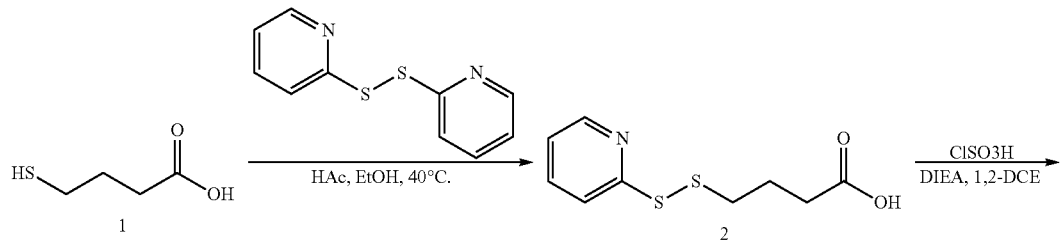
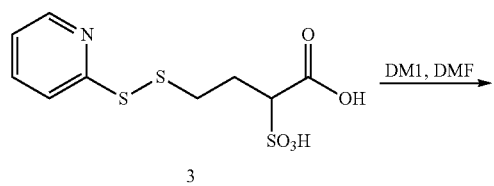
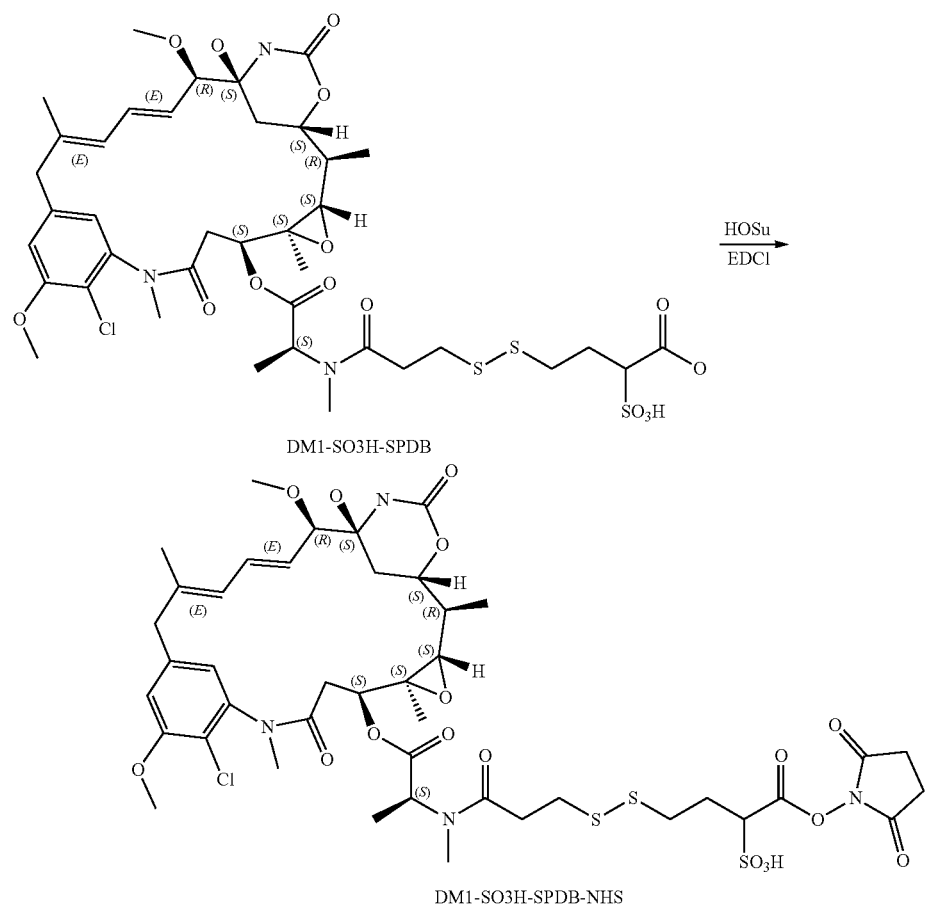

Compound 2

To a solution of 4-sulfanylbutanoic acid (2.0 g, 16.64 mmol, 1 eq) and 2-(2-pyridyldisulfanyl)pyridine (11.0 g, 49.93 mmol, 3 eq) in EtOH (50 mL) was added AcOH (1.05 g, 17.48 mmol, 1 mL, 1.05 eq). The mixture was stirred at 40° C. for 16 hr under $N_2$. LC-MS showed one main peak with desired mass was detected and TLC indicated 4-sulfanylbutanoic acid was consumed completely. The reaction mixture was concentrated under reduced pressure to remove solvent to give a residue. The residue was purified by preparative HPLC (neutral condition). Compound 2 (2.0 g, 8.72 mmol, 52.4% yield) was obtained as yellow solid.

$^1$H NMR: 400 MHz CDCl$_3$

δ ppm 2.03-2.11 (m, 2H), 2.54 (t, J=7.20 Hz, 2H), 2.88 (t, J=7.20 Hz, 2H), 7.11-7.14 (m, 1H), 7.67-7.74 (m, 2H), 8.50 (d, J=4.80 Hz, 1H).

| LCMS (ESI): | 230 [M + H]$^+$ |
|---|---|
| Molecular weight | 229.31 |

Compound 3

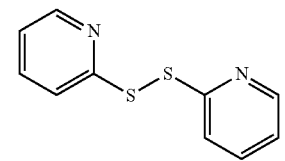

To a solution of compound 2 (0.5 g, 2.18 mmol, 1 eq) in DCE (5 mL) was added chlorosulfonic acid (1.5 g, 13.08 mmol, 0.89 mL, 6 eq) in three portions and DIEA (1.13 g, 8.72 mmol, 1.52 mL, 4 eq) in two portions. The mixture was stirred at 75° C. for 2 hr. LC-MS showed compound 2 was consumed completely and one main peak with desired mass was detected. The reaction mixture was quenched by addition 3 mL of H$_2$O and the DCE was removed. The residue was The mixture was directly purified by preparative HPLC (neutral conditions). Compound 3 (0.68 g, 1.76 mmol, 80.6% yield, 80% purity) was obtained as light yellow oil.

$^1$H NMR: 400 MHz CDCl$_3$

δ ppm 2.49-2.54 (m, 2H), 3.63-3.67 (m, 2H), 3.90 (t, J=6.60 Hz, 2H), 7.09-7.12 (m, 1H), 7.66-7.76 (m, 2H), 8.47 (dd, J=4.80 Hz, 0.80 Hz, 1H), 8.56 (s, 1H).

| LCMS (ESI): | 310.0 [M + H]$^+$ |
|---|---|
| Molecular weight | 309.37 |

DM1-SO$_3$H-SPDB

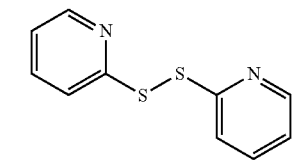

DM1-SO3H-SPDB

To a solution of DM1 (1.0 g, 1.35 mmol, 1 eq) and compound 3 (502.9 mg, 1.63 mmol, 1.2 eq) in DMF (10 mL) was added NaHCO$_3$(aq) until the pH reached 8. The mixture was stirred at 25° C. for 1 hr. LC-MS showed DM1 was consumed completely and one main peak with desired mass was detected. The residue was The mixture was directly purified by preparative HPLC (neutral condition). Compound DM1-SO$_3$H-SPDB (0.28 g, 299.0 μmol, 22.1% yield) was obtained as a white solid.

| LCMS (ESI): | 918.2 [M + H − H$_2$O]$^+$ |
|---|---|
| Molecular weight | 936.50 |

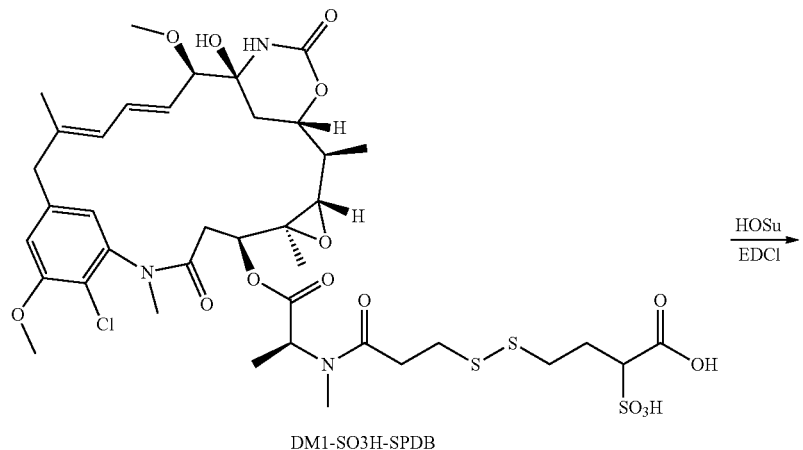

DM1-SO3H-SPDB $\xrightarrow[\text{EDCl}]{\text{HOSu}}$

DM1-SO$_3$H-SPDB-NHS

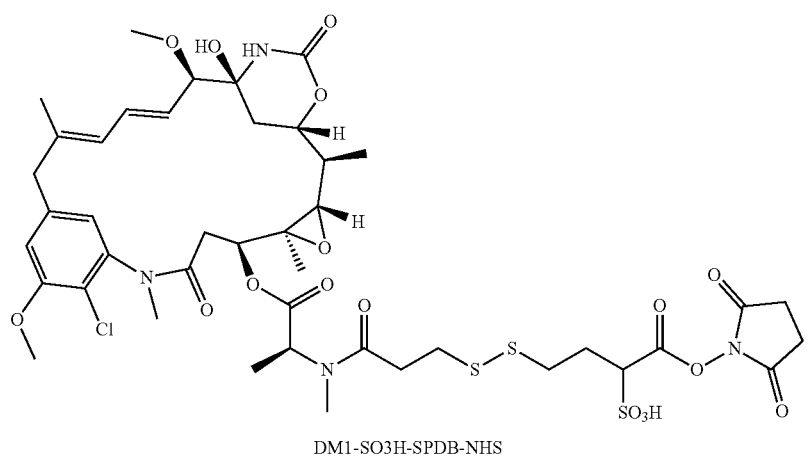

DM1-SO3H-SPDB-NHS

To a solution of DM1-SO$_3$H-SPDB (103.2 mg, 896.95 μmol, 3 eq), 1-Hydroxypyrrolidine-2,5-dione (103.2 mg, 896.95 μmol, 3 eq) in DMA (6 mL) and DCM (2 mL) was added EDCI (171.9 mg, 896.95 μmol, 3 eq). The mixture was stirred at 25° C. for 16 hr. LC-MS showed DM1-SO$_3$H-SPDB was consumed completely and one main peak with desired mass was detected. DCM was removed. The residue was The mixture was directly purified by preparative HPLC (neutral condition). Compound DM1-SO$_3$H-SPDB-NHS (0.22 g, 212.85 μmol, 71.2% yield) was obtained as a white solid.

| LCMS (ESI): | 1015.2 [M + H − H$_2$O]$^+$ |
|---|---|
| Molecular weight | 1033.57 |

General Procedure for Coupling DM1-SO$_3$H-SPDB-NHS with Targeting Bicycles

To a solution of targeting Bicycle (1.1-1.3 eq) in DMA was added DIEA (3 eq) and DM1-SO$_3$H-SPDB-NHS (1 eq). The mixture was stirred at 25° C. for 16 hr. The reaction was monitored by LC-MS and once complete, the mixture was directly purified by preparative HPLC.

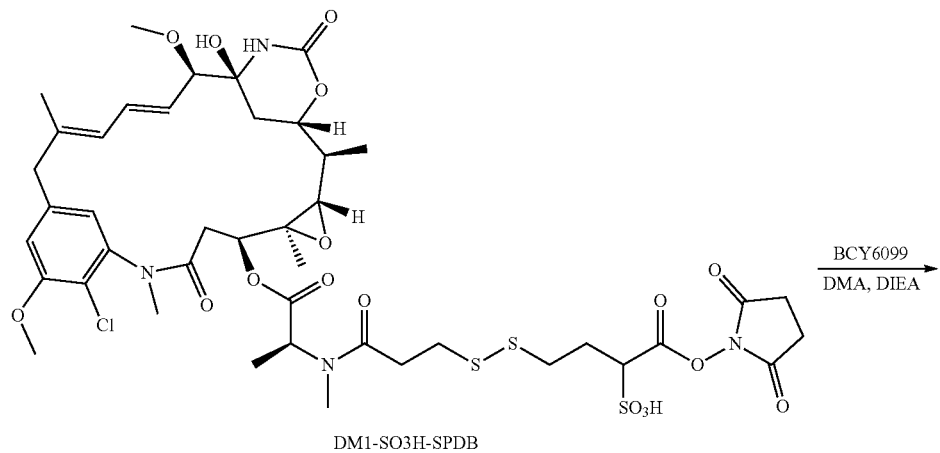
DM1-SO3H-SPDB

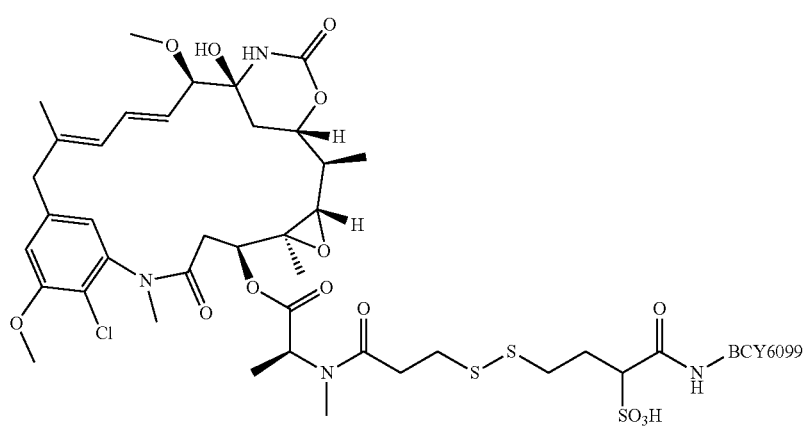
BCY6173

BCY6099 (200.15 mg, 62.89 μmol) was used as the bicycle reagent. 57.1 mg compound BCY6173 (3.40 μmol, 22.79% yield, 95.80% purity) was obtained as a white solid.

BCY6173 Analytical Data

| | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

BCY6173 Analytical Data

| | |
|---|---|
| Method: | 28-68% B over 30 minutes, then 3 min 95% B |
| Retention Time: | 10.30 min |
| LCMS (ESI): | m/z 1361.9 [M + 3H − H2O]$^{3+}$, 1021.8 [M + 4H − H2O]$^{4+}$ |
| Peptide mw | 4101.15 |

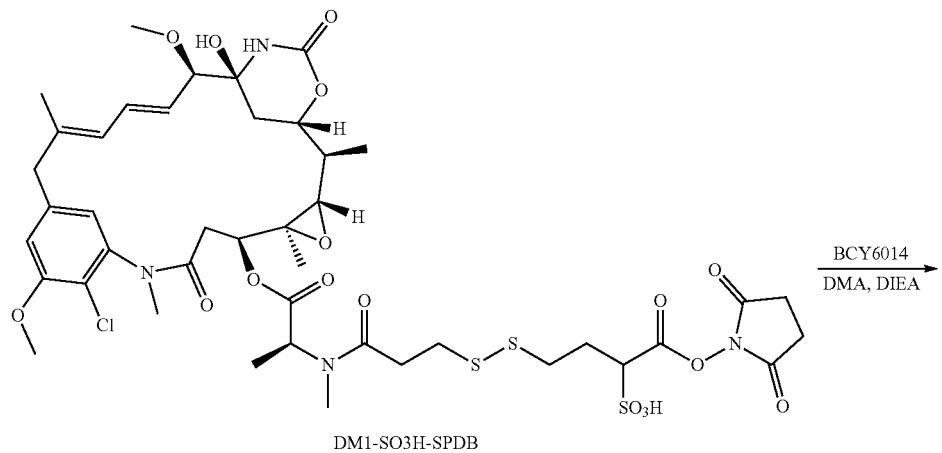

DM1-SO3H-SPDB → BCY6014 / DMA, DIEA → BCY6082

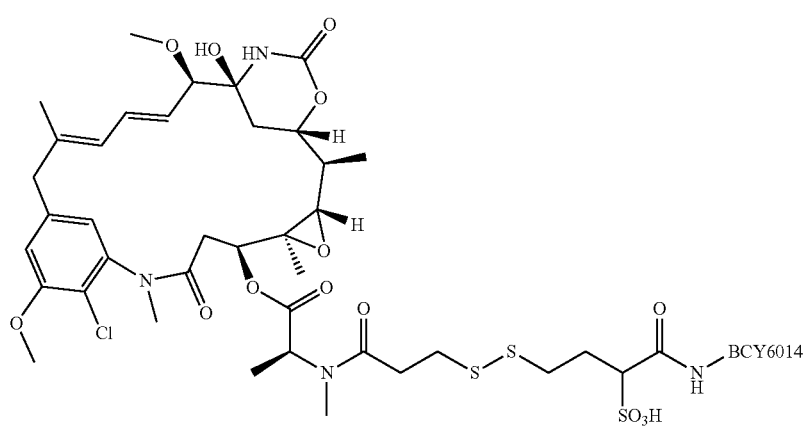

BCY6082

BCY6014 (711.9 mg, 234.14 μmol) was used as the bicycle reagent. 308 mg compound BCY6082 (74.97 μmol, 35.2% yield, 96.36% purity) was obtained as a white solid.

| BCY6082 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |

-continued

| BCY6082 Analytical Data | |
|---|---|
| Method: | 28-68% B over 30 minutes, then 3 min 95% B |
| Retention Time: | 11.95 min |
| LCMS (ESI): | m/z 1299.3 [M + 3H − H2O]$^{3+}$, 975.0 [M + 4H − H2O]$^{4+}$ |
| Peptide mw | 3911.04 |

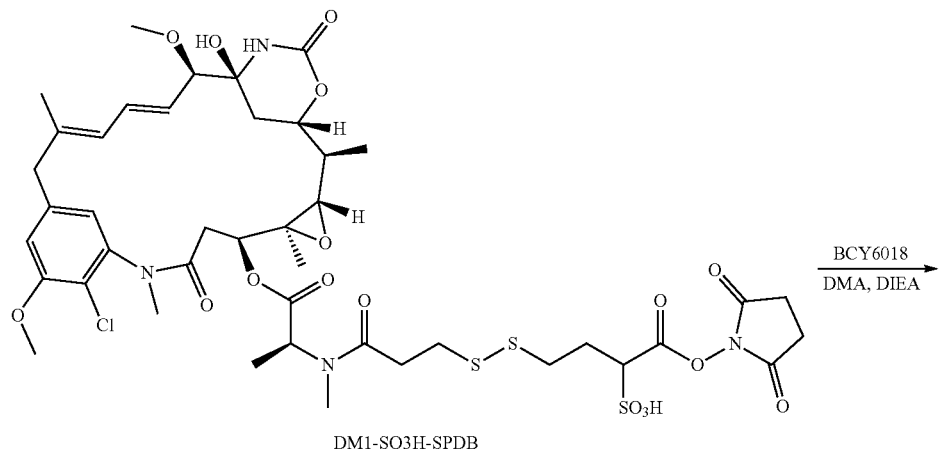
DM1-SO3H-SPDB
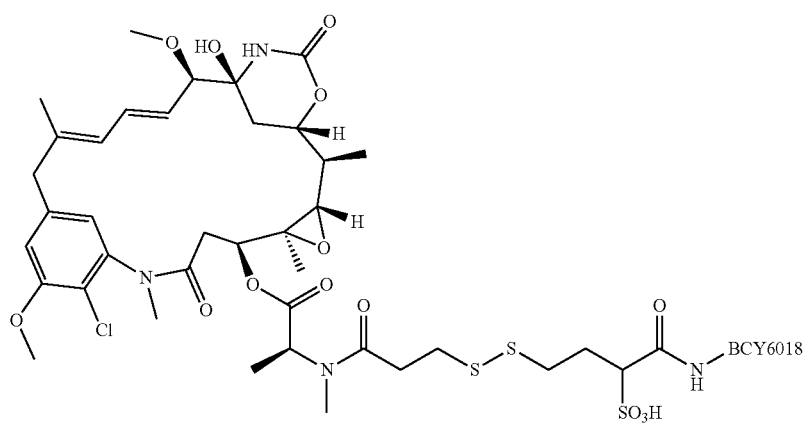
BCY6150
BCY6018 (77.91 mg, 29.03 μmol, 1 eq) was used as the bicycle reagent. BCY6150 (0.0249 g, 6.61 μmol, 22.78% yield) was obtained as a white solid.
| BCY6150 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6150 Analytical Data | |
|---|---|
| Method: | 28-68% B over 30 minutes, then 3 min 95% B |
| Retention Time: | 12.31 min |
| LCMS (ESI): | m/z 1195.4 [M + 3H − H2O]$^{3+}$ |
| Peptide mw | 3602.63 |

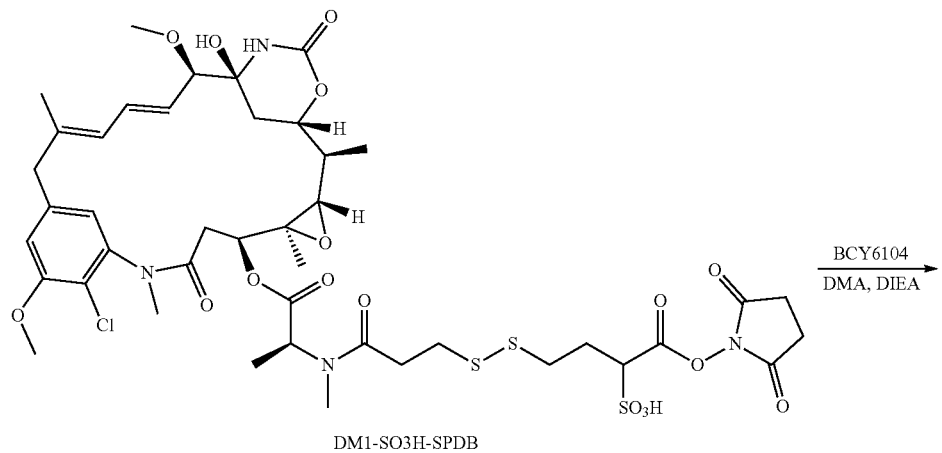
DM1-SO3H-SPDB
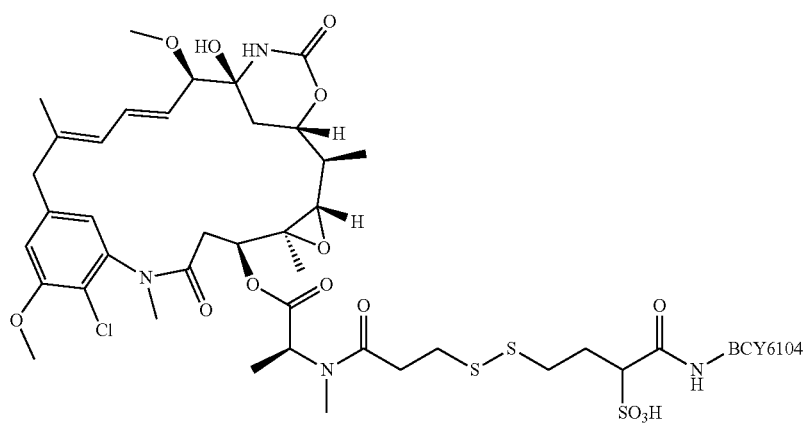
BCY6151
BCY6104 (120.17 mg, 37.73 μmol, 1.3 eq) was used as the bicycle reagent. BCY6151 (0.0256 g, 6.16 μmol, 21.22% yield) was obtained as a white solid.
| BCY6151 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6151 Analytical Data | |
|---|---|
| Method: | 28-68% B over 30 minutes, then 3 min 95% B |
| Retention Time: | 8.68 min |
| LCMS (ESI): | m/z 1362.3 [M + 3H − H2O]$^{3+}$ |
| Peptide mw | 4105.16 |

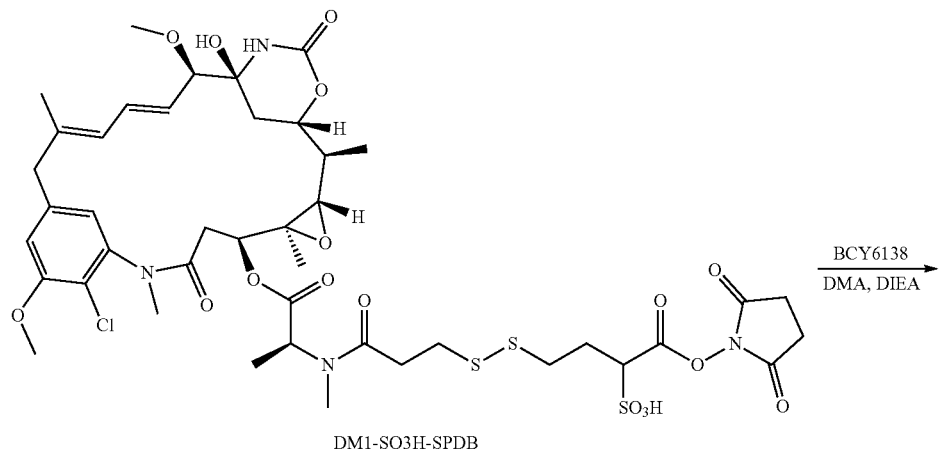
DM1-SO3H-SPDB → BCY6138 / DMA, DIEA → BCY6162
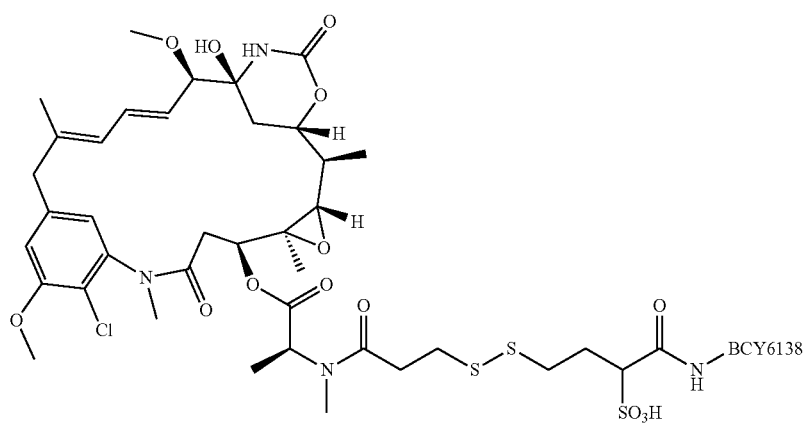
BCY6162
BCY6138 (82.80 mg, 26.61 μmol, 1.1 eq) was used as the bicycle reagent. BCY6162 (0.0362 g, 8.98 μmol, 37.13% yield) was obtained as a white solid.
| BCY6162 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 28-68% B over 30 minutes, then 3 min 95% B |
| Retention Time: | 21.09 min |
| LCMS (ESI): | m/z 1323.5 [M + 3H − H2O − 44]$^{3+}$ |
| Peptide mw | 4026.74 |

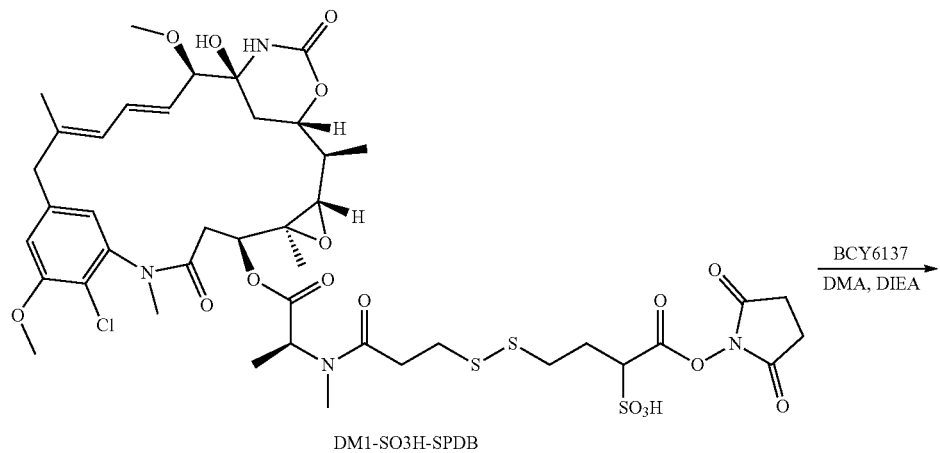
DM1-SO3H-SPDB
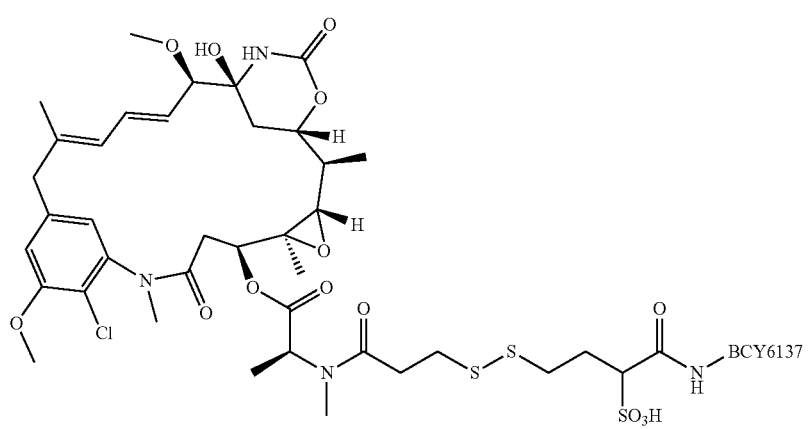
BCY6161
BCY6137 (79.67 mg, 24.48 μmol, 1.1 eq) was used as the bicycle reagent. BCY6161 (0.0232 g, 5.26 μmol, 21.76% yield) was obtained as a white solid.
| BCY6161 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6161 Analytical Data | |
|---|---|
| Method: | 28-68% B over 30 minutes, then 3 min 95% B |
| Retention Time: | 10.22 min |
| LCMS (ESI): | m/z 1392 [M + 3H − H2O]$^{3+}$ |
| Peptide mw | 4192.33 |

DM1-SS-Me Series
DM1-SS-Me Linker
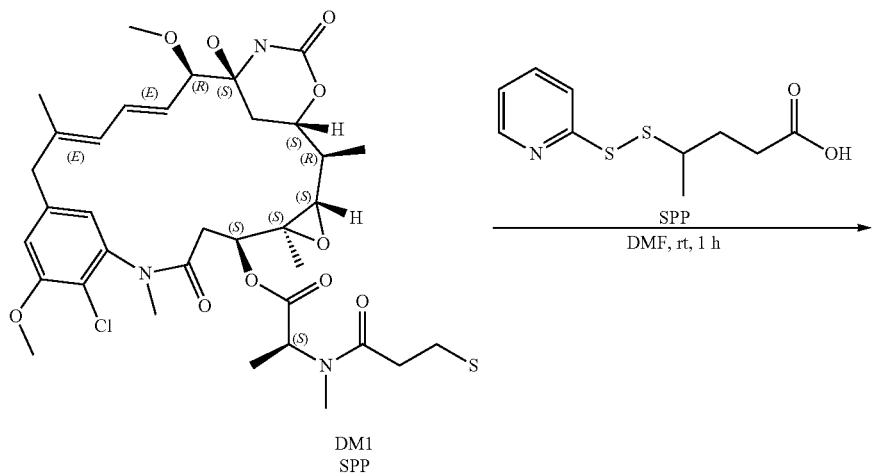
DM1
SPP
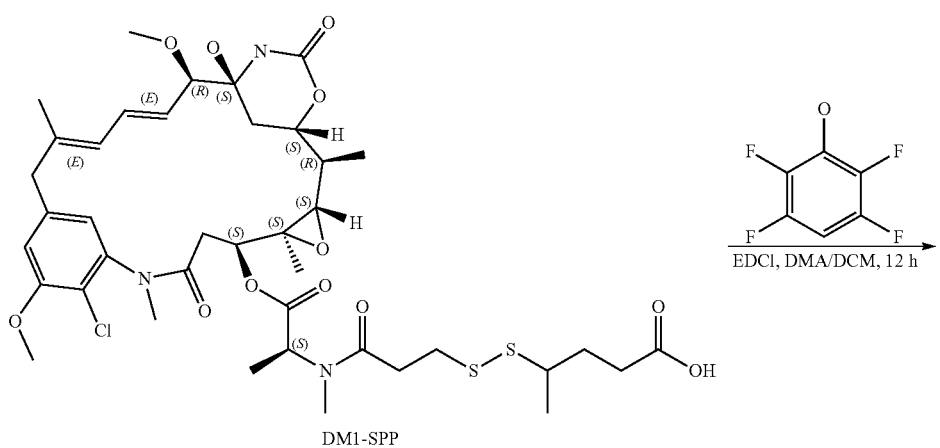
DM1-SPP
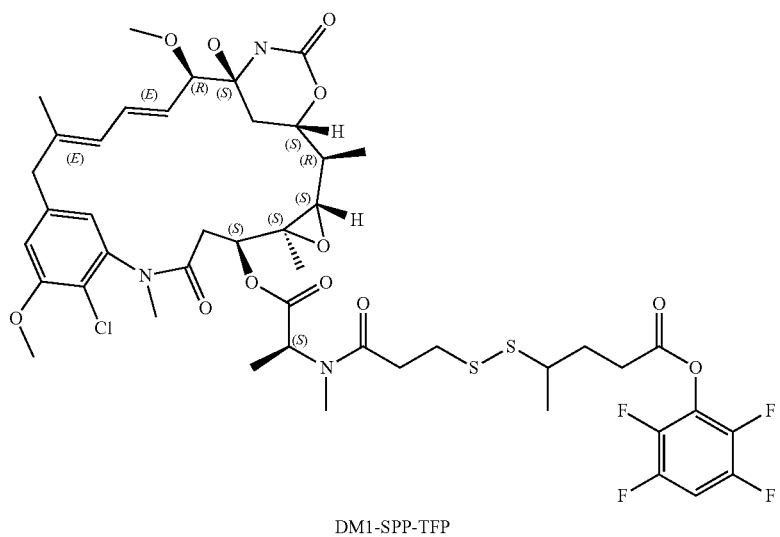
DM1-SPP-TFP

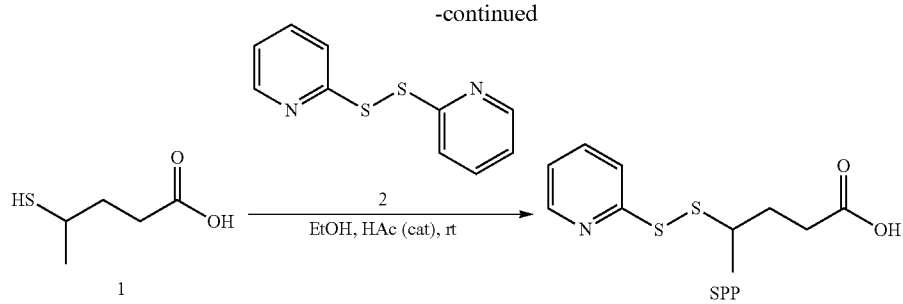

To a solution of 2-(2-pyridyldisulfanyl)pyridine (2.46 g, 11.18 mmol, 1.50 eq) and AcOH (1.05 g, 17.49 mmol, 1.00 mL, 2.35 eq) in EtOH (50.00 mL) was added 4-sulfanylpentanoic acid (1.00 g, 7.45 mmol, 1.00 eq). The mixture was stirred at 40° C. for 18 hours under $N_2$. LC-MS showed compound 1 was consumed completely and one main peak with desired mass was detected. The reaction mixture was concentrated under reduced pressure to remove solvent to give a residue. The residue was purified by preparative HPLC (neutral condition). Compound SPP (1.61 g, 6.62 mmol, 88.81% yield) was obtained as a yellow solid.

$^1$H NMR: 400 MHz DMSO-$d_6$

δ ppm 1.36 (d, J=6.78 Hz, 3H), 1.88-2.07 (m, 2H), 2.56 (td, J=7.53, 1.76 Hz, 2H), 3.00-3.09 (m, 1H), 7.11 (ddd, J=7.34, 4.96, 1.00 Hz, 1H), 7.66 (td, J=7.78, 1.76 Hz, 1H), 7.73-7.77 (m, 1H), 8.48 (dt, J=4.02, 0.88 Hz, 1H).

| LCMS (ESI): | 243.8 [M + H]$^+$ |
|---|---|
| Molecular weight | 243.34 |

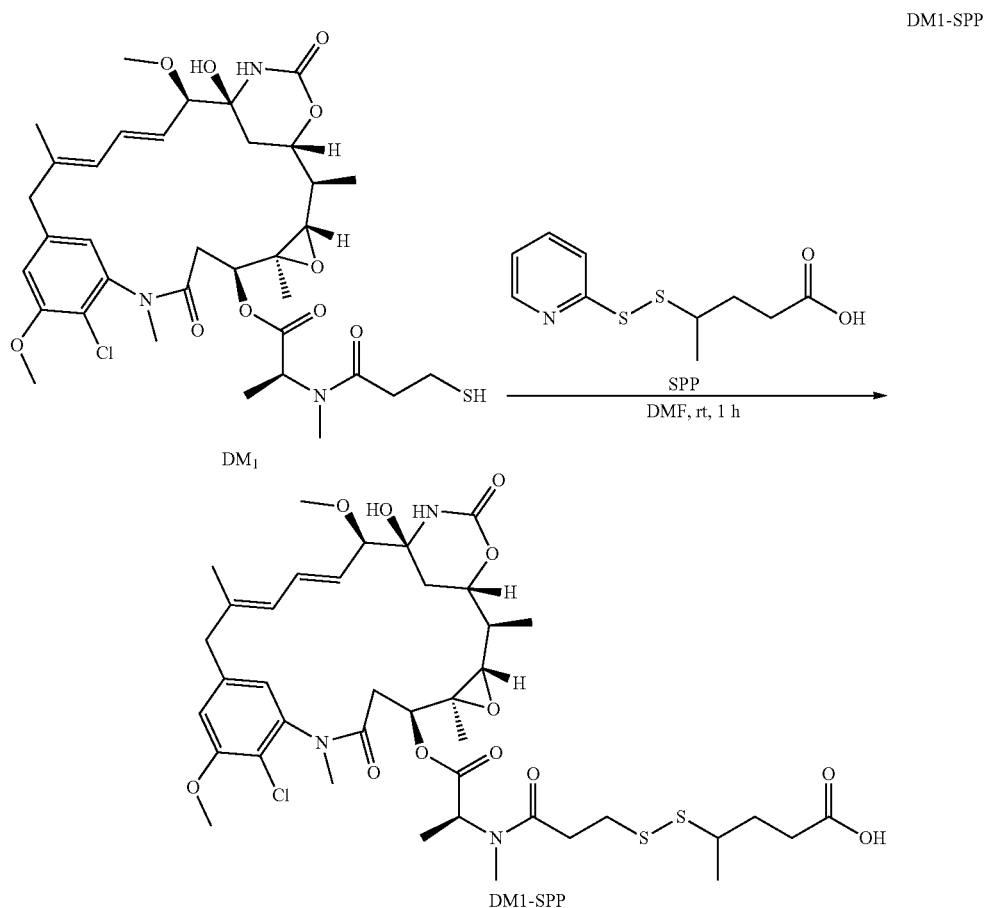

A solution of DM1 (200 mg, 270.90 μmol, 1.00 eq), 4-(2-pyridyldisulfanyl)pentanoic acid (98.89 mg, 406.35 μmol, 1.50 eq) in $H_2O$ (5.00 mL) was adjusted PH=8 using NaHCO$_3$ (aq). The mixture was stirred at 15° C. for 1 hour. LC-MS showed DM1 was consumed completely and one main peak with desired mass was detected (main MS was M+1-18). The mixture was directly purified by preparative HPLC (neutral condition). Compound DM1-SPP (120 mg, 137.86 μmol, 50.89% yield) was obtained as a white solid.

| LCMS (ESI): | 852.0 [M + H − H₂O]⁺ |
|---|---|
| Molecular weight | 870.47 |

DM1-SPP-TFP (0.123 g, 120.76 μmol, 60.07% yield) was obtained as a white solid.

| LCMS (ESI): | 999.9 [M + H − H₂O]⁺ |
|---|---|
| Molecular weight | 1018.53 |

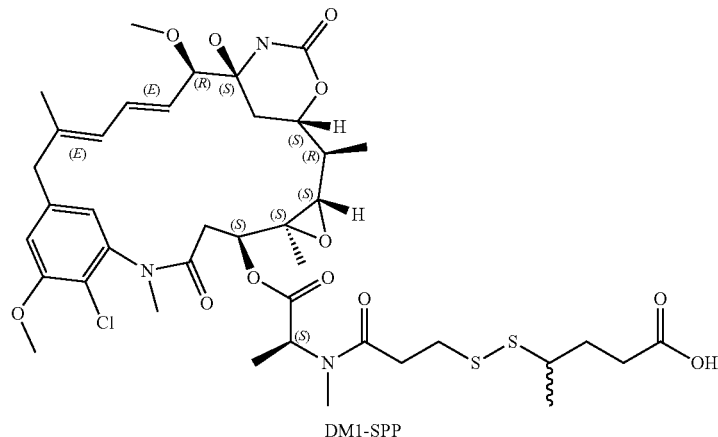

DM1-SPP

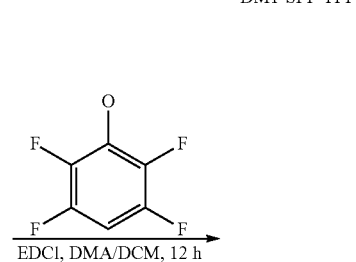

DM1-SPP-TFP

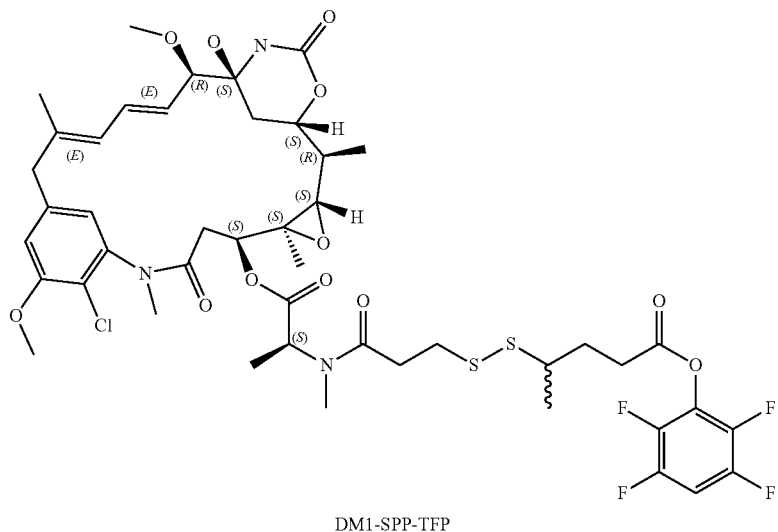

DM1-SPP-TFP

To a solution of DM1-SPP (0.175 g, 201.04 μmol, 1.0 eq), 2,3,5,6-tetrafluorophenol (100.16 mg, 603.13 μmol, 3.0 eq) in DCM (1.0 mL) and DMA (3.0 mL) was added EDCI (115.62 mg, 603.13 μmol, 3.0 eq). The mixture was stirred at 15° C. for 12 hour. LC-MS showed DM1-SPP was consumed completely and one main peak with desired MS was detected. The DCM was removed and the residue was purified by prep-HPLC (neutral condition). Compound General Procedure for Coupling DM1-SPP-TFP with Targeting Bicycles To a solution of targeting Bicycle (1.1-1.3 eq) in DMA was added DIEA (3 eq) and DM1-SPP-TFP (1 eq). The mixture was stirred at 25° C. for 16 hr. The reaction was monitored by LC-MS and once complete, the mixture was directly purified by preparative HPLC.

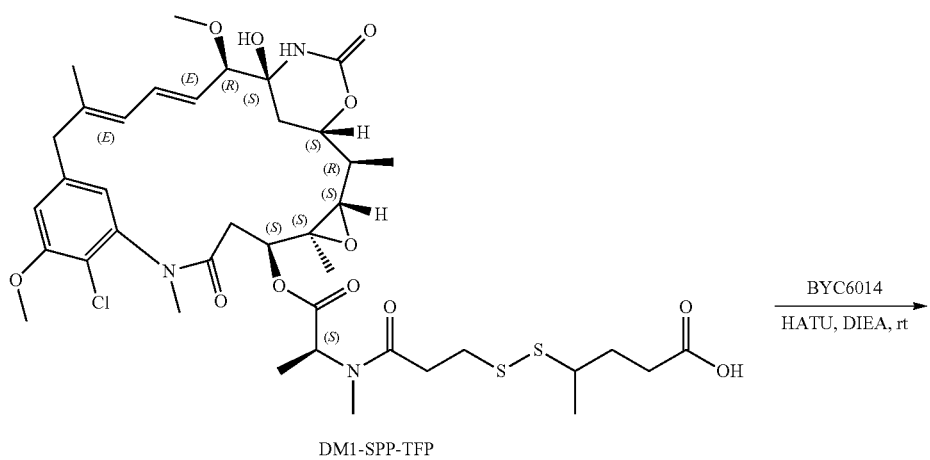

DM1-SPP-TFP

BCY6032

→ BYC6014
HATU, DIEA, rt

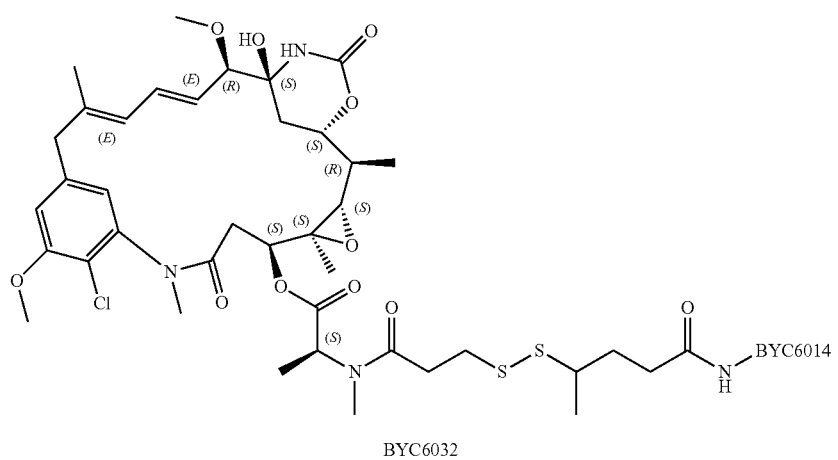

BYC6032

To a solution of DM1-SPP (30.00 mg, 34.46 μmol, 1.00 eq) in DMF (5.00 mL) was added DIEA (13.36 mg, 103.38 μmol, 18.05 μL, 3.00 eq) and HATU (13.10 mg, 34.46 μmol, 1.00 eq). After 1 h, BCY6014 (104.79 mg, 34.46 μmol, 1.00 eq) was added and the mixture was stirred at 15° C. for 2 hours. LC-MS showed 40% of DM1-SPP was remained. Several new peaks were observed on LC-MS and 20% of desired compound was detected. The mixture was directly purified by preparative HPLC (TFA condition). Compound BCY6032 (10.00 mg, 2.57 μmol, 7.45% yield) was obtained as a white solid.

| BCY6032 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 25-55% B over 20 minutes, then 3 min 95% B |
| Retention Time: | 13.38 min |
| LCMS (ESI): | m/z 1292.1 [M + 3H − H2O]$^{3+}$, 969.0 [M + 4H − H2O]$^{4+}$ |
| Peptide mw | 3892.94 |

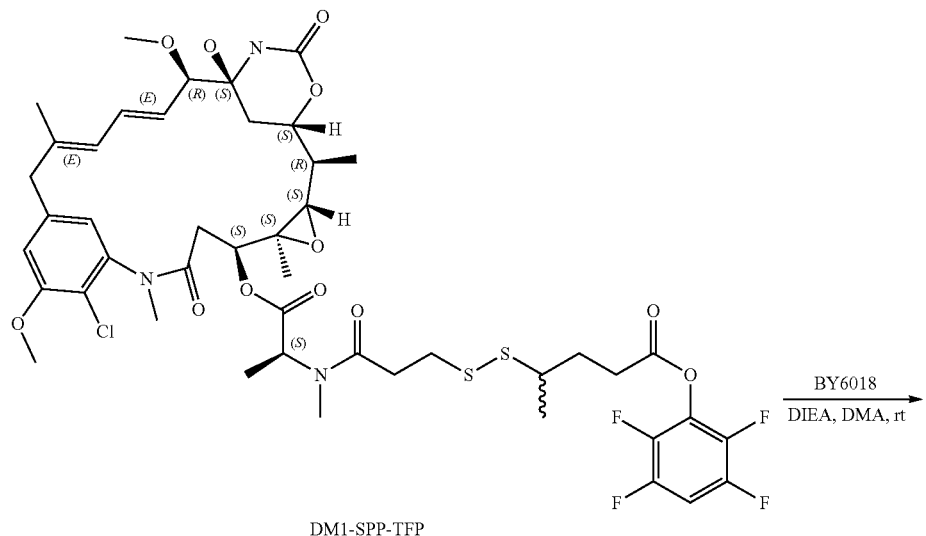

DM1-SPP-TFP → BY6018 / DIEA, DMA, rt → BCY6052

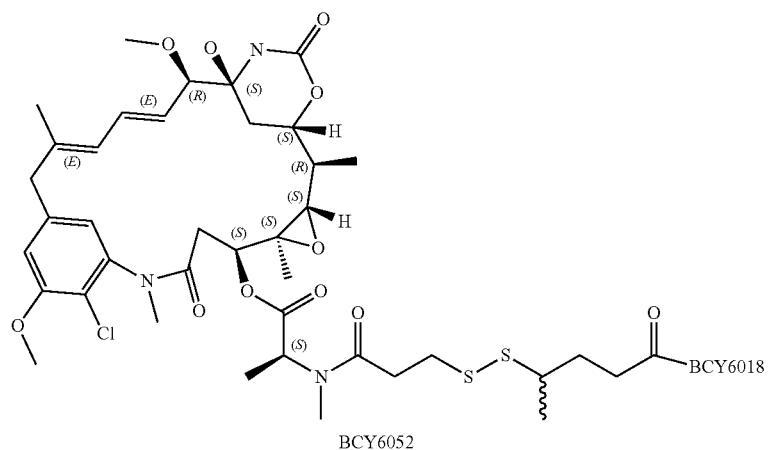

BCY6052

BCY6018 (86.96 mg, 32.40 μmol, 1.1 eq) was used as the bicycle reagent. BCY6052 (32.30 mg, 9.13 μmol, 31.01% yield) was obtained as a white solid.

| BCY6052 Analytical Data | |
|---|---|
| Mobile Phase: | A: 0.1% Formic acid in H2O B: ACN |
| Flow: | 1.0 ml/min |
| Column: | Eclipse XDB-Phenyl 3.5 um 100 * 3.0 mm |
| Instrument: | Agilent 1200 HPLC-BE(1-614) |
| Method: | 35-65% B over 20 minutes, then 3 min 95% B |

-continued

| BCY6052 Analytical Data | |
|---|---|
| Retention Time: | 6.96 min |
| LCMS (ESI): | m/z 1173.4 $[M + 3H - H2O]^{3+}$, 884.6 $[M + 4H]^{4+}$ |
| Peptide mw | 3536.58 |

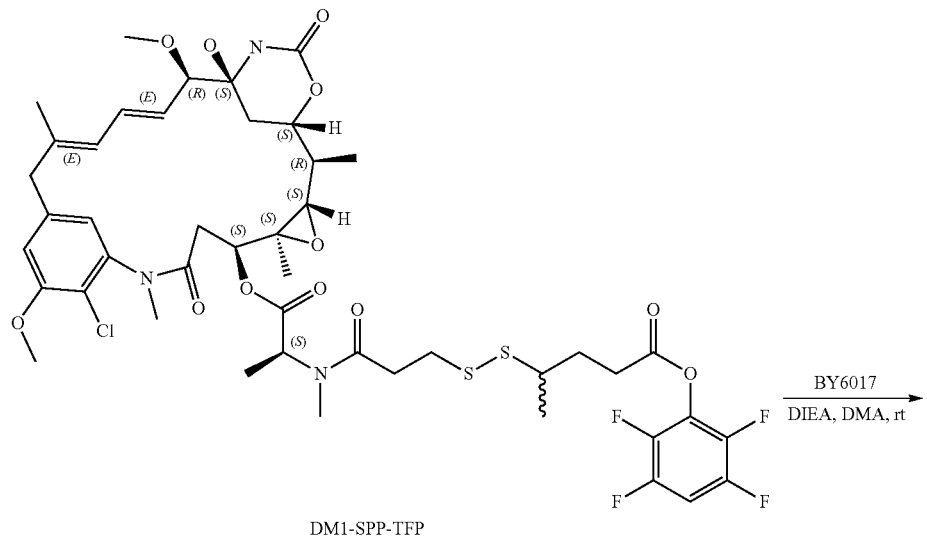

DM1-SPP-TFP → BY6017 / DIEA, DMA, rt

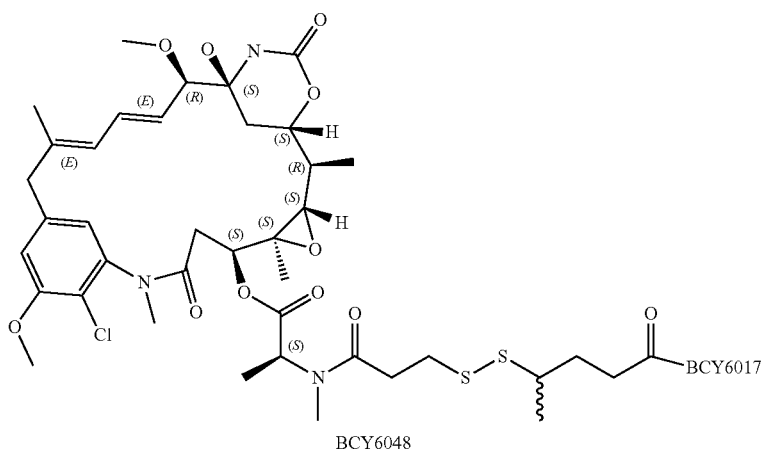

BCY6048

BCY6017 (66.50 mg, 29.45 µmol, 1.2 eq) was used as the bicycle reagent. BCY6048 (40.80 mg, 13.12 µmol, 53.45% yield) was obtained as a white solid.

| BCY6048 Analytical Data | |
|---|---|
| Mobile Phase: | A: 0.1% Formic acid in H2O B: ACN |
| Flow: | 1.0 ml/min |
| Column: | Eclipse XDB-Phenyl 3.5 um 100 * 3.0 mm |
| Instrument: | Agilent 1200 HPLC-BE(1-614) |
| Method: | 35-65% B over 20 minutes, then 3 min 95% B |

-continued

| BCY6048 Analytical Data | |
|---|---|
| Retention Time: | 7.56 min |
| LCMS (ESI): | m/z 1031.0 $[M + 3H - H2O]^{3+}$, 884.6 $[M + 4H]^{4+}$ |
| Peptide mw | 3110.13 |

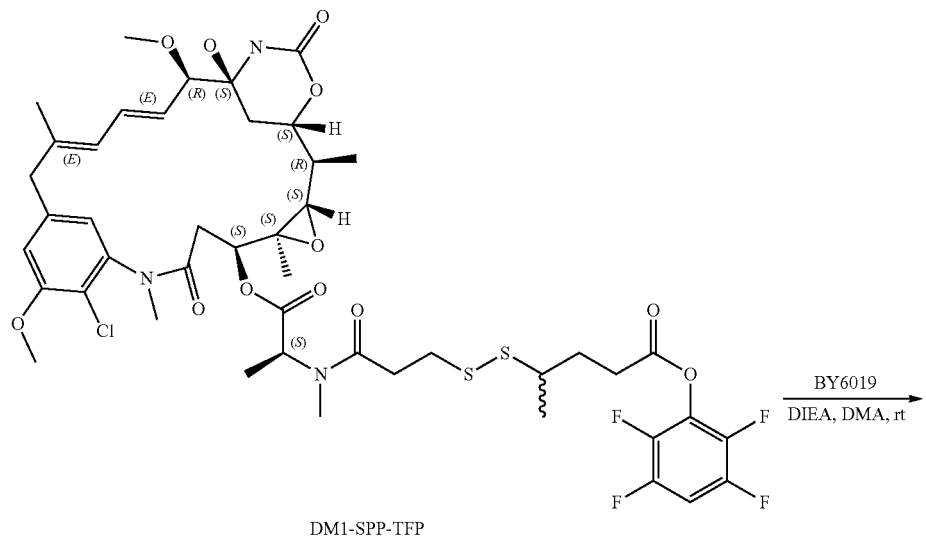
DM1-SPP-TFP → BY6019, DIEA, DMA, rt
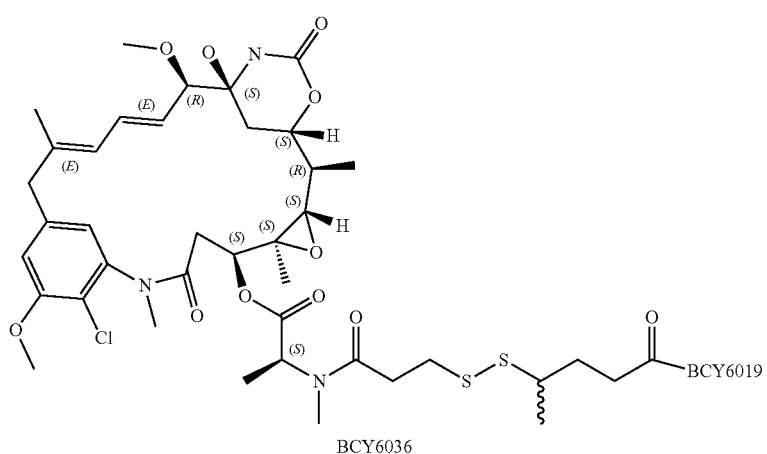
BCY6036
BCY6019 (113.60 mg, 32.40 μmol, 1.10 eq) was used as the bicycle reagent. BCY6036 (53.20 mg, 14.00 μmol, 47.54% yield, 96.26% purity) was obtained as a white solid.
| BCY6036 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
| Method: | 35-65% B over 20 minutes, then 3 min 95% B |
| Retention Time: | 8.19 min |
| LCMS (ESI): | m/z 1213.6 $[M + 3H - H2O]^{3+}$, 914.7 $[M + 4H]^{4+}$ |
| Peptide mw | 3657.76 |

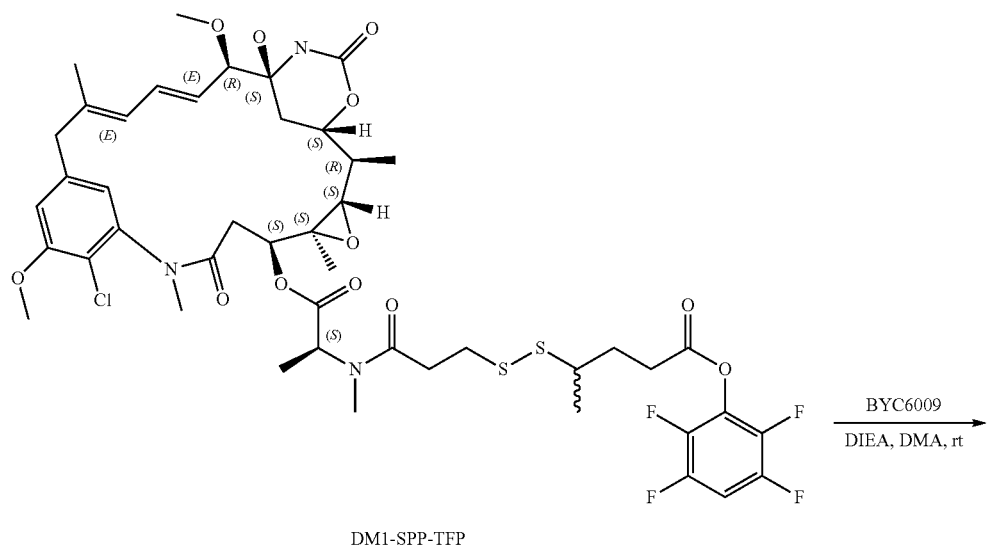
DM1-SPP-TFP
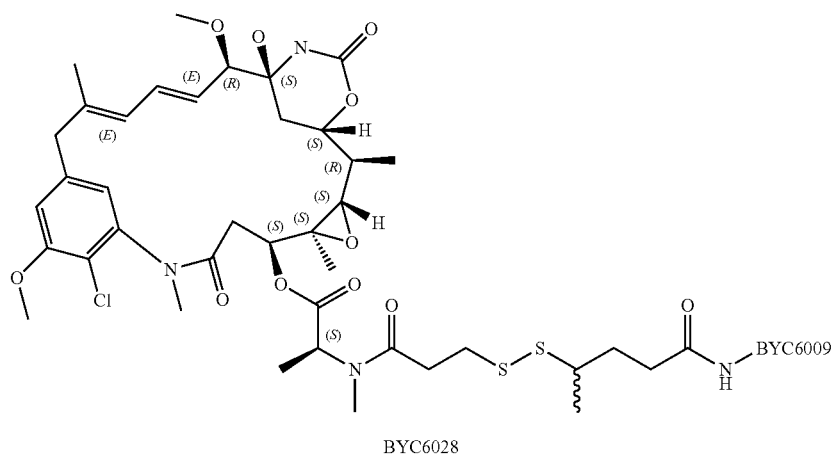
BCY6028
BCY6009 (99.00 mg, 29.45 μmol, 1.00 eq) was used as the bicycle reagent. BCY6028 (24.30 mg, 6.05 μmol, 20.56% yield, 96.61% purity) was obtained as a white solid.
| BCY6028 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE(1-614) |
-continued
| BCY6028 Analytical Data | |
|---|---|
| Method: | 35-65% B over 20 minutes, then 3 min 95% B |
| Retention Time: | 6.43 min |
| LCMS (ESI): | m/z 965.6 [M + 4H − H2O]$^{4+}$ |
| Peptide mw | 3877.96 |

Disulfide Linkers (Various Hindrances)
BCY6039 (DM1-Me-SS-Me-Bicycle)
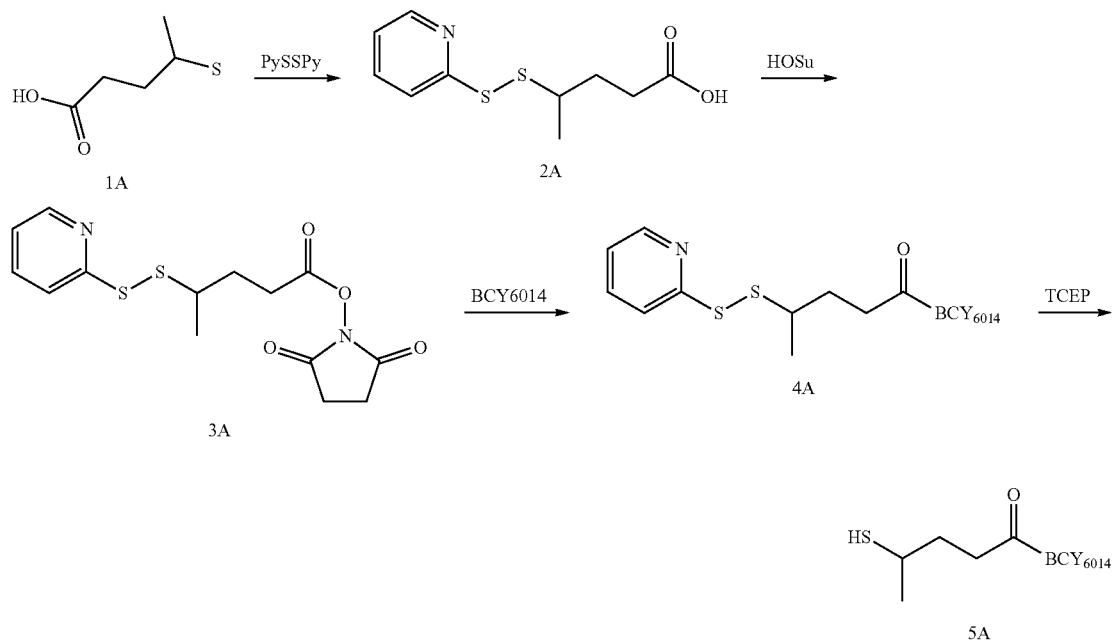
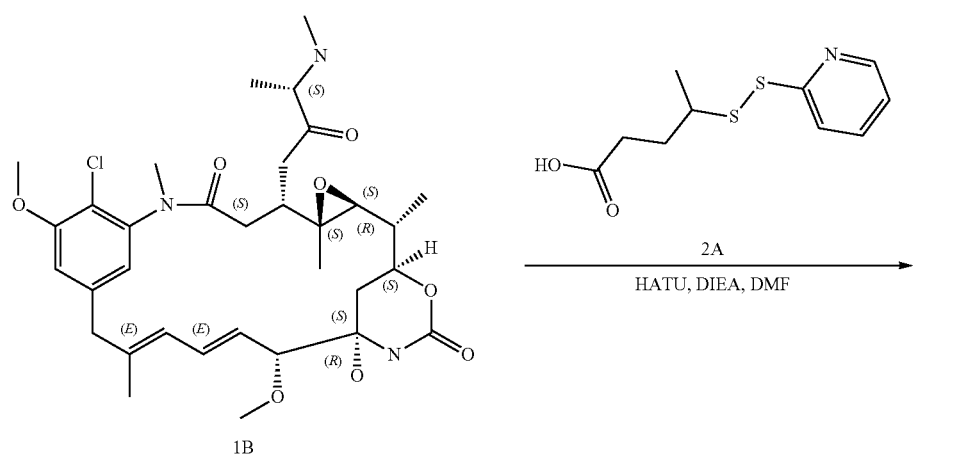
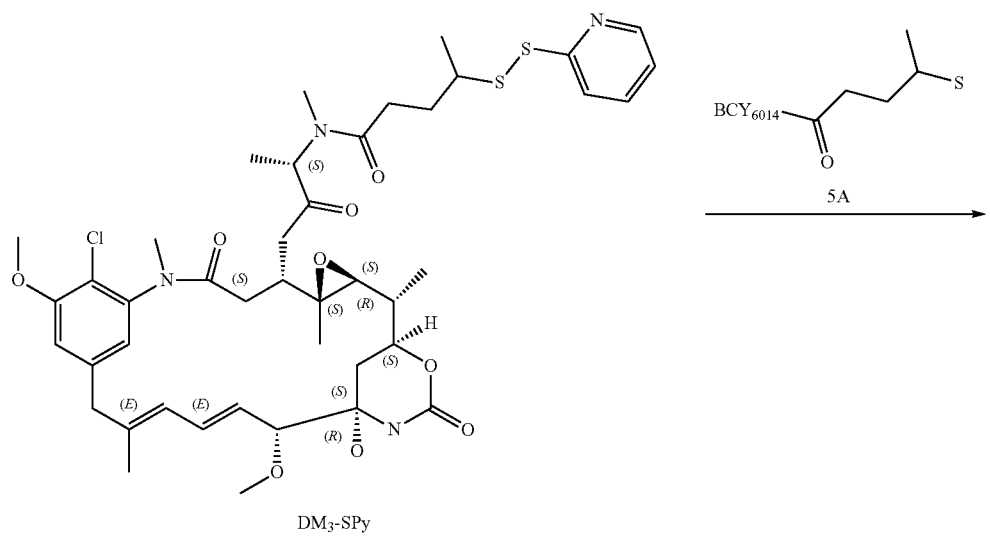

-continued

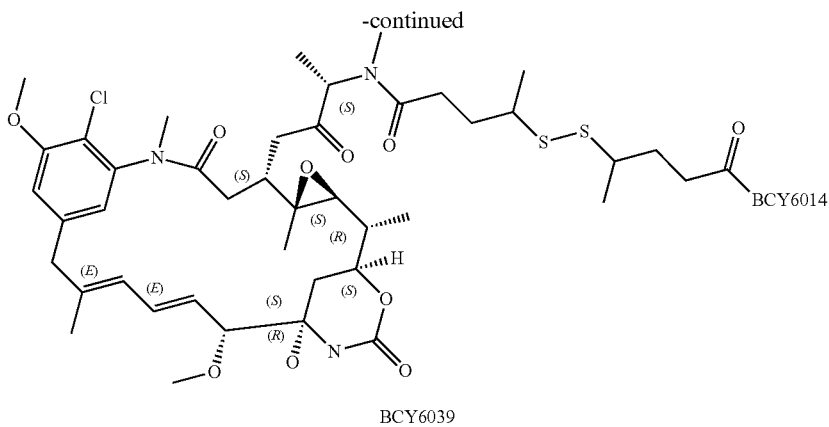

BCY6039

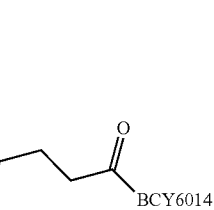

Compound 2A

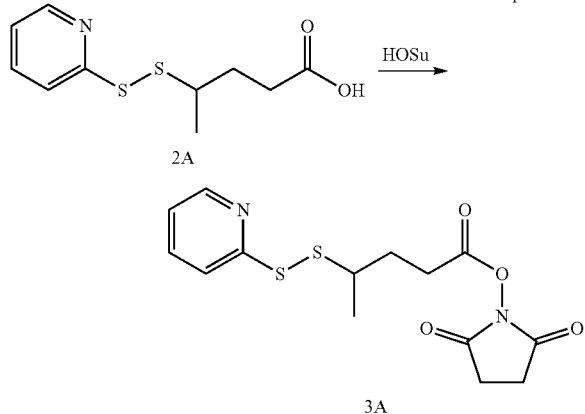

To a solution of 2-(2-pyridyldisulfanyl)pyridine (2.46 g, 11.18 mmol, 1.50 eq) and AcOH (1.05 g, 17.49 mmol, 1.00 mL, 2.35 eq) in EtOH (50.00 mL) was added 4-sulfanyl-pentanoic acid (1A) (1.00 g, 7.45 mmol, 1.00 eq). The mixture was stirred at 40° C. for 18 hours under N$_2$. LC-MS showed 1A was consumed completely and one main peak with the desired mass was detected. The reaction mixture was concentrated under reduced pressure to give a residue, which was purified by preparative HPLC (neutral condition). Compound 2A (1.61 g, 6.62 mmol, 88.81% yield) was obtained as a light yellow solid.

| LCMS (ESI): | 243.9 [M + H]$^+$ |
|---|---|
| Molecular weight | 243.34 |

Compound 3A

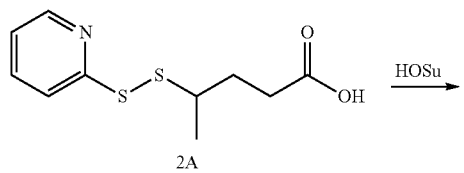

-continued

3A

To a solution of 2A (0.01 g, 41.09 μmol, 1.00 eq), 1-hydroxypyrrolidine-2,5-dione (14.19 mg, 123.28 μmol, 3.00 eq) in DMA (1 mL) was added EDCI (23.63 mg, 123.28 μmol, 3.00 eq). The mixture was stirred at 15° C. for 16 hr. LC-MS showed 2A was consumed completely and one main peak with the desired mass was detected. The residue was purified by preparative HPLC (neutral condition). Compound 3A (0.011 g, 32.31 μmol, 78.63% yield) was obtained as a white solid.

| LCMS (ESI): | 340.8 [M + H]$^+$ |
|---|---|
| Molecular weight | 340.41 |

Compound 4A

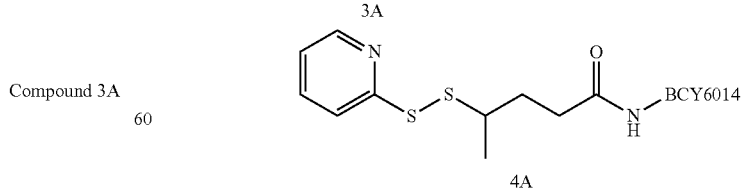

To a solution of BCY6014 (98.25 mg, 32.31 μmol, 1.00 eq) in DMA (3 mL) was added DIEA (8.26 mg, 64.62 μmol, 11.26 μL, 2.00 eq) and 3A (0.011 g, 32.31 μmol, 1.00 eq).

The mixture was stirred at 15° C. for 18 hr. LC-MS showed 3A was consumed completely and one main peak with desired mass was detected. The mixture was directly purified by preparative HPLC (neutral condition). Compound 4A (0.04 g, 12.25 μmol, 37.90% yield) was obtained as a white solid.

| LCMS (ESI): | 1088.7 [M + 3H]$^{3+}$, 816.5 [M + 4H]$^{4+}$ |
|---|---|
| Molecular weight | 3264.88 |

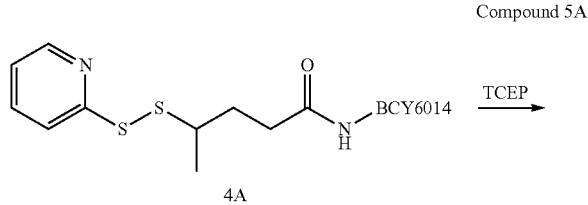

4A

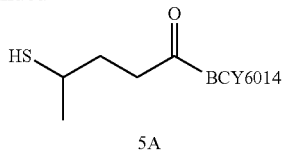

5A

To a solution of 4A (0.04 g, 12.25 μmol, 1.00 eq) in MeCN (4 mL) and H$_2$O (2 mL) was added TCEP (4.21 mg, 14.70 μmol, 4.05 μL, 1.20 eq). The mixture was stirred at 15° C. for 1 hr. LC-MS showed 4A was consumed completely and one main peak with the desired mass was detected. The residue was purified by preparative HPLC (neutral condition). Compound 5A (0.035 g, 11.09 μmol, 90.53% yield) was obtained as a white solid.

| LCMS (ESI): | 1052.2 [M + 3H]$^{3+}$ |
|---|---|
| Molecular weight | 3155.73 |

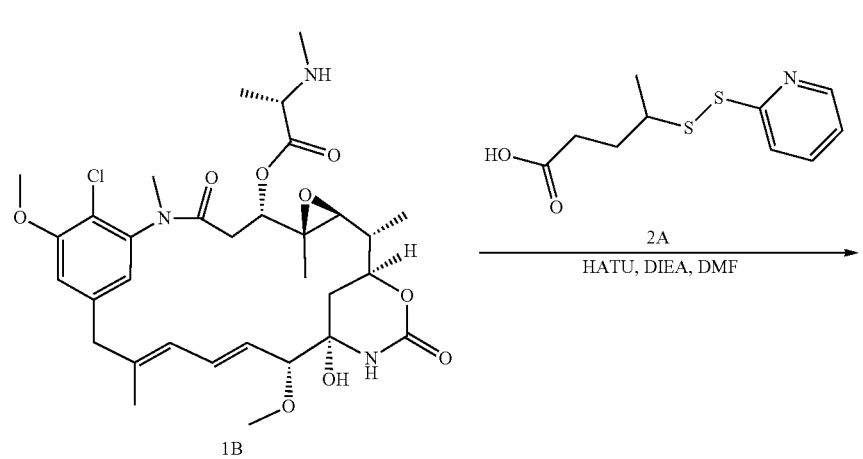

1B

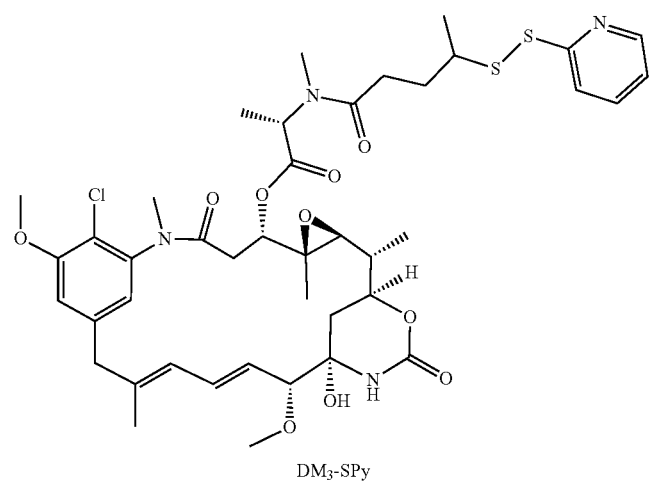

DM$_3$-SPy

249

To a solution of 4-(2-pyridyldisulfanyl)pentanoic acid (2A) (22.46 mg, 92.29 μmol, 1.20 eq), HATU (35.09 mg, 92.29 μmol, 1.20 eq), DIEA (29.82 mg, 230.71 μmol, 40.19 μL, 3.00 eq) in DMF (5 mL) was added 1B (0.05 g, 76.90 μmol, 1.00 eq). The mixture was stirred at 15° C. for 1 hr. LC-MS showed 1B was consumed completely and one main peak with the desired mass was detected. The residue was purified by preparative HPLC (neutral condition). Compound DM3-SPy (0.025 q, 28.56 μmol, 37.13% yield) was obtained as a white solid.

| LCMS (ESI): | 875.1 [M + H]⁺ |
| Molecular weight | 875.49 |

250

A solution of DM3-SPy (0.015 g, 17.13 μmol, 1.00 eq) and 5A (54.08 mg, 17.13 μmol, 1.00 eq) in DMF (3 mL) was adjusted to pH=8 using NaHCO$_3$(aq). The mixture was stirred at 15° C. for 1 hr. LC-MS showed DM3-SPy was consumed completely and one main peak with desired mass was detected. The mixture was directly purified by preparative HPLC (TFA condition). Compound BCY6039 (0.0263 g, 6.58 μmol, 38.39% yield) was obtained as a white solid.

| BCY6039 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE (1-614) |
| Method: | 28-68% B over 30 minutes, then 3 min 95% B |
| Retention Time: | 13.01 min |
| LCMS (ESI): | m/z 976.1 [M + 4H − H2O]⁴⁺ |
| Peptide mw | 3921.01 |

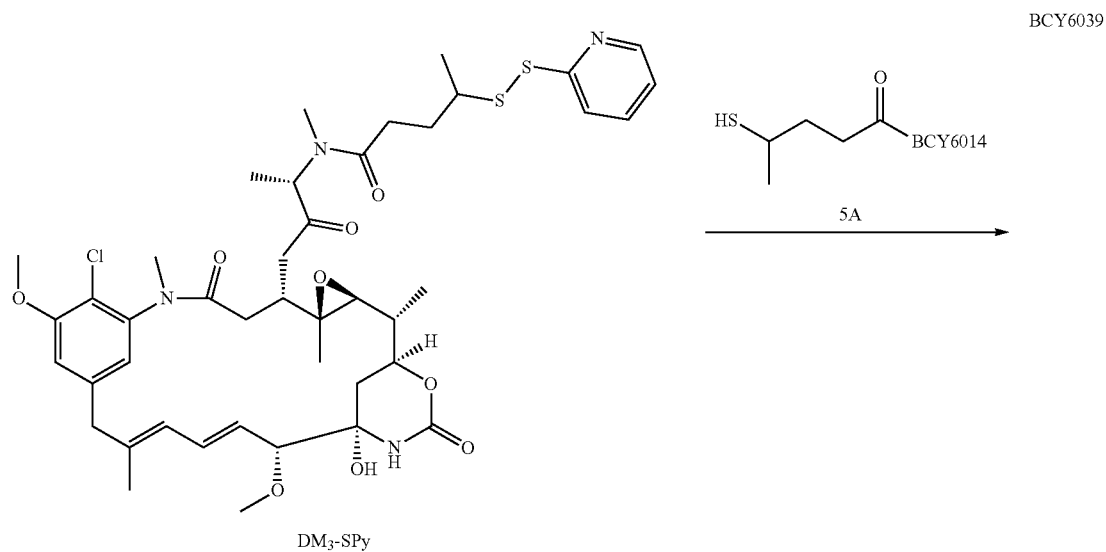

DM$_3$-SPy

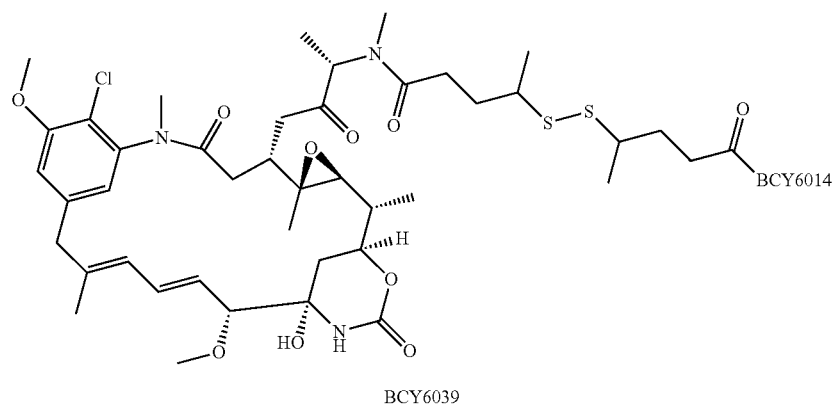

BCY6039

251 252
BCY6055 (DM1-SS-Me₂-Bicycle)
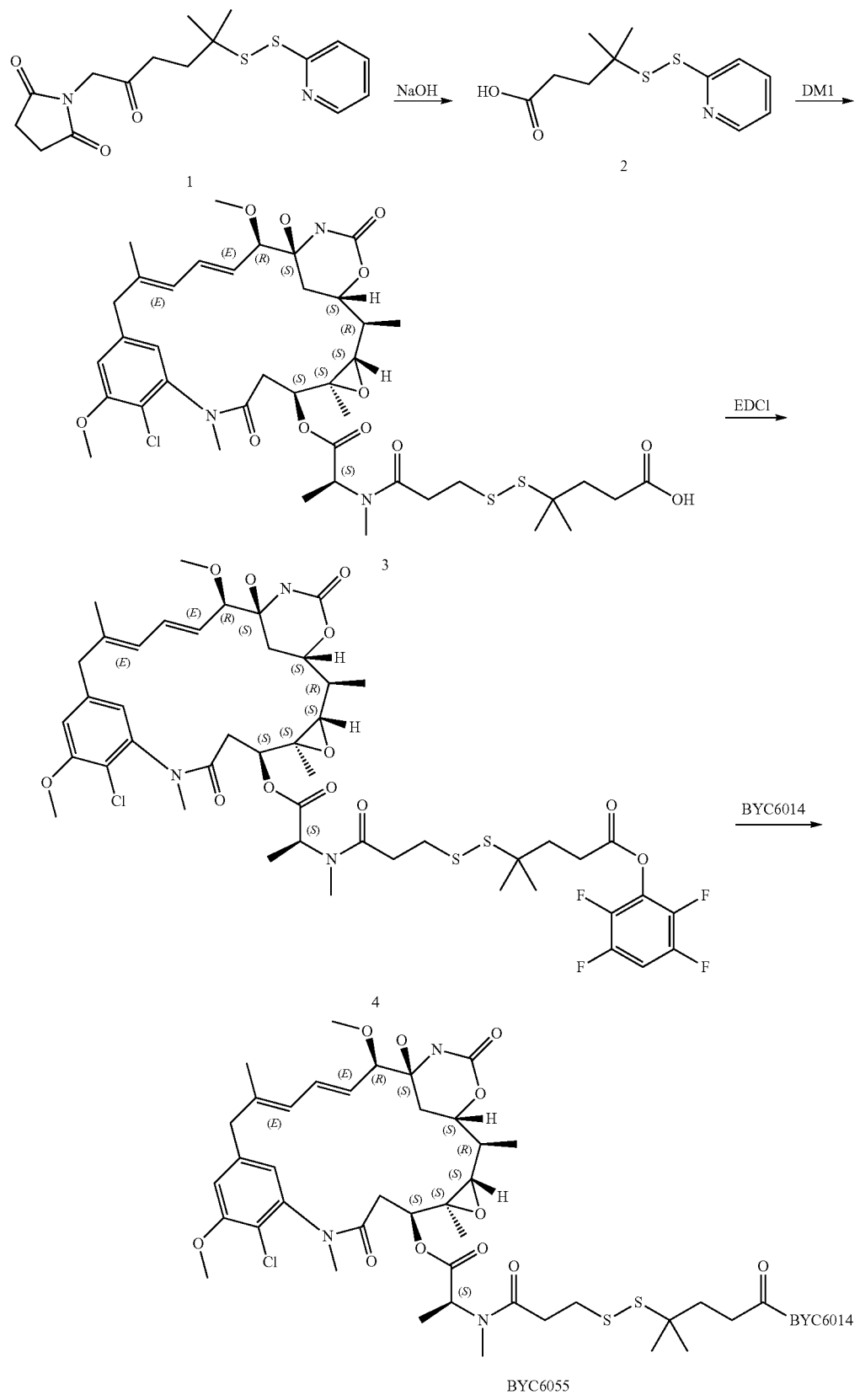

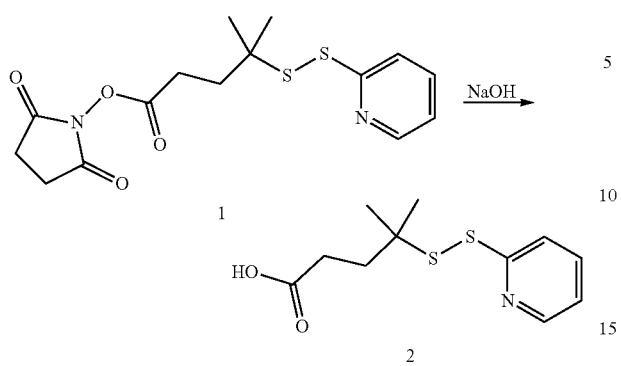

Compound 2

To a solution of compound 1 (0.045 g, 126.96 μmol, 1 eq) in H$_2$O (1 mL) was adjusted pH=13 using 1N NaOH solution. The mixture was stirred at 15° C. for 16 hr. LC-MS showed compound 1 was consumed completely and one main peak with the desired mass was detected. The residue was purified by preparative HPLC (neutral condition). Compound 2 (0.03 g, 116.56 μmol, 91.81% yield) was obtained as a yellow solid.

| LCMS (ESI): | 257.9 [M + H]$^+$ |
|---|---|
| Molecular weight | 257.37 |

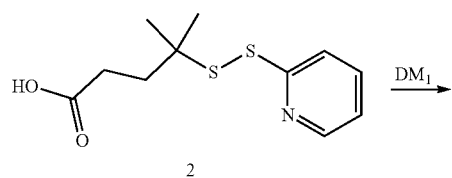

Compound 3

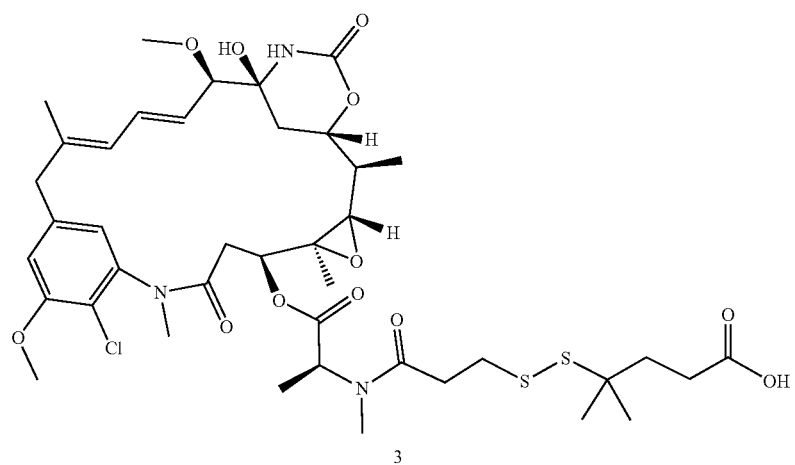

A solution of compound 2 (0.03, 116.56 μmol, 1.0 eq) and DM1 (111.87 mg, 151.53 μmol, 1.3 eq) in DMF (5 mL) was stirred at 15° C. for 2 hours. LC-MS showed DM1 was consumed completely and one main peak with desired mass was detected. The mixture was directly purified by preparative HPLC (NH$_4$HCO$_3$ condition). Compound 3 (0.05 g, 56.53 μmol, 48.50% yield) was obtained as a white solid.

| LCMS (ESI): | 866.0 [M + H − H$_2$O]$^+$ |
|---|---|
| Molecular weight | 884.49 |

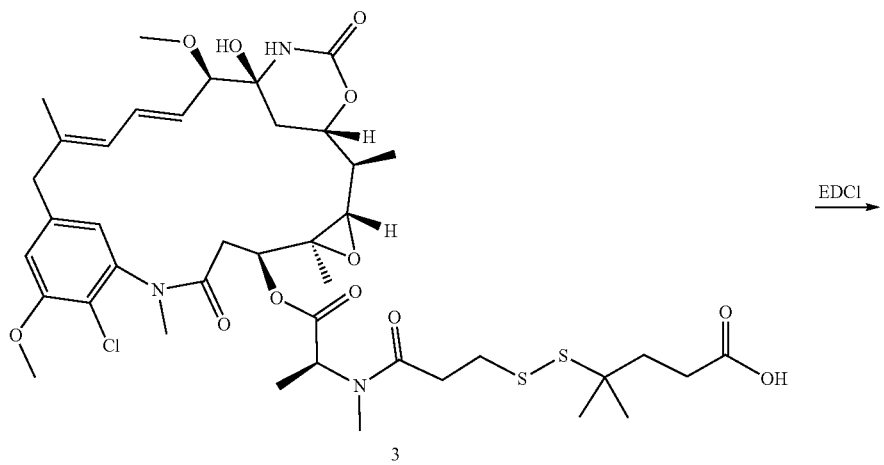

Compound 4

EDCl

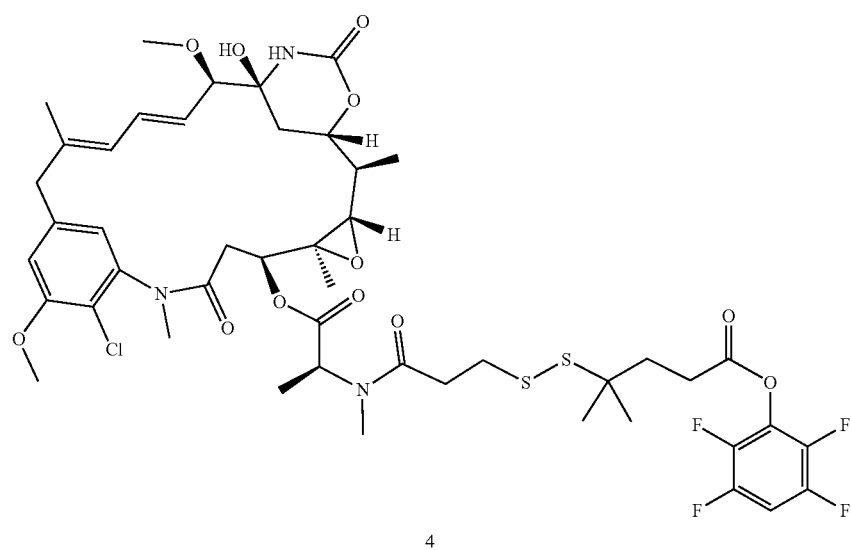

4

To a solution of compound 3 (0.05 g, 56.53 μmol, 1.0 eq) and 2,3,5,6-tetrafluorophenol (28.16 mg, 169.59 μmol, 3.0 eq) in DMA (3 mL) and DCM (1 mL) was added EDCI (32.51 mg, 169.59 μmol, 3 eq). The mixture was stirred at 15° C. for 16 hr. LC-MS showed compound 3 was consumed completely and one main peak with desired mass was detected. DCM was removed and the mixture was directly purified by preparative HPLC (neutral condition). Compound 4 (0.03 g, 29.05 μmol, 51.40% yield) was obtained as a white solid.

| | |
|---|---|
| LCMS (ESI): | 1014.0 [M + H − H$_2$O]$^+$ |
| Molecular weight | 1032.55 |

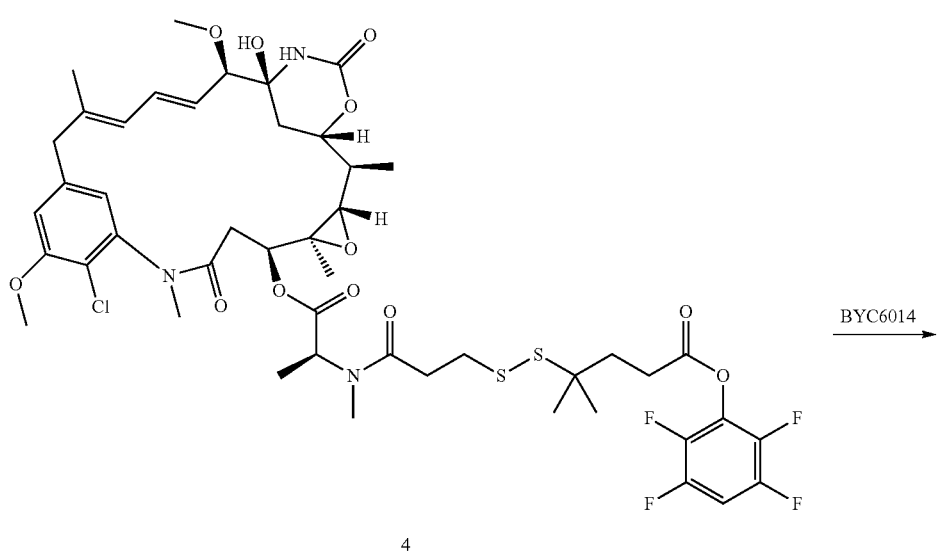

BYC6055

To a solution of BCY6014 (106.01 mg, 34.87 μmol, 1.2 eq) in DMA (3 mL) was added DIEA (11.27 mg, 87.16 μmol, 15.18 μL, 3.0 eq) and compound 4 (0.03 g, 29.05 μmol, 1.0 eq). The mixture was stirred at 15° C. for 16 hr. LC-MS showed compound 4 was consumed completely and one main peak with desired mass was detected. The mixture was directly purified by preparative HPLC (TFA condition). Compound BCY6055 (0.0352 g, 9.01 μmol, 31.01% yield) was obtained as a white solid.

| BCY6055 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE (1-614) |
| Method: | 28-68% B over 30 minutes, then 3 min 95% B |
| Retention Time: | 12.68 min |
| LCMS (ESI): | m/z 1296.1 [M + 3H − H2O]$^{3+}$, 972.4 [M + 4H − H2O]$^{4+}$ |
| Peptide mw | 3906.98 |

BCY6077 (DM1-SS-Me-(SO3H)-Bicycle)

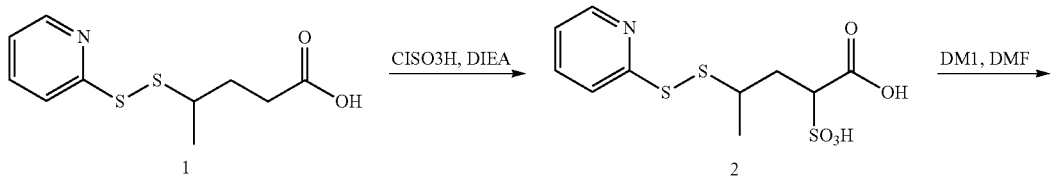

259    260
-continued
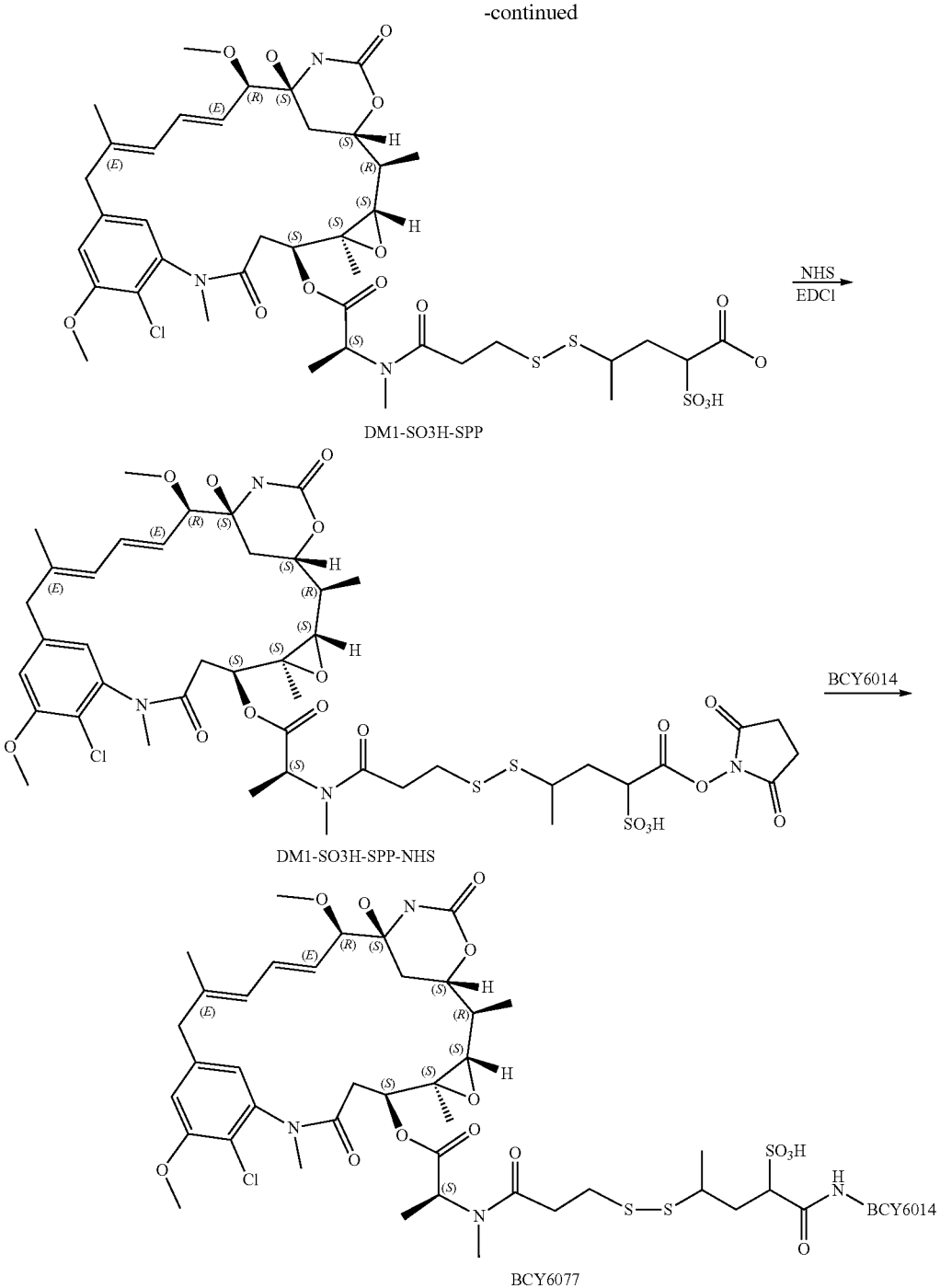
55
General Procedure for Preparation of Compound 2
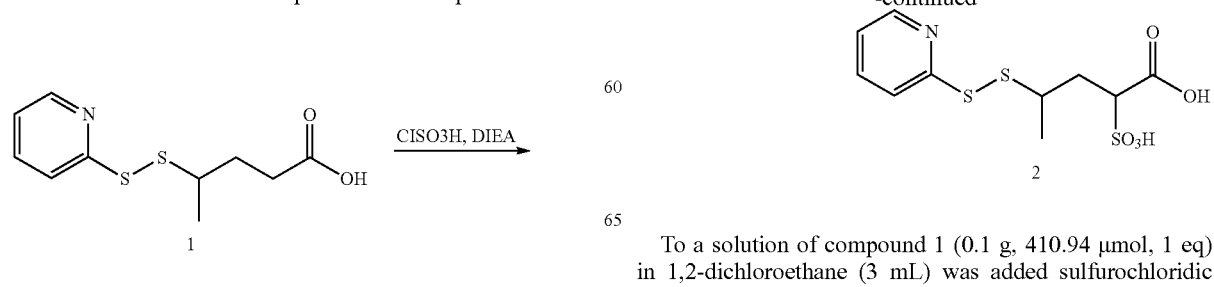
To a solution of compound 1 (0.1 g, 410.94 μmol, 1 eq) in 1,2-dichloroethane (3 mL) was added sulfurochloridic acid (0.86 g, 7.38 mmol, 491.43 μL, 17.96 eq) on three parts and DIEA (318.67 mg, 2.47 mmol, 429.47 μL, 6 eq) was added on two parts. The mixture was stirred at 75° C. for 16 hr. LC-MS showed compound 1 was consumed completely and one main peak with desired MS was detected MS324, one main peak of byproduct MS 221 was PySSPy. The solvent was removed and dissolved in H2O/MeCN=15/1. Directly purified by prep-HPLC (neutral condition: MeCN/H$_2$O). Compound 2 (0.055 g, 170.06 μmol, 41.38% yield) was obtained as a yellow oil.

| LCMS (ESI): | 323.6 [M + H]$^+$ |
|---|---|
| Molecular weight | 323.4 |

General Procedure for Preparation of DM1-SO$_3$H-SPP

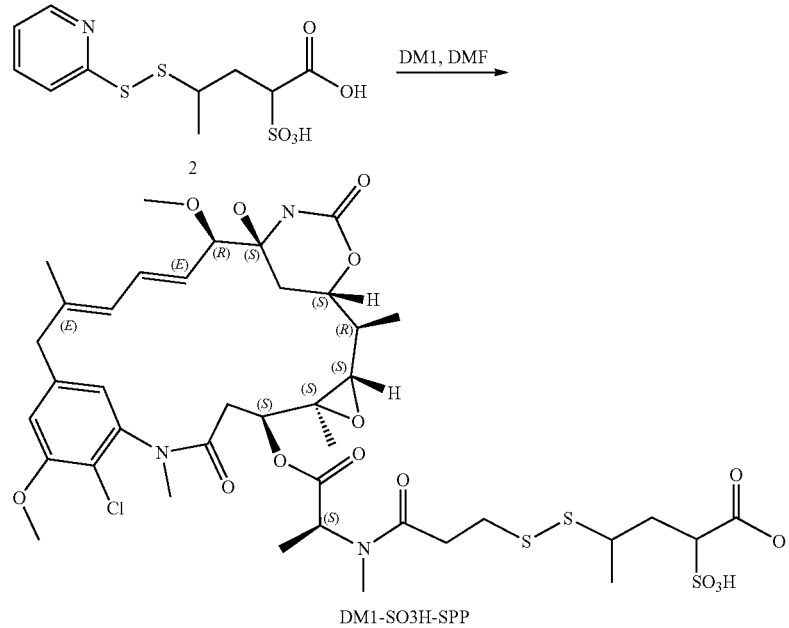

To a solution of DM1 (113.00 mg, 153.06 μmol, 1.1 eq), compound 2 (0.045 g, 139.14 μmol, 1 eq) in DMF (2 mL) was adjusted PH=8 used for NaHCO$_3$(aq). The mixture was stirred at 15° C. for 1 hr. LC-MS showed DM1 was consumed completely and one main peak with desired MS was detected. Directly purified by prep-HPLC (neutral condition). Compound DM1-SO$_3$H-SPP (0.075 g, 78.90 μmol, 56.71% yield) was obtained as a white solid.

| LCMS (ESI): | 931.9 [M + H − H2O]$^+$ |
|---|---|
| Molecular weight | 950.52 |

General Procedure for Preparation of DM1-SO$_3$H-SPP—NHS

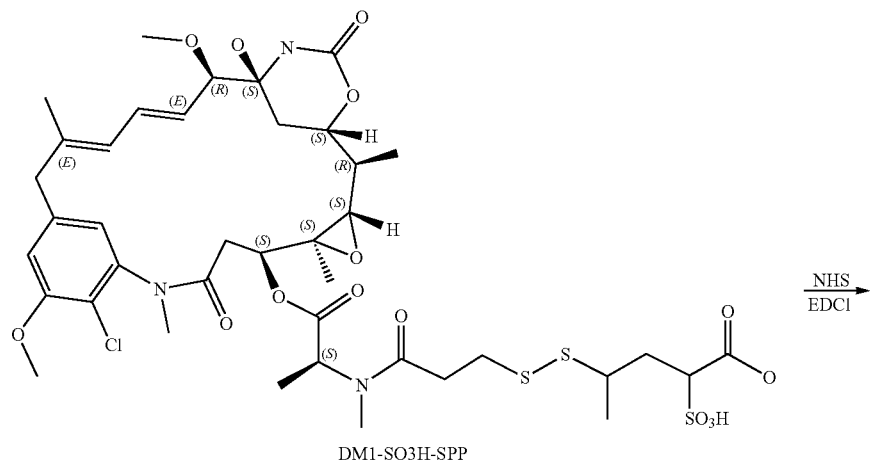

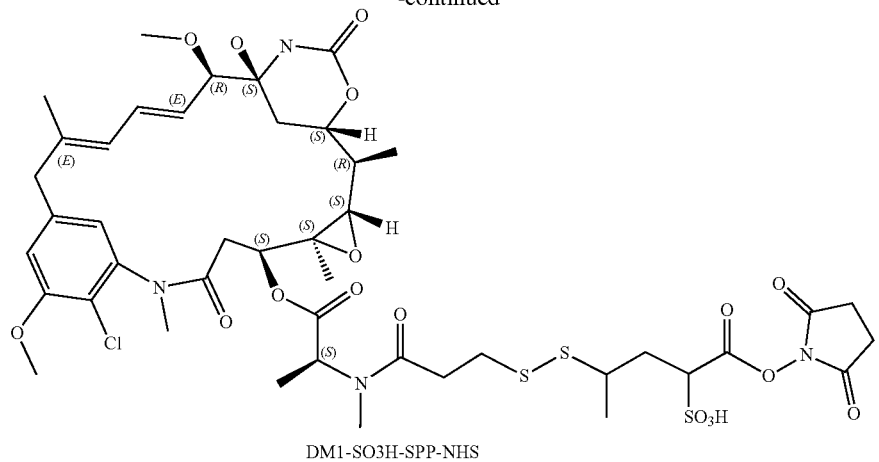

DM1-SO3H-SPP-NHS

To a solution of DM1-SO₃H-SPP (0.06 g, 63.12 μmol, 1 eq), 1-hydroxypyrrolidine-2, 5-dione (7.99 mg, 69.43 μmol, 1.1 eq) in DMA (1.5 mL) and DCM (0.5 mL) was added EDCI (13.31 mg, 69.43 μmol, 1.1 eq). The mixture was stirred at 15° C. for 18 hr. LC-MS showed DM1-SO₃H-SPP was consumed completely and one main peak with desired MS was detected. Directly purified by prep-HPLC (neutral condition: MeCN/H₂O). Compound DM1-SO₃H-SPP—NHS (0.045 g, 42.96 μmol, 68.05% yield) was obtained as a white solid.

| LCMS (ESI): | 984 [M − NHS + K]⁺ |
|---|---|
| Molecular weight | 1047.6 |

General Procedure for Preparation of BCY6077

To a solution of BCY6014 (101.58 mg, 33.41 μmol, 1 eq) in DMA (1 mL) was added DIEA (12.95 mg, 100.23 μmol, 17.46 μL, 3 eq) and DM1-SO₃H-SPP-TFP (0.035 g, 33.41 μmol, 1 eq). The mixture was stirred at 15° C. for 16 hr. LC-MS showed DM1-SO₃H-SPP-TFP was consumed completely and one main peak with desired MS was detected. Directly purified by prep-HPLC (TFA condition). Compound BCY6077 (41.30 mg, 10.03 μmol, 30.01% yield, 96.44% purity) was obtained as a white solid.

| BCY6077 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150 * 4.6 mm |
| Instrument: | Agilent 1200 HPLC-BE (1-614) |
| Method: | 28-68% B over 30 minutes, then 3 min 95% B |
| Retention Time: | 11.80 min |
| LCMS (ESI): | m/z 978.2 [M + 4H − 18 − 44]⁴⁺ |
| Peptide mw | 3972.06 |

Non-Cleavable Series
BCY6063 (MMAE)

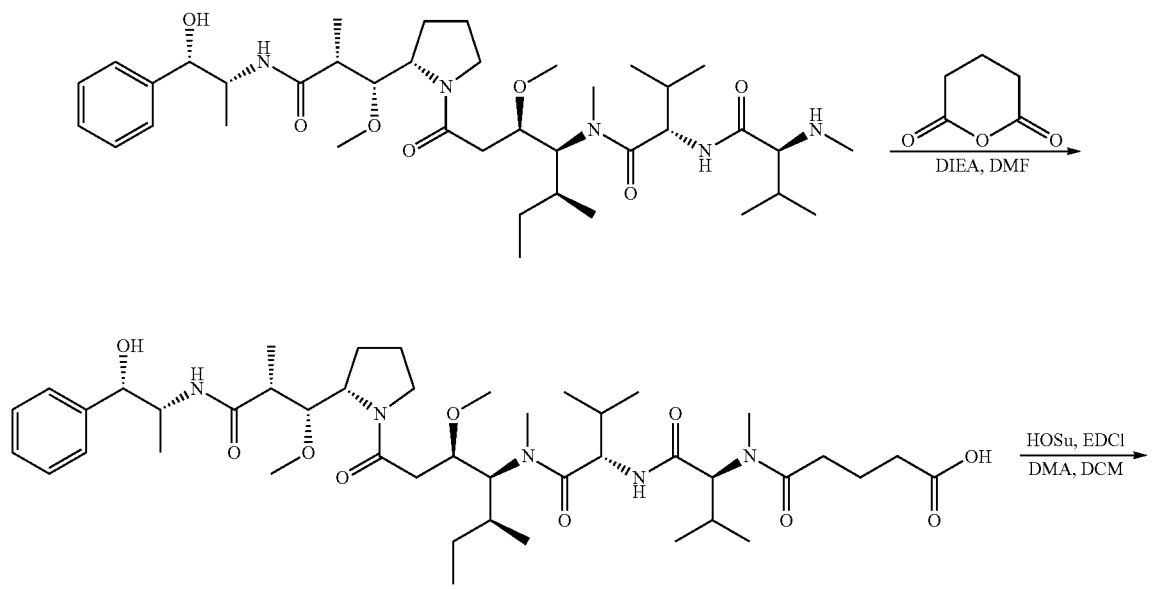

-continued

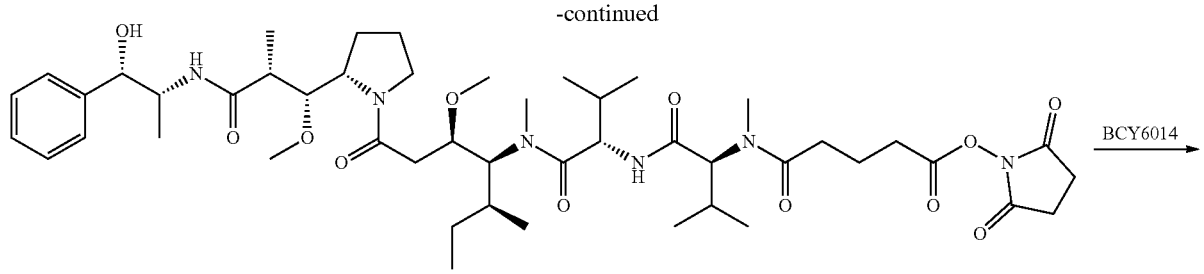

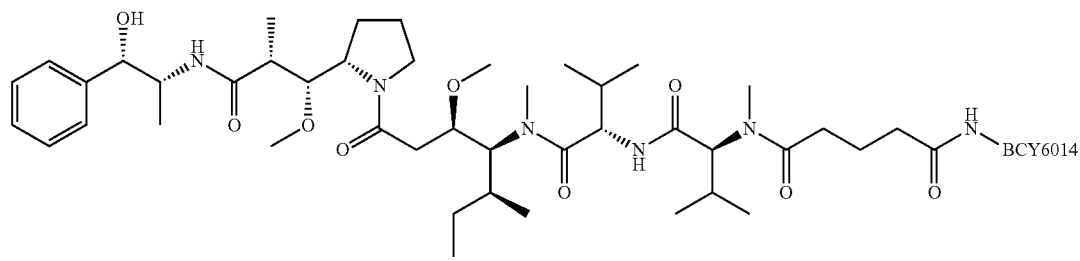

Glutarate-(MMAE)

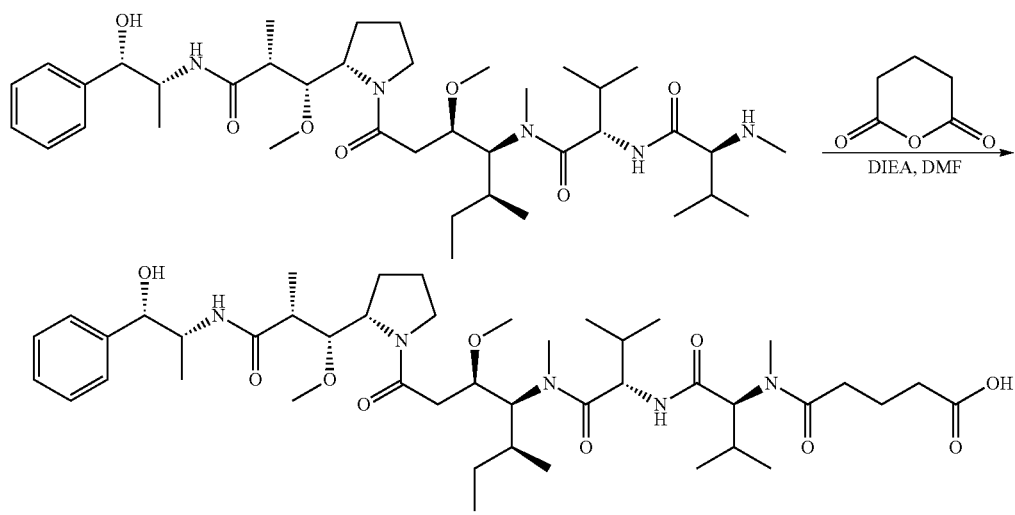

To a solution of MMAE (0.2 g, 278.56 μmol, 1.0 eq) in DMA (3 mL) was added DIEA (108.01 mg, 835.68 μmol, 145.56 μL, 3.0 eq) and tetrahydropyran-2,6-dione (63.57 mg, 557.12 μmol, 2.0 eq). The mixture was stirred at 15° C. for 16 hr. LC-MS showed MMAE was consumed completely and one main peak with desired mass was detected. The mixture was The mixture was directly purified by preparative HPLC (neutral condition). Compound Glutarate-MMAE (0.12 g, 144.22 μmol, 51.77% yield) was obtained as a white solid.

| LCMS (ESI): | 832.3 [M + H]+ |
|---|---|
| Molecular weight | 832.09 |

Glutarate-MMAE-NHS

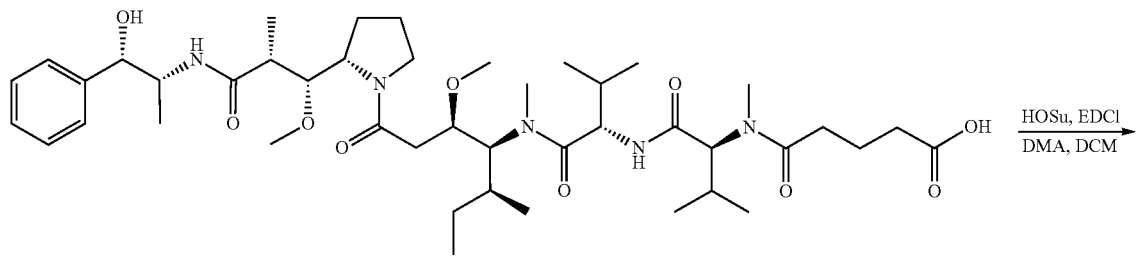

-continued

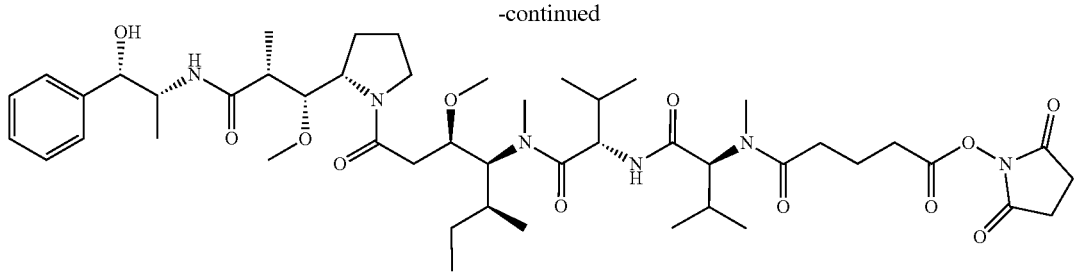

To a solution of Glutarate-MMAE (0.12 g, 144.22 µmol, 1.0 eq), 1-hydroxypyrrolidine-2, 5-dione (49.79 mg, 432.65 µmol, 3.0 eq) in DMA (3 mL) and DCM (1 mL) was added EDCI (82.94 mg, 432.65 µmol, 3.0 eq). The mixture was stirred at 15° C. for 16 hr. LC-MS showed Glutarate-MMAE was consumed completely and one main peak with desired mass was detected. The mixture was The mixture was directly purified by preparative HPLC (TFA condition). Compound Glutarate-MMAE-NHS (0.055 g, 59.19 µmol, 41.04% yield) was obtained as a white solid.

| LCMS (ESI): | 929.2 [M + H]+ |
|---|---|
| Molecular weight | 929.17 |

To a solution of BCY6014 (98.17 mg, 32.29 µmol, 1.2 eq) in DMA (2 mL) were added DIEA (10.43 mg, 80.72 µmol, 14.06 µL, 3 eq) and Glutarate-MMAE-NHS (0.025 g, 26.91 µmol, 1 eq). The mixture was stirred at 15° C. for 16 hr. LC-MS showed Glutarate-MMAE-NHS was consumed completely and one main peak with desired mass was detected. The mixture was directly purified by preparative HPLC (TFA condition). Compound BCY6063 (32.10 mg, 8.33 µmol, 30.95% yield) was obtained as a white solid.

| BCY6063 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150*4.6 mm |
| Instrument: | Agilent 1200 HPLC-BE(1-614) |
| Method: | 28-68% B over 30 minutes, then 3 min 95% B |
| Retention Time: | 10.86 min |
| LCMS (ESI): | m/z 963.8 [M + 4H]$^{4+}$, 771.1 [M + 5H]$^{5+}$ |
| Peptide mw | 3854.56 |

BCY6063

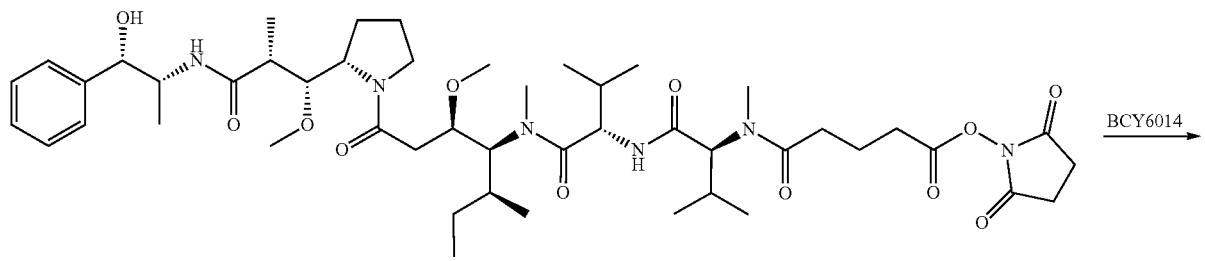

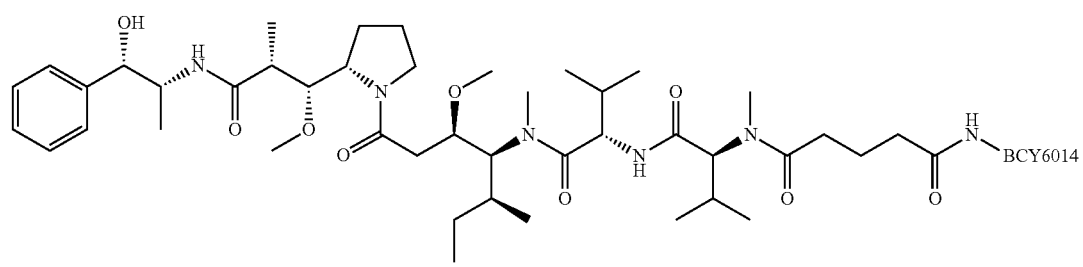

BCY6064 (DM1)
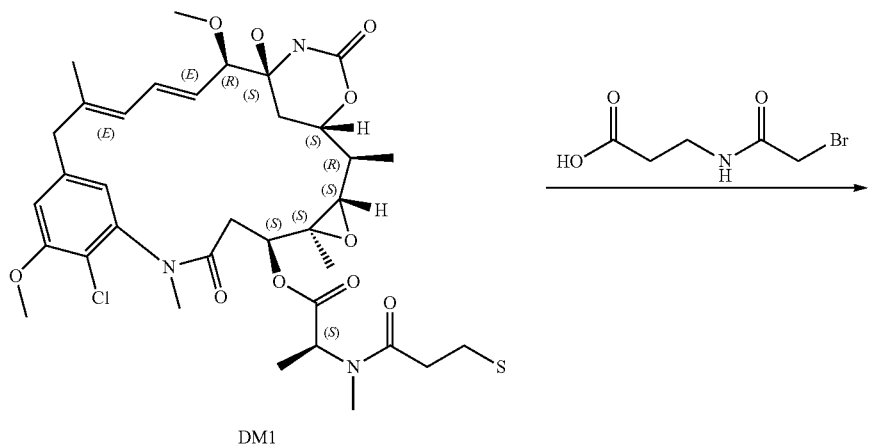
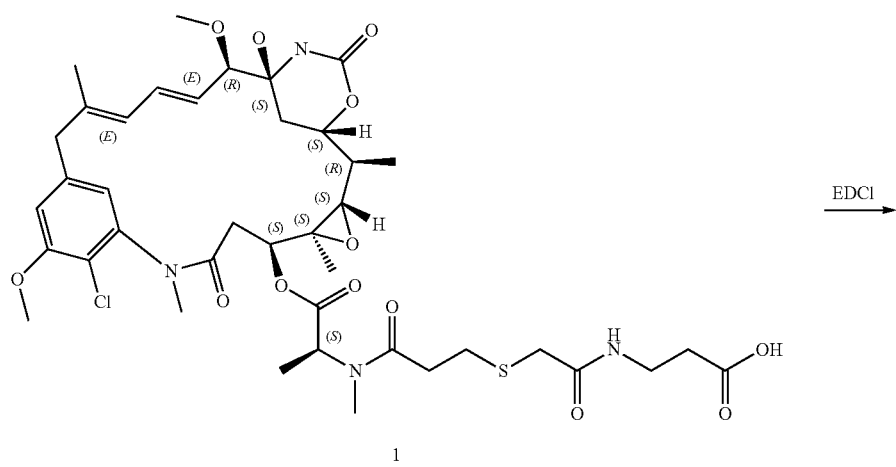
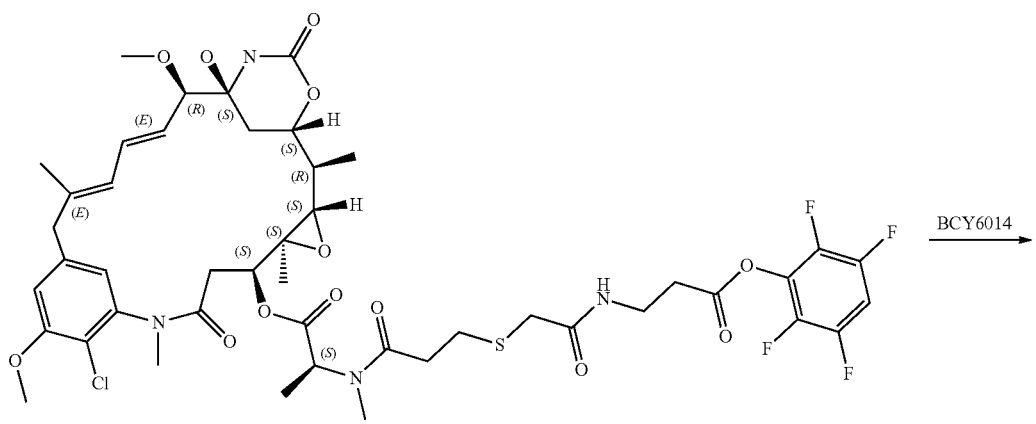

-continued

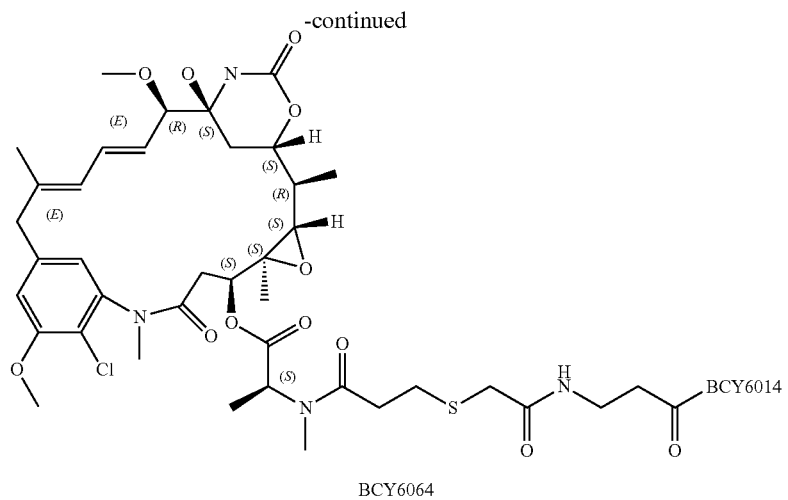

BCY6064

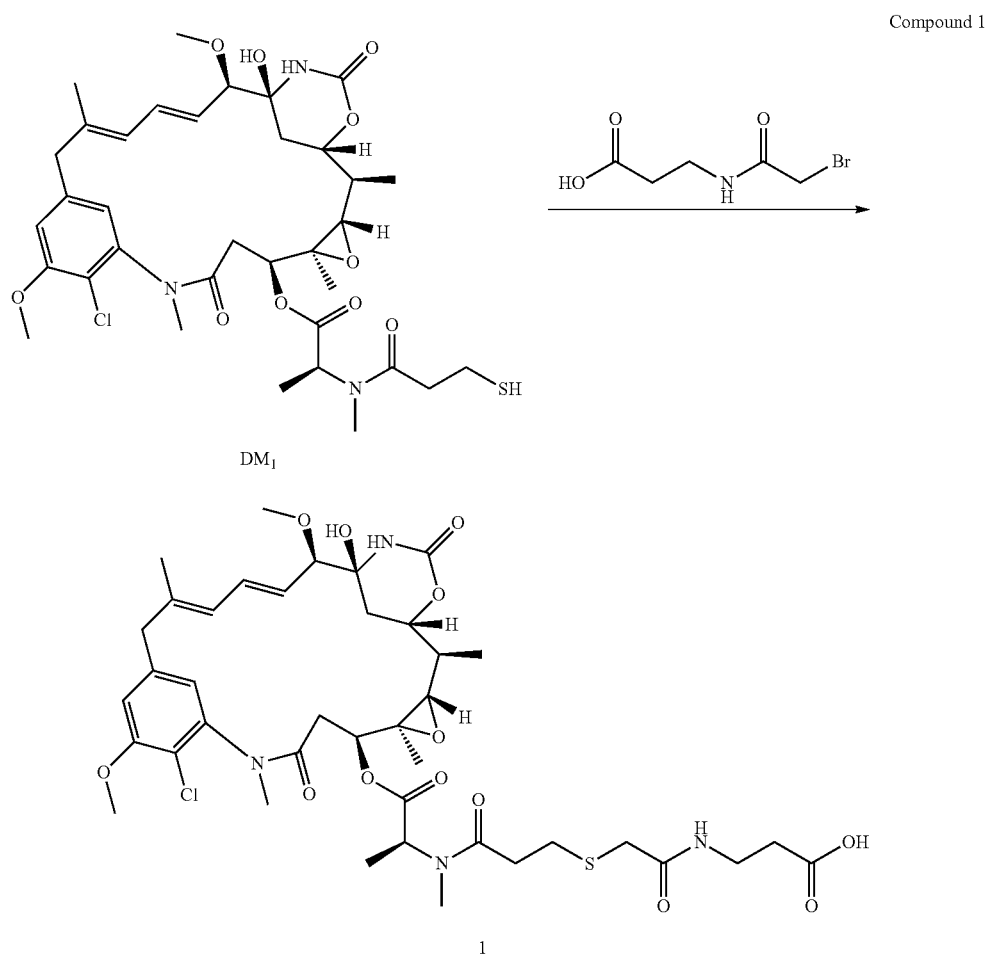

To a solution of DM1 (0.1 g, 135.45 μmol, 1 eq), 3-[(2-bromoacetyl)amino]propanoic acid (34.14 mg, 162.54 μmol, 1.2 eq) in DMF (5 mL) was added TEA (41.12 mg, 406.35 μmol, 56.56 μL, 3 eq). The mixture was stirred at 15° C. for 1 hr. LC-MS showed DM1 was consumed completely and one main peak with the desired mass was detected. The mixture was directly purified by preparative HPLC (neutral conditions). Compound 1 (0.08 g, 92.23 μmol, 68.09% yield) was obtained as a white solid.

| LCMS (ESI): | 849.1 [M + H—H$_2$O]$^+$ |
|---|---|
| Molecular weight | 867.41 | and one main peak with desired mass was detected. The mixture was directly purified by preparative HPLC (neutral condition). Compound 2 (0.06 g, 59.09 µmol, 64.06% yield) was obtained as a white solid.

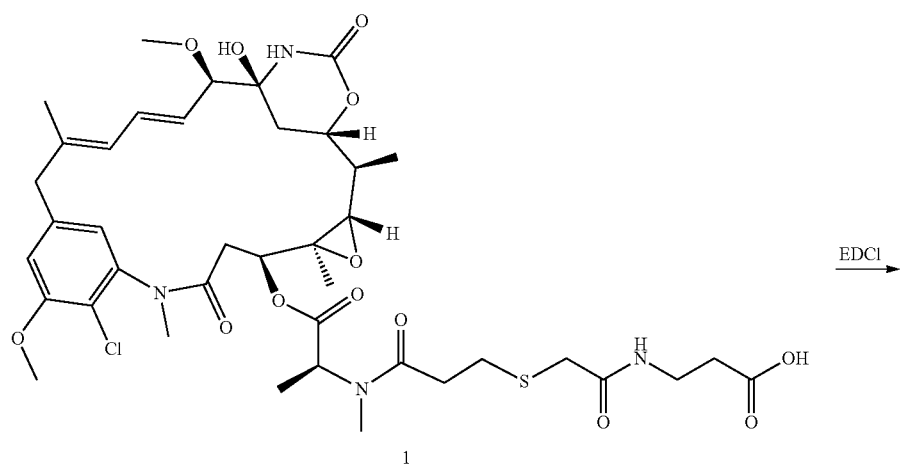

Compound 2

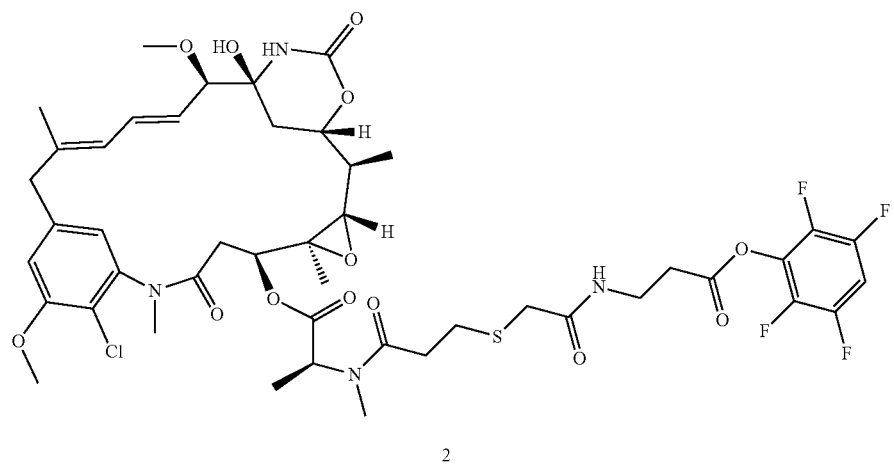

To a solution of compound 1 (0.08 g, 92.23 µmol, 1 eq), 2,3,5,6-tetrafluorophenol (45.95 mg, 276.69 µmol, 3 eq) in DMA (3 mL) and DCM (1 mL) was added EDCI (53.04 mg, 276.69 µmol, 3 eq). The mixture was stirred at 15° C. for 4 hr. LC-MS showed compound 1 was consumed completely

| LCMS (ESI): | 997.0 [M + H—H$_2$O]$^+$ |
|---|---|
| Molecular weight | 1015.46 |

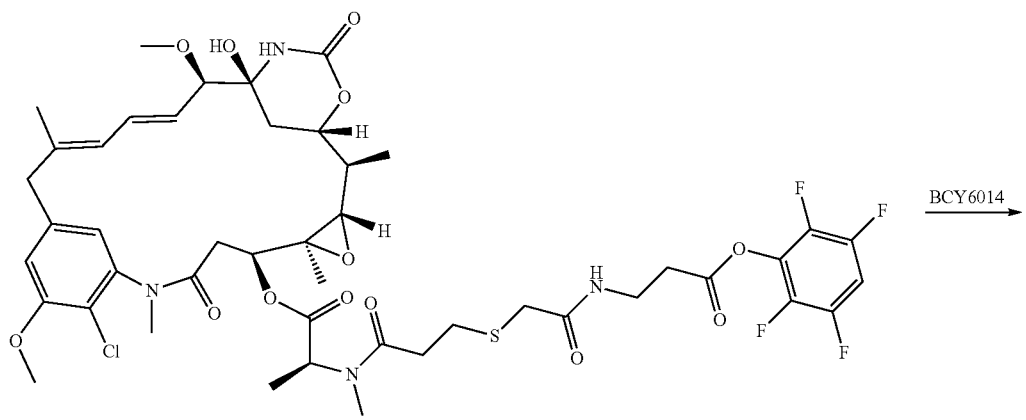

2

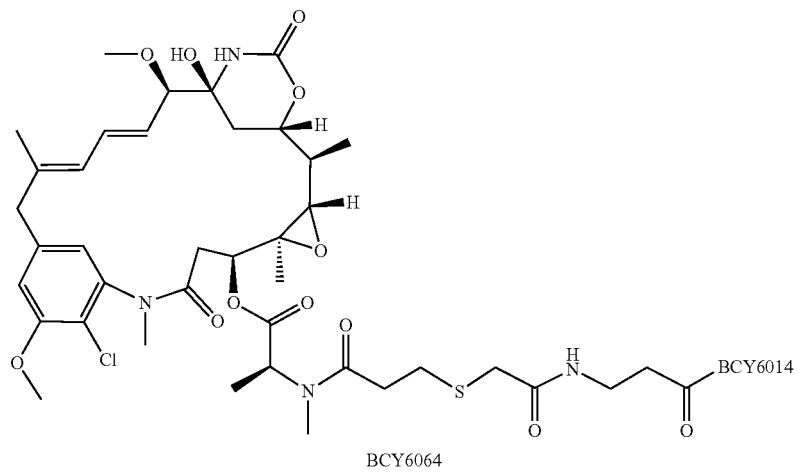

BCY6064

To a solution of BCY6014 (107.79 mg, 35.45 µmol, 1.2 eq) in DMA (3 mL) was added DIEA (11.45 mg, 88.63 µmol, 15.44 µL, 3.0 eq) and compound 2 (0.030 g, 29.54 µmol, 1 eq). The mixture was stirred at 15° C. for 16 hr. LC-MS showed compound 2 was consumed completely and one main peak with desired mass was detected. The mixture was directly purified by preparative HPLC (TFA condition). Compound BCY6064 (28.40 mg, 7.30 µmol, 24.71% yield) was obtained as a white solid.

| BCY6064 Analytical Data | |
|---|---|
| Mobile Phase: | A: 0.1% TFA in H2O B: 0.1% TFA in ACN |
| Flow: | 1.0 ml/min |
| Column: | Gemini-NX C18 5 um 110A 150*4.6 mm |
| Instrument: | Agilent 1200 HPLC-BE(1-614) |
| Method: | 28-68% B over 30 minutes, then 3 min 95% B |
| Retention Time: | 10.26 min |
| LCMS (ESI): | m/z 968.4 [M + 4H—H2O]$^{4+}$ |
| Peptide mw | 3889.89 |

BCY6105
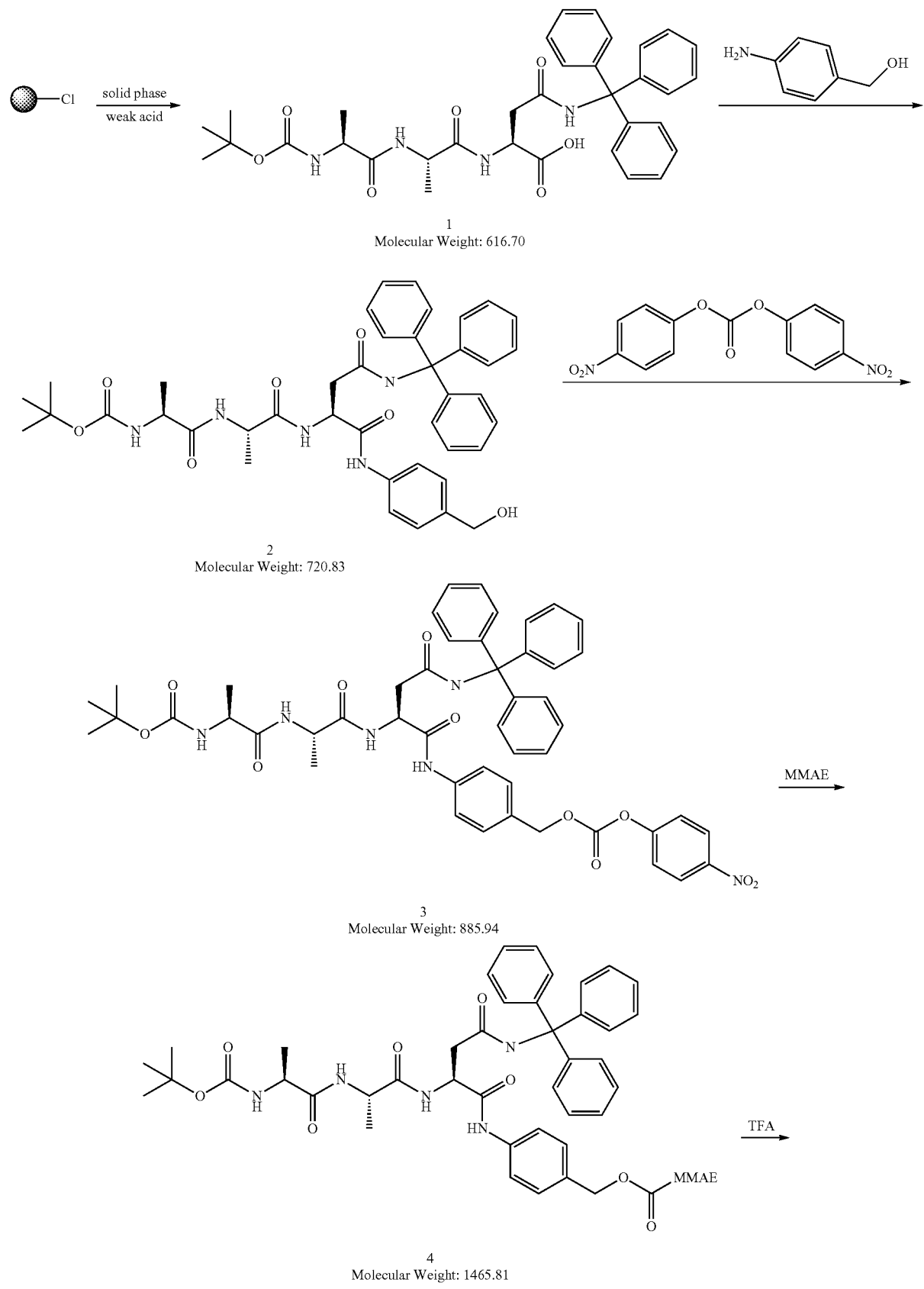

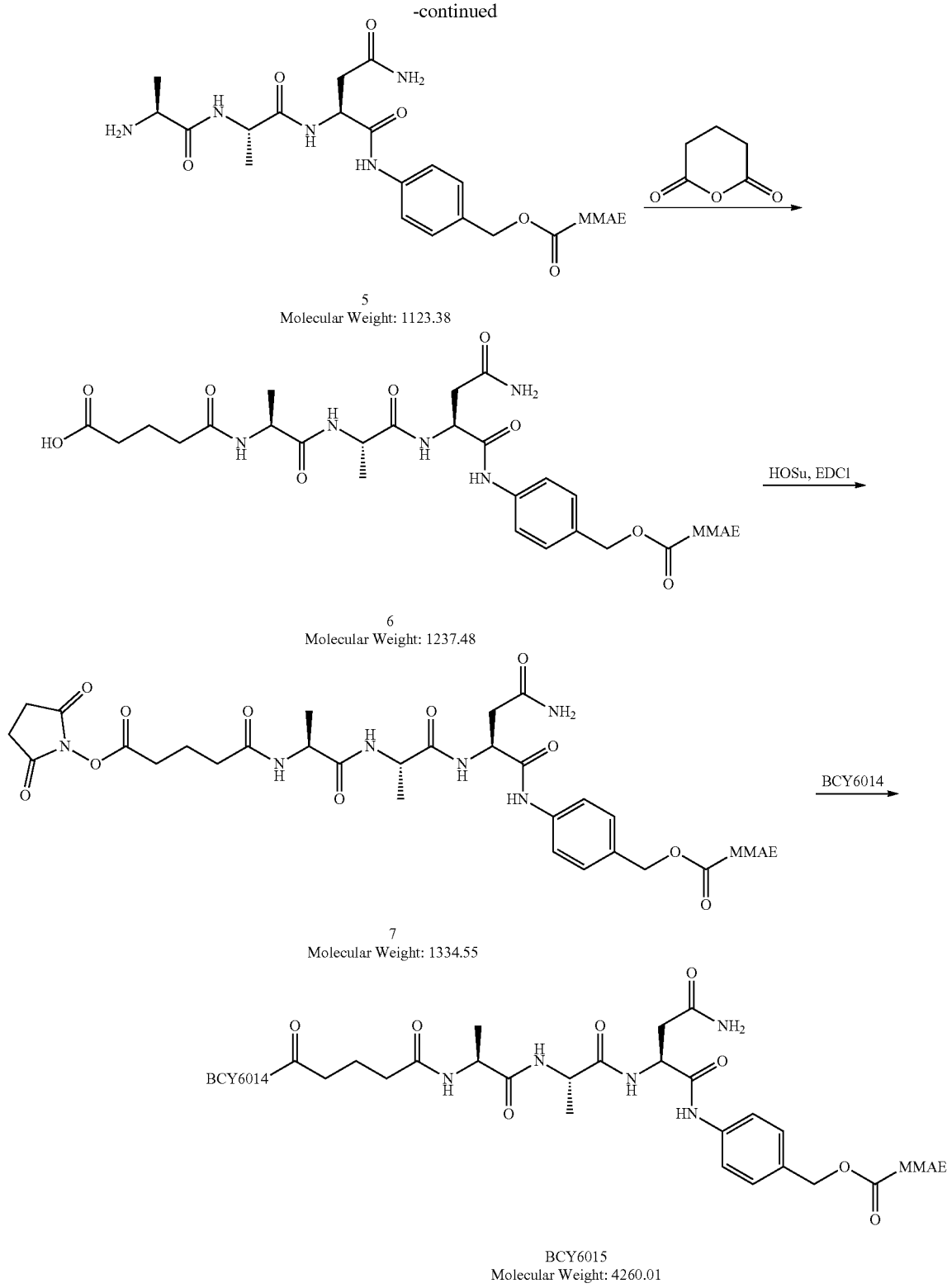

5
Molecular Weight: 1123.38

6
Molecular Weight: 1237.48

7
Molecular Weight: 1334.55

BCY6015
Molecular Weight: 4260.01

General Procedure for Preparation of Compound 2

To a solution of compound 1 (3.5 g, 5.68 mmol, 1.0 eq) in DCM (20 mL) and MeOH (10 mL), (4-aminophenyl) methanol (978.5 mg, 7.95 mmol, 1.4 eq) and EEDQ (2.81 g, 11.35 mmol, 2.0 eq) were added in the dark, and the mixture was stirred at 25° C. for 18 hr. LC-MS showed compound 1 was consumed completely and one main peak with desired MS was detected ([M+H⁺]=722.0). The resulting reaction mixture was concentrated under reduced pressure to give a residue. The residue was purified by flash silica gel chromatography (ISCO®; 220 g SepaFlash® Silica Flash Column, Eluent of 0~10% Methanol/Dichloromethane @ 80 mL/min). Compound 2 (3.0 g, 4.16 mmol, 73.2% yield) was obtained as a yellow solid.

General Procedure for Preparation of Compound 3

To a solution of compound 2 (2.5 g, 3.46 mmol, 1.0 eq) in THF (30 mL) was added DIEA (2.69 g, 20.78 mmol, 3.62 mL, 6.0 eq) and bis(4-nitrophenyl) carbonate (6.32 g, 20.78 mmol, 6.0 eq), and the mixture was stirred at 25° C. for 16 hr. TLC indicated compound 2 was consumed completely and one new spot formed. The reaction was clean according to TLC. The reaction mixture was concentrated under reduced pressure to give a residue. The residue was purified by flash silica gel chromatography (ISCO®; 220 g SepaFlash® Silica Flash Column, Eluent of 0~5% Methanol/Dichloromethane @ 100 mL/min). Compound 3 (2.2 g, 2.48 mmol, 71.6% yield) was obtained as a yellow solid.

General Procedure for Preparation of Compound 4

To a solution of compound 3 (0.3 g, 338.24 umol, 1.0 eq) in DMF (5 mL), HOBt (50.3 mg, 372.06 umol, 1.1 eq), DIEA (131.1 mg, 1.01 mmol, 176.7 μL, 3.0 eq), and MMAE (218.6 mg, 304.42 umol, 0.9 eq) were added. The mixture was stirred at 40° C. for 16 hr. LC-MS showed one peak with desired MS ([M+H$^+$]=1466.4, [M+2H$^+$]/2=733.2). The reaction mixture was then directly purified by prep-HPLC (neutral condition), and compound 4 (0.2 g, 136.44 umol, 40.3% yield) was obtained as a white solid.

General Procedure for Preparation of Compound 5

Compound 4 (0.175 g, 119.39 umol, 1.0 eq) was first dissolved in TFA (1.8 mL), and then triisopropylsilane (13.5 g, 85.20 mmol, 17.5 mL, 713.7 eq) was added. The mixture was stirred at 0° C. for 30 min. LC-MS showed one peak with desired MS ([M+H$^+$]=1123.4, [M+2H$^+$]/2=562.2). The reaction mixture was concentrated under reduced pressure to remove solvent to give a residue. The residue was purified by prep-HPLC (neutral condition). Compound 5 (0.1 g, 89.02 umol, 74.6% yield) was obtained as a yellow solid.

General Procedure for Preparation of Compound 6

To a solution of compound 5 (0.07 g, 62.31 umol, 1.0 eq) in DMA (1.0 mL), DIEA (24.2 mg, 186.94 umol, 32.6 μL, 3.0 eq) and tetrahydropyran-2,6-dione (14.2 mg, 124.62 umol, 2.0 eq) were added. The mixture was stirred at 25° C. for 2 hr. LC-MS showed compound 5 was consumed completely and one main peak with desired MS was detected ([M+H$^+$]=1237.4, [M+2H$^+$]/2=619.3). The reaction mixture was then directly purified by prep-HPLC (neutral condition), and compound 6 (0.04 g, 32.32 umol, 51.8% yield) was obtained as a light yellow solid.

General Procedure for Preparation of Compound 7

To a solution of compound 6 (0.04 g, 32.32 umol, 1.0 eq), 1-hydroxypyrrolidine-2,5-dione (11.2 mg, 96.97 umol, 3.0 eq) in DMA (3.0 mL) and DCM (1.0 mL), EDCI (18.6 mg, 96.97 umol, 3.0 eq) was added. The mixture was stirred at 25° C. for 18 hr. LC-MS showed compound 6 was consumed completely and one main peak with desired MS was detected ([M+H$^+$]=1334.5, [M+2H$^+$]/2=667.7). The reaction mixture was then directly purified by prep-HPLC (TFA condition), and compound 7 (0.025 g, 18.73 umol, 57.9% yield) was obtained as a white solid.

General Procedure for Preparation of BCY6105

To a solution of BCY6014 (82.0 mg, 26.98 umol, 1.2 eq) in DMA (4 mL), DIEA (8.7 mg, 67.44 umol, 11.7 μL, 3.0 eq) and compound 7 (0.03 g, 22.48 umol, 1.0 eq) were added. The mixture was stirred at 25° C. for 18 hr. LC-MS showed compound 7 was consumed completely and one main peak with desired MS was detected ([M+4H$^+$]/4=1065.2). The reaction mixture was then directly purified by prep-HPLC (TFA condition). Compound BCY6105 (0.024 g, 5.41 umol, 24.1% yield, 96.06% purity) was obtained as a white solid.

BCY6106

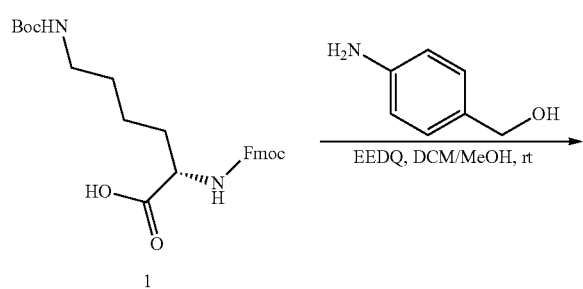

1

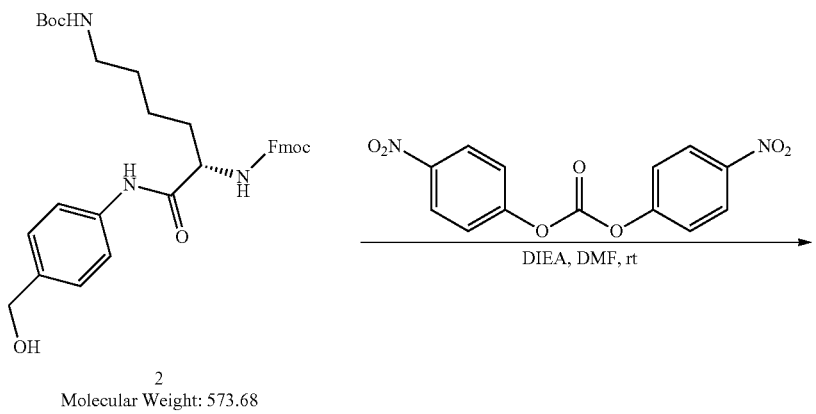

2
Molecular Weight: 573.68

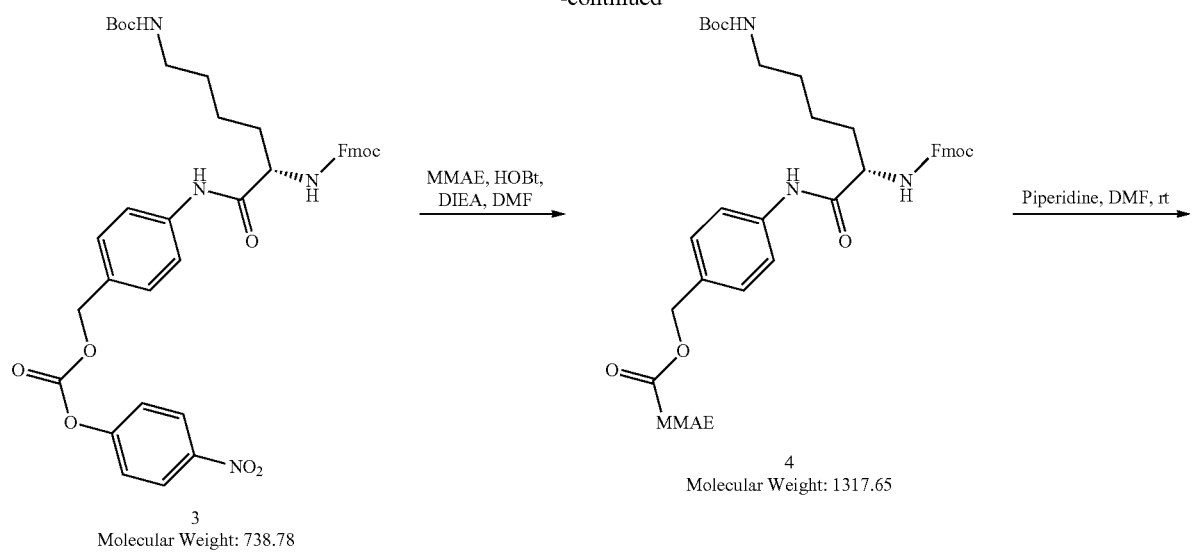
-continued
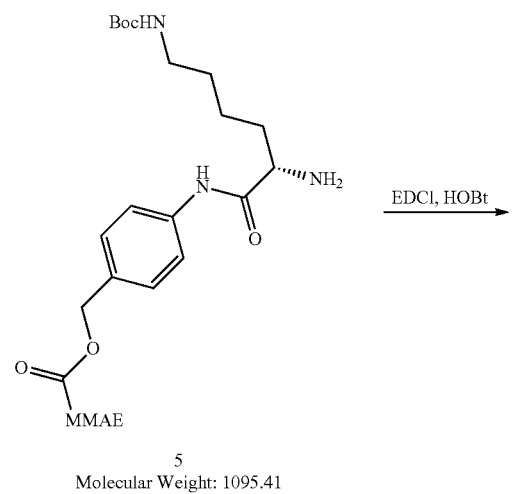
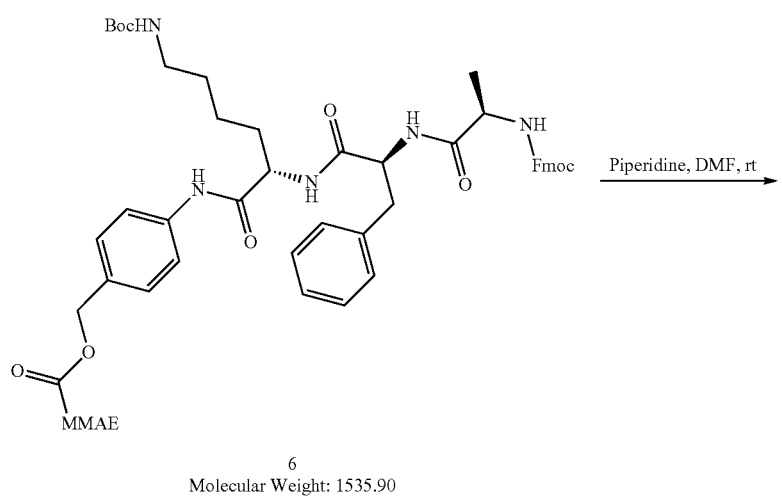

-continued
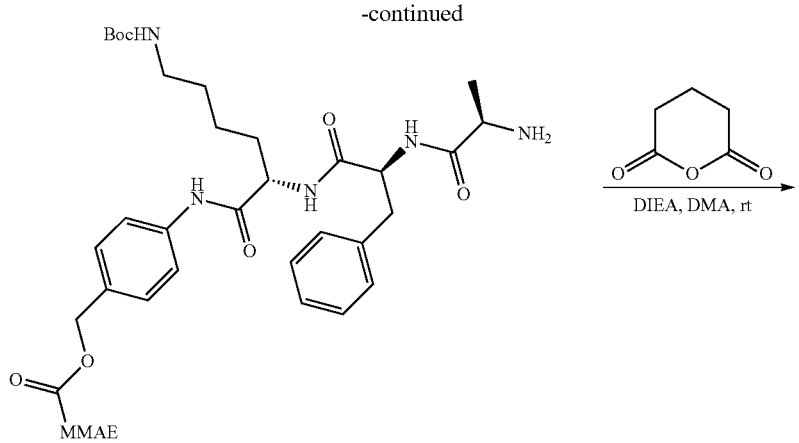
7
Molecular Weight: 1313.66
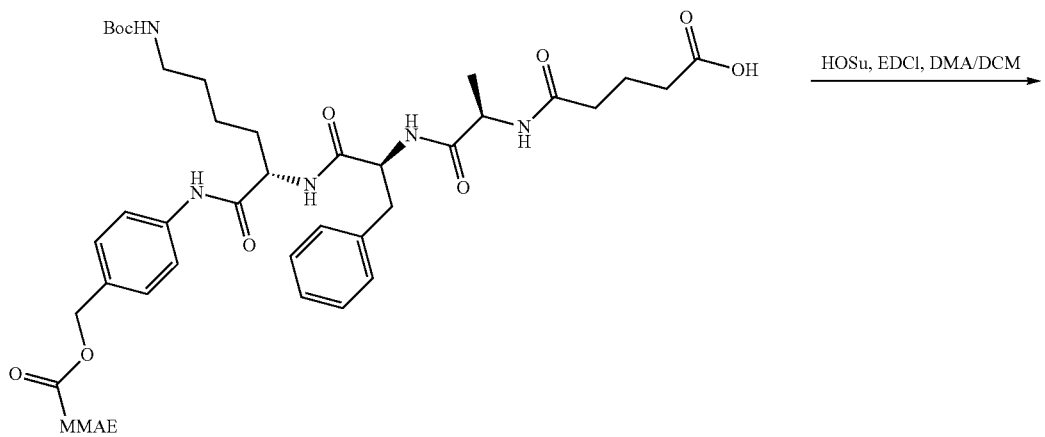
8
Molecular Weight: 1427.76
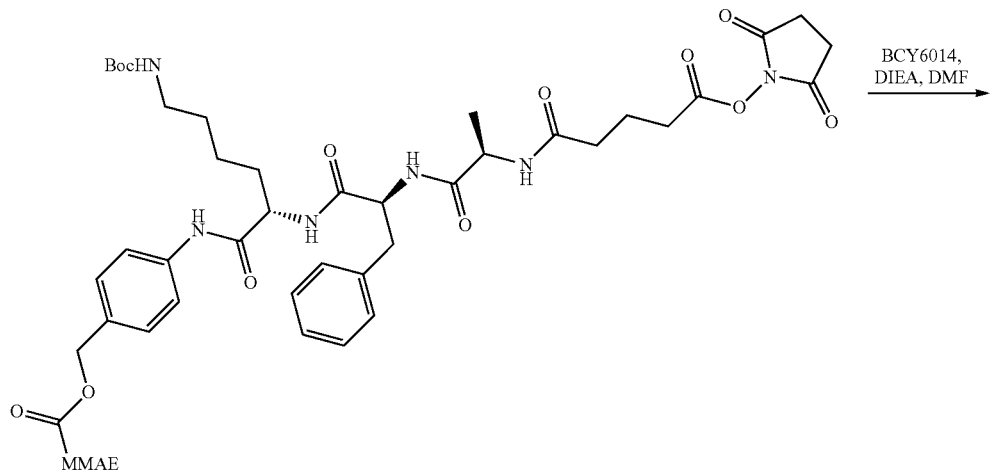
9
Molecular Weight: 1524.83

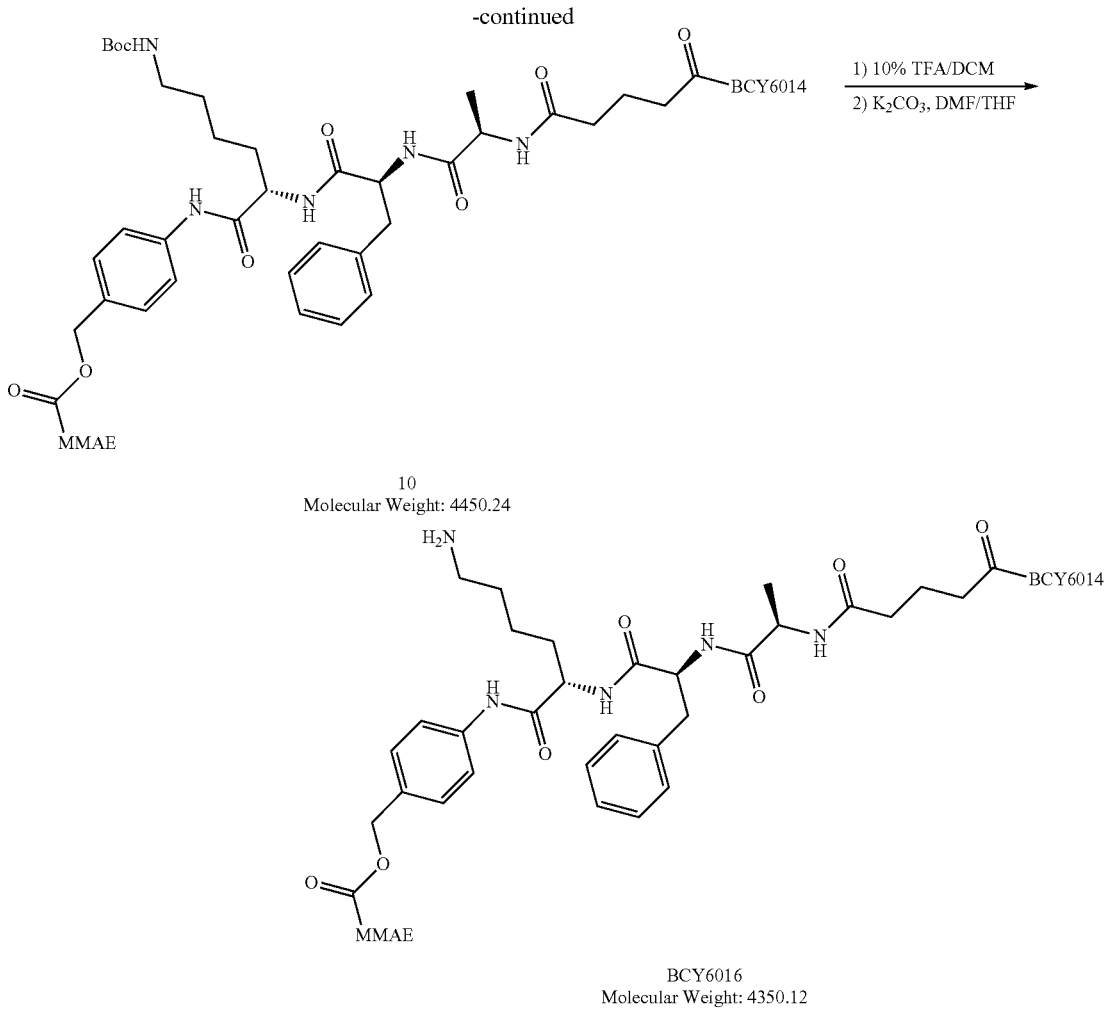

10
Molecular Weight: 4450.24

BCY6016
Molecular Weight: 4350.12

General Procedure for Preparation of Compound 2

To a solution of compound 1 (5.0 g, 10.67 mmol, 1.0 eq) in DCM (30 mL) and MeOH (10 mL), EEDQ (5.28 g, 21.34 mmol, 2.0 eq) and (4-aminophenyl)methanol (2.63 g, 21.34 mmol, 2.0 eq) were added. The mixture was stirred at 20° C. for 18 hr. LC-MS showed compound 1 was consumed completely and one main peak with desired MS was detected (desired m/z=574, while Boc group falling off and partially falling off corresponded to m/z=474 and 518, respectively). The reaction mixture was concentrated under reduced pressure to remove solvent to give a residue. The residue was purified by prep-HPLC (neutral condition). Compound 2 (3.7 g, 6.45 mmol, 60.4% yield) was obtained as a yellow solid.

General Procedure for Preparation of Compound 3

To a solution of compound 2 (3.4 g, 5.93 mmol, 1.0 eq) in DMF (20 mL) was added DIEA (5.36 g, 41.49 mmol, 7.23 mL, 7.0 eq) and bis(4-nitrophenyl) carbonate (10.82 g, 35.56 mmol, 6.0 eq) in one part. The mixture was stirred at 25° C. for 2 hr. LC-MS showed one peak with desired MS (m/z=639 corresponded to the mass with Boc group falling off during ESI). The reaction mixture was directly purified by prep-HPLC (neutral condition). Compound 3 (3.0 g, 4.06 mmol, 68.5% yield) was obtained as a yellow solid.

General Procedure for Preparation of Compound 4

To a solution of compound 3 (707.4 mg, 957.55 umol, 1.0 eq) in DMF (15 mL), HOBt (155.3 mg, 1.15 mmol, 1.2 eq), DIEA (371.3 mg, 2.87 mmol, 500.4 µL, 3.0 eq), and MMAE (0.55 g, 766.04 umol, 0.8 eq) were added. The mixture was stirred at 30° C. for 16 hr. LC-MS showed one peak with desired MS (desired m/z=1317, and m/z=609 corresponded to the mass with two protons and Boc group falling off during ESI). The reaction mixture was then directly purified by prep-HPLC (neutral condition). Compound 4 (0.53 g, 402.23 umol, 42.0% yield) was obtained as a yellow solid.

General Procedure for Preparation of Compound 5

To a solution of compound 4 (0.526 g, 399.20 umol, 1.0 eq) in DMF (4 mL), piperidine (862.2 mg, 10.13 mmol, 1.0 mL, 25.4 eq) was added. The mixture was stirred at 25° C. for 30 min. LC-MS showed compound 4 was consumed completely and one main peak with desired MS was detected (desired m/z=1095, and m/z=265 corresponded to Fmoc-piperidine adduct). The reaction mixture was then directly purified by prep-HPLC (neutral condition). Compound 5 (0.230 g, 209.97 umol, 52.6% yield) was obtained as a white solid.

General Procedure for Preparation of Compound 6

To a solution of Fmoc-(D-Ala)-Phe-OH (125.6 mg, 273.87 umol, 1.2 eq) in DMF (10 mL), EDCI (52.5 mg, 273.87 umol, 1.2 eq), HOBt (37.0 mg, 273.87 umol, 1.2 eq), and compound 5 (0.25 g, 228.23 umol, 1 eq) were added. The mixture was stirred at 25° C. for 3 hr. LC-MS showed compound 5 was consumed completely and one peak with desired MS was detected (m/z=718 corresponded to the mass with two protons and Boc group falling off during ESI). The reaction mixture was then directly purified by prep-HPLC (neutral condition). Compound 6 (0.18 g, 117.20 umol, 51.3% yield) was obtained as a white solid.

General Procedure for Preparation of Compound 7

To a solution of compound 6 (0.18 g, 117.20 umol, 1.0 eq) in DMF (8 mL), piperidine (1.72 g, 20.25 mmol, 2.0 mL, 172.8 eq) was added. The mixture was stirred at 25° C. for 1 hr. LC-MS showed compound 7 was consumed completely and one main peak with desired MS was detected (m/z=1314 and 657 corresponded to the desired mass, and m/z=265 corresponded to Fmoc-piperidine adduct). The reaction mixture was then directly purified by prep-HPLC (neutral condition). Compound 7 (0.13 g, 98.96 umol, 84.4% yield) was obtained as a white solid.

General Procedure for Preparation of Compound 8

To a solution of compound 7 (0.105 g, 79.93 umol, 1.0 eq) in DMA (4 mL), DIEA (31.0 mg, 239.79 umol, 41.8 µL, 3.0 eq) and tetrahydropyran-2,6-dione (27.4 mg, 239.79 umol, 3.0 eq) were added. The mixture was stirred at 25° C. for 2 hr. LC-MS showed compound 7 was consumed completely and one main peak with desired MS was detected (m/z 664.5 corresponded to the mass with two protons and Boc group falling off during ESI). The reaction mixture was then directly purified by prep-HPLC (neutral condition), and compound 8 (0.09 g, 63.04 umol, 78.8% yield) was obtained as a white solid.

General Procedure for Preparation of Compound 9

To a solution of compound 8 (0.09 g, 63.04 umol, 1.0 eq), 1-hydroxypyrrolidine-2,5-dione (21.7 mg, 189.11 umol, 3.0 eq) in DMA (3 mL) and DCM (1 mL), EDCI (36.2 mg, 189.11 umol, 3.0 eq) dissolved in 1 mL DCM was added. The mixture was stirred at 25° C. for 18 hr. LC-MS showed compound 8 was consumed completely and one main peak with desired MS was detected (desired m/z=1524 (one proton) and 763 (two protons), while m/z=713 corresponded to the mass with Boc group falling off during ESI). The reaction mixture was directly purified by prep-HPLC (neutral condition). Compound 9 (0.07 g, 45.91 umol, 72.8% yield) was obtained as a white solid.

General Procedure for Preparation of Compound 10

To a solution of BCY6014 (167.5 mg, 55.09 umol, 1.2 eq) in DMF (3 mL), DIEA (11.8 mg, 91.81 umol, 16.0 µL, 2.0 eq) and compound 9 (0.07 g, 45.91 umol, 1.0 eq) were added. The mixture was stirred at 25° C. for 16 hr. LC-MS showed compound 9 was consumed completely and one main peak with desired MS was detected ([M+4H+]/4=1112.9, [M+5H+]/5=890.5). The reaction mixture was concentrated under reduced pressure to remove solvent to give a residue. The crude product 10 (0.220 g, crude) was used in the next step without further purification.

General Procedure for Preparation of BCY6106

To a solution of compound 10 (0.200 g, 44.95 umol, 1.0 eq) in DCM (4 mL), 1 mL TFA was added. The mixture was stirred at 25° C. for 1 hr. LC-MS showed one main peak with desired MS ([M+4H+]/4=1088.0, [M+5H+]/5=870.8). The reaction mixture was concentrated under reduced pressure to give a residue, which was then directly purified by prep-HPLC (TFA condition). Compound BCY6106 (0.0297 g, 20.06 umol, 14.5% yield, 95.46% purity) was obtained as a white solid.

BCY6175

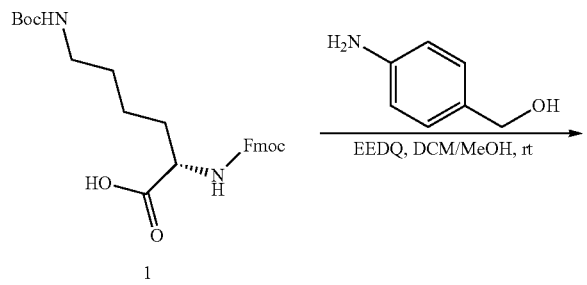

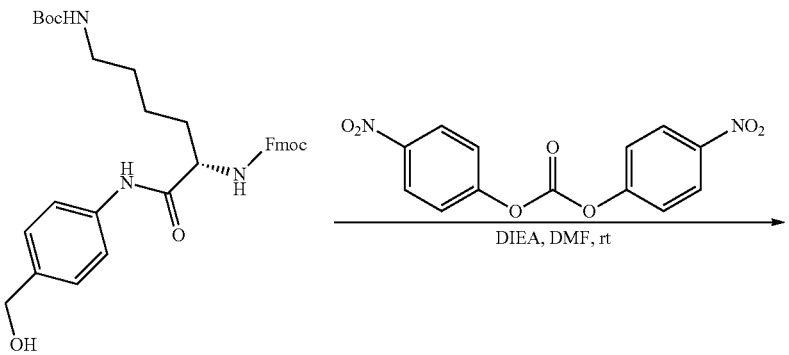

291 292
-continued
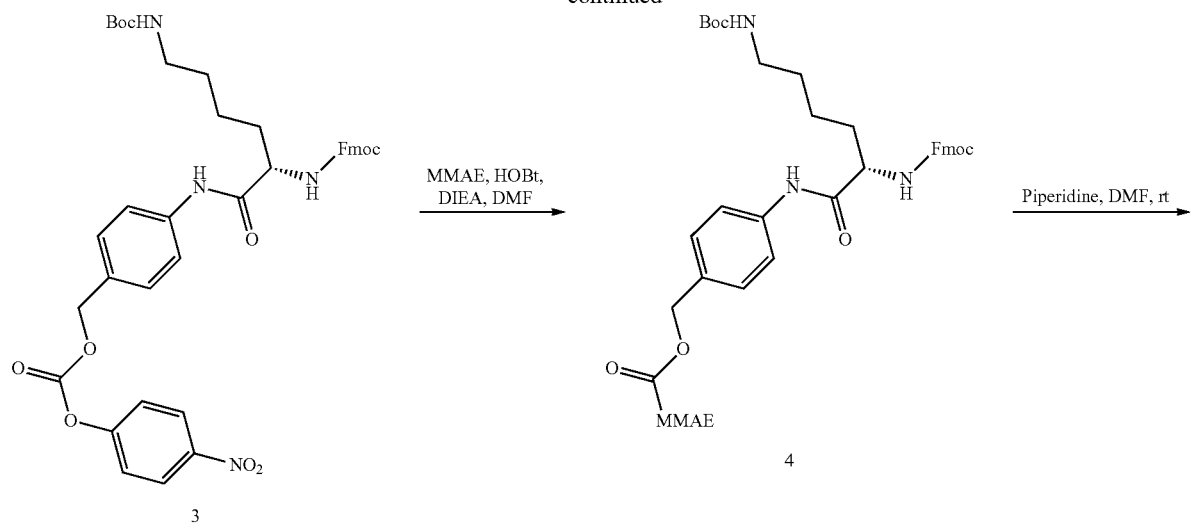
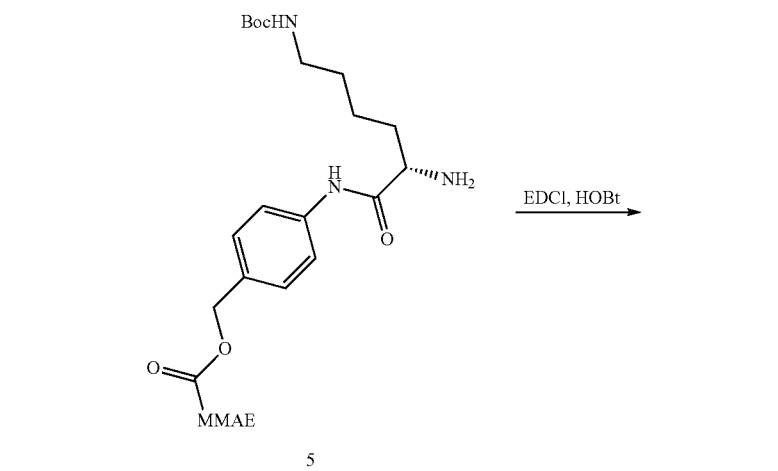
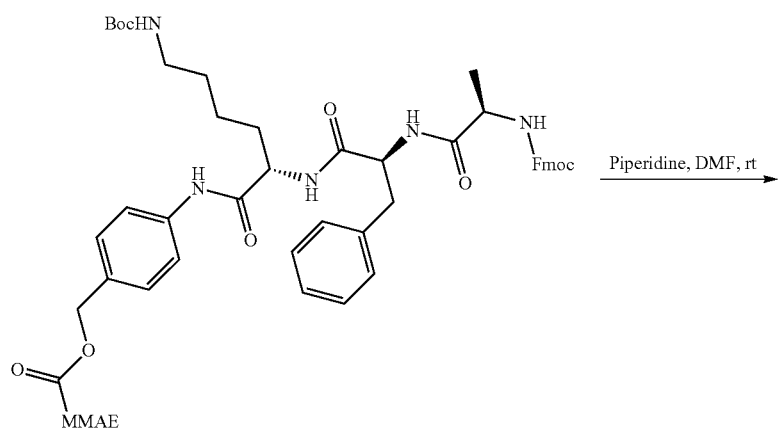

293
-continued
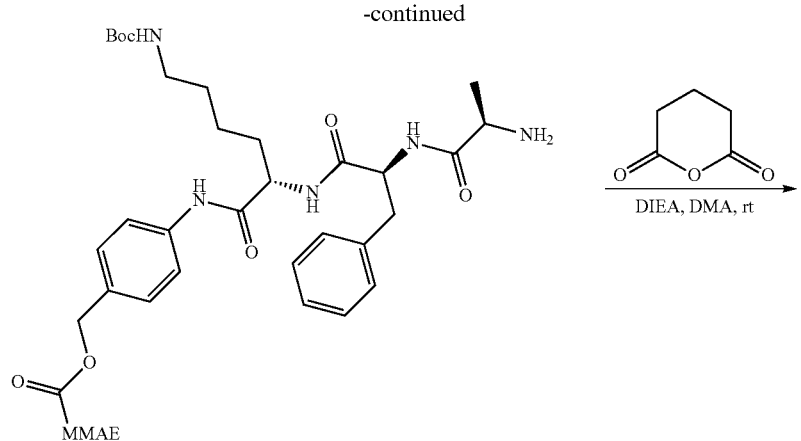
7
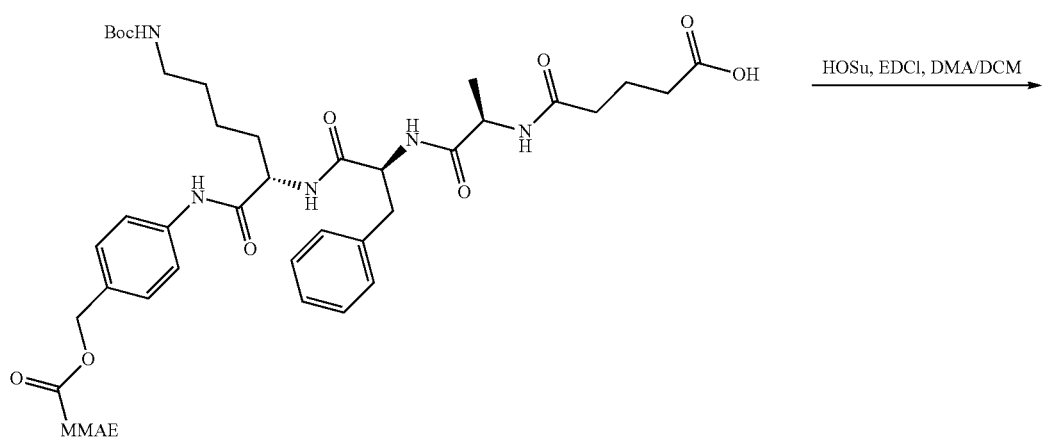
8
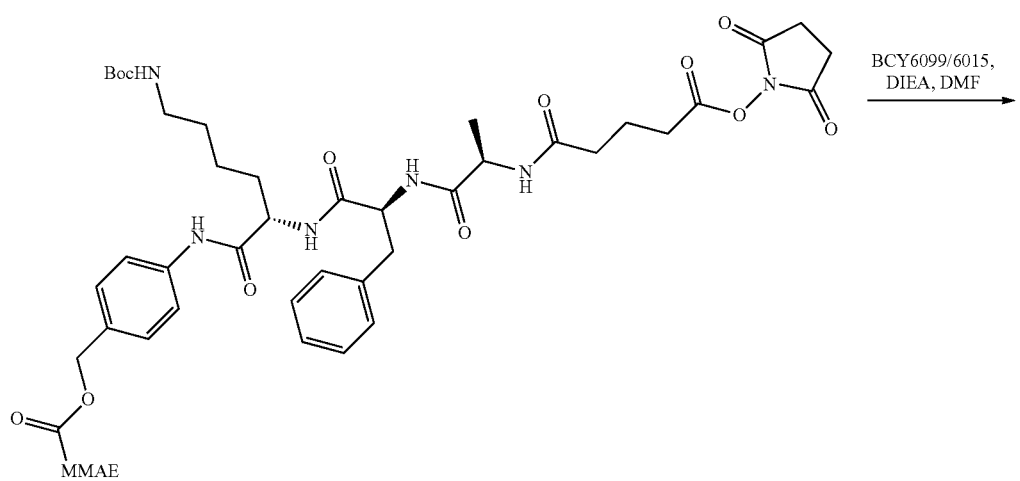
9

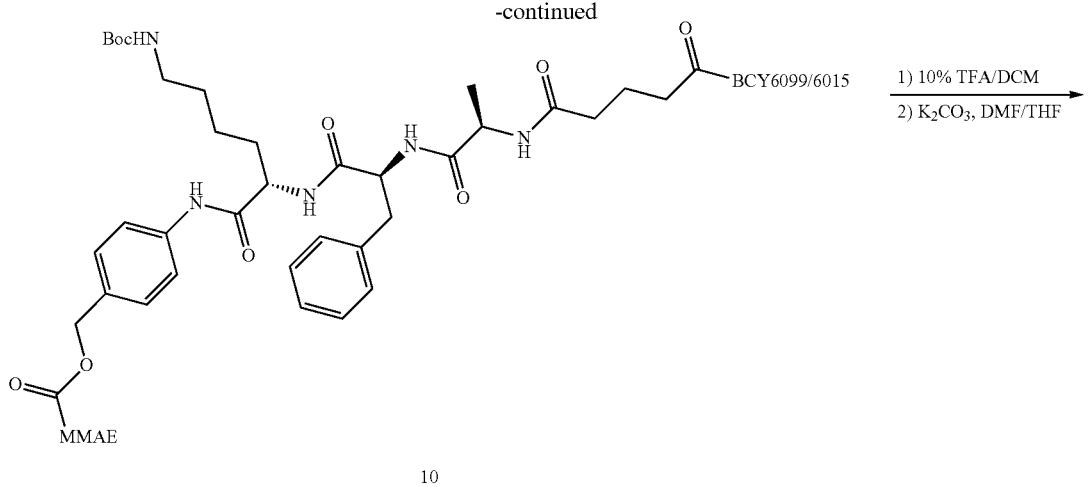

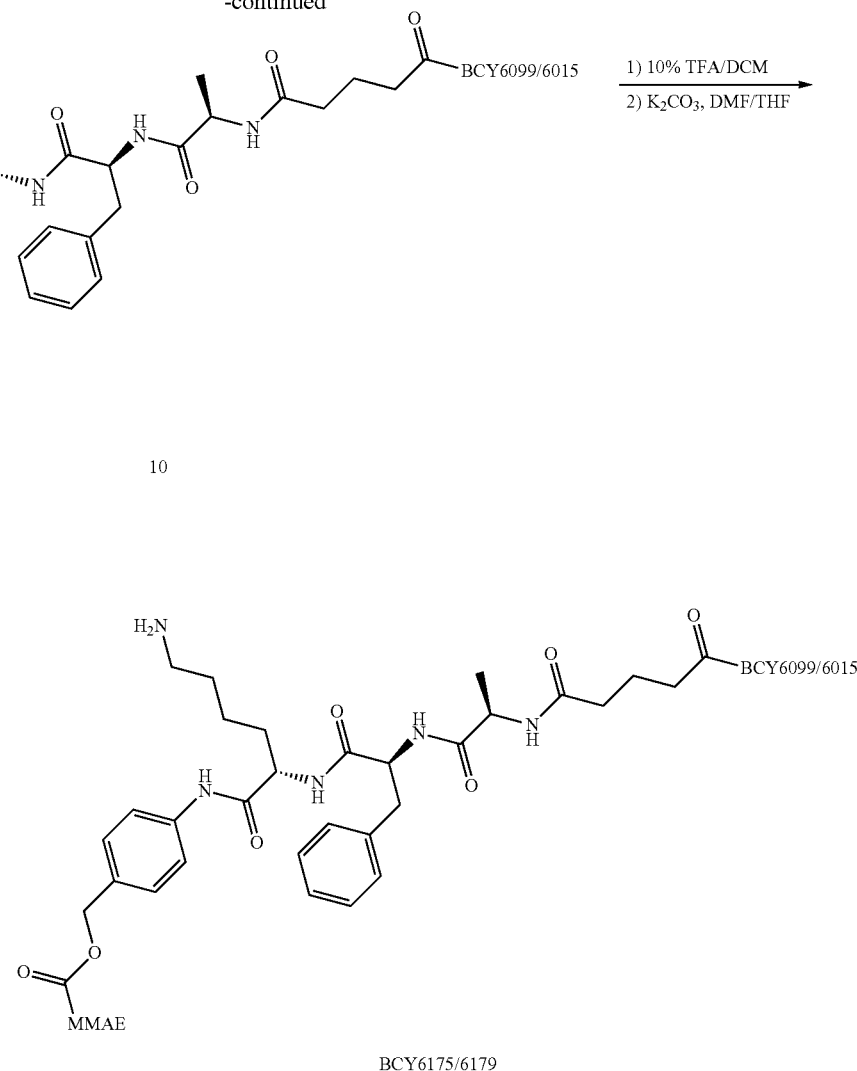

BCY6175/6179

General Procedure for Preparation of Compound 9

The synthesis of Compound 9 was performed in an analogous to manner to that described in BCY6106.

General Procedure for Preparation of Compound 10A

To a solution of BCY6099 (195.15 mg, 61.32 μmol, 1.1 eq) in DMA (3 mL) were added DIEA (21.61 mg, 167.23 μmol, 29.13 μL, 3 eq) and compound 9 (0.085 g, 55.74 μmol, 1.0 eq). The mixture was stirred at 25° C. for 16 hr. LC-MS showed compound 9 was consumed completely and one main peak with desired m/z was detected. The reaction mixture was concentrated under reduced pressure to remove solvent to afford a residue (light yellow oil). The reaction was directly purified by prep-HPLC (neutral condition). Compound 10A (0.160 g, 34.84 μmol, 62.50% yield) was obtained as a white solid.

General Procedure for Preparation of BCY6175

To a solution of compound 10A in DCM (4.5 mL) was added TFA (4.5 mL). The mixture was stirred at 0° C. for 30 min. LC-MS showed compound 10A was consumed completely and one main peak with desired m/z was detected. The reaction mixture was concentrated under reduced pressure to remove solvent to afford a residue, which was purified by prep-HPLC (TFA condition). Compound BCY6175 (61.40 mg, 13.56 μmol, 31.13% yield) was obtained as a white solid.

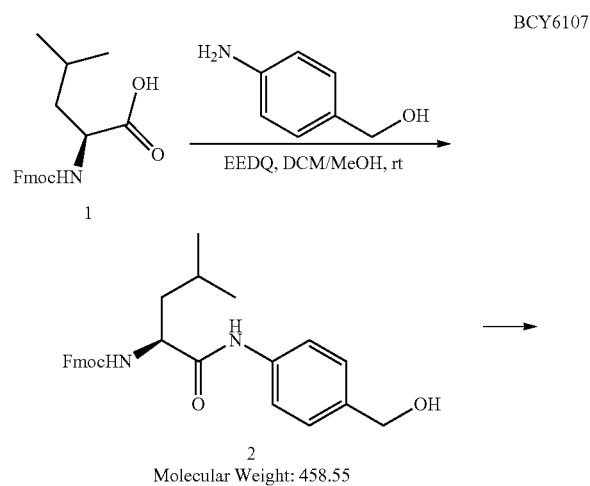

BCY6107

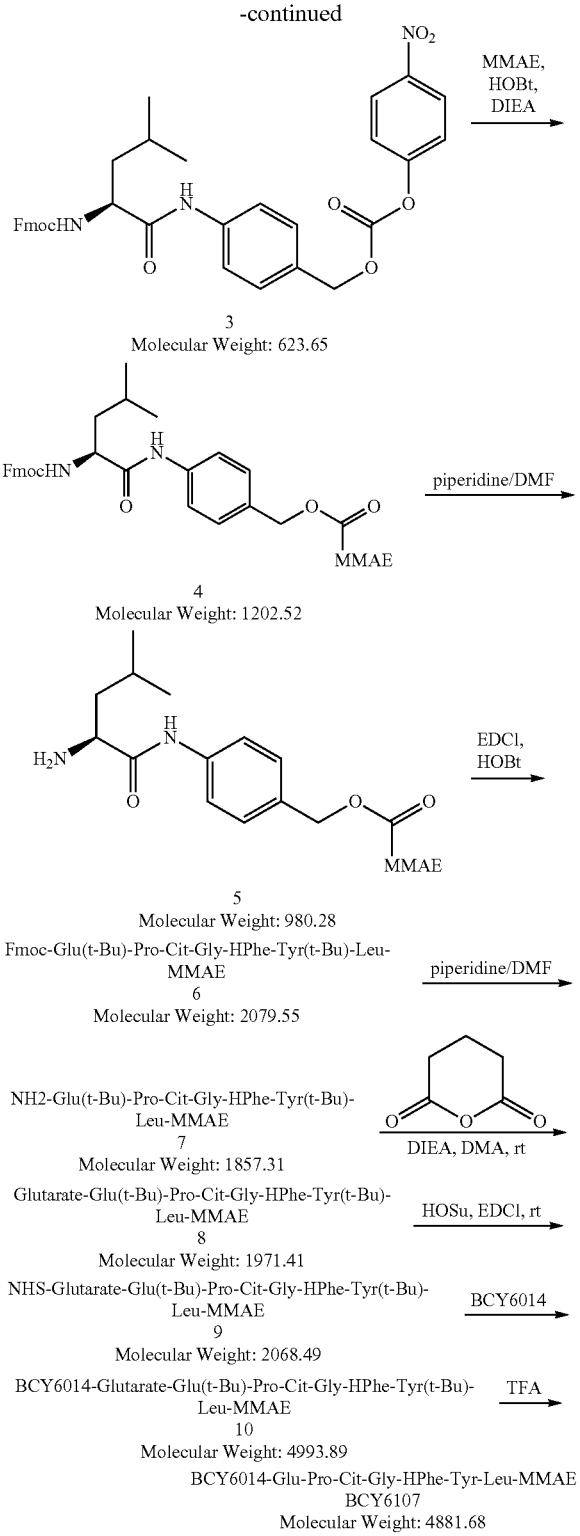

3
Molecular Weight: 623.65

4
Molecular Weight: 1202.52

5
Molecular Weight: 980.28

Fmoc-Glu(t-Bu)-Pro-Cit-Gly-HPhe-Tyr(t-Bu)-Leu-MMAE
6
Molecular Weight: 2079.55

NH2-Glu(t-Bu)-Pro-Cit-Gly-HPhe-Tyr(t-Bu)-Leu-MMAE
7
Molecular Weight: 1857.31

Glutarate-Glu(t-Bu)-Pro-Cit-Gly-HPhe-Tyr(t-Bu)-Leu-MMAE
8
Molecular Weight: 1971.41

NHS-Glutarate-Glu(t-Bu)-Pro-Cit-Gly-HPhe-Tyr(t-Bu)-Leu-MMAE
9
Molecular Weight: 2068.49

BCY6014-Glutarate-Glu(t-Bu)-Pro-Cit-Gly-HPhe-Tyr(t-Bu)-Leu-MMAE
10
Molecular Weight: 4993.89

BCY6014-Glu-Pro-Cit-Gly-HPhe-Tyr-Leu-MMAE
BCY6107
Molecular Weight: 4881.68

General Procedure for Preparation of Compound 2

To a solution of compound 1 (3.0 g, 8.49 mmol, 1.0 eq) in DCM (30 mL) and MeOH (10 mL), EEDQ (2.52 g, 10.19 mmol, 1.2 eq) and (4-aminophenyl)methanol (1.25 g, 10.19 mmol, 1.2 eq) were added. The mixture was stirred at 25° C. for 16 hr. LC-MS showed compound 1 was consumed completely and one main peak with desired MS was detected ([M+H]$^+$ 459.5). In addition, TLC indicated compound 1 was consumed completely and new spots formed. The reaction mixture was concentrated under reduced pressure to remove solvent to give a residue. The residue was purified by flash silica gel chromatography (ISCO®; 120 g SepaFlash® Silica Flash Column, Eluent of 0-60% Ethylacetate/Petroleum ether gradient @ 80 mL/min). Compound 2 (3.5 g, 7.63 mmol, 89.9% yield) was obtained as a yellow solid.

General Procedure for Preparation of Compound 3

To a solution of compound 2 (3.3 g, 7.20 mmol, 1.0 eq) in THF (100 mL), DIEA (4.65 g, 35.98 mmol, 6.27 mL, 5.0 eq) and bis(4-nitrophenyl) carbonate (8.76 g, 28.79 mmol, 4.0 eq) were added. The mixture was stirred at 25° C. for 16 hr. LC-MS showed compound 2 was consumed completely and one main peak with desired MS was detected ([M+H]$^+$ 624.0). In addition, TLC indicated compound 2 was consumed completely and new spots formed. The reaction mixture was concentrated under reduced pressure to remove solvent to give a residue. The residue was purified by flash silica gel chromatography (ISCO®; 120 g SepaFlash® Silica Flash Column, Eluent of 0-15% Ethylacetate/Petroleum ether gradient @ 80 mL/min). Compound 3 (3.0 g, 4.81 mmol, 66.8% yield) was obtained as a yellow solid.

General Procedure for Preparation of Compound 4

To a solution of compound 3 (124.09 mg, 198.97 umol, 1.0 eq) in DMF (5 mL), HOBt (32.3 mg, 238.77 umol, 1.2 eq), DIEA (77.1 mg, 596.92 μmol, 103.9 μL, 3.0 eq), and MMAE (0.1 g, 139.28 umol, 0.7 eq) were added. The mixture was stirred at 25° C. for 1 hr. LC-MS showed compound 3 was consumed completely and one main peak with desired MS was detected ([M+H]$^+$ 1202.5, [M+Na]+ 1224.5). The reaction mixture was then directly purified by prep-HPLC (neutral condition). After lyophilization, compound 4 (0.08 g, 66.53 umol, 33.4% yield) was obtained as a white solid.

General Procedure for Preparation of Compound 5

To a solution of compound 4 (0.08 g, 66.53 umol, 1.0 eq) in DMF (4 mL), piperidine (862.2 mg, 10.13 mmol, 1 mL, 152.2 eq) was added. The mixture was stirred at 25° C. for 1 hr. LC-MS showed compound 4 was consumed completely and one main peak with desired MS was detected ([M+H]$^+$ 981.5, [M+Na]$^+$1003.5, while m/z=264.0 corresponded to Fmoc-piperidine adduct). The reaction mixture was directly purified by prep-HPLC (neutral condition). Compound 5 (0.055 g, 56.11 umol, 84.3% yield) was obtained as a white solid.

General Procedure for Preparation of Compound 6

To a solution of Fmoc-Glu(t-Bu)-Pro-Cit-Gly-HPhe-Tyr (t-Bu)-OH (74.1 mg, 66.31 umol, 1.3 eq) in DMF (4 mL), EDCI (12.7 mg, 66.31 umol, 1.3 eq), HOBt (8.9 mg, 66.31 umol, 1.3 eq), and compound 5 (0.05 g, 51.01 umol, 1.0 eq) were added. The mixture was stirred at 25° C. for 30 min. LC-MS indicated 20% of compound 5 remained, several new peaks formed, and 60% of the reaction mixture was desired product ([M+2H+]/2=1040.4). The reaction mixture was directly purified by prep-HPLC (neutral condition). Compound 6 (0.07 g, 33.66 umol, 66.0% yield) was obtained as a white solid.

General Procedure for Preparation of Compound 7

To a solution of compound 6 (0.07 g, 33.66 umol, 1.0 eq) in DMF (4 mL), piperidine (2.9 mg, 33.66 umol, 3.3 μL, 1.0 eq) was added. The mixture was stirred at 25° C. for 15 min. LC-MS showed compound 6 was consumed completely and one main peak with desired MS was detected ([M+2H$^+$]/2=929.1, while m/z=264.2 corresponded to Fmoc-piperidine adduct). The reaction mixture was directly purified by prep-HPLC (neutral condition). Compound 7 (0.045 g, 24.23 umol, 72.0% yield) was obtained as a white solid.

General Procedure for Preparation of Compound 8

To a solution of compound 7 (0.04 g, 21.54 umol, 1.0 eq) in DMA (1 mL), DIEA (8.3 mg, 64.61 umol, 11.2 µL, 3.0 eq) and tetrahydropyran-2,6-dione (7.4 mg, 64.61 umol, 3.0 eq) were added. The mixture was stirred at 25° C. for 1 hr. LC-MS showed compound 7 was consumed completely and one main peak with desired MS was detected ([M+2H+]/2=986.4). The reaction mixture was then directly purified by prep-HPLC (neutral condition). Compound 8 (0.035 g, 17.75 umol, 82.4% yield) was obtained as a white solid.

General Procedure for Preparation of Compound 9

To a solution of compound 8 (0.035 g, 17.75 umol, 1.0 eq), 1-hydroxypyrrolidine-2,5-dione (6.1 mg, 53.26 umol, 3.0 eq) in DMA (3 mL) and DCM (1 mL), EDCI (10.2 mg, 53.26 umol, 3.0 eq) was added. The mixture was stirred at 25° C. for 16 hr. LC-MS showed compound 8 was partially remained and one peak with desired MS was detected ([M+2H+]/2=1034.7). DCM was then removed, following by mixture being purified by prep-HPLC (neutral condition). Compound 9 (0.03 g, 14.50 umol, 81.7% yield) was obtained as a white solid.

General Procedure for Preparation of Compound 10

To a solution of BCY6014 (52.9 mg, 17.40 umol, 1.59 µL, 1.2 eq) in DMF (2 mL), DIEA (5.6 mg, 43.51 umol, 7.6 µL, 3.0 eq) and compound 9 (0.03 g, 14.50 umol, 1.0 eq) were added. The mixture was stirred at 25° C. for 16 hr. LC-MS showed one main peak with desired MS ([M+4H+]/4=1249.2, [M+5H+]/5=999.3). The solvent was then removed and the resulting crude product 10 (0.06 g, crude) was used into the next step without further purification.

General Procedure for Preparation of BCY6107

To a solution of compound 10 (0.055 g, 11.01 umol, 1.0 eq) in DCM (1 mL), 1 mL TFA was added. The mixture was stirred at 0° C. for 15 min. LC-MS showed compound 10 was consumed completely and one main peak with desired MS was detected ([M+4H+]/4=1221.0, [M+5H+]/5=977.0). The reaction mixture was concentrated under reduced pressure to remove solvent, resulting a residue which was then directly purified by prep-HPLC (TFA condition). Compound BCY6107 (20.4 mg, 4.03 umol, 36.6% yield, 96.36% purity) was obtained as a white solid.

Biological Data

Study 1: Fluorescence Polarisation Measurements (a) Direct Binding Assay

Peptides with a fluorescent tag (either fluorescein, SIGMA or Alexa Fluor488™, Fisher Scientific) were diluted to 2.5 nM in PBS with 0.01% tween 20 or 50 mM HEPES with 100 mM NaCl and 0.01% tween pH 7.4 (both referred to as assay buffer). This was combined with a titration of protein in the same assay buffer as the peptide to give 1 nM peptide in a total volume of 25 µL in a black walled and bottomed low bind low volume 384 well plates, typically 5 µL assay buffer, 10 µL protein (Table 1) then 10 µL fluorescent peptide. One in two serial dilutions were used to give 12 different concentrations with top concentrations ranging from 500 nM for known high affinity binders to 10 µM for low affinity binders and selectivity assays. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. The gain used for analysis was determined for each tracer at the end of the 60 minutes where there was no protein in the well.

Data was analysed using Systat Sigmaplot version 12.0. mP values were fit to a user defined quadratic equation to generate a Kd value: f=ymin+(ymax−ymin)/Lig*((x+Lig+Kd)/2−sqrt((((x+Lig+Kd)/2)^2)−(Lig*x))). "Lig" was a defined value of the concentration of tracer used.

(b) Competition Binding Assay

Peptides without a fluorescent tag were tested in competition with a peptide with a fluorescent tag and a known Kd (Table 2). Reference Compound A has the sequence FI-G-Sar$_5$-ACPWGPAWCPVNRPGCA (FI-G-Sar$_5$-(SEQ ID NO: 94)). Reference Compound B has the sequence FI-G-Sar$_5$-ACPWGPFWCPVNRPGCA (FI-G-Sar$_5$-(SEQ ID NO: 95)). Reference Compound C has the sequence FI-G-Sar$_5$-AD-VTCPWGPFWCPVNRPGCA (FI-G-Sar$_5$-(SEQ ID NO: 96). Each of Reference Compounds A, B and C contain a TBMB molecular scaffold. Peptides were diluted to an appropriate concentration in assay buffer as described in the direct binding assay with a maximum of 5% DMSO, then serially diluted 1 in 2. Five µL of diluted peptide was added to the plate followed by 10 µL of human or mouse EphA2 (Table 1) at a fixed concentration which was dependent on the fluorescent peptide used (Table 2), then 10 µL fluorescent peptide added. Measurements were conducted as for the direct binding assay, however the gain was determined prior to the first measurement. Data analysis was in Systat Sigmaplot version 12.0 where the mP values were fit to a user defined cubic equation to generate a Ki value:

$$f=y\ min+(y\ max-y\ min)/Lig*((Lig*((2*((Klig+Kcomp+Lig+Comp-Prot*c)^2-3*(Kcomp*(Lig-Prot*c)+Klig*(Comp-Prot*c)+Klig*Kcomp))^0.5*COS(ARCCOS((-2*(Klig+Kcomp+Lig+Comp-Prot*c)^3+9*(Klig+Kcomp+Lig+Comp-Prot*c)*(Kcomp*(Lig-Prot*c)+Klig*(Comp-Prot*c)+Klig*Kcomp)-27*(-1*Klig*Kcomp*Prot*c))/(2*((((Klig+Kcomp+Lig+Comp-Prot*c)^2-3*(Kcomp*(Lig-Prot*c)+Klig*(Comp-Prot*c)+Klig*Kcomp))^3)^0.5)))/3))-(Klig+Kcomp+Lig+Comp-Prot*c)))/((3*Klig)+((2*((Klig+Kcomp+Lig+Comp-Prot*c)^2-3*(Kcomp*(Lig-Prot*c)+Klig*(Comp-Prot*c)+Klig*Kcomp))^0.5*COS(ARCCOS((-2*(Klig+Kcomp+Lig+Comp-Prot*c)^3+9*(Klig+Kcomp+Lig+Comp-Prot*c)*(Kcomp*(Lig-Prot*c)+Klig*(Comp-Prot*c)+Klig*Kcomp)-27*(-1*Klig*Kcomp*Prot*c))/(2*((((Klig+Kcomp+Lig+Comp-Prot*c)^2-3*(Kcomp*(Lig-Prot*c)+Klig*(Comp-Prot*c)+Klig*Kcomp))^3)^0.5)))/3))-(Klig+Kcomp+Lig+Comp-Prot*c)))).$$

"Lig", "KLig" and "Prot" were all defined values relating to: fluorescent peptide concentration, the Kd of the fluorescent peptide and EphA2 concentration respectively.

TABLE 1

Ephrin receptors and source

| Receptor (domain) | Species | Format/tag | Supplier | Catalogue number |
|---|---|---|---|---|
| EphA1 (Ecto) | Human | Fc fusion | R&D systems | 7146-A1 |
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | Fc fusion | R&D Systems | 639-A2 |
| EphA2 (Ecto) | Mouse | C-terminal polyHis | Sino Biological | 50586-M08H |
| EphA2 (ligand binding) | Rat | C-terminal polyHis | In-house | N/A |
| EphA2 (ligand binding) | Dog | C-terminal polyHis | In-house | N/A |
| EphA3 (Ecto) | Human | Fc fusion | R&D systems | 6444-A3 |

TABLE 1-continued

Ephrin receptors and source

| Receptor (domain) | Species | Format/tag | Supplier | Catalogue number |
|---|---|---|---|---|
| EphA3 (Ecto) | Human | N-terminal polyHis | In-house | N/A |
| EphA3 (Ecto) | Rat | C-terminal polyHis | Sino Biological | 80465-R08H |
| EphA4 (Ecto) | Human | Fc fusion | R&D systems | 6827-A4 |
| EphA4 (Ecto) | Human | C-terminal polyHis | Sino Biological | 11314-H08H |
| EphA4 (Ecto) | Rat | C-terminal polyHis | Sino Biological | 80123-R08H |
| EphA6 (Ecto) | Human | Fc fusion | R&D systems | 5606-A6 |
| EphA7 (Ecto) | Human | Fc fusion | R&D systems | 6756-A7 |
| EphB1 (Ecto) | Rat | Fc fusion | R&D systems | 1596-B1 |
| EphB4 (Ecto) | human | C-terminal polyHis | R&D systems | 3038-B4 |

TABLE 2

Final concentrations of fluorescent peptide and EphA2 as used with Competition Binding Assays

| Fluorescent peptide | Concentration of fluorescent peptide (nM) | Concentration of Human EphA2 (nM) | Concentration of Mouse EphA2 (nM) |
|---|---|---|---|
| Reference Compound A | 10 | 75 | |
| Reference Compound B | 1 | 30 | |
| Reference Compound C | 0.8 (human) 1 (mouse) | 2.4 | 50 |

Certain peptide ligands of the invention were tested in the above mentioned assays and the results are shown in Tables 3-7:

TABLE 3

Biological Assay Data for Peptide Ligands of the Invention (TATA peptides, Direct Binding Assay)

| Bicycle Compound Number | Sequence | Human EphA2 ($K_D$, nM ± 95% CI) |
|---|---|---|
| 1 | ACMNDVVVVCAMGWKCA-Sar$_6$-K(FI) ((SEQ ID NO: 3)-Sar$_6$-K(FI)) | 304 ± 91.99 |
| 2 | ACVPDRRCAYMNVCA-Sar$_6$-K(FI) ((SEQ ID NO: 4)-Sar$_{6+l-K(FI)}$) | 74.91 ± 6.6 |
| 3 | ACVVDGRCAYMNVCA-Sar$_6$-K(FI) ((SEQ ID NO: 5)-Sar$_6$-K(FI)) | 129.8 ± 80.75 |
| 4 | ACVVDSRCAYMNVCA-Sar$_6$-K(FI) ((SEQ ID NO: 6)-Sar$_6$-K(FI)) | 124.6 ± 51.74 |
| 5 | ACVPDSRCAYMNVCA-Sar$_6$-K(FI) ((SEQ ID NO: 7)-Sar$_6$-K(FI)) | 93.95 ± 23.62 |
| 6 | ACYVGKECAIRNVCA-Sar$_6$-K(FI) ((SEQ ID NO: 8)-Sar$_6$-K(FI)) | 168.5 ± 20.58 |
| 7 | ACYVGKECACYMNVCA-Sar$_6$-K(FI) ((SEQ ID NO: 9)-Sar$_6$-K(FI)) | 149.73 ± 39.2 |
| 8 | FI-G-Sar$_5$-ACYVGKECAYMNVCA (FI-G-Sar$_5$-(SEQ ID NO: 9)) | 218.33 ± 10.51 |
| 9 | FI-(β-Ala)-Sar$_{10}$-ARDCPLVNPLCLHPGWTC (FI-(β-Ala)-Sar$_{10}$-(SEQ ID NO: 10)) | 6.43 ± 1.15 |
| 10 | FI-(β-Ala)-Sar$_{10}$-A(HArg)DCPLVNPLCLHPGWTC (FI-(β-Ala)-Sar$_{10}$-(SEQ ID NO: 11)) | 9.07 ± 2.49 |
| 11 | Ac-CPLVNPLCLHPGWTCLHG-Sar$_6$-(D-K[FI]) (Ac-(SEQ ID NO: 12)-Sar$_6$-(D-K[FI])) | 3.08 ± 0.43 |
| 12 | Ac-CPLVNPLCLHPGWTCL(D-His)G-Sar$_6$-(D-K[FI]) (Ac-SEQ ID NO: 13)-Sar$_6$-(D-K[FI])) | 10.56 ± 0.77 |
| 13 | Ac-CPLVNPLCLHPGWSCRGQ-Sar$_6$-(D-K[FI]) (Ac-(SEQ ID NO: 14)-Sar$_6$-(D-K[FI])) | 5.29 ± 0.79 |
| 14 | Ac-CPLVNPLCLHPGWSC(HArg)GQ-Sar$_6$-(D-K[FI]) (Ac-(SEQ ID NO: 15)-Sar$_6$-(D-K[FI])) | 9.96 ± 0.55 |

TABLE 4

Biological Assay Data for Peptide Ligands of the Invention (TATA peptides, Competition Binding Assay)

| Bicycle Compound Number | Sequence | Ki, nM ± 95% CI Human EphA2 Fluorescent Peptide Reference Compound C | Reference Compound B | Reference Compound A | Mouse EphA2 Reference Compound C |
|---|---|---|---|---|---|
| 15 | ACMNDVVVVCAMGWKCA (SEQ ID NO: 3) | 277.5 ± 38.22 | | | |
| 16 | ACVPDRRCAYMNVCA (SEQ ID NO: 4) | 69.97 ± 8.67 | | | |
| 17 | (β-Ala)-Sar$_{10}$-ACVPDRRCAYMNVC ((β-Ala)-Sar$_{10}$-(SEQ ID NO: 16)) | 85.05 ± 1.08 | | | |
| 18 | DLRCGGDPRCAYMNVCA (SEQ ID NO: 17) | 70.8 ± 2.35 | | | |
| 19 | SRPCVIDSRCAYMNVCA (SEQ ID NO: 18) | 94.75 ± 24.01 | | | |
| 20 | ESRCSPDARCAYMNVCA (SEQ ID NO: 19) | 57.05 ± 4.61 | | | |
| 21 | HSGCRPDPRCAYMNVCA (SEQ ID NO: 20) | 62.15 ± 4.61 | | | |
| 22 | GSGCKPDSRCAYMNVCA (SEQ ID NO: 21) | 63.25 ± 13.82 | | | |
| 23 | ETVCLPDSRCAYMNVCA (SEQ ID NO: 22) | 130 ± 15.68 | | | |
| 24 | GQVCIVDARCAYMNVCA (SEQ ID NO: 23) | 168.5 ± 16.66 | | | |
| 25 | ACVPDRRCAFENVCVDH (SEQ ID NO: 24) | 97.3 ± 3.33 | | | |

TABLE 4-continued

Biological Assay Data for Peptide Ligands of the Invention (TATA peptides, Competition Binding Assay)

| Bicycle Compound Number | Sequence | Ki, nM ± 95% CI Human EphA2 Fluorescent Peptide Reference Compound C | Reference Compound B | Reference Compound A | Mouse EphA2 Reference Compound C |
|---|---|---|---|---|---|
| 26 | ACVPDRRCAFMNVCEDR (SEQ ID NO: 25) | 39.05 ± 10.29 | | | |
| 27 | ACVPDRRCAFQDVCDHE (SEQ ID NO: 26) | 159 n=1 | | | |
| 28 | ACVPDRRCAFRDVCLTG (SEQ ID NO: 27) | 1700 n=1 | | | |
| 29 | ACYVGKECAYMNVCA (SEQ ID NO: 9) | 209.5 ± 110.74 | 106.65 ± 24.94 | 87.7 n = 1 | |
| 30 | ACQPSNHCAFMNYCA (SEQ ID NO: 28) | 293 n=1 | 186.53 ± 86.86 | 137 n = 1 | |
| 31 | ACSPTPACAVQNLCA (SEQ ID NO: 29) | 223 n=1 | 177 ± 60.76 | | |
| 32 | ACTSCWAYPDSFCA (SEQ ID NO: 30) | 232 ± 52.19 | | | 151 n = 1 |
| 33 | ACTKPTGFCAYPDTICA (SEQ ID NO: 31) | 268.5 ± 16.66 | | | |
| 34 | ACRGEWGYCAYPDTICA (SEQ ID NO: 32) | 347.5 ± 57.82 | | | |
| 35 | ACRNWGMYCAYPDTICA (SEQ ID NO: 33) | 282.5 ± 65.66 | | | |
| 36 | ACPDWGKYCAYPDTICA (SEQ ID NO: 34) | 160 ± 1.96 | | | |
| 37 | ACRVYGPYCAYPDTICA (SEQ ID NO: 35) | 294.5 ± 20.58 | | | |
| 38 | ACSSCWAYPDSVCA (SEQ ID NO: 36) | 400.33 ± 205.19 | | | |
| 39 | ACQSCWAYPDTYCA (SEQ ID NO: 37) | 321.33 ± 119.53 | | | |
| 40 | ACGFMGLEPCETFCA (SEQ ID NO: 38) | 187.5 ± 20.58 | | | |
| 41 | ACGFMGLVPCEVHCA (SEQ ID NO: 39) | 155 ± 9.8 | | | |
| 42 | ACGFMGLEPCEMVCA (SEQ ID NO: 40) | 320.5 ± 14.7 | | | |
| 43 | ACGFMGLEPCVTYCA (SEQ ID NO: 41) | 233.5 ± 20.58 | | | |
| 44 | ACGFMGLEPCELVCA (SEQ ID NO: 42) | 126.8 ± 21.17 | | | |
| 45 | ACGFMGLVPCNVFCA (SEQ ID NO: 43) | 142 ± 41.16 | | | |
| 46 | ACGFMGLEPCELFCA (SEQ ID NO: 44) | 81.7 ± 7.06 | | | |
| 47 | ACGFMGLEPCELFCMPK (SEQ ID NO: 45) | 185'74.48 | | | |
| 48 | ACGFMGLEPCELYCA (SEQ ID NO: 46) | 127.5 ± 14.7 | | | |
| 49 | ACGFMGLEPCELYCAHT (SEQ ID NO: 47) | 144 ± 17.64 | | | |
| 50 | ACGFMGLEPCEMYCA (SEQ ID NO: 48) | 140 ± 45.08 | | | |
| 51 | ACGFMGLVPCELYCADN (SEQ ID NO: 49) | 84.4 ± 36.46 | | | |
| 52 | ACPLVNPLCLTSGWKCA (SEQ ID NO: 50) | 115.33 ± 11.33 | | | |
| 53 | ACPMVNPLCLHPGWICA (SEQ ID NO: 51) | 15.4 ± 3.17 | | | |
| 54 | ACPLVNPLCLHPGWICA (SEQ ID NO: 52) | 15.25 ± 2.84 | | | |
| 55 | ACPLVNPLCLHPGWRCA (SEQ ID NO: 53) | 20.55 ± 0.88 | | | |
| 56 | ACPLVNPLCNLPGVVTCA (SEQ ID NO: 54) | 184 ± 115.64 | | | |
| 57 | ACPLVNPLCLVPGWSCA (SEQ ID NO: 55) | 35.4 ± 10 | | | |
| 58 | ACPLVNPLCLLDGVVTCA (SEQ ID NO: 56) | 38.35 ± 5.39 | | | |
| 59 | ACPLVNPLCLMPGWGCA (SEQ ID NO: 57) | 114.5 ± 10.78 | | | |
| 60 | ACPLVNPLCMIGNWTCA (SEQ ID NO: 58) | 96.2 ± 0.59 | | | |

TABLE 4-continued

Biological Assay Data for Peptide Ligands of the Invention (TATA peptides, Competition Binding Assay)

| Bicycle Compound Number | Sequence | Ki, nM ± 95% CI Human EphA2 Fluorescent Peptide Reference Compound C | Reference Compound B | Reference Compound A | Mouse EphA2 Reference Compound C |
|---|---|---|---|---|---|
| 61 | ACPLVNPLCLMTGWSCA (SEQ ID NO: 59) | 241.5 ± 44.1 | | | |
| 62 | ACPLVNPLCMMGGWKCA (SEQ ID NO: 60) | 67.1 ± 19.21 | | | |
| 63 | ACPLVNPLCLYGSWKCA (SEQ ID NO: 61) | 59.05 ± 28.32 | | | |
| 64 | ACPLVNPLCLHPGVVTCA (SEQ ID NO: 62) | 30 n = 1 | | | |
| 65 | ARDCPLVNPLCLHPGVVTCA (SEQ ID NO: 63) | 6.05 ± 1.38 | | | 39.1 ± 0.39 |
| 66 (BCY6099) | (β-Ala)-Sar$_{10}$-A(HArg)DC(HyP)LVNPLCLHP(D-Asp)W(HArg)C (SEQ ID NO: 2) | 4.94 ± 1.41 | | | 57.6 ± 24.86 |
| 67 (BCY6014) | (β-Ala)-Sar$_{10}$-A(HArg)DCPLVNPLCLHPGVVTC ((β-Ala)-Sar$_{10}$-(SEQ ID NO: 11)) | 8.51 ± 0.17 | | | 61.7 ± 15.48 |
| 68 | Ac-ARDCPLVNPLCLHPGWTCA-Sar$_6$-(D-K) (Ac-(SEQ ID NO: 63)-Sar$_6$-(D-K)) | 19.3 ± 4.92 | | | 166.5 ± 30.38 |
| 69 | Ac-A(HArg)DCPLVNPLCLHPGWTCA-Sar$_6$-(D-K) (Ac-(SEQ ID NO: 11)-A-Sar$_6$-(D-K)) | 17.5 ± 0.98 | | | 164.5 ± 2.94 |
| 70 | RPACPLVNPLCLHPGVVTCA (SEQ ID NO: 64) | 10.06 ± 2.96 | | | |
| 71 | RPPCPLVNPLCLHPGVVTCA (SEQ ID NO: 65) | 11.11 ± 2.25 | | | |
| 72 | KHSCPLVNPLCLHPGVVTCA (SEQ ID NO: 66) | 11.92 ± 6.04 | | | |
| 73 | ACPLVNPLCLHPGVVTCLHG (SEQ ID NO: 67) | 1.98 ± 0.49 | | | 72.7 ± 1.09 |
| 74 | Ac-CPLVNPLCLHPGWTCLHG (Ac-(SEQ ID NO: 12)) | 1.76 ± 0.54 | | | |
| 75 | (β-Ala)-Sar$_{10}$-ACPLVNPLCLHPGVVTCLHG ((β-Ala)-Sar$_{10}$-(SEQ ID NO: 67)) | 2.48 ± 0.27 | | | 18 ± 1.18 |
| 76 | (β-Ala)-Sar$_{10}$-ACPLVNPLCLHPGVVTCL(D-His)G ((β-Ala)-Sar$_{10}$-(SEQ ID NO: 68)) | 10.01 ± 1.55 | | | 75.15 ± 14.41 |
| 77 (BCY6019) | Ac-CPLVNPLCLHPGVVTCLHG-Sar$_6$-(D-K) (Ac-(SEQ ID NO: 12)-Sar$_6$-(D-K)) | 5.41 ± 0.86 | | | 48.23 ± 15.72 |
| 78 | Ac-CPLVNPLCLHPGVVTCL(D-His)G-Sar$_6$-(D-K) (Ac-(SEQ ID NO: 13)-Sar$_6$-(D-K)) | 15.6 ± 4.7 | | | 115.03 ± 41.16 |
| 79 | ACPLVNPLCLHPG(2Nal)TCLHG (SEQ ID NO: 69) | 162 ± 17.64 | | | |
| 80 | RHDCPLVNPLCLLPGVVTCA (SEQ ID NO: 70) | 7.11 ± 0.72 | | | |
| 81 | TPRCPLVNPLCLMPGVVTCA (SEQ ID NO: 71) | 9.8 ± 2.61 | | | |
| 82 | ACPLVNPLCLAPGVVTCA (SEQ ID NO: 72) | 46.2 n=1 | | | |
| 83 | ACPLVNPLCLAPGWTCSRS (SEQ ID NO: 73) | 7.05 ± 1.11 | | | |
| 84 | ACPLVNPLCLEPGVVTCA (SEQ ID NO: 74) | 53.9 n=1 | | | |
| 85 | ACPLVNPLCLEPGVVTCAKR (SEQ ID NO: 75) | 10.95 ± 1.6 | | | |
| 86 | ACPLVNPLCLHPGWSCA (SEQ ID NO: 76) | 56.15 ± 11.27 | | | |
| 87 (BCY6026) | ACPLVNPLCLHPGWSCRGQ (SEQ ID NO: 77) | 2.57 ± 0.63 | | | 18.6 ± 0.59 |
| 88 | Ac-CPLVNPLCLHPGWSCRGQ (Ac-(SEQ ID NO: 14)) | 1.64 ± 0.75 | | | |
| 89 | β13-Ala)-Sar$_{10}$-ACPLVNPLCLHPGWSCRGQ ((β-Ala)-Sar$_{10}$-(SEQ ID NO: 77) | 2.86 ± 1.29 | | | 29.55 ± 4.61 |
| 90 | (β-Ala)-Sar$_{10}$-ACPLVNPLCLHPGWSC(HArg)GQ (β-Ala)-Sar$_{10}$-(SEQ ID NO: 78)) | 5.41 ± 0.67 | | | 47.05 ± 11.47 |
| 91 (BCY6042) | Ac-CPLVNPLCLHPGWSCRGQ-Sar$_6$-(D-K) (Ac-(SEQ ID NO: 14)-Sar$_6$-(D-K)) | 5.98 ± 1.42 | | | 49.87 ± 14.44 |
| 92 | Ac-CPLVNPLCLHPGWSC(HArg)GQ-Sar$_6$-(D-K) (Ac-(SEQ ID NO: 15)-Sar$_6$-(D-K)) | 10.56 ± 6.56 | | | 75.27 ± 21.72 |
| 93 | ACPLVNPLCLHPG(2Nal)SCRGQ (SEQ ID NO: 79) | 228 ± 103.88 | | | |
| 94 | ACPLVNPLCLTPGVVTCTNT (SEQ ID NO: 80) | 13.25 ± 4.05 | | | |

TABLE 4-continued

Biological Assay Data for Peptide Ligands of the Invention (TATA peptides, Competition Binding Assay)

| Bicycle Compound Number | Sequence | Ki, nM ± 95% CI | | | |
|---|---|---|---|---|---|
| | | Human EphA2 Fluorescent Peptide | | | Mouse EphA2 |
| | | Reference Compound C | Reference Compound B | Reference Compound A | Reference Compound C |
| 95 | ACPMVNPLCLHPGWKCA (SEQ ID NO: 81) | 11.91 ± 3.73 | | | |
| 96 | ACPMVNPLCLTPGWICA (SEQ ID NO: 82) | 16.07 ± 4.58 | | | |
| 97 | ACPMVNPLCLHPGVVTCA (SEQ ID NO: 83) | 20 ± 1.02 | | | |

TABLE 5

Biological Assay Data for TATA Peptide Ligands of the Invention (Competition Binding Assay)

| Bicycle Compound Number | Sequence | Ki, nM ± 95% Cl | |
|---|---|---|---|
| | | Human EphA2 Fluorescent peptide | Mouse EphA2 |
| | | Reference Compound C | Reference Compound C |
| 98 | (β-Ala)-Sar$_{10}$-H(D-Asp)VT-C(Aib)(1Nal)G(Aib)F(1Nal)CP(tBuGly)N(HArg)P(D-Asp)C ((β-Ala)-Sar$_{10}$-(SEQ ID NO: 84)) | 251.5 ± 73.5 | |

TABLE 6

Biological Assay Data for Peptide Ligands of the Invention (BDC competition binding data with TATA Scaffolds)

| BDC Compound Number | Bicycle precursor | General Formula | Ki, nM | |
|---|---|---|---|---|
| | | | Human EphA2 Fluorescent Peptide | Mouse EphA2 |
| | | | Reference Compound C | Reference Compound C |
| BCY6027 | BCY6099 | Formula (A) | 10.23 | |
| BCY6028 | BCY6099 | Formula (B) | 13.04 | |
| BCY6031 | BCY6014 | Formula (A) | 12.62 | 34.70 |
| BCY6032 | BCY6014 | Formula (B) | 11.42 | 35.90 |

TABLE 7

Selectivity Data for Peptide Ligands of the Invention (Selectivity Direct Binding Assay)

| Bicycle Compound Number | mouse EphA2 | rat EphA2 | dog EphA2 | Human & mouse EphA3 | rat EphA3 | human EphA4 | rat & mouse EphA4 | rat EphB1 |
|---|---|---|---|---|---|---|---|---|
| 2 | 516.5 ± 236.1 | 210 ± 1.96 | | >1000 | >1000 | >1000 | 10890 n = 1 | |
| 7 | 216 | 252.5 ± 6.86 | | | | | | |
| 9 | | | | | | >3000 | | |
| 11 | | | | | | >3000 | | |
| 12 | | | | | | >3000 | | |
| 13 | | | | | | >3000 | | |
| 14 | | | | | | >3000 | | |

TABLE 7-continued

Selectivity Data for Peptide Ligands of the Invention (Selectivity Direct Binding Assay)

| Bicycle Compound Number | Human EphB4 | Human EphA7 | Human EphA6 | Human EphA1 | human Factor XIIa | human Carbonic anhydrase 9 | human CD38 |
|---|---|---|---|---|---|---|---|
| 2 | | | | | | | >6000 |
| 7 | | | | | | | |
| 9 | | | | | | | |
| 11 | | | | | | | |
| 12 | | | | | | | |
| 13 | | | | | | | |
| 14 | | | | | | | |

Study 2: Fluorescence Polarisation Measurements (Alternative Protocol)

(a) Competition Binding

Peptides without a fluorescent tag were tested in competition with a peptide with a fluorescent tag and a known Kd (Table 9). Five μL of increasing (2 fold) concentrations of test compound was added to the plate followed by 10 μL of EphA2 protein (Table 8) at a fixed concentration which was dependent on the fluorescent peptide used (Table 9), then 10 μL fluorescent peptide added. Buffer was assay buffer as above with DMSO<1%. Measurements were conducted on a BMG PHERAstar FS equipped with an "FP 485 520 520" optic module which excites at 485 nm and detects parallel and perpendicular emission at 520 nm. The PHERAstar FS was set at 25° C. with 200 flashes per well and a positioning delay of 0.1 second, with each well measured at 5 to 10 minute intervals for 60 minutes. Alternatively, measurements were done on at similar time intervals on a Perkin Elmer Envision equipped with FITC FP Dual Mirror, FITC FP 480 excitation filter and FITC FP P-pol 535 and FITC FP S-pol emission filters with 30 flashes and a G-Factor of 1.2. Data analysis was in Systat Sigmaplot version 12.0 or 13.0 where the mP values at 60 minutes were fit to a user defined cubic equation to generate a Ki value:

$f = y\ min + (y\ max - y\ min)/Lig*((Lig*((2*((Klig+Kcomp+Lig+Comp-Prot*c)^2 - 3*(Kcomp*(Lig-Prot*c) + Klig*(Comp-Prot*c) + Klig*Kcomp))^0.5*COS(ARCCOS((-2*(Klig+Kcomp+Lig+Comp-Prot*c)^3 + 9*(Klig+Kcomp+Lig+Comp-Prot*c)*(Kcomp*(Lig-Prot*c) + Klig*(Comp-Prot*c) + Klig*Kcomp) - 27*(-1*Klig*Kcomp*Prot*c))/(2*(((( Klig+Kcomp+Lig+Comp-Prot*c)^2 - 3*(Kcomp*(Lig-Prot*c) + Klig*(Comp-Prot*c) + Klig*Kcomp))^3)^0.5)))/3) - (Klig+Kcomp+Lig+Comp-Prot*c)))/((3*Klig) + ((2*((Klig+Kcomp+Lig+Comp-Prot*c)^2 - 3*(Kcomp*(Lig-Prot*c) + Klig*(Comp-Prot*c) + Klig*Kcomp))^0.5*COS(ARCCOS((-2*(Klig+Kcomp+Lig+Comp-Prot*c)^3 + 9*(Klig+Kcomp+Lig+Comp-Prot*c)*(Kcomp*(Lig-Prot*c) + Klig*(Comp-Prot*c) + Klig*Kcomp) - 27*(-1*Klig*Kcomp*Prot*c))/(2*(((( Klig+Kcomp+Lig+Comp-Prot*c)^2 - 3*(Kcomp*(Lig-Prot*c) + Klig*(Comp-Prot*c) + Klig*Kcomp))^3)^0.5)))/3) - (Klig+Kcomp+Lig+Comp-Prot*c))))$ "Lig", "KLig" and "Prot" were all defined values relating to: fluorescent peptide concentration, the Kd of the fluorescent peptide and EphA2 concentration respectively.

TABLE 8

Eph receptors and source

| Receptor (domain) | Species | Format/tag | Supplier | Catalogue number |
|---|---|---|---|---|
| EphA2 (Ecto) | Human | C-terminal polyHis | R&D systems | 3035-A2 |
| EphA2 (Ecto) | Human | C-terminal polyHis | In-house | N/A |
| EphA2 (Ecto) | Mouse | C-terminal polyHis | Sino Biological | 50586-M08H |
| EphA2 (ligand binding) | Rat | C-terminal polyHis | In-house | N/A |

TABLE 9

Final concentrations of fluorescent peptide and EphA2 as used with competition binding assays

| Fluorescent peptide | Concentration of fluorescent peptide (nM) | Concentration of human EphA2 (nM) | Concentration of mouse EphA2 (nM) | Concentration of rat EphA2 (nM) |
|---|---|---|---|---|
| Reference Compound C | 0.8 | 2.4 or 25 | 50 or 15 nM | 25 |

Certain peptide ligands and bicycle drug conjugates of the invention were tested in the above mentioned competition binding assay and the results are shown in Tables 10 to 11:

TABLE 10

Competition Binding with Selected Bicyclic Peptides

| Bicycle No. | Human Ki (nM) | Mouse Ki (nM) | Rat Ki (nM) |
|---|---|---|---|
| BCY6009 (Compound 108) | 12.7 | 26.7 | 18.0 |
| BCY6014 (Compound 67) | 14.5 | 39.6 | 24.4 |
| BCY6017 (Compound 109) | 8.3 | | |
| BCY6018 (Compound 110) | 13.1 | | |
| BCY6019 (Compound 77) | 6.4 | 16.0 | |
| BCY6026 (Compound 87) | 4.4 | | |
| BCY6042 (Compound 91) | 6.7 | | |
| BCY6059 (Compound 106) | 43.2 | | |
| BCY6099 (Compound 66) | 2.7 | 4.5 | 1.9 |

TABLE 10-continued

Competition Binding with Selected Bicyclic Peptides

| Bicycle No. | Human Ki (nM) | Mouse Ki (nM) | Rat Ki (nM) |
|---|---|---|---|
| BCY6101 (Compound 101) | 9.7 | 6.9 | |
| BCY6102 (Compound 102) | 14.6 | 25.1 | |
| BCY6103 (Compound 100) | 14.8 | 20.8 | |
| BCY6104 (Compound 99) | 5.1 | 19.8 | |
| BCY6137 (Compound 105) | 2.2 | | |
| BCY6138 (Compound 104) | 566.0 | | |
| BCY6139 (Compound 103) | 5.7 | | |
| BCY6141 (Compound 112) | 90.4 | | |
| BCY6152 (Compound 111) | 23.3 | | |
| BCY6153 (Compound 113) | 18.2 | | |
| BCY6160 (Compound 107) | 14.0 | | |
| BCY6039 | 9.4 | | |
| BCY6105 | 8.86 | | |
| BCY6106 | 12.9 | | |
| BCY6175 | 1 | | |
| BCY6107 | 19.18 | | |

The results from the competition binding assay in Table 10 show that Bicycle peptides targeting human EphA2 (BCY6014 and BCY6099) bind with high affinity to mouse and rat EphA2. Similarly, BCY6019 binds to both human and mouse EphA2. These results show that certain peptides of the invention can be used in in vivo mouse and rat efficacy and toxicology models.

TABLE 11

Competition Binding with Selected Bicycle Drug Conjugates (BDCs)

| Bicycle ID | Human Ki (nM) | Mouse Ki (nM) | Rat Ki (nM) |
|---|---|---|---|
| BCY6061 | 12.0 | 32.3 | 14.2 |
| BCY6174 | 1.7 | 3.9 | 3.0 |
| BCY6029 | 2.3 | | |
| BCY6033 | 9.9 | 34.2 | 13.4 |
| BCY6037 | 7.3 | | |
| BCY6049 | 8.8 | 28.1 | |
| BCY6053 | 48.2 | 29.7 | |
| BCY6122 | 13.7 | 10.4 | |
| BCY6136 | 1.9 | 5.5 | 3.2 |
| BCY6030 | 5.6 | | |
| BCY6034 | 5.9 | 35.9 | |
| BCY6038 | 2.8 | | |
| BCY6050 | 168.1 | 62.2 | |
| BCY6054 | 53.6 | 73.6 | |
| BCY6027 | 10.2 | | |
| BCY6031 | 12.5 | 35.1 | 20.0 |
| BCY6035 | 15.2 | | |
| BCY6047 | 53.2 | 34.2 | |
| BCY6051 | 54.0 | 43.6 | |
| BCY6134 | 7.4 | 12.6 | |
| BCY6135 | 2.4 | 5.0 | 2.9 |
| BCY6154 | 8.0 | | |
| BCY6155 | 12.5 | | |
| BCY6063 | 7.8 | 66.8 | |
| BCY6028 | 13.0 | | |
| BCY6032 | 11.4 | 35.9 | |
| BCY6036 | 18.6 | | |
| BCY6048 | 120.7 | 87.2 | |

TABLE 11-continued

Competition Binding with Selected Bicycle Drug Conjugates (BDCs)

| Bicycle ID | Human Ki (nM) | Mouse Ki (nM) | Rat Ki (nM) |
|---|---|---|---|
| BCY6052 | 30.5 | 27.1 | |
| BCY6064 | 12.5 | 40.7 | |
| BCY6162 | 44.9 | | |
| BCY6082 | 10.5 | 34.1 | 13.9 |
| BCY6150 | 17.9 | | |
| BCY6151 | 9.0 | | |
| BCY6161 | 2.1 | | |
| BCY6173 | 1.7 | 4.3 | 2.5 |
| BCY6077 | 6.5 | 25.3 | |
| BCY6055 | 15.8 | | |
| BCY6062 | 12.9 | 20.3 | |

Table 11 shows that certain Bicycle Drug Conjugates of the invention exhibit excellent cross reactivity between human, mouse and rodent EphA2. Peptides of the invention can therefore be used in mouse and rat efficacy and toxicology in vivo models.

(b) SPR Measurements

Non-Fc fusion proteins were biotinylated with EZ-Link™ Sulfo-NHS-LC-Biotin for 1 hour in 4 mM sodium acetate, 100 mM NaCl, pH 5.4 with a 3× molar excess of biotin over protein. The degree of labelling was determined using a Fluorescence Biotin Quantification Kit (Thermo) after dialysis of the reaction mixture into PBS. For analysis of peptide binding, a Biacore T200 instrument was used utilising a XanTec CMD500D chip. Streptavidin was immobilized on the chip using standard amine-coupling chemistry at 25° C. with HBS—N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 µl/min. For capture of streptavidin, the protein was diluted to 0.2 mg/ml in 10 mM sodium acetate (pH 4.5) and captured by injecting 120 µl onto the activated chip surface. Residual activated groups were blocked with a 7 min injection of 1 M ethanolamine (pH 8.5):HBS—N(1:1). Buffer was changed to PBS/0.05% Tween 20 and biotinylated EphA2 was captured to a level of 500-1500 RU using a dilution of protein to 0.2 µM in buffer. A dilution series of the peptides was prepared in this buffer with a final DMSO concentration of 0.5% with a top peptide concentration was 50 or 100 nM and 6 further 2-fold dilutions. The SPR analysis was run at 25° C. at a flow rate of 90 µl/min with 60 seconds association and 900-1200 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

For binding of Bicycle Drug Conjugates a Biacore 3000 instrument was used. For biotinylated proteins immobilisation levels were 1500 RU and the top concentration was 100 nM. Otherwise the method was the same as described above using either the CMD500D or a CM5 chip (GE Healthcare). For the Fc-tagged proteins, a CM5 chip was activated as described above and then goat anti-human IgG antibody (Thermo-Fisher H10500) was diluted to 20 µg/ml in 10 mM sodium acetate pH5.0 and captured to approximately 3000 RU. The surface was then blocked as described above.

Subsequent capture of the Fc-tagged proteins was carried out to obtain approximately 200-400 RU of the target protein. The proteins used are described below. All proteins were reconstituted as per manufacturer's suggested buffers and concentrations and captured using 5-10 µg/ml protein in PBS/0.05% Tween 20.

TABLE 12

| Receptor | Species | Format/tag | Supplier | Catalogue number |
|---|---|---|---|---|
| EphA1 | Human | Fc fusion | Sino Biologics | 15789-H02H |
| EphA2 | Human | 0.95 mol biotin/monomer | In house | N/A |
| EphA2 | Mouse | Fc fusion | R&D Systems | 639-A2 |
| EphA2 | Rat | 1.4 mol biotin/monomer | In house | N/A |
| EphA3 | Human | Fc fusion | R&D Systems | 6444-A3 |
| EphA3 | Mouse | Fc fusion | Sino Biologics | 51122-M02H |
| EphA3 | Rat | Fc fusion | Sino Biologics | 80465-R02H |

TABLE 12-continued

| Receptor | Species | Format/tag | Supplier | Catalogue number |
|---|---|---|---|---|
| EphA4 | Human | Fc fusion | Sino Biologics | 11314-H03H |
| EphA4 | Mouse | Fc fusion | Sino Biologics | 50575-M02H |
| EphA4 | Rat | Fc fusion | Sino Biologics | 80123-R02H |
| EphA5 | Human | 3.1 mol biotin/monomer | R&D Systems | 3036-A5 |
| EphA6 | Human | Fc fusion | R&D Systems | 5606-A6 |
| EphA7 | Human | Fc fusion | R&D Systems | 6756-A7 |
| EphB1 | Rat | Fc fusion | R&D Systems | 1596-B1 |
| EphB4 | Human | Fc fusion | Sino Biologics | 10235-H02H |

Certain peptide ligands and bicycle drug conjugates of the invention were tested in the above mentioned competition binding assay and the results are shown in Tables 13 to 15:

TABLE 13

SPR Binding Analysis with Selected Bicyclic Peptides and Bicycle Drug Conjugates of the Invention

| Bicycle/BDC No. | Human | | | | Mouse | | | | Rat | | | |
|---|---|---|---|---|---|---|---|---|---|---|---|---|
| | $K_D$ (nM) | $K_{off}$ (s-1) | $t_{1/2}$ (min) | $K_{on}$ (M-1s-1) | $K_D$ (nM) | $K_{off}$ (s-1) | $t_{1/2}$ (min) | $K_{on}$ (M-1s-1) | $K_D$ (nM) | $K_{off}$ (s-1) | $t_{1/2}$ (min) | $K_{on}$ (M-1s-1) |
| BCY6026 | 1.02 | 1.02E−03 | 11.3 | 9.92E+05 | | | | | | | | |
| BCY6031 | 1.99 | 4.95E−03 | 2.3 | 2.49E+06 | | | | | | | | |
| BCY6032 | 2.10 | 5.27E−03 | 2.2 | 2.52E+06 | | | | | | | | |
| BCY6033 | 3.41 | 3.43E−03 | 3.5 | 9.99E+05 | 21.8 | 6.37E−03 | 1.8 | 2.92E+05 | 166 | 4.42E−03 | 2.6 | 2.67E+04 |
| BCY6034 | 1.64 | 3.65E−03 | 3.2 | 2.23E+06 | | | | | | | | |
| BCY6082 | 2.42 | 2.42E−03 | 4.8 | 9.87E+05 | 18.3 | 5.97E−03 | 1.9 | 3.27E+05 | 28.8 | 3.64E−03 | 3.2 | 1.26E+05 |
| BCY6136 | 1.17 | 1.15E−03 | 10.0 | 9.86E+05 | 2.53 | 1.11E−03 | 10.4 | 4.37E+05 | 2.96 | 9.11E−04 | 12.6 | 3.07E+05 |
| BCY6173 | 0.73 | 1.24E−03 | 9.3 | 1.69E+06 | 2.95 | 1.14E−03 | 10.1 | 3.86E+05 | 1.10 | 9.60E−04 | 12.0 | 8.81E+05 |

Table 13 details binding affinities and kinetic parameters (Koff and Kon) for binding of selected Bicycle Drug Conjugates to human EphA2 determined using the SPR assay.

TABLE 14

SPR Binding Analysis with Selected Bicycle Drug Conjugates of the Invention with Human Eph Homologs

| BDC No. | EphA1 | EphA3 | EphA4 | EphA5 | EphA6 | EphA7 | EphB4 |
|---|---|---|---|---|---|---|---|
| BCY6033 | no binding @ 5 µM | no binding @ 5 µM | no binding @ 5 µM | no binding @ 25 µM | no binding @ 20 µM | no binding @ 20 µM | no binding @ 20 µM |
| BCY6082 | no binding @ 5 µM | no binding @ 5 µM | no binding @ 5 µM | no binding @ 25 µM | no binding @ 20 µM | no binding @ 20 µM | no binding @ 20 µM |
| BCY6136 | no binding @ 5 µM | no binding @ 5 µM | no binding @ 5 µM | no binding @ 25 µM | no binding @ 20 µM | no binding @ 20 µM | no binding @ 20 µM |
| BCY6173 | no binding @ 5 µM | no binding @ 5 µM | no binding @ 5 µM | no binding @ 25 µM | no binding @ 20 µM | no binding @ 20 µM | no binding @ 20 µM |

Table 14 illustrates binding results with four Bicycle Drug Conjugates (BCY6033, BCY6082, BCY6136 and BCY6173) in the SPR assay with closely related human Ephrin homologs. The results show that compounds of the invention exhibit no significant binding to closely related human homologs: EphA1, EphA3, EphA4, EphA5, EphA6, EphA7 and EphB4.

TABLE 15

SPR Binding Analysis with Selected Bicycle Drug Conjugates of the Invention with Mouse and Rat Eph Orthologs

| BDC No. | Mouse EphA3 | Mouse EphA4 | Rat EphA3 | Rat EphB1 |
|---|---|---|---|---|
| BCY6033 | no binding @ 20 µM | no binding @ 20 µM | no binding @ 20 µM | no binding @ 20 µM |
| BCY6082 | no binding @ 20 µM | no binding @ 20 µM | no binding @ 20 µM | no binding @ 20 µM |
| BCY6136 | no binding @ 20 µM | no binding @ 20 µM | no binding @ 20 µM | no binding @ 20 µM |
| BCY6173 | no binding @ 20 µM | no binding @ 20 µM | no binding @ 20 µM | no binding @ 20 µM |

The results in Table 15 show that certain Bicycle Drug Conjugates of the invention (BCY6033, BCY6082, BCY6136 and BCY6173) are also selective for mouse and rat EphA2 and exhibit no significant binding to closely related homologs: mouse EphA3 and EphA4; and rat EphA3 and EphB1.

Studies 3 and 7-23

In each of Studies 3 and 7-23, the following methodology was adopted for each study:

(a) Materials (i) Animals and Housing Condition

Animals

Species: *Mus Musculus*

Strain: Balb/c nude or CB17-SCID

Age: 6-8 weeks

Body weight: 18-22 g

Number of animals: 9-90 mice

Animal supplier: Shanghai Lingchang Biotechnology Experimental Animal Co. Limited Housing Condition The mice were kept in individual ventilation cages at constant temperature and humidity with 3-5 animals in each cage.

Temperature: 20-26° C.

Humidity 40-70%.

Cages: Made of polycarbonate. The size is 300 mm×180 mm×150 mm. The bedding material is corn cob, which is changed twice per week.

Diet: Animals had free access to irradiation sterilized dry granule food during the entire study period.

Water: Animals had free access to sterile drinking water.

Cage identification: The identification labels for each cage contained the following information: number of animals, sex, strain, the date received, treatment, study number, group number and the starting date of the treatment.

Animal identification: Animals were marked by ear coding.

(ii) Test and Positive Control Articles

| Number | Physical Description | Molecular Weight | Purity | Storage Condition |
|---|---|---|---|---|
| BCY6031 | Lyophilised powder | 3878.92 | 97.99% | Stored at −80° C. |
| BCY6033 | Lyophilised powder | 4260.01 | 99.12% | Stored at −80° C. |
| BCY6082 | Lyophilised powder | 3911.04 | 96.8% | Stored at −80° C. |
| BCY6135 | Lyophilised powder | 4021 | 95.14% | Stored at −80° C. |
| BCY6136 | Lyophilised powder | 4402.23 | 97.5-98.6% | Stored at −80° C. |
| BCY6173 | Lyophilised powder | 4101.15 | 95.80% | Stored at −80° C. |
| BCY6174 | Lyophilised powder | 4537 | 99.50% | Stored at −80° C. |
| BCY6175 | Lyophilised powder | 4492.29 | 96.20% | Stored at −80° C. |
| BCY8245 | Lyophilised powder | 4173.85 | 99.30% | Stored at −80° C. |
| BCY8781 | Lyophilised powder | 4173.83 | 99.00% | Stored at −80° C. |
| ADC (MEDI-547)[1] | Solution (10.47 mg/ml concentration) | — | >99.00% | Stored at −80° C. |

[1]Full details of MEDI-547 (a fully human monoclonal antibody 1C1 (recognizing both human and murine EphA2) conjugated to MMAF via an mc linker) are described in Jackson et al (2008) Cancer Res 68, 9367-74.

(b) Experimental Methods and Procedures

Observations

All the procedures related to animal handling, care and the treatment in the study were performed according to the guidelines approved by the Institutional Animal Care and Use Committee (IACUC) of WuXi AppTec, following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss, eye/hair matting and any other abnormal effect as stated in the protocol. Death and observed clinical signs were recorded on the basis of the numbers of animals within each subset.

(ii) Tumor Measurements and the Endpoints

The major endpoint was to see if the tumor growth could be delayed or mice could be cured. Tumor volume was measured three times weekly in two dimensions using a caliper, and the volume was expressed in $mm^3$ using the formula: $V=0.5 \ a \times b^2$ where a and b are the long and short diameters of the tumor, respectively. The tumor size was then used for calculations of T/C value. The T/C value (in percent) is an indication of antitumor effectiveness; T and C are the mean volumes of the treated and control groups, respectively, on a given day. TGI was calculated for each group using the formula: TGI $(\%)=[1-(T_i-T_0)/(V_i-V_0)]\times 100$; $T_i$ is the average tumor volume of a treatment group on a given day, $T_0$ is the average tumor volume of the treatment group on the day of treatment start, $V_i$ is the average tumor volume of the vehicle control group on the same day with $T_i$, and $V_0$ is the average tumor volume of the vehicle group on the day of treatment start.

(iii) Sample Collection

At the end of study the tumors of all groups were collected for FFPE.

(iv) Statistical Analysis

Summary statistics, including mean and the standard error of the mean (SEM), are provided for the tumor volume of each group at each time point.

Statistical analysis of difference in tumor volume among the groups was conducted on the data obtained at the best therapeutic time point after the final dose.

A one-way ANOVA was performed to compare tumor volume among groups, and when a significant F-statistics (a ratio of treatment variance to the error variance) was obtained, comparisons between groups were carried out with Games-Howell test. All data were analyzed using GraphPad Prism 5.0. P<0.05 was considered to be statistically significant.

Study 3: In Vivo Efficacy in the LU-01-0046 PDX Model

Cancer cell lines (CCL) are originally derived from patient tumors, but acquire the ability to proliferate within in vitro cell cultures. As a result of in vitro manipulation, CCL that have been traditionally used in cancer research undergo genetic transformations that are not restored when cells are allowed to grow in vivo. Because of the cell culturing process cells that are better adapted to survive in culture are selected, tumor resident cells and proteins that interact with cancer cells are eliminated, and the culture becomes phenotypically homogeneous. Researchers are beginning to attribute the reason that only 5% of anti-cancer agents are approved by the Food and Drug Administration after pre-clinical testing to the lack of tumor heterogeneity and the absence of the human stromal microenvironment. Specifically, CCL-xenografts often are not predictive of the drug response in the primary tumors because CCL do not follow pathways of drug resistance or the effects of the microenvironment on drug response found in human primary tumors. To overcome these problems, the inventors have used PDX models to improve the predictive power of pre-clinical models.

PDX are created when cancerous tissue from a patient's primary tumor is implanted directly into an immunodeficient mouse. PDX can maintain patient histology, including the presence of non-tumor cells (eg stromal cells) and thus better mimic the tumor microenvironment. In general PDX are therefore more reflective of the heterogeneity and histology of primary tumors than CCL-xenografts.

BCY6031 was screened in a primary adenocarcinoma PDX xenograft (LU-01-0046) derived from a patient with non-small cell lung carcinomas (NSCLC). LU-01-0046 has been shown to express high levels of EphA2 using RNA sequencing. BCY6031 exhibited excellent efficacy in the LU-01-0046 model and is therefore a promising novel therapy for the treatment of non-small cell lung cancer.

(a) Treatment Arms

The experiment was designed to compare tumour growth in vehicle treated animals and animals treated with BCY6031 at 5 mg/kg qw for four weeks.

TABLE 16

| Gr | n | Treatment | Dose (mg/kg) | Dosing Volume (µl/g) | Dosing Route | Schedule |
|---|---|---|---|---|---|---|
| 1 | 6 | Vehicle | — | 10 | i.v. | biw*1 week |
| 2 | 3 | BCY6031 | 5 | 10 | i.v. | qw*4 weeks |

Note:
n: animal number;
Dosing volume: adjust dosing volume based on body weight.

(b) Experimental Method
(i) PDX Information

TABLE 17

| Model Name | Cancer Type | Tumor growth speed | Array | RSQ | EPH2 expression |
|---|---|---|---|---|---|
| LU-01-0046 | NSCLC | Tumor size can reach 1000 mm$^3$ in 40 days after tumor inoculation | 6.790 | 31.312 | High |

(ii) Tumor Inoculation

Each mouse was inoculated subcutaneously in the right flank with an approximately 30 mm$^3$ LU-01-0046 tumor fragment. Drug treatment was started when the average tumor volume reached 943 mm$^3$. The test article, route of administration, dosing frequency and the animal numbers in each group are described above.

(iii) Testing Article Formulation Preparation

TABLE 18

| Test article | Dose(mg/kg) | Formulation |
|---|---|---|
| Vehicle | — | 50 mM Acetate, 10% Sucrose pH 5 (without DMSO) |
| BCY6031 | 5 | Dissolve 4.59 mg BCY6031 into 4.498 ml formulation buffer to get the 1 mg/ml BCY6031 stock solution; Dilute 450 µl 1 mg/ml BCY6031 with 450 µl formulation buffer. |

(c) Results
(i) Mortality, Morbidity, and Body Weight Gain or Loss

Animal body weight was monitored regularly as an indirect measure of toxicity. Body weight change in female Balb/C nude mice bearing LU-01-0046 tumor dosed with BCY6031 is shown in FIG. 1.

Figure 2:
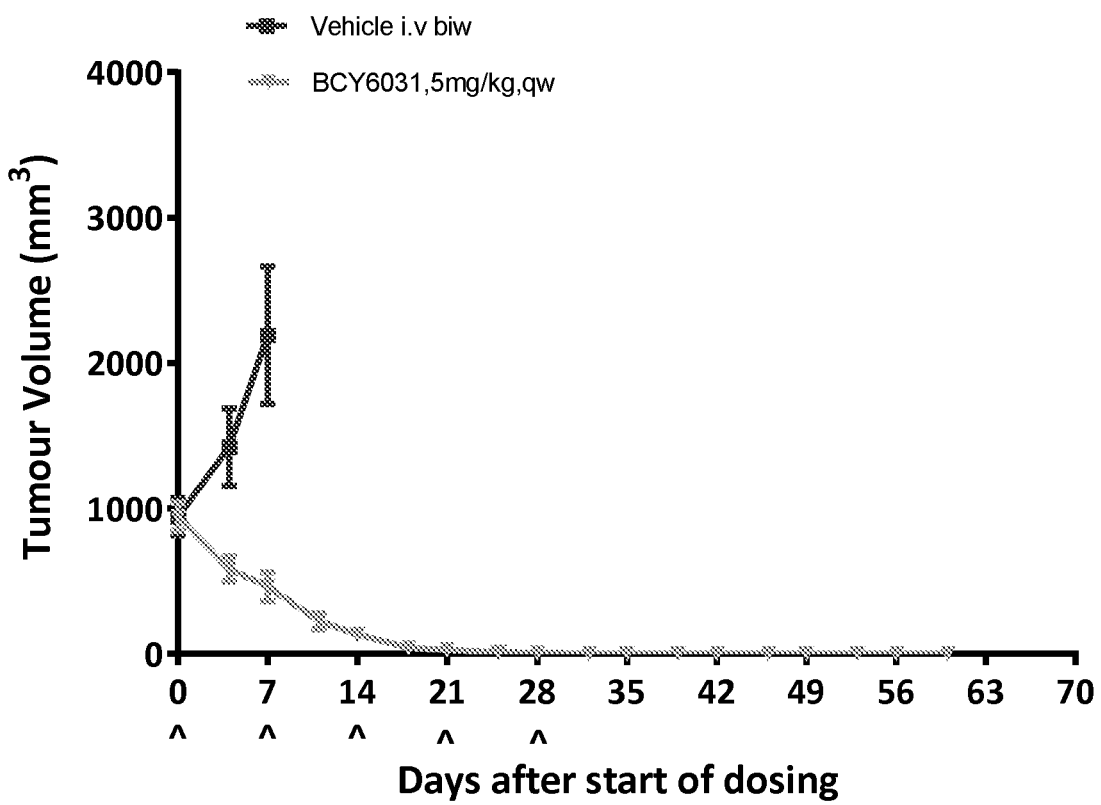
FIG. 2: Tumor volume trace after administering BCY6031 to female Balb/C nude mice bearing LU-01-0046 tumor. Data points represent group mean. The treatment was ceased from day 28.

(ii) Tumor Growth Curve
The tumor growth curve is shown in FIG. 2.
(iii) Tumor Growth Inhibition Analysis Tumor growth inhibition rate for BCY6031 in the PDX model LU-01-0046 was calculated based on tumor volume measurements on day 7 after the start of treatment.

TABLE 19

Tumor growth inhibition analysis (T/C and TGI) on Day 7

| Group | Treatment | Tumor Volume (mm$^3$)$^a$ | T/C$^b$ (%) | TGI (%) | P value |
|---|---|---|---|---|---|
| 1 | Vehicle, biw | 2191 ± 473 | — | — | — |
| 2 | BCY6031, 5 mpk, qw | 463 ± 158 | 21.1 | 138.6 | p < 0.05 |

$^a$Mean ± SEM.
$^b$Tumor Growth Inhibition is calculated by dividing the group average tumor volume for the treated group by the group average tumor volume for the control group (T/C).

(e) Discussion

The study evaluated the therapeutic efficacy of BCY6031 in the LU-01-0046 PDX model. The measured body weights are shown in the FIG. 1. Tumor volumes of the treatment group at various time points are shown in Table 19 and FIG. 2.

The mean tumor size of vehicle treated mice reached 2191 mm$^3$ on day 7. BCY6031 at 5 mg/kg produced potent antitumor activity with tumor measured as 463 mm$^3$ (TGI=138.6%, p<0.05) by day 7. Furthermore, the BCY6031 treatment completely eradicated the tumors from day 32 and no tumour regrowth occurred following dosing suspension on day 28. BCY6031 gave rise to no significant body weight loss (FIG. 1) and there were no adverse clinical observations on drug treated mice throughout the study.

Study 4: In Vivo Efficacy of BCY6136 in CDX Xenograft Models

The study evaluated the therapeutic efficacy of BCY6136 in three Cancer Cell Line Derived (CDX) models: the HT1080 fibrosarcoma line, the MDA-MB-231 triple negative breast cancer line and the NCI-H1975 non-small cell lung cancer (NSCLC) line.

(a) Experimental Method

Balb/c mice were inoculated subcutaneously with tumour cells at the right flank and drug treatment started when the average the average tumour volume reached between 150 and 200 mm$^3$. Tumour measurements and statistical analysis were performed as described above. Tumour bearing animals were treated once weekly with BCY6136 or vehicle.

(b) Discussion

Figure 4:
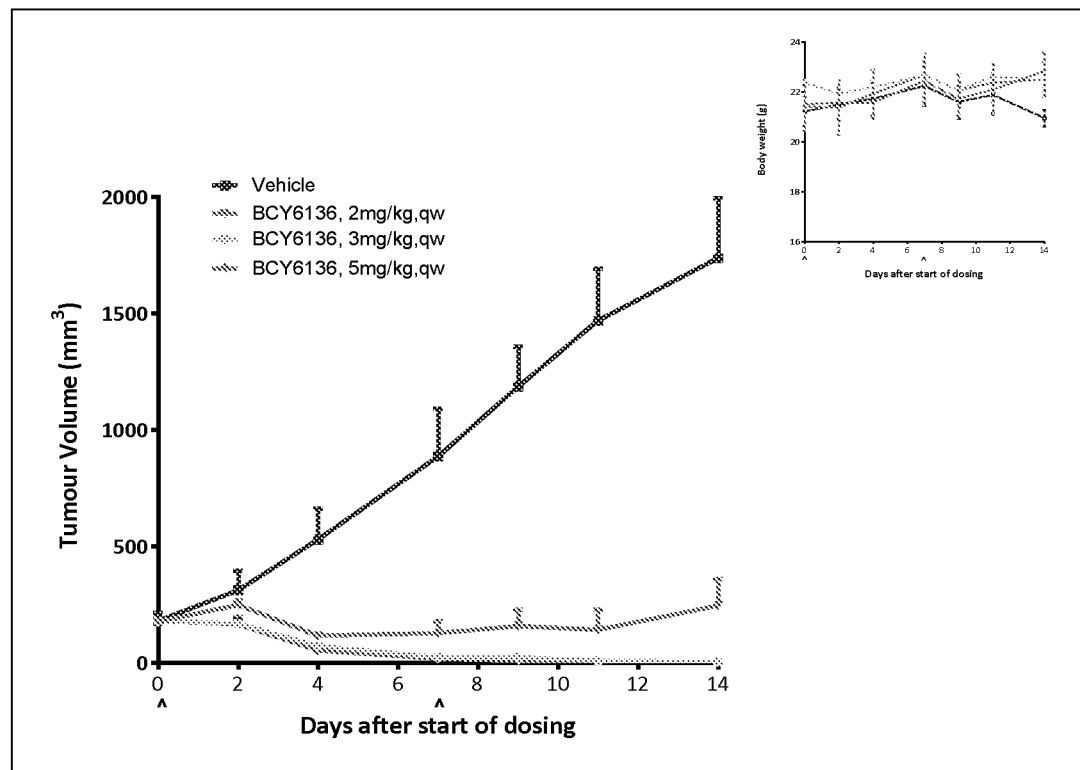
FIG. 4: Plot of mean tumour volume versus time for BCY6136 in HT1080 xenograft mice. Doses (2, 3 and 5 mg/kg) were administered on days 0 and 7. Body weight changes during treatment indicative of tumour burden, drug-associated toxicology and overall animal health are illustrated in the top right inset.
Figure 5:
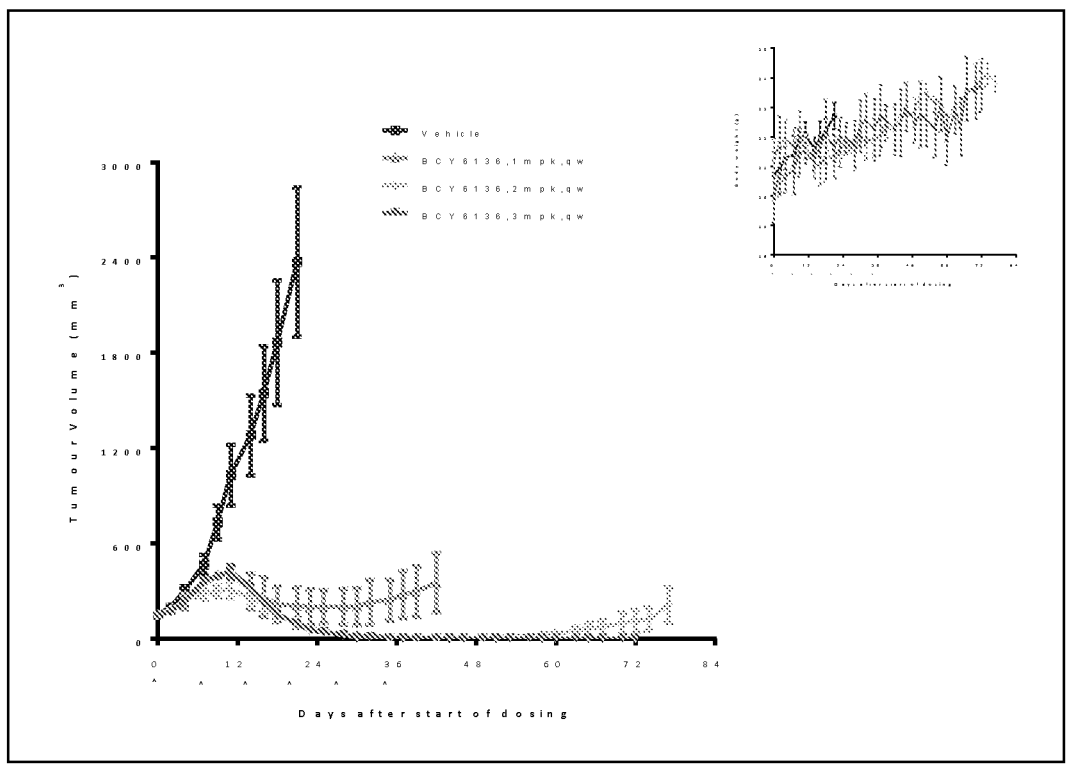
FIG. 5: Plot of mean tumour volume versus time for BCY6136 in NCI-H1975 xenograft mice. Doses (1, 2 and 3 mg/kg) were administered on days 0, 7, 14, 21, 28 and 35. Body weight changes during treatment indicative of tumour burden, drug-associated toxicology and overall animal health are illustrated in the top right inset.
Figure 6:
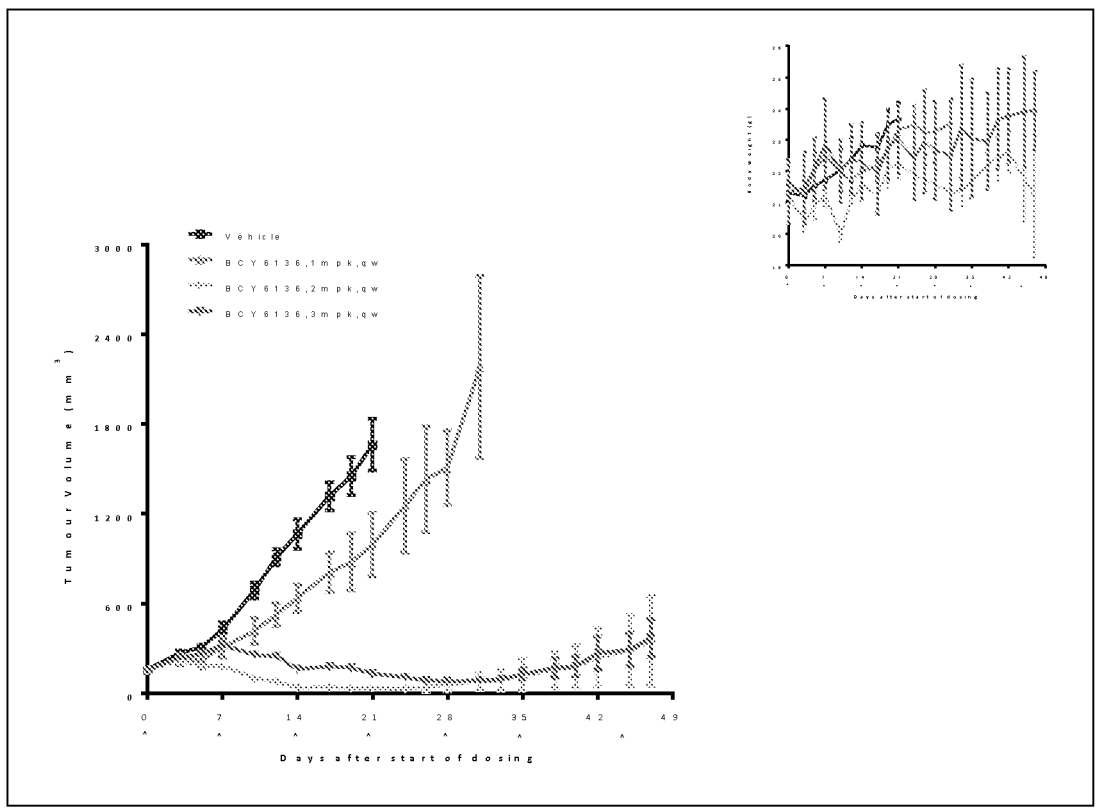
FIG. 6: Plot of mean tumour volume versus time for BCY6136 in MDA-MB-231 xenograft mice. Doses (1, 2 and 3 mg/kg) were administered on day 0, 7, 14, 21, 28, 35 and 45. Body weight changes during treatment indicative of tumour burden, drug-associated toxicology and overall animal health are illustrated in the top right inset.

FIGS. 4-6 show that BCY6136 is effective in breast, lung and fibrosarcoma xenograft models following once weekly dosing.

The HT1080 Fibrosarcoma Model:

In the HT1080 model complete regression of tumour growth was achieved by day 14 following once weekly dosing with BCY6136 on days 0 and 7 at 3 and 5 mg/kg (FIG. 4). Once weekly dosing with BCY6136 at 2 mg/kg on days 0 and 7 gave rise to tumour stasis (partial regression) (FIG. 4). BCY6136 treatment gave rise to no significant body weight loss (FIG. 4 inset) and there were no adverse clinical observations on drug treated mice throughout the study.

The NCI-H1975 NSCLC Model:

Complete regression of tumour growth in the NCI-H1975 model was observed by around day 28 following 2 and 3 mg/kg once weekly dosing with BCY6136 (FIG. 5). Following dosing cessation on day 35 no tumour regrowth was observed in the 3 mg/kg treated animals from day 35 to day 72 when the 3 mg/kg arm measurements ended (FIG. 5). Dosing with BCY6136 at 2 mg/kg gave rise to complete regression in this model from around day 28. Following dosing cessation on day 35 there was no tumour regrowth until around day 51 at the 2 mg/kg dose. At this dose level moderate tumour re-growth was observed from around day 51 until study termination on day 77. 1 mg/kg treatment with BCY6136 gave rise to tumour stasis (partial regression) (FIG. 5). BCY6136 treatment gave rise to no significant body weight loss (FIG. 5 inset) and there were no adverse clinical observations on drug treated mice throughout the study.

The MDA-MB-231 Breast Model:

Tumour stasis (partial regression) was observed in the MDA-MB231 model following once weekly dosing at 2 and 3 mg/kg from days 0 to day 45 (FIG. 6). Some body weight loss (attributed to tumour burden) was observed in the 2 mg/kg treated animals (FIG. 6 inset).

These results demonstrate that BCY6136 gives rise to profound tumour growth inhibition in mice implanted with fibrosarcoma, breast and lung CDX xenografts following once daily dosing.

Study 5: Safety Studies in the Rat

Six (6) female rats were randomly assigned to 3 groups of 2 rats/group to determine the toxicity of BCY6136, following administered by IV bolus injection at 5, 7.5 and 10 mg/kg on days 1 and 8. The study was terminated on day 15. No significant effects on coagulation parameters (Pro-thrombin time (sec), Activated partial thromboplastin time (sec) or Fibrinogen levels (g/L) were observed on days 2, 12 and 15 (data not shown). No in-life bleeding events were reported and no evidence of internal bleeding was detected following pathology examination.

Study 6: Safety Studies in the Cynomolgous Monkeys

Twenty eight day toxicology studies with BCY6136 we conducted in cynomolgous monkeys. BCY6136 was dosed at 1.0 and 2.0 mg/kg on days 1, 8, 15 and 22. Animals were euthanised and necropsied on day 29 (7 days after the final dose).

No significant effects on coagulation parameters relative to baseline were observed on days 18, 22 and 25 (data not shown) and day 29 (Table 20). No in-life bleeding events were reported and no evidence of internal bleeding was detected following pathology examination.

TABLE 20

Day 29 coagulation parameters following 1.0 and 2.0 mg/kg BCY6136 dosing to cynomolgus monkeys

|  | 1.0 mg/kg × 4 | | 2.0 mg/kg × 4 | |
| --- | --- | --- | --- | --- |
|  | Baseline | Day 29 | Baseline | Day 29 |
| PT(s) | 13.4 | 11.7 | 9.4 | 9.7 |
| PT(s) | 11 | 9.2 | 11.2 | 11.0 |
| APTT(s) | 18.9 | 19.4 | 19.4 | 20.9 |
| APTT(s) | 16.1 | 15.7 | 18.7 | 18.2 |
| FIB(g/L) | 2.08 | 2.42 | 1.86 | 6.1 |
| FIB(g/L) | 2.28 | 2.35 | 1.82 | 3.1 |

Study 7: In Vivo Efficacy Study of BCY6033 and BCY6136 and ADC in Treatment of PC-3 Xenograft in Balb/c Nude Mice (a) Study Objective The objective of the research is to evaluate the in vivo anti-tumor efficacy of BCY6033 and BCY6136 in treatment of PC-3 xenograft.

(b) Experimental Design

| Group | Treatment | n | Dose (mg/kg) | Dosing Volume (μl/g) | Dosing Route | Schedule |
| --- | --- | --- | --- | --- | --- | --- |
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |
| 5 | ADC | 3 | 3 | 10 | iv | qw |
| 6 | BCY6033 | 3 | 3 | 10 | iv | qw |

(c) Experimental Methods and Procedures (i) Cell Culture

The PC-3 tumor cells will be maintained in F12K medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

(ii) Tumor Inoculation

Each mouse will be inoculated subcutaneously at the right flank with PC-3 ($10*10^6$) tumor cells for tumor development. The animals will be randomized and treatment will be started when the average tumor volume reaches approximately 150 mm$^3$. The test article administration and the animal numbers in each group are shown in the following experimental design table.

(iii) Testing Article Formulation Preparation

| Test article | Con. (mg/ml) | Formulation |
| --- | --- | --- |
| Vehicle | — | 50 mM Acetate/acetic acid pH 5 10% sucrose |
| BCY6136 | 0.1 | Dilute 90 μl 1 mg/ml BCY6136 stock with 810 μl vehicle buffer |
|  | 0.2 | Dilute 180 μl 1 mg/ml BCY6136 stock with 720 μl vehicle buffer |
|  | 0.3 | Dilute 270 μl 1 mg/ml BCY6136 stock with 630 μl vehicle buffer |

| Test article | Con. (mg/ml) | Formulation |
|---|---|---|
| ADC | 0.3 | Dilute 26 μl 10.47 mg/ml ADC stock with 874 μl ADC buffer |
| BCY6033 | 0.3 | Dilute 270 μl 1 mg/ml BCY6033 stock with 630 μl vehicle buffer |

Figure 7:
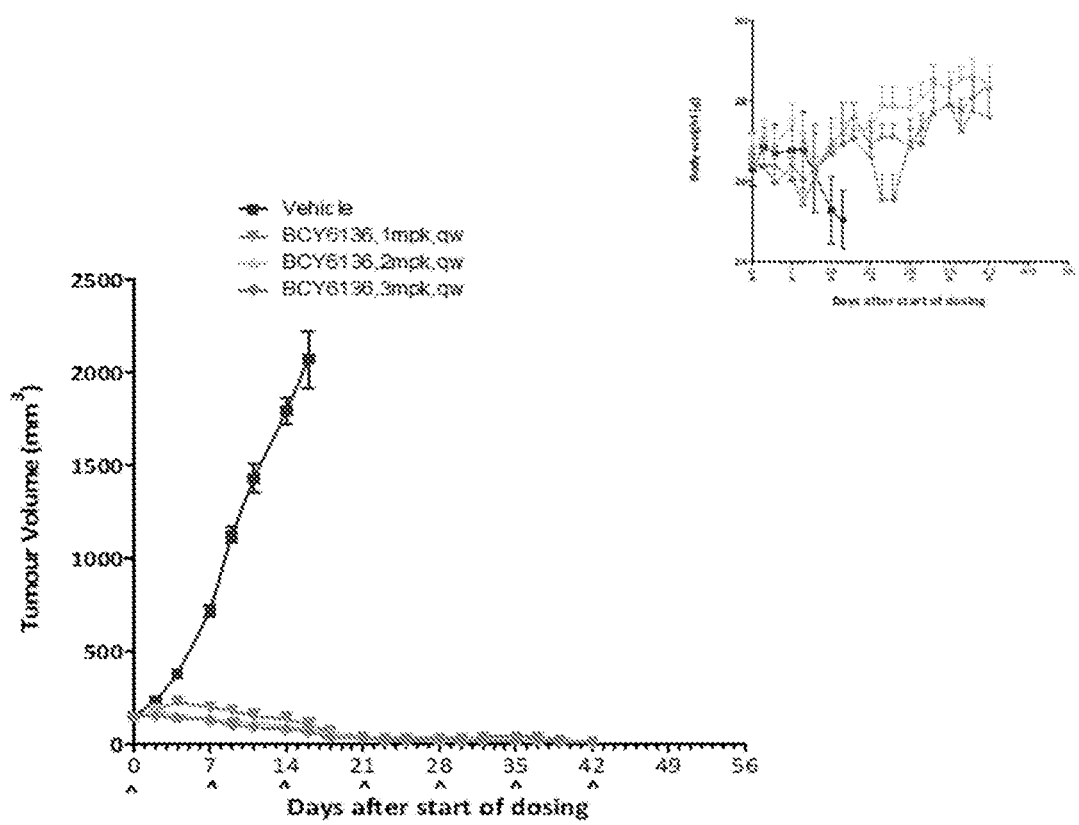
FIGS. 7 to 9: Body weight changes and tumor volume traces after administering BCY6136 (FIG. 7), ADC (FIG. 8) and BCY6033 (FIG. 9) to female BALB/c nude mice bearing PC-3 xenograft. Data points represent group mean body weight.
Figure 8:
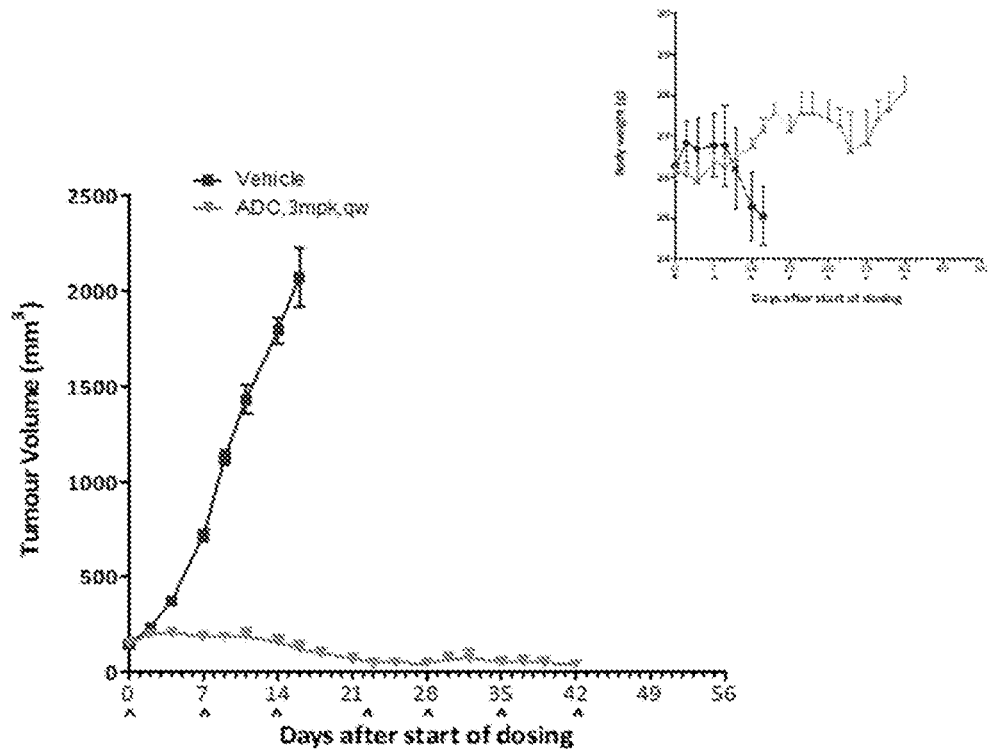
Figure 9:
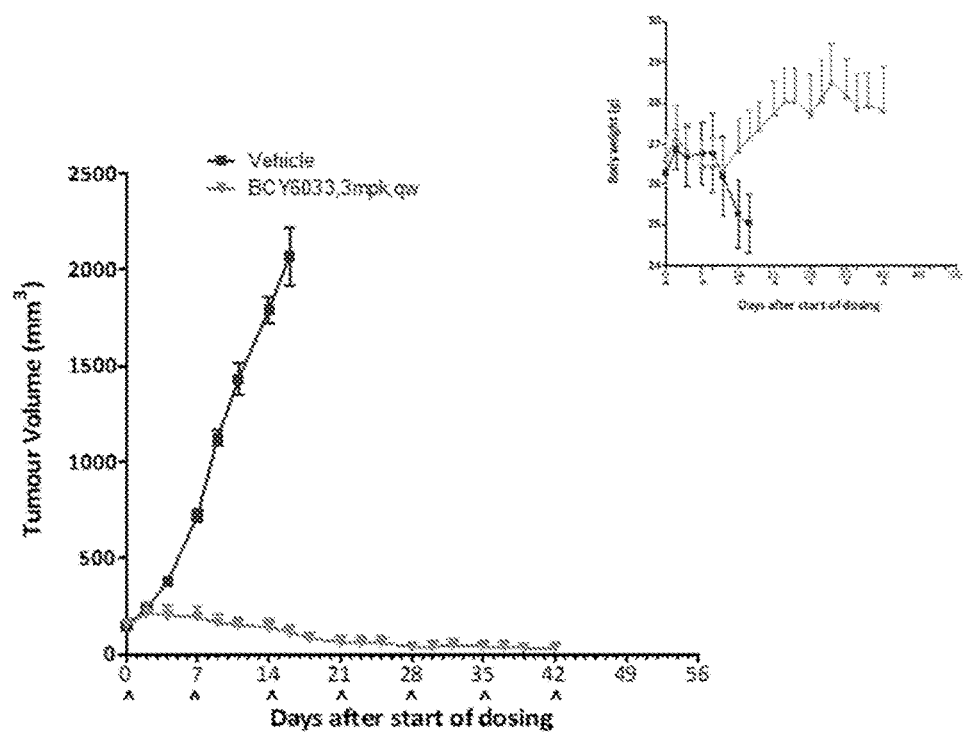

(d) Results
(i) Body Weight change and Tumor Growth Curve
Body weight and tumor growth curve are shown in FIGS. 7 to 9.
(ii) Tumor Volume Trace
Mean tumor volume over time in female Balb/c nude mice bearing PC-3 xenograft is shown in Table 21.

TABLE 21

Tumor volume trace over time

| Gr | Treatment | 0 | 2 | 4 | 7 | 9 | 11 | 14 | 16 | 18 | 21 |
|---|---|---|---|---|---|---|---|---|---|---|---|
| 1 | Vehicle, qw | 149 ± 9 | 235 ± 9 | 377 ± 9 | 718 ± 30 | 1126 ± 41 | 1431 ± 79 | 1792 ± 69 | 2070 ± 152 | | |
| 2 | BCY6136, 1mpk, qw | 150 ± 11 | 185 ± 25 | 228 ± 31 | 201 ± 17 | 183 ± 23 | 153 ± 38 | 137 ± 33 | 107 ± 32 | 64 ± 28 | 45 ± 23 |
| 3 | BCY6136, 2 mpk, qw | 149 ± 18 | 179 ± 28 | 158 ± 22 | 137 ± 16 | 122 ± 15 | 114 ± 20 | 101 ± 16 | 79 ± 20 | 57 ± 19 | 42 ± 17 |
| 4 | BCY6136 3 mpk, qw | 149 ± 2 | 155 ± 8 | 144 ± 16 | 132 ± 20 | 107 ± 28 | 94 ± 23 | 83 ± 22 | 70 ± 27 | 38 ± 16 | 35 ± 17 |
| 5 | ADC 3 mpk, qw | 151 ± 27 | 203 ± 10 | 210 ± 12 | 189 ± 11 | 185 ± 16 | 190 ± 37 | 158 ± 36 | 124 ± 35 | 103 ± 27 | 74 ± 14 |
| 6 | BCY6033, 3mpk, qw | 151 ± 33 | 214 ± 53 | 204 ± 51 | 192 ± 53 | 163 ± 43 | 151 ± 40 | 141 ± 39 | 116 ± 36 | 83 ± 28 | 63 ± 32 |

| Gr | Treatment | 23 | 25 | 28 | 30 | 32 | 35 | 37 | 39 | 42 |
|---|---|---|---|---|---|---|---|---|---|---|
| 1 | Vehicle, qw | | | | | | | | | |
| 2 | BCY6136, 1mpk, qw | 35 ± 18 | 28 ± 14 | 37 ± 19 | 34 ± 17 | 42 ± 21 | 42 ± 23 | 43 ± 21 | 28 ± 14 | 18 ± 9 |
| 3 | BCY6136, 2 mpk, qw | 21 ± 11 | 22 ± 12 | 22 ± 12 | 24 ± 12 | 33 ± 16 | 22 ± 11 | 26 ± 14 | 22 ± 12 | 16 ± 9 |
| 4 | BCY6136 3 mpk, qw | 21 ± 10 | 23 ± 12 | 27 ± 14 | 22 ± 11 | 24 ± 12 | 20 ± 11 | 27 ± 14 | 12 ± 6 | 12 ± 6 |
| 5 | ADC 3 mpk, qw | 53 ± 16 | 50 ± 22 | 46 ± 23 | 70 ± 35 | 78 ± 39 | 53 ± 27 | 60 ± 30 | 53 ± 27 | 40 ± 22 |
| 6 | BCY6033, 3mpk, qw | 59 ± 31 | 44 ± 27 | 39 ± 24 | 40 ± 29 | 47 ± 32 | 41 ± 27 | 41 ± 30 | 34 ± 24 | 33 ± 27 |

(iii) Tumor Growth Inhibition Analysis

Tumor growth inhibition rate for test articles in the PC-3 xenograft model was calculated based on tumor volume measurements at day 16 after the start of treatment.

TABLE 22

Tumor growth inhibition analysis

| Gr | Treatment | Tumor Volume (mm³)[a] | T/C[b] (%) | TGI (%) | P value compare with vehicle |
|---|---|---|---|---|---|
| 1 | Vehicle, qw | 2070 ± 152 | — | — | — |
| 2 | BCY6136, 1 mpk, qw | 107 ± 32 | 5.2 | 102.2 | p < 0.001 |
| 3 | BCY6136, 2 mpk, qw | 79 ± 20 | 3.8 | 103.6 | p < 0.001 |
| 4 | BCY6136, 3 mpk, qw | 70 ± 27 | 3.4 | 104.1 | p < 0.001 |
| 5 | ADC, 3 mpk, qw | 124 ± 35 | 6.0 | 101.4 | p < 0.001 |
| 6 | BCY6033, 3 mpk, qw | 116 ± 36 | 5.6 | 101.8 | p < 0.001 |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of test articles in the PC-3 xenograft model was evaluated. The measured body weights and tumor volumes of all treatment groups at various time points are shown in the FIGS. 7 to 9 and Tables 21 and 22.

The mean tumor size of vehicle treated mice reached 2070 mm³ on day 16. BCY6136 at 1 mg/kg, qw (TV=107 mm³, TGI=102.2%, p<0.001), BCY6136 at 2 mg/kg, qw (TV=79 mm³, TGI=103.6%, p<0.001) and BCY6136 at 3 mg/kg, qw (TV=70 mm³, TGI=104.1%, p<0.001) showed potent anti-tumor effect.

BCY6033 at 3 mg/kg, qw (TV=116 mm³, TGI=101.8%, p<0.001) and ADC at 3 mg/kg, qw (TV=124 mm³, TGI=101.4%, p<0.001) showed comparable anti-tumor effect.

In this study, animal body weight was monitored regularly. All mice maintained their body weight well.

Study 8. In Vivo Efficacy Study of BCY6136 in Treatment of PC-3 Xenograft in Balb/c Nude Mice (a) Study Objective The objective of the research is to evaluate the in vivo anti-tumor efficacy of BCY6136 in treatment of PC-3 xenograft in Balb/c nude mice.

(b) Experimental Design

| Group | Treatment | Dose (mg/kg) | N[a] | Dosing Route | Schedule |
|---|---|---|---|---|---|
| 1 | Vehicle | — | 4 | i.v. | qw × 4 weeks |
| 2 | BCY6136 | 0.167 | 4 | i.v. | qw × 4 weeks |
| 3[b] | BCY6136 | 0.5 | 4 | i.v. | qw × 4 weeks |
| 4 | BCY6136 | 1.5 | 4 | i.v. | qw × 4 weeks |
| 5[b] | BCY6136 | 0.5 | 4 | i.v. | q2w × 2 weeks |
| 6[b] | BCY6136 | 1.5 | 4 | i.v. | q2w × 2 weeks |
| 7 | EphA2-ADC | 0.33 | 4 | i.v. | qw × 4 weeks |
| 8 | EphA2-ADC | 1 | 4 | i.v. | qw × 4 weeks |
| 9 | EphA2-ADC | 3 | 4 | i.v. | qw × 4 weeks |
| 10[c] | Docetaxel | 15 | 4 | i.v. | qw × 4 weeks |

[a]N, the number of animals in each group.
[b]After 4 weeks' treatment demonstrated in the experimental design table, the mice of group 3, 5 and 6 were treated with BCY6136 1.5 mg/kg qw from day 52 during the monitoring schedule.
[c]Due to the severe body weight loss of the Docetaxel treated mice after the first dosing, the treatment was suspended for 2 weeks, then a lower dosage (Docetaxel, 10 mg/kg) was performed on day 28. After that, the mice were treated with BCY6136 1.5 mg/kg qw from day 42 to day 70.

(c) Experimental Methods and Procedures
(i) Cell Culture

The tumor cells were maintained in F-12K medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with PC-3 tumor cells ($10 \times 10^6$) in 0.2 ml of PBS for tumor development. 52 animals were randomized when the average tumor volume reached 454 mm³. The test article administration and the animal numbers in each group were shown in the experimental design table.

(iii) Testing Article Formulation Preparation

| Test article | Purity | Conc. (mg/ml) | Formulation |
|---|---|---|---|
| Vehicle | — | — | 25 mM Histidine pH 7 10% sucrose |
| BCY6136 | 98.6% | — | 50 mM Acetate 10% sucrose pH 5 |
|  |  | 1 | Dissolve 2.70 mg BCY6136 in 2.662 ml Acetate buffer |
|  |  | 0.3 | Dilute 300 μl 1 mg/ml BCY6136 stock with 700 μl Acetate buffer[1] |
|  |  | 0.15 | Dilute 600 μl 0.3 mg/ml BCY6136 stock with 600 μl Acetate buffer |
|  |  | 0.05 | Dilute 200 μl 0.3 mg/ml BCY6136 stock with 1000 μl Acetate buffer |
|  |  | 0.0167 | Dilute 66.7 μl 0.3 mg/ml BCY6136 stock with 1133.3 μl Acetate buffer |
| EphA2-ADC | — | — | 25 mM Histidine pH 5.5 |
|  |  | 0.033 | Dilute 9.3 μl 4.24 mg/ml EphA2-ADC stock with 1191 μl His buffer |
|  |  | 0.1 | Dilute 28 μl 4.24 mg/ml EphA2-ADC stock with 1172 μl His buffer |
|  |  | 0.3 | Dilute 84.9 μl 4.24 mg/ml EphA2-ADC stock with 1115 μl His buffer |
| Docetaxel | — | 10 | Mix 0.5 ml 20 mg Docetaxel with 1.5 ml buffer |
|  |  | 1.5 | Dilute 180 μl 10 mg/ml Docetaxel stock with 1020 μl saline buffer |

[1]50 mM Acetate 10% sucrose pH 5 3.25 mM Histidine pH 5.5

Figure 10:
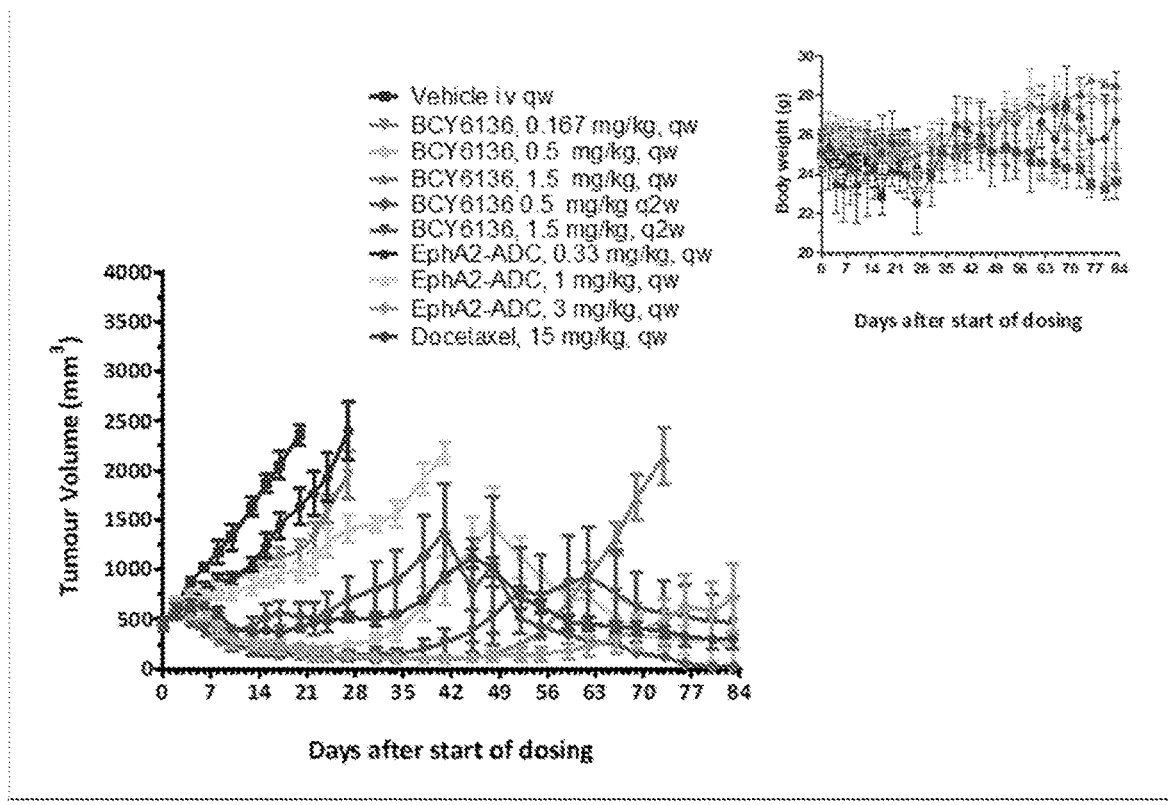
FIG. 10: Body weight changes and tumor volume traces after administering BCY6136, EphA2-ADC or Docetaxel to male Balb/c nude mice bearing PC-3 xenograft. Data points represent group mean body weight.

(c) Results
(i) Body Weight change and Tumor Growth Curve
Body weight and tumor growth curve is shown in FIG. 10.
(ii) Tumor Volume Trace
Mean tumor volume over time in male Balb/c nude mice bearing PC-3 xenograft is shown in Table 23.

TABLE 23

Tumor volume trace over time (Day 0 to day 20)

| Gr. | Treatment | Days after the start of treatment | | | | | | | | | |
|---|---|---|---|---|---|---|---|---|---|---|---|
|  |  | 0 | 2 | 4 | 6 | 8 | 10 | 13 | 15 | 17 | 20 |
| 1 | Vehicle, qw | 456 ± 25 | 648 ± 50 | 880 ± 23 | 1022 ± 29 | 1178 ± 118 | 1327 ± 133 | 1631 ± 93 | 1868 ± 90 | 2052 ± 139 | 2364 ± 102 |
| 2 | BCY6136 0.167 mpk, qw | 450 ± 33 | 631 ± 55 | 695 ± 78 | 739 ± 39 | 850 ± 68 | 904 ± 73 | 975 ± 47 | 1089 ± 74 | 1124 ± 92 | 1188 ± 111 |
| 3 | BCY6136 0.5 mpk, qw | 451 ± 47 | 622 ± 96 | 519 ± 70 | 460 ± 55 | 398 ± 50 | 329 ± 38 | 260 ± 33 | 249 ± 33 | 231 ± 38 | 234 ± 42 |
| 4 | BCY6136 1.5 mpk, qw | 458 ± 49 | 587 ± 63 | 494 ± 54 | 363 ± 32 | 283 ± 32 | 237 ± 24 | 192 ± 13 | 164 ± 16 | 155 ± 20 | 131 ± 19 |
| 5 | BCY6136 0.5 mpk, q2w | 454 ± 37 | 643 ± 25 | 531 ± 37 | 458 ± 33 | 411 ± 32 | 382 ± 49 | 430 ± 88 | 522 ± 124 | 560 ± 129 | 530 ± 147 |
| 6 | BCY6136 1.5 mpk, q2w 1.5 mpk, qw | 452 ± 42 | 590 ± 75 | 457 ± 49 | 375 ± 44 | 328 ± 47 | 242 ± 63 | 206 ± 61 | 197 ± 62 | 182 ± 55 | 128 ± 36 |
| 7 | EphA2-ADC 0.33 mpk, qw | 457 ± 43 | 636 ± 57 | 712 ± 70 | 792 ± 78 | 870 ± 87 | 900 ± 58 | 1049 ± 66 | 1242 ± 123 | 1443 ± 12 | 1637 ± 181 |
| 8 | EphA2-ADC 1 mpk, qw | 450 ± 49 | 617 ± 48 | 673 ± 50 | 721 ± 61 | 782 ± 78 | 755 ± 67 | 840 ± 93 | 913 ± 91 | 978 ± 100 | 981 ± 100 |
| 9 | EphA2-ADC 3 mpk, qw | 452 ± 60 | 593 ± 98 | 643 ± 141 | 593 ± 106 | 433 ± 103 | 290 ± 81 | 268 ± 64 | 232 ± 60 | 225 ± 66 | 184 ± 62 |
| 10 | Docetaxel 15 mpk, qw | 453 ± 62 | 584 ± 72 | 632 ± 56 | 636 ± 48 | 568 ± 50 | 408 ± 31 | 374 ± 26 | 388 ± 36 | 361 ± 25 | 419 ± 31 |

(iii) Tumor Growth Inhibition Analysis

Tumor growth inhibition ratefor test articles in the PC-3 xenograft model was calculated based on tumor volume measurements at day 20 after the start of the treatment. for test articles in the PC-3 xenograft model was calculated based on tumor volume measurements at day 20 after the start of the treatment.

TABLE 24

Tumor growth inhibition analysis

| Gr | Treatment | Tumor Volume (mm$^3$)$^a$ | T/C$^b$ (%) | TGI (%) | P value compared with vehicle |
|---|---|---|---|---|---|
| 1 | Vehicle, qw | 2364 ± 102 | — | — | — |
| 2 | BCY6136, 0.167 mpk, qw | 1188 ± 111 | 50.2 | 61.4 | p < 0.001 |
| 3 | BCY6136, 0.5 mpk, qw | 234 ± 42 | 9.9 | 111.4 | p < 0.001 |
| 4 | BCY6136, 1.5 mpk, qw | 131 ± 19 | 5.5 | 117.2 | p < 0.001 |
| 5 | BCY6136, 0.5 mpk, q2w | 530 ± 147 | 22.4 | 96.0 | p < 0.001 |
| 6 | BCY6136, 1.5 mpk, q2w | 128 ± 36 | 5.4 | 117.0 | p < 0.001 |
| 7 | EphA2-ADC, 0.33 mpk, qw | 1637 ± 181 | 69.2 | 38.1 | p < 0.001 |
| 8 | EphA2-ADC, 1 mpk, qw | 981 ± 100 | 41.5 | 72.2 | p < 0.001 |
| 9 | EphA2-ADC, 3 mpk, qw | 184 ± 62 | 7.8 | 114.0 | p < 0.001 |
| 10 | Docetaxel, 15 mpk, qw | 419 ± 31 | 17.7 | 101.8 | p < 0.001 |

$^a$Mean ± SEM.
$^b$Tumor Growth Inhibition is calculated by dividing the group average tumor volume for the treated group by the group average tumor volume for the control group (T/C).

(d) Results Summary and Discussion

In this study, the therapeutic efficacy of test articles in the PC-3 xenograft model was evaluated. The measured body weights and tumor volumes of all treatment groups at various time points are shown in the FIG. 10 and Tables 23 and 24.

The mean tumor size of vehicle treated mice reached 2364 mm$^3$ on day 20. BCY6136 at 0.167 mg/kg, qw (TV=1188 mm$^3$, TGI=61.4%, p<0.001), 0.5 mg/kg, q2w (TV=530 mm$^3$, TGI=96.0%, p<0.001), 0.5 mg/kg, qw (TV=234 mm$^3$, TGI=111.4%, p<0.001) and 1.5 mg/kg, qw (TV=131 mm$^3$, TGI=117.2%, p<0.001) produced significant anti-tumor activity in dose or dose-frequency dependent manner on day 20. BCY6136 at 1.5 mg/kg, q2w (TV=128 mm$^3$, TGI=117.0%, p<0.001) produced comparable anti-tumor activity with BCY6136 1.5 mg/kg qw. Among them, the mice treated with BCY6136, 0.5 mg/kg qw or BCY6136, 0.5 mg/kg q2w showed obvious tumor relapse after ceasing the treatment, further treatment with BCY6136, 1.5 mg/kg qw from day 52 worked well on the tumor regression. The mice treated with BCY6136, 1.5 mg/kg q2w also showed tumor relapse after ceasing the treatment, but further dosing didn't work on complete tumor regression. The mice treated with BCY6136, 1.5 mpk qw didn't show any tumor relapse until day 48.

EphA2-ADC at 0.33 mg/kg, qw (TV=1637 mm$^3$, TGI=38.1%, p<0.001), 1 mg/kg, qw (TV=981 mm$^3$, TGI=72.2%, p<0.001) and 3 mg/kg, qw (TV=184 mm$^3$, TGI=114.0%, p<0.001) produced significant anti-tumor activity in dose dependent manner on day 20. The mice treated with EphA2-ADC, 3 mg/kg qw didn't show any tumor relapse until day 59.

Docetaxel at 15 mg/kg, qw (TV=419 mm$^3$, TGI=101.8%, p<0.001) produced significant anti-tumor activity but caused severe animal body weight loss. After ceasing the treatment, the mice showed obvious tumor relapse. The treatment with BCY6136, 1.5 mg/kg qw from day 42 worked well on tumor regression of these mice.

Study 9. In Vivo Efficacy Test of BCY6033, BCY6136 and BCY6082 in Treatment of NCI-H1975 Xenograft in Balb/c Nude Mice (a) Study Objective The objective of the research was to evaluate the in vivo anti-tumor efficacy of BCY6033, BCY6136 and BCY6082 in treatment of NCI-H1975 xenograft model in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6033 | 3 | 1 | 10 | iv | qw |
| 3 | BCY6033 | 3 | 2 | 10 | iv | qw |
| 4 | BCY6033 | 3 | 3 | 10 | iv | qw |
| 5 | BCY6136 | 3 | 1 | 10 | iv | qw |
| 6 | BCY6136 | 3 | 2 | 10 | iv | qw |
| 7 | BCY6136 | 3 | 3 | 10 | iv | qw |
| 8 | BCY6082 | 3 | 2 | 10 | iv | qw |
| 9 | BCY6082 | 3 | 5 | 10 | iv | qw |

(c) Experimental Methods and Procedures (i) Cell Culture

The cells growing in an exponential growth phase were harvested and counted for tumor inoculation.

(ii) Tumor Inoculation

Each mouse was inoculated subcutaneously at the right flank with NCI-H1975 tumor cells (10×10^6) in 0.2 ml of PBS for tumor development. 36 animals were randomized when the average tumor volume reached 149 mm$^3$. The test article administration and the animal numbers in each group were shown in the experimental design table.

(iii) Testing Article Formulation Preparation

| Treatment | Dose (mg/ml) | Formulation |
|---|---|---|
| Vehicle | | 50 mM Acetate, 10% sucrose pH = 5 |
| BCY6033 | 1 | Dissolve 6.71 mg BCY6033 in 6.710 ml formulation buffer |
| | 0.3 | Dilute 270 μl 1 mg/ml BCY6033 with 630 μl formulation buffer |
| | 0.2 | Dilute 180 μl 1 mg/ml BCY6033 with 720 μl formulation buffer |
| | 0.1 | Dilute 90 μl 1 mg/ml BCY6033 with 810 μl formulation buffer |
| BCY6136 | 1 | Dissolve 3.79 mg BCY6136 in 3.695 ml formulation buffer |
| | 0.3 | Dilute 270 μl 1 mg/ml BCY6136 with 630 μl formulation buffer |
| | 0.2 | Dilute 180 μl 1 mg/ml BCY6136 with 720 μl formulation buffer |
| | 0.1 | Dilute 90 μl 1 mg/ml BCY6136 with 810 μl formulation buffer |
| BCY6082 | 1 | Weigh and dissolve 4.30 mg BCY6082 in 4.162 ml formulation buffer |
| | 0.5 | Dilute 450 μl 1 mg/ml BCY6082 with 450 μl formulation buffer |
| | 0.2 | Dilute 180 μl 1 mg/ml BCY6082 with 720 μl formulation buffer |

Figure 11:
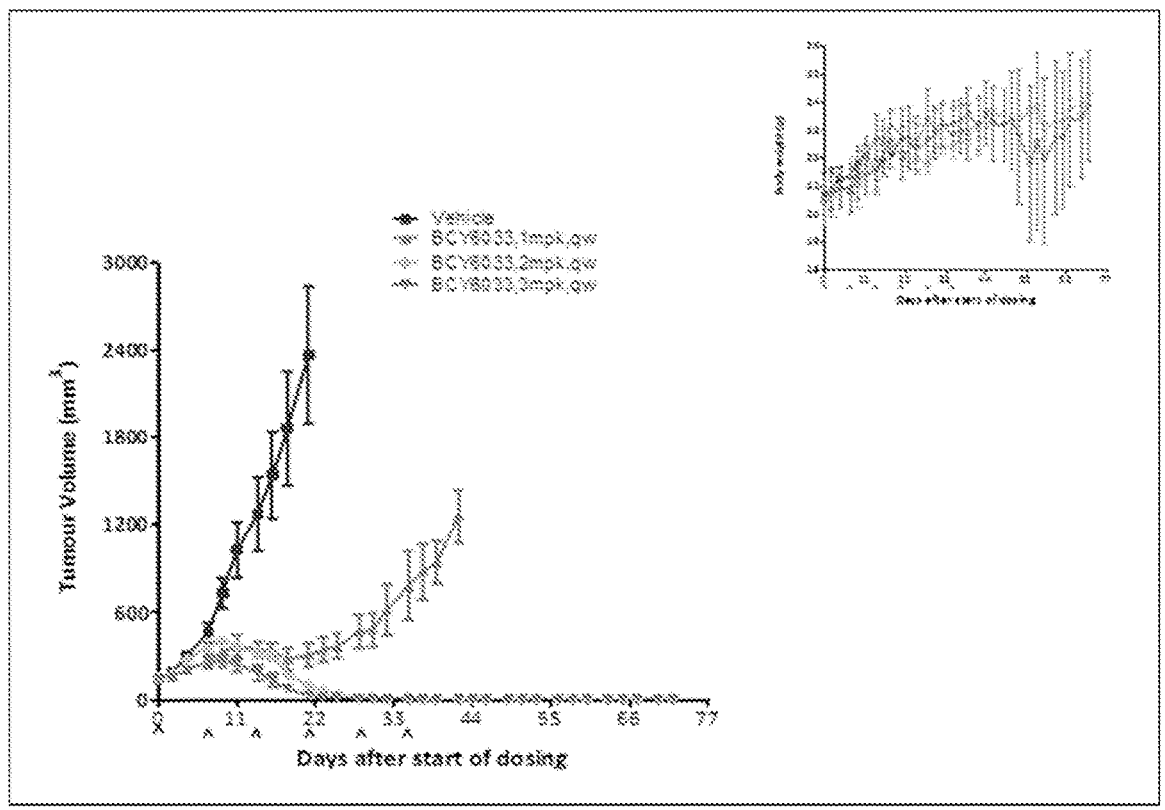
FIGS. 11 to 13: Body weight changes and tumor volume trace after administering BCY6033 (FIG. 11), BCY6136 (FIG. 12) and BCY6082 (FIG. 13) to female Balb/c nude mice bearing NCI-H1975 xenograft. Data points represent group mean tumor volume and body weight.
Figure 12:
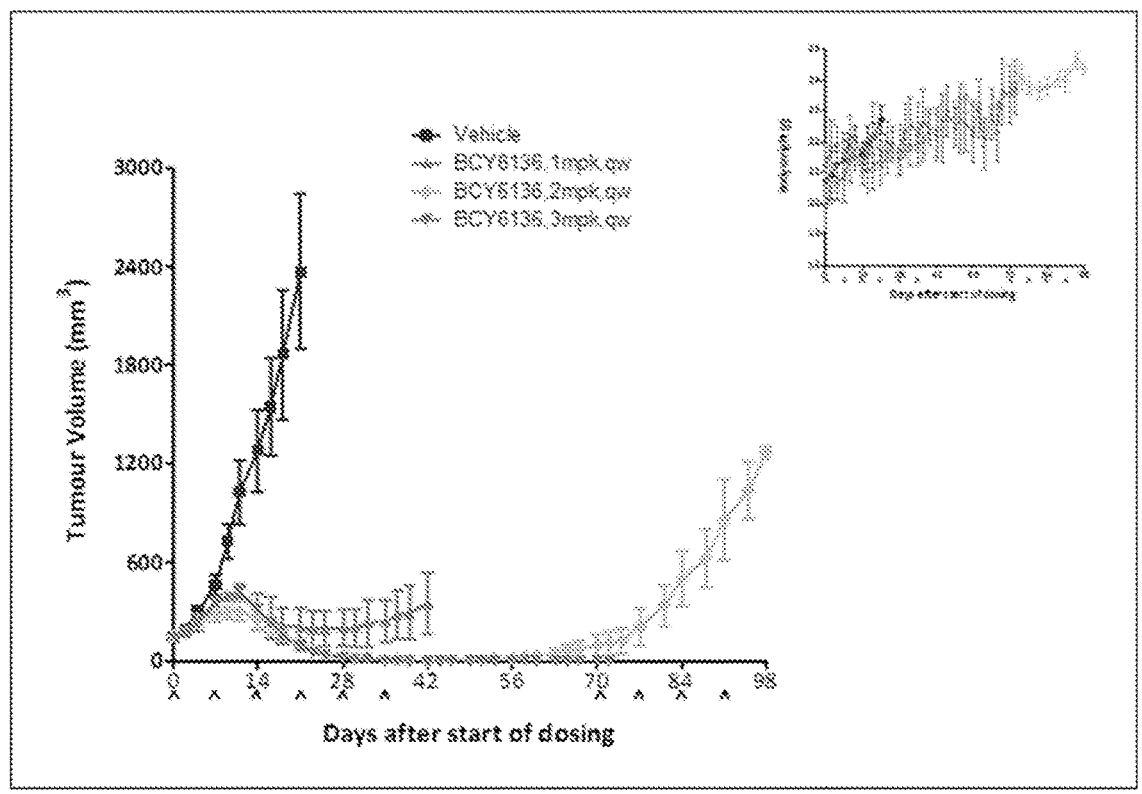
Figure 13:
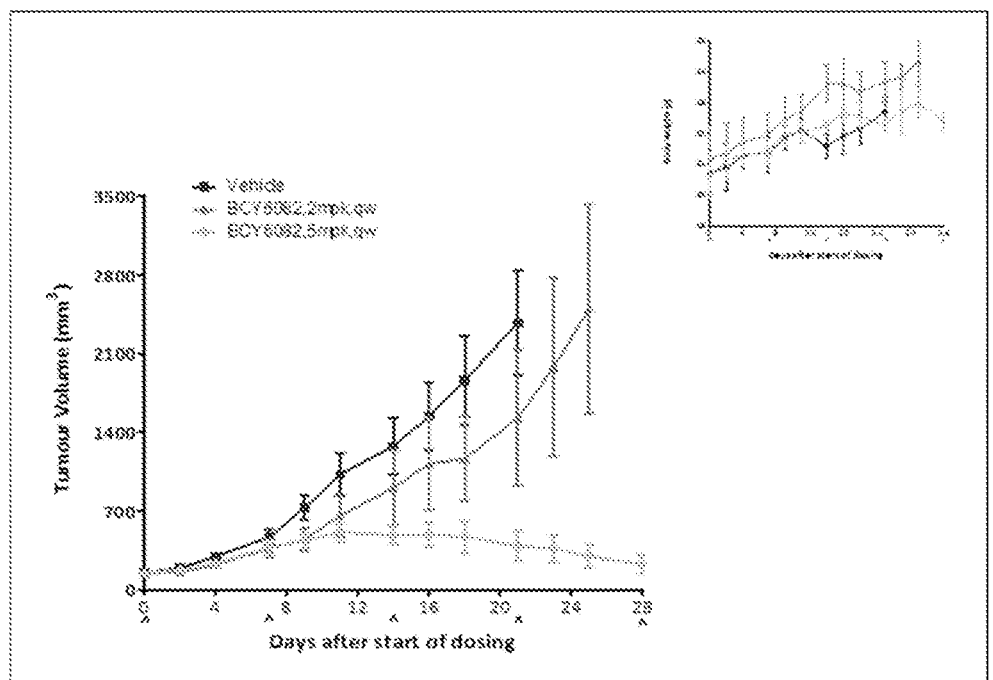

(iv) Sample Collection
On PG-D23, we fixed the tumors of Group 1 for FFPE.
On PG-D44, we fixed the tumors of Group 2 and 5 for FFPE.
At the end of study, we the tumors of Group 6 for FFPE.
(d) Results
(i) Body Weight change and Tumor Growth Curve Body weight and tumor growth are shown in FIGS. 11 to 13.

(ii) Tumor Volume Trace

Mean tumor volume over time in female Balb/c nude mice bearing NCI-H1975 xenograft is shown in Table 25 to 29.

TABLE 25

Tumor volume trace (PG-DO-PG-017)

| Gr. | Treatment | \multicolumn{8}{c}{Days after the start of treatment} |
|---|---|---|---|---|---|---|---|---|---|
| | | 0 | 2 | 4 | 7 | 9 | 11 | 14 | 17 |
| 1 | Vehicle, qw | 148 ± 4 | 195 ± 11 | 297 ± 33 | 466 ± 64 | 732 ± 107 | 1028 ± 192 | 1278 ± 252 | 1543 ± 298 |
| 2 | BCY6033, 1 mpk, qw | 149 ± 10 | 160 ± 4 | 207 ± 13 | 259 ± 49 | 330 ± 69 | 365 ± 83 | 341 ± 59 | 336 ± 54 |
| 3 | BCY6033, 2 mpk, qw | 149 ± 10 | 183 ± 11 | 276 ± 24 | 365 ± 42 | 405 ± 20 | 364 ± 19 | 319 ± 32 | 304 ± 33 |
| 4 | BCY6033, 3 mpk, qw | 149 ± 6 | 161 ± 4 | 207 ± 26 | 260 ± 21 | 270 ± 42 | 243 ± 52 | 187 ± 53 | 131 ± 43 |
| 5 | BCY6136, 1 mpk, qw | 150 ± 6 | 178 ± 20 | 232 ± 49 | 336 ± 43 | 400 ± 24 | 407 ± 42 | 299 ± 113 | 261 ± 127 |
| 6 | BCY6136, 2 mpk, qw | 150 ± 14 | 181 ± 26 | 237 ± 27 | 277 ± 36 | 297 ± 37 | 306 ± 55 | 256 ± 53 | 218 ± 49 |
| 7 | BCY6136, 3 mpk, qw | 148 ± 9 | 168 ± 10 | 231 ± 6 | 365 ± 16 | 390 ± 13 | 423 ± 42 | 319 ± 26 | 228 ± 16 |
| 8 | BCY6082, 2 mpk, qw | 148 ± 5 | 157 ± 4 | 223 ± 19 | 370 ± 84 | 447 ± 102 | 658 ± 188 | 906 ± 332 | 1123 ± 410 |
| 9 | BCY6082, 5 mpk, qw | 148 ± 6 | 176 ± 12 | 235 ± 19 | 378 ± 59 | 436 ± 68 | 510 ± 82 | 484 ± 78 | 491 ± 103 |

TABLE 26

Tumor volume trace (PG-018-PG-035)

| Gr. | Treatment | \multicolumn{8}{c}{Days after the start of treatment} |
|---|---|---|---|---|---|---|---|---|---|
| | | 18 | 21 | 23 | 25 | 28 | 30 | 33 | 35 |
| 1 | Vehicle, qw | 1864 ± 395 | 2371 ± 470 | — | — | — | — | — | — |
| 2 | BCY6033, 1 mpk, qw | 278 ± 71 | 306 ± 81 | 343 ± 86 | 366 ± 89 | 466 ± 115 | 481 ± 112 | 619 ± 170 | 780 ± 236 |
| 3 | BCY6033, 2 mpk, qw | 172 ± 25 | 95 ± 12 | 61 ± 6 | 39 ± 4 | 13 ± 1 | 12 ± 1 | 6 ± 3 | 6 ± 3 |
| 4 | BCY6033, 3 mpk, qw | 75 ± 15 | 29 ± 4 | 20 ± 6 | 13 ± 2 | 6 ± 0 | 4 ± 0 | 1 ± 0 | 2 ± 1 |
| 5 | BCY6136, 1 mpk, qw | 215 ± 113 | 205 ± 117 | 197 ± 113 | 200 ± 105 | 202 ± 112 | 202 ± 117 | 230 ± 142 | 241 ± 127 |
| 6 | BCY6136, 2 mpk, qw | 149 ± 31 | 99 ± 30 | 69 ± 22 | 42 ± 13 | 30 ± 10 | 16 ± 8 | 20 ± 9 | 4 ± 2 |
| 7 | BCY6136, 3 mpk, qw | 149 ± 17 | 94 ± 30 | 50 ± 15 | 41 ± 21 | 21 ± 8 | 6 ± 6 | 10 ± 6 | 3 ± 1 |
| 8 | BCY6082, 2 mpk, qw | 1199 ± 408 | 1528 ± 604 | 1978 ± 792 | 2499 ± 931 | — | — | — | — |
| 9 | BCY6082, 5 mpk, qw | 471 ± 143 | 390 ± 133 | 368 ± 122 | 295 ± 102 | 227 ± 86 | — | — | — |

TABLE 27

Tumor volume trace (PG-037-PG-053)

| Gr. | Treatment | \multicolumn{7}{c}{Days after the start of treatment} |
|---|---|---|---|---|---|---|---|---|
| | | 37 | 39 | 42 | 44 | 46 | 49 | 51 | 53 |
| 2 | BCY6033, 1 mpk, qw | 877 ± 188 | 945 ± 145 | 1258 ± 173 | — | — | — | — | — |
| 3 | BCY6033, 2 mpk, qw | 3 ± 1 | 1 ± 0 | 1 ± 0 | 1 ± 0 | 1 ± 0 | 1 ± 0 | 1 ± 0 | 1 ± 0 |

TABLE 27-continued

Tumor volume trace (PG-037-PG-053)

| | | Days after the start of treatment | | | | | | |
|---|---|---|---|---|---|---|---|---|
| Gr. | Treatment | 37 | 39 | 42 | 44 | 46 | 49 | 51 | 53 |
| 4 | BCY6033, 3 mpk, qw | 0 ± 0 | 0 ± 0 | 0 ± 0 | 0 ± 0 | 1 ± 0 | 0 ± 0 | 1 ± 0 | 1 ± 0 |
| 5 | BCY6136, 1 mpk, qw | 277 ± 149 | 294 ± 159 | 351 ± 188 | — | — | — | — | — |
| 6 | BCY6136, 2 mpk, qw | 7 ± 4 | 2 ± 1 | 1 ± 0 | 3 ± 1 | 2 ± 1 | 3 ± 2 | 6 ± 3 | 14 ± 10 |
| 7 | BCY6136, 3 mpk, qw | 3 ± 3 | 2 ± 1 | 1 ± 0 | 0 ± 0 | 0 ± 0 | 0 ± 0 | 1 ± 0 | 1 ± 0 |

TABLE 28

Tumor volume trace (PG-056-PG-074)

| | | Days after the start of treatment | | | | | | | |
|---|---|---|---|---|---|---|---|---|---|
| Gr. | Treatment | 56 | 58 | 60 | 63 | 65 | 67 | 70 | 72 | 74 |
| 3 | BCY6033, 2 mpk, qw | 1 ± 0 | 1 ± 0 | 1 ± 0 | 1 ± 0 | 1 ± 0 | 2 ± 1 | 4 ± 3 | 7 ± 6 | — |
| 4 | BCY6033, 3 mpk, qw | 1 ± 0 | 1 ± 0 | 0 ± 0 | 0 ± 0 | 0 ± 0 | 0 ± 0 | 0 ± 0 | 0 ± 0 | — |
| 6 | BCY6136, 2 mpk, qw | 16 ± 11 | 27 ± 18 | 34 ± 23 | 45 ± 31 | 63 ± 40 | 71 ± 47 | 95 ± 70 | 111 ± 73 | 122 ± 75 |
| 7 | BCY6136, 3 mpk, qw | 1 ± 0 | 1 ± 0 | 1 ± 0 | 0 ± 0 | 0 ± 0 | 0 ± 0 | 0 ± 0 | 0 ± 0 | — |

TABLE 29

Tumor volume trace (PG-D77~PG-D98)

| | | Days after the start of treatment | | | | | |
|---|---|---|---|---|---|---|---|
| Gr. | Treatment | 77 | 81 | 84 | 88 | 91 | 95 | 98 |
| 6 | BCY6136, 2 mpk, qw | 208 ± 112 | 337 ± 123 | 501 ± 172 | 626 ± 182 | 856 ± 245 | 1035 ± 169 | 1266 ± 39 |

(iii) Tumor Growth Inhibition Analysis

Tumor growth inhibition rate for BCY6033, BCY6136 and BCY6082 in the NCI-H1975 xenograft model was calculated based on tumor volume measurements at day 21 after the start of treatment.

TABLE 30

Tumor growth inhibition analysis

| Gr | Treatment | Tumor Volume (mm$^3$)$^a$ | T/C$^b$ (%) | TGI (%) | P value |
|---|---|---|---|---|---|
| 1 | Vehicle, qw | 2371 ± 470 | — | — | — |
| 2 | BCY6033, 1 mpk, qw | 306 ± 81 | 12.9 | 92.9 | p < 0.001 |
| 3 | BCY6033, 2 mpk, qw | 95 ± 12 | 4.0 | 102.5 | p < 0.001 |
| 4 | BCY6033, 3 mpk, qw | 29 ± 4 | 1.2 | 105.4 | p < 0.001 |
| 5 | BCY6136, 1 mpk, qw | 205 ± 117 | 8.6 | 97.5 | p < 0.001 |
| 6 | BCY6136, 2 mpk, qw | 99 ± 30 | 4.2 | 102.3 | p < 0.001 |
| 7 | BCY6136, 3 mpk, qw | 94 ± 30 | 4.0 | 102.4 | p < 0.001 |
| 8 | BCY6082, 2 mpk, qw | 1528 ± 604 | 64.4 | 37.9 | p > 0.05 |
| 9 | BCY6082, 5 mpk, qw | 390 ± 133 | 16.4 | 89.1 | p < 0.001 |

$^a$Mean ± SEM.
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6033, BCY6136 and BCY6082 in the NCI-H1975 xenograft model was evaluated. The measured body weights and tumor volumes of all treatment groups at various time points are shown in the FIGS. 11 to 13 and Tables 25 to 30.

The mean tumor size of vehicle treated mice reached 2371 mm$^3$ on day 21. BCY6033 at 1 mg/kg (TV=306 mm$^3$, TGI=92.9%, p<0.001), 2 mg/kg (TV=95 mm$^3$, TGI=102.5%, p<0.001) and 3 mg/kg (TV=29 mm$^3$, TGI=105.4%, p<0.001) produced dose-dependent antitumor activity. BCY6033 at 2 mg/kg and 3 mg/kg eradicated the tumors or regressed the tumor to small size, the treatments was suspended from day 35, and the tumors didn't show obvious re-growth in following 5-6 weeks monitoring.

BCY6136 at 1 mg/kg (TV=205 mm$^3$, TGI=97.5%, p<0.001), 2 mg/kg (TV=99 mm$^3$, TGI=102.3%, p<0.001) and 3 mg/kg (TV=94 mm$^3$, TGI=102.4%, p<0.001) produced potent antitumor activity. BCY6136 at 2 mg/kg and 3 mg/kg eradicated the tumors or regressed the tumor to small size. The treatments was suspended from day 35, and the tumors in 3 mg/kg group didn't show obvious re-growth in following 5-6 weeks monitoring, however tumors in 2 mg/kg group showed obvious regrowth and didn't show significant tumor inhibition when resuming the dosing.

BCY6082 at 2 mg/kg (TV=1528 mm3, TGI=37.9%, p>0.05) didn't show obvious antitumor activity, BCY6082 at 5 mg/kg (TV=390 mm3, TGI=89.1%, p<0.001) produced significant antitumor activity.

In this study, one mouse treated with BCY60333 mg/kg lost over 15% bodyweight during the monitoring, other mice maintained the bodyweight well.

Study 10. In Vivo Efficacy Study of BCY6136 in the LU-01-0251 PDX Model in Balb/c Nude Mice (a) Study Objective The objective of the research is to evaluate the in vivo anti-tumor efficacy of BCY6136 in the LU-01-0251 PDX model in Balb/c nude mice.

(b) Experimental Design

| Group | Treatment | n | Dose (mg/kg) | Dosing Volume (µl/g) | Dosing Route | Schedule |
|---|---|---|---|---|---|---|
| 1 | Vehicle | 5 | — | 10 | iv | qw |
| 2 | BCY6136 | 5 | 1 | 10 | iv | qw |
| 3 | BCY6136 | 5 | 2 | 10 | iv | qw |
| 4 | BCY6136 | 5 | 3 | 10 | iv | qw |
| 5 | ADC | 5 | 3 | 10 | iv | qw |

(c) Experimental Methods and Procedures (i) Tumor Inoculation

Each mouse was inoculated subcutaneously at the right flank with LU-01-0251 of tumor fragment (~30 mm$^3$) for tumor development. The treatment was started when the average tumor volume reached 174 mm$^3$ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.3 | Dissolve 6.11 mg BCY6136 in 20 ml Acetate buffer[1] |
|  | 0.2 | Dilute 940 µl 0.3 mg/ml BCY6136 stock with 470 µl Acetate buffer |
|  | 0.1 | Dilute 470 µl 0.3 mg/ml BCY6136 stock with 940 µl Acetate buffer |
| ADC | 0.3 | Dilute 43 µl 10.47 mg/ml ADC stock with 1457 µl ADC buffer[2] |

[1]Acetate buffer: 50 mM Acetate 10% sucrose pH 5
[2]ADC buffer: 20 mM Histidine pH 5.5

(d) Results (i) Body Weight change and Tumor Growth Curve

Figure 14:
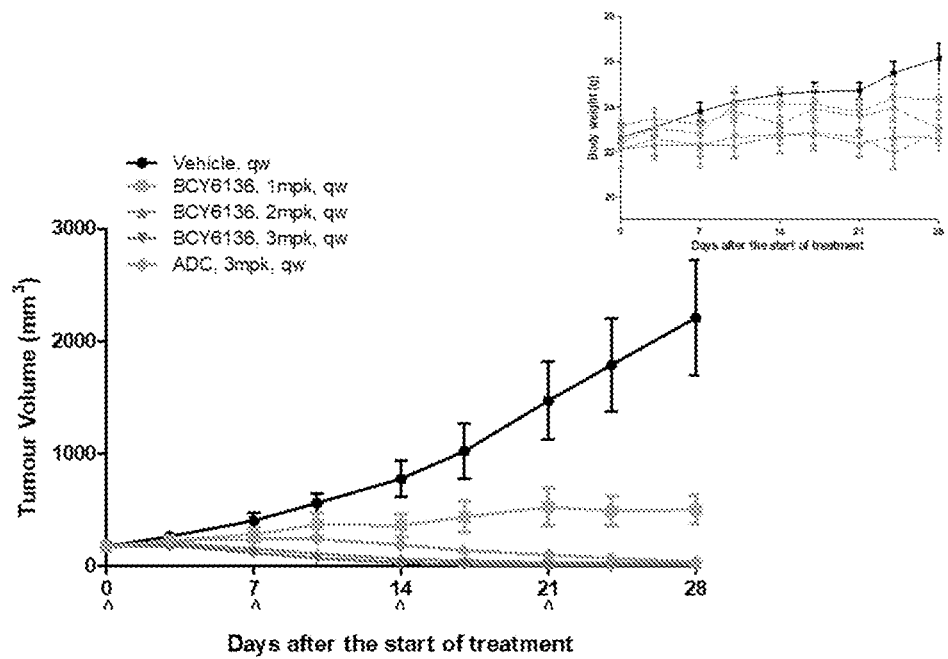
FIGS. 14 and 15: Body weight changes and tumor volume traces after administering BCY6136 and ADC to female Balb/c nude mice bearing LU-01-0251 xenograft. Data points represent group mean body weight.

Body weight and tumor growth curve are shown in FIG. 14.

(ii) Tumor Volume Trace

Mean tumor volume on day 28 after the start of treatment in female Balb/c nude mice bearing LU-01-0251 xenograft is shown in Table 31.

TABLE 31

Tumor volume trace over time

| Day | Group 1 Vehicle | Group 2 BCY6136, 1 mpk, qw | Group 3 BCY6136, 2 mpk, qw | Group 4 BCY6136, 3 mpk, qw | Group 5 ADC, 3 mpk, qw |
|---|---|---|---|---|---|
| 0 | 174 ± 17 | 175 ± 15 | 174 ± 17 | 175 ± 14 | 174 ± 16 |
| 3 | 264 ± 33 | 230 ± 29 | 205 ± 21 | 187 ± 19 | 227 ± 12 |
| 7 | 403 ± 68 | 281 ± 55 | 154 ± 21 | 118 ± 13 | 239 ± 42 |
| 10 | 562 ± 83 | 370 ± 104 | 111 ± 19 | 72 ± 12 | 241 ± 46 |
| 14 | 777 ± 163 | 362 ± 104 | 62 ± 17 | 30 ± 5 | 191 ± 47 |
| 17 | 1021 ± 246 | 437 ± 136 | 46 ± 13 | 17 ± 3 | 139 ± 39 |
| 21 | 1472 ± 342 | 526 ± 167 | 30 ± 18 | 4 ± 3 | 101 ± 31 |
| 24 | 1790 ± 417 | 491 ± 132 | 32 ± 24 | 1 ± 1 | 70 ± 23 |
| 28 | 2208 ± 512 | 499 ± 128 | 32 ± 30 | 0 ± 0 | 39 ± 14 |

(iii) Tumor Growth Inhibition Analysis

Tumor growth inhibition rate for BCY6136 and ADC in the LU-01-0251 PDX model was calculated based on tumor volume measurements at day 28 after the start of the treatment.

TABLE 32

Tumor growth inhibition analysis

| Group | Treatment | Tumor Volume (mm$^3$)$^a$ | T/C$^b$ (%) | TGI (%) | P value |
|---|---|---|---|---|---|
| 1 | Vehicle, qw | 2208 ± 512 | — | — | — |
| 2 | BCY6136, 1 mpk, qw | 499 ± 128 | 22.6 | 84.0 | p < 0.001 |
| 3 | BCY6136, 2 mpk, qw | 32 ± 30 | 1.4 | 107.0 | p < 0.001 |
| 4 | BCY6136, 3 mpk, qw | 0 ± 0 | 0.0 | 108.6 | p < 0.001 |
| 5 | ADC, 3 mpk, qw | 39 ± 14 | 1.8 | 106.6 | p < 0.001 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 and ADC in LU-01-0251 PDX model was evaluated. The measured body weight and tumor volume of all treatment groups at various time points are shown in the FIG. 14 and Tables 31 and 32.

In this study, the mean tumor volume of vehicle treated mice reached 2208 mm$^3$ on day 28 after the start of treatment. BCY6136 at 1 mg/kg, qw (TV=499 mm$^3$, TGI=84.0%, p<0.001), 2 mg/kg, qw (TV=32 mm$^3$, TGI=107.0%, p<0.001) and 3 mg/kg, qw (TV=0 mm$^3$, TGI=108.6%, p<0.001) produced dose-dependent anti-tumor activity. ADC at 3 mg/kg, qw (TV=39 mm$^3$, TGI=106.6%, p<0.001) showed significant anti-tumor activity.

Study 11: In Vivo Efficacy Study of BCY6136 in the LU-01-0251 PDX Model in Balb/c Nude Mice (a) Study Objective The objective of the research is to evaluate the in vivo anti-tumor efficacy of BCY6136 in the LU-01-0251 PDX model in Balb/c nude mice.

(b) Experimental Design

| Group | Treatment | Dose n | Dose (mg/kg) | Dosing Volume (μl/g) | Dosing Route | Schedule |
|---|---|---|---|---|---|---|
| 1 | Vehicle | 5 | — | 10 | iv | Qw*21 |
| 2 | BCY6136 | 5 | 1 | 10 | iv | Qw*28 |
| 3[a] | BCY6136 | 5 | 2 | 10 | iv | Qw*70 |
| 4[b] | BCY6136 | 5 | 3 | 10 | iv | Qw*56 |
| 5[c] | ADC | 5 | 3 | 10 | iv | Qw*70 | a. The dosing schedule was kept from day 0 to day 70 for all the mice of this group, then the mouse 3-2 and mouse 3-4 were further dosed with BCY6136 3 mg/kg qw from day 77 while the treatment of the other 3 mice was suspended. The dosing schedule was kept from day 0 to day 56 for all the mice of this group.
b. The dosing schedule was kept from day 0 to day 70 for all the mice of this group.

(c) Experimental Methods and Procedures
(i) Tumor Inoculation

Each mouse was inoculated subcutaneously at the right flank with LU-01-0251 of tumor fragment (~30 mm$^3$) for tumor development. The treatment was started when the average tumor volume reached 960 mm$^3$ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 25 mM Histidine 10% sucrose pH 7 |
| BCY6136 | 0.3 | 0.3 mg/ml BCY6136 was prepared as in Study 10 hereinbefore |
|  | 0.2 | Dilute 940 μl 0.3 mg/ml BCY6136 stock with 470 μl His-buffer[1] |
|  | 0.1 | Dilute 470 μl 0.3 mg/ml BCY6136 stock with 940 μl His-buffer |
| ADC | 0.3 | Dilute 43 μl 10.47 mg/ml ADC stock with 1457 μl ADC-buffer[2] |

[1]His-buffer: 25 mM Histidine 10% sucrose pH 7
[2]ADC-buffer: 20 mM Histidine pH 5.5

(iii) Sample Collection

Tumor of mouse #3-2 was collected for FFPE on Day 94. Tumors of mice #5-2 and 5-3 were collected and embed into 1 FFPE block on Day 140.

(d) Results
(i) Body Weight change and Tumor Growth Curve

Figure 15:
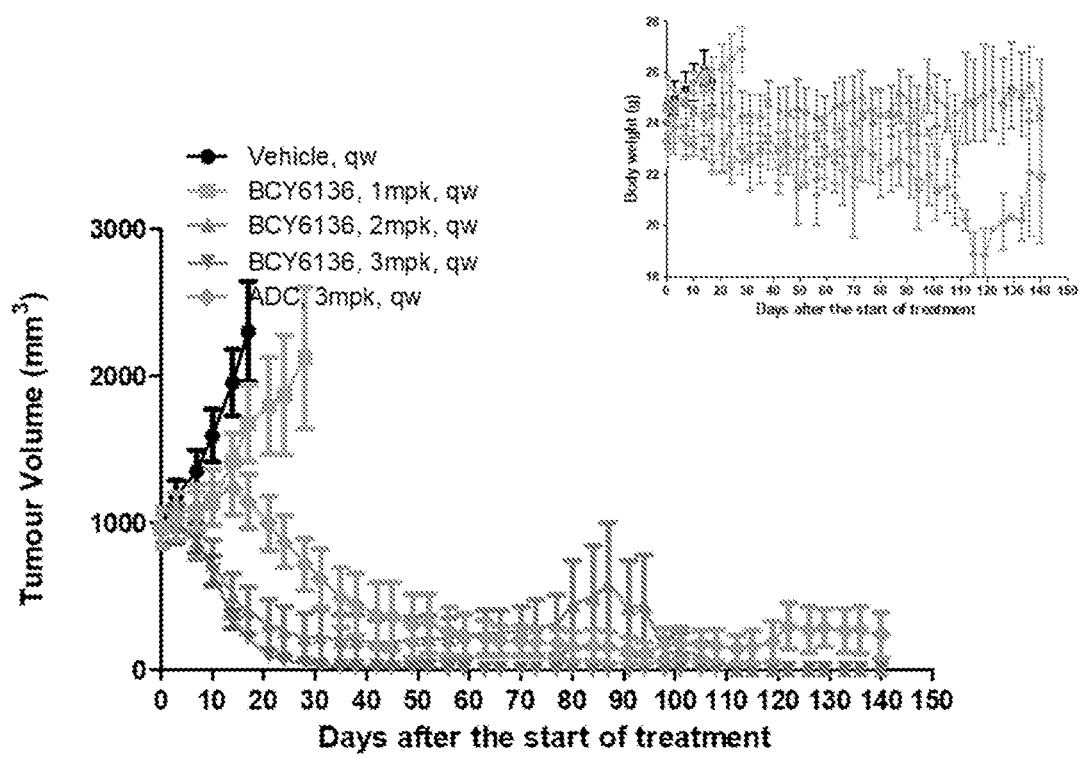

Body weight and tumor growth curve are shown in FIG. 15.

(ii) Tumor Volume Trace

Mean tumor volume on day 0 to day 28 after the start of treatment in female Balb/c nude mice bearing LU-01-0251 xenograft is shown in Table 33.

TABLE 33

Tumor volume trace over time

| Day | Group 1 Vehicle | Group 2 BCY6136, 1 mpk, qw | Group 3 BCY6136, 2 mpk, qw | Group 4 BCY6136, 3 mpk, qw | Group 5 ADC, 3 mpk, qw |
|---|---|---|---|---|---|
| 0 | 962 ± 102 | 963 ± 97 | 962 ± 137 | 960 ± 103 | 959 ± 124 |
| 3 | 1176 ± 108 | 1003 ± 121 | 973 ± 105 | 989 ± 128 | 1043 ± 158 |
| 7 | 1351 ± 142 | 1056 ± 151 | 873 ± 125 | 890 ± 98 | 1100 ± 156 |
| 10 | 1591 ± 179 | 1122 ± 139 | 722 ± 157 | 674 ± 96 | 1172 ± 188 |
| 14 | 1951 ± 225 | 1417 ± 191 | 503 ± 151 | 342 ± 64 | 1228 ± 174 |
| 17 | 2301 ± 344 | 1672 ± 262 | 398 ± 160 | 216 ± 43 | 1143 ± 186 |
| 21 |  | 1794 ± 328 | 307 ± 169 | 94 ± 26 | 996 ± 187 |
| 24 |  | 1867 ± 408 | 261 ± 168 | 62 ± 14 | 867 ± 178 |
| 28 |  | 2120 ± 483 | 217 ± 167 | 45 ± 16 | 713 ± 178 |

(iii) Tumor Growth Inhibition Analysis

Tumor growth inhibition rate for BCY6136 and ADC in the LU-01-0251 PDX model was calculated based on tumor volume measurements at day 17 after the start of the treatment.

TABLE 34

Tumor growth inhibition analysis

| Group | Treatment | Tumor Volume (mm$^3$)[a] | T/C[b] (%) | TGI (%) | P value |
|---|---|---|---|---|---|
| 1 | Vehicle, qw | 2301 ± 344 | — | — | — |
| 2 | BCY6136, 1 mpk, qw | 1672 ± 262 | 72.7 | 47.0 | p > 0.05 |
| 3 | BCY6136, 2 mpk, qw | 398 ± 160 | 17.3 | 142.1 | p < 0.001 |
| 4 | BCY6136, 3 mpk, qw | 216 ± 43 | 9.4 | 155.6 | p < 0.001 |
| 5 | ADC, 3 mpk, qw | 1143 ± 186 | 49.7 | 86.3 | p < 0.01 |

[a]Mean ± SEM;
[b]Tumor Growth Inhibition is calculated by dividing the group average tumor volume for the treated group by the group average tumor volume for the control group (T/C).

(e) Results Summary and Discussion

In this study, the therapeutic efficacy of BCY6136 and ADC in LU-01-0251 PDX model was evaluated. The measured body weight and tumor volume of all treatment groups at various time points are shown in the FIG. 15 and Tables 33 and 34.

In this study, the treatment was started when the average tumor volume reached 960 mm$^3$.

On day 17 after the start of treatment, the mean tumor volume of vehicle treated mice reached 2301 mm$^3$. BCY6136 at 1 mg/kg qw (TV=1672 mm$^3$, TGI=47.0%, p>0.05) didn't show obvious antitumor activity; BCY6136 at 2 mg/kg qw (TV=398 mm$^3$, TGI=142.1%, p<0.001) and 3 mg/kg qw (TV=216 mm$^3$, TGI=155.6%, p<0.001) produced dose-dependent anti-tumor activity on day 17.

After 70 days' treatment with BCY6136 at 2 mg/kg qw, 3 in 5 of these mice showed complete tumor regression, the other 2 mice showed obvious tumor relapse from day 42 to day 77. Then further treatment with BCY6136 3 mg/kg qw was performed to the two relapse tumors from day 7, one of tumor showed obvious tumor regress while another one showed resistance to the treatment.

After 56 days' treatment with BCY6136 at 3 mg/kg qw, all the mice of this group showed complete tumor regression.

ADC at 3 mg/kg qw (TV=1143 mm$^3$, TGI=86.3%, p<0.01) showed obvious anti-tumor activity on day 17, after another 53 day' treatment, these mice showed further but not complete tumor regression.

In this study, there were some mice showed sudden bodyweight loss, this may have the relationship with the long term feeding of the immune-deficiency mice.

Study 12: In Vivo Efficacy Study of BCY6033, BCY6136, BCY6082 and BCY6031 in the LU-01-0046 NSCLC PDX Model in Balb/c Nude Mice (a) Study Objective The objective of the research is to evaluate the in vivo anti-tumor efficacy of BCY6033, BCY6136, BCY6082 and BCY6031 in large LU-01-0046 PDX tumors in Balb/c nude mice.

(b) Experimental Design

| Group | Treatment | n | Dose (mg/kg) | Dosing Volume (μl/g) | Dosing Route | Schedule |
|---|---|---|---|---|---|---|
| BCYs | | | | | | |
| 1 | Vehicle | 5 | — | 10 | iv | qw |
| 2 | BCY6082 | 5 | 1 | 10 | iv | qw |
| 3 | BCY6082 | 5 | 3 | 10 | iv | qw |
| 4 | BCY6033 | 5 | 1 | 10 | iv | qw |
| 5 | BCY6033 | 5 | 3 | 10 | iv | qw |
| 6 | BCY6136 | 5 | 1 | 10 | iv | qw |
| 7 | BCY6136 | 5 | 3 | 10 | iv | qw |
| 8 | ADC | 5 | 3 | 10 | iv | qw |
| 9 | BCY6031 | 5 | 3 | 10 | iv | qw |

(c) Experimental Methods and Procedures (i) Tumor Inoculation

Each mouse was inoculated subcutaneously at the right flank with LU-01-0046 of tumor fragment (~30 mm$^3$) for tumor development. The treatment was started when the average tumor volume reaches 955 mm$^3$ for BT17BDCs study and 1039 mm$^3$ for BCYs study. The test article administration and the animal numbers in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6033 | 0.1 | Dilute 150 μl 1 mg/ml BCY6033 stock with 1350 μl Acetate buffer[1] |
|  | 0.3 | Dilute 450 μl 1 mg/ml BCY6033 stock with 1050 μl Acetate buffer |
| BCY6136 | 0.1 | Dilute 150 μl 1 mg/ml BCY6136 stock with 1350 μl Acetate buffer |
|  | 0.3 | Dilute 450 μl 1 mg/ml BCY6136 stock with 1050 μl Acetate buffer |
| BCY6082 | 0.1 | Dilute 150 μl 1 mg/ml BCY6082 stock with 1350 μl Acetate buffer |
|  | 0.3 | Dilute 450 μl 1 mg/ml BCY6082 stock with 1050 μl Acetate buffer |
| BCY6031 | 0.3 | Dissolve 5.72 mg BCY6031 in 5.6 ml Acetate buffer to make 1 mg/ml stock. Dilute 450 μl 1 mg/ml BCY6031 with 1050 μl Acetate buffer |
| ADC | 0.3 | Dilute 43 μl 10.47 mg/ml ADC stock solution into 1457 μl with buffer[2] |

[1]Acetate buffer: 50 mM Acetate 10% sucrose pH 5
[2]Dissolve 0.419 g His. hydrochloride in 100 ml water, use 1M HCl adjust PH to 5.5

(d) Results (i) Body Weight change and Tumor Growth Curve

Figure 16:
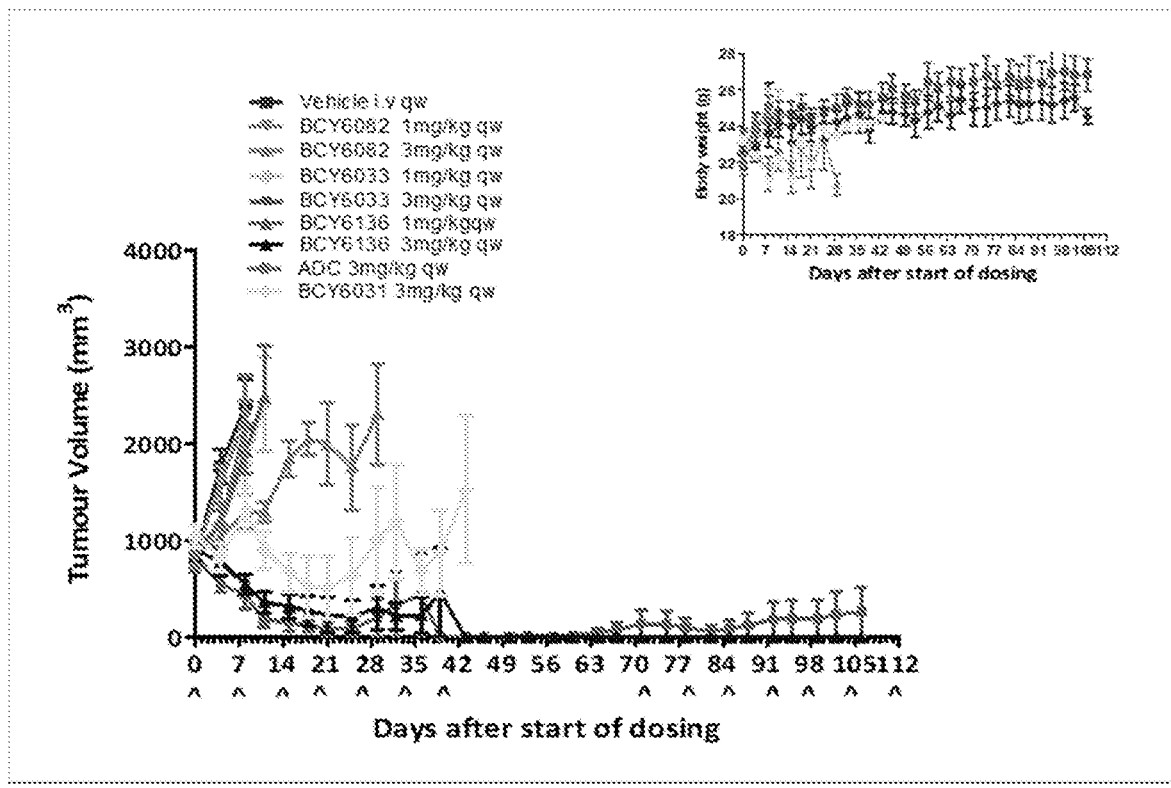
FIG. 16: Body weight changes and tumor volume traces after administering BCY6033, BCY6136, BCY6082 and BCY6031 to female Balb/c nude mice bearing LU-01-0046. Data points represent group mean body weight.

Body weight and tumor growth curve are shown in FIG. 16.

(ii) Tumor Volume Trace

Mean tumor volume over time in female Balb/c nude mice bearing LU-01-0046 is shown in Table 35.

TABLE 35

Tumor volume trace over time (BCYs Section)

| | | Days after the start of treatment | | | | | | |
|---|---|---|---|---|---|---|---|---|
| Group | Treatment | 0 | 4 | 8 | 11 | 15 | 18 | 22 |
| 1 | Vehicle, qw | 1044 ± 115 | 1762 ± 178 | 2404 ± 262 | — | — | — | — |
| 2 | BCY6082, 1 mpk, qw | 1049 ± 133 | 1592 ± 178 | 2279 ± 168 | — | — | — | — |
| 3 | BCY6082, 3 mpk, qw | 1033 ± 111 | 1040 ± 124 | 1294 ± 182 | 1298 ± 101 | 1849 ± 189 | 2052 ± 168 | 1999 ± 425 |
| 4 | BCY6033, 1 mpk, qw | 1030 ± 124 | 1173 ± 227 | 1791 ± 324 | 2408 ± 484 | — | — | — |
| 5 | BCY6033, 3 mpk, qw | 1046 ± 128 | 555 ± 85 | 441 ± 144 | 182 ± 76 | 163 ± 94 | 114 ± 54 | 88 ± 76 |
| 6 | BCY6136, 1 mpk, qw | 1037 ± 130 | 1163 ± 146 | 1927 ± 283 | 2483 ± 530 | — | — | — |
| 7 | BCY6136, 3 mpk, qw | 1036 ± 100 | 784 ± 146 | 548 ± 107 | 362 ± 110 | 325 ± 122 | 275 ± 152 | 233 ± 187 |
| 8 | ADC, 3 mpk, qw | 1033 ± 114 | 1155 ± 230 | 2200 ± 505 | — | — | — | — |
| 9 | BCY6031, 3 mpk, qw | 1042 ± 117 | 820 ± 149 | 1319 ± 233 | 901 ± 188 | 672 ± 198 | 522 ± 315 | 515 ± 323 |

Note:
the tumor volume trace didn't show after the day22 for the group3, 5, 7 and 9.

(iii) Tumor Growth Inhibition Analysis

Tumor growth inhibition rate for test articles in the LU-01-0046 PDX model was calculated based on tumor volume measurements at day 22 and day 28 respectively for the two section studies after the start of the treatment.

TABLE 36

Tumor growth inhibition analysis (BCYs section on day 22)

| Group | Treatment | Tumor Volume | T/C[b] (%) | TGI (%) | P value |
|---|---|---|---|---|---|
| 1 | Vehicle, qw | 6186 ± 596* | — | — | — |
| 2 | BCY6082, 1 mpk, qw | 5805 ± 428* | 93.8 | 7.5 | p > 0.05 |
| 3 | BCY6082, 3 mpk, qw | 1999 ± 425 | 32.3 | 81.2 | p < 0.01 |
| 4 | BCY6033, 1 mpk, qw | 4384 ± 881* | 70.9 | 34.8 | p > 0.05 |
| 5 | BCY6033, 3 mpk, qw | 88 ± 76 | 1.4 | 118.6 | P < 0.001 |
| 6 | BCY6136, 1 mpk, qw | 4564 ± 981* | 73.8 | 31.4 | p > 0.05 |
| 7 | BCY6136, 3 mpk, qw | 233 ± 187 | 3.8 | 115.6 | p < 0.001 |
| 8 | ADC, 3 mpk, qw | 5446 ± 1250* | 88.0 | 14.2 | p > 0.05 |
| 9 | BCY6031, 3 mpk, qw | 515 ± 323 | 8.3 | 110.2 | p < 0.001 |

[a]Mean ± SEM;
[b]Tumor Growth Inhibition is calculated by dividing the average tumor volume of the treated group by the average tumor volume of the control group (T/C).
*Some groups was terminated before day 22, and the tumor size was calculated by exponential growth equation acquisition as below:
Vehicle group: Y = 995.4 × exp (0.1134 × X).
BCY6082, 1 mpk group: Y = 939.1 × exp (0.1128 × X).
BCY6033, 1 mpk group: Y = 846.6 × exp (0.0945 × X).
BCY6136, 1 mpk group: Y = 855.0 × exp (0.0974 × X).
ADC, 3 mpk group: Y = 757.4 × exp (0.1312 × X).

(e) Results Summary and Discussion

In this study, the therapeutic efficacy of test articles in large LU-01-0046 tumors was evaluated. The measured body weights and tumor volumes of all treatment groups at various time points are shown in the FIG. 16 and Tables 35 and 36.

In BCYs study, the mean tumor size of vehicle treated mice was calculated as 6186 mm$^3$ on day 22. BCY6082, BCY6033, BCY6136 at 1 mg/kg and ADC at 3 mg/kg didn't show obvious anti-tumor activity when starting treatment from tumor size of 1000 mm$^3$.

BCY6082 (TV=1999 mm$^3$, TGI=81.2%, p<0.01), BCY6033 (TV=88 mm$^3$, TGI=118.6%, p<0.001), BCY6136 (TV=233 mm$^3$, TGI=115.6%, p<0.001) and BCY6031 (TV=115 mm$^3$, TGI=110.2%, p<0.001) at 3 mg/kg produced significant anti-tumor antitumor activity. Among them, BCY6033 and BCY6136 eradicated 2/5 and 4/5 tumors completely.

Study 13: In Vivo Efficacy of BCY6136 in Balb/c Nude Mice Bearing LU-01-0046 NSCLC PDX Model (a) Study Objective The objective of the research was to evaluate the in vivo therapeutic efficacy of BCY6136 in Balb/c nude mice bearing LU-01-0046 NSCLC PDX model.

(b) Experimental Design

| Group | Treatment | n | Dose (mg/kg) | Dosing Route | Schedule |
|---|---|---|---|---|---|
| 1 | Vehicle | 5 | — | i.v. | qw * 2 w |
| 2 | BCY6136 | 5 | 1 | i.v. | qw * 3 w |
| 3 | BCY6136 | 5 | 2 | i.v. | qw * 4 w |
| 4 | BCY6136 | 5 | 3 | i.v. | qw * 4 w |
| 5 | ADC | 5 | 3 | i.v. | qw * 3 w |
| 6 | ADC | 5 | 5 | i.v. | qw * 3 w |

Note:
Groups were terminated when average tumor volume reached over 2000 mm$^3$ and tumors were harvested for FFPE: Group 1 on PG-D14, group 5 on PG-D18, group 2 & 6 on PG-D21 and group 3 & 4 on PG-D31.

(c) Experimental Methods and Procedures (i) Tumor Inoculation

Each mouse was inoculated subcutaneously at the right flank with certain kind of tumor fragment (~30 mm$^3$) for tumor development. The treatments were started when the average tumor volume reached approximately 198 mm$^3$. The test article administration and the animal numbers in each group are shown in the experimental design table.

(ii) Testing Article Formulation Preparation

| Gr | Compounds | Dose (mg/kg) | Con. (mg/ml) | Formulation |
|---|---|---|---|---|
| 1 | Vehicle | — | — | 50 mM Acetate, 10% Sucrose pH 5 (without DMSO) |
| 2 | BCY6136 | 1 | 0.1 | Dissolve 10.93 mg BCY6136 in 10.766 ml vehicle, ultrasonic simply to make the 1 mg/ml BCY6136 stock solution Dilute 150 μl 1 mg/ml BCY6136 stock solution with 1350 μl vehicle |
| 3 | BCY6136 | 2 | 0.2 | Dilute 300 μl 1 mg/ml BCY6136 stock solution with 1200 μl vehicle |
| 4 | BCY6136 | 3 | 0.3 | Dilute 450 μl 1 mg/ml BCY6136 stock solution with 1050 μl vehicle |
|  | Buffer 2: Dissolve 0.419 g His. hydrochloride in 100 ml water, use 1M HCl adjust pH to 5.5 | | | |
| 5 | ADC | 3 | 0.3 | Dilute 43 μl 10.47 mg/ml ADC stock solution with 1457 μl with buffer 2 |
| 6 | ADC | 5 | 0.5 | Dilute 71.6 μl 10.47 mg/ml ADC stock solution with 1428.4 μl with buffer 2 |

Note
The dosing formulation frequently is fresh prepared timely.

(iii) Sample Collection

Groups were terminated when average tumor volume reached over 2000 mm$^3$ and tumors were harvested for FFPE after the last measurement: Group 1 on PG-D14, group 5 on PG-D18, group 2 & 6 on PG-D21 and group 3 & 4 on PG-D31.

(d) Results (i) Body Weight change and Tumor Growth Curve

Figure 17:
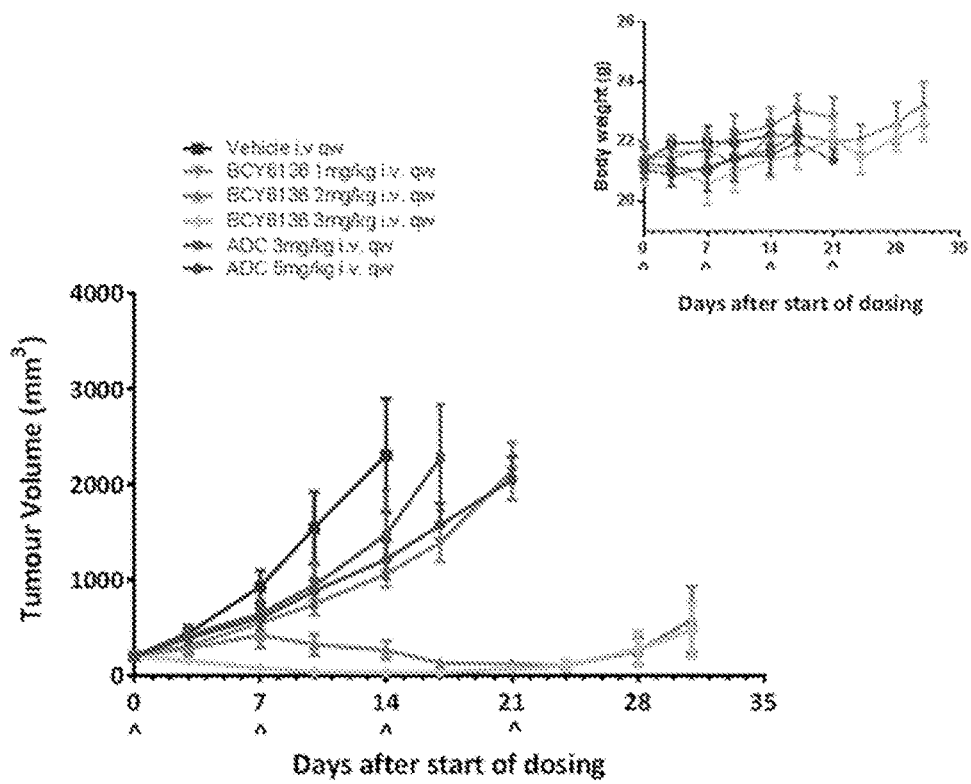
FIG. 17: Body weight changes and tumor volume traces after administering BCY6136 or ADC to female Balb/c nude mice bearing LU-01-0046 NSCLC PDX model. Data points represent group mean body weight.
Figure 18:
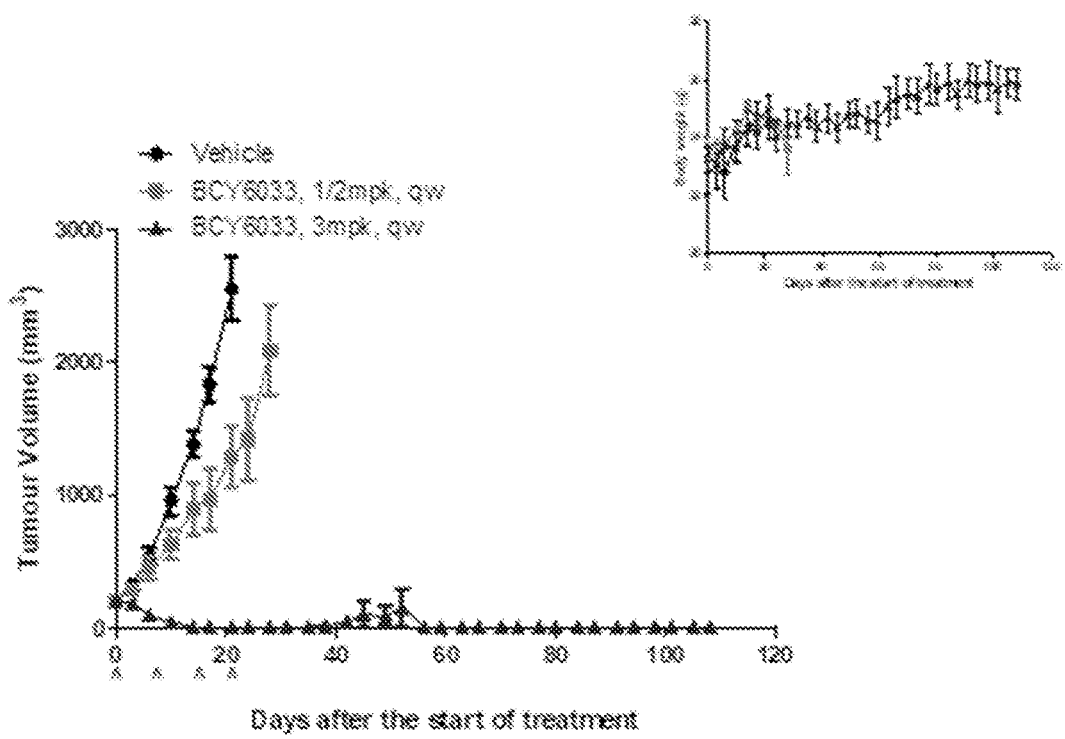
FIGS. 18 to 22: Body weight changes and tumor volume traces after administering BCY6033 (FIG. 18), BCY6136 (FIG. 19), BCY6082 (FIG. 20), BCY6173 (FIG. 21) and BCYs 6175 and 6031 (FIG. 22) to female Balb/c nude mice bearing LU-01-0046. Data points represent group mean body weight.
Figure 19:
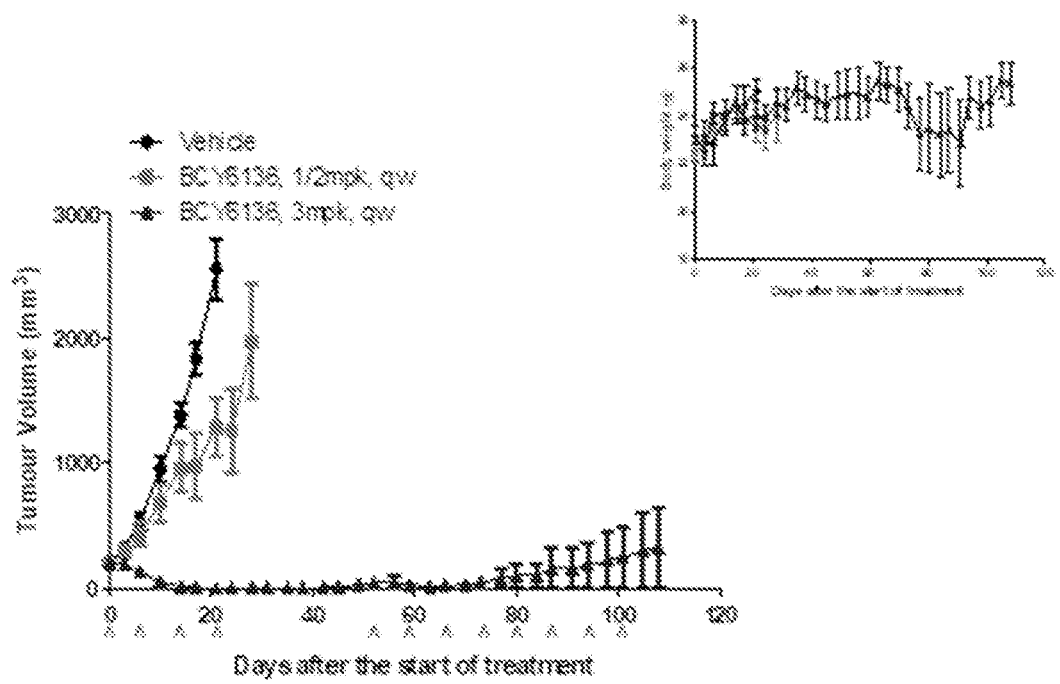
Figure 20:
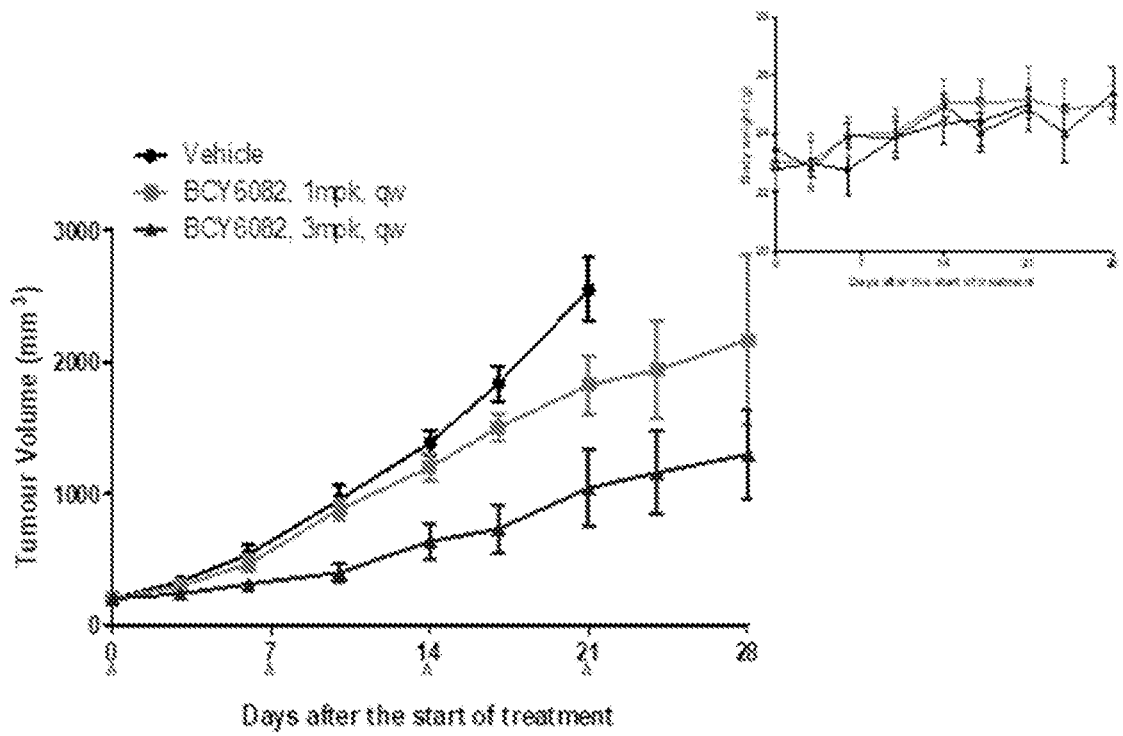
Figure 21:
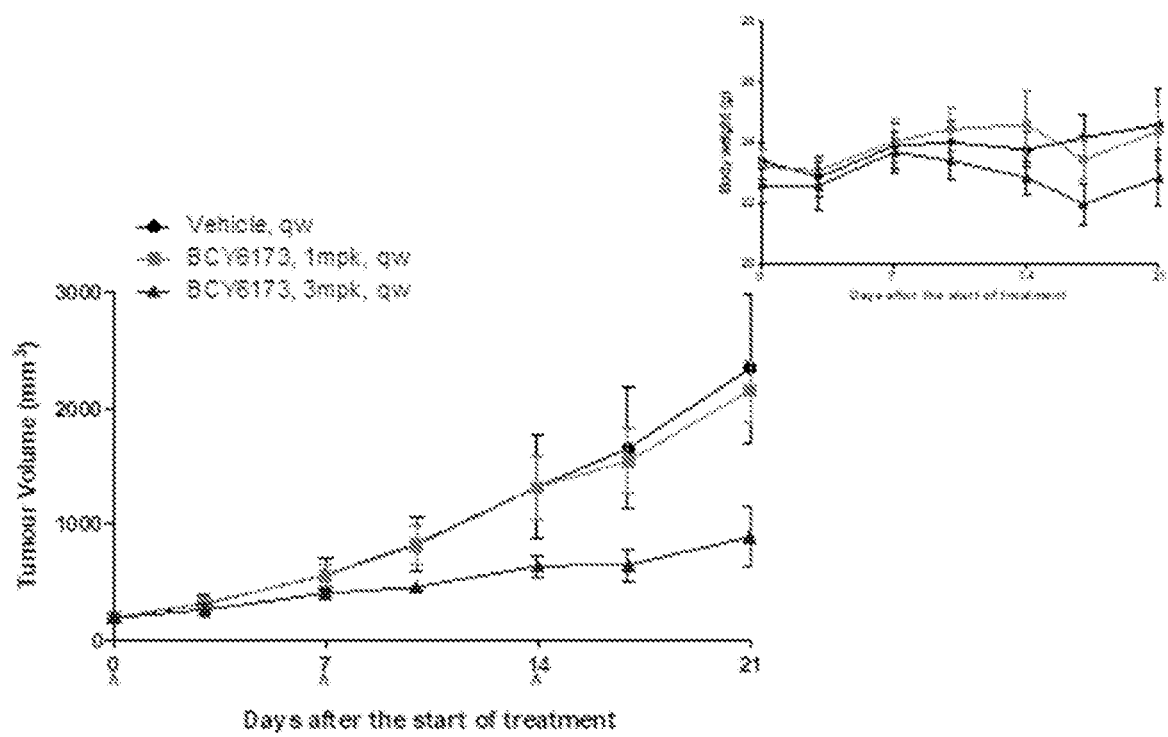
Figure 22:
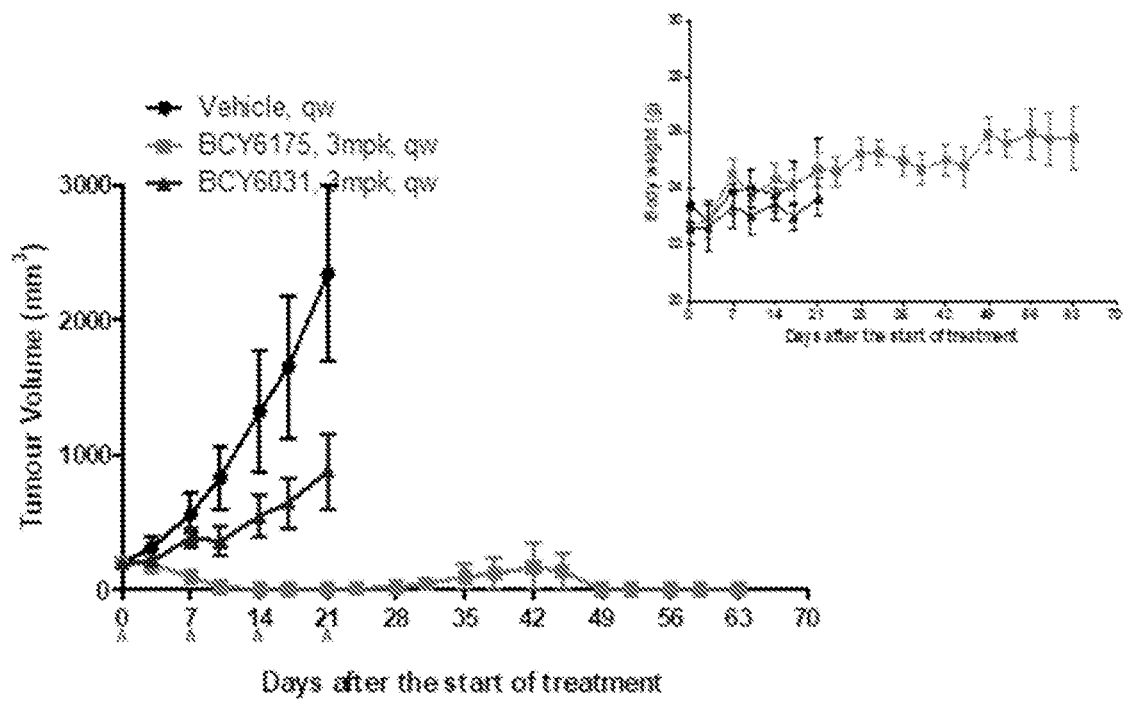

Body weight and tumor growth curve are shown in FIG. 17.

(ii) Tumor Volume Trace

Mean tumor volume over time in female Balb/c nude mice bearing LU-01-0046 NSCLC PDX model is shown in Table 37.

TABLE 37

| | 1 | 2 | 3 | 4 | 5 | 6 |
|---|---|---|---|---|---|---|
| Gr Treatment | Vehicle qw | BCY6136 1 mpk, qw | BCY6136 2 mpk, qw | BCY6136 3 mpk, qw | ADC 3 mpk, qw | ADC 5 mpk, qw |
| 0 | 201 ± 37 | 198 ± 39 | 201 ± 40 | 200 ± 46 | 195 ± 28 | 195 ± 40 |
| 3 | 441 ± 82 | 310 ± 59 | 283 ± 77 | 155 ± 40 | 418 ± 99 | 389 ± 68 |
| 7 | 927 ± 171 | 547 ± 88 | 423 ± 132 | 74 ± 19 | 643 ± 159 | 596 ± 116 |
| 10 | 1546 ± 377 | 747 ± 121 | 321 ± 108 | 31 ± 8 | 938 ± 230 | 882 ± 134 |
| 14 | 2307 ± 594 | 1058 ± 140 | 264 ± 95 | 26 ± 11 | 1475 ± 466 | 1215 ± 193 |
| 17 | — | 1390 ± 205 | 127 ± 41 | 26 ± 13 | 2281 ± 556 | 1576 ± 228 |
| 21 | — | 2138 ± 301 | 118 ± 34 | 64 ± 42 | — | 2049 ± 242 |
| 24 | — | — | 101 ± 40 | 99 ± 63 | — | — |
| 28 | — | — | 255 ± 140 | 276 ± 176 | — | — |
| 31 | — | — | 582 ± 346 | 477 ± 283 | — | — |

Tumor volume trace over time (mm$^3$)

(iii) Tumor Growth Inhibition Analysis

Tumor growth inhibition rate for test articles in Balb/c nude mice bearing LU-01-0046 PDX model was calculated based on tumor volume measured on PG-D14.

TABLE 38

Tumor growth inhibition analysis

| Gr | Treatment | Tumor Volume (mm$^3$)[a] | T/C (%)[b] | TGI (%)[c] | P value compared with vehicle |
|---|---|---|---|---|---|
| 1 | Vehicle qw | 2307 ± 594 | — | — | — |
| 2 | BCY6136 1 mpk, qw | 1058 ± 140 | 45.9 | 59.1 | p < 0.05 |
| 3 | BCY6136 2 mpk, qw | 264 ± 95 | 11.4 | 97.0 | p < 0.001 |
| 4 | BCY6136 3 mpk, qw | 26 ± 11 | 1.1 | 108.3 | p < 0.001 |
| 5 | ADC 3 mpk, qw | 1475 ± 466 | 63.9 | 39.2 | p > 0.05 |
| 6 | ADC 5 mpk, qw | 1215 ± 193 | 52.7 | 51.6 | p > 0.05 |

[a] Mean ± SEM.
[b] Tumor Growth Inhibition was calculated by dividing the group average tumor volume for the treated group by the group average tumor volume for the control group (T/C).
[c] TGI was calculated for each group using the formula: TGI (%) = [1 − (T$_i$ − T$_0$)/(V$_i$ − V$_0$)] × 100

(e) Results Summary and Discussion

In the present study, the therapeutic efficacy of test articles in the LU-01-0046 PDX model was evaluated. The measured body weights and tumor volumes of all treatment groups at various time points were shown in the FIG. 17 and Tables 37 and 38.

The mean tumor size of vehicle treated mice reached 2307 mm$^3$ on PG-D14. BCY6136 at 1 mg/kg (TV=1058 mm$^3$, TGI=59.1%, p<0.05), at 2 mg/kg (TV=264 mm$^3$, TGI=97.0%, p<0.001) and at 3 mg/kg (TV=26 mm$^3$, TGI=108.3%, p<0.001) produced dose-dependent antitumor activity. ADC at 3 mg/kg and 5 mg/kg did not show obvious antitumor activity (p>0.05).

In this study, all of the group's animals maintained the body weight well.

Study 14: In Vivo Efficacy Study of BCY6033, BCY6136, BCY6082, BCY6173, BCY6175 and BCY6031 in the LU-01-0046 NSCLC PDX Model in Balb/c Nude Mice (a) Study Objective The objective of the research is to evaluate the in vivo anti-tumor efficacy of test articles in the LU-01-0046 NSCLC PDX model in Balb/c nude mice.

(b) Experimental Design

| Group | Treatment | n | Dose (mg/kg) | Dosing Volume (μl/g) | Dosing Route | Schedule |
|---|---|---|---|---|---|---|
| Part 1 | | | | | | |
| 1 | Vehicle | 5 | — | 10 | iv | qw |
| 2 | BCY6033 | 5 | ½ | 10 | iv | qw |
| 3 | BCY6033 | 5 | 3 | 10 | iv | qw |
| 4 | BCY6136 | 5 | ½ | 10 | iv | qw |
| 5 | BCY6136 | 5 | 3 | 10 | iv | qw |
| 6 | BCY6082 | 5 | 1 | 10 | iv | qw |
| 7 | BCY6082 | 5 | 3 | 10 | iv | qw |
| Part 2 | | | | | | |
| 8 | Vehicle | 5 | — | 10 | iv | qw |
| 9 | BCY6173 | 5 | 1 | 10 | iv | qw |
| 10 | BCY6173 | 5 | 3 | 10 | iv | qw |
| 11 | BCY6175 | 5 | 3 | 10 | iv | qw |
| 12 | BCY6031 | 5 | 3 | 10 | iv | qw |

(c) Experimental Methods and Procedures (i) Tumor Inoculation

Each mouse was inoculated subcutaneously at the right flank with LU-01-0046 of tumor fragment (~30 mm$^3$) for tumor development. The treatment was started when the average tumor volume reaches 200 mm$^3$ for part 1 study and 192 mm$^3$ for part 2 study. The test article administration and the animal numbers in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6033 | 0.1 | Dilute 150 μl 1 mg/ml BCY6033 stock with 1350 μl Acetate buffer[1] |
| | 0.3 | Dilute 450 μl 1 mg/ml BCY6033 stock with 1050 μl Acetate buffer |
| BCY6136 | 0.1 | Dilute 150 μl 1 mg/ml BCY6136 stock with 1350 μl Acetate buffer |
| | 0.3 | Dilute 450 μl 1 mg/ml BCY6136 stock with 1050 μl Acetate buffer |
| BCY6082 | 0.1 | Dilute 150 μl 1 mg/ml BCY6082 stock with 1350 μl Acetate buffer |
| | 0.3 | Dilute 450 μl 1 mg/ml BCY6082 stock with 1050 μl Acetate buffer |

| Test article | Conc. (mg/ml) | Formulation |
|---|---|---|
| BCY6173 | 0.1 | Dissolve 3.65 mg BCY6173 in 3.5 ml Acetate buffer to make 1 mg/ml stock. Dilute 150 μl 1 mg/ml BCY6173 with 1350 μl Acetate buffer |
| | 0.3 | Dilute 450 μl 1 mg/ml BCY6173 stock with 1050 μl Acetate buffer |
| BCY6175 | 0.3 | Dissolve 3.02 mg BCY6175 in 2.9 ml Acetate buffer to make 1 mg/ml stock. Dilute 450 μl 1 mg/ml BCY6175 with 1050 μl Acetate buffer |
| BCY6031 | 0.3 | Dissolve 5.72 mg BCY6031 in 5.6 ml Acetate buffer to make 1 mg/ml stock. Dilute 450 μl 1 mg/ml BCY6031 with 1050 μl Acetate buffer |

[1]Acetate buffer: 50 mM Acetate 10% sucrose pH 5

(d) Results (i) Body Weight change and Tumor Growth Curve

Body weight and tumor growth curve are shown in FIGS. 18 to 22.

(ii) Tumor Volume Trace

Mean tumor volume on day 21 after the start of treatment in female Balb/c nude mice bearing LU-01-0046 is shown in Tables 39 and 40.

TABLE 39

Tumor volume trace over time (Part 1)

| Gr | Treatment | Days after the start of treatment | | | | | | |
|---|---|---|---|---|---|---|---|---|
| | | 0 | 3 | 6 | 10 | 14 | 17 | 21 |
| 1 | Vehicle, qw | 202 ± 26 | 328 ± 48 | 536 ± 68 | 953 ± 107 | 1386 ± 97 | 1833 ± 132 | 2551 ± 242 |
| 2 | BCY6033, 1 mpk, qw | 201 ± 23 | 285 ± 47 | 449 ± 87 | 623 ± 112 | 891 ± 196 | 967 ± 228 | 1285 ± 234 |
| 3 | BCY6033, 3 mpk, qw | 201 ± 26 | 187 ± 43 | 91 ± 34 | 37 ± 14 | 3 ± 3 | 0 ± 0 | 0 ± 0 |
| 4 | BCY6136, 1 mpk, qw | 200 ± 33 | 293 ± 56 | 426 ± 91 | 682 ± 151 | 964 ± 194 | 976 ± 258 | 1285 ± 234 |
| 5 | BCY6136, 3 mpk, qw | 201 ± 33 | 194 ± 31 | 135 ± 27 | 52 ± 18 | 13 ± 9 | 4 ± 4 | 0 ± 0 |
| 6 | BCY6082, 1 mpk, qw | 201 ± 29 | 295 ± 43 | 466 ± 65 | 877 ± 80 | 1201 ± 106 | 1502 ± 108 | 1826 ± 224 |
| 7 | BCY6082, 3 mpk, qw | 201 ± 34 | 235 ± 36 | 310 ± 44 | 398 ± 65 | 634 ± 136 | 729 ± 184 | 1042 ± 290 |

TABLE 40

Tumor volume trace over time (Part 2)

| Gr | Treatment | Days after the start of treatment | | | | | | |
|---|---|---|---|---|---|---|---|---|
| | | 0 | 3 | 7 | 10 | 14 | 17 | 21 |
| 8 | Vehicle, qw | 192 ± 30 | 311 ± 83 | 562 ± 146 | 830 ± 230 | 1320 ± 444 | 1652 ± 528 | 2342 ± 651 |
| 9 | BCY6173, 1 mpk, qw | 191 ± 33 | 318 ± 58 | 553 ± 88 | 817 ± 165 | 1314 ± 276 | 1546 ± 276 | 2151 ± 262 |
| 10 | BCY6173, 3 mpk, qw | 192 ± 37 | 259 ± 51 | 400 ± 53 | 455 ± 28 | 636 ± 92 | 646 ± 138 | 890 ± 260 |
| 11 | BCY6175, 3 mpk, qw | 192 ± 42 | 186 ± 57 | 92 ± 38 | 19 ± 11 | 0 ± 0 | 0 ± 0 | 0 ± 0 |
| 12 | BCY6031, 3 mpk, qw | 191 ± 38 | 207 ± 46 | 387 ± 70 | 355 ± 110 | 544 ± 159 | 643 ± 185 | 874 ± 281 |

(iii) Tumor Growth Inhibition Analysis

Tumor growth inhibition rate for test articles in the LU-01-0046 PDX model was calculated based on tumor volume measurements at day 21 after the start of the treatment.

TABLE 41

Tumor growth inhibition analysis (Part 1)

| Group | Treatment | Tumor Volume$^a$ | T/C$^b$ (%) | TGI (%) | P value |
|---|---|---|---|---|---|
| 1 | Vehicle, qw | 2551 ± 242 | — | — | — |
| 2 | BCY6033, 1 mpk, qw | 1285 ± 234 | 50.4 | 53.9 | p < 0.001 |
| 3 | BCY6033, 3 mpk, qw | 0 ± 0 | 0.0 | 108.6 | p < 0.001 |
| 4 | BCY6136, 1 mpk, qw | 1285 ± 234 | 50.4 | 53.9 | p < 0.001 |
| 5 | BCY6136, 3 mpk, qw | 0 ± 0 | 0.0 | 108.5 | p < 0.001 |
| 6 | BCY6082, 1 mpk, qw | 1826 ± 224 | 71.6 | 30.8 | p < 0.05 |
| 7 | BCY6082, 3 mpk, qw | 1042 ± 290 | 40.8 | 64.2 | p < 0.001 |

$^a$Mean ± SEM;
$^b$Tumor Growth Inhibition is calculated by dividing the group average tumor volume for the treated group by the group average tumor volume for the control group (T/C).

TABLE 42

Tumor growth inhibition analysis (Part 2)

| Group | Treatment | Tumor Volume$^a$ | T/C$^b$ (%) | TGI (%) | P value |
|---|---|---|---|---|---|
| 8 | Vehicle, qw | 2342 ± 651 | — | — | — |
| 9 | BCY6173, 1 mpk, qw | 2151 ± 262 | 91.8 | 8.9 | p > 0.05 |
| 10 | BCY6173, 3 mpk, qw | 890 ± 260 | 38.0 | 67.5 | p < 0.05 |
| 11 | BCY6175, 3 mpk, qw | 0 ± 0 | 0.0 | 108.9 | p < 0.001 |
| 12 | BCY6031, 3 mpk, qw | 874 ± 281 | 37.3 | 68.2 | p < 0.05 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of test articles in the LU-01-0046 PDX model was evaluated. The measured body weights and tumor volumes of all treatment groups at various time points are shown in the FIGS. 18 to 22 and Tables 39 to 42.

In part 1 study, the mean tumor size of vehicle treated mice reached 2551 mm$^3$ on day 21 after the start of treatment.

BCY6033 at ½ mg/kg, qw (TV=1285 mm$^3$, TGI=53.9%, p<0.001) and BCY6136 at ½ mg/kg, qw (TV=1285 mm$^3$, TGI=53.9%, p<0.001) produced significant anti-tumor activity, but didn't exhibit any tumor regression. BCY6033 at 3 mg/kg, qw (TV=0 mm$^3$, TGI=108.6%, p<0.001) and BCY6136 at 3 mg/kg, qw (TV=0 mm$^3$, TGI=108.5%, p<0.001) completely eradicated the tumors, 1 of 5 tumors respectively in BCY6033 and BCY6136 3 mg/kg groups showed regrowth after the dosing suspension and the tumors were resistant to BCY6033 or BICY6136 treatment when resuming the dosing. The remaining tumors in the BCY6033 and BCY6136 groups (4/5 for each group) showed no regrowth after 80 days of dosing suspension. BCY6082 at 1 mg/kg, qw (TV=1826 mm$^3$, TGI=30.8%, p<0.05) and 3 mg/kg, qw (TV=1042 mm$^3$, TGI=64.2%, p<0.001) produced dose-dependent anti-tumor activity, but didn't show tumor regression.

In part 2 study, the mean tumor size of vehicle treated mice reached 2342 mm$^3$ on day 21 after the start of treatment. BCY6173 at 1 mg/kg, qw (TV=2151 mm$^3$, TGI=8.9%, p>0.05) did not show anti-tumor antitumor activity. BCY6173 at 3 mg/kg, qw (TV=890 mm$^3$, TGI=67.5%, p<0.05) produced obvious anti-tumor activity. BCY6175 at 3 mg/kg, qw (TV=0 mm$^3$, TGI=108.9%, p<0.001) completely eradicated 4/5 tumors on day 14. BCY6031 at 3 mg/kg, qw (TV=874 mm$^3$, TGI=68.2%, p<0.05) produced obvious anti-tumor activity, but didn't show any tumor regression.

Study 15: In Vivo Efficacy Study of BCY6136 in the LU-01-0412 NSCLC PDX Model in Balb/c Nude Mice (a) Study Objective The objective of the project is to evaluate the in vivo therapeutic efficacy of BCY6136 in the LU-01-0412 NSCLC PDX model in BALB/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 6 | — | 10 | iv | Qw, 4 |
| 2 | BCY6136 | 6 | 1 | 10 | iv | Qw, 4 |
| 3 | BCY6136 | 6 | 3 | 10 | iv | Qw, 4 |
| 4 | BCY8245 | 6 | 3 | 10 | iv | Qw, 4 |
| 5 | BCY8781 | 6 | 3 | 10 | iv | Qw, 4 |

(c) Experimental Methods and Procedures (i) Tumor Inoculation

Each mouse was inoculated subcutaneously at the right flank with LU-01-0412 tumor fragment (~30 mm$^3$) for tumor development. Animals were randomized when the average tumor volume reached 159 mm$^3$. The test article administration and the animal numbers in each group were shown in the experimental design table.

(ii) Testing Article Formulation Preparation

| Test article | Conc. (mg/ml) | Formulation |
|---|---|---|
| Vehicle | — | 25 mM Histidine 10% sucrose pH 7 |
| BCY6136 | 1 | Dissolve 6.06 mg BCY6136 in 5.969 ml 50 mM Acetate/ acetic acid pH 5 10% sucrose |
|  | 0.1 | Dilute 180 μl 1 mg/ml BT5528 with 1620 μl 50 mM Acetate/acetic acid pH 5 10% sucrose |
|  | 0.3 | Dilute 540 μl 1 mg/ml BT5528 with 1260 ul 50 mM Acetate/acetic acid pH 5 10% sucrose |
| BCY8245 | 1 | Dissolve 4.15 mg BCY8245 powder in 4.121 ml vehicle buffer |
|  | 0.3 | Dilute 540 μl 1 mg/ml BCY8245 with 1260 μl vehicle buffer |
| BCY8781 | 1 | Dissolve 4.08 mg BCY8781 powder in 80.8 μl DMSO, then dilute to 1 mg/ml with 3.958 vehicle buffer |
|  | 0.3 | Dilute 540 μl 1 mg/ml BCY8781 with 1260 μl vehicle buffer |

(iii) Sample Collection

Plasma from vehicle and 3 extra mice treated with BCY6136, BCY8245 and BCY8781 were collected at 30 min and 24 h post dosing. Tumor from vehicle and 3 extra mice treated with BCY6136, BCY8245 and BCY8781 were collected at 24 h post dosing.

(d) Results (i) Body Weight change and Tumor Growth Curve

Body weight and tumor growth curves are shown in FIG. 23.

(ii) Tumor Volume Trace

Mean tumor volume over time in female BALB/c nude mice bearing LU-01-0412 xenograft is shown in Table 43.

TABLE 43

Tumor volume trace over time

| Days | Group 1 Vehicle Qw * 4 | Group 2 BCY6136 1 mpk, Qw * 4 | Group 3 BCY6136 3 mpk, Qw * 4 | Group 4 BCY8245 3 mpk, Qw * 4 | Group 5 BCY8781 3 mpk, Qw * 4 |
|---|---|---|---|---|---|
| 0 | 159 ± 11 | 159 ± 13 | 159 ± 11 | 159 ± 12 | 159 ± 11 |
| 4 | 255 ± 12 | 214 ± 16 | 197 ± 16 | 168 ± 18 | 176 ± 21 |
| 7 | 309 ± 20 | 237 ± 16 | 195 ± 16 | 132 ± 10 | 167 ± 13 |
| 11 | 395 ± 31 | 246 ± 19 | 156 ± 18 | 78 ± 4 | 107 ± 15 |
| 14 | 464 ± 31 | 300 ± 18 | 177 ± 29 | 45 ± 5 | 72 ± 12 |
| 18 | 521 ± 26 | 369 ± 32 | 210 ± 32 | 21 ± 2 | 44 ± 8 |
| 21 | 611 ± 33 | 470 ± 46 | 225 ± 32 | 11 ± 1 | 31 ± 6 |
| 25 | 737 ± 68 | 632 ± 47 | 252 ± 37 | 6 ± 1 | 20 ± 6 |
| 28 | 788 ± 80 | 664 ± 52 | 299 ± 37 | 2 ± 1 | 14 ± 5 |
| 32 | 1104 ± 142 | 758 ± 70 | 416 ± 52 | 1 ± 1 | 12 ± 5 |

(iii) Tumor Growth Inhibition Analysis

Tumor growth inhibition rate for BCY6136, BCY8245 and BCY8781 in the LU-01-0412 xenograft model was calculated based on tumor volume measurements on day 32 after the start of the treatment.

TABLE 44

Tumor growth inhibition analysis

| Group | Treatment | Tumor Volume (mm$^3$)$^a$ | T/C$^b$ (%) | TGI (%) | P value |
|---|---|---|---|---|---|
| 1 | Vehicle, qw * 4 | 1104 ± 142 | — | — | — |
| 2 | BCY6136, 1 mpk, qw * 4 | 758 ± 70 | 68.6 | 36.7 | p < 0.05 |
| 3 | BCY6136, 3 mpk, qw * 4 | 416 ± 52 | 37.6 | 72.9 | p < 0.001 |
| 4 | BCY8245, 3 mpk, qw * 4 | 1 ± 1 | 0.1 | 116.8 | p < 0.001 |
| 5 | BCY8781, 3 mpk, qw * 4 | 12 ± 5 | 1.0 | 115.6 | p < 0.001 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136, BCY8245 and BCY8781 in the LU-01-0412 xenograft model was evaluated. The measured body weight and tumor volume of all treatment groups at various time points are shown in FIG. 23 and Tables 43 and 44.

The mean tumor volume of vehicle treated mice reached 1104 mm$^3$ on day 32 after the start of treatment. BCY6136 at 1 mg/kg, qw*4 (TV=758 mm$^3$, TGI=36.7%, p<0.05) and 3 mg/kg, qw*4 (TV=416 mm$^3$, TGI=72.9%, p<0.001) produced dose-dependent antitumor activity, but didn't show any tumor regression. BCY8245 at 3 mg/kg, qw*4 (TV=1 mm$^3$, TGI=116.8%, p<0.001) and BCY8781 at 3 mg/kg, qw*4 (TV=12 mm$^3$, TGI=115.6%, p<0.001) regressed the tumors obviously. Among them, 5 of 6 tumor treated with BCY8245 3 mg/kg and 2 of 6 tumor treated with d BCY8781 3 mg/kg were completely eradicated on day 32.

In this study, animals in all groups maintained the body weight well.

Study 16: In Vivo Efficacy Study of BCY6136 in Treatment of LU-01-0486 PDX Model in Balb/c Nude Mice (a) Study Objective The objective of the research is to evaluate the in vivo anti-tumor efficacy of BCY6136 in the LU-01-0486 PDX model in Balb/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 5 | — | 10 | iv | qw |
| 2 | BCY6136 | 5 | 1 | 10 | iv | qw |
| 3 | BCY6136 | 5 | 2 | 10 | iv | qw |
| 4 | BCY6136 | 5 | 3 | 10 | iv | qw |

(c) Experimental Methods and Procedures (i) Tumor Inoculation

Each mouse was inoculated subcutaneously at the right flank with LU-01-0486 of tumor fragment (~30 mm$^3$) for tumor development. The treatment was started when the average tumor volume reached 180 mm$^3$ for efficacy study. The test article administration and the animal number in each group are shown in the experimental design table.

(ii) Testing Article Formulation Preparation

| Test article | Conc. (mg/ml) | Formulation |
|---|---|---|
| Vehicle | — | 50 mM Acetate 10% sucrose pH 5 |
| BCY6136 | 0.3 | 0.3 mg/ml BCY6136 was prepared as described in Study 10 |
|  | 0.2 | Dilute 940 μl 0.3 mg/ml BCY6136 with 470 μl Acetate buffer$^1$ |
|  | 0.1 | Dilute 470 μl 0.3 mg/ml BCY6136 with 940 μl Acetate buffer |

$^1$Acetate buffer: 50 mM Acetate 10% sucrose pH 5

(d) Results (i) Body Weight change and Tumor Growth Curve

Body weight and tumor growth curve are shown in FIG. 24.

(ii) Tumor Volume Trace

Mean tumor volume on day 14 after the start of treatment in female Balb/c nude mice bearing LU-01-0486 xenograft is shown in Table 45.

TABLE 45

Tumor volume trace over time

| Group | Treatment | \multicolumn{5}{c}{Days after the start of treatment} |
|---|---|---|---|---|---|---|
| | | 0 | 3 | 7 | 10 | 14 |
| 1 | Vehicle, qw | 179 ± 20 | 232 ± 30 | 358 ± 45 | 450 ± 47 | 651 ± 112 |
| 2 | BCY6136, 1 mpk, qw | 180 ± 23 | 221 ± 20 | 326 ± 34 | 420 ± 34 | 638 ± 71 |
| 3 | BCY6136, 2 mpk, qw | 179 ± 27 | 222 ± 26 | 365 ± 44 | 459 ± 82 | 645 ± 105 |
| 4 | BCY6136, 3 mpk, qw | 180 ± 25 | 209 ± 37 | 304 ± 51 | 348 ± 77 | 449 ± 115 |

(iii) Tumor Growth Inhibition Analysis

Tumor growth inhibition rate for BCY6136 in the LU-01-0486 PDX model was calculated based on tumor volume measurement at day 14 after the start of the treatment.

TABLE 46

Tumor growth inhibition analysis

| Group | Treatment | Tumor Volume (mm³)$^a$ | T/C$^b$ (%) | TGI (%) | P value |
|---|---|---|---|---|---|
| 1 | Vehicle, qw | 651 ± 112 | — | — | — |
| 2 | BCY6136, 1 mpk, qw | 638 ± 71 | 98.0 | 3.0 | p > 0.05 |
| 3 | BCY6136, 2 mpk, qw | 645 ± 105 | 99.1 | 1.2 | p > 0.05 |
| 4 | BCY6136, 3 mpk, qw | 449 ± 115 | 68.9 | 43.1 | p > 0.05 |

$^a$Mean ± SEM;
$^b$Tumor Growth Inhibition is calculated by dividing the group average tumor volume for the treated group by the group average tumor volume for the control group (T/C).

(e) Results Summary and Discussion

In this study, the therapeutic efficacy of BCY6136 in LU-01-0486 PDX model was evaluated. The measured body weight and tumor volume of all treatment groups at various time points are shown in the FIG. 24 and Tables 45 and 46.

In this study, the mean tumor volume of vehicle treated mice reached 651 mm³ on day 14 after the start of treatment. BCY6136 at 1 mg/kg, qw (TV=638 mm³, TGI=3.0%, p>0.05) and 2 mg/kg, qw (TV=645 mm³, TGI=1.2%, p>0.05) didn't show any anti-tumor activity. BCY6136 at 3 mg/kg, qw (TV=449 mm³, TGI=43.1%, p>0.05) produced slight anti-tumor activity without statistical significance.

Study 17: In Vivo Efficacy Test of BCY6033, BCY6136 and BCY6082 in Treatment of MDA-MB-231-Luc Xenograft in Balb/c Nude Mice (a) Study Objective The objective of the research was to evaluate the in vivo anti-tumor efficacy of BCY6033, BCY6136 and BCY6082 in treatment of MDA-MB-231-luc xenograft model in Balb/c nude mice.

(b) Experimental Design

| Gr | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6033 | 3 | 1 | 10 | iv | qw |
| 3 | BCY6033 | 3 | 2 | 10 | iv | qw |
| 4 | BCY6033 | 3 | 3 | 10 | iv | qw |
| 5 | BCY6136 | 3 | 1 | 10 | iv | qw |
| 6 | BCY6136 | 3 | 2 | 10 | iv | qw |
| 7 | BCY6136 | 3 | 2 | 10 | iv | qw |
| 8 | BCY6082 | 3 | 2 | 10 | iv | qw |
| 9 | BCY6082 | 3 | 5 | 10 | iv | qw |

(c) Experimental Methods and Procedures (i) Cell Culture

The cells growing in an exponential growth phase were harvested and counted for tumor inoculation.

(ii) Tumor Inoculation

Each mouse was inoculated subcutaneously at the right flank with MDA-MB-231-luc tumor cells (10×10^6) in 0.1 ml of PBS with 0.1 ml matrigel for tumor development. 36 animals were randomized when the average tumor volume reached 159 mm³. The test article administration and the animal numbers in each group were shown in the experimental design table.

(iii) Testing Article Formulation Preparation

| Treatment | Dose (mg/ml) | Formulation |
|---|---|---|
| Vehicle | | 50 mM Acetate, 10% sucrose pH = 5 |
| BCY6033 | 1 | Dissolve 6.71 mg BCY6033 into 6.710 ml formulation buffer |
| | 0.3 | Dilute 270 μl 1 mg/ml BCY6033 into 630 μl formulation buffer |
| | 0.2 | Dilute 180 μl 1 mg/ml BCY6033 into 720 μl formulation buffer |
| | 0.1 | Dilute 90 μl 1 mg/ml BCY6033 into 810 μl formulation buffer |
| BCY6136 | 1 | Dissolve 3.79 mg BCY6136 into 3.695 ml formulation buffer |
| | 0.3 | Dilute 270 μl 1 mg/ml BCY6136 into 630 μl formulation buffer |
| | 0.2 | Dilute 180 μl 1 mg/ml BCY6136 into 720 μl formulation buffer |
| | 0.1 | Dilute 90 μl 1 mg/ml BCY6136 into 810 μl formulation buffer |
| BCY6082 | 1 | Weigh and dissolve 4.30 mg BCY6082 into 4.162 ml formulation buffer |
| | 0.5 | Dilute 450 μl 1 mg/ml BCY6082 into 450 μl formulation buffer |
| | 0.2* | Dilute 180 μl 1 mg/ml BCY6082 into 720 μl formulation buffer |

(iv) Sample Collection

On PG-D24, we collected and fixed the tumors of Group 1, 8 and 9 for FFPE.

On PG-D33, we collected and fixed the tumors of Group 2 and 5 for FFPE.

At the end of study, we collected and fixed the tumors of Group 3, 4, 6 and 7 for FFPE.

(d) Results (i) Body Weight change and Tumor Growth Curve

Figure 25:
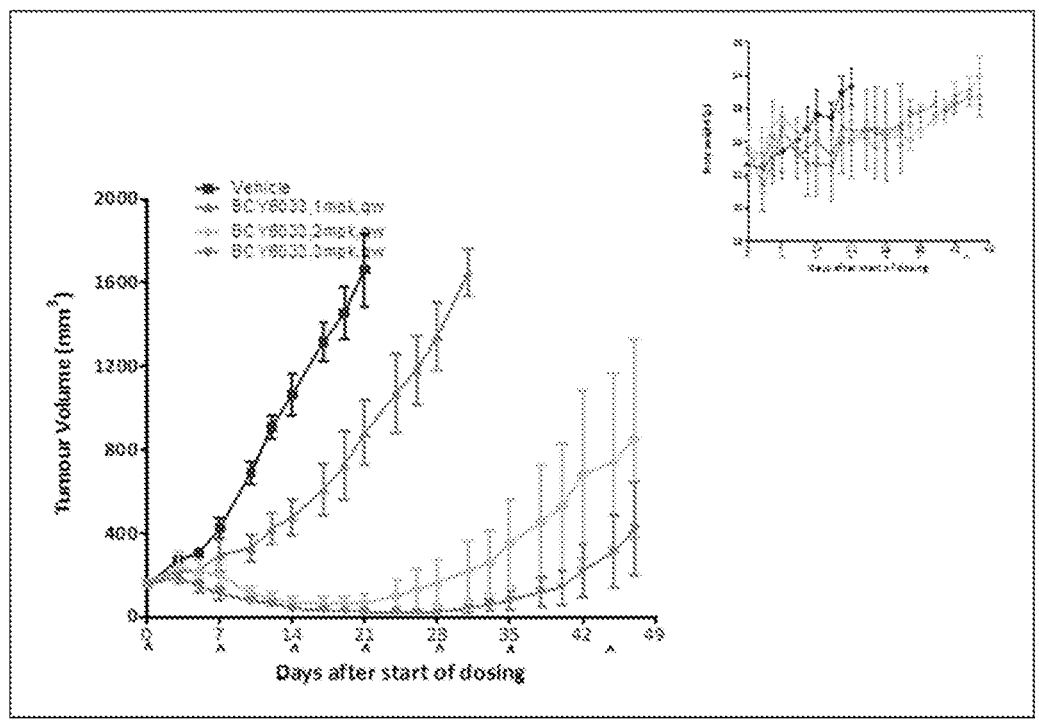
FIGS. 25 to 27: Body weight changes and tumor volume trace after administering BCY6033 (FIG. 25), BCY6136 (FIG. 26) and BCY6082 (FIG. 27) to female Balb/c nude mice bearing MDA-MB-231-luc xenograft. Data points represent group mean tumor volume and body weight.
Figure 26:
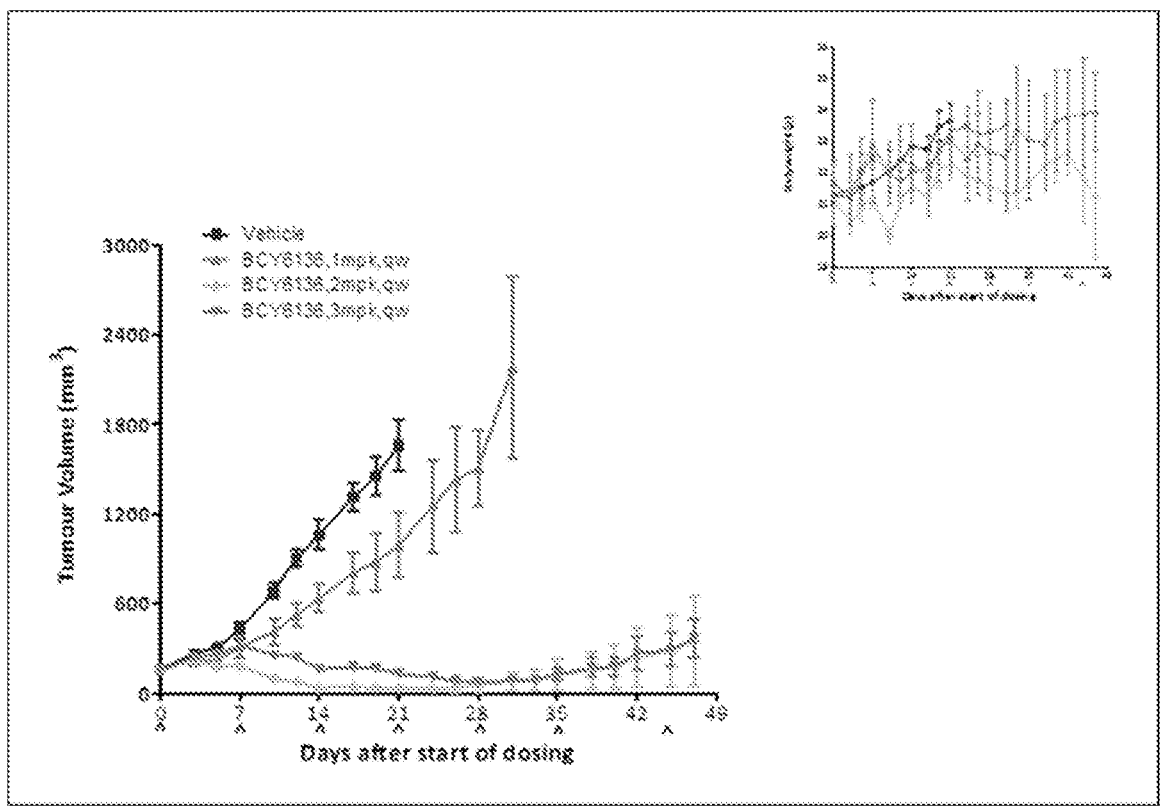
Figure 27:
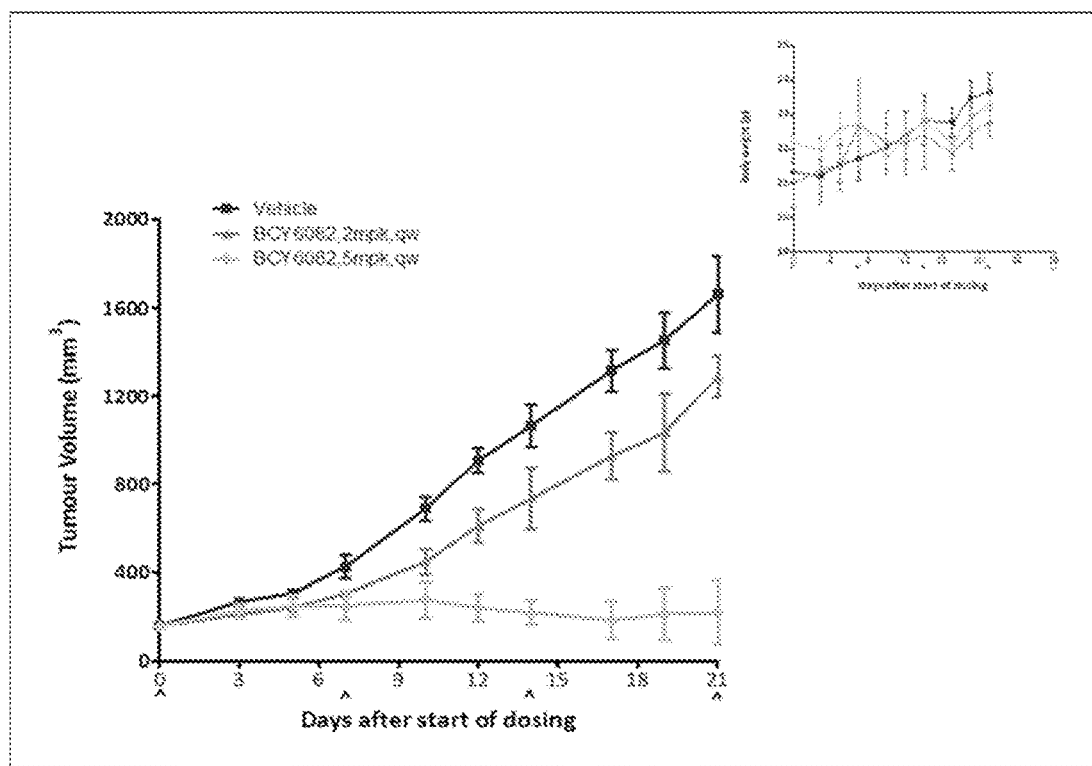
Figure 28:
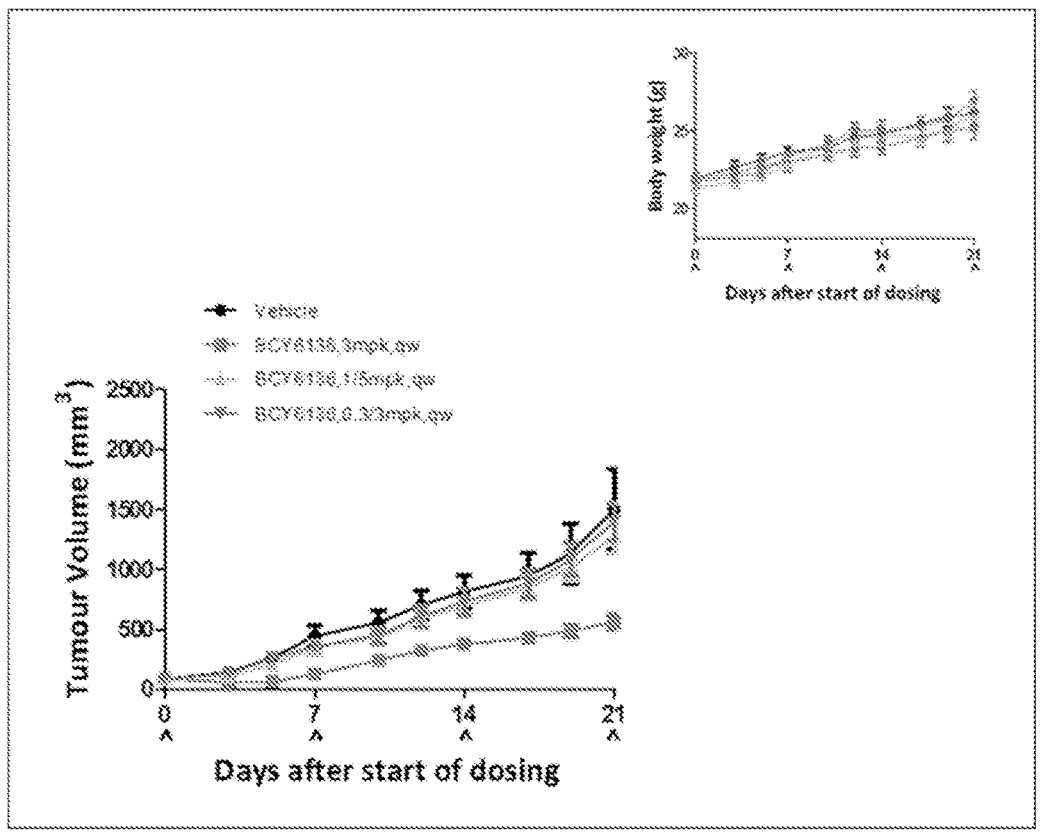
FIG. 28: Body weight changes and tumor volume traces after administering BCY6136 to female BALB/c mice bearing EMT-6 syngeneic. Data points represent group mean body weight. The dosage of group 3 and group 4 was changed to 5 mpk and 3 mpk from Day 14.

Body weight and tumor growth are shown in FIGS. 25 to 27.

(ii) Tumor Volume Trace

Mean tumor volume over time in female Balb/c nude mice bearing MDA-MB-231-luc xenograft is shown in Tables 47 to 49.

TABLE 47

Tumor volume trace (PG-D0~PG-D17)

| Gr. | Treatment | Days after the start of treatment | | | | | | | |
|---|---|---|---|---|---|---|---|---|---|
| | | 0 | 2 | 4 | 7 | 9 | 11 | 14 | 17 |
| 1 | Vehicle, qw | 159 ± 14 | 269 ± 8 | 306 ± 19 | 425 ± 52 | 688 ± 54 | 908 ± 54 | 1064 ± 98 | 1315 ± 95 |
| 2 | BCY6033, 1 mpk, qw | 159 ± 6 | 219 ± 19 | 221 ± 55 | 296 ± 76 | 329 ± 64 | 421 ± 77 | 479 ± 84 | 609 ± 122 |
| 3 | BCY6033, 2 mpk, qw | 159 ± 10 | 240 ± 73 | 215 ± 57 | 201 ± 47 | 109 ± 36 | 84 ± 34 | 64 ± 32 | 59 ± 35 |
| 4 | BCY6033, 3 mpk, qw | 158 ± 7 | 189 ± 27 | 147 ± 32 | 109 ± 26 | 79 ± 11 | 66 ± 7 | 41 ± 5 | 31 ± 6 |
| 5 | BCY6136, 1 mpk, qw | 159 ± 10 | 226 ± 36 | 221 ± 54 | 310 ± 72 | 416 ± 89 | 526 ± 77 | 636 ± 92 | 809 ± 135 |
| 6 | BCY6136, 2 mpk, qw | 159 ± 16 | 218 ± 17 | 182 ± 22 | 182 ± 26 | 101 ± 20 | 77 ± 24 | 36 ± 4 | 41 ± 10 |
| 7 | BCY6136, 3 mpk, qw | 158 ± 5 | 241 ± 12 | 259 ± 6 | 325 ± 14 | 258 ± 12 | 246 ± 15 | 162 ± 19 | 178 ± 10 |
| 8 | BCY6082, 2 mpk, qw | 159 ± 13 | 210 ± 10 | 242 ± 16 | 305 ± 19 | 445 ± 58 | 611 ± 76 | 734 ± 139 | 926 ± 105 |
| 9 | BCY6082, 5 mpk, qw | 159 ± 7 | 227 ± 31 | 247 ± 47 | 250 ± 65 | 276 ± 79 | 241 ± 61 | 220 ± 56 | 184 ± 85 |

TABLE 48

Tumor volume trace (PG-D19~PG-D33)

| Gr. | Treatment | Days after the start of treatment | | | | | | |
|---|---|---|---|---|---|---|---|---|
| | | 19 | 21 | 24 | 26 | 28 | 31 | 33 |
| 1 | Vehicle, qw | 1453 ± 128 | 1661 ± 173 | — | — | — | — | — |
| 2 | BCY6033, 1 mpk, qw | 724 ± 162 | 880 ± 156 | 1069 ± 189 | 1182 ± 164 | 1342 ± 166 | 1647 ± 113 | — |
| 3 | BCY6033, 2 mpk, qw | 61 ± 35 | 67 ± 44 | 100 ± 76 | 133 ± 96 | 163 ± 106 | 221 ± 143 | 257 ± 152 |
| 4 | BCY6033, 3 mpk, qw | 29 ± 7 | 22 ± 12 | 22 ± 8 | 21 ± 9 | 21 ± 10 | 43 ± 20 | 57 ± 29 |
| 5 | BCY6136, 1 mpk, qw | 879 ± 190 | 994 ± 213 | 1253 ± 313 | 1431 ± 353 | 1507 ± 253 | 2181 ± 609 | — |
| 6 | BCY6136, 2 mpk, qw | 35 ± 9 | 33 ± 9 | 31 ± 17 | 41 ± 32 | 59 ± 45 | 82 ± 59 | 87 ± 71 |
| 7 | BCY6136, 3 mpk, qw | 171 ± 21 | 132 ± 19 | 108 ± 19 | 85 ± 15 | 81 ± 8 | 87 ± 14 | 92 ± 18 |
| 8 | BCY6082, 2 mpk, qw | 1034 ± 178 | 1287 ± 94 | — | — | — | — | — |
| 9 | BCY6082, 5 mpk, qw | 214 ± 120 | 218 ± 146 | — | — | — | — | — |

TABLE 49

Tumor volume trace (PG-D35~PG-D47)

| Gr. | Treatment | Days after the start of treatment | | | | | |
|---|---|---|---|---|---|---|---|
| | | 35 | 38 | 40 | 42 | 45 | 47 |
| 3 | BCY6033, 2 mpk, qw | 352 ± 210 | 456 ± 271 | 525 ± 302 | 683 ± 400 | 738 ± 429 | 853 ± 476 |
| 4 | BCY6033, 3 mpk, qw | 79 ± 47 | 118 ± 71 | 139 ± 82 | 220 ± 125 | 312 ± 176 | 423 ± 222 |

TABLE 49-continued

Tumor volume trace (PG-D35~PG-D47)

| | | Days after the start of treatment | | | | | |
|---|---|---|---|---|---|---|---|
| Gr. | Treatment | 35 | 38 | 40 | 42 | 45 | 47 |
| 6 | BCY6136, 2 mpk, qw | 124 ± 106 | 156 ± 120 | 179 ± 142 | 239 ± 197 | 285 ± 239 | 350 ± 298 |
| 7 | BCY6136, 3 mpk, qw | 129 ± 38 | 173 ± 65 | 181 ± 65 | 269 ± 113 | 293 ± 114 | 371 ± 128 |

(iii) Tumor Growth Inhibition Analysis

Tumor growth inhibition rate for BCY6033, BCY6136 and BCY6082 in the MDA-MB-231-luc xenograft model was calculated based on tumor volume measurements at day 21 after the start of treatment.

TABLE 50

Tumor growth inhibition analysis

| Gr | Treatment | Tumor Volume $(mm^3)^a$ | $T/C^b$ (%) | TGI (%) | P value |
|---|---|---|---|---|---|
| 1 | Vehicle, qw | 1661 ± 173 | — | — | — |
| 2 | BCY6033, 1 mpk, qw | 880 ± 156 | 53.0 | 52.0 | p < 0.001 |
| 3 | BCY6033, 2 mpk, qw | 67 ± 44 | 4.1 | 106.1 | p < 0.001 |
| 4 | BCY6033, 3 mpk, qw | 22 ± 12 | 1.3 | 109.1 | p < 0.001 |
| 5 | BCY6136, 1 mpk, qw | 994 ± 213 | 59.8 | 44.4 | p < 0.01 |
| 6 | BCY6136, 2 mpk, qw | 33 ± 9 | 2.0 | 108.4 | p < 0.001 |
| 7 | BCY6136, 3 mpk, qw | 132 ± 19 | 8.0 | 101.7 | p < 0.001 |
| 8 | BCY6082, 2 mpk, qw | 1287 ± 94 | 77.5 | 24.9 | p > 0.05 |
| 9 | BCY6082, 5 mpk, qw | 218 ± 146 | 13.1 | 96.1 | p < 0.001 |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCY6033, BCY6136 and BCY6082 in the MDA-MB-231-luc xenograft model was evaluated. The measured body weights and tumor volumes of all treatment groups at various time points are shown in the FIGS. 25 to 27 and Tables 47 to 50.

The mean tumor size of vehicle treated mice reached 1661 mm$^3$ on day 21. BCY6033 at 1 mg/kg (TV=880 mm$^3$, TGI=52.0%, p<0.001), 2 mg/kg (TV=67 mm$^3$, TGI=106.1%, p<0.001) and 3 mg/kg (TV=22 mm$^3$, TGI=109.1%, p<0.001) produced dose-dependent antitumor activity. BCY6033 at 2 mg/kg and 3 mg/kg regressed the tumors potently, but the tumors showed obvious re-growth from day 21.

BCY6136 at 1 mg/kg (TV=994 mm$^3$, TGI=44.4%, p<0.01) showed moderate antitumor activity, BCY6136 at 2 mg/kg (TV=33 mm$^3$, TGI=108.4%, p<0.001) and 3 mg/kg (TV=132 mm$^3$, TGI=101.1%, p<0.001) produced potent antitumor activity, but the tumors showed obvious re-growth from day 28.

BCY6082 at 2 mg/kg (TV=1287 mm3, TGI=24.9%, p>0.05) didn't show obvious antitumor activity, BCY6082 at 5 mg/kg (TV=218 mm3, TGI=96.1%, p<0.001) produced significant antitumor activity.

In this study, one mouse treated with BCY6136 2 mg/kg lost over 15% bodyweight during the treatment schedule, other mice maintained the bodyweight well.

Study 18: In Vivo Efficacy Test of BCY6136 in Treatment of EMT-6 Syngeneic Model in BALB/c Mice (a) Study Objective The objective of the research was to evaluate the in vivo anti-tumor efficacy of BCY6136 in treatment of EMT-6 syngeneic model in BALB/c mice.

(b) Experimental Design

| Group | Treatment | Dose (mg/kg) | N | Dosing Route | Schedule | Sample Collection |
|---|---|---|---|---|---|---|
| 1 | Vehicle | — | 5 | iv | qw*4 | tumors from spare mice will be collected for FACS |
| 2 | BCY6136 | 3 | 5 | iv | qw*4 | |
| 3 | BCY6136 | $1/5^b$ | 5 | iv | qw*4 | |
| 4 | BCY6136 | $0.3/3^b$ | 5 | iv | qw*4 | |

[a]The injection volume of each mouse is 10 ml/kg.
[b]The dosage of group 3 and group 4 was changed to 5 mpk and 3 mpk from Day 14.

(c) Experimental Methods and Procedures (i) Cell Culture

The EMT-6 tumor cells were maintained in vitro as a monolayer culture in EMEM medium supplemented with 10% heat inactivated fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

(ii) Tumor Inoculation

Each mouse was inoculated subcutaneously at the right flank with EMT-6 tumor cells ($5 \times 10^6$) in 0.1 ml of PBS for tumor development. 44 animals were randomized when the average tumor volume reached 75 mm$^3$. The test article administration and the animal numbers in each group were shown in the experimental design table.

(iii) Testing Article Formulation Preparation

BCY6136 formulation

| Treatment | Conc.(mg/ml) | Formulation |
|---|---|---|
| Vehicle/ buffer | — | 50 mM Acetate, 10% sucrose pH = 5 |
| BCY6136 | 1 | Dissolve 6.2 mg BCY6136 with 6113 ul buffer |
| BCY6136 | 0.3 | Dilute 450 µl 1 mg/ml BCY6136 stock with 1050 µl buffer |
| BCY6136 | 0.1 | Dilute 150 µl 1 mg/ml BCY6136 stock with 1350 µl buffer |
| BCY6136 | 0.03 | Dilute 45 µl 1 mg/ml BCY6136 stock with 1455 µl buffer |

| BCY6136 formulation | | |
|---|---|---|
| Treatment | Conc.(mg/ml) | Formulation |
| Vehicle/buffer | — | 50 mM Acetate, 10% sucrose pH = 5 |
| BCY6136 | 1 | stock |
| BCY6136 | 0.3 | Dilute 420 μl 1 mg/ml BCY6136 stock with 980 μl buffer |
| BCY6136 | 0.3 | Dilute 420 μl 1 mg/ml BCY6136 stock with 980 μl buffer |
| BCY6136 | 0.5 | Dilute 700 μl 1 mg/ml BCY6136 stock with 700 μl buffer |

(iv) Sample Collection 3 tumors from spare mice were collected for FACS on day 11. The data was supplied by biology team.

(d) Results (i) Body Weight change and Tumor Growth Curve

Body weight and tumor growth curve are shown in FIG. 28.

(ii) Tumor Volume Trace

Mean tumor volume over time in female BALB/c mice bearing EMT-6 syngeneic is shown in Table 51.

TABLE 51

Tumor volume trace over time

| | | Days after the start of treatment | | | | | | | | |
|---|---|---|---|---|---|---|---|---|---|---|
| Gr. | Treatment | 0 | 3 | 5 | 7 | 10 | 12 | 14 | 17 | 19 | 21 |
| 1 | Vehicle, qw | 82 ± 4 | 141 ± 11 | 260 ± 24 | 443 ± 90 | 557 ± 99 | 703 ± 119 | 812 ± 139 | 948 ± 191 | 1129 ± 248 | 1499 ± 340 |
| 2 | BCY6136, 3 mpk, qw | 82 ± 4 | 58 ± 1 | 59 ± 2 | 125 ± 18 | 240 ± 23 | 322 ± 23 | 374 ± 22 | 431 ± 37 | 486 ± 50 | 561 ± 61 |
| 3 | BCY6136, 1/5$^a$ mpk, qw | 82 ± 4 | 108 ± 18 | 204 ± 27 | 350 ± 57 | 426 ± 49 | 588 ± 72 | 691 ± 65 | 850 ± 98 | 1018 ± 115 | 1272 ± 140 |
| 4 | BCY6136, 0.3/3$^a$ mpk, qw | 82 ± 4 | 130 ± 16 | 255 ± 35 | 358 ± 34 | 450 ± 67 | 607 ± 94 | 731 ± 112 | 872 ± 119 | 1082 ± 133 | 1394 ± 161 |

The dosage of group 3 and group 4 was changed to 5 mpk and 3 mpk from Day 14.

(iii) Tumor Growth Inhibition Analysis

Tumor growth inhibition rate for BCY6136 in EMT-6 syngeneic model was calculated based on tumor volume measurements on day 21 after the start of treatment.

TABLE 52

Tumor growth inhibition analysis

| Gr | Treatment | Tumor Volume (mm$^3$)$^a$ | T/C$^b$ (%) | TGI (%) | P value compare with vehicle |
|---|---|---|---|---|---|
| 1 | Vehicle, qw | 1499 ± 340 | — | — | — |
| 2 | BCY6136, 3 mpk, qw | 561 ± 61 | 37.4 | 66.2 | p < 0.05 |
| 3 | BCY6136, 1/5$^c$ mpk, qw | 1272 ± 140 | 84.8 | 16.1 | ns |
| 4 | BCY6136, 0.3/3$^c$ mpk, qw | 1394 ± 161 | 93.0 | 7.4 | ns |

$^a$Mean ± SEM.
$^b$Tumor Growth Inhibition is calculated by dividing the group average tumor volume for the treated group by the group average tumor volume for the control group (T/C).
$^c$The dosage of group 3 and group 4 was changed to 5 mpk and 3 mpk from Day 14.

(e) Results Summary and Discussion

In this study, the therapeutic efficacy of BCY6136 in EMT-6 syngeneic model was evaluated. The measured body weights and tumor volumes of all treatment groups at various time points are shown in the FIG. 28 and Tables 51 and 52.

The mean tumor size of vehicle treated mice reached 1499 mm$^3$ on day 21. BCY6136 at 3 mg/kg, qw (TV=561 mm$^3$, TGI=66.2%, p<0.05) showed obvious antitumor activity. BCY6136 at 1/5 mg/kg, qw (TV=1272 mm$^3$, TGI=16.1%, p>0.05) and BCY6136 at 0.3/3 mg/kg, qw (TV=1394 mm$^3$, TGI=7.4%, p>0.05) didn't show any antitumor activity.

The dosage of group 3 and group 4 was changed to 5 mpk and 3 mpk from day 14. Tumor ulceration was found in mouse 3-5 on Day 14, and the mice was deal with antibiotic cream. In this study, all mice maintained the bodyweight well.

Study 19: In Vivo Efficacy Study of BCY6136 in Treatment of NCI-N87 Xenograft in Balb/c Nude Mice (a) Study Objective The objective of the research is to evaluate the in vivo anti-tumor efficacy of BCY6136 in treatment of NCI-N87 xenograft in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | Qw |
| 2 | BCY6136 | 3 | 1 | 10 | iv | Qw |
| 3 | BCY6136 | 3 | 2 | 10 | iv | Qw |
| 4 | BCY6136 | 3 | 3 | 10 | iv | Qw |

(c) Experimental Methods and Procedures (i) Cell Culture

The NCI-N87 tumor cells were maintained in RPMI-1640 medium supplemented with 10% heat inactivated fetal bovine serum at 37° C. in an atmosphere of 5% CO$_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with NCI-N87 tumor cells (10×10$^6$) with matrigel (1:1) in 0.2 ml of PBS for tumor development. The animals were randomized and treatment was started when the average tumor volume reached approximately 176 mm$^3$. The test article administration and the animal number in each group are shown in the experimental design table.

(iii) Testing Article Formulation Preparation

| Test article | Conc. (mg/ml) | Formulation |
|---|---|---|
| Vehicle | — | 50 mM Acetate 10% sucrose pH 5 |
| BCY6136 | 1 | Dissolve 4.295 mg BCY6136 in 4.214 ml Acetate buffer[1] |
| | 0.1 | Dilute 90 µl 1 mg/ml BCY6136 stock with 810 µl Acetate buffer |
| | 0.2 | Dilute 180 µl 1 mg/ml BCY6136 stock with 720 µl Acetate buffer |
| | 0.3 | Dilute 270 µl 1 mg/ml BCY6136 stock with 630 µl Acetate buffer |

[1]Acetate buffer: 50 mM Acetate 10% sucrose pH 5

(d) Results (i) Body Weight change and Tumor Growth Curve

Figure 29:
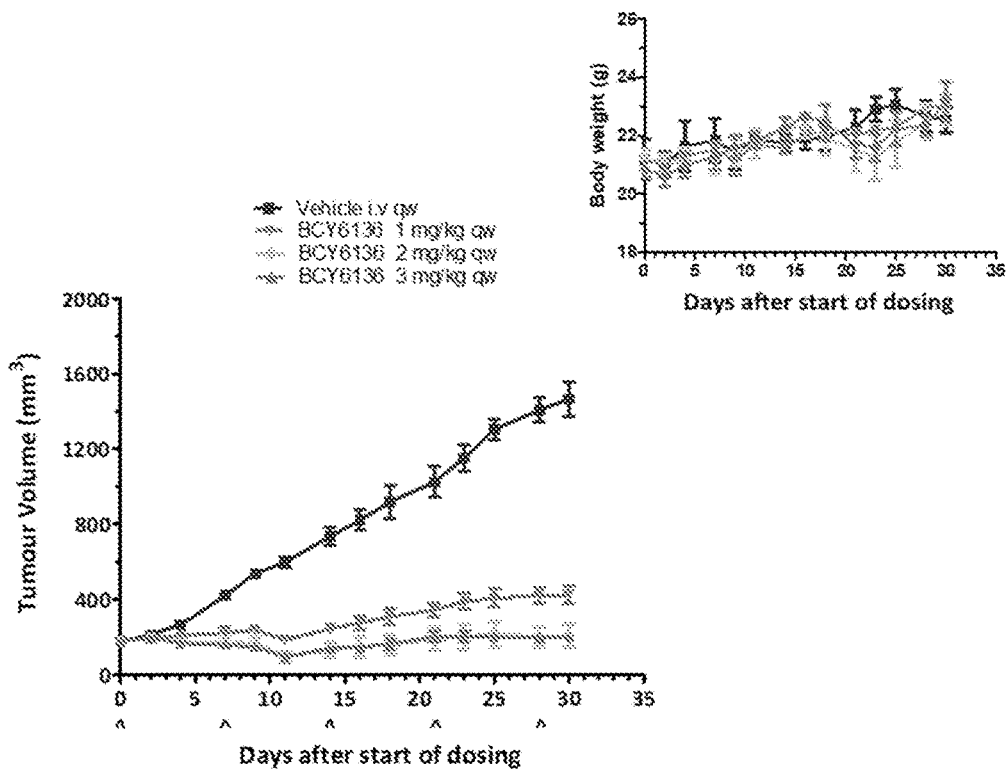
FIG. 29: Body weight changes and tumor volume traces after administering BCY6136 to female Balb/c nude mice bearing NCI-N87 xenograft. Data points represent group mean body weight.

Body weight and tumor growth curve is shown in FIG. 29.

(ii) Tumor Volume Trace

Mean tumor volume over time in female Balb/c nude mice bearing NCI-N87 xenograft is shown in Table 53.

TABLE 53

Tumor volume trace over time

| Gr. | Treatment | Days after the start of treatment | | | | | | |
|---|---|---|---|---|---|---|---|---|
| | | 0 | 2 | 4 | 7 | 9 | 11 | 14 |
| 1 | Vehicle, qw | 174 ± 7 | 213 ± 5 | 266 ± 6 | 421 ± 10 | 537 ± 17 | 598 ± 30 | 734 ± 46 |
| 2 | BCY6136, 1 mpk, qw | 176 ± 7 | 200 ± 8 | 210 ± 14 | 224 ± 27 | 238 ± 21 | 184 ± 18 | 244 ± 23 |
| 3 | BCY6136, 2 mpk, qw | 176 ± 18 | 197 ± 25 | 168 ± 25 | 170 ± 26 | 165 ± 34 | 96 ± 27 | 133 ± 35 |
| 4 | BCY6136, 3 mpk, qw | 177 ± 8 | 197 ± 9 | 169 ± 7 | 158 ± 3 | 148 ± 8 | 95 ± 16 | 141 ± 12 |

| Gr. | Treatment | Days after the start of treatment | | | | | | |
|---|---|---|---|---|---|---|---|---|
| | | 16 | 18 | 21 | 23 | 25 | 28 | 30 |
| 1 | Vehicle, qw | 821 ± 55 | 918 ± 91 | 1024 ± 83 | 1151 ± 68 | 1305 ± 57 | 1407 ± 64 | 1465 ± 90 |
| 2 | BCY6136, 1 mpk, qw | 276 ± 35 | 308 ± 44 | 343 ± 37 | 390 ± 43 | 406 ± 48 | 422 ± 42 | 425 ± 47 |
| 3 | BCY6136, 2 mpk, qw | 150 ± 52 | 160 ± 49 | 190 ± 63 | 203 ± 65 | 218 ± 66 | 201 ± 53 | 210 ± 60 |
| 4 | BCY6136, 3 mpk, qw | 145 ± 24 | 164 ± 28 | 202 ± 28 | 205 ± 30 | 201 ± 16 | 196 ± 21 | 201 ± 22 |

(iii) Tumor Growth Inhibition Analysis

Tumor growth inhibition rate for BCY6136 in the NCI-N87 xenograft was calculated based on tumor volume measurements at day 30 after the start of treatment.

TABLE 54

Tumor growth inhibition analysis

| Group | Treatment | Tumor Volume (mm³)[a] | T/C[b] (%) | TGI (%) | P value |
|---|---|---|---|---|---|
| 1 | Vehicle, qw | 1465 ± 90 | — | — | — |
| 2 | BCY6136, 1 mpk, qw | 425 ± 47 | 29.0 | 80.7 | p < 0.001 |
| 3 | BCY6136, 2 mpk, qw | 210 ± 60 | 14.3 | 97.4 | p < 0.001 |
| 4 | BCY6136, 3 mpk, qw | 201 ± 22 | 13.7 | 98.1 | p < 0.001 |

[a]Mean ± SEM.
[b]Tumor growth inhibition is calculated by dividing the group average tumor volume for the treated group by the group average tumor volume for the control group (T/C).

(e) Results Summary and Discussion

In this study, the therapeutic efficacy of BCY6136 in the NCI-N87 model was evaluated. The measured body weight and tumor volume of all treatment groups at various time points are shown in the FIG. 29 and Tables 53 and 54.

The mean tumor size of vehicle treated mice reached 1465 mm³ on day 30. BCY6136 at 1 mg/kg, qw (TV=425 mm³, TGI=80.7%, p<0.001) and 2 mg/kg, qw (TV=210 mm³, TGI=97.4%, p<0.001) produced significant antitumor activity in a dose-dependent manner, BCY6136 at 3 mg/kg, qw (TV=201 mm³, TGI=98.1%, p<0.001) showed comparable antitumor activity with BCY6136 at 2 mpk.

In this study, no obvious body weight loss was found in all the groups during the treatment schedule.

Study 20: In Vivo Efficacy Study of BCY6136 in Treatment of SK-OV-3 Xenograft in Balb/c Nude Mice (a) Study Objective The objective of the research is to evaluate the in vivo anti-tumor efficacy of BCY6136 in treatment of SK-OV-3 xenograft in Balb/c nude mice.

(b) Experimental Design

| Group | Treatment | n | Dose (mg/kg) | Dosing Volume (µl/g) | Dosing Route | Schedule |
|---|---|---|---|---|---|---|
| 1 | Vehicle | 3 | — | 10 | iv | Qw |
| 2 | ADC | 3 | 3 | 10 | iv | Qw |
| 3 | BCY6136 | 3 | 1 | 10 | iv | Qw |
| 4 | BCY6136 | 3 | 2 | 10 | iv | Qw |
| 5 | BCY6136 | 3 | 3 | 10 | iv | Qw |

(c) Experimental Methods and Procedures (i) Cell Culture

The SK-OV-3 tumor cells were maintained in McCoy's 5a medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with SK-OV-3 tumor cells ($10 \times 10^6$) with matrigel (1:1) in 0.2 ml of PBS for tumor development. The animals were randomized and treatment was started when the average tumor volume reached approximately 186 mm$^3$. The test article administration and the animal number in each group are shown in the experimental design table.

(iii) Testing Article Formulation Preparation

| Test article | Purity | Conc. (mg/ml) | Formulation |
|---|---|---|---|
| Vehicle | — | — | 50 mM Acetate 10% sucrose pH 5 |
| BCY6136 | 98.5% | 1 | Dissolve 3.65 mg BCY6136 in 3.60 ml 50 mM Acetate buffer[1] |
| | | 0.1 | Dilute 90 μl 1 mg/ml BCY6136 stock with 810 μl Acetate buffer[1] |
| | | 0.2 | Dilute 180 μl 1 mg/ml BCY6136 stock with 720 μl Acetate buffer[1] |
| | | 0.3 | Dilute 270 μl 1 mg/ml BCY6136 stock with 630 μl Acetate buffer[1] |
| ADC | ADC | 0.3 | Dilute 69 μl 10.47 mg/ml ADC stock with 2331 μl ADC buffer[2] |

[1]Acetate buffer: 50 mM Acetate 10% sucrose pH 5
[2]ADC buffer: 25 mM Histidine 10% sucrose pH 5.5

(d) Results (i) Body Weight change and Tumor Growth Curve

Figure 30:
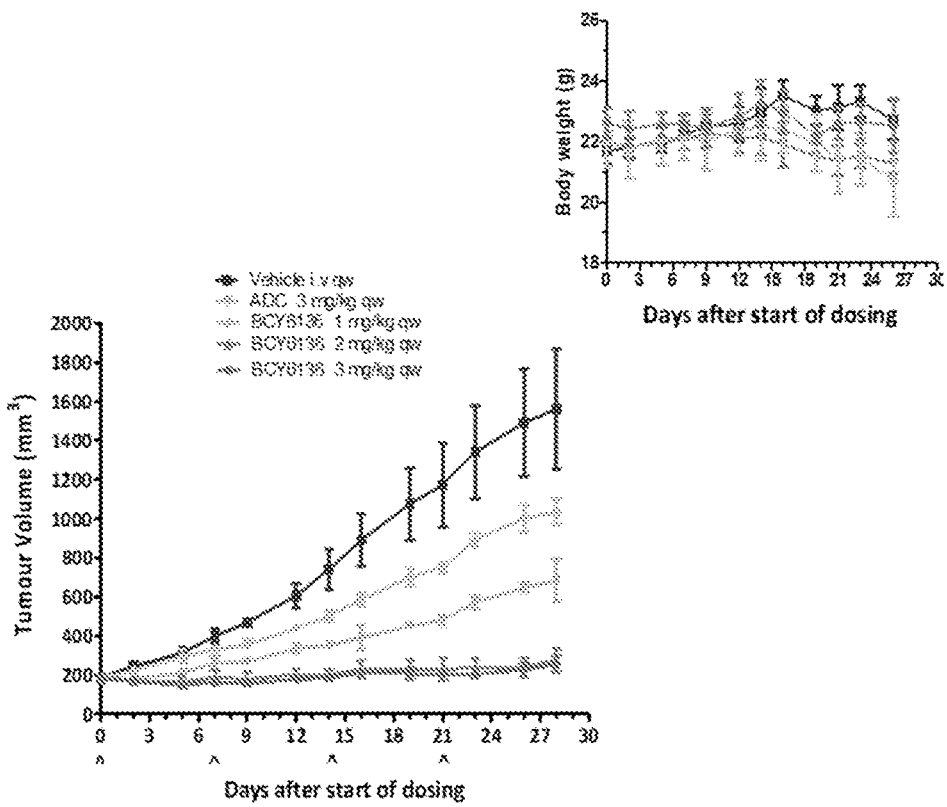
FIG. 30: Body weight changes and tumor volume traces after administering BCY6136 to female Balb/c nude mice bearing SK-OV-3 xenograft. Data points represent group mean body weight.

Body weight and tumor growth curve is shown in FIG. 30.

(ii) Tumor Volume Trace

Mean tumor volume over time in female Balb/c nude mice bearing SK-OV-3 xenograft is shown in Table 55.

TABLE 55

Tumor volume trace over time

| | | Days after the start of treatment | | | | | | |
|---|---|---|---|---|---|---|---|---|
| Gr. | Treatment | 0 | 2 | 5 | 7 | 9 | 12 | 14 |
| 1 | Vehicle, qw | 187 ± 16 | 243 ± 24 | 313 ± 28 | 399 ± 37 | 470 ± 23 | 606 ± 61 | 742 ± 103 |
| 2 | ADC, 3 mpk, qw | 187 ± 16 | 181 ± 15 | 212 ± 16 | 263 ± 35 | 268 ± 14 | 335 ± 23 | 353 ± 18 |
| 3 | BCY6136, 2 mpk, qw | 186 ± 23 | 222 ± 19 | 293 ± 34 | 331 ± 21 | 356 ± 23 | 440 ± 8 | 503 ± 28 |
| 4 | BCY6136, 2 mpk, qw | 186 ± 23 | 170 ± 18 | 164 ± 28 | 188 ± 33 | 180 ± 34 | 202 ± 29 | 200 ± 29 |
| 5 | BCY6136, 3 mpk, qw | 184 ± 24 | 168 ± 18 | 150 ± 12 | 164 ± 12 | 158 ± 8 | 180 ± 8 | 187 ± 4 |

| | | Days after the start of treatment | | | | | |
|---|---|---|---|---|---|---|---|
| Gr. | Treatment | 16 | 19 | 21 | 23 | 26 | 28 |
| 1 | Vehicle, qw | 891 ± 133 | 1076 ± 185 | 1173 ± 214 | 1340 ± 236 | 1490 ± 273 | 1560 ± 305 |
| 2 | ADC, 3 mpk, qw | 392 ± 63 | 449 ± 4 | 481 ± 27 | 573 ± 33 | 647 ± 26 | 684 ± 111 |
| 3 | BCY6136, 2 mpk, qw | 587 ± 33 | 702 ± 43 | 752 ± 26 | 893 ± 34 | 1002 ± 68 | 1035 ± 67 |
| 4 | BCY6136, 2 mpk, qw | 230 ± 46 | 229 ± 48 | 231 ± 58 | 236 ± 49 | 240 ± 48 | 277 ± 58 |
| 5 | BCY6136, 3 mpk, qw | 212 ± 17 | 208 ± 29 | 204 ± 12 | 205 ± 17 | 227 ± 31 | 254 ± 48 |

(iii) Tumor Growth Inhibition Analysis

Tumor growth inhibition rate for BCY6136 in the SK-OV-3 xenograft was calculated based on tumor volume measurements at day 28 after the start of treatment.

TABLE 56

Tumor growth inhibition analysis

| Group | Treatment | Tumor Volume (mm$^3$)[a] | T/C[b] (%) | TGI (%) | P value |
|---|---|---|---|---|---|
| 1 | Vehicle, qw | 1560 ± 305 | — | — | — |
| 2 | ADC, 3 mpk, qw | 684 ± 111 | 43.9 | 63.8 | p < 0.01 |
| 3 | BCY6136, 1 mpk, qw | 1035 ± 67 | 66.4 | 38.1 | p > 0.05 |
| 4 | BCY6136, 2 mpk, qw | 277 ± 58 | 17.8 | 93.3 | p < 0.001 |
| 5 | BCY6136, 3 mpk, qw | 254 ± 48 | 16.3 | 95.0 | p < 0.001 |

[a]Mean ± SEM.
[b]Tumor growth inhibition is calculated by dividing the group average tumor volume for the treated group by the group average tumor volume for the control group (T/C).

(e) Results Summary and Discussion

In this study, the therapeutic efficacy of BCY6136 in the SK-OV-3 model was evaluated. The measured body weight and tumor volume of all treatment groups at various time points are shown in the FIG. 30 and Tables 55 and 56.

The mean tumor size of vehicle treated mice reached 1560 mm$^3$ on day 28. ADC at 3 mg/kg, qw (TV=684 mm$^3$, TGI=63.8%, p<0.01) showed moderate anti-tumor efficacy. BCY6136 at 1 mg/kg, qw (TV=1035 mm$^3$, TGI=38.1%, p>0.05) didn't show obvious anti-tumor activity. BCY6136 at 2 mg/kg, qw (TV=277 mm$^3$, TGI=93.3%, p<0.001) and 3 mg/kg, qw (TV=254 mm$^3$, TGI=95.0%, p<0.001) produced significant anti-tumor activity.

In this study, no obvious body weight loss was found in all the groups during the treatment schedule.

Study 21: In Vivo Efficacy Study of BCY6136 in Treatment of OE21 Xenograft in Balb/c Nude Mice (a) Study Objective The objective of the research is to evaluate the in vivo anti-tumor efficacy of BCY6136 in treatment of OE21 xenograft in Balb/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |

(c) Experimental Methods and Procedures
(i) Cell Culture

The OE21 tumor cells were maintained in RPMI-1640 medium supplemented with 10% heat inactivated fetal bovine serum at 37° C. in an atmosphere of 5% $CO_2$ in air. The tumor cells were routinely subcultured twice weekly. The cells growing in an exponential growth phase were harvested and counted for tumor inoculation.

(ii) Tumor Inoculation

Each mouse was inoculated subcutaneously at the right flank with OE21 tumor cells ($5 \times 10^6$) with matrigel (1:1) in 0.2 ml of PBS for tumor development. The animals were randomized and treatment was started when the average tumor volume reached approximately 157 $mm^3$. The test article administration and the animal number in each group are shown in the experimental design table.

(iii) Testing Article Formulation Preparation

| Test article | Conc. (mg/ml) | Formulation |
|---|---|---|
| Vehicle | — | 50 mM Acetate 10% sucrose pH 5 |
| BCY6136 | 1 | Dissolve 4.295 mg BCY6136 in 4.214 ml Acetate buffer[1] |
| | 0.1 | Dilute 90 μl 1 mg/ml BCY6136 stock with 810 μl Acetate buffer |
| | 0.2 | Dilute 180 μl 1 mg/ml BCY6136 stock with 720 μl Acetate buffer |
| | 0.3 | Dilute 270 μl 1 mg/ml BCY6136 stock with 630 μl Acetate buffer |

[1]Acetate buffer: 50 mM Acetate 10% sucrose pH 5

(d) Results
(i) Body Weight change and Tumor Growth Curve

Figure 31:
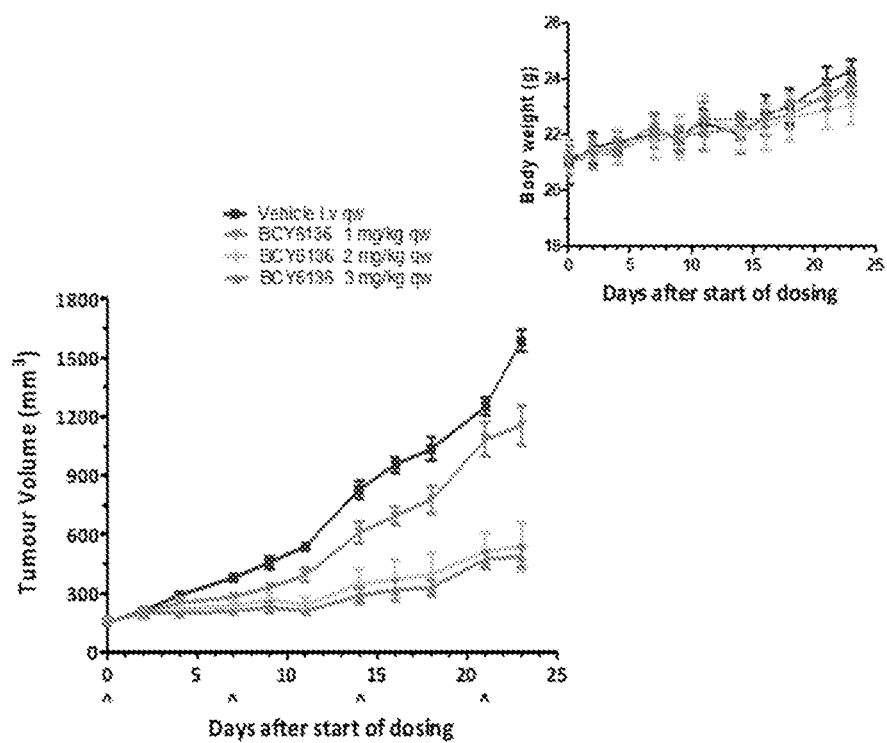
FIG. 31: Body weight changes and tumor volume traces after administering BCY6136 to female Balb/c nude mice bearing OE21 xenograft. Data points represent group mean body weight.

Body weight and tumor growth curve is shown in FIG. 31.

(ii) Tumor Volume Trace

Mean tumor volume over time in female Balb/c nude mice bearing OE21 xenograft is shown in Table 57.

TABLE 57

Tumor volume trace over time

| | | Days after the start of treatment | | | | |
|---|---|---|---|---|---|---|
| Gr. | Treatment | 0 | 2 | 4 | 7 | 9 |
| 1 | Vehicle, qw | 155 ± 9 | 211 ± 16 | 291 ± 16 | 379 ± 14 | 456 ± 32 |
| 2 | BCY6136, 1 mpk, qw | 159 ± 14 | 202 ± 28 | 251 ± 29 | 282 ± 6 | 331 ± 19 |
| 3 | BCY6136, 2 mpk, qw | 157 ± 19 | 197 ± 13 | 219 ± 6 | 235 ± 27 | 268 ± 35 |
| 4 | BCY6136, 3 mpk, qw | 155 ± 19 | 200 ± 16 | 197 ± 7 | 209 ± 11 | 229 ± 26 |

| | Days after the start of treatment | | | | |
|---|---|---|---|---|---|
| Gr. | 11 | 14 | 16 | 18 | 21 | 23 |
| 1 | 539 ± 13 | 828 ± 42 | 955 ± 40 | 1035 ± 58 | 1250 ± 46 | 1586 ± 57 |
| 2 | 392 ± 35 | 609 ± 56 | 694 ± 44 | 777 ± 68 | 1083 ± 85 | 1155 ± 98 |
| 3 | 243 ± 37 | 346 ± 78 | 371 ± 98 | 396 ± 109 | 515 ± 94 | 537 ± 122 |
| 4 | 211 ± 14 | 289 ± 38 | 318 ± 53 | 330 ± 40 | 474 ± 42 | 489 ± 51 |

(iii) Tumor Growth Inhibition Analysis

Tumor growth inhibition rate for BCY6136 in the OE21 xenograft was calculated based on tumor volume measurements at day 23 after the start of treatment.

TABLE 58

Tumor growth inhibition analysis

| Group | Treatment | Tumor Volume ($mm^3$)[a] | T/C[b] (%) | TGI (%) | P value |
|---|---|---|---|---|---|
| 1 | Vehicle, qw | 1586 ± 57 | — | — | — |
| 2 | BCY6136, 1 mpk, qw | 1155 ± 98 | 72.8 | 30.4 | p < 0.05 |
| 3 | BCY6136, 2 mpk, qw | 537 ± 122 | 33.9 | 73.4 | p < 0.001 |
| 4 | BCY6136, 3 mpk, qw | 489 ± 51 | 30.8 | 76.7 | p < 0.001 |

[a]Mean ± SEM.
[b]Tumor growth inhibition is calculated by dividing the group average tumor volume for the treated group by the group average tumor volume for the control group (T/C).

(e) Results Summary and Discussion

In this study, the therapeutic efficacy of BCY6136 in the OE21 model was evaluated. The measured body weight and tumor volume of all treatment groups at various time points are shown in the FIG. 31 and Tables 57 and 58.

The mean tumor size of vehicle treated mice reached 1586 $mm^3$ on day 23. BCY6136 at 1 mg/kg, qw (TV=1155 $mm^3$, TGI=30.4% p<0.05) showed slight anti-tumor activity. BCY6136 at 2 mg/kg, qw (TV=537 mm³, TGI=73.4%, p<0.001) and 3 mg/kg, qw (TV=489 mm³, TGI=76.7%, p<0.001) produced significant anti-tumor activity.

In this study, no obvious body weight loss was found in all the groups during the treatment schedule.

Study 22: In Vivo Efficacy Test of BCY6136 and BCY6082 in Treatment of MOLP-8 Xenograft in CB17-SCID Mice (a) Study Objective The objective of the research is to evaluate the in vivo anti-tumor efficacy of BCY6136 and BCY6082 in treatment of MOLP-8 xenograft in CB17-SCID mice.

(b) Experimental Design

| Group | Treatment | n | Dose (mg/kg) | Dosing Volume (µl/g) | Dosing Route | Schedule |
|---|---|---|---|---|---|---|
| 1 | Vehicle | 3 | — | 10 | iv | qw |
| 2 | BCY6136 | 3 | 1 | 10 | iv | qw |
| 3 | BCY6136 | 3 | 2 | 10 | iv | qw |
| 4 | BCY6136 | 3 | 3 | 10 | iv | qw |
| 5 | BCY6082 | 3 | 1 | 10 | iv | qw |
| 6 | BCY6082 | 3 | 2 | 10 | iv | qw |
| 7 | BCY6082 | 3 | 3 | 10 | iv | qw |

(iii) Testing Article Formulation Preparation

| Treatment | Concentration (mg/ml) | Formulation |
|---|---|---|
| Vehicle | — | 50 mM Acetate, 10% sucrose pH = 5 |
| BCY6136 | 0.1 | Dilute 90 µl 1 mg/ml BCY6136 stocks* with 810 µl buffer*** |
|  | 0.2 | Dilute 180 µl 1 mg/ml BCY6136 stocks* with 720 µl buffer*** |
|  | 0.3 | Dilute 270 µl 1 mg/ml BCY6136 stocks* with 630 µl buffer*** |
| BCY6082 | 0.1 | Dilute 90 µl 1 mg/ml BCY6082 stocks** with 810 µl buffer*** |
|  | 0.2 | Dilute 180 µl 1 mg/ml BCY6082 stocks** with 720 µl buffer*** |
|  | 0.3 | Dilute 270 µl 1 mg/ml BCY6082 stocks** with 630 µl buffer*** |

*BCY6136 stocks: 10.93 mg BCY6136 dissolved to 10.93 mL 50 mM Acetate, 10% sucrose, pH = 5, and separated into individual tubes and stored at −80° C.
**BCY6082 stocks: 2.43 mg BCY6136 dissolved to 2.43 mL 50 mM Acetate, 10% sucrose, pH = 5, and separated into individual tubes and stored at −80° C.
***Buffer: 50 mM Acetate, 10% sucrose pH = 5

(d) Results (i) Body Weight change and Tumor Growth Curve

Figure 32:
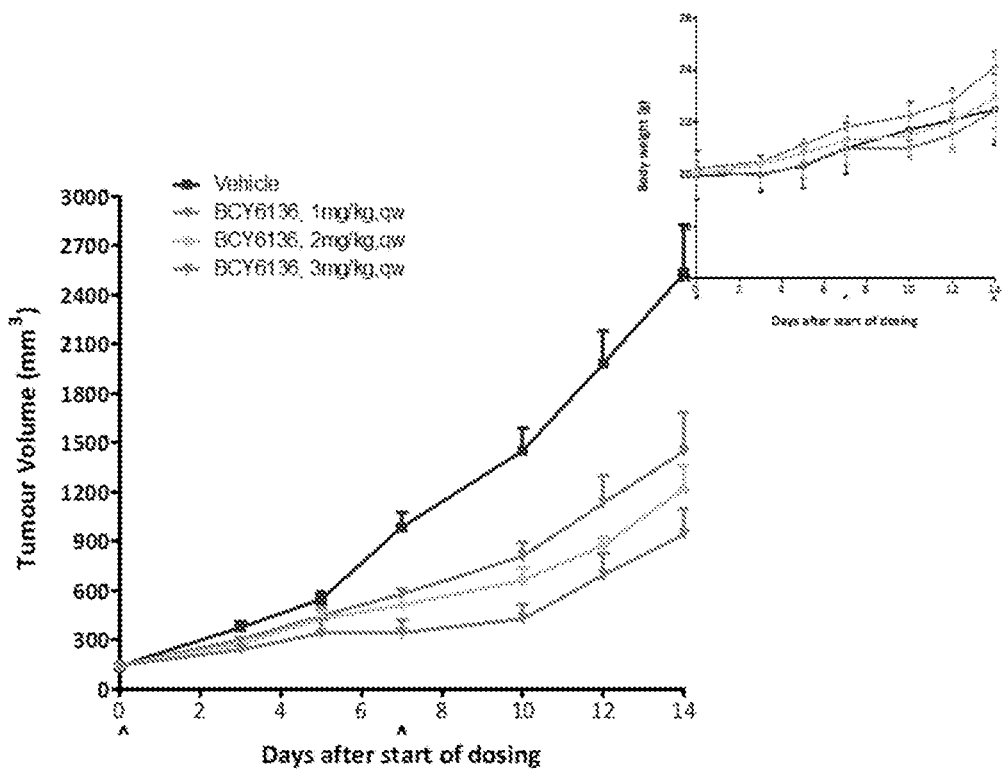
FIG. 32: Body weight changes and tumor volume traces after administering BCY6136 to female CB17-SCID mice bearing MOLP-8 xenograft. Data points represent group mean body weight.
Figure 33:
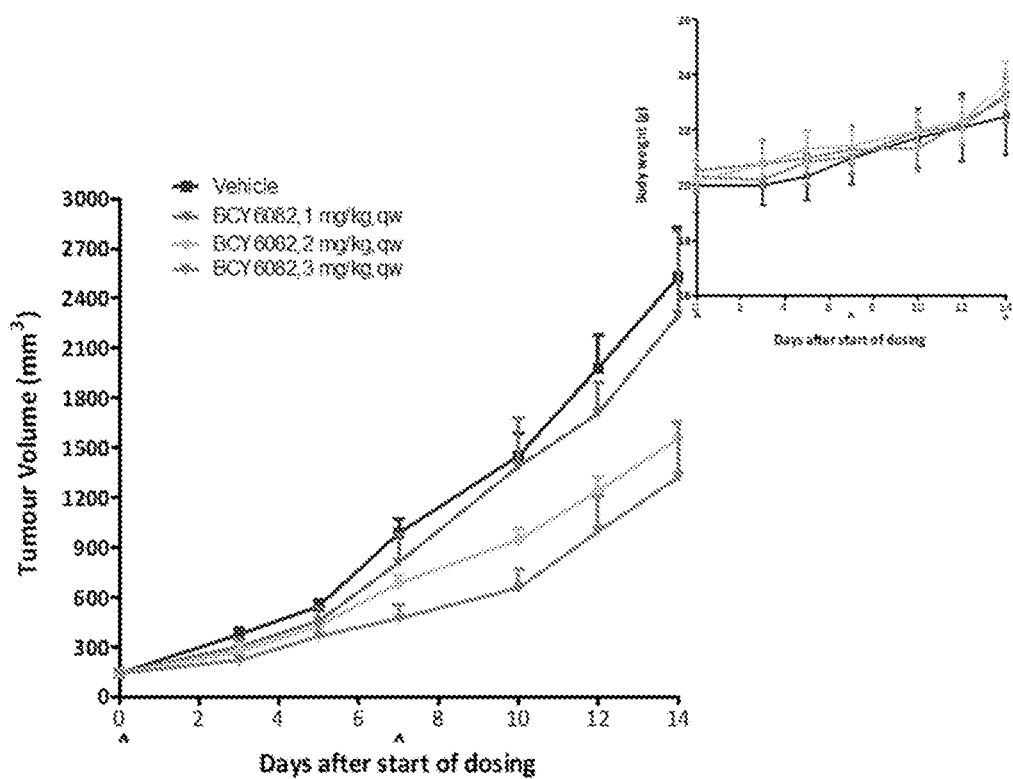
FIG. 33: Body weight changes and Tumor volume traces after administering BCY6082 to female CB17-SCID mice bearing MOLP-8 xenograft. Data points represent group mean body weight.
Figure 34:
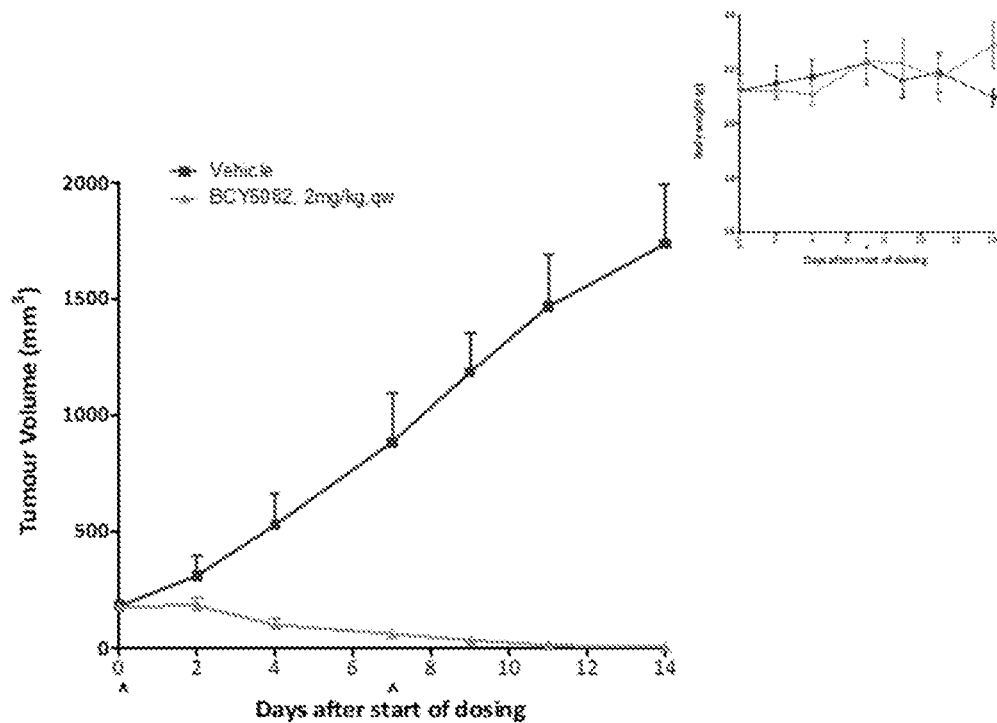
FIGS. 34 to 42: Body weight changes and tumor volume traces after administering BCY6082 (FIG. 34, BCY6031 (FIG. 35), BCY6173 (FIG. 36), BCY6135 (FIG. 37), BCY6033 (FIG. 38), BCY6136 (FIG. 39), BCY6174 (FIG. 40), BCY6175 (FIG. 41) and ADC (FIG. 42) to female BALB/c nude mice bearing HT1080 xenograft. Data points represent group mean body weight.
Figure 35:
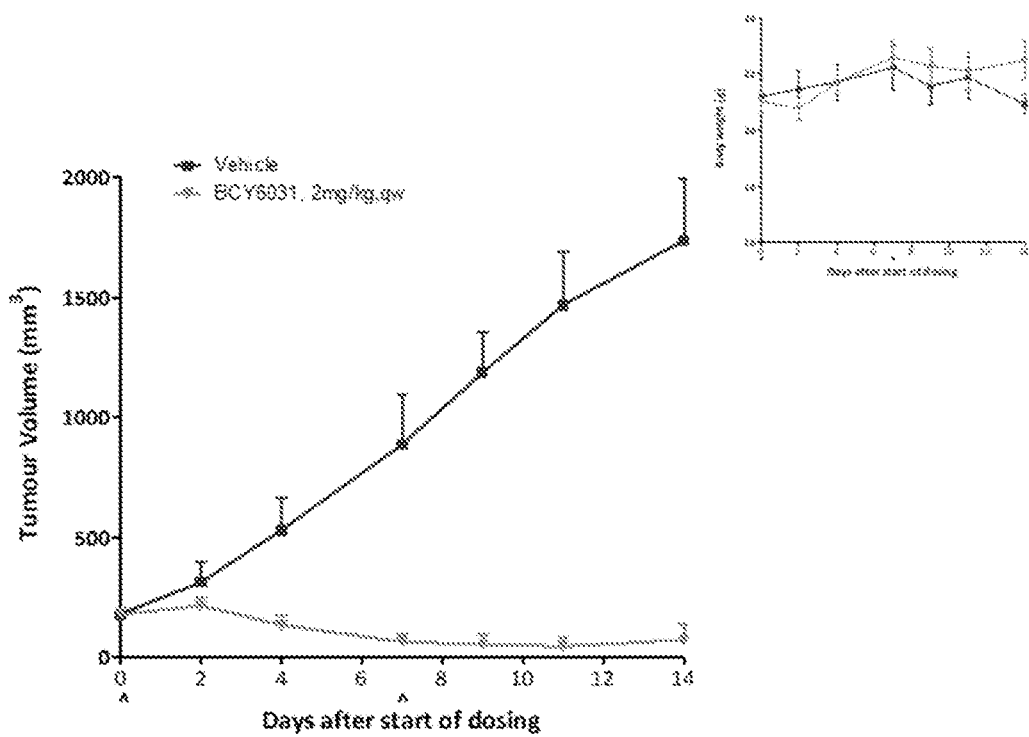
Figure 36:
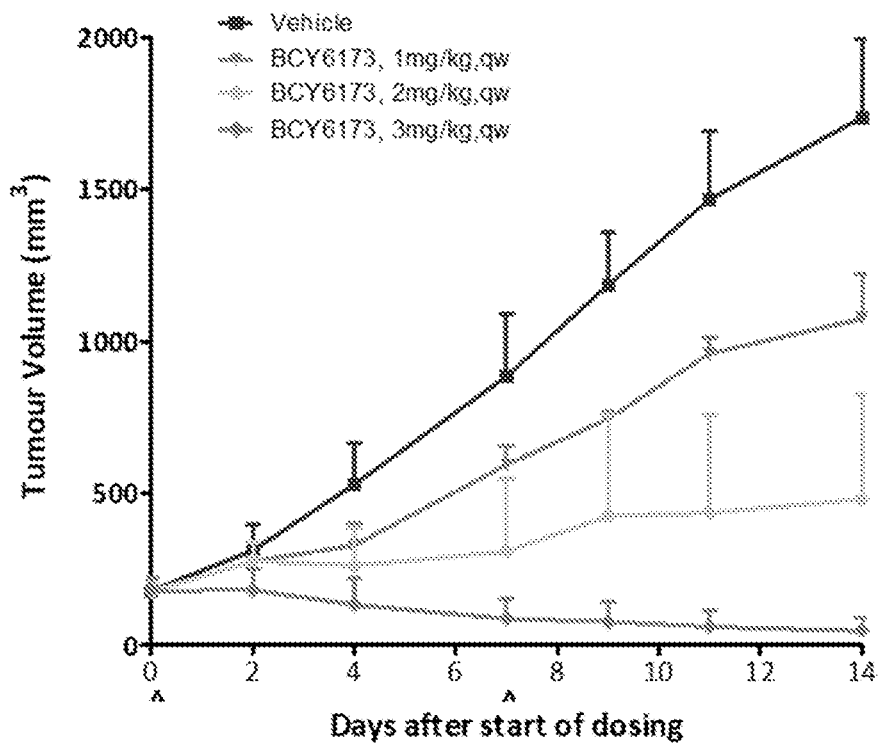
Figure 37:
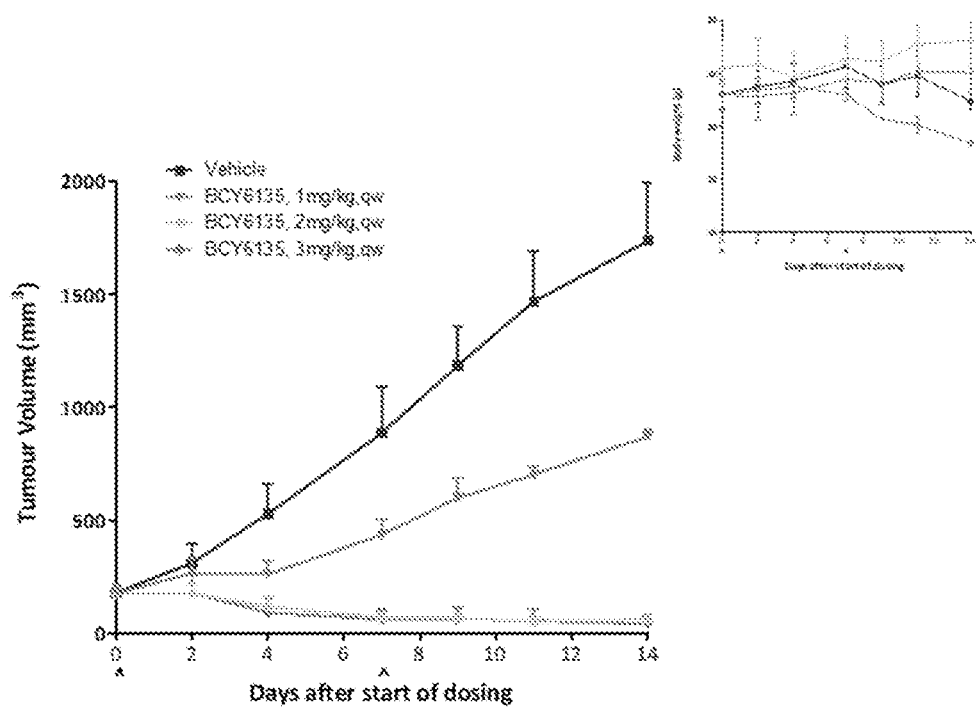
Figure 38:
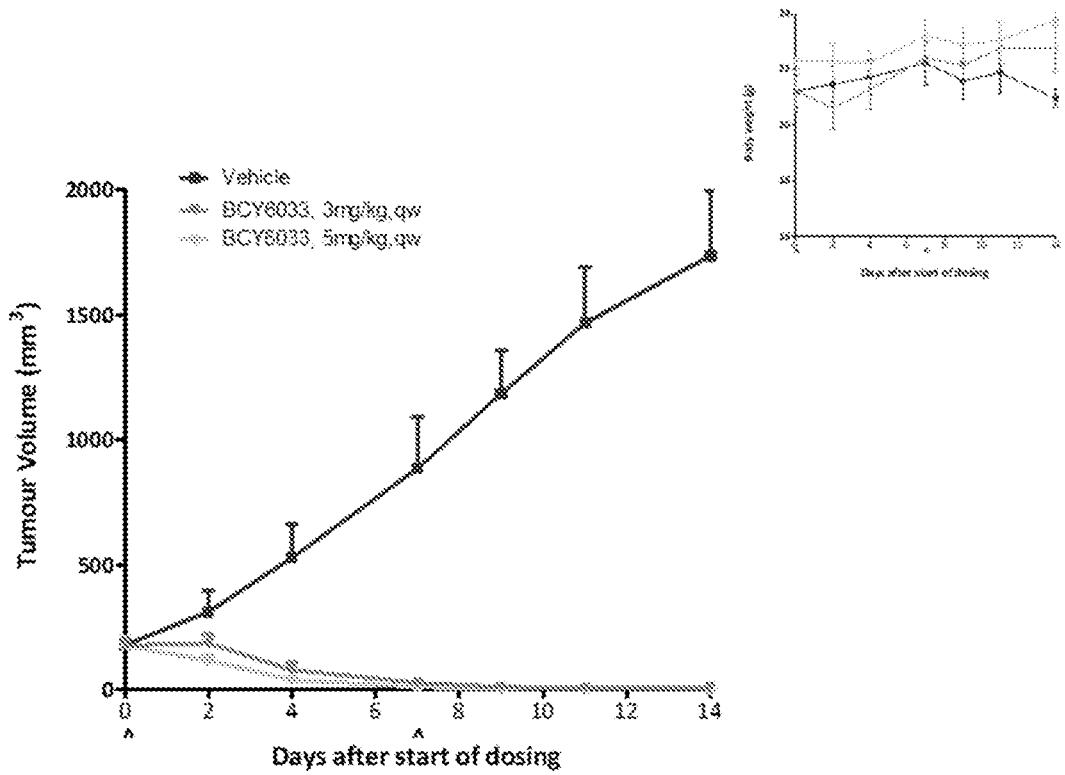
Figure 39:
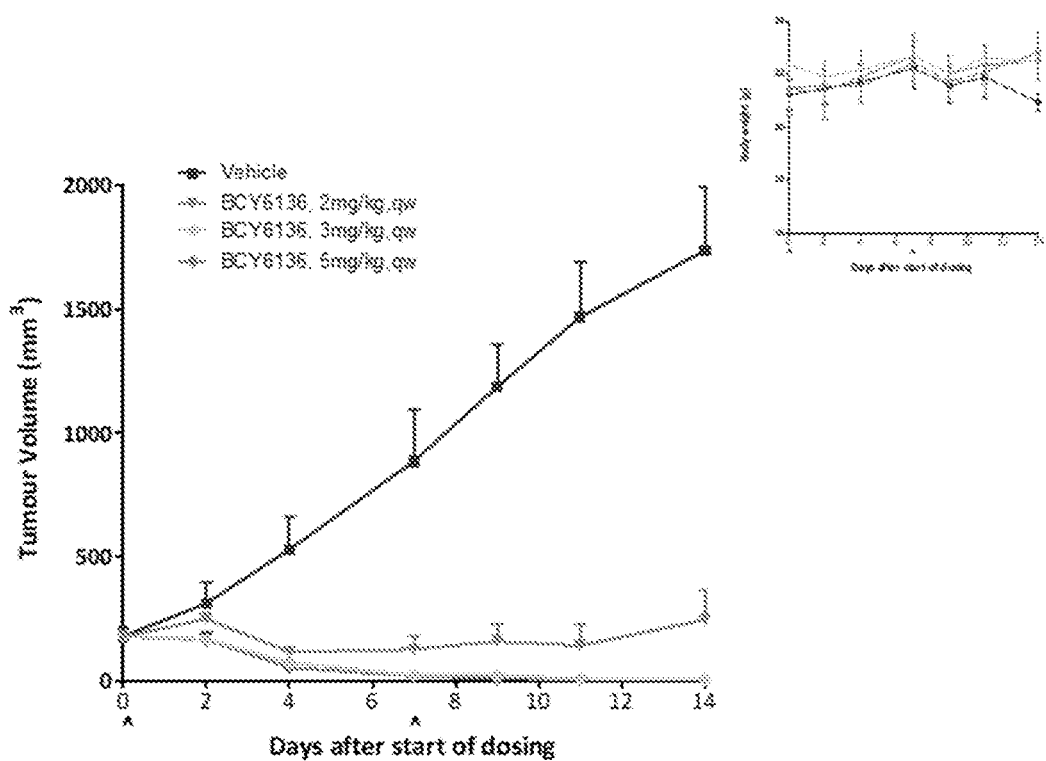
Figure 40:
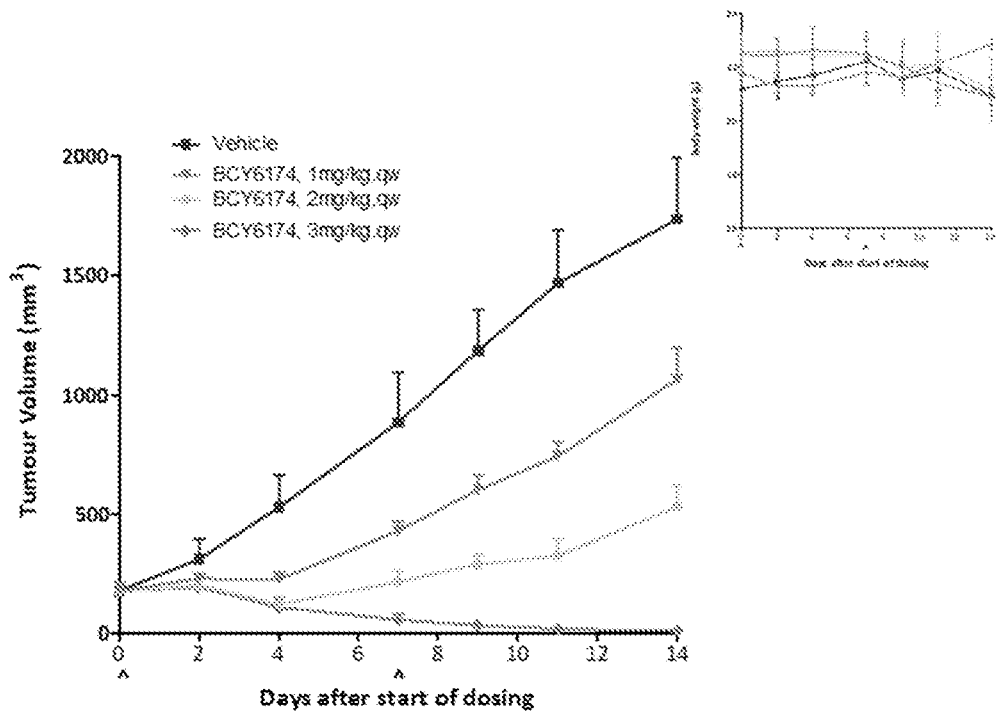
Figure 41:
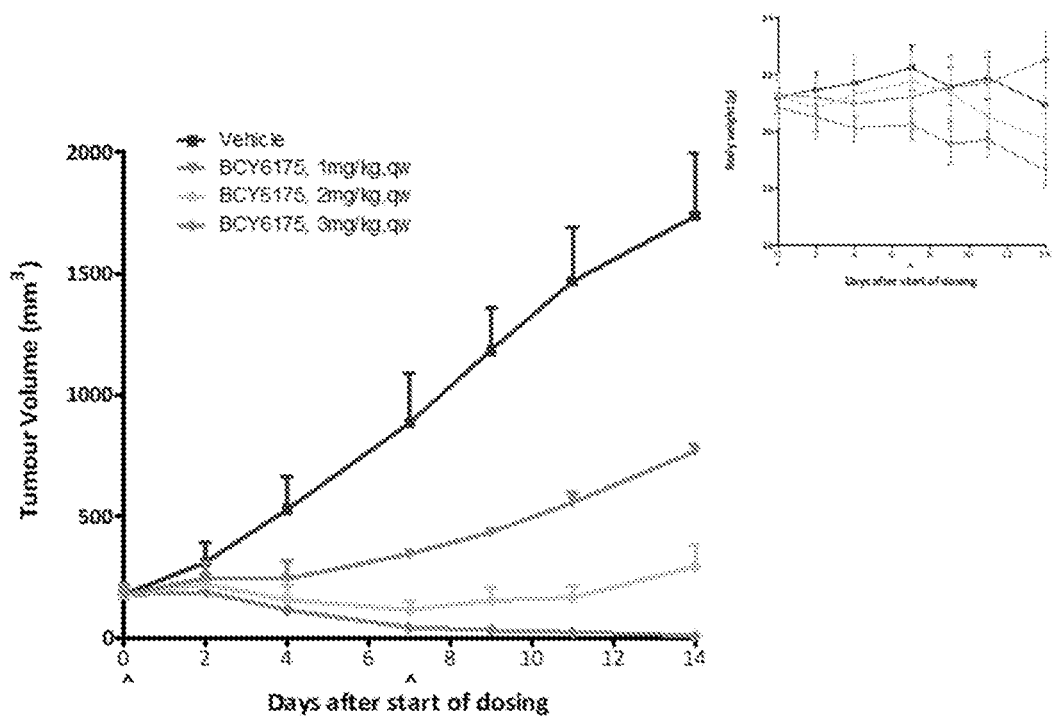
Figure 42:
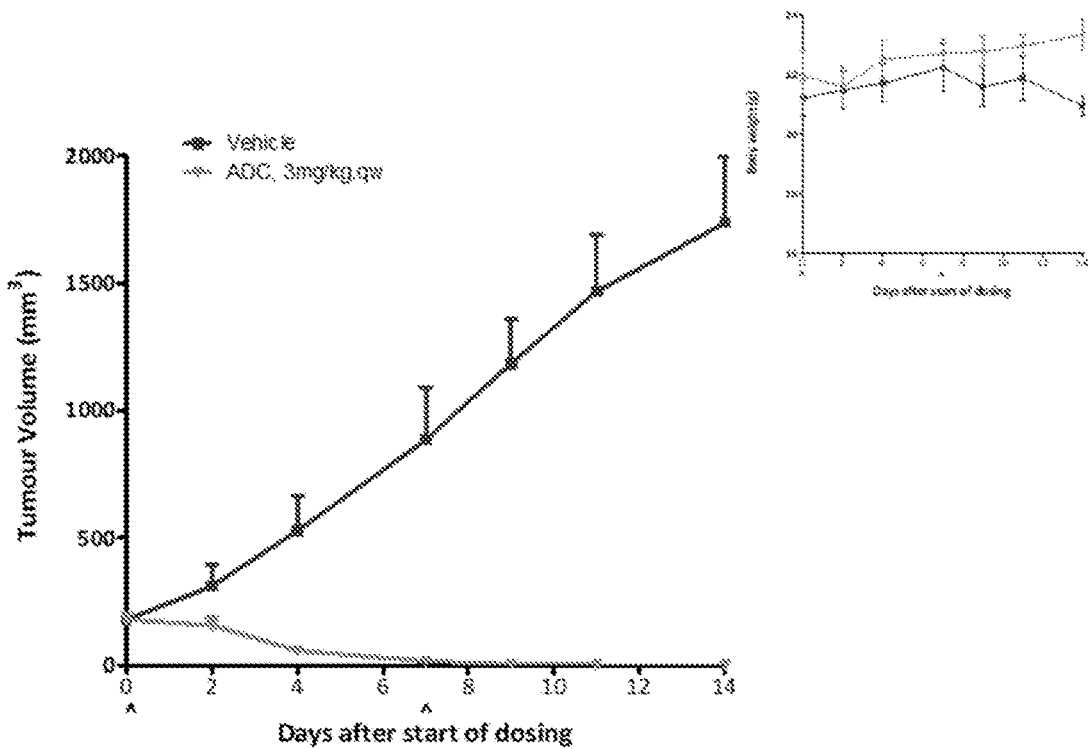

Body weight and tumor growth curve are shown in FIGS. 32 and 33.

(ii) Tumor Volume Trace

Mean tumor volume over time in female CB17-SCID mice bearing MOLP-8 xenograft is shown in Table 59.

TABLE 59

Tumor volume trace over time

| Gr. | Treatment | \multicolumn{7}{c}{Days after the start of treatment} |
|---|---|---|---|---|---|---|---|---|

| Gr. | Treatment | 0 | 2 | 4 | 7 | 9 | 11 | 14 |
|---|---|---|---|---|---|---|---|---|
| 1 | Vehicle, qw | 139 ± 2 | 375 ± 36 | 604 ± 28 | 984 ± 88 | 1451 ± 135 | 1981 ± 196 | 2528 ± 295 |
| 2 | BCY6136, 1 mpk, qw | 143 ± 13 | 299 ± 6 | 444 ± 49 | 576 ± 31 | 806 ± 85 | 1132 ± 170 | 1446 ± 234 |
| 3 | BCY6136, 2 mpk, qw | 140 ± 15 | 271 ± 43 | 250 ± 2 | 509 ± 23 | 662 ± 78 | 873 ± 49 | 1218 ± 144 |
| 4 | BCY6136, 3 mpk, qw | 142 ± 19 | 239 ± 67 | 197 ± 20 | 342 ± 78 | 425 ± 90 | 693 ± 133 | 938 ± 155 |
| 5 | BCY6082, 1 mpk, qw | 142 ± 4 | 303 ± 49 | 456 ± 83 | 809 ± 169 | 1365 ± 277 | 1708 ± 190 | 2296 ± 511 |
| 6 | BCY6082, 2 mpk, qw | 139 ± 5 | 273 ± 46 | 428 ± 18 | 682 ± 50 | 945 ± 73 | 1240 ± 85 | 1554 ± 84 |
| 7 | BCY6082, 3 mpk, qw | 142 ± 4 | 219 ± 7 | 369 ± 77 | 471 ± 81 | 656 ± 115 | 997 ± 212 | 1321 ± 336 |

(c) Experimental Methods and Procedures (i) Cell Culture

The MOLP-8 tumor cells were maintained in vitro as a monolayer culture in RMPI-1640 supplemented with 20% heat inactivated fetal bovine serum at 37° C. in an atmosphere of 5% $CO_2$ in air. The tumor cells were routinely subcultured by trypsin-EDTA treatment. The cells growing in an exponential growth phase were harvested and counted for tumor inoculation.

(ii) Tumor Inoculation

Each mouse was inoculated subcutaneously at the right flank with MOLP-8 tumor cells (10×10⁶) in 0.2 ml PBS with 50% matrigel for tumor development. 36 animals were randomized when the average tumor volume reached 141 mm³. The test article administration and the animal numbers in each group were shown in the experimental design table.

(iii) Tumor Growth Inhibition Analysis

Tumor growth inhibition rate for BCY6136 and BCY6082 in the MOLP-8 xenograft model was calculated based on tumor volume measurements at day 14 after the start of treatment.

TABLE 60

Tumor growth inhibition analysis

| Gr | Treatment | Tumor Volume (mm³)$^a$ | T/C$^b$ (%) | TGI (%) | P value compared with vehicle |
|---|---|---|---|---|---|
| 1 | Vehicle, qw | 2528 ± 295 | — | — | — |
| 2 | BCY6136, 1 mpk, qw | 1446 ± 234 | 57.2 | 45.5 | p > 0.05 |
| 3 | BCY6136, 2 mpk, qw | 1218 ± 144 | 48.2 | 54.9 | p < 0.05 |
| 4 | BCY6136, 3 mpk, qw | 938 ± 155 | 37.1 | 66.7 | p < 0.01 |

TABLE 60-continued

Tumor growth inhibition analysis

| Gr | Treatment | Tumor Volume (mm³)[a] | T/C[b] (%) | TGI (%) | P value compared with vehicle |
|---|---|---|---|---|---|
| 5 | BCY6082, 1 mpk, qw | 2296 ± 511 | 90.8 | 9.8 | p > 0.05 |
| 6 | BCY6082, 2 mpk, qw | 1554 ± 84 | 61.5 | 40.8 | p > 0.05 |
| 7 | BCY6082, 3 mpk, qw | 1321 ± 336 | 52.3 | 50.6 | p < 0.05 |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCY6136 and BCY6082 in the MOLP-8 xenograft model was evaluated. The measured body weights and tumor volumes of all treatment groups at various time points are shown in the FIGS. 32 and 33 and Tables 59 and 60.

The mean tumor size of vehicle treated mice reached 2528 mm³ on day 14. BCY6136 at 1 mg/kg (TV=1146 mm³, TGI=45.5%, p>0.05), 2 mg/kg (TV=1218 mm³, TGI=54.9%, p<0.05) and 3 mg/kg (TV=938 mm³, TGI=66.7%, p<0.01) produced dose-dependent antitumor activity, but all of dosage didn't regress the tumors in MOLP-8 xenografts.

BCY6082 at 1 mg/kg (TV=2296 mm³, TGI=9.8%, p>0.05) and 2 mg/kg (TV=1554 mm³, TGI=40.8%, p>0.05) didn't show obvious anti-tumor activity. BCY6082 at 3 mg/kg inhibited the tumor growth significantly (TV=1321 mm³, TGI=50.6%, p<0.05), but didn't regress the tumors in MOLP-8 xenografts.

In this study, all of mice maintained the bodyweight well.

Study 23: In Vivo Efficacy Test of BCYs in Treatment of HT1080 Xenograft in BALB/c Nude Mice (a) Study Objective The objective of the research was to evaluate the in vivo anti-tumor efficacy of BCYs in treatment of HT1080 xenograft model in BALB/c nude mice.

(b) Experimental Design

| Group | Treatment | n | Dose (mg/kg) | Dosing Volume (μl/g) | Dosing Route | Schedule |
|---|---|---|---|---|---|---|
| 1 | Vehicle | 3 | — | 10 | iv | qw |
| 2 | BCY6082 | 3 | 2 | 10 | iv | qw |
| 3 | BCY6031 | 3 | 2 | 10 | iv | qw |
| 4 | BCY6173 | 3 | 1 | 10 | iv | qw |
| 5 | BCY6173 | 3 | 2 | 10 | iv | qw |
| 6 | BCY6173 | 3 | 3 | 10 | iv | qw |
| 7 | BCY6135 | 3 | 1 | 10 | iv | qw |
| 8 | BCY6135 | 3 | 2 | 10 | iv | qw |
| 9 | BCY6135 | 3 | 3 | 10 | iv | qw |
| 10 | BCY6033 | 3 | 3 | 10 | iv | qw |
| 11 | BCY6033 | 3 | 5 | 10 | iv | qw |
| 12 | BCY6136 | 3 | 2 | 10 | iv | qw |
| 13 | BCY6136 | 3 | 3 | 10 | iv | qw |
| 14 | BCY6136 | 3 | 5 | 10 | iv | qw |
| 15 | BCY6174 | 3 | 1 | 10 | iv | qw |
| 16 | BCY6174 | 3 | 2 | 10 | iv | qw |
| 17 | BCY6174 | 3 | 3 | 10 | iv | qw |
| 18 | BCY6175 | 3 | 1 | 10 | iv | qw |
| 19 | BCY6175 | 3 | 2 | 10 | iv | qw |
| 20 | BCY6175 | 3 | 3 | 10 | iv | qw |
| 21 | ADC | 3 | 3 | 10 | iv | qw |

Note:
n: animal number;
Dosing volume: adjust dosing volume based on body weight 10 μl/g.

(c) Experimental Methods and Procedures (i) Cell Culture

The HT1080 tumor cells will be maintained in medium supplemented with 10% heat inactivated fetal bovine serum at 37° C. in an atmosphere of 5% $CO_2$ in air. The tumor cells will be routinely subcultured twice weekly. The cells growing in an exponential growth phase will be harvested and counted for tumor inoculation.

(ii) Tumor Inoculation

Each mouse will be inoculated subcutaneously at the right flank with HT1080 tumor cells ($5*10^6$) for tumor development. The animals will be randomized and treatment will be started when the average tumor volume reaches approximately 150-200 mm³. The test article administration and the animal numbers in each group are shown in the following experimental design table.

(iii) Testing Article Formulation Preparation

| Treatment | Dose (mg/ml) | Formulation |
|---|---|---|
| Vehicle | — | 50 mM Acetate/acetic acid pH 5 10% sucrose |
| BCY6082 | 0.2 | Dilute 160 μl 1 mg/ml BCY6082 stock with 640 μl buffer |
| BCY6031 | 0.2 | Dilute 180 μl 1 mg/ml BCY6031 stock with 720 μl buffer |
| BCY6173 | 1 | Dissolve 2.13 mg BCY6173 with 2.04 ml buffer |
| | 0.1 | Dilute 90 μl 1 mg/ml BCY6173 stock with 810 μl buffer |
| | 0.2 | Dilute 180 μl 1 mg/ml BCY6173 stock with 720 μl buffer |
| | 0.3 | Dilute 270 μl 1 mg/ml BCY6173 stock with 630 μl buffer |
| BCY6135 | 1 | Dissolve 2 mg BCY6135 with 1.9 ml buffer |
| | 0.1 | Dilute 90 μl 1 mg/ml BCY6135 stock with 810 μl buffer |
| | 0.2 | Dilute 180 μl 1 mg/ml BCY6135 stock with 720 μl buffer |
| | 0.3 | Dilute 270 μl 1 mg/ml BCY6135 stock with 630 μl buffer |
| BCY6033 | 0.3 | Dilute 270 μl 1 mg/ml BCY6033 stock with 630 μl buffer |
| | 0.5 | Dilute 450 μl 1 mg/ml BCY6033 stock with 450 μl buffer |
| BCY6136 | 0.2 | Dilute 200 μl 1 mg/ml BCY6136 stock with 800 μl buffer |
| | 0.3 | Dilute 300 μl 1 mg/ml BCY6136 stock with 700 μl buffer |
| | 0.5 | Dilute 500 μl 1 mg/ml BCY6136 stock with 500 μl buffer |
| BCY6174 | 1 | Dissolve 2.69 mg BCY6174 with 2.677 ml buffer |
| | 0.1 | Dilute 90 μl 1 mg/ml BCY6174 stock with 810 μl buffer |
| | 0.2 | Dilute 180 μl 1 mg/ml BCY6174 stock with 720 μl buffer |
| | 0.3 | Dilute 270 μl 1 mg/ml BCY6174 stock with 630 μl buffer |

-continued

| Treatment | Dose (mg/ml) | Formulation |
|---|---|---|
| BCY6175 | 1 | Dissolve 2 mg BCY6175 with 1.924 ml buffer |
|  | 0.1 | Dilute 90 µl 1 mg/ml BCY6175 stock with 810 µl buffer |
|  | 0.2 | Dilute 180 µl 1 mg/ml BCY6175 stock with 720 µl buffer |
|  | 0.3 | Dilute 270 µl 1 mg/ml BCY6175 stock with 630 µl buffer |
| ADC | 0.3 | Dilute 25.78 µl 10.47 mg/ml ADC stock with 874.22 µl 25 mM Histidine pH 7 10% sucrose |

(d) Results (i) Body Weight change and Tumor Growth Curve

Body weight and tumor growth curve are shown in FIGS. 34 to 42.

(ii) Tumor Volume Trace

Mean tumor volume over time in female Balb/c nude mice bearing HT1080 xenograft is shown in Table 61.

TABLE 61

Tumor volume trace over time

| Gr | Treatment | Days after the start of treatment | | | | | | |
|---|---|---|---|---|---|---|---|---|
|  |  | 0 | 2 | 4 | 7 | 9 | 11 | 14 |
| 1 | Vehicle, qw | 179 ± 22 | 312 ± 84 | 529 ± 135 | 886 ± 207 | 1185 ± 172 | 1467 ± 224 | 1737 ± 258 |
| 2 | BCY6082, 2 mpk, qw | 177 ± 16 | 183 ± 31 | 99 ± 27 | 61 ± 17 | 33 ± 10 | 12 ± 5 | 5 ± 3 |
| 3 | BCY6031, 2 mpk, qw | 177 ± 24 | 215 ± 35 | 133 ± 37 | 63 ± 31 | 53 ± 37 | 45 ± 36 | 71 ± 67 |
| 4 | BCY6173 1 mpk, qw | 178 ± 26 | 276 ± 8 | 328 ± 73 | 594 ± 62 | 745 ± 22 | 960 ± 53 | 1074 ± 150 |
| 5 | BCY6173, 2 mpk, qw | 178 ± 28 | 277 ± 61 | 262 ± 125 | 309 ± 238 | 425 ± 334 | 436 ± 323 | 480 ± 347 |
| 6 | BCY6173, 3 mpk, qw | 179 ± 43 | 182 ± 71 | 133 ± 88 | 87 ± 68 | 77 ± 65 | 60 ± 54 | 47 ± 42 |
| 7 | BCY6135, 1 mpk, qw | 178 ± 22 | 267 ± 66 | 262 ± 58 | 436 ± 67 | 599 ± 89 | 703 ± 36 | 871 ± 28 |
| 8 | BCY6135, 2 mpk, qw | 178 ± 23 | 176 ± 48 | 117 ± 43 | 70 ± 23 | 67 ± 23 | 52 ± 21 | 62 ± 7 |
| 9 | BCY6135, 3 mpk, qw | 177 ± 39 | 178 ± 79 | 92 ± 67 | 62 ± 46 | 62 ± 51 | 57 ± 51 | 44 ± 40 |
| 10 | BCY6033 3 mpk, qw | 178 ± 26 | 186 ± 34 | 79 ± 30 | 29 ± 15 | 12 ± 8 | 6 ± 4 | 9 ± 7 |
| 11 | BCY6033 5 mpk, qw | 178 ± 36 | 117 ± 20 | 41 ± 10 | 12 ± 4 | 6 ± 2 | 4 ± 0 | 0 ± 0 |
| 12 | BCY6136 2mpk, qw | 178 ± 19 | 249 ± 22 | 115 ± 8 | 126 ± 53 | 158 ± 71 | 140 ± 89 | 245 ± 116 |
| 13 | BCY6136 3 mpk, qw | 178 ± 36 | 168 ± 21 | 72 ± 18 | 22 ± 7 | 21 ± 15 | 8 ± 6 | 3 ± 2 |
| 14 | BCY6136 5 mpk, qw | 178 ± 26 | 165 ± 33 | 52 ± 10 | 18 ± 7 | 9 ± 4 | 5 ± 2 | 2 ± 1 |
| 15 | BCY6174 1 mpk, qw | 180 ± 35 | 231 ± 19 | 226 ± 29 | 432 ± 37 | 602 ± 63 | 742 ± 62 | 1066 ± 130 |
| 16 | BCY6174 2 mpk, qw | 178 ± 31 | 203 ± 50 | 123 ± 29 | 216 ± 47 | 291 ± 40 | 326 ± 68 | 532 ± 91 |
| 17 | BCY6174 3 mpk, qw | 178 ± 33 | 195 ± 13 | 110 ± 39 | 58 ± 23 | 34 ± 17 | 21 ± 11 | 11 ± 7 |
| 18 | BCY6175 1 mpk, qw | 178 ± 27 | 248 ± 62 | 244 ± 74 | 347 ± 18 | 435 ± 18 | 558 ± 38 | 769 ± 26 |
| 19 | BCY6175 2 mpk, qw | 178 ± 22 | 223 ± 42v | 158 ± 59 | 116 ± 35 | 156 ± 52 | 166 ± 51 | 295 ± 88 |
| 20 | BCY6175 3 mpk, qw | 179 ± 39 | 189 ± 48 | 116 ± 50 | 43 ± 18 | 33 ± 18 | 25 ± 13 | 11 ± 9 |
| 21 | ADC 3 mpk, qw | 180 ± 26 | 158 ± 30 | 58 ± 8 | 18 ± 2 | 7 ± 1 | 2 ± 2 | 0 ± 0 |

(iii) Tumor Growth Inhibition Analysis

Tumor growth inhibition rate for BCYs in the HT1080 xenograft model was calculated based on tumor volume measurements at day 14 after the start of treatment.

TABLE 62

Tumor growth inhibition analysis

| Gr | Treatment | Tumor Volume (mm$^3$)$^a$ | T/C$^b$ (%) | TGI (%) | P value compare |
|---|---|---|---|---|---|
| 1 | Vehicle, qw | 1737 ± 258 | — | — | — |
| 2 | BCY6082, 2 mpk, | 5 ± 3 | 0.3 | 111.1 | p < 0.01 |
| 3 | BCY6031, 2 mpk, | 71 ± 67 | 4.1 | 106.8 | p < 0.01 |
| 4 | BCY6173, 1 mpk, | 1074 ± 150 | 61.8 | 42.5 | p > 0.05 |
| 5 | BCY6173, 2 mpk, | 480 ± 347 | 27.6 | 80.6 | p < 0.05 |
| 6 | BCY6173, 3 mpk, | 47 ± 42 | 2.7 | 108.4 | p < 0.01 |
| 7 | BCY6135, 1 mpk, | 871 ± 28 | 50.1 | 55.5 | p < 0.01 |
| 8 | BCY6135, 2 mpk, | 62 ± 7 | 3.5 | 107.5 | p < 0.001 |

TABLE 62-continued

Tumor growth inhibition analysis

| Gr | Treatment | Tumor Volume (mm³)[a] | T/C[b] (%) | TGI (%) | P value compare |
|---|---|---|---|---|---|
| 9 | BCY6135, 3 mpk, | 44 ± 40 | 2.5 | 108.6 | p < 0.001 |
| 10 | BCY6033, 3 mpk, | 9 ± 7 | 0.5 | 110.8 | p < 0.001 |
| 11 | BCY6033, 5 mpk, | 0 ± 0 | 0.0 | 111.4 | p < 0.001 |
| 12 | BCY6136, 2 mpk, qw | 245 ± 116 | 14.1 | 95.7 | p < 0.001 |
| 13 | BCY6136, 3 mpk, | 3 ± 2 | 0.2 | 111.2 | p < 0.001 |
| 14 | BCY6136, 5 mpk, | 2 ± 1 | 0.1 | 111.3 | p < 0.001 |
| 15 | BCY6174, 1 mpk, | 1066 ± 130 | 61.4 | 43.1 | p < 0.05 |
| 16 | BCY6174, 2 mpk, qw | 532 ± 91 | 30.6 | 77.3 | p < 0.01 |
| 17 | BCY6174, 3 mpk, | 11 ± 7 | 0.6 | 110.7 | p < 0.001 |
| 18 | BCY6175, 1 mpk, | 769 ± 26 | 44.3 | 62.1 | p < 0.01 |
| 19 | BCY6175, 2 mpk, | 295 ± 88 | 17.0 | 92.5 | p < 0.001 |
| 20 | BCY6175, 3 mpk, | 11 ± 9 | 0.6 | 110.8 | p < 0.001 |
| 21 | ADC, 3 mpk, qw | 0 ± 0 | 0.0 | 111.5 | — |

[a]Mean ± SEM.
[b]Tumor Growth Inhibition is calculated by dividing the group average tumor volume for the treated group by the group average tumor volume for the control group (T/C).

(e) Results Summary and Discussion

In this study, the therapeutic efficacy of BCYs in the HT1080 xenograft model was evaluated.

The measured body weights and tumor volumes of all treatment groups at various time points are shown in the FIGS. 34 to 42 and Tables 61 and 62.

The mean tumor size of vehicle treated mice reached 1737 mm³ on day 14.

BCY6082 at 2 mg/kg, qw (TV=5 mm³, TGI=111.1%, p<0.01) and BCY6031 at 2 mg/kg qw (TV=7 mm³, TGI=106.8%, p<0.01) showed potent anti-tumor activity.

BCY6173 at 1 mg/kg, qw (TV=1074 mm³, TGI=42.5%, p>0.05), 2 mg/kg, qw (TV=480 mm³, TGI=80.6%, p<0.05) and 3 mg/kg, qw (TV=7 mm³, TGI=108.4%, p<0.01) produced dose-dependent antitumor activity.

BCY6135 at 1 mg/kg, qw (TV=871 mm³, TGI=55.5%, p<0.01), 2 mg/kg, qw (TV=62 mm³, TGI=107.5%, p<0.001) and 3 mg/kg, qw (TV=44 mm³, TGI=108.6%, p<0.001) produced dose-dependent antitumor activity.

BCY6033 at 3 mg/kg, qw (TV=9 mm³, TGI=110.8%, p<0.001) and 5 mg/kg, qw (TV=0 mm³, TGI=111.4%, p<0.001) showed potent anti-tumor activity, and completely eradicated the tumors by day 14 at 5 mg/kg.

BCY6136 at 2 mg/kg, qw (TV=345 mm³, TGI=95.7%, p<0.001), 3 mg/kg, qw (TV=3 mm³, TGI=111.2%, p<0.001) and 5 mg/kg, qw (TV=2 mm³, TGI=111.3%, p<0.001) showed potent anti-tumor activity.

BCY6174 at 1 mg/kg, qw (TV=1066 mm³, TGI=43.1%, p<0.05), 2 mg/kg, qw (TV=532 mm³, TGI=77.3%, p<0.01) and 3 mg/kg, qw (TV=11 mm³, TGI=110.7%, p<0.001) produced dose-dependent antitumor activity.

BCY6175 at 1 mg/kg, qw (TV=769 mm³, TGI=62.1%, p<0.01), 2 mg/kg, qw (TV=295 mm³, TGI=92.5%, p<0.001) and 3 mg/kg, qw (TV=11 mm³, TGI=110.8%, p<0.001) produced dose-dependent antitumor activity.

ADC at 3 mg/kg, qw (TV=0 mm³, TGI=111.5%) completely eradicated the tumors by day 14.

Study 24: Investigation of Association Between Copy Number Variation (CNV) and Gene Expression for EphA2 from Multiple Tumour Types Methods 1. Select all studies in cBioPortal (cbioportal.org) and search for EPHA2.
   (a) Remove provisional studies.
   (b) Deselect studies with overlapping samples to prevent sample bias (based on warning in cBioPortal)—always keep PanCancer study if this is an option.
   (c) Studies selected for analysis (Table 63).

TABLE 63

Studies analysed from cBioPortal and units in study

| Study Name | Units |
|---|---|
| Breast Invasive Carcinoma (TCGA, PanCancer Atlas) | mRNA Expression Batch Normalized/Merged from Illumina HiSeq_RNASeqV2 syn4976369 |
| Lung Squamous Cell Carcinoma (TCGA, PanCancer Atlas) | mRNA Expression Batch Normalized/Merged from Illumina HiSeq_RNASeqV2 syn4976369 |
| Kidney Renal Papillary Cell Carcinoma (TCGA, PanCancer Atlas) | mRNA Expression, RSEM (Batch normalized from Illumina HiSeq_RNASeqV2) |
| Kidney Renal Clear Cell Carcinoma (TCGA, PanCancer Atlas) | mRNA Expression, RSEM (Batch normalized from Illumina HiSeq_RNASeqV2) |
| Colon Adenocarcinoma (TCGA, PanCancer Atlas) | RSEM (Batch normalized from Illumina HiSeq_RNASeqV2) |
| Head and Neck Squamous Cell Carcinoma (TCGA, PanCancer Atlas) | mRNA Expression, RSEM (Batch normalized from Illumina HiSeq_RNASeqV2) |
| Bladder Urothelial Carcinoma (TCGA, PanCancer Atlas) | RSEM (Batch normalized from Illumina HiSeq_RNASeqV2) |
| Uveal Melanoma (TCGA, PanCancer Atlas) | mRNA Expression Batch Normalized/Merged from Illumina HiSeq_RNASeqV2 syn4976369 |
| Lung Adenocarcinoma (TCGA, PanCancer Atlas) | mRNA Expression, RSEM (Batch normalized from Illumina HiSeq_RNASeqV2) |
| Ovarian Serous Cystadenocarcinoma (TCGA, PanCancer Atlas) | mRNA Expression Batch Normalized/Merged from Illumina HiSeq_RNASeqV2 syn4976369 |
| Breast Cancer (METABRIC, Nature 2012 & Nat Commun 2016) | mRNA expression (microarray) |
| Mesothelioma (TCGA, PanCancer Atlas) | mRNA Expression Batch Normalized/Merged from Illumina HiSeq_RNASeqV2 syn4976369 |
| Colorectal Adenocarcinoma (TCGA, Nature 2012) | RNA Seq RPKM |

TABLE 63-continued

Studies analysed from cBioPortal and units in study

| Study Name | Units |
|---|---|
| Cervical Squamous Cell Carcinoma (TCGA, PanCancer Atlas) | RSEM (Batch normalized from Illumina HiSeq_RNASeqV2) |
| Sarcoma (TCGA, PanCancer Atlas) | mRNA Expression Batch Normalized/Merged from Illumina HiSeq_RNASeqV2 syn4976369 |
| Cancer Cell Line Encyclopedia (Novartis/Broad, Nature 2012) | mRNA expression (microarray) |
| Rectum Adenocarcinoma (TCGA, PanCancer Atlas) | mRNA Expression Batch Normalized/Merged from Illumina HiSeq_RNASeqV2 syn4976369 |
| Liver Hepatocellular Carcinoma (TCGA, PanCancer Atlas) | EPHA2: mRNA Expression, RSEM (Batch normalized from Illumina HiSeq_RNASeqV2) |
| Stomach Adenocarcinoma (TCGA, PanCancer Atlas) | mRNA Expression Batch Normalized/Merged from Illumina HiSeq_RNASeqV2 syn4976369 |
| Uterine Corpus Endometrial Carcinoma (TCGA, PanCancer Atlas) | mRNA Expression Batch Normalized/Merged from Illumina HiSeq_RNASeqV2 syn4976369 |
| Skin Cutaneous Melanoma (TCGA, PanCancer Atlas) | mRNA Expression Batch Normalized/Merged from Illumina HiSeq_RNASeqV2 syn4976369 |
| Prostate Adenocarcinoma (TCGA, PanCancer Atlas) | mRNA Expression, RSEM (Batch normalized from Illumina HiSeq_RNASeqV2) |
| Kidney Chromophobe (TCGA, PanCancer Atlas) | mRNA Expression, RSEM (Batch normalized from Illumina HiSeq_RNASeqV2) |
| Pediatric Wilms' Tumor (TARGET, 2018) | Epha2: mRNA expression (RNA-Seq RPKM) |
| Pheochromocytoma and Paraganglioma (TCGA, PanCancer Atlas) | mRNA Expression Batch Normalized/Merged from Illumina HiSeq_RNASeqV2 syn4976369 |
| Thyroid Carcinoma (TCGA, PanCancer Atlas) | mRNA Expression Batch Normalized/Merged from Illumina HiSeq_RNASeqV2 syn4976369 |
| Esophageal Adenocarcinoma (TCGA, PanCancer Atlas) | RSEM (Batch normalized from Illumina HiSeq_RNASeqV2) |
| Cholangiocarcinoma (TCGA, PanCancer Atlas) | RSEM (Batch normalized from Illumina HiSeq_RNASeqV2) |
| Brain Lower Grade Glioma (TCGA, PanCancer Atlas) | RSEM (Batch normalized from Illumina HiSeq_RNASeqV2) |
| Thymoma (TCGA, PanCancer Atlas) | mRNA Expression Batch Normalized/Merged from Illumina HiSeq_RNASeqV2 syn4976369 |
| Pediatric Acute Lymphoid Leukemia-Phase II (TARGET, 2018) | Epha2: mRNA expression (RNA-Seq RPKM) |
| Diffuse Large B-Cell Lymphoma (TCGA, PanCancer Atlas) | mRNA Expression, RSEM (Batch normalized from Illumina HiSeq_RNASeqV2) |
| Glioblastoma Multiforme (TCGA, PanCancer Atlas) | mRNA Expression, RSEM (Batch normalized from Illumina HiSeq_RNASeqV2) |
| Metastatic Prostate Cancer, SU2C/PCF Dream Team (Robinson et al., Cell 2015) | mRNA expression/capture (RNA Seq RPKM) |
| Acute Myeloid Leukemia (TCGA, PanCancer Atlas) | mRNA Expression, RSEM (Batch normalized from Illumina HiSeq_RNASeqV2) |
| Testicular Germ Cell Tumors (TCGA, PanCancer Atlas) | mRNA Expression Batch Normalized/Merged from Illumina HiSeq_RNASeqV2 syn4976369 |
| Adrenocortical Carcinoma (TCGA, PanCancer Atlas) | RSEM (Batch normalized from Illumina HiSeq_RNASeqV2) |
| Uterine Carcinosarcoma (TCGA, PanCancer Atlas) | mRNA Expression Batch Normalized/Merged from Illumina HiSeq_RNASeqV2 syn4976369 |
| Pancreatic Adenocarcinoma (TCGA, PanCancer Atlas) | mRNA Expression Batch Normalized/Merged from Illumina HiSeq_RNASeqV2 syn4976369 |
| Prostate Adenocarcinoma (MSKCC, Cancer Cell 2010) | mRNA Expression |
| Prostate Adenocarcinoma (Fred Hutchinson CRC, Nat Med 2016) | mRNA expression |

2. Export CNV and RNA expression data from cBioPortal.

3. Test if CNVs are statistically significantly associated with changes in mRNA expression for EphA2 (log 2 not applied).
  (a) Run non-parametric Kruskal-Wallis test in GraphPad Prism (7.04) and R/R studio (threshold for significance: p<0.01).
    (i) GraphPad Prism: set up column table, run non-parametric test with no matching or pairing and do not assume Gaussian distribution.

(ii) Packages used in R:
      1. XLConnect
      2. dplyr
      3. Kruskal-Wallis Rank Sum Test: Kruskal.test.
  4. Adjust for multiple comparisons (include all possible comparisons even if n=1 within a group) in R/Rstudio using Dunn's test (threshold for significance: p<0.025).
    (a) dunn.test with multiple comparison method="bonferonni".

Results

The results are shown in Table 64 below. Across 41 publicly available datasets compiled in cBioPortal that report both Copy Number Variation (CNV) and mRNA gene expression for EphA2, there are numerous cancer types where cases have been reported with EphA2 shallow-deletions (<2 copies). Although less common, in these same cancer types a subset of tumors harbored EphA2 deep deletions (>1 copy loss or biallelic loss), EphA2 gains (2-3 copies) or EphA2 amplifications (>3 copies). Indications where >33% of tumors had either shallow-deletions or deep deletions in EphA2 included: kidney chromophobe, cholangiocarcinoma, pheochromocytoma and paraganglioma, lung squamous cancer, breast, rectum, brain lower grade glioma, liver, adrenocortical carcinoma, mesothelioma, esophageal adenocarcinoma and colon cancer. In contrast, there were no studies where >33% of samples had either gains or amplification in EphA2. Taken together these results demonstrate that deletions in EphA2 DNA are found across a variety of indications.

Approximately one third of all samples analyzed in the 41 studies harbored EphA2 CNVs. Based on this high percentage of CNVs across studies, and the high percentage of shallow deletions within specific tumor types, statistical testing was performed to identify possible associations between copy number changes and RNA expression. Tumors per indication were allocated to 1 of 5 classes:
a) Deep deletion;
b) Shallow deletion;
c) Diploid;
d) Gain; or
e) Amplification.

Kruskall-Wallis testing was then performed to detect if the distributions of mRNA expression values per classes differed between classes (P<0.01). For those TOGA data sets with P<0.01 and to identify which classes were different to one another post-hoc testing was performed by calculating Z-statistics with adjusted P-values calculated (Bonferroni). For simplicity of interpretation pair-wise comparisons vs. diploid per indication were reviewed (although all pair-wise P-values were calculated). 19/41 of these studies had a Kruskall-Wallis p-value of <0.01 demonstrating that copy number is statistically significantly associated with RNA expression. Of these 19 studies, 17 of them had a Bonferroni adjusted P<0.025 for Diploid vs. Shallow Deletion indicating an association of decreased EphA2 mRNA expression with decreased EphA2 copy number. Only 2 of these 19 studies had a Bonferroni adjusted P<0.025 for Diploid vs. Gain and both were breast cancer studies. Furthermore, one of these breast cancer studies (Breast Invasive Carcinoma (TOGA, PanCancer Atlas)) had a Bonferroni adjusted P<0.025 for both Diploid vs. Shallow Deletion and Diploid vs. Gain suggesting that copy number alterations may have a strong impact on EphA2 RNA expression in breast cancer.

The central dogma of genetics suggests that reduced copy number in EphA2 lead to reduced RNA and protein expression. Therefore, the observed associations between copy number loss of EphA2 and reduced mRNA expression in a variety of tumor types suggest that EphA2 protein expression may also be reduced. Similarly, copy number gains of EphA2 in breast cancer that were associated with increased mRNA expression may also suggest increased EphA2 protein expression. Moreover, higher EphA2 protein expression (measured by FACS) is associated with increased efficacy of certain EphA2 bicyclic drug conjugates of the invention (measured by tumor volume) in preclinical in vivo models. Taken together if copy number alterations that are associated with mRNA expression changes do predict protein expression levels then patients with tumors containing copy number deletions of EphA2 may be less likely to respond to EphA2 bicyclic drug conjugates of the invention. Similarly, if patients with tumor copy number gains in EphA2 (e.g. breast cancer) it is possible that these patients would be more likely to respond to EphA2 bicyclic drug conjugates of the invention. Therefore, if patients were stratified by EphA2 copy number status, then this information could be used to both exclude and select patients for treatment with EphA2 bicyclic drug conjugates of the invention to increase efficacy.

TABLE 64

Results of Investigation of Association between Copy Number Variation (CNV) and gene expression for EphA2

| Study name | Units | Number of samples/group (n = X) | | | | |
| --- | --- | --- | --- | --- | --- | --- |
| | | Deep deletion | Shallow deletion | Diploid | Gain | Amplification |
| Breast Invasive Carcinoma (TCGA, PanCancer Atlas) | mRNA Expression Batch Normalized/ Merged from Illumina HiSeq_RNASeqV2 syn4976369 | 5 | 415 | 511 | 61 | 2 |
| Lung Squamous Cell Carcinoma (TCGA, PanCancer Atlas) | mRNA Expression Batch Normalized/ Merged from Illumina HiSeq_RNASeqV2 syn4976369 | 3 | 207 | 201 | 55 | 0 |

TABLE 64-continued

Results of Investigation of Association between Copy Number Variation (CNV) and gene expression for EphA2

| | | | | | | |
|---|---|---|---|---|---|---|
| Kidney Renal Papillary Cell Carcinoma (TCGA, PanCancer Atlas) | mRNA Expression, RSEM (Batch normalized from Illumina HiSeq_RNASeqV2) | 1 | 48 | 224 | 0 | 1 |
| Kidney Renal Clear Cell Carcinoma (TCGA, PanCancer Atlas) | mRNA Expression, RSEM (Batch normalized from Illumina HiSeq_RNASeqV2) | 0 | 69 | 278 | 5 | 0 |
| Colon Adenocarcinoma (TCGA, PanCancer Atlas) | RSEM (Batch normalized from Illumina HiSeq_RNASeqV2) | 3 | 132 | 245 | 8 | 0 |
| Head and Neck Squamous Cell Carcinoma (TCGA, PanCancer Atlas) | mRNA Expression, RSEM (Batch normalized from Illumina HiSeq_RNASeqV2) | 3 | 86 | 345 | 54 | 0 |
| Bladder Urothelial Carcinoma (TCGA, PanCancer Atlas) | RSEM (Batch normalized from Illumina HiSeq_RNASeqV2) | 0 | 73 | 245 | 80 | 4 |
| Uveal Melanoma (TCGA, PanCancer Atlas) | mRNA Expression Batch Normalized/ Merged from Illumina HiSeq_RNASeqV2 syn4976369 | 0 | 24 | 56 | 0 | 0 |
| Lung Adenocarcinoma (TCGA, PanCancer Atlas) | mRNA Expression, RSEM (Batch normalized from Illumina HiSeq_RNASeqV2) | 1 | 115 | 263 | 121 | 3 |
| Ovarian Serous Cystadenocarcinoma (TCGA, PanCancer Atlas) | mRNA Expression Batch Normalized/ Merged from Illumina HiSeq_RNASeqV2 syn4976369 | 0 | 59 | 78 | 60 | 4 |
| Breast Cancer (METABRIC, Nature 2012 & Nat Commun 2016) | mRNA expression (microarray) | 1 | 491 | 1349 | 25 | 0 |
| Mesothelioma (TCGA, PanCancer Atlas) | mRNA Expression Batch Normalized/ Merged from Illumina HiSeq_RNASeqV2 syn4976369 | 0 | 29 | 50 | 3 | 0 |

TABLE 64-continued

Results of Investigation of Association between Copy Number Variation (CNV) and gene expression for EphA2

| | | | | | | |
|---|---|---|---|---|---|---|
| Colorectal Adenocarcinoma (TCGA, Nature 2012) | RNA Seq RPKM | 0 | 53 | 138 | 2 | 0 |
| Cervical Squamous Cell Carcinoma (TCGA, PanCancer Atlas) | RSEM (Batch normalized from Illumina HiSeq_RNASeqV2) | 1 | 31 | 167 | 76 | 0 |
| Sarcoma (TCGA, PanCancer Atlas) | mRNA Expression Batch Normalized/ Merged from Illumina HiSeq_RNASeqV2 syn4976369 | 0 | 43 | 113 | 70 | 4 |
| Cancer Cell Line Encyclopedia (Novartis/Broad, Nature 2012) | mRNA expression (microarray) | 17 | 279 | 418 | 150 | 13 |
| Rectum Adenocarcinoma (TCGA, PanCancer Atlas) | mRNA Expression Batch Normalized/ Merged from Illumina HiSeq_RNASeqV2 syn4976369 | 1 | 54 | 78 | 3 | 0 |
| Liver Hepatocellular Carcinoma (TCGA, PanCancer Atlas) | EPHA2: mRNA Expression, RSEM (Batch normalized from Illumina HiSeq_RNASeqV2) | 1 | 130 | 194 | 21 | 2 |
| Stomach Adenocarcinoma (TCGA, PanCancer Atlas) | mRNA Expression Batch Normalized/ Merged from Illumina HiSeq_RNASeqV2 syn4976369 | 2 | 90 | 264 | 44 | 7 |
| Uterine Corpus Endometrial Carcinoma (TCGA, PanCancer Atlas) | mRNA Expression Batch Normalized/ Merged from Illumina HiSeq_RNASeqV2 syn4976369 | 3 | 61 | 395 | 43 | 5 |
| Skin Cutaneous Melanoma (TCGA, PanCancer Atlas) | mRNA Expression Batch Normalized/ Merged from Illumina HiSeq_RNASeqV2 syn4976369 | 2 | 70 | 216 | 72 | 3 |
| Prostate Adenocarcinoma (TCGA, PanCancer Atlas) | mRNA Expression, RSEM (Batch normalized from Illumina HiSeq_RNASeqV2) | 0 | 44 | 438 | 4 | 1 |

TABLE 64-continued

Results of Investigation of Association between Copy Number Variation (CNV) and gene expression for EphA2

| | | | | | | |
|---|---|---|---|---|---|---|
| Kidney Chromophobe (TCGA, PanCancer Atlas) | mRNA Expression, RSEM (Batch normalized from Illumina HiSeq_RNASeqV2) | 0 | 52 | 12 | 1 | 0 |
| Pediatric Wilms' Tumor (TARGET, 2018) | Epha2: mRNA expression (RNA-Seq RPKM) | 0 | 22 | 74 | 5 | 0 |
| Pheochromocytoma Paraganglioma (TCGA, PanCancer Atlas) | mRNA and Expression Batch Normalized/ Merged from Illumina HiSeq_RNASeqV2 syn4976369 | 4 | 96 | 60 | 1 | 0 |
| Thyroid Carcinoma (TCGA, PanCancer Atlas) | mRNA Expression Batch Normalized/ Merged from Illumina HiSeq_RNASeqV2 syn4976369 | 0 | 4 | 474 | 2 | 0 |
| Esophageal Adenocarcinoma (TCGA, PanCancer Atlas) | RSEM (Batch normalized from Illumina HiSeq_RNASeqV2) | 1 | 64 | 83 | 32 | 1 |
| Cholangiocarcinoma (TCGA, PanCancer Atlas) | RSEM (Batch normalized from Illumina HiSeq_RNASeqV2) | 2 | 27 | 7 | 0 | 0 |
| Brain Lower Grade Glioma (TCGA, PanCancer Atlas) | RSEM (Batch normalized from Illumina HiSeq_RNASeqV2) | 0 | 191 | 303 | 13 | 0 |
| Thymoma (TCGA, PanCancer Atlas) | mRNA Expression Batch Normalized/ Merged from Illumina HiSeq_RNASeqV2 syn4976369 | 0 | 8 | 110 | 1 | 0 |
| Pediatric Acute Lymphoid Leukemia-Phase II (TARGET, 2018) | Epha2: mRNA expression (RNA-Seq RPKM) | 1 | 6 | 70 | 4 | 0 |
| Diffuse Large B-Cell Lymphoma (TCGA, PanCancer Atlas) | mRNA Expression, RSEM (Batch normalized from Illumina HiSeq_RNASeqV2) | 0 | 4 | 33 | 0 | 0 |
| Glioblastoma Multiforme (TCGA, PanCancer Atlas) | mRNA Expression, RSEM (Batch normalized from Illumina HiSeq_RNASeqV2) | 0 | 13 | 104 | 28 | 0 |

TABLE 64-continued

Results of Investigation of Association between Copy Number Variation (CNV) and gene expression for EphA2

| Study | Data type | | | | | |
|---|---|---|---|---|---|---|
| Metastatic Prostate Cancer, SU2C/PCF Dream Team (Robinson et al., Cell 2015) | mRNA expression/ capture (RNA Seq RPKM) | 2 | 21 | 87 | 7 | 0 |
| Acute Myeloid Leukemia (TCGA, PanCancer Atlas) | mRNA Expression, RSEM (Batch normalized from Illumina HiSeq_RNASeqV2) | 0 | 1 | 160 | 4 | 0 |
| Testicular Germ Cell Tumors (TCGA, PanCancer Atlas) | mRNA Expression Batch Normalized/ Merged from Illumina HiSeq_RNASeqV2 syn4976369 | 1 | 29 | 92 | 22 | 0 |
| Adrenocortical Carcinoma (TCGA, PanCancer Atlas) | RSEM (Batch normalized from Illumina HiSeq_RNASeqV2) | 0 | 28 | 47 | 1 | 0 |
| Uterine Carcinosarcoma (TCGA, PanCancer Atlas) | mRNA Expression Batch Normalized/ Merged from Illumina HiSeq_RNASeqV2 syn4976369 | 0 | 16 | 22 | 16 | 2 |
| Pancreatic Adenocarcinoma (TCGA, PanCancer Atlas) | mRNA Expression Batch Normalized/ Merged from Illumina HiSeq_RNASeqV2 syn4976369 | 2 | 50 | 106 | 9 | 1 |
| Prostate Adenocarcinoma (MSKCC, Cancer Cell 2010) | mRNA Expression | 0 | 5 | 77 | 3 | 0 |
| Prostate Adenocarcinoma (Fred Hutchinson CRC, Nat Med 2016) | mRNA expression | 0 | 39 | 84 | 10 | 0 |

| | Kruskal-wallis test | | Pairwise comparison, Z statistic (adjusted p-value), Bonferonni | | | |
|---|---|---|---|---|---|---|
| Study name | Kruskal-wallis statstic | p-value | Deep Deletion-Diploid | Diploid-Shallow deletion | Diploid-Gain | Amplification-Diploid |
| Breast Invasive Carcinoma (TCGA, PanCancer Atlas) | 80.816 | <2.2e−16 | 0.176118 (1.0000) | 6.460580 (0.0000)* | -4.603180 (0.0000)* | 0.713978 (1.0000) |
| Lung Squamous Cell Carcinoma (TCGA, PanCancer Atlas) | 52.942 | 1.89E−11 | -1.584610 (0.3392) | 6.786501 (0.0000)* | -0.019607 (1.0000) | N/A |

TABLE 64-continued

Results of Investigation of Association between Copy Number Variation (CNV) and gene expression for EphA2

| Cancer Type | | | | | | |
|---|---|---|---|---|---|---|
| Kidney Renal Papillary Cell Carcinoma (TCGA, PanCancer Atlas) | 42.161 | 3.71E−09 | −1.586207 (0.3381)* | 6.097375 (0.0000)* | N/A | 1.549107 (0.3641) |
| Kidney Renal Clear Cell Carcinoma (TCGA, PanCancer Atlas) | 38.342 | 4.72E−09 | N/A | 6.133219 (0.0000)* | −0.487059 (0.9393) | N/A |
| Colon Adenocarcinoma (TCGA, PanCancer Atlas) | 35.397 | 1.00E−07 | −2.158194 (0.0927) | 5.670600 (0.0000)* | 0.781046 (1.0000) | N/A |
| Head and Neck Squamous Cell Carcinoma (TCGA, PanCancer Atlas) | 32.72 | 3.69E−07 | −2.444914 (0.0435) | 4.680789 (0.0000)* | −1.530670 (0.3776) | N/A |
| Bladder Urothelial Carcinoma (TCGA, PanCancer Atlas) | 28.906 | 2.34E−06 | N/A | 5.203251 (0.0000)* | 0.211744 (1.0000) | 0.581704 (1.0000) |
| Uveal Melanoma (TCGA, PanCancer Atlas) | 21.051 | 4.47E−06 | N/A | 4.588095 (0.0000)* | N/A | N/A |
| Lung Adenocarcinoma (TCGA, PanCancer Atlas) | 28.874 | 8.29E−06 | −0.690460 (1.0000) | 4.280100 (0.0001)* | −0.626707 (1.0000) | 2.276458 (0.1141) |
| Ovarian Serous Cystadenocarcinoma (TCGA, PanCancer Atlas) | 25.349 | 1.31E−05 | N/A | 4.390097 (0.0000)* | −0.239249 (1.0000) | 0.240543 (1.0000) |
| Breast Cancer (METABRIC, Nature 2012 & Nat Commun 2016) | 23.875 | 2.65E−05 | 0.568937 (1.0000) | 2.274564 (0.0688) | −4.115288 (0.0001)* | N/A |
| Mesothelioma (TCGA, PanCancer Atlas) | 18.866 | 8.00E−05 | N/A | 4.319425 (0.0000)* | 0.170478 (1.0000) | N/A |
| Colorectal Adenocarcinoma (TCGA, Nature 2012) | 18.847 | 8.08E−05 | N/A | 4.298092 (0.0000)* | −0.338975 (1.0000) | N/A |
| Cervical Squamous Cell Carcinoma (TCGA, PanCancer Atlas) | 19.435 | 2.22E−04 | −1.618248 (0.3168) | 3.429609 (0.0018)* | −1.446339 (0.4442) | N/A |
| Sarcoma (TCGA, PanCancer Atlas) | 19.389 | 2.27E−04 | N/A | 3.666949 (0.0007)* | −0.852454 (1.0000) | 0.953027 (1.0000) |
| Cancer Cell Line Encyclopedia (Novartis/Broad, Nature 2012) | 20.977 | 0.00032 | −2.084879 (0.1854) | −3.615935 (0.0015)* | −2.007004 (0.2237) | −0.108880 (1.0000) |
| Rectum Adenocarcinoma (TCGA, PanCancer Atlas) | 18.215 | 0.0003971 | −1.926519 (0.1621) | 3.877166 (0.0003)* | 1.167400 (0.7291) | N/A |

TABLE 64-continued

Results of Investigation of Association between Copy Number Variation (CNV) and gene expression for EphA2

| Cancer Type | | | | | | |
|---|---|---|---|---|---|---|
| Liver Hepatocellular Carcinoma (TCGA, PanCancer Atlas) | 15.514 | 0.003745 | 0.302341 (1.0000) | 3.697218 (0.0011)* | -0.336659 (1.0000) | 0.454454 (1.0000) |
| Stomach Adenocarcinoma (TCGA, PanCancer Atlas) | 13.966 | 0.007404 | -2.072978 (0.1909) | 1.606072 (0.5413) | -1.750466 (0.4002) | 1.602806 (0.5449) |
| Uterine Corpus Endometrial Carcinoma (TCGA, PanCancer Atlas) | 12.916 | 0.0117 | -1.905863 (0.2833) | 1.039307 (1.0000) | -1.597383 (0.5509) | 2.268798 (0.1164) |
| Skin Cutaneous Melanoma (TCGA, PanCancer Atlas) | 12.242 | 0.01564 | 1.094526 (1.0000) | 2.674493 (0.0374) | 0.095966 (1.0000) | 1.692628 (0.4526) |
| Prostate Adenocarcinoma (TCGA, PanCancer Atlas) | 10.112 | 0.01764 | N/A | 2.905502 (0.0110)* | 1.374609 (0.5078) | -0.082790 (1.0000) |
| Kidney Chromophobe (TCGA, PanCancer Atlas) | 7.8781 | 0.01947 | N/A | 2.498340 (0.0187)* | 1.863169 (0.0937) | N/A |
| Pediatric Wilms' Tumor (TARGET, 2018) | 7.4912 | 0.02362 | N/A | 2.690766 (0.0107)* | -0.173274 (1.0000) | N/A |
| Pheochromocytoma Paraganglioma (TCGA, PanCancer Atlas) | 8.8074 | 0.03196 | -1.411567 (0.4742) | 2.201344 (0.0831) | 1.946134 (0.1549) | N/A |
| Thyroid Carcinoma (TCGA, PanCancer Atlas) | 5.1773 | 0.08 | N/A | 2.221884 (0.0394) | 0.503577 (0.9218) | N/A |
| Esophageal Adenocarcinoma (TCGA, PanCancer Atlas) | 7.6886 | 0.1037 | -1.462679 (0.7178) | 0.910990 (1.0000) | -1.682311 (0.4625) | -0.362298 (1.0000) |
| Cholangiocarcinoma (TCGA, PanCancer Atlas) | 4.1691 | 0.1244 | -2.037840 (0.0623) | 0.972100 (0.4965) | N/A | N/A |
| Brain Lower Grade Glioma (TCGA, PanCancer Atlas) | 4.0473 | 0.1322 | N/A | 0.722383 (0.7051) | -1.771514 (0.1147) | N/A |
| Thymoma (TCGA, PanCancer Atlas) | 4.0322 | 1.33E-01 | N/A | 1.982334 (0.0712) | 0.369115 (1.0000) | N/A |
| Pediatric Acute Lymphoid Leukemia-Phase II (TARGET, 2018) | 5.5309 | 0.1368 | 1.437404 (0.4518) | -0.805100 (1.0000) | 1.607586 (0.3238) | N/A |
| Diffuse Large B-Cell Lymphoma (TCGA, PanCancer Atlas) | 1.744 | 0.1866 | N/A | 1.320613 (0.0933) | N/A | N/A |

TABLE 64-continued

Results of Investigation of Association between Copy Number Variation (CNV) and gene expression for EphA2

| | | | | | | |
|---|---|---|---|---|---|---|
| Glioblastoma Multiforme (TCGA, PanCancer Atlas) | 2.9376 | 0.2302 | N/A | 1.428778 (0.2296) | -0.716110 (0.7109) | N/A |
| Metastatic Prostate Cancer, SU2C/PCF Dream (Robinson et al., Cell 2015) | 4.069 | 0.254 | -1.812613 (0.2097) | 0.992571 (0.9628) | 0.3140 (1.0000) | N/A |
| Acute Myeloid Leukemia (TCGA, PanCancer Atlas) | 2.4016 | 0.301 | N/A | -1.539142 (0.1857) | -0.199532 (1.0000) | N/A |
| Testicular Germ Cell Tumors (TCGA, PanCancer Atlas) | 3.3144 | 0.3456 | 0.574846 (1.0000) | -0.443110 (1.0000) | -1.751161 (0.2398) | N/A |
| Adrenocortical Carcinoma (TCGA, PanCancer Atlas) | 2.0003 | 0.3678 | N/A | 1.346397 (0.2673) | 0.550103 (0.8734) | N/A |
| Uterine Carcinosarcoma (TCGA, PanCancer Atlas) | 2.44 | 0.4862 | N/A | 0.476071 (1.0000) | -0.550292 (1.0000) | 1.2151 (0.6730) |
| Pancreatic Adenocarcinoma (TCGA, PanCancer Atlas) | 3.3833 | 4.96E-01 | -1.195082 (1.0000) | 0.159442 (1.0000) | -0.602558 (1.0000) | 1.217697 (1.0000) |
| Prostate Adenocarcinoma (MSKCC, Cancer Cell 2010) | 1.3139 | 0.5184 | N/A | -0.406579 (1.0000) | -1.089948 (0.4136) | N/A |
| Prostate Adenocarcinoma (Fred Hutchinson CRC, Nat Med 2016) | 0.028351 | 0.9859 | N/A | 0.160404 (1.0000) | 0.079785 (1.0000) | N/A |

The invention claimed is:

1. A peptide ligand specific for EphA2, or a pharmaceutically acceptable salt or modified derivative thereof, the peptide ligand comprising a polypeptide comprising at least three cysteine residues, separated by at least two loop sequences, and a non-aromatic molecular scaffold which forms covalent bonds with the cysteine residues of the polypeptide such that at least two polypeptide loops are formed on the molecular scaffold, wherein the polypeptide comprises an amino acid sequence selected from C(HyP)LVNPLCLHP(D-Asp)W(HArg)C; (SEQ ID NO: 1)

(β-Ala)-Sar$_{10}$-A(HArg)DC(HyP)LVNPLCLHP(D-Asp)W(HArg)C; (SEQ ID NO: 2)

ACMNDWWCAMGWKCA; (SEQ ID NO: 3)

ACVPDRRCAYMNVCA; (SEQ ID NO: 4)

ACVVDGRCAYMNVCA; (SEQ ID NO: 5)

ACVVDSRCAYMNVCA; (SEQ ID NO: 6)

ACVPDSRCAYMNVCA; (SEQ ID NO: 7)

ACYVGKECAIRNVCA; (SEQ ID NO: 8)

ACYVGKECAYMNVCA; (SEQ ID NO: 9)

ARDCPLVNPLCLHPGWTC; (SEQ ID NO: 10)

A(HArg)DCPLVNPLCLHPGWTC; (SEQ ID NO: 11)

CPLVNPLCLHPGWTCLHG; (SEQ ID NO: 12)

CPLVNPLCLHPGWTCL(D-His)G; (SEQ ID NO: 13)

CPLVNPLCLHPGWSCRGQ; (SEQ ID NO: 14)

CPLVNPLCLHPGWSC(HArg)GQ; (SEQ ID NO: 15)

ACVPDRRCAYMNVC; (SEQ ID NO: 16)

DLRCGGDPRCAYMNVCA; (SEQ ID NO: 17)

SRPCVIDSRCAYMNVCA; (SEQ ID NO: 18)

ESRCSPDARCAYMNVCA; (SEQ ID NO: 19)

HSGCRPDPRCAYMNVCA; (SEQ ID NO: 20)

GSGCKPDSRCAYMNVCA; (SEQ ID NO: 21)

ETVCLPDSRCAYMNVCA; (SEQ ID NO: 22)

GQVCIVDARCAYMNVCA; (SEQ ID NO: 23)

ACVPDRRCAFENVCVDH; (SEQ ID NO: 24)

ACVPDRRCAFMNVCEDR; (SEQ ID NO: 25)

ACVPDRRCAFQDVCDHE; (SEQ ID NO: 26)

ACVPDRRCAFRDVCLTG; (SEQ ID NO: 27)

ACQPSNHCAFMNYCA; (SEQ ID NO: 28)

ACSPTPACAVQNLCA; (SEQ ID NO: 29)

ACTSCWAYPDSFCA; (SEQ ID NO: 30)

ACTKPTGFCAYPDTICA; (SEQ ID NO: 31)

ACRGEWGYCAYPDTICA; (SEQ ID NO: 32)

ACRNWGMYCAYPDTICA; (SEQ ID NO: 33)

ACPDWGKYCAYPDTICA; (SEQ ID NO: 34)

ACRVYGPYCAYPDTICA; (SEQ ID NO: 35)

ACSSCWAYPDSVCA; (SEQ ID NO: 36)

ACQSCWAYPDTYCA; (SEQ ID NO: 37)

ACGFMGLEPCETFCA; (SEQ ID NO: 38)

ACGFMGLVPCEVHCA; (SEQ ID NO: 39)

ACGFMGLEPCEMVCA; (SEQ ID NO: 40)

ACGFMGLEPCVTYCA; (SEQ ID NO: 41)

ACGFMGLEPCELVCA; (SEQ ID NO: 42)

ACGFMGLVPCNVFCA; (SEQ ID NO: 43)

ACGFMGLEPCELFCA; (SEQ ID NO: 44)

ACGFMGLEPCELFCMPK; (SEQ ID NO: 45)

ACGFMGLEPCELYCA; (SEQ ID NO: 46)

ACGFMGLEPCELYCAHT; (SEQ ID NO: 47)

ACGFMGLEPCEMYCA; (SEQ ID NO: 48)

ACGFMGLVPCELYCADN; (SEQ ID NO: 49)

ACPLVNPLCLTSGWKCA; (SEQ ID NO: 50)

ACPMVNPLCLHPGWICA; (SEQ ID NO: 51)

ACPLVNPLCLHPGWICA; (SEQ ID NO: 52)

ACPLVNPLCLHPGWRCA; (SEQ ID NO: 53)

ACPLVNPLCNLPGWTCA; (SEQ ID NO: 54)

ACPLVNPLCLVPGWSCA; (SEQ ID NO: 55)

ACPLVNPLCLLDGWTCA; (SEQ ID NO: 56)

ACPLVNPLCLMPGWGCA; (SEQ ID NO: 57)

ACPLVNPLCMIGNWTCA; (SEQ ID NO: 58)

ACPLVNPLCLMTGWSCA; (SEQ ID NO: 59)

ACPLVNPLCMMGGWKCA; (SEQ ID NO: 60)

ACPLVNPLCLYGSWKCA; (SEQ ID NO: 61)

ACPLVNPLCLHPGWTCA; (SEQ ID NO: 62)

ARDCPLVNPLCLHPGWTCA; (SEQ ID NO: 63)

RPACPLVNPLCLHPGWTCA; (SEQ ID NO: 64)

RPPCPLVNPLCLHPGWTCA; (SEQ ID NO: 65)

KHSCPLVNPLCLHPGWTCA; (SEQ ID NO: 66)

ACPLVNPLCLHPGWTCLHG; (SEQ ID NO: 67)

ACPLVNPLCLHPGWTCL(D-His)G; (SEQ ID NO: 68)

ACPLVNPLCLHPG(2Nal)TCLHG; (SEQ ID NO: 69)

RHDCPLVNPLCLLPGWTCA; (SEQ ID NO: 70)

TPRCPLVNPLCLMPGWTCA; (SEQ ID NO: 71)

ACPLVNPLCLAPGWTCA; (SEQ ID NO: 72)

ACPLVNPLCLAPGWTCSRS; (SEQ ID NO: 73)

ACPLVNPLCLEPGWTCA; (SEQ ID NO: 74)

ACPLVNPLCLEPGWTCAKR; (SEQ ID NO: 75)

ACPLVNPLCLHPGWSCA; (SEQ ID NO: 76)

ACPLVNPLCLHPGWSCRGQ; (SEQ ID NO: 77)

ACPLVNPLCLHPGWSC(HArg)GQ; (SEQ ID NO: 78)

ACPLVNPLCLHPG(2Nal)SCRGQ; (SEQ ID NO: 79)

ACPLVNPLCLTPGWTCTNT; (SEQ ID NO: 80)

ACPMVNPLCLHPGWKCA; (SEQ ID NO: 81)

ACPMVNPLCLTPGWICA; (SEQ ID NO: 82)

ACPMVNPLCLHPGWTCA; (SEQ ID NO: 83)

H(D-Asp)VT-C(Aib)(1Nal)G(Aib)F(1Nal)CP(tBuGly)N(HArg)P(D-Asp)C; (SEQ ID NO: 84)

A(HArg)DC(HyP)(Hse(Me))VNPLCLHP(D-Asp)W(HArg)C; (SEQ ID NO: 85)

A(HArg)DC(HyP)(Hse(Me))VNPLCLHP(D-Asp)WTC; (SEQ ID NO: 86)

A(HArg)DC(HyP)LVNPLCLHP(D-Ala)WTC; (SEQ ID NO: 87)

```
A(HArg)DCPLVNPLCLHP(D-Ala)WTC;           (SEQ ID NO: 88)

ARDC(HyP)LVNPLCLHPGWTC;                  (SEQ ID NO: 89)

ARDCPLVNPLCL(D-3,3-DPA)PGWTC;            (SEQ ID NO: 90)

ARDCPLVNPLCLHPGWTCLH;                    (SEQ ID NO: 91)

A(HArg)DCPLVNPLCLHP(D-Cya)WTC;           (SEQ ID NO: 92)

A(D-Arg)DC(HyP)LVNPLCL(D-3,3-DPA)P(D-Asp)W(HArg)C;   (SEQ ID NO: 93)

ACPWGPAWCPVNRPGCA;                       (SEQ ID NO: 94)

ACPWGPFWCPVNRPGCA;                       (SEQ ID NO: 95)

ADVTCPWGPFWCPVNRPGCA;                    (SEQ ID NO: 96)
and

CPLVNPLCLHPGWTC;                         (SEQ ID NO: 97)
``` wherein HyP is hydroxyproline, HArg is homoarginine, Sar is sarcosine, HArg is homoarginine, D-Asp is D-aspartic acid, 2Nal is 2-naphthylalanine, 1Nal is 1-naphthylalanine, Aib is 2-aminoisobutyric acid, tBuGly is tert-leucine, hSerMe is homoserine(methyl), D-Ala is D-alanine, D-3,3-DPA is 3,3-diphenyl-D-alanine, D-Cya is D-cysteic acid, D-Arg is D-arginine, HPhe is homophenylalanine, and D-His is D-histidine.

2. The peptide ligand as defined in claim 1, wherein the molecular scaffold is 1,1',1''-(1,3,5-triazinane-1,3,5-triyl)triprop-2-en-1-one (TATA).

3. The peptide ligand as defined in claim 1, which is selected from

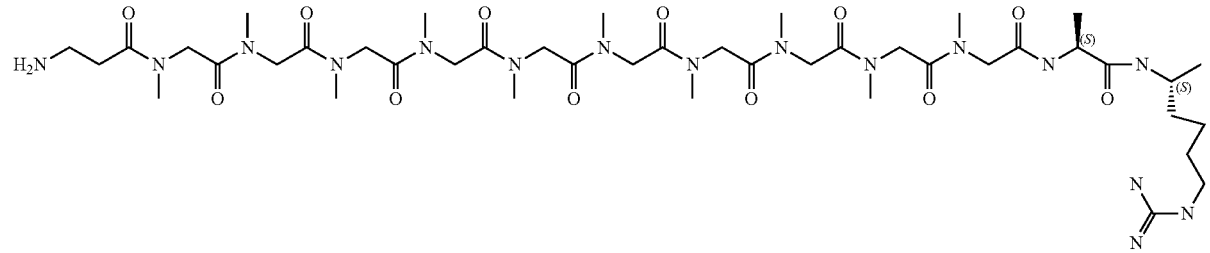

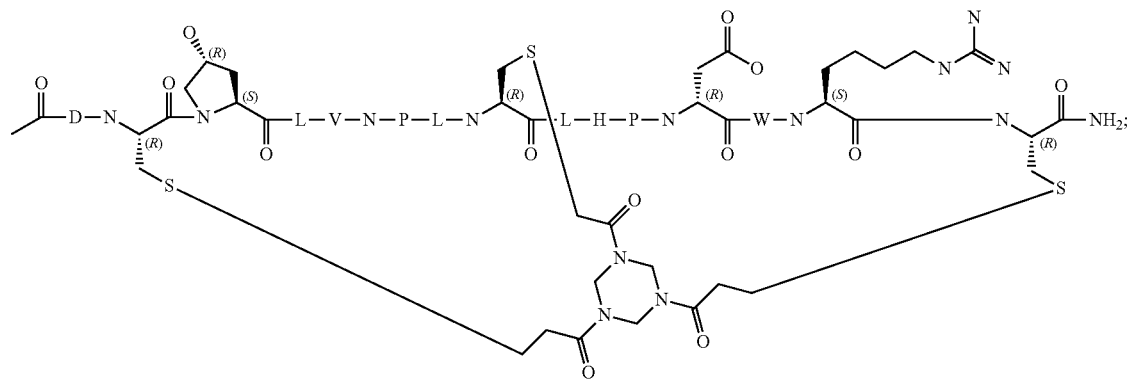

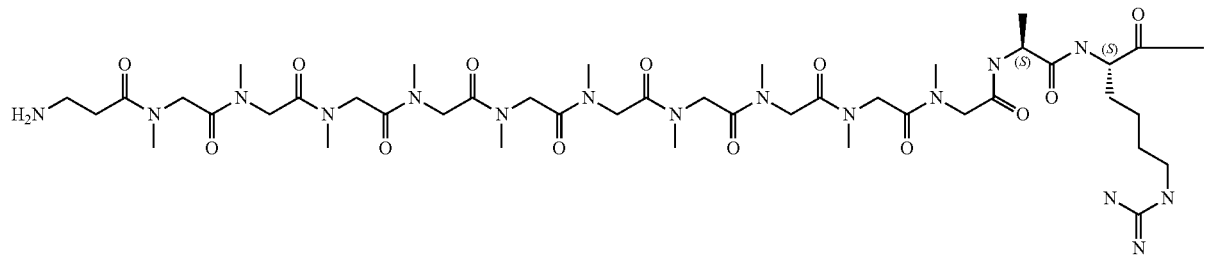

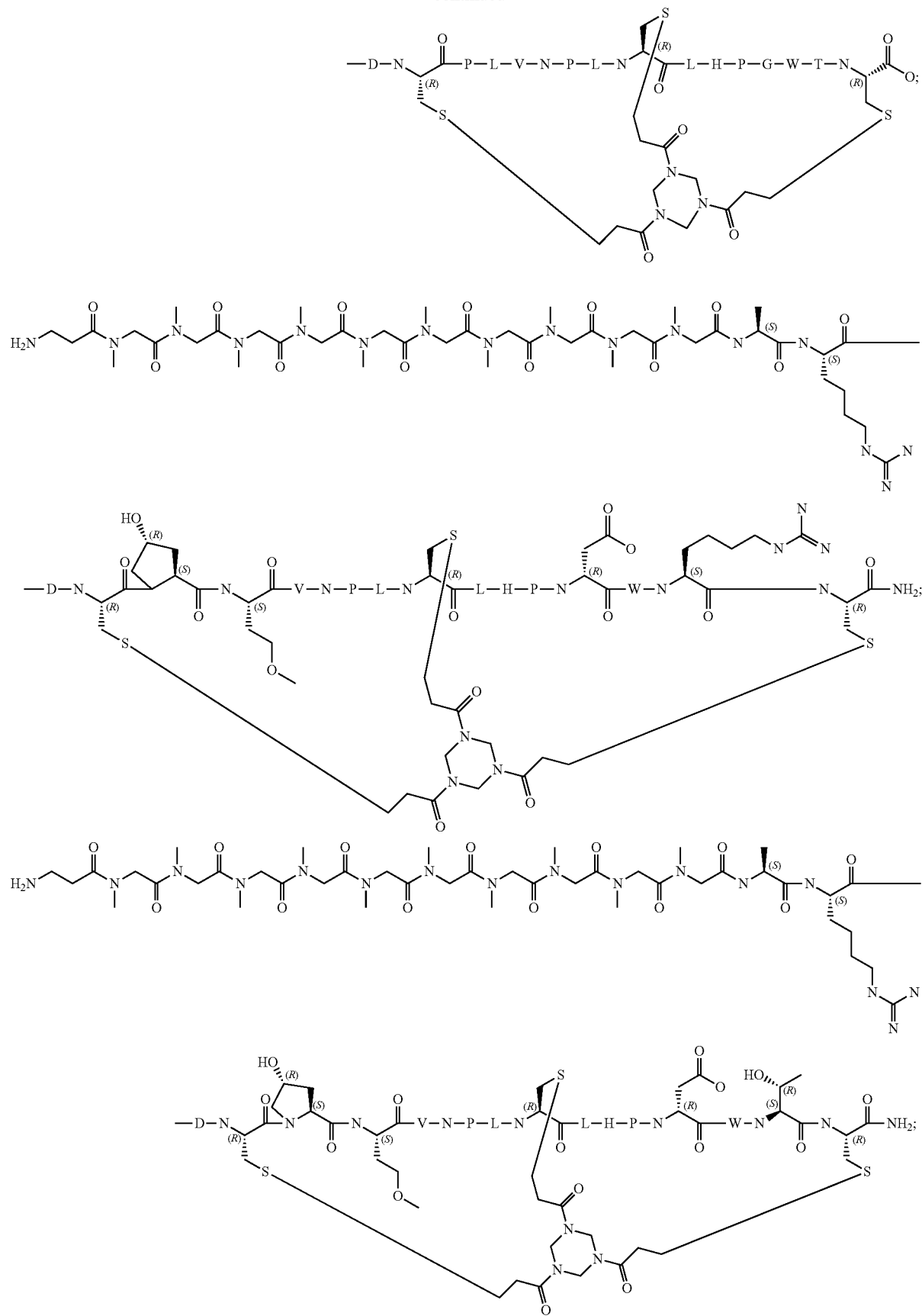

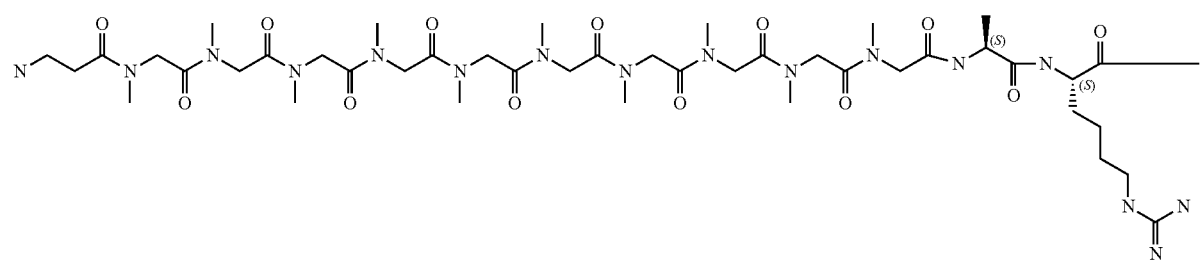
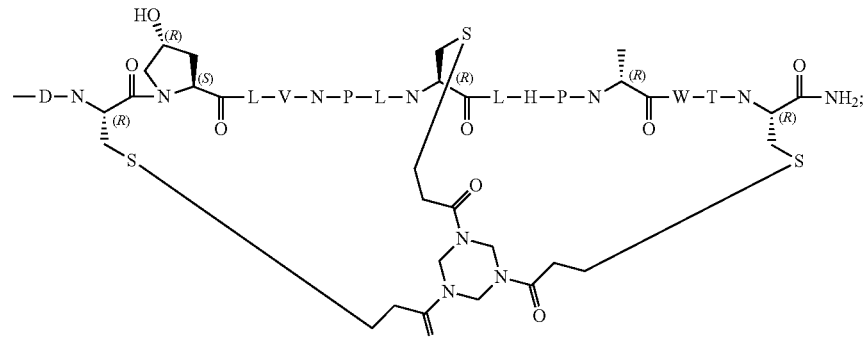
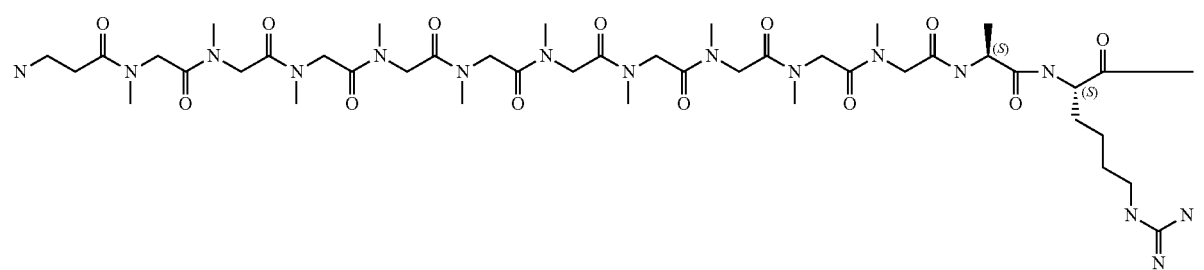
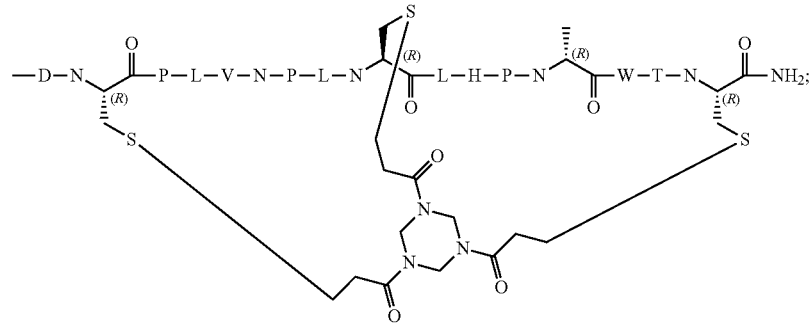
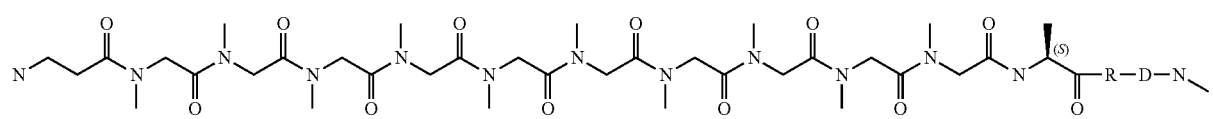
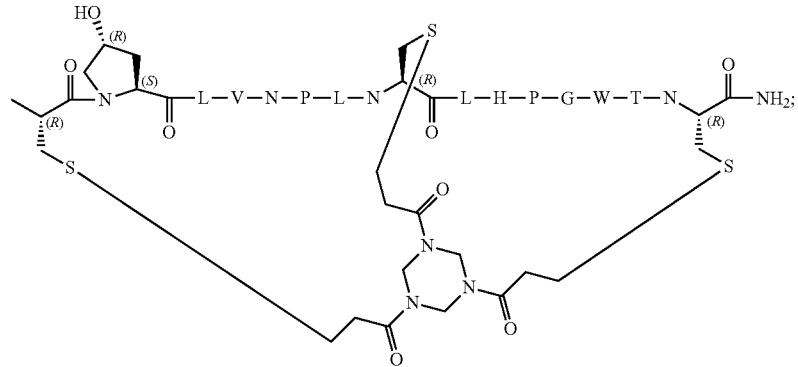

437
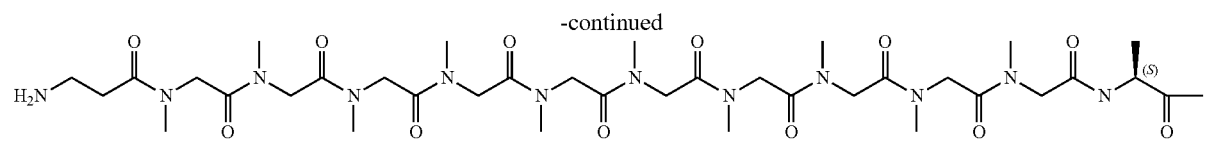
-continued
438
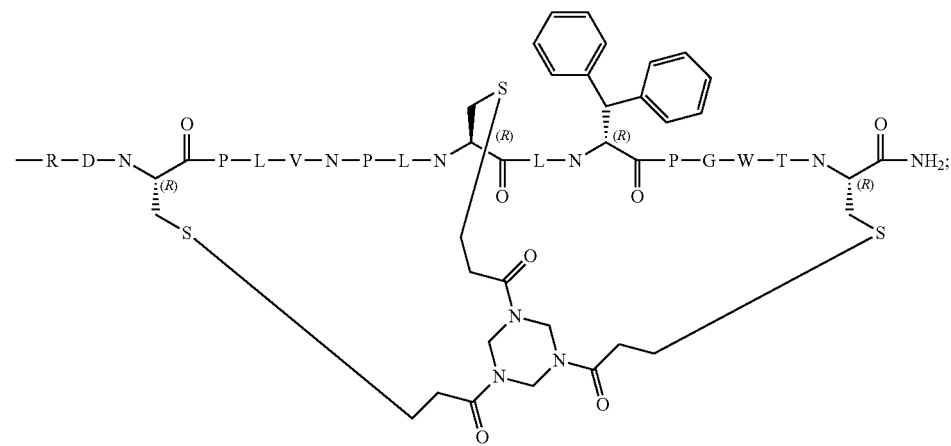
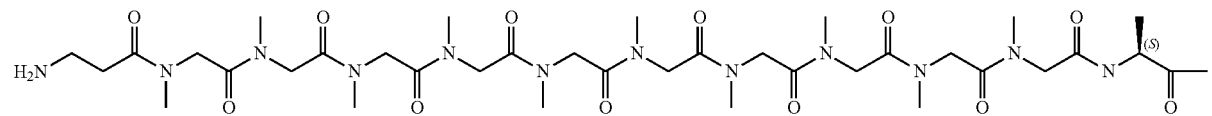
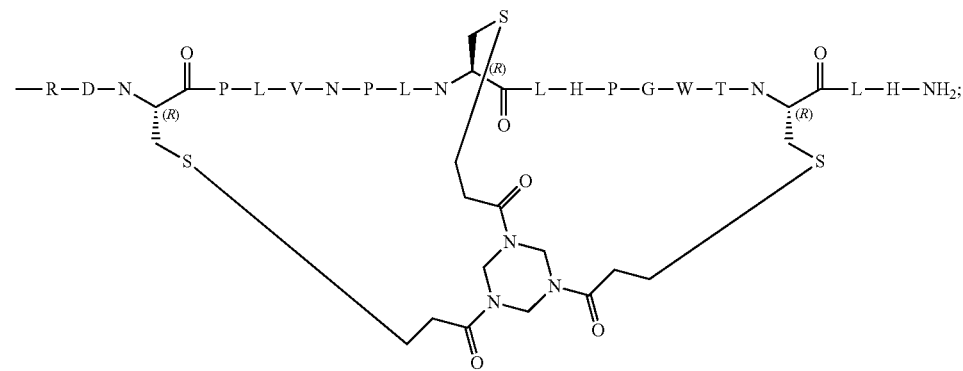
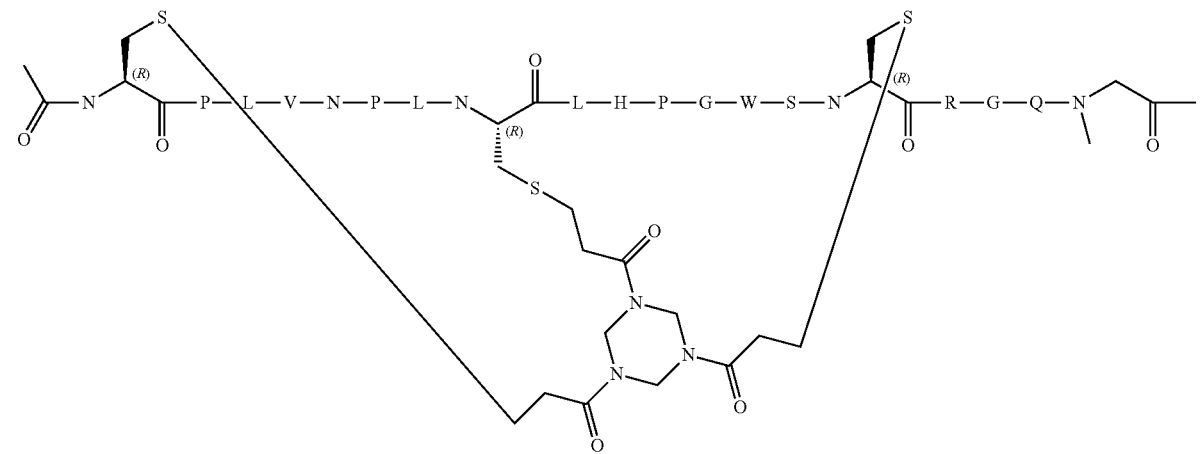

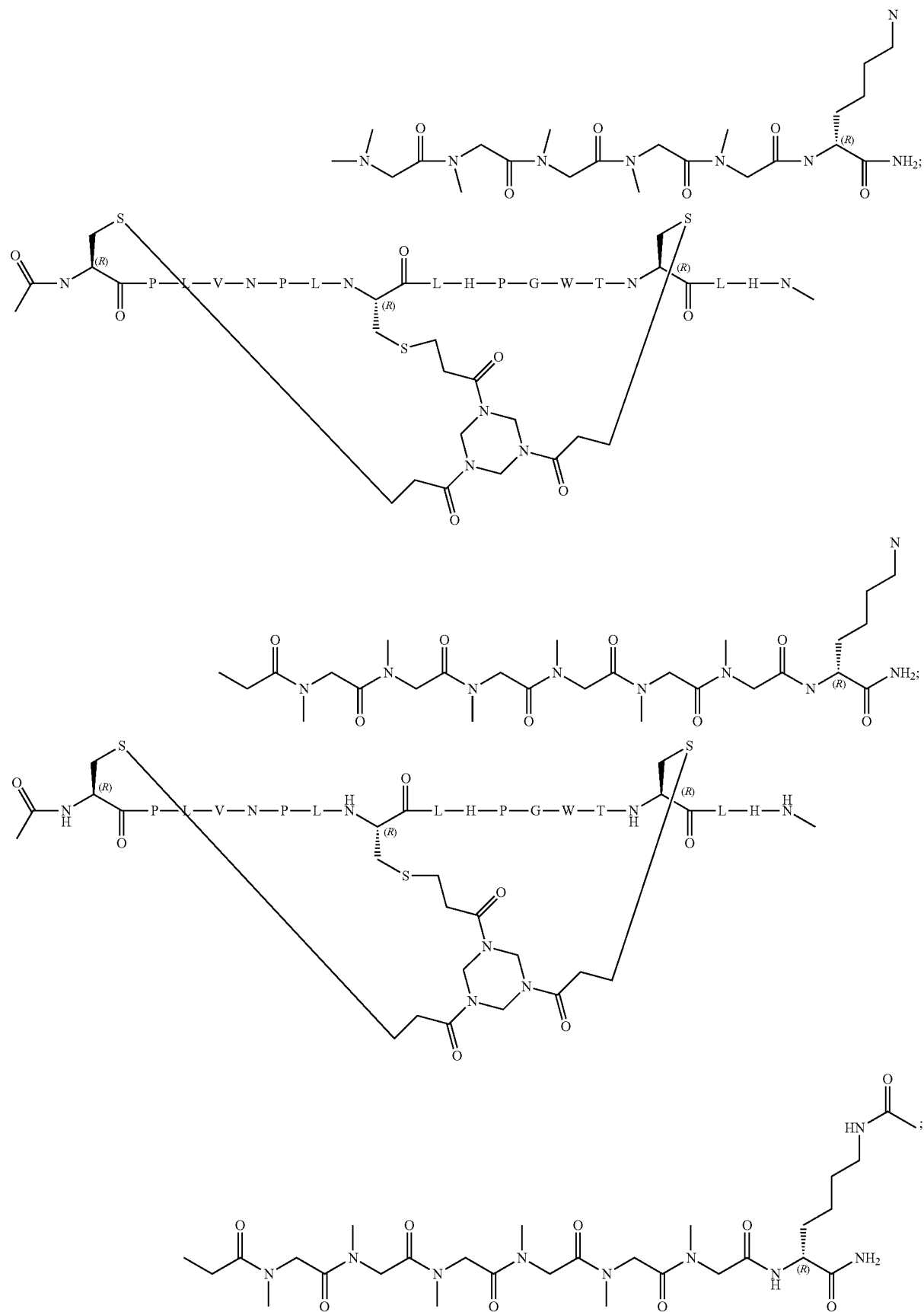

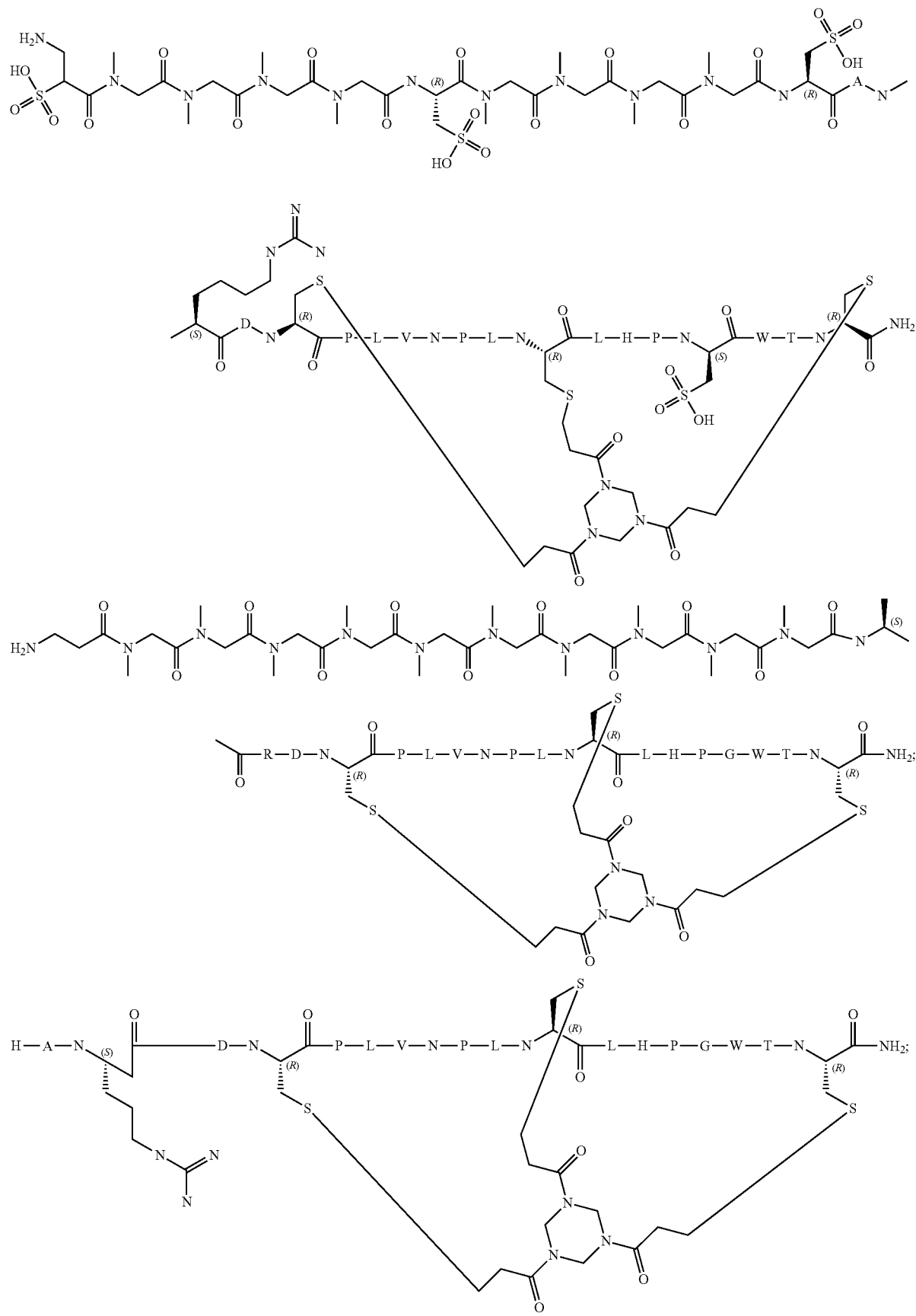

443                                        444
-continued
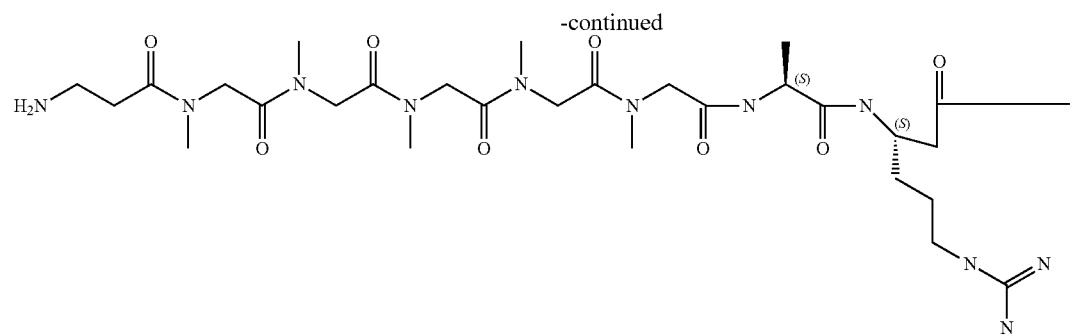
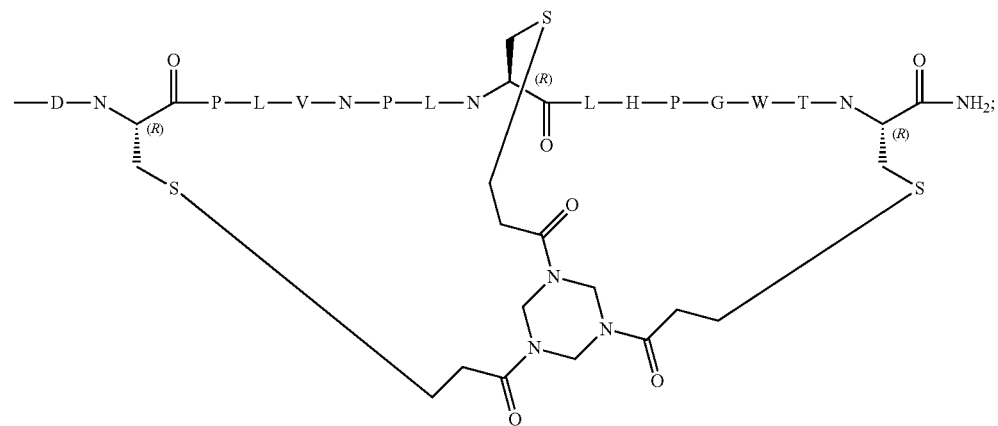
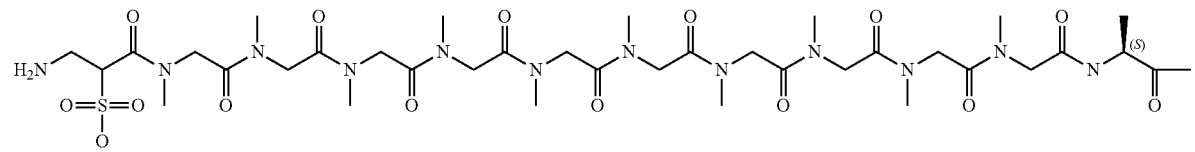
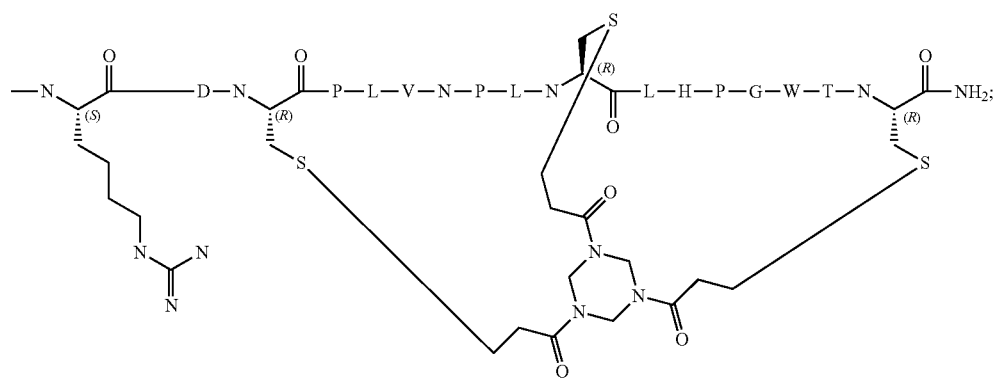
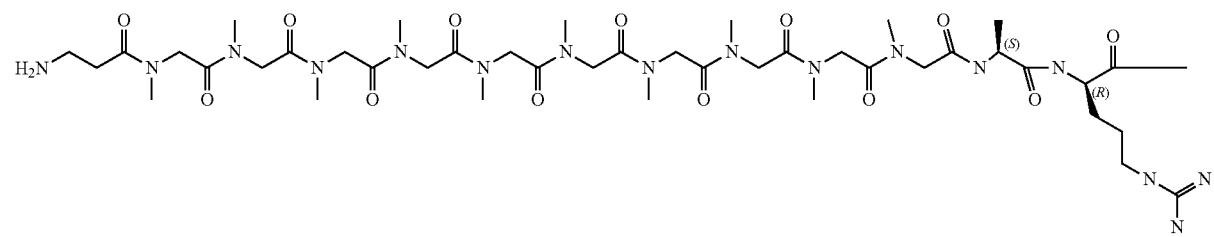

-continued
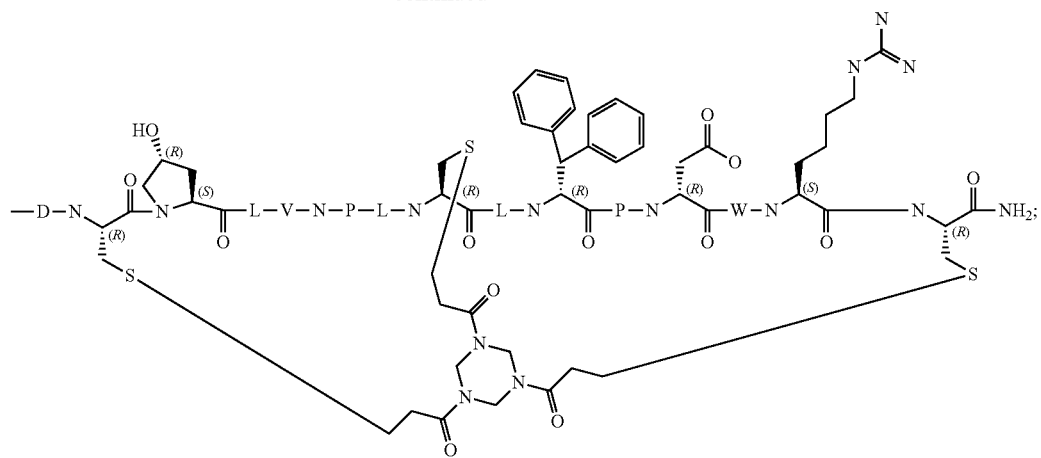
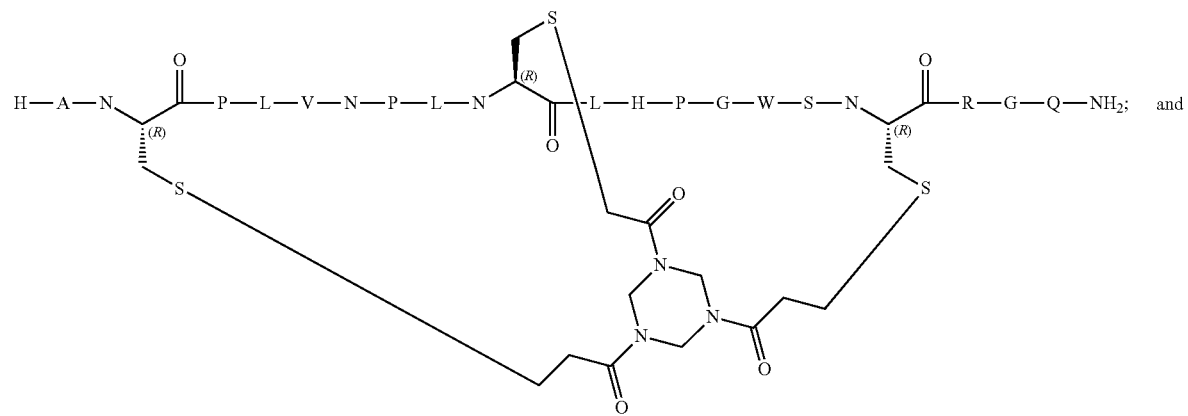
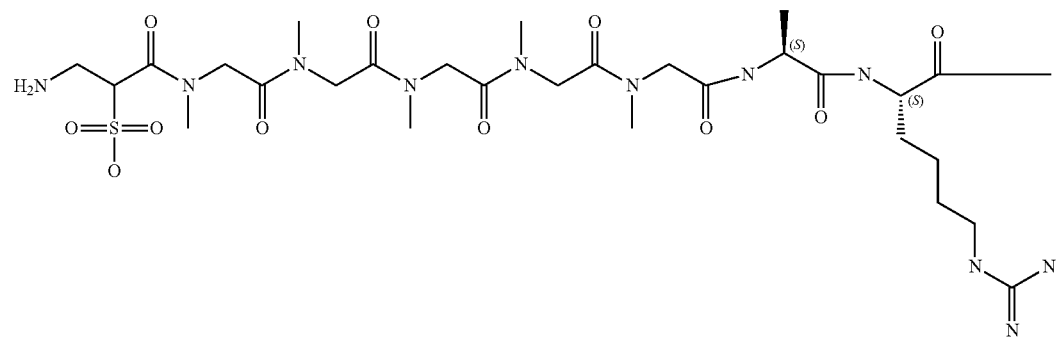

-continued

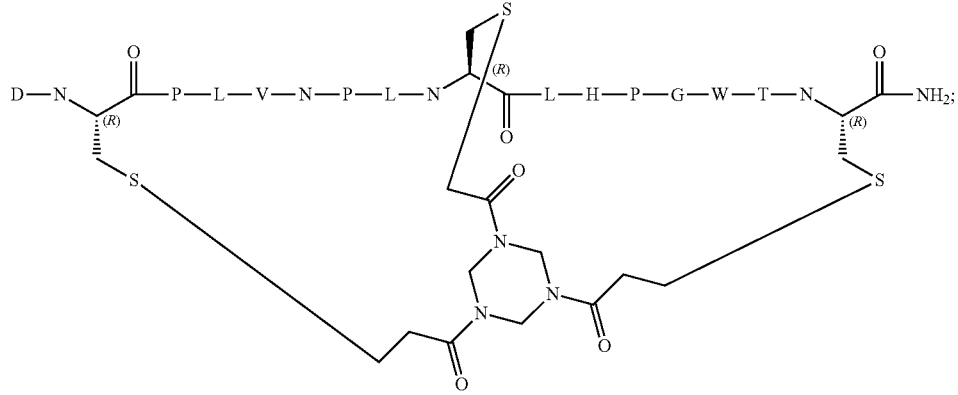

or a pharmaceutically acceptable salt thereof.

4. The peptide ligand as defined in claim 1, wherein the pharmaceutically acceptable salt is selected from a free acid or a sodium, potassium, calcium, or ammonium salt.

5. The peptide ligand as defined in claim 1, wherein the EphA2 is human EphA2.

6. A drug conjugate comprising the peptide ligand as defined in claim 1, conjugated to one or more effector and/or functional groups.

7. A pharmaceutical composition which comprises the drug conjugate of claim 6, in combination with one or more pharmaceutically acceptable excipients.

8. The peptide ligand as defined in claim 1, wherein the polypeptide comprises an amino acid sequence selected from ACMNDWWCAMGWKCA-Sar$_6$-K(Fl) ((SEQ ID NO: 3)-Sar$_6$-K(Fl));
ACVPDRRCAYMNVCA-Sar$_6$-K(Fl) ((SEQ ID NO: 4)-Sar$_6$-K(Fl));
ACVVDGRCAYMNVCA-Sar$_6$-K(Fl) ((SEQ ID NO: 5)-Sar$_6$-K(Fl));
ACVVDSRCAYMNVCA-Sar$_6$-K(Fl) ((SEQ ID NO: 6)-Sar$_6$-K(Fl));
ACVPDSRCAYMNVCA-Sar$_6$-K(Fl) ((SEQ ID NO: 7)-Sar$_6$-K(Fl));
ACYVGKECAIRNVCA-Sar$_6$-K(Fl) ((SEQ ID NO: 8)-Sar$_6$-K(Fl));
ACYVGKECAYMNVCA-Sar$_6$-K(Fl) ((SEQ ID NO: 9)-Sar$_6$-K(Fl));
Fl-G-Sar$_5$-ACYVGKECAYMNVCA (Fl-G-Sar$_5$-(SEQ ID NO: 9));
Fl-(β-Ala)-Sar$_{10}$-ARDCPLVNPLCLHPGWTC (Fl-(β-Ala)-Sar$_{10}$-(SEQ ID NO: 10));
Fl-(β-Ala)-Sar$_{10}$-A(HArg)DCPLVNPLCLHPGWTC (Fl-(β-Ala)-Sar$_{10}$-(SEQ ID NO: 11);
Ac-CPLVNPLCLHPGWTCLHG-Sar$_6$-(D-K[Fl]) (Ac-(SEQ ID NO: 12)-Sar$_6$-(D-K[Fl]));
Ac-CPLVNPLCLHPGWTCL(D-His)G-Sar$_6$-(D-K[Fl]) (Ac-SEQ ID NO: 13)-Sar$_6$-(D-K[Fl]));
Ac-CPLVNPLCLHPGWSCRGQ-Sar$_6$-(D-K[Fl]) (Ac-(SEQ ID NO: 14)-Sar$_6$-(D-K[Fl]));
Ac-CPLVNPLCLHPGWSC(HArg)GQ-Sar$_6$-(D-K[Fl]) (Ac-(SEQ ID NO: 15)-Sar$_6$-(D-K[Fl]));
(β-Ala)-Sar$_{10}$-ACVPDRRCAYIVINVC ((β-Ala)-Sar$_{10}$-(SEQ ID NO: 16));
(β-Ala)-Sar$_{10}$-A(HArg)DCPLVNPLCLHPGWTC ((β-Ala)-Sar$_{10}$-(SEQ ID NO: 11);

Ac-ARDCPLVNPLCLHPGWTCA-Sar$_6$-(D-K) (Ac-(SEQ ID NO: 63)-Sar$_6$-(D-K));
Ac-A(HArg)DCPLVNPLCLHPGWTCA-Sar$_6$-(D-K) (Ac-(SEQ ID NO: 11)-A-Sar$_6$-(D-K));
Ac-CPLVNPLCLHPGWTCLHG (Ac-(SEQ ID NO: 12));
(β-Ala)-Sar$_{10}$-ACPLVNPLCLHPGWTCLHG ((β-Ala)-Sar$_{10}$-(SEQ ID NO: 67));
(β-Ala)-Sar$_{10}$-ACPLVNPLCLHPGWTCL(D-His)G ((β-Ala)-Sar$_{10}$-(SEQ ID NO: 68));
Ac-CPLVNPLCLHPGWTCLHG-Sar$_6$-(D-K) (Ac-(SEQ ID NO: 12)-Sar$_6$-(D-K));
Ac-CPLVNPLCLHPGWTCL(D-His)G-Sar$_6$-(D-K) (Ac-(SEQ ID NO: 13)-Sar$_6$-(D-K));
Ac-CPLVNPLCLHPGWSCRGQ (Ac-(SEQ ID NO: 14));
(β-Ala)-Sar$_{10}$-ACPLVNPLCLHPGWSCRGQ ((β-Ala)-Sar$_{10}$-(SEQ ID NO: 77);
(β-Ala)-Sar$_{10}$-ACPLVNPLCLHPGWSC(HArg)GQ ((β-Ala)-Sar$_{10}$-(SEQ ID NO: 78));
Ac-CPLVNPLCLHPGWSCRGQ-Sar$_6$-(D-K) (Ac-(SEQ ID NO: 14)-Sar$_6$-(D-K));
Ac-CPLVNPLCLHPGWSC(HArg)GQ-Sar$_6$-(D-K) (Ac-(SEQ ID NO: 15)-Sar$_6$-(D-K));
(β-Ala)-Sar$_{10}$-H(D-Asp)VT-C(Aib)(1Nal)G(Aib)F(1Nal)CP(tBuGly)N(HArg)P(D-Asp)C ((β-Ala)-Sar$_{10}$-(SEQ ID NO: 84));
(β-Ala)-Sar$_{10}$-(SEQ ID NO: 10);
(β-Ala)-Sar$_{10}$-(SEQ ID NO: 11)-CONH$_2$;
(β-Ala)-Sar$_5$-(SEQ ID NO: 11);
Ac-(SEQ ID NO: 12)-Sar$_6$-(D-K);
Ac-(SEQ ID NO: 14)-Sar$_6$-(D-K);
Ac-(SEQ ID NO: 12)-Sar$_6$-(D-K[Ac]);
(β-Ala)-Sar$_{10}$-(SEQ ID NO: 2)-CONH$_2$;
(β-Ala)-Sar$_{10}$-(SEQ ID NO: 87);
(β-Ala)-Sar$_{10}$-(SEQ ID NO: 88);
(β-Ala)-Sar$_{10}$-(SEQ ID NO: 86);
(β-Ala)-Sar$_{10}$-(SEQ ID NO: 85);
(β-Ala)-Sar$_{10}$-(SEQ ID NO: 91);
(β-Ala)-Sar$_{10}$-(SEQ ID NO: 90);
(β-Ala)-Sar$_{10}$-(SEQ ID NO: 89);
(β-Ala)-Sar$_{10}$-(SEQ ID NO: 93);
(β-AlaSO$_3$H)-Sar$_{10}$-(SEQ ID NO: 11);
(β-AlaSO$_3$H)-Sar$_5$-(SEQ ID NO: 11); and
(β-AlaSO$_3$H)-Sar$_4$-(Cya)-Sar$_4$-(Cya)-(SEQ ID NO: 92).

9. The peptide ligand as defined in claim 1, wherein the polypeptide comprises the amino acid sequence C(HyP)LVNPLCLHP(D-Asp)W(HArg)C (SEQ ID NO: 1).

10. The peptide ligand as defined in claim 1, wherein the polypeptide comprises the amino acid sequence (β-Ala)-Sar₁₀-A(HArg)DC(HyP)LVNPLCHP(D-Asp)W(HArg)C (SEQ ID NO: 2); or
(SEQ ID NO: 2)-CONH₂.

11. The peptide ligand as defined in claim 1, wherein the polypeptide comprises the amino acid sequence selected from
A(HArg)DCPLVNPLCLHPGWTC (SEQ ID NO: 11);
Fl-(β-Ala)-Sar₁₀-(SEQ ID NO: 11);
(β-Ala)-Sar₁₀-(SEQ ID NO: 11);
Ac-(SEQ ID NO: 11)-A-Sar₆-(D-K);
(β-Ala)-Sar₁₀-(SEQ ID NO: 11)-CONH₂;
(β-Ala)-Sar₅-(SEQ ID NO: 11);
(β-AlaSO₃H)-Sar₁₀-(SEQ ID NO: 11); and
(β-AlaSO₃H)-Sar₅-(SEQ ID NO: 11).

12. The peptide ligand as defined in claim 1, wherein the polypeptide comprises the amino acid sequence CPLVNPLCLHPGWTC (SEQ ID NO: 97).

13. A pharmaceutical composition which comprises the peptide ligand of claim 1, in combination with one or more pharmaceutically acceptable excipients.

14. The drug conjugate as defined in claim 6, wherein said effector and/or functional groups is a cytotoxic agent selected from DM1 and MMAE.

15. The drug conjugate as defined in claim 14, which additionally comprises a linker between said peptide ligand and said cytotoxic agent.

16. The drug conjugate as defined in claim 15, wherein said cytotoxic agent is MMAE and the linker is selected from: -Val-Cit-, -Trp-Cit-, -Val-Lys-, -D-Trp-Cit-, -Ala-Ala-Asn-, D-Ala-Phe-Lys-, and -Glu-Pro-Cit-Gly-hPhe-Tyr-Leu- (SEQ ID NO: 98).

17. The drug conjugate as defined in claim 16, wherein said cytotoxic agent is MMAE and the linker is -Val-Cit-.

18. The drug conjugate as defined in claim 15, wherein said cytotoxic agent is DM1 and the linker is selected from: —S—S—, —SS(SO₃H)—, —SS-(Me)-, -(Me)-SS-(Me)-, —SS-(Me₂)-, and —SS-(Me)-SO₃H—.

19. The drug conjugate as defined in claim 6, which is selected from

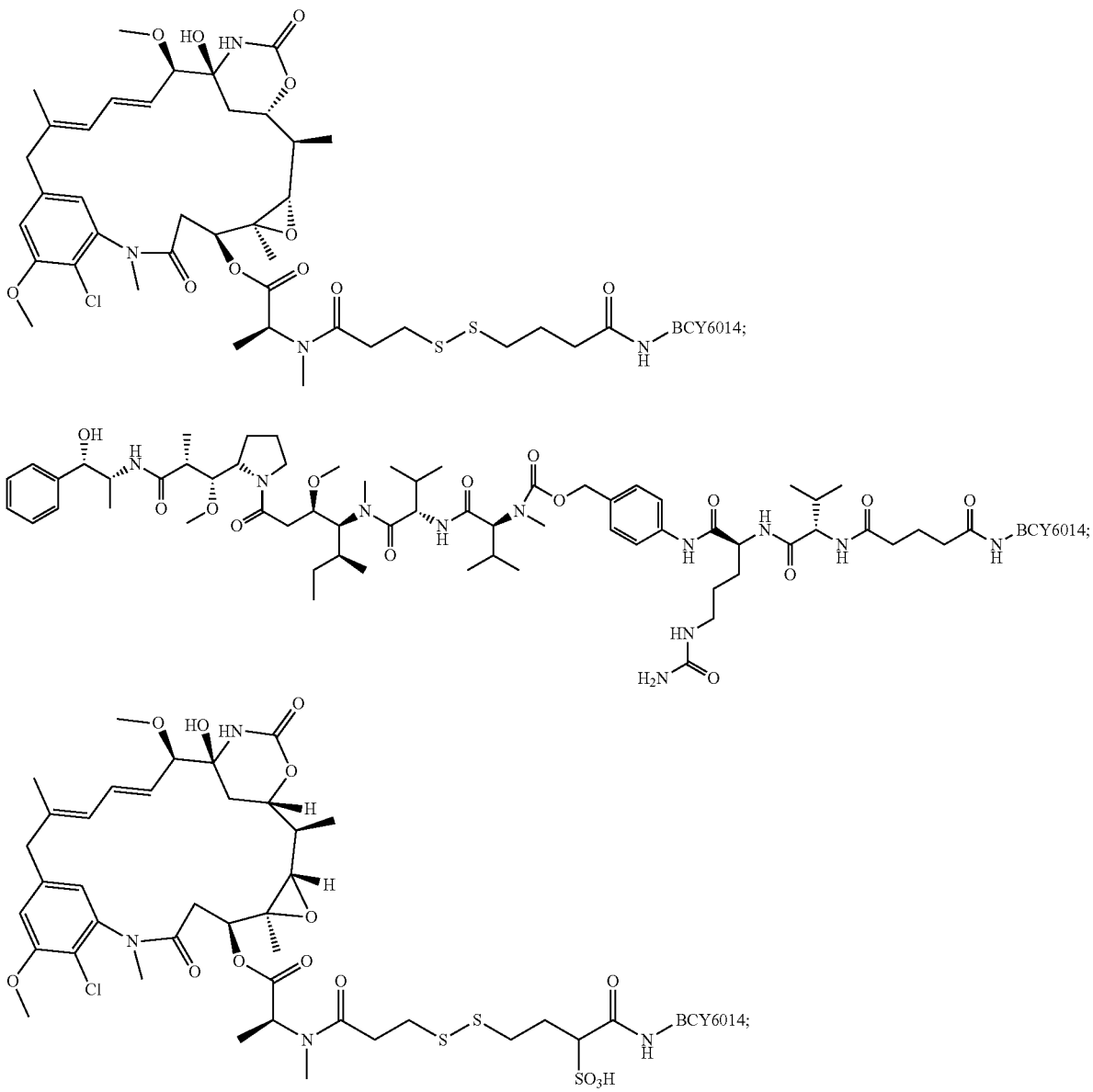

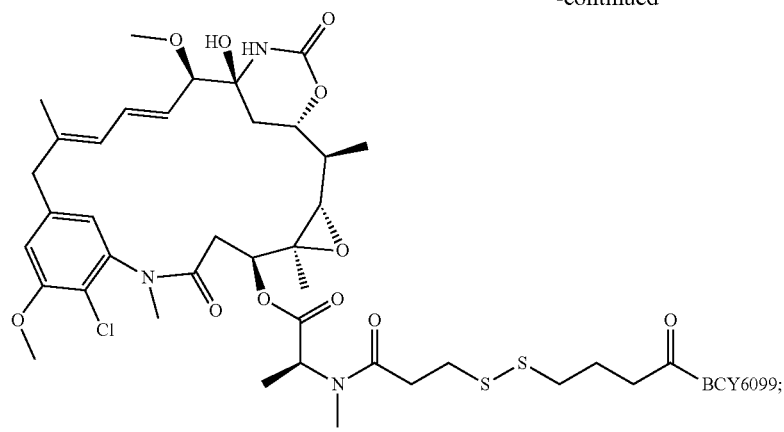
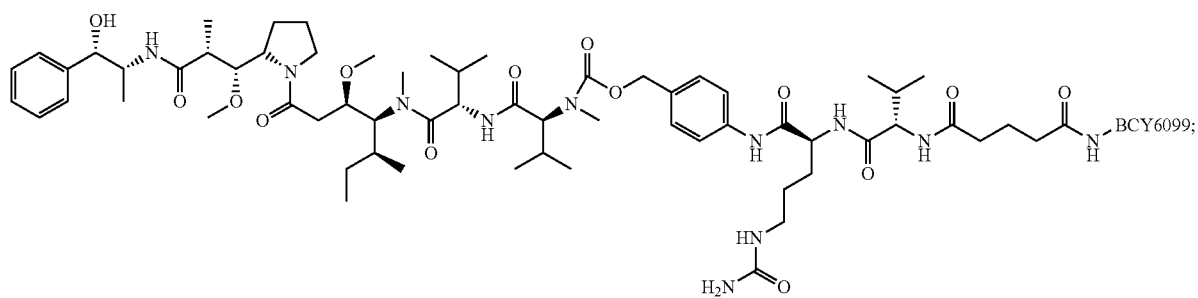
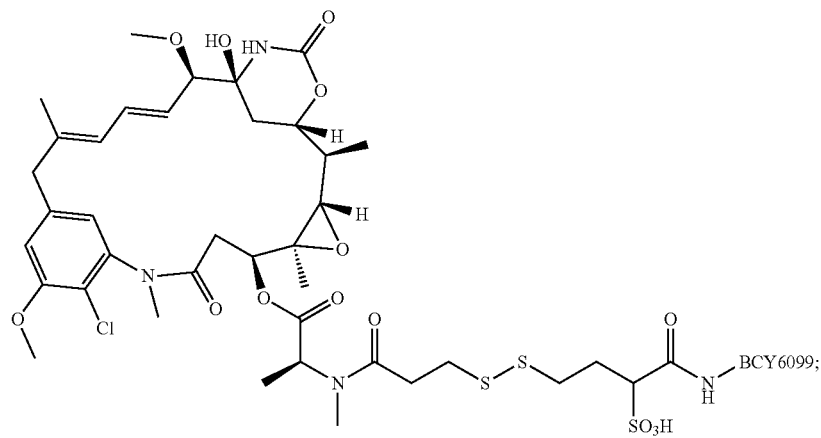
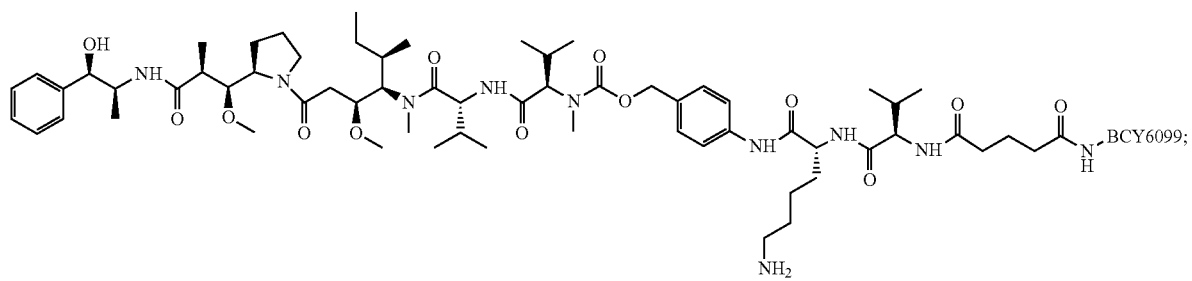

-continued
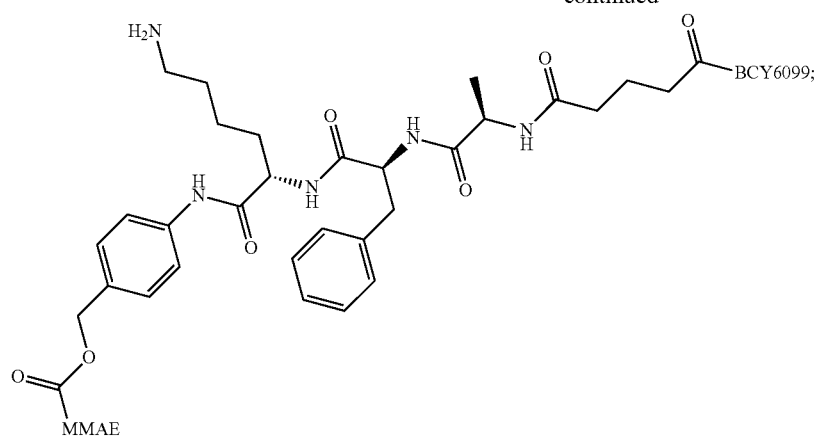
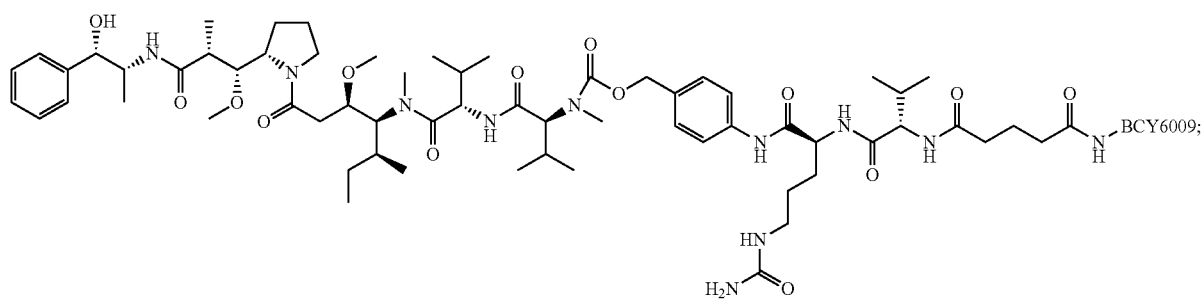
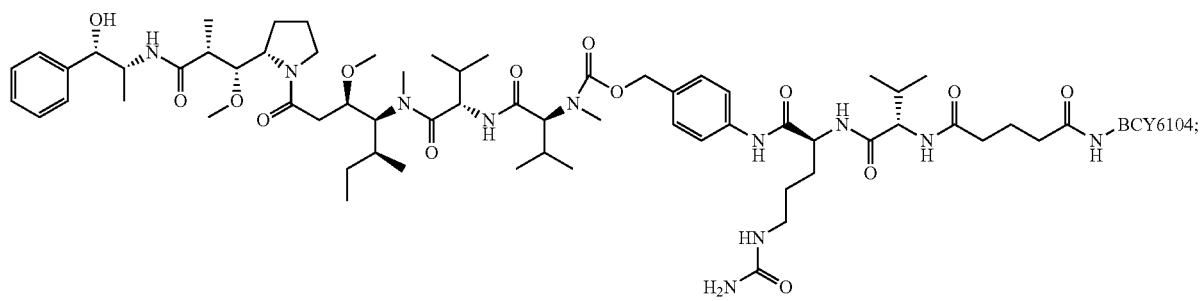
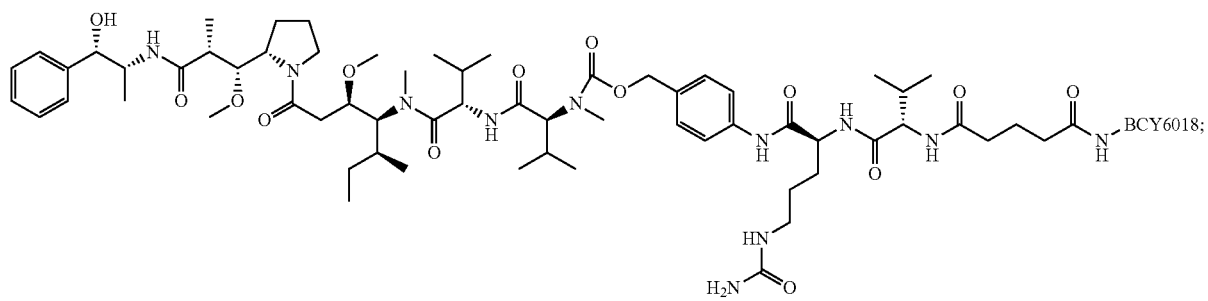
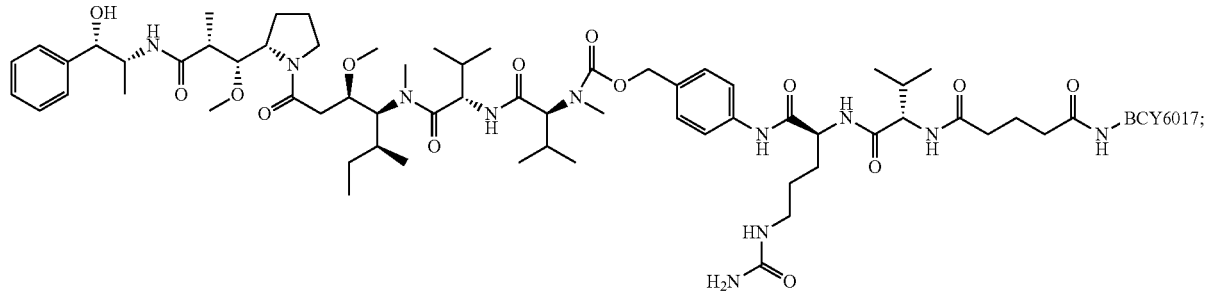

-continued
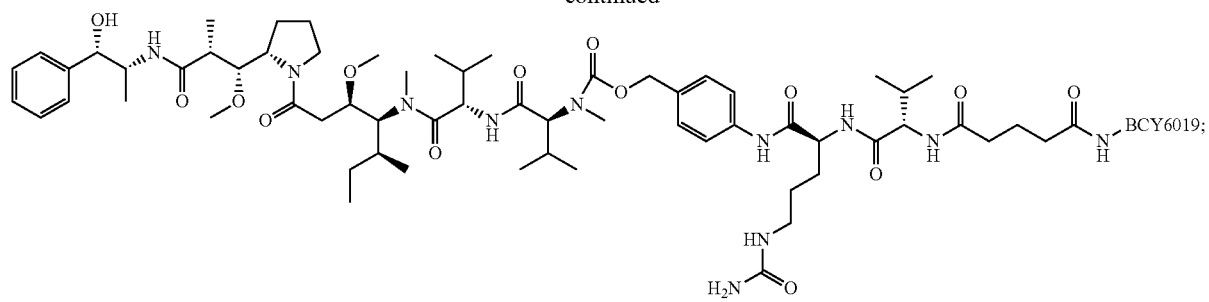
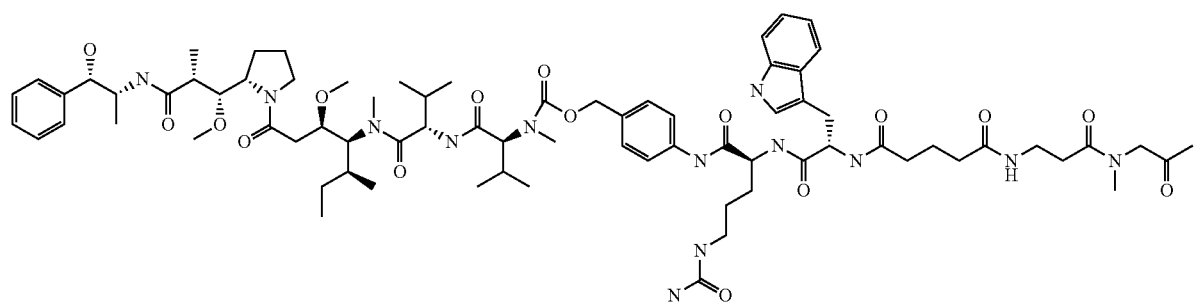
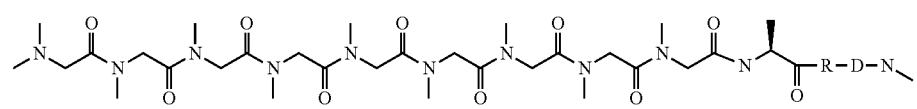
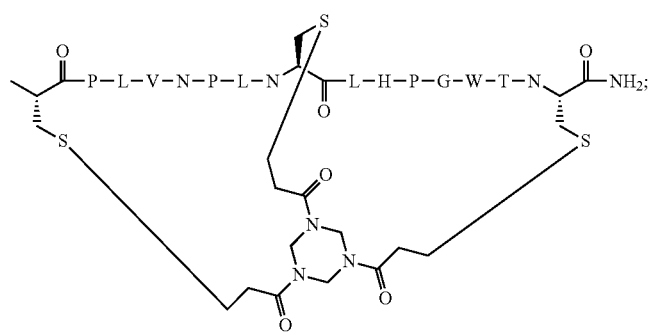
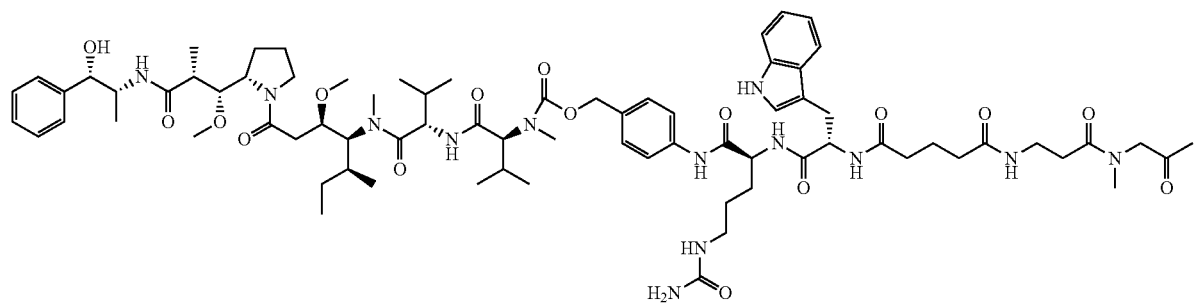
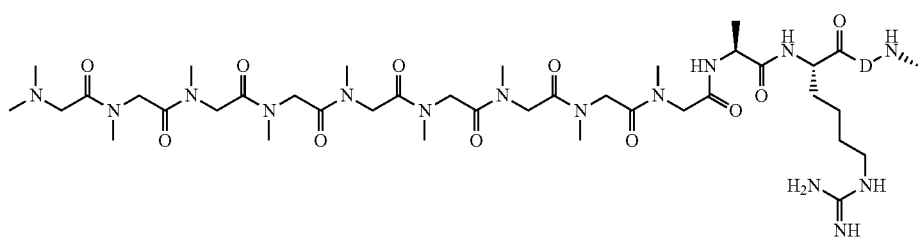

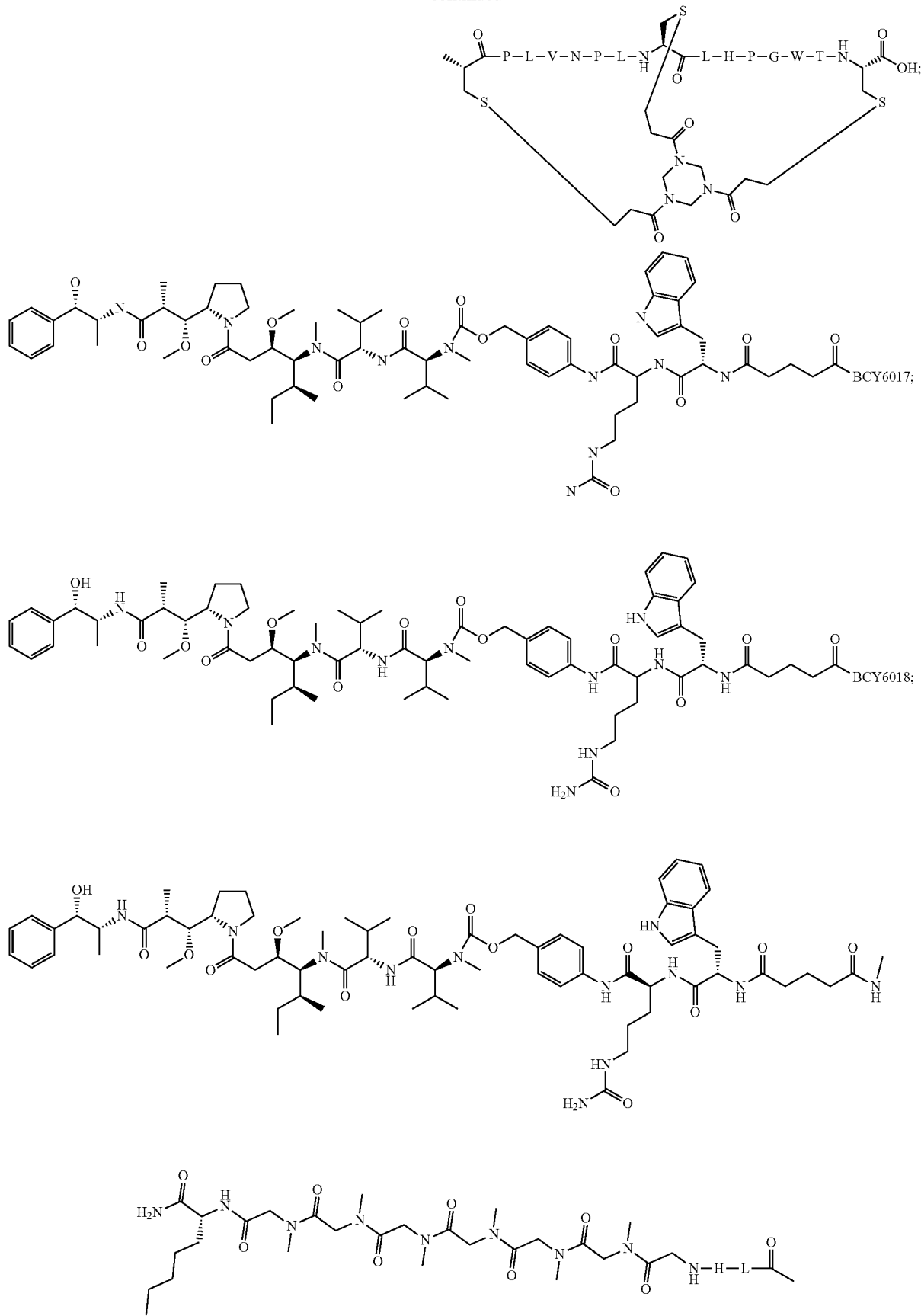

-continued
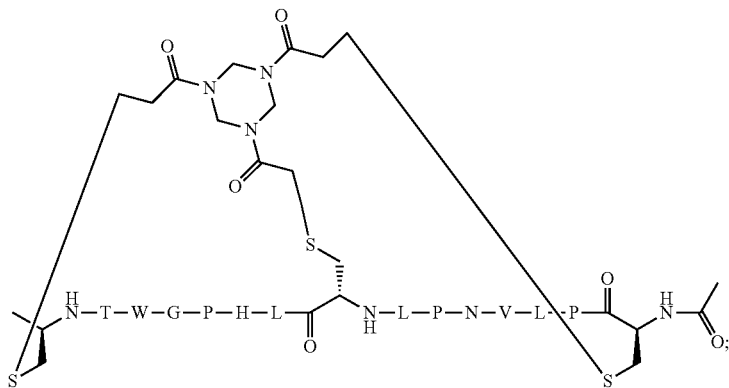
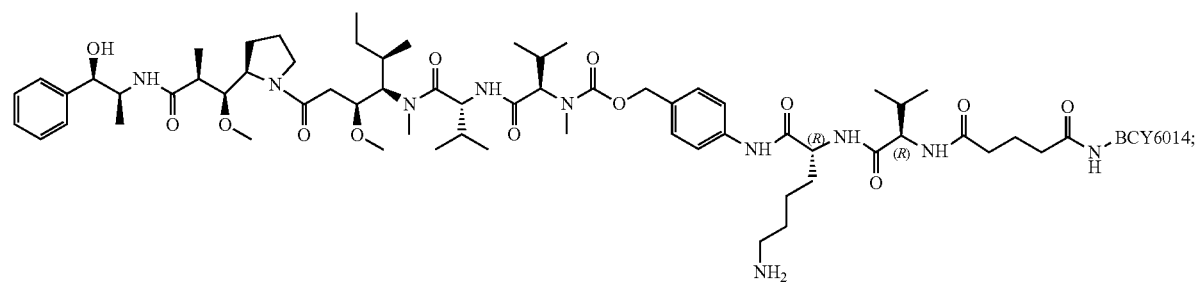
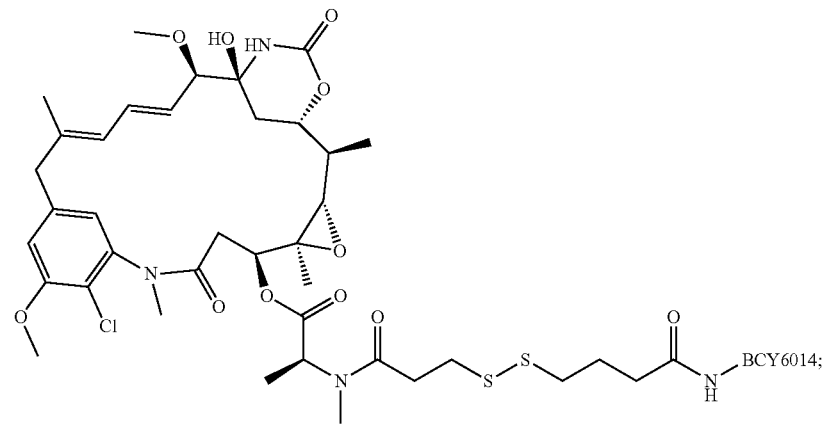
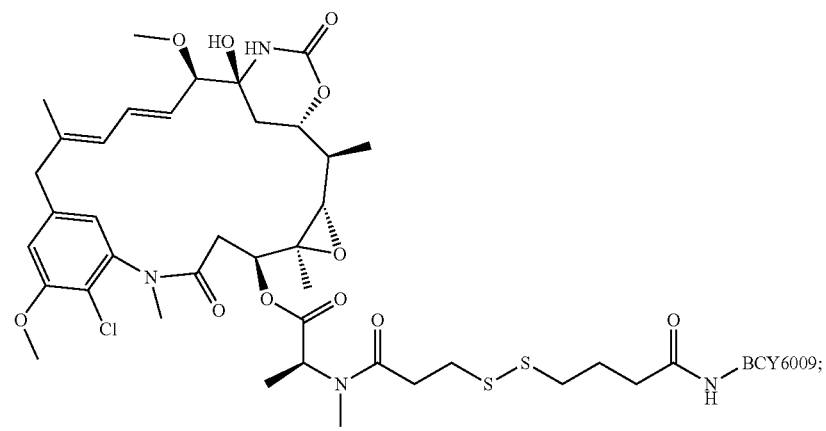

-continued
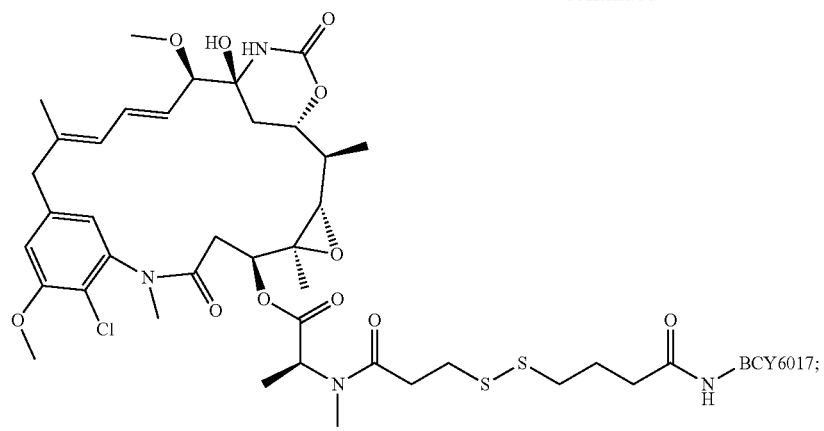
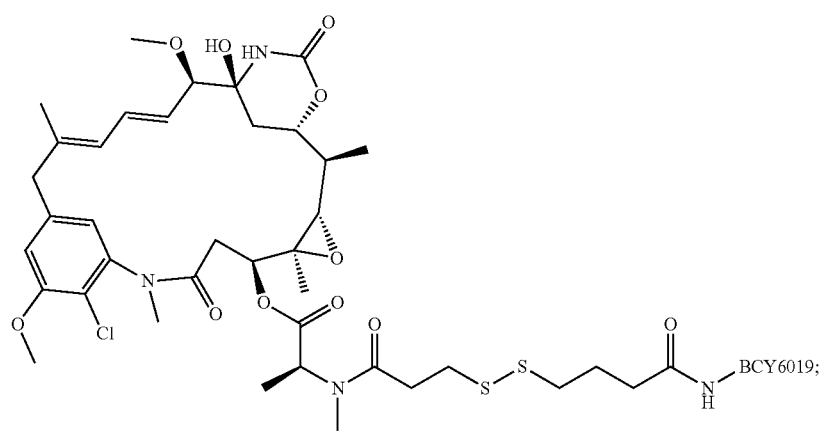
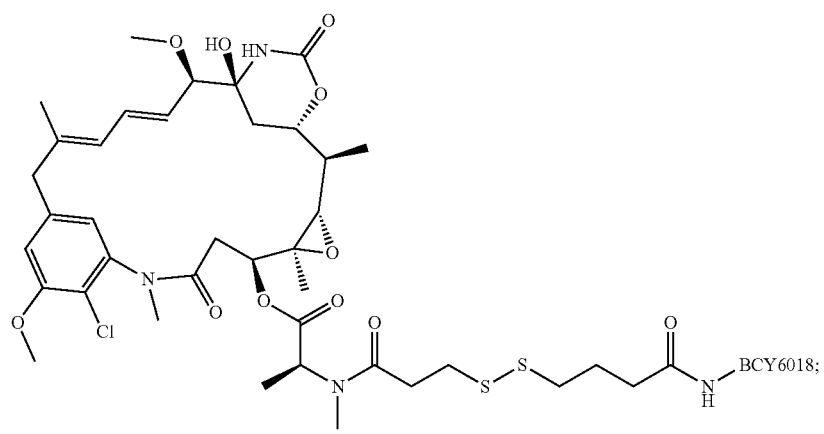
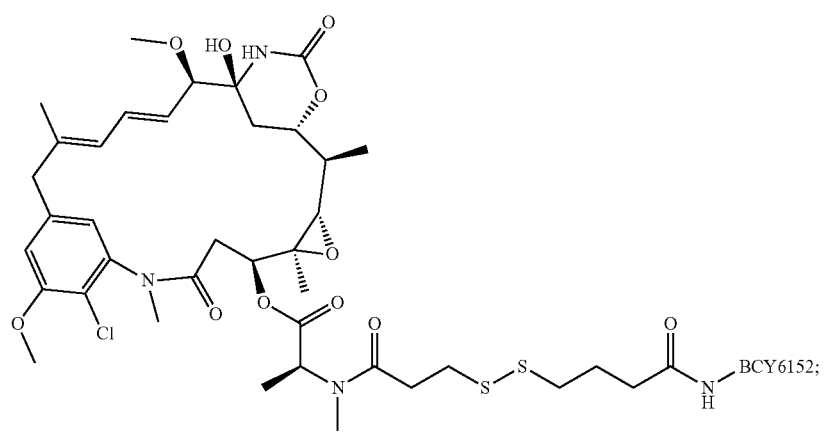

-continued
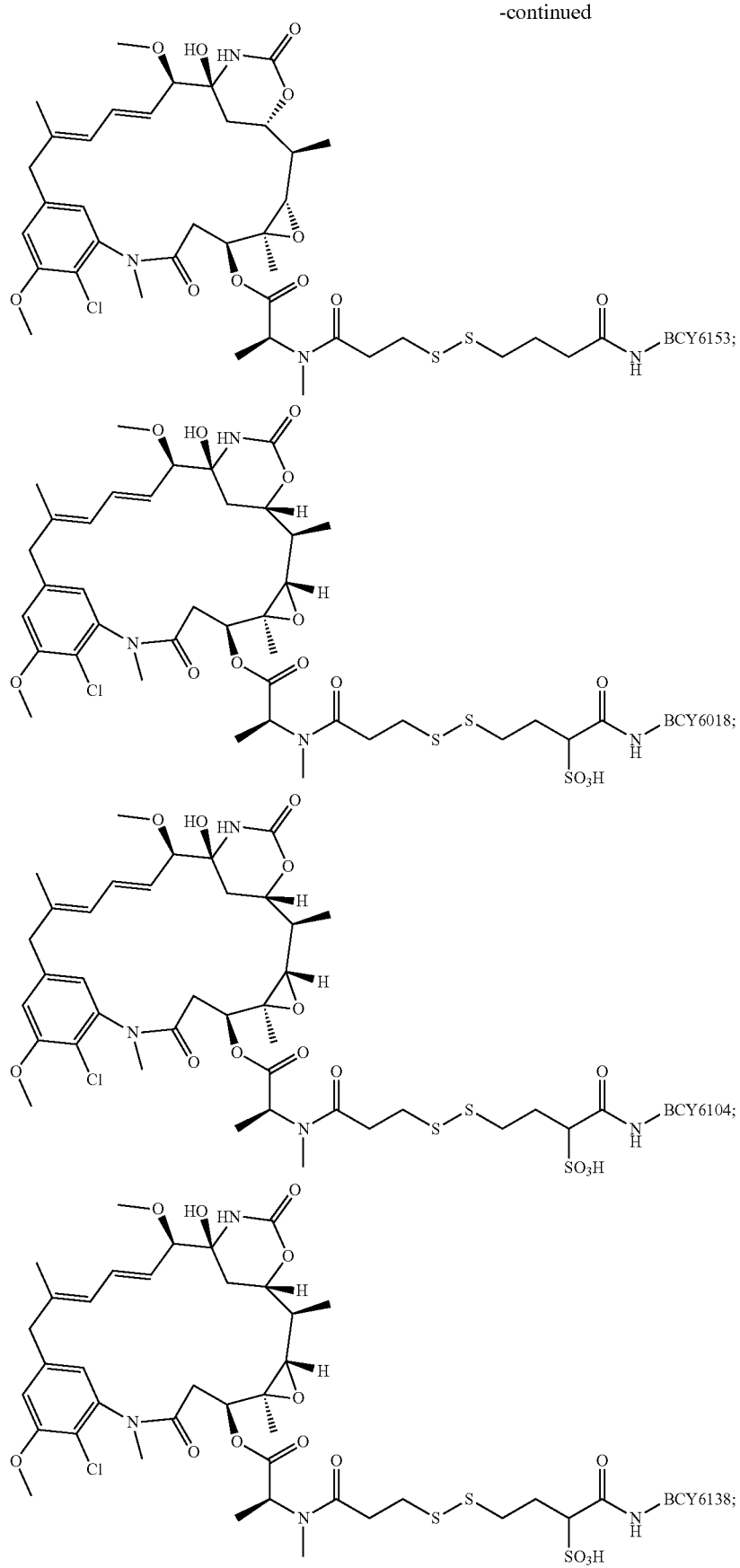

-continued
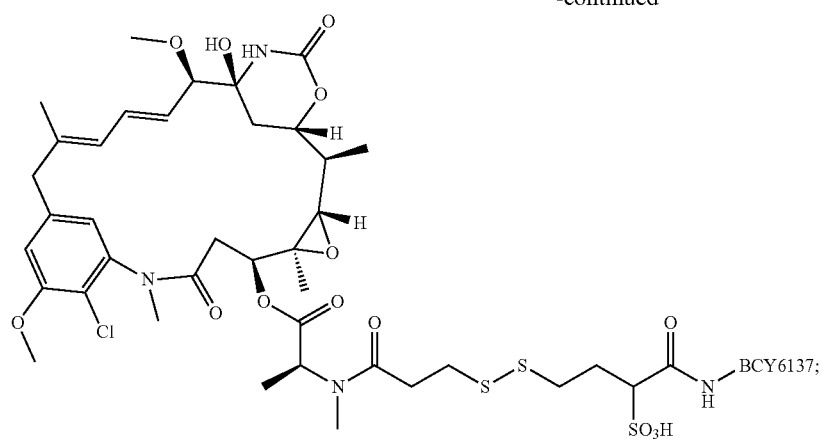
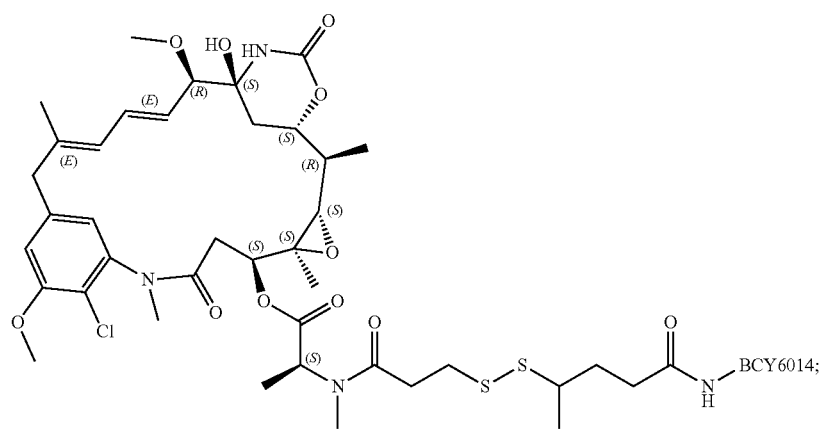
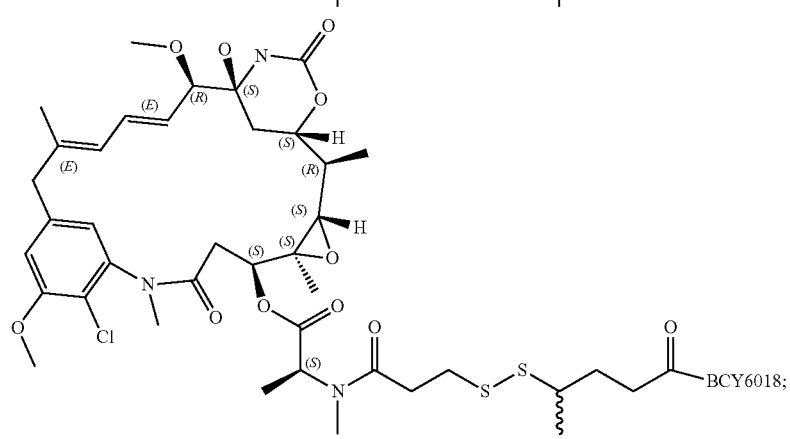
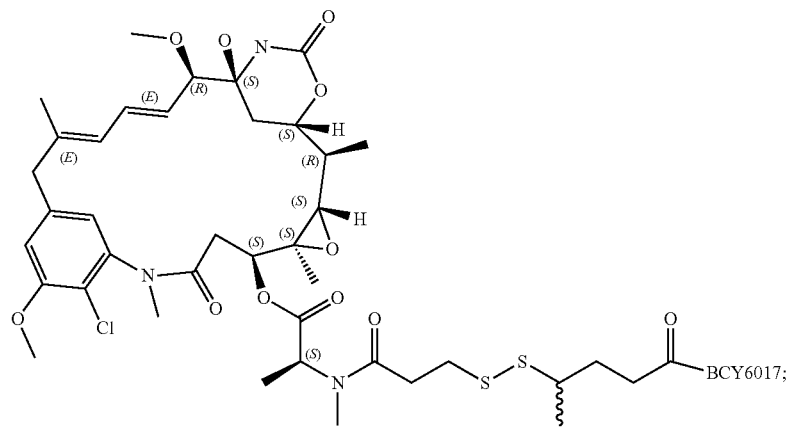

-continued
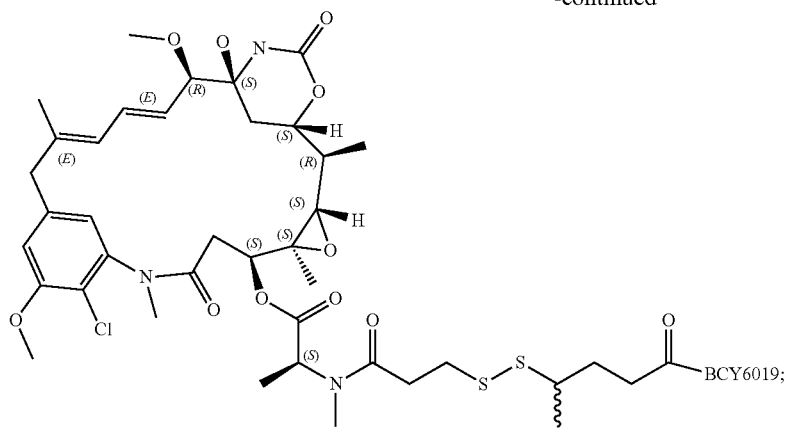
BCY6019;
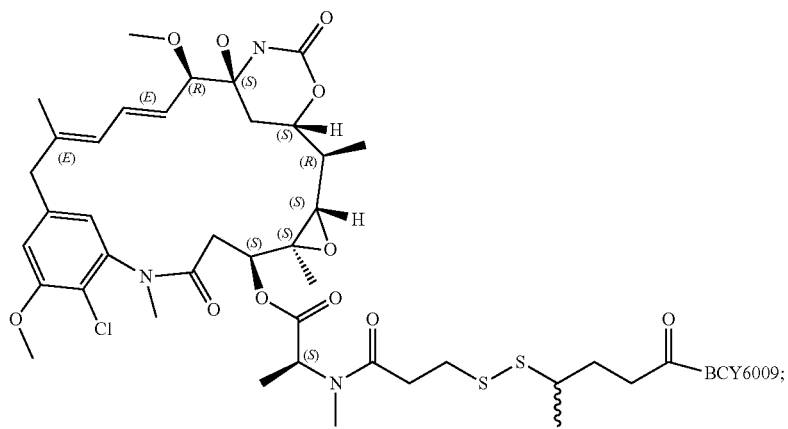
BCY6009;
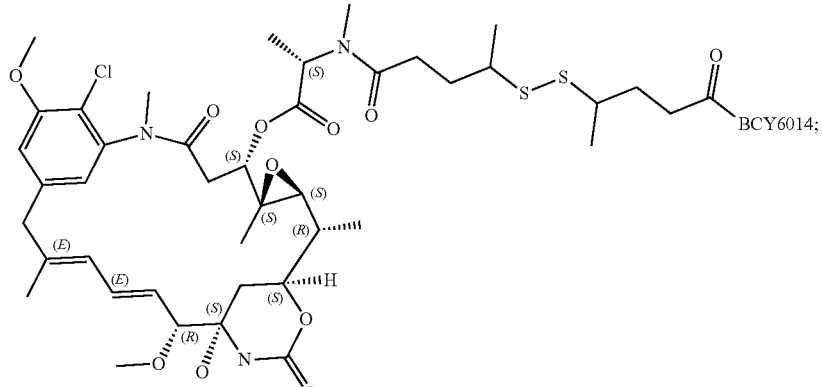
BCY6014;
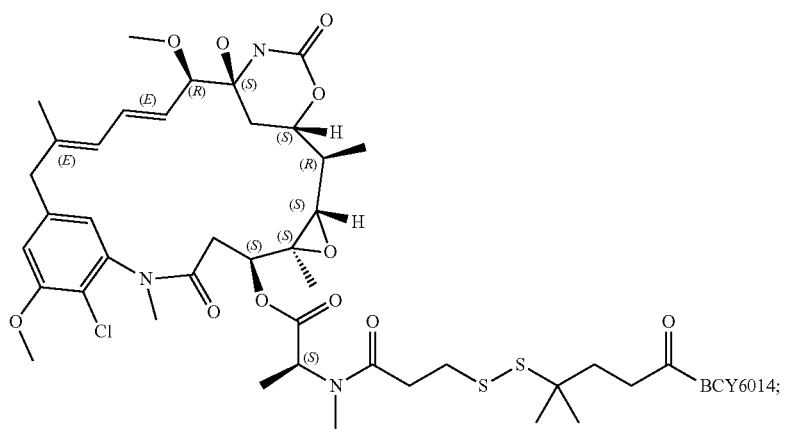
BCY6014;

-continued
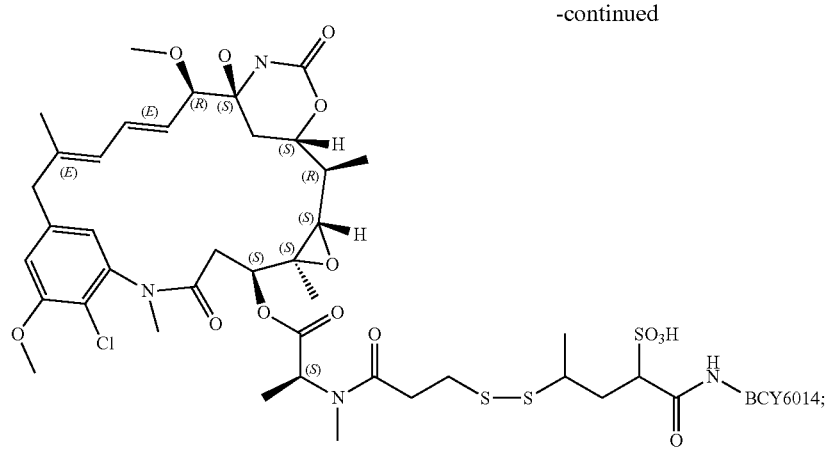
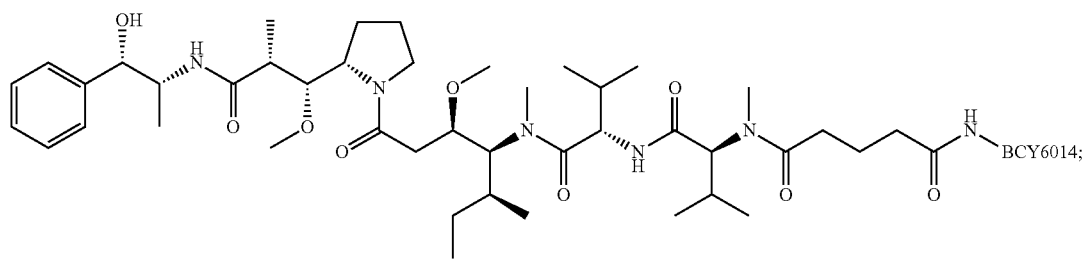
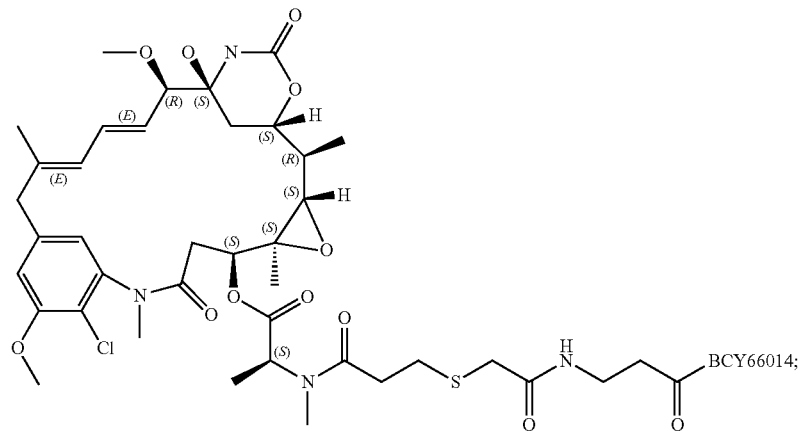
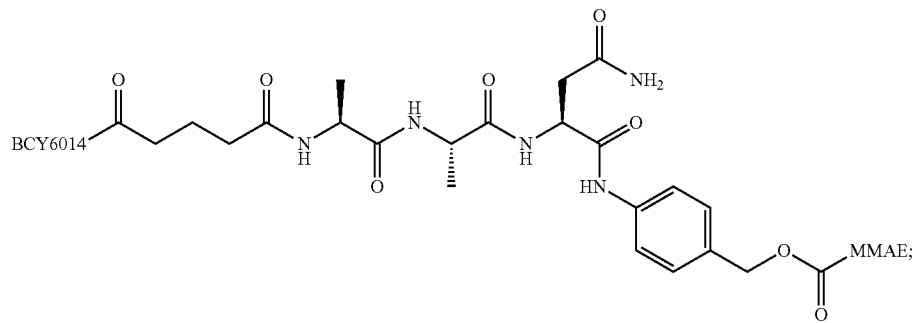

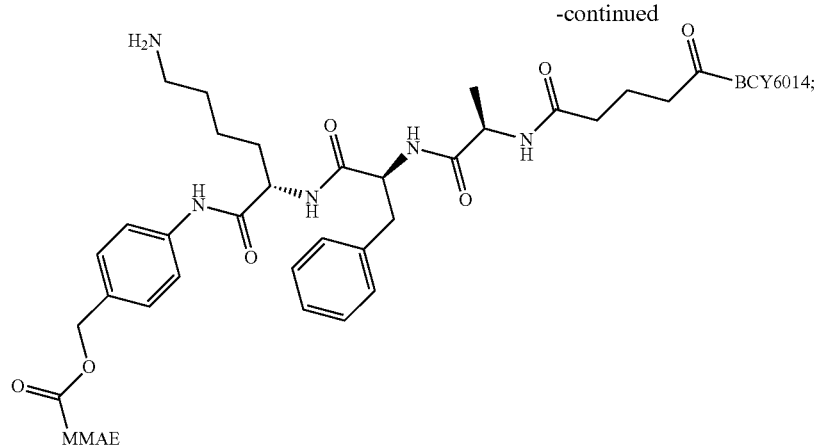
and
BCY6014-Glu-Pro-Cit-Gly-H Phe-Tyr-Leu-MMAE
   wherein BCY6099 has a structure
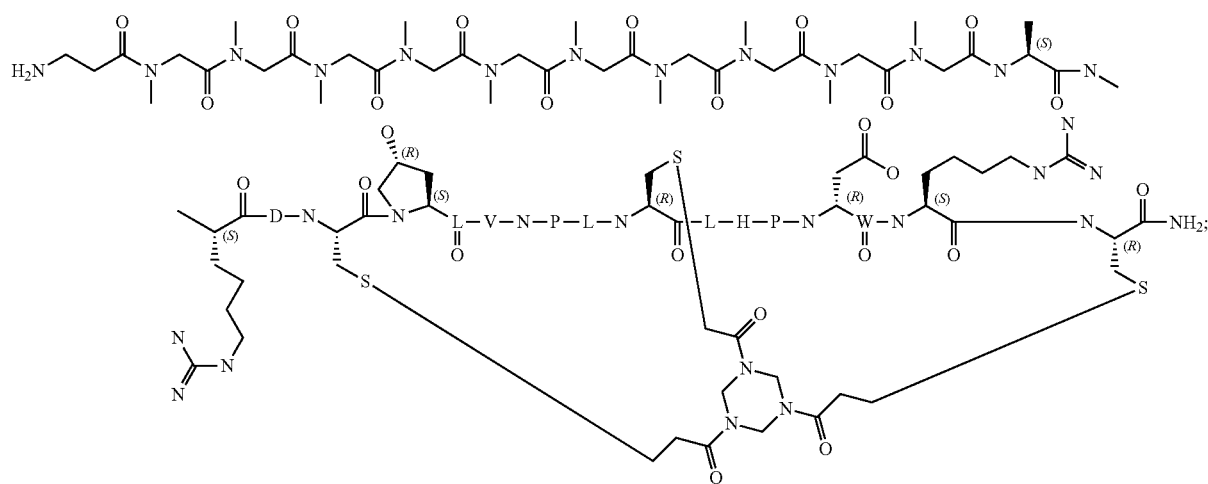
wherein BCY6014 has a structure
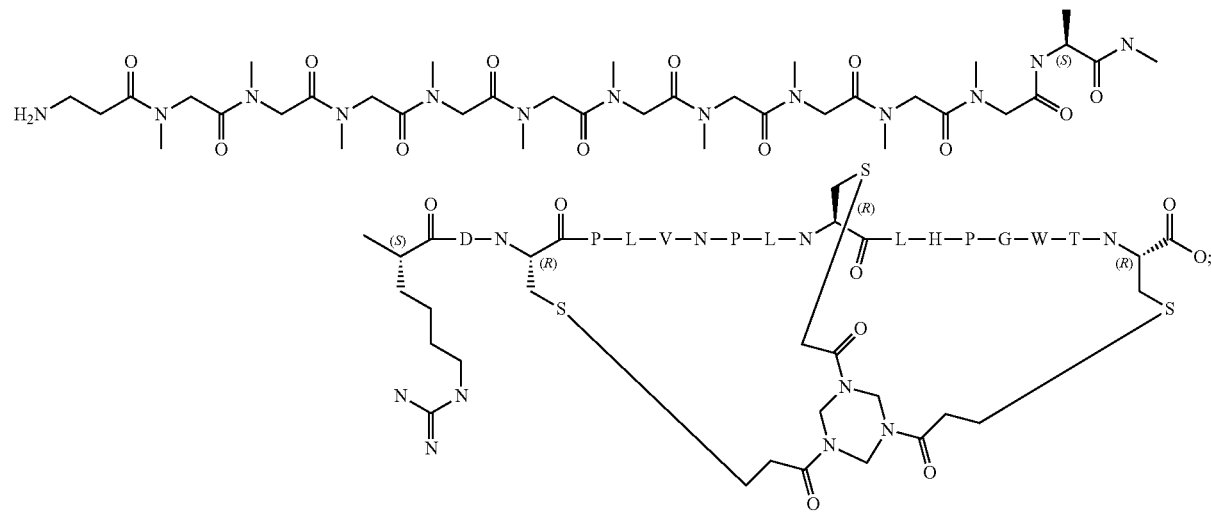

wherein BCY6104 has a structure
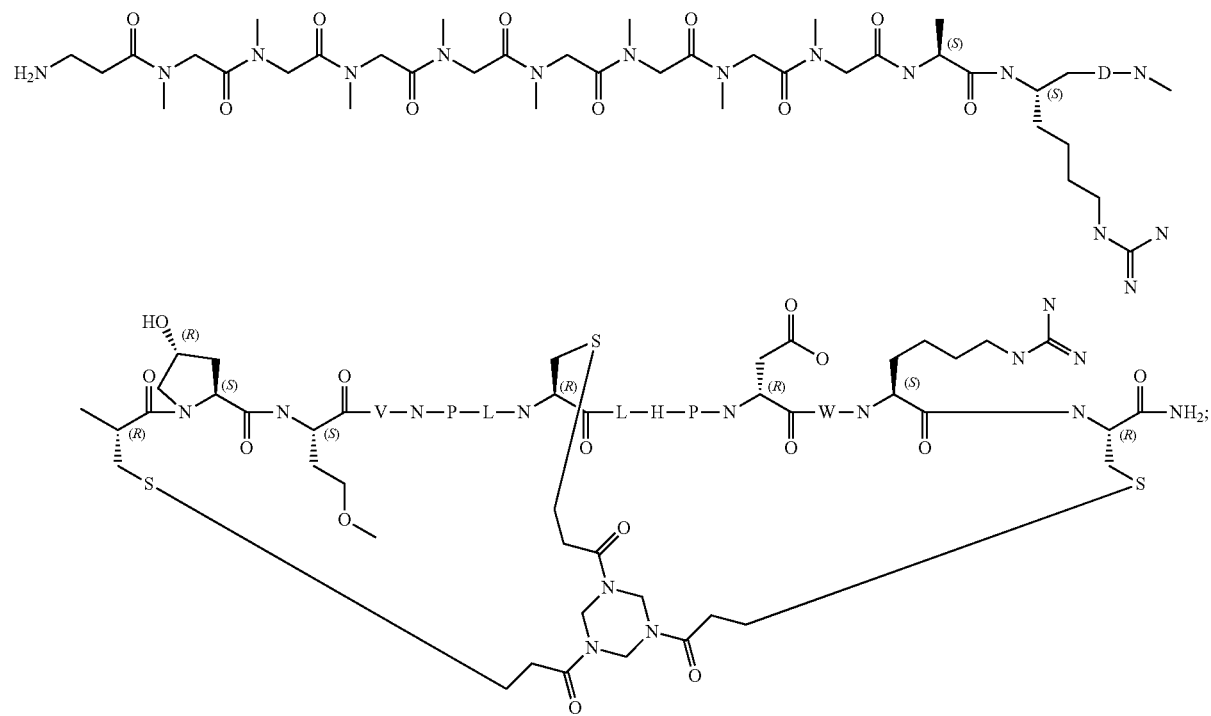
wherein BCY6018 has a structure
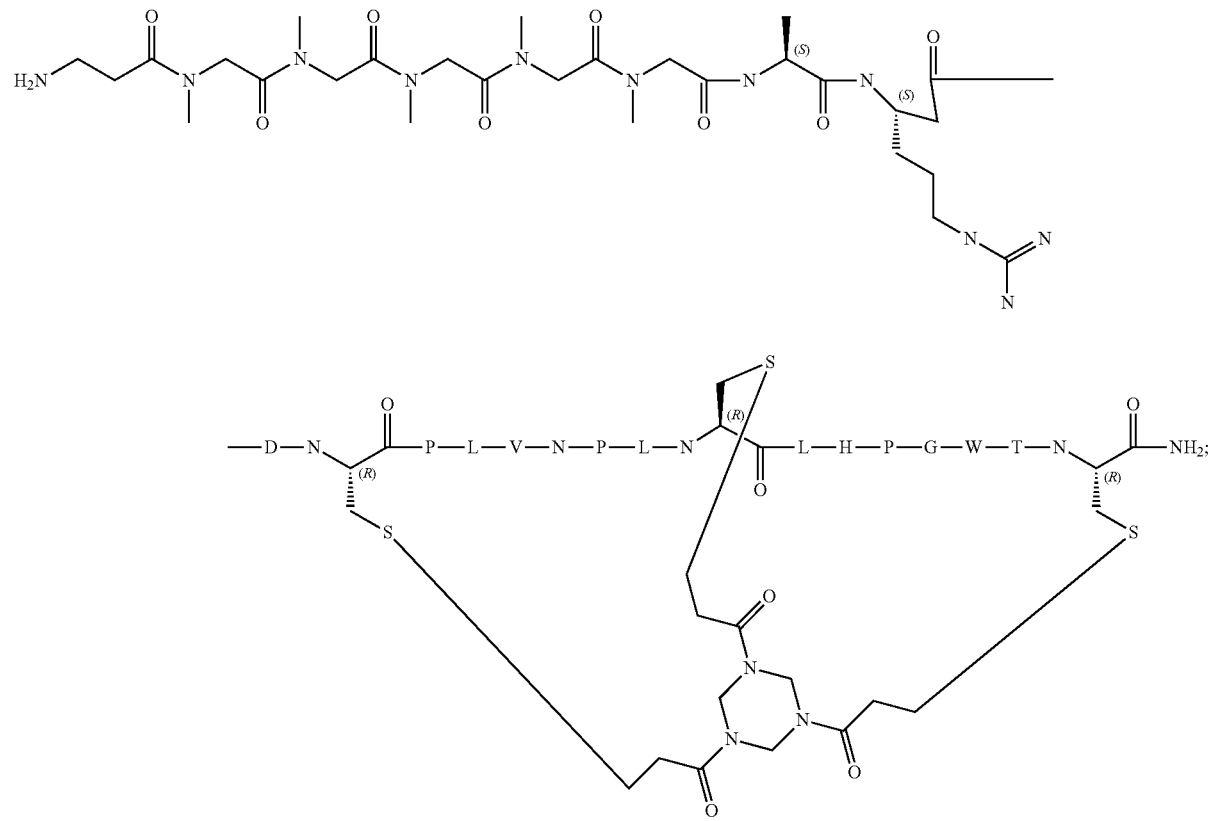

wherein BCY 6017 has a structure
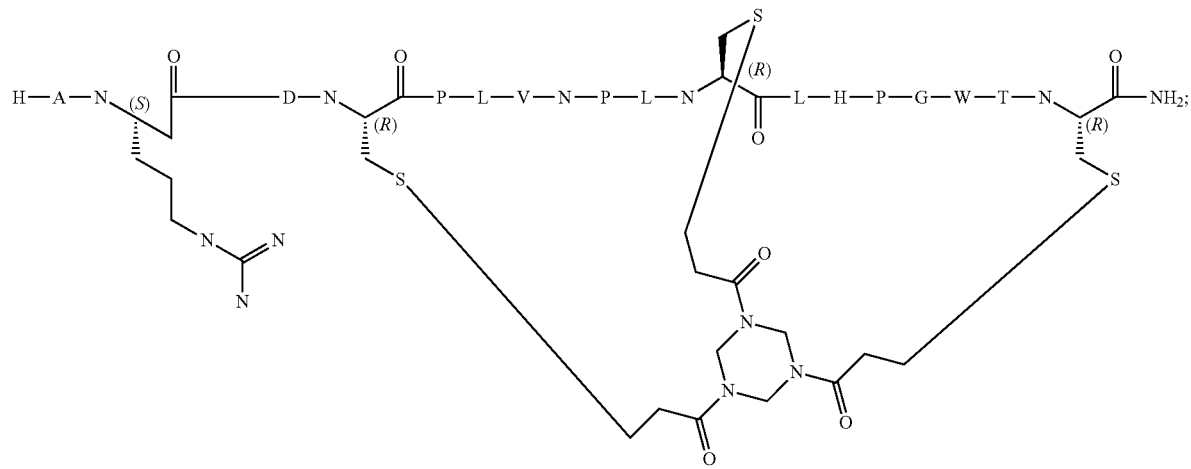
wherein BCY6019 has a structure
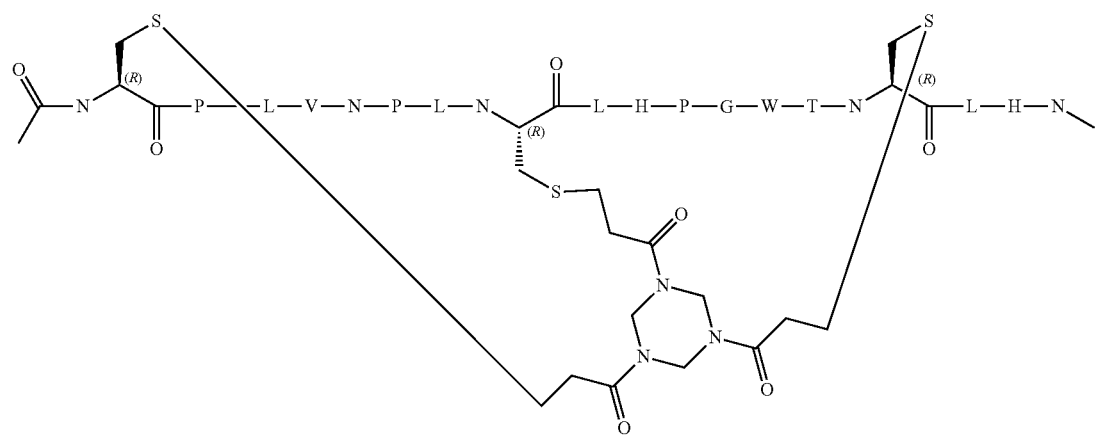
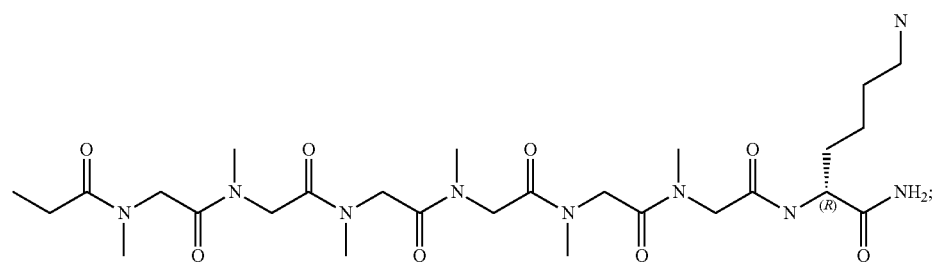
wherein BCY 6009 has a structure
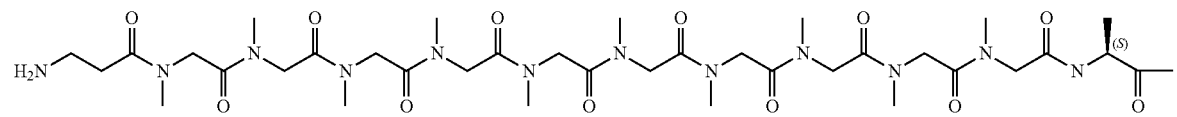

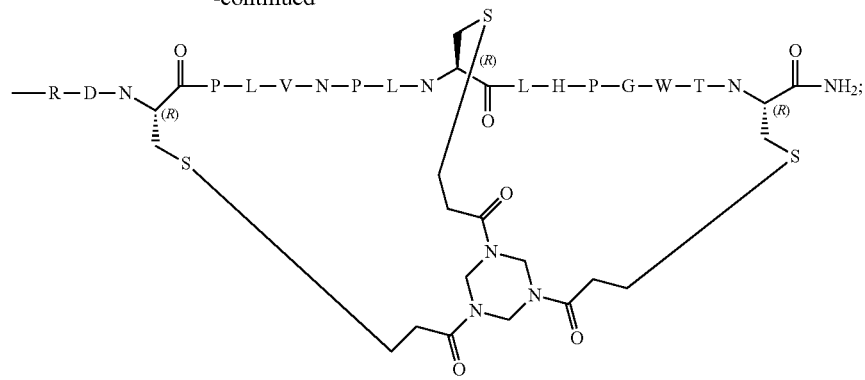
wherein BCY6152 has a structure
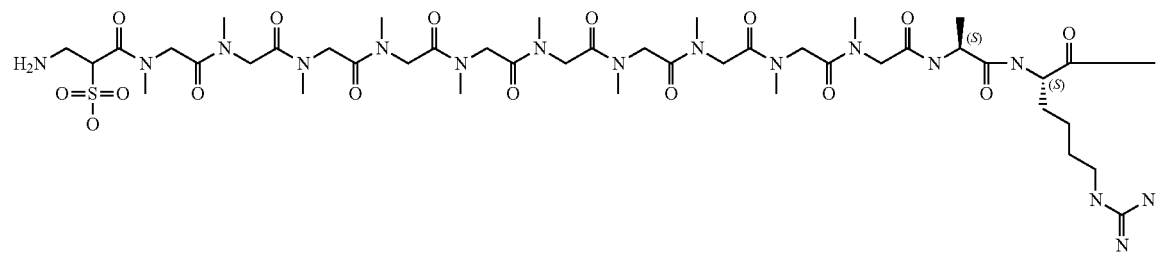
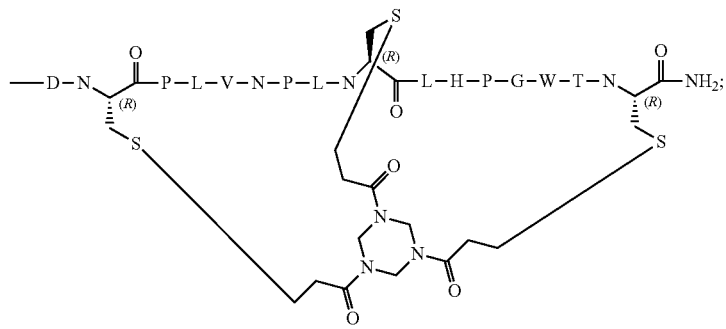
wherein BCY6153 has a structure
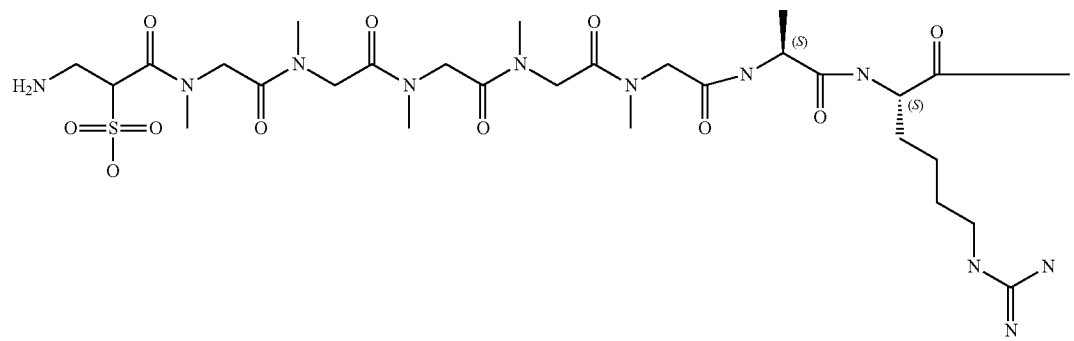

-continued
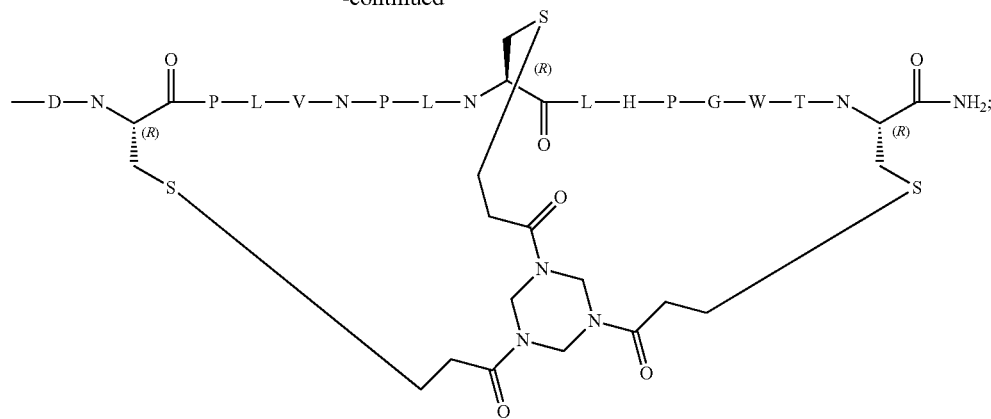
wherein BCY6138 has a structure
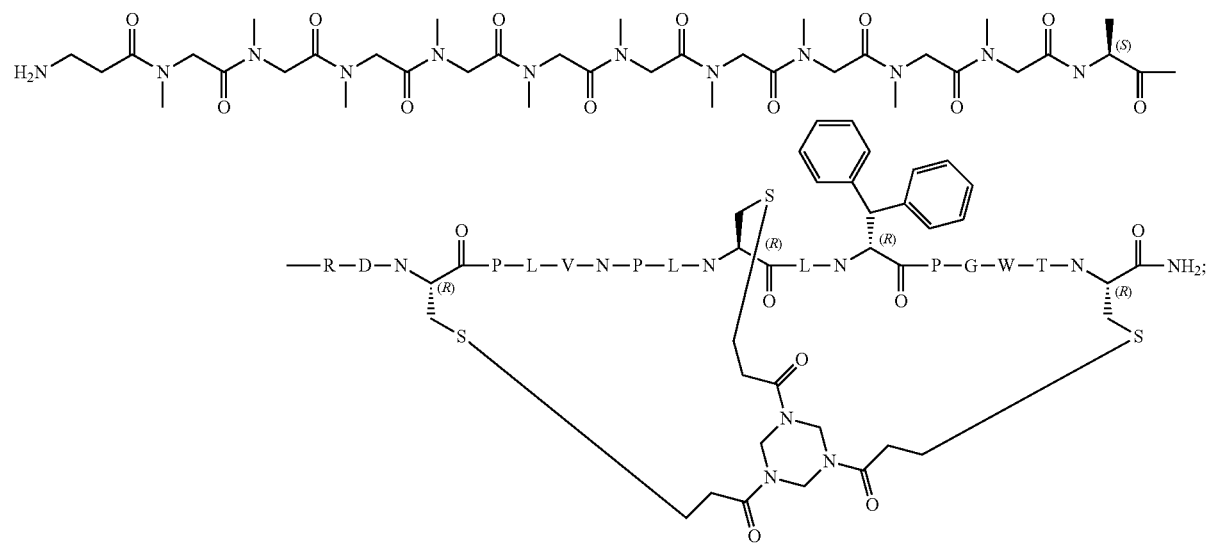
and
wherein BCY6137 has a structure
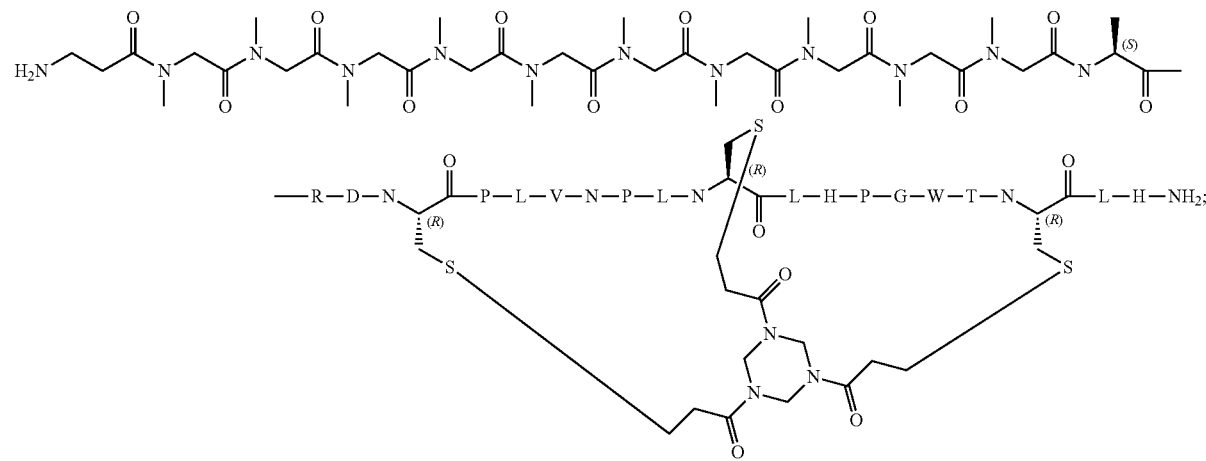
or a pharmaceutically acceptable salt thereof.
* * * * *

SEQUENCE LISTING

<160> NUMBER OF SEQ ID NOS: 98

<210> SEQ ID NO 1
<211> LENGTH: 15
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: X represents HyP
<220> FEATURE:
<221> NAME/KEY: Xaa
<222> LOCATION: (12)..(12)
<223> OTHER INFORMATION: Xaa represents D-Asp
<220> FEATURE:
<221> NAME/KEY: Xaa
<222> LOCATION: (14)..(14)
<223> OTHER INFORMATION: Xaa represents HArg

<400> SEQUENCE: 1

```
Cys Xaa Leu Val Asn Pro Leu Cys Leu His Pro Xaa Trp Xaa Cys
1               5                   10                  15

<210> SEQ ID NO 2
<211> LENGTH: 20
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (1)..(1)
<223> OTHER INFORMATION: Xaa represents Beta-Ala
<220> FEATURE:
<221> NAME/KEY: Xaa
<222> LOCATION: (2)..(2)
<223> OTHER INFORMATION: Xaa represents Sar10
<220> FEATURE:
<221> NAME/KEY: Xaa
<222> LOCATION: (4)..(4)
<223> OTHER INFORMATION: Xaa represents HArg
<220> FEATURE:
<221> NAME/KEY: Xaa
<222> LOCATION: (7)..(7)
<223> OTHER INFORMATION: Xaa represents HyP
<220> FEATURE:
<221> NAME/KEY: Xaa
<222> LOCATION: (17)..(17)
<223> OTHER INFORMATION: Xaa represents D-Asp
<220> FEATURE:
<221> NAME/KEY: Xaa
<222> LOCATION: (19)..(19)
<223> OTHER INFORMATION: Xaa represents HArg

<400> SEQUENCE: 2

Xaa Xaa Ala Xaa Asp Cys Xaa Leu Val Asn Pro Leu Cys Leu His Pro
1               5                   10                  15

Xaa Trp Xaa Cys
            20

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Ala Cys Met Asn Asp Trp Trp Cys Ala Met Gly Trp Lys Cys Ala
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic peptide

<400> SEQUENCE: 4

Ala Cys Val Pro Asp Arg Arg Cys Ala Tyr Met Asn Val Cys Ala
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5
```

```
Ala Cys Val Val Asp Gly Arg Cys Ala Tyr Met Asn Val Cys Ala
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Ala Cys Val Val Asp Ser Arg Cys Ala Tyr Met Asn Val Cys Ala
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

Ala Cys Val Pro Asp Ser Arg Cys Ala Tyr Met Asn Val Cys Ala
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Ala Cys Tyr Val Gly Lys Glu Cys Ala Ile Arg Asn Val Cys Ala
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Ala Cys Tyr Val Gly Lys Glu Cys Ala Tyr Met Asn Val Cys Ala
1               5                   10                  15

<210> SEQ ID NO 10
<211> LENGTH: 18
<212> TYPE: PRT
<213> ORGANISM: Artificial
<220> FEATURE:
<223> OTHER INFORMATION: Synthetic peptide

<400> SEQUENCE: 10

Ala Arg Asp Cys Pro Leu Val Asn Pro Leu Cys Leu His Pro Gly Trp
1               5                   10                  15

Thr Cys

<210> SEQ ID NO 11
<211> LENGTH: 18
<212> TYPE: PRT
<213> ORGANISM: Artificial
<220> FEATURE:
<223> OTHER INFORMATION: Synthetic peptide
<220> FEATURE:
```

```
<221> NAME/KEY: Xaa
<222> LOCATION: (2)..(2)
<223> OTHER INFORMATION: Xaa is HArg

<400> SEQUENCE: 11

Ala Xaa Asp Cys Pro Leu Val Asn Pro Leu Cys Leu His Pro Gly Trp
1               5                   10                  15

Thr Cys

<210> SEQ ID NO 12
<211> LENGTH: 18
<212> TYPE: PRT
<213> ORGANISM: Artificial
<220> FEATURE:
<223> OTHER INFORMATION: Synthetic peptide

<400> SEQUENCE: 12

Cys Pro Leu Val Asn Pro Leu Cys Leu His Pro Gly Trp Thr Cys Leu
1               5                   10                  15

His Gly

<210> SEQ ID NO 13
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (17)..(17)
<223> OTHER INFORMATION: Xaa is D-His

<400> SEQUENCE: 13

Cys Pro Leu Val Asn Pro Leu Cys Leu His Pro Gly Trp Thr Cys Leu
1               5                   10                  15

Xaa Gly

<210> SEQ ID NO 14
<211> LENGTH: 18
<212> TYPE: PRT
<213> ORGANISM: Artificial
<220> FEATURE:
<223> OTHER INFORMATION: Synthetic peptide

<400> SEQUENCE: 14

Cys Pro Leu Val Asn Pro Leu Cys Leu His Pro Gly Trp Ser Cys Arg
1               5                   10                  15

Gly Gln

<210> SEQ ID NO 15
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (16)..(16)
<223> OTHER INFORMATION: Xaa is HArg

<400> SEQUENCE: 15

Cys Pro Leu Val Asn Pro Leu Cys Leu His Pro Gly Trp Ser Cys Xaa
1               5                   10                  15

Gly Gln
```

<210> SEQ ID NO 16
<211> LENGTH: 14
<212> TYPE: PRT
<213> ORGANISM: Artificial
<220> FEATURE:
<223> OTHER INFORMATION: Synthetic peptide

<400> SEQUENCE: 16

Ala Cys Val Pro Asp Arg Arg Cys Ala Tyr Met Asn Val Cys
1               5                   10

<210> SEQ ID NO 17
<211> LENGTH: 17
<212> TYPE: PRT
<213> ORGANISM: Artificial
<220> FEATURE:
<223> OTHER INFORMATION: Synthetic peptide

<400> SEQUENCE: 17

Asp Leu Arg Cys Gly Gly Asp Pro Arg Cys Ala Tyr Met Asn Val Cys
1               5                   10                  15

Ala

<210> SEQ ID NO 18
<211> LENGTH: 17
<212> TYPE: PRT
<213> ORGANISM: Artificial
<220> FEATURE:
<223> OTHER INFORMATION: Synthetic peptide

<400> SEQUENCE: 18

Ser Arg Pro Cys Val Ile Asp Ser Arg Cys Ala Tyr Met Asn Val Cys
1               5                   10                  15

Ala

<210> SEQ ID NO 19
<211> LENGTH: 17
<212> TYPE: PRT
<213> ORGANISM: Artificial
<220> FEATURE:
<223> OTHER INFORMATION: Synthetic peptide

<400> SEQUENCE: 19

Glu Ser Arg Cys Ser Pro Asp Ala Arg Cys Ala Tyr Met Asn Val Cys
1               5                   10                  15

Ala

<210> SEQ ID NO 20
<211> LENGTH: 17
<212> TYPE: PRT
<213> ORGANISM: Artificial
<220> FEATURE:
<223> OTHER INFORMATION: Synthetic peptide

<400> SEQUENCE: 20

His Ser Gly Cys Arg Pro Asp Pro Arg Cys Ala Tyr Met Asn Val Cys
1               5                   10                  15

Ala

<210> SEQ ID NO 21
<211> LENGTH: 17
<212> TYPE: PRT
<213> ORGANISM: Artificial
<220> FEATURE:

```
<223> OTHER INFORMATION: Synthetic peptide

<400> SEQUENCE: 21

Gly Ser Gly Cys Lys Pro Asp Ser Arg Cys Ala Tyr Met Asn Val Cys
1               5                   10                  15
Ala

<210> SEQ ID NO 22
<211> LENGTH: 17
<212> TYPE: PRT
<213> ORGANISM: Artificial
<220> FEATURE:
<223> OTHER INFORMATION: Synthetic peptide

<400> SEQUENCE: 22

Glu Thr Val Cys Leu Pro Asp Ser Arg Cys Ala Tyr Met Asn Val Cys
1               5                   10                  15
Ala

<210> SEQ ID NO 23
<211> LENGTH: 17
<212> TYPE: PRT
<213> ORGANISM: Artificial
<220> FEATURE:
<223> OTHER INFORMATION: Synthetic peptide

<400> SEQUENCE: 23

Gly Gln Val Cys Ile Val Asp Ala Arg Cys Ala Tyr Met Asn Val Cys
1               5                   10                  15
Ala

<210> SEQ ID NO 24
<211> LENGTH: 17
<212> TYPE: PRT
<213> ORGANISM: Artificial
<220> FEATURE:
<223> OTHER INFORMATION: Synthetic peptide

<400> SEQUENCE: 24

Ala Cys Val Pro Asp Arg Arg Cys Ala Phe Glu Asn Val Cys Val Asp
1               5                   10                  15
His

<210> SEQ ID NO 25
<211> LENGTH: 17
<212> TYPE: PRT
<213> ORGANISM: Artificial
<220> FEATURE:
<223> OTHER INFORMATION: Synthetic peptide

<400> SEQUENCE: 25

Ala Cys Val Pro Asp Arg Arg Cys Ala Phe Met Asn Val Cys Glu Asp
1               5                   10                  15
Arg

<210> SEQ ID NO 26
<211> LENGTH: 17
<212> TYPE: PRT
<213> ORGANISM: Artificial
<220> FEATURE:
<223> OTHER INFORMATION: Synthetic peptide

<400> SEQUENCE: 26
```

```
Ala Cys Val Pro Asp Arg Arg Cys Ala Phe Gln Asp Val Cys Asp His
1               5                   10                  15

Glu

<210> SEQ ID NO 27
<211> LENGTH: 17
<212> TYPE: PRT
<213> ORGANISM: Artificial
<220> FEATURE:
<223> OTHER INFORMATION: Synthetic peptide

<400> SEQUENCE: 27

Ala Cys Val Pro Asp Arg Arg Cys Ala Phe Arg Asp Val Cys Leu Thr
1               5                   10                  15

Gly

<210> SEQ ID NO 28
<211> LENGTH: 15
<212> TYPE: PRT
<213> ORGANISM: Artificial
<220> FEATURE:
<223> OTHER INFORMATION: Synthetic peptide

<400> SEQUENCE: 28

Ala Cys Gln Pro Ser Asn His Cys Ala Phe Met Asn Tyr Cys Ala
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Ala Cys Ser Pro Thr Pro Ala Cys Ala Val Gln Asn Leu Cys Ala
1               5                   10                  15

<210> SEQ ID NO 30
<211> LENGTH: 14
<212> TYPE: PRT
<213> ORGANISM: Artificial
<220> FEATURE:
<223> OTHER INFORMATION: Synthetic peptide

<400> SEQUENCE: 30

Ala Cys Thr Ser Cys Trp Ala Tyr Pro Asp Ser Phe Cys Ala
1               5                   10

<210> SEQ ID NO 31
<211> LENGTH: 17
<212> TYPE: PRT
<213> ORGANISM: Artificial
<220> FEATURE:
<223> OTHER INFORMATION: Synthetic peptide

<400> SEQUENCE: 31

Ala Cys Thr Lys Pro Thr Gly Phe Cys Ala Tyr Pro Asp Thr Ile Cys
1               5                   10                  15

Ala

<210> SEQ ID NO 32
<211> LENGTH: 17
<212> TYPE: PRT
<213> ORGANISM: Artificial
```

```
<220> FEATURE:
<223> OTHER INFORMATION: Synthetic peptide

<400> SEQUENCE: 32

Ala Cys Arg Gly Glu Trp Gly Tyr Cys Ala Tyr Pro Asp Thr Ile Cys
1               5                   10                  15

Ala

<210> SEQ ID NO 33
<211> LENGTH: 17
<212> TYPE: PRT
<213> ORGANISM: Artificial
<220> FEATURE:
<223> OTHER INFORMATION: Synthetic peptide

<400> SEQUENCE: 33

Ala Cys Arg Asn Trp Gly Met Tyr Cys Ala Tyr Pro Asp Thr Ile Cys
1               5                   10                  15

Ala

<210> SEQ ID NO 34
<211> LENGTH: 17
<212> TYPE: PRT
<213> ORGANISM: Artificial
<220> FEATURE:
<223> OTHER INFORMATION: Synthetic peptide

<400> SEQUENCE: 34

Ala Cys Pro Asp Trp Gly Lys Tyr Cys Ala Tyr Pro Asp Thr Ile Cys
1               5                   10                  15

Ala

<210> SEQ ID NO 35
<211> LENGTH: 17
<212> TYPE: PRT
<213> ORGANISM: Artificial
<220> FEATURE:
<223> OTHER INFORMATION: Synthetic peptide

<400> SEQUENCE: 35

Ala Cys Arg Val Tyr Gly Pro Tyr Cys Ala Tyr Pro Asp Thr Ile Cys
1               5                   10                  15

Ala

<210> SEQ ID NO 36
<211> LENGTH: 14
<212> TYPE: PRT
<213> ORGANISM: Artificial
<220> FEATURE:
<223> OTHER INFORMATION: Synthetic peptide

<400> SEQUENCE: 36

Ala Cys Ser Ser Cys Trp Ala Tyr Pro Asp Ser Val Cys Ala
1               5                   10

<210> SEQ ID NO 37
<211> LENGTH: 14
<212> TYPE: PRT
<213> ORGANISM: Artificial
<220> FEATURE:
<223> OTHER INFORMATION: Synthetic peptide

<400> SEQUENCE: 37

Ala Cys Gln Ser Cys Trp Ala Tyr Pro Asp Thr Tyr Cys Ala
```

-continued

```
1               5                  10

<210> SEQ ID NO 38
<211> LENGTH: 15
<212> TYPE: PRT
<213> ORGANISM: Artificial
<220> FEATURE:
<223> OTHER INFORMATION: Synthetic peptide

<400> SEQUENCE: 38

Ala Cys Gly Phe Met Gly Leu Glu Pro Cys Glu Thr Phe Cys Ala
1               5                  10                  15

<210> SEQ ID NO 39
<211> LENGTH: 15
<212> TYPE: PRT
<213> ORGANISM: Artificial
<220> FEATURE:
<223> OTHER INFORMATION: Synthetic peptide

<400> SEQUENCE: 39

Ala Cys Gly Phe Met Gly Leu Val Pro Cys Glu Val His Cys Ala
1               5                  10                  15

<210> SEQ ID NO 40
<211> LENGTH: 15
<212> TYPE: PRT
<213> ORGANISM: Artificial
<220> FEATURE:
<223> OTHER INFORMATION: Synthetic peptide

<400> SEQUENCE: 40

Ala Cys Gly Phe Met Gly Leu Glu Pro Cys Glu Met Val Cys Ala
1               5                  10                  15

<210> SEQ ID NO 41
<211> LENGTH: 15
<212> TYPE: PRT
<213> ORGANISM: Artificial
<220> FEATURE:
<223> OTHER INFORMATION: Synthetic peptide

<400> SEQUENCE: 41

Ala Cys Gly Phe Met Gly Leu Glu Pro Cys Val Thr Tyr Cys Ala
1               5                  10                  15

<210> SEQ ID NO 42
<211> LENGTH: 15
<212> TYPE: PRT
<213> ORGANISM: Artificial
<220> FEATURE:
<223> OTHER INFORMATION: Synthetic peptide

<400> SEQUENCE: 42

Ala Cys Gly Phe Met Gly Leu Glu Pro Cys Glu Leu Val Cys Ala
1               5                  10                  15

<210> SEQ ID NO 43
<211> LENGTH: 15
<212> TYPE: PRT
<213> ORGANISM: Artificial
<220> FEATURE:
<223> OTHER INFORMATION: Synthetic peptide

<400> SEQUENCE: 43

Ala Cys Gly Phe Met Gly Leu Val Pro Cys Asn Val Phe Cys Ala
1               5                  10                  15
```

```
<210> SEQ ID NO 44
<211> LENGTH: 15
<212> TYPE: PRT
<213> ORGANISM: Artificial
<220> FEATURE:
<223> OTHER INFORMATION: Synthetic peptide

<400> SEQUENCE: 44

Ala Cys Gly Phe Met Gly Leu Glu Pro Cys Glu Leu Phe Cys Ala
1               5                   10                  15

<210> SEQ ID NO 45
<211> LENGTH: 17
<212> TYPE: PRT
<213> ORGANISM: Artificial
<220> FEATURE:
<223> OTHER INFORMATION: Synthetic peptide

<400> SEQUENCE: 45

Ala Cys Gly Phe Met Gly Leu Glu Pro Cys Glu Leu Phe Cys Met Pro
1               5                   10                  15

Lys

<210> SEQ ID NO 46
<211> LENGTH: 15
<212> TYPE: PRT
<213> ORGANISM: Artificial
<220> FEATURE:
<223> OTHER INFORMATION: Synthetic peptide

<400> SEQUENCE: 46

Ala Cys Gly Phe Met Gly Leu Glu Pro Cys Glu Leu Tyr Cys Ala
1               5                   10                  15

<210> SEQ ID NO 47
<211> LENGTH: 17
<212> TYPE: PRT
<213> ORGANISM: Artificial
<220> FEATURE:
<223> OTHER INFORMATION: Synthetic peptide

<400> SEQUENCE: 47

Ala Cys Gly Phe Met Gly Leu Glu Pro Cys Glu Leu Tyr Cys Ala His
1               5                   10                  15

Thr

<210> SEQ ID NO 48
<211> LENGTH: 15
<212> TYPE: PRT
<213> ORGANISM: Artificial
<220> FEATURE:
<223> OTHER INFORMATION: Synthetic peptide

<400> SEQUENCE: 48

Ala Cys Gly Phe Met Gly Leu Glu Pro Cys Glu Met Tyr Cys Ala
1               5                   10                  15

<210> SEQ ID NO 49
<211> LENGTH: 17
<212> TYPE: PRT
<213> ORGANISM: Artificial
<220> FEATURE:
<223> OTHER INFORMATION: Synthetic peptide

<400> SEQUENCE: 49
```

Ala Cys Gly Phe Met Gly Leu Val Pro Cys Glu Leu Tyr Cys Ala Asp
1               5                   10                  15

Asn

<210> SEQ ID NO 50
<211> LENGTH: 17
<212> TYPE: PRT
<213> ORGANISM: Artificial
<220> FEATURE:
<223> OTHER INFORMATION: Synthetic peptide

<400> SEQUENCE: 50

Ala Cys Pro Leu Val Asn Pro Leu Cys Leu Thr Ser Gly Trp Lys Cys
1               5                   10                  15

Ala

<210> SEQ ID NO 51
<211> LENGTH: 17
<212> TYPE: PRT
<213> ORGANISM: Artificial
<220> FEATURE:
<223> OTHER INFORMATION: Synthetic peptide

<400> SEQUENCE: 51

Ala Cys Pro Met Val Asn Pro Leu Cys Leu His Pro Gly Trp Ile Cys
1               5                   10                  15

Ala

<210> SEQ ID NO 52
<211> LENGTH: 17
<212> TYPE: PRT
<213> ORGANISM: Artificial
<220> FEATURE:
<223> OTHER INFORMATION: Synthetic peptide

<400> SEQUENCE: 52

Ala Cys Pro Leu Val Asn Pro Leu Cys Leu His Pro Gly Trp Ile Cys
1               5                   10                  15

Ala

<210> SEQ ID NO 53
<211> LENGTH: 17
<212> TYPE: PRT
<213> ORGANISM: Artificial
<220> FEATURE:
<223> OTHER INFORMATION: Synthetic peptide

<400> SEQUENCE: 53

Ala Cys Pro Leu Val Asn Pro Leu Cys Leu His Pro Gly Trp Arg Cys
1               5                   10                  15

Ala

<210> SEQ ID NO 54
<211> LENGTH: 17
<212> TYPE: PRT
<213> ORGANISM: Artificial
<220> FEATURE:
<223> OTHER INFORMATION: Synthetic peptide

<400> SEQUENCE: 54

Ala Cys Pro Leu Val Asn Pro Leu Cys Asn Leu Pro Gly Trp Thr Cys
1               5                   10                  15

Ala

<210> SEQ ID NO 55
<211> LENGTH: 17
<212> TYPE: PRT
<213> ORGANISM: Artificial
<220> FEATURE:
<223> OTHER INFORMATION: Synthetic peptide

<400> SEQUENCE: 55

Ala Cys Pro Leu Val Asn Pro Leu Cys Leu Val Pro Gly Trp Ser Cys
 1               5                  10                  15

Ala

<210> SEQ ID NO 56
<211> LENGTH: 17
<212> TYPE: PRT
<213> ORGANISM: Artificial
<220> FEATURE:
<223> OTHER INFORMATION: Synthetic peptide

<400> SEQUENCE: 56

Ala Cys Pro Leu Val Asn Pro Leu Cys Leu Leu Asp Gly Trp Thr Cys
 1               5                  10                  15

Ala

<210> SEQ ID NO 57
<211> LENGTH: 17
<212> TYPE: PRT
<213> ORGANISM: Artificial
<220> FEATURE:
<223> OTHER INFORMATION: Synthetic peptide

<400> SEQUENCE: 57

Ala Cys Pro Leu Val Asn Pro Leu Cys Leu Met Pro Gly Trp Gly Cys
 1               5                  10                  15

Ala

<210> SEQ ID NO 58
<211> LENGTH: 17
<212> TYPE: PRT
<213> ORGANISM: Artificial
<220> FEATURE:
<223> OTHER INFORMATION: Synthetic peptide

<400> SEQUENCE: 58

Ala Cys Pro Leu Val Asn Pro Leu Cys Met Ile Gly Asn Trp Thr Cys
 1               5                  10                  15

Ala

<210> SEQ ID NO 59
<211> LENGTH: 17
<212> TYPE: PRT
<213> ORGANISM: Artificial
<220> FEATURE:
<223> OTHER INFORMATION: Synthetic peptide

<400> SEQUENCE: 59

Ala Cys Pro Leu Val Asn Pro Leu Cys Leu Met Thr Gly Trp Ser Cys
 1               5                  10                  15

Ala

<210> SEQ ID NO 60

```
<211> LENGTH: 17
<212> TYPE: PRT
<213> ORGANISM: Artificial
<220> FEATURE:
<223> OTHER INFORMATION: Synthetic peptide

<400> SEQUENCE: 60

Ala Cys Pro Leu Val Asn Pro Leu Cys Met Met Gly Gly Trp Lys Cys
1               5                   10                  15
Ala

<210> SEQ ID NO 61
<211> LENGTH: 17
<212> TYPE: PRT
<213> ORGANISM: Artificial
<220> FEATURE:
<223> OTHER INFORMATION: Synthetic peptide

<400> SEQUENCE: 61

Ala Cys Pro Leu Val Asn Pro Leu Cys Leu Tyr Gly Ser Trp Lys Cys
1               5                   10                  15
Ala

<210> SEQ ID NO 62
<211> LENGTH: 17
<212> TYPE: PRT
<213> ORGANISM: Artificial
<220> FEATURE:
<223> OTHER INFORMATION: Synthetic peptide

<400> SEQUENCE: 62

Ala Cys Pro Leu Val Asn Pro Leu Cys Leu His Pro Gly Trp Thr Cys
1               5                   10                  15
Ala

<210> SEQ ID NO 63
<211> LENGTH: 19
<212> TYPE: PRT
<213> ORGANISM: Artificial
<220> FEATURE:
<223> OTHER INFORMATION: Synthetic peptide

<400> SEQUENCE: 63

Ala Arg Asp Cys Pro Leu Val Asn Pro Leu Cys Leu His Pro Gly Trp
1               5                   10                  15
Thr Cys Ala

<210> SEQ ID NO 64
<211> LENGTH: 19
<212> TYPE: PRT
<213> ORGANISM: Artificial
<220> FEATURE:
<223> OTHER INFORMATION: Synthetic peptide

<400> SEQUENCE: 64

Arg Pro Ala Cys Pro Leu Val Asn Pro Leu Cys Leu His Pro Gly Trp
1               5                   10                  15
Thr Cys Ala

<210> SEQ ID NO 65
<211> LENGTH: 19
<212> TYPE: PRT
<213> ORGANISM: Artificial
<220> FEATURE:
```

<223> OTHER INFORMATION: Synthetic peptide

<400> SEQUENCE: 65

Arg Pro Pro Cys Pro Leu Val Asn Pro Leu Cys Leu His Pro Gly Trp
1               5                   10                  15

Thr Cys Ala

<210> SEQ ID NO 66
<211> LENGTH: 19
<212> TYPE: PRT
<213> ORGANISM: Artificial
<220> FEATURE:
<223> OTHER INFORMATION: Synthetic peptide

<400> SEQUENCE: 66

Lys His Ser Cys Pro Leu Val Asn Pro Leu Cys Leu His Pro Gly Trp
1               5                   10                  15

Thr Cys Ala

<210> SEQ ID NO 67
<211> LENGTH: 19
<212> TYPE: PRT
<213> ORGANISM: Artificial
<220> FEATURE:
<223> OTHER INFORMATION: Synthetic peptide

<400> SEQUENCE: 67

Ala Cys Pro Leu Val Asn Pro Leu Cys Leu His Pro Gly Trp Thr Cys
1               5                   10                  15

Leu His Gly

<210> SEQ ID NO 68
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (18)..(18)
<223> OTHER INFORMATION: Xaa is D-His

<400> SEQUENCE: 68

Ala Cys Pro Leu Val Asn Pro Leu Cys Leu His Pro Gly Trp Thr Cys
1               5                   10                  15

Leu Xaa Gly

<210> SEQ ID NO 69
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is 2Nal

<400> SEQUENCE: 69

Ala Cys Pro Leu Val Asn Pro Leu Cys Leu His Pro Gly Xaa Thr Cys
1               5                   10                  15

Leu His Gly

<210> SEQ ID NO 70

```
<211> LENGTH: 19
<212> TYPE: PRT
<213> ORGANISM: Artificial
<220> FEATURE:
<223> OTHER INFORMATION: Synthetic peptide

<400> SEQUENCE: 70

Arg His Asp Cys Pro Leu Val Asn Pro Leu Cys Leu Leu Pro Gly Trp
1               5                   10                  15
Thr Cys Ala

<210> SEQ ID NO 71
<211> LENGTH: 19
<212> TYPE: PRT
<213> ORGANISM: Artificial
<220> FEATURE:
<223> OTHER INFORMATION: Synthetic peptide

<400> SEQUENCE: 71

Thr Pro Arg Cys Pro Leu Val Asn Pro Leu Cys Leu Met Pro Gly Trp
1               5                   10                  15
Thr Cys Ala

<210> SEQ ID NO 72
<211> LENGTH: 17
<212> TYPE: PRT
<213> ORGANISM: Artificial
<220> FEATURE:
<223> OTHER INFORMATION: Synthetic peptide

<400> SEQUENCE: 72

Ala Cys Pro Leu Val Asn Pro Leu Cys Leu Ala Pro Gly Trp Thr Cys
1               5                   10                  15
Ala

<210> SEQ ID NO 73
<211> LENGTH: 19
<212> TYPE: PRT
<213> ORGANISM: Artificial
<220> FEATURE:
<223> OTHER INFORMATION: Synthetic peptide

<400> SEQUENCE: 73

Ala Cys Pro Leu Val Asn Pro Leu Cys Leu Ala Pro Gly Trp Thr Cys
1               5                   10                  15
Ser Arg Ser

<210> SEQ ID NO 74
<211> LENGTH: 17
<212> TYPE: PRT
<213> ORGANISM: Artificial
<220> FEATURE:
<223> OTHER INFORMATION: Synthetic peptide

<400> SEQUENCE: 74

Ala Cys Pro Leu Val Asn Pro Leu Cys Leu Glu Pro Gly Trp Thr Cys
1               5                   10                  15
Ala

<210> SEQ ID NO 75
<211> LENGTH: 19
<212> TYPE: PRT
<213> ORGANISM: Artificial
<220> FEATURE:
```

<223> OTHER INFORMATION: Synthetic peptide

<400> SEQUENCE: 75

Ala Cys Pro Leu Val Asn Pro Leu Cys Leu Glu Pro Gly Trp Thr Cys
1               5                   10                  15

Ala Lys Arg

<210> SEQ ID NO 76
<211> LENGTH: 17
<212> TYPE: PRT
<213> ORGANISM: Artificial
<220> FEATURE:
<223> OTHER INFORMATION: Synthetic peptide

<400> SEQUENCE: 76

Ala Cys Pro Leu Val Asn Pro Leu Cys Leu His Pro Gly Trp Ser Cys
1               5                   10                  15

Ala

<210> SEQ ID NO 77
<211> LENGTH: 19
<212> TYPE: PRT
<213> ORGANISM: Artificial
<220> FEATURE:
<223> OTHER INFORMATION: Synthetic peptide

<400> SEQUENCE: 77

Ala Cys Pro Leu Val Asn Pro Leu Cys Leu His Pro Gly Trp Ser Cys
1               5                   10                  15

Arg Gly Gln

<210> SEQ ID NO 78
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (17)..(17)
<223> OTHER INFORMATION: Xaa is HArg

<400> SEQUENCE: 78

Ala Cys Pro Leu Val Asn Pro Leu Cys Leu His Pro Gly Trp Ser Cys
1               5                   10                  15

Xaa Gly Gln

<210> SEQ ID NO 79
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is 2Nal

<400> SEQUENCE: 79

Ala Cys Pro Leu Val Asn Pro Leu Cys Leu His Pro Gly Xaa Ser Cys
1               5                   10                  15

Arg Gly Gln

<210> SEQ ID NO 80

```
<211> LENGTH: 19
<212> TYPE: PRT
<213> ORGANISM: Artificial
<220> FEATURE:
<223> OTHER INFORMATION: Synthetic peptide

<400> SEQUENCE: 80

Ala Cys Pro Leu Val Asn Pro Leu Cys Leu Thr Pro Gly Trp Thr Cys
1               5                   10                  15

Thr Asn Thr

<210> SEQ ID NO 81
<211> LENGTH: 17
<212> TYPE: PRT
<213> ORGANISM: Artificial
<220> FEATURE:
<223> OTHER INFORMATION: Synthetic peptide

<400> SEQUENCE: 81

Ala Cys Pro Met Val Asn Pro Leu Cys Leu His Pro Gly Trp Lys Cys
1               5                   10                  15

Ala

<210> SEQ ID NO 82
<211> LENGTH: 17
<212> TYPE: PRT
<213> ORGANISM: Artificial
<220> FEATURE:
<223> OTHER INFORMATION: Synthetic peptide

<400> SEQUENCE: 82

Ala Cys Pro Met Val Asn Pro Leu Cys Leu Thr Pro Gly Trp Ile Cys
1               5                   10                  15

Ala

<210> SEQ ID NO 83
<211> LENGTH: 17
<212> TYPE: PRT
<213> ORGANISM: Artificial
<220> FEATURE:
<223> OTHER INFORMATION: Synthetic peptide

<400> SEQUENCE: 83

Ala Cys Pro Met Val Asn Pro Leu Cys Leu His Pro Gly Trp Thr Cys
1               5                   10                  15

Ala

<210> SEQ ID NO 84
<211> LENGTH: 19
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Asp
<220> FEATURE:
<221> NAME/KEY: Xaa
<222> LOCATION: (6)..(6)
<223> OTHER INFORMATION: Xaa is Aib
<220> FEATURE:
<221> NAME/KEY: Xaa
<222> LOCATION: (7)..(7)
<223> OTHER INFORMATION: Xaa is 1Nal
<220> FEATURE:
<221> NAME/KEY: Xaa
```

```
<222> LOCATION: (9)..(9)
<223> OTHER INFORMATION: Xaa is Aib
<220> FEATURE:
<221> NAME/KEY: Xaa
<222> LOCATION: (11)..(11)
<223> OTHER INFORMATION: Xaa is 1Nal
<220> FEATURE:
<221> NAME/KEY: Xaa
<222> LOCATION: (14)..(14)
<223> OTHER INFORMATION: Xaa is tBuGly
<220> FEATURE:
<221> NAME/KEY: Xaa
<222> LOCATION: (16)..(16)
<223> OTHER INFORMATION: Xaa is HArg
<220> FEATURE:
<221> NAME/KEY: Xaa
<222> LOCATION: (18)..(18)
<223> OTHER INFORMATION: Xaa is D-Asp

<400> SEQUENCE: 84

His Xaa Val Thr Cys Xaa Xaa Gly Xaa Phe Xaa Cys Pro Xaa Asn Xaa
1               5                   10                  15

Pro Xaa Cys

<210> SEQ ID NO 85
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
<223> OTHER INFORMATION: Xaa is Hse(Me)
<220> FEATURE:
<221> NAME/KEY: Xaa
<222> LOCATION: (15)..(15)
<223> OTHER INFORMATION: Xaa is D-Asp
<220> FEATURE:
<221> NAME/KEY: Xaa
<222> LOCATION: (17)..(17)
<223> OTHER INFORMATION: Xaa is HArg

<400> SEQUENCE: 85

Ala Xaa Asp Cys Xaa Xaa Val Asn Pro Leu Cys Leu His Pro Xaa Trp
1               5                   10                  15

Xaa Cys

<210> SEQ ID NO 86
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (6)..(6)
```

```
<223> OTHER INFORMATION: Xaa is Hse(Me)
<220> FEATURE:
<221> NAME/KEY: Xaa
<222> LOCATION: (15)..(15)
<223> OTHER INFORMATION: Xaa is D-Asp

<400> SEQUENCE: 86

Ala Xaa Asp Cys Xaa Xaa Val Asn Pro Leu Cys Leu His Pro Xaa Trp
1               5                   10                  15

Thr Cys

<210> SEQ ID NO 87
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (15)..(15)
<223> OTHER INFORMATION: Xaa is D-Ala

<400> SEQUENCE: 87

Ala Xaa Asp Cys Xaa Leu Val Asn Pro Leu Cys Leu His Pro Xaa Trp
1               5                   10                  15

Thr Cys

<210> SEQ ID NO 88
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (15)..(15)
<223> OTHER INFORMATION: Xaa is D-Ala

<400> SEQUENCE: 88

Ala Xaa Asp Cys Pro Leu Val Asn Pro Leu Cys Leu His Pro Xaa Trp
1               5                   10                  15

Thr Cys

<210> SEQ ID NO 89
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is HyP

<400> SEQUENCE: 89

Ala Arg Asp Cys Xaa Leu Val Asn Pro Leu Cys Leu His Pro Gly Trp
1               5                   10                  15
```

Thr Cys

<210> SEQ ID NO 90
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (13)..(13)
<223> OTHER INFORMATION: Xaa is D-3,3-DPA

<400> SEQUENCE: 90

Ala Arg Asp Cys Pro Leu Val Asn Pro Leu Cys Leu Xaa Pro Gly Trp
1               5                   10                  15

Thr Cys

<210> SEQ ID NO 91
<211> LENGTH: 20
<212> TYPE: PRT
<213> ORGANISM: Artificial
<220> FEATURE:
<223> OTHER INFORMATION: Synthetic peptide

<400> SEQUENCE: 91

Ala Arg Asp Cys Pro Leu Val Asn Pro Leu Cys Leu His Pro Gly Trp
1               5                   10                  15

Thr Cys Leu His
            20

<210> SEQ ID NO 92
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is HArg
<220> FEATURE:
<221> NAME/KEY: Xaa
<222> LOCATION: (15)..(15)
<223> OTHER INFORMATION: Xaa is Cya

<400> SEQUENCE: 92

Ala Xaa Asp Cys Pro Leu Val Asn Pro Leu Cys Leu His Pro Xaa Trp
1               5                   10                  15

Thr Cys

<210> SEQ ID NO 93
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is D-Arg
<220> FEATURE:
<221> NAME/KEY: Xaa
<222> LOCATION: (5)..(5)
<223> OTHER INFORMATION: Xaa is HyP
<220> FEATURE:
<221> NAME/KEY: Xaa
<222> LOCATION: (13)..(13)

```
<223> OTHER INFORMATION: Xaa is D-3,3-DPA
<220> FEATURE:
<221> NAME/KEY: Xaa
<222> LOCATION: (15)..(15)
<223> OTHER INFORMATION: Xaa is D-Asp
<220> FEATURE:
<221> NAME/KEY: Xaa
<222> LOCATION: (17)..(17)
<223> OTHER INFORMATION: Xaa is HArg

<400> SEQUENCE: 93

Ala Xaa Asp Cys Xaa Leu Val Asn Pro Leu Cys Leu Xaa Pro Xaa Trp
1               5                   10                  15

Xaa Cys

<210> SEQ ID NO 94
<211> LENGTH: 17
<212> TYPE: PRT
<213> ORGANISM: Artificial
<220> FEATURE:
<223> OTHER INFORMATION: Synthetic peptide

<400> SEQUENCE: 94

Ala Cys Pro Trp Gly Pro Ala Trp Cys Pro Val Asn Arg Pro Gly Cys
1               5                   10                  15

Ala

<210> SEQ ID NO 95
<211> LENGTH: 17
<212> TYPE: PRT
<213> ORGANISM: Artificial
<220> FEATURE:
<223> OTHER INFORMATION: Synthetic peptide

<400> SEQUENCE: 95

Ala Cys Pro Trp Gly Pro Phe Trp Cys Pro Val Asn Arg Pro Gly Cys
1               5                   10                  15

Ala

<210> SEQ ID NO 96
<211> LENGTH: 20
<212> TYPE: PRT
<213> ORGANISM: Artificial
<220> FEATURE:
<223> OTHER INFORMATION: Synthetic peptide

<400> SEQUENCE: 96

Ala Asp Val Thr Cys Pro Trp Gly Pro Phe Trp Cys Pro Val Asn Arg
1               5                   10                  15

Pro Gly Cys Ala
            20

<210> SEQ ID NO 97
<211> LENGTH: 15
<212> TYPE: PRT
<213> ORGANISM: Artificial
<220> FEATURE:
<223> OTHER INFORMATION: Synthetic peptide

<400> SEQUENCE: 97

Cys Pro Leu Val Asn Pro Leu Cys Leu His Pro Gly Trp Thr Cys
1               5                   10                  15

<210> SEQ ID NO 98
<211> LENGTH: 7
```

```
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (3)..(3)
<223> OTHER INFORMATION: Xaa is Cit
<220> FEATURE:
<221> NAME/KEY: Xaa
<222> LOCATION: (5)..(5)
<223> OTHER INFORMATION: Xaa is hPhe

<400> SEQUENCE: 98

Glu Pro Xaa Gly Xaa Tyr Leu
1               5
```